(12) United States Patent
Grant et al.

(10) Patent No.: US 10,994,871 B2
(45) Date of Patent: May 4, 2021

(54) APPARATUS, SYSTEM AND METHOD FOR FLUID DELIVERY

(71) Applicant: DEKA Products Limited Partnership, Manchester, NH (US)

(72) Inventors: Kevin L. Grant, Litchfield, NH (US); Richard J. Lanigan, Concord, NH (US); Cory L. Adams, Pembroke, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 16/393,270

(22) Filed: Apr. 24, 2019

(65) Prior Publication Data

US 2019/0248518 A1 Aug. 15, 2019

Related U.S. Application Data

(63) Continuation-in-part of application No. 15/961,238, filed on Apr. 24, 2018, which is a continuation-in-part
(Continued)

(51) Int. Cl.
*A61M 5/14* (2006.01)
*B65B 3/00* (2006.01)
(Continued)

(52) U.S. Cl.
CPC ......... *B65B 3/003* (2013.01); *A61M 5/14224* (2013.01); *A61M 5/14248* (2013.01);
(Continued)

(58) Field of Classification Search
CPC ............... B65B 3/003; A61M 5/16809; A61M 5/14224; A61M 5/14586; A61M 5/14248; A61M 2205/3306; A61M 2205/0266; A61M 2205/18; A61M 2205/0294; A61M 2205/3576; A61M 2205/8237; A61M 2205/3546; A61M 2205/3331; A61M 2205/3375; A61M 2205/8206; A61M 2005/14268; A61M 2005/3114; A61M 2209/086; A61M 2209/045; A61M 2039/1077
See application file for complete search history.

(56) References Cited

U.S. PATENT DOCUMENTS 3,486,539 A * 12/1969 Jacuzzi ................. A61M 5/152
141/329
3,702,609 A * 11/1972 Steiner ................ A61M 5/2033
604/139
(Continued)

*Primary Examiner* — Nicolas A Arnett
(74) *Attorney, Agent, or Firm* — Reid Knott Cunningham

(57) ABSTRACT

A filling aid device for filling a reservoir. The device includes a cover portion comprising a septum window; a slider beam comprising a septum cover; and a first filling aid tab attached to the slider beam, the first filling aid tab in slidable relation to the cover from a first position to a second position, wherein when the filling aid device is in an unlocked position, the septum cover is located below the septum window, wherein when the first filling aid tab is moved from the first position to the second position, the septum cover is moved from below the septum window, and the filling aid device is in the locked position.

29 Claims, 408 Drawing Sheets

Related U.S. Application Data of application No. 15/483,490, filed on Apr. 10, 2017, now Pat. No. 10,773,836, which is a continuation of application No. 14/323,672, filed on Jul. 3, 2014, now Pat. No. 9,617,020.

(60) Provisional application No. 62/662,018, filed on Apr. 24, 2018, provisional application No. 62/489,154, filed on Apr. 24, 2017, provisional application No. 61/905,533, filed on Nov. 18, 2013, provisional application No. 61/842,553, filed on Jul. 3, 2013.

(51) Int. Cl.
*A61M 5/142* (2006.01)
*A61M 5/168* (2006.01)
*A61M 5/145* (2006.01)
*A61M 5/31* (2006.01)
*A61M 39/10* (2006.01)

(52) U.S. Cl.
CPC .... *A61M 5/14586* (2013.01); *A61M 5/16809* (2013.01); *A61M 2005/14268* (2013.01); *A61M 2005/3114* (2013.01); *A61M 2039/1077* (2013.01); *A61M 2205/0266* (2013.01); *A61M 2205/0294* (2013.01); *A61M 2205/18* (2013.01); *A61M 2205/3306* (2013.01); *A61M 2205/3331* (2013.01); *A61M 2205/3375* (2013.01); *A61M 2205/3546* (2013.01); *A61M 2205/3576* (2013.01); *A61M 2205/8206* (2013.01); *A61M 2205/8237* (2013.01); *A61M 2206/22* (2013.01); *A61M 2209/045* (2013.01); *A61M 2209/086* (2013.01)

(56) References Cited

U.S. PATENT DOCUMENTS

| | | | | |
|---|---|---|---|---|
| 5,681,291 | A * | 10/1997 | Galli | A61M 5/2033 604/156 |
| 7,361,160 | B2 * | 4/2008 | Hommann | A61M 5/2033 604/198 |
| 7,682,345 | B2 * | 3/2010 | Savage | A61M 5/007 604/228 |
| 7,882,863 | B2 * | 2/2011 | Pestotnik | A61J 1/2089 141/27 |
| 8,409,138 | B2 * | 4/2013 | James | A61M 5/2033 604/110 |
| 9,180,244 | B2 * | 11/2015 | Anderson | A61M 5/14248 |
| 2004/0158205 | A1 * | 8/2004 | Savage | A61M 5/14546 604/151 |
| 2010/0049125 | A1 * | 2/2010 | James | A61M 5/2033 604/110 |
| 2010/0198182 | A1 * | 8/2010 | Lanigan | A61M 5/16809 604/406 |
| 2010/0243099 | A1 * | 9/2010 | Yodfat | A61M 5/14244 141/2 |
| 2010/0249697 | A1 * | 9/2010 | Matusch | A61M 5/30 604/68 |
| 2010/0256486 | A1 * | 10/2010 | Savage | A61M 5/007 600/432 |
| 2011/0054390 | A1 * | 3/2011 | Searle | A61M 5/1413 604/66 |
| 2014/0311624 | A1 * | 10/2014 | Eilertsen | A61J 1/2089 141/18 |
| 2014/0360623 | A1 * | 12/2014 | Nielsen | A61J 1/2096 141/27 |
| 2018/0237174 | A1 * | 8/2018 | Grant | A61M 5/16809 |
| 2019/0248518 | A1 * | 8/2019 | Grant | A61M 5/14224 |
| 2019/0321260 | A1 * | 10/2019 | Grant | A61J 1/2037 |

* cited by examiner

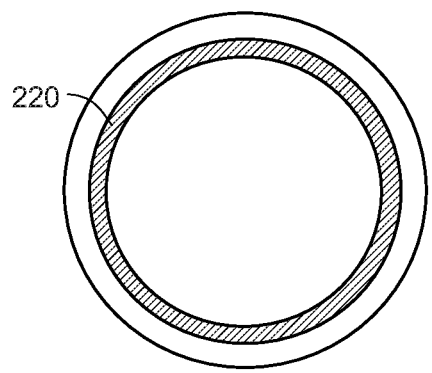
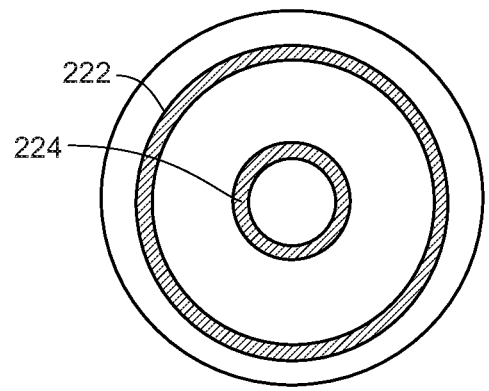
FIG. 10A  FIG. 10B
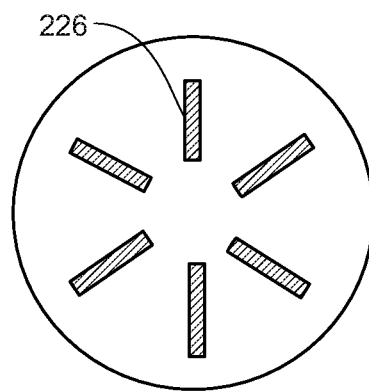
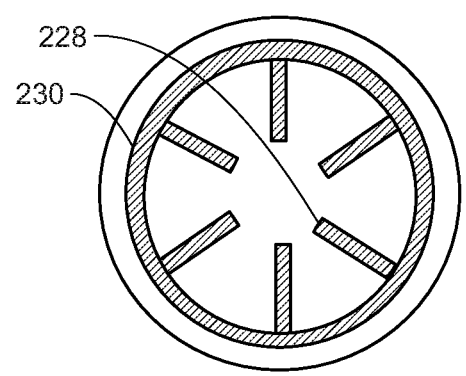
FIG. 10C  FIG. 10D
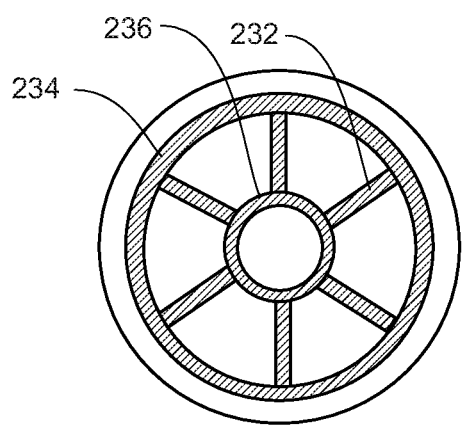
FIG. 10E Each HW interface has its own Driver instance
Driver Interaction Data Flow Diagram

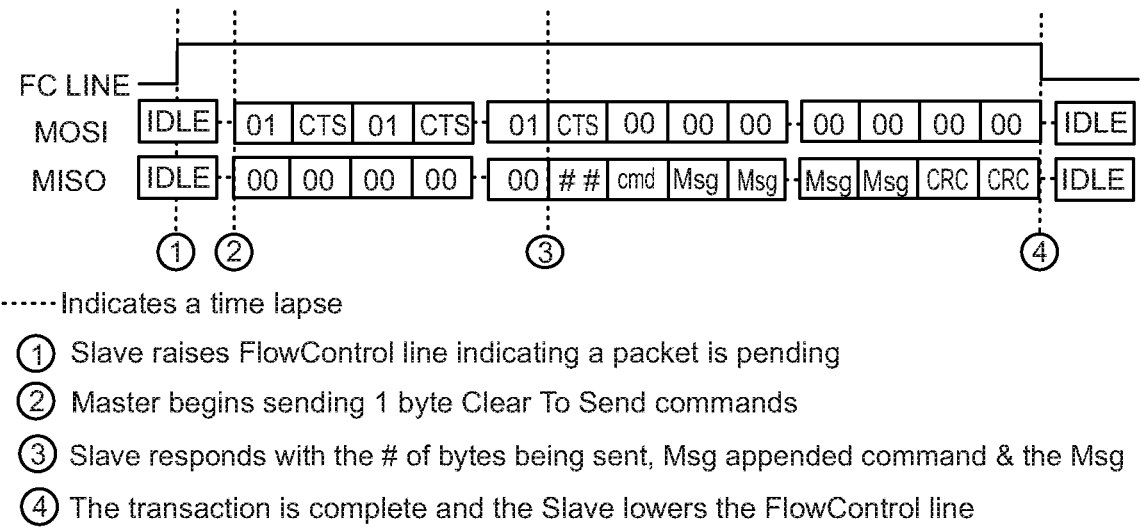

------ Indicates a time lapse

① Slave raises FlowControl line indicating a packet is pending
② Master begins sending 1 byte Clear To Send commands
③ Slave responds with the # of bytes being sent, Msg appended command & the Msg
④ The transaction is complete and the Slave lowers the FlowControl line

FIG.11Q

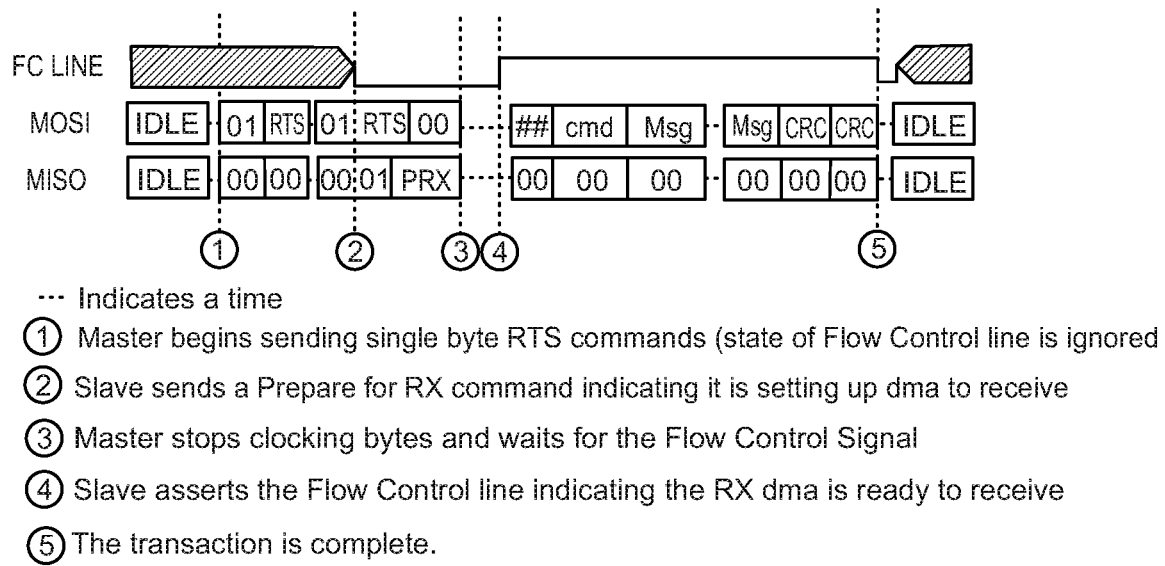

--- Indicates a time

① Master begins sending single byte RTS commands (state of Flow Control line is ignored)
② Slave sends a Prepare for RX command indicating it is setting up dma to receive
③ Master stops clocking bytes and waits for the Flow Control Signal
④ Slave asserts the Flow Control line indicating the RX dma is ready to receive
⑤ The transaction is complete.

FIG.11R

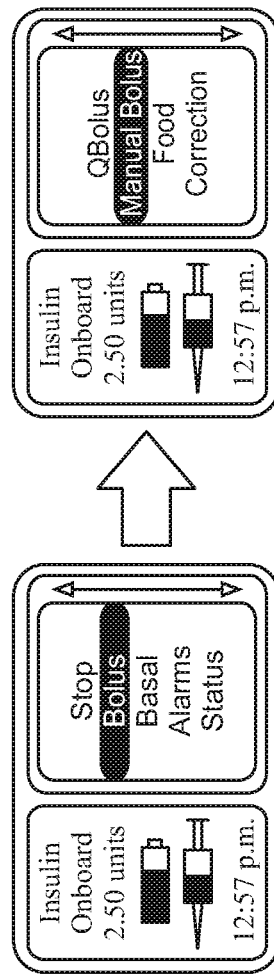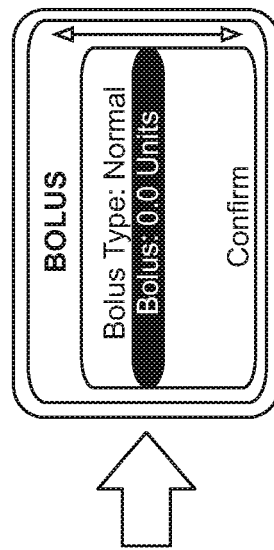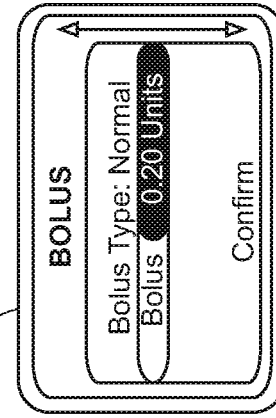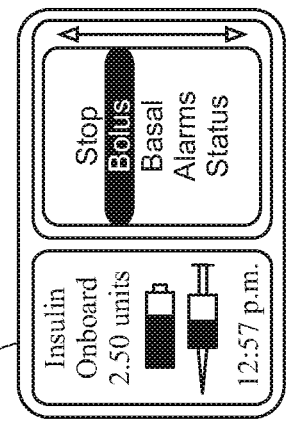

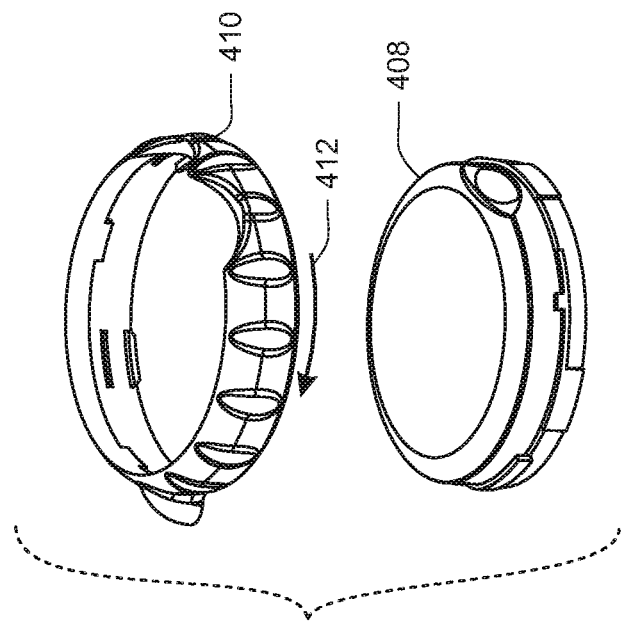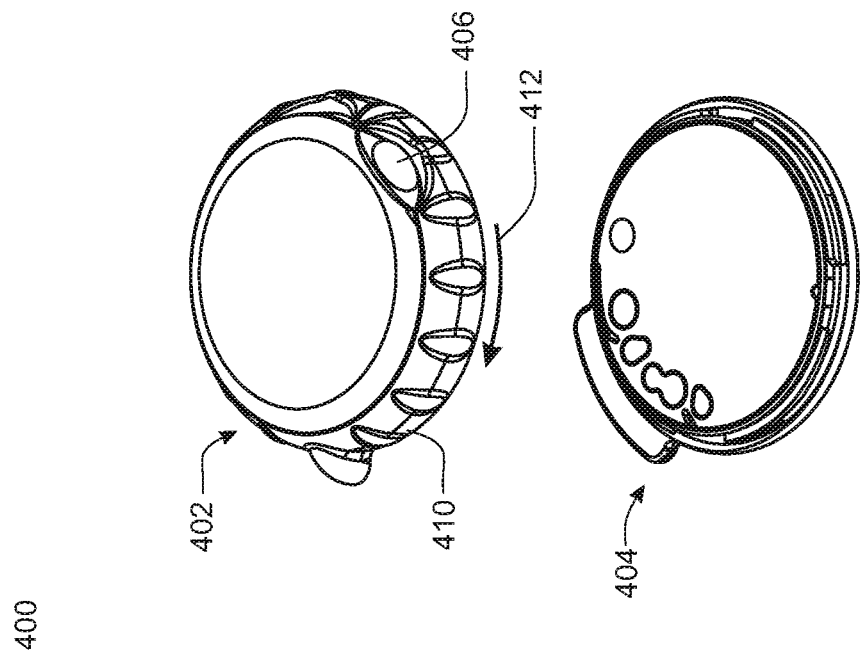
FIG. 13

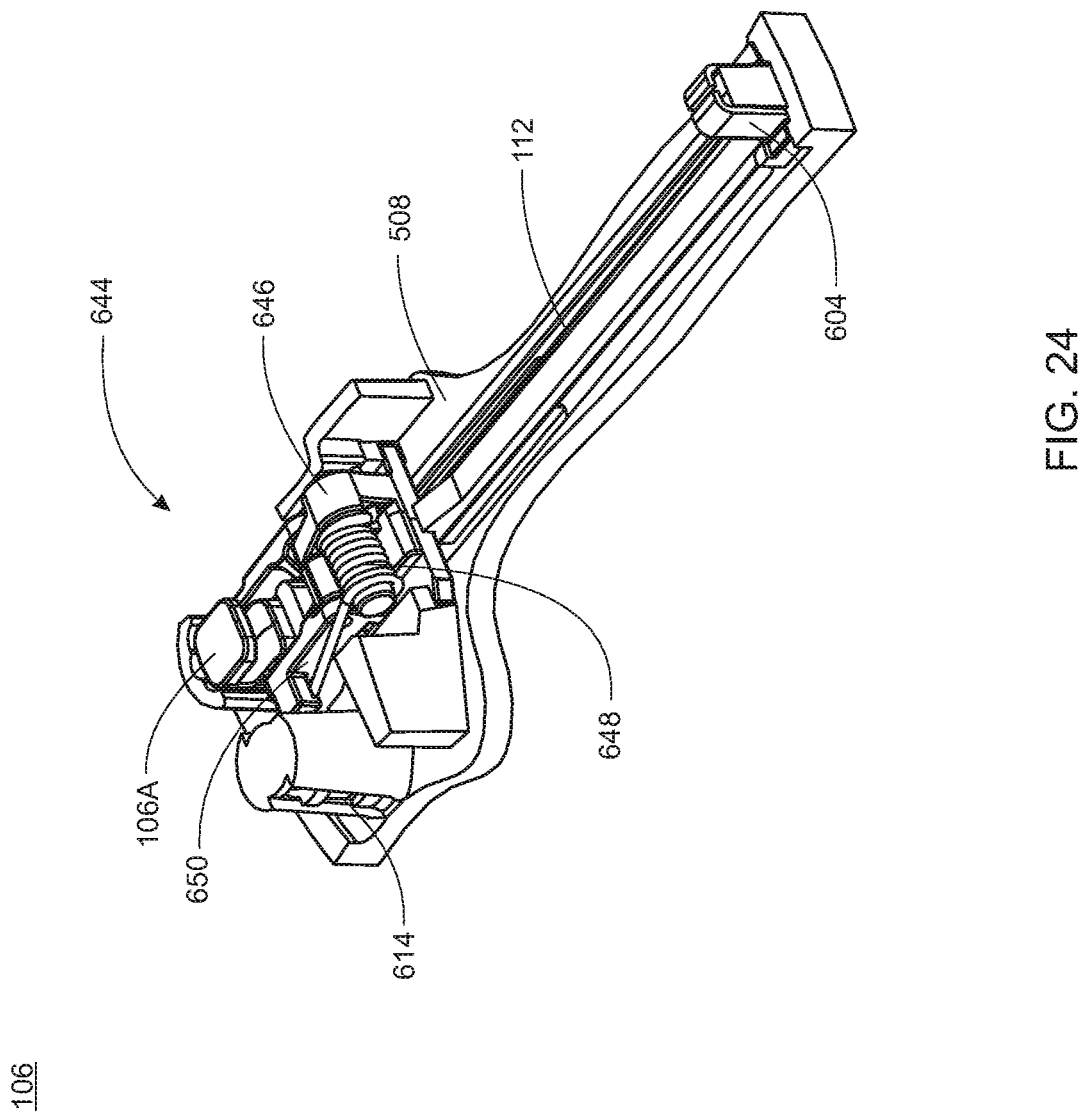

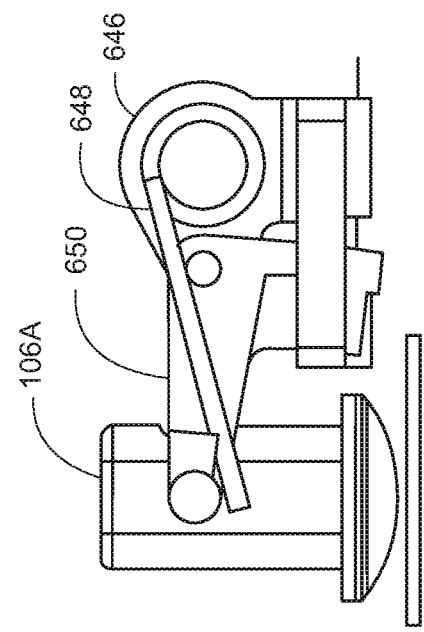
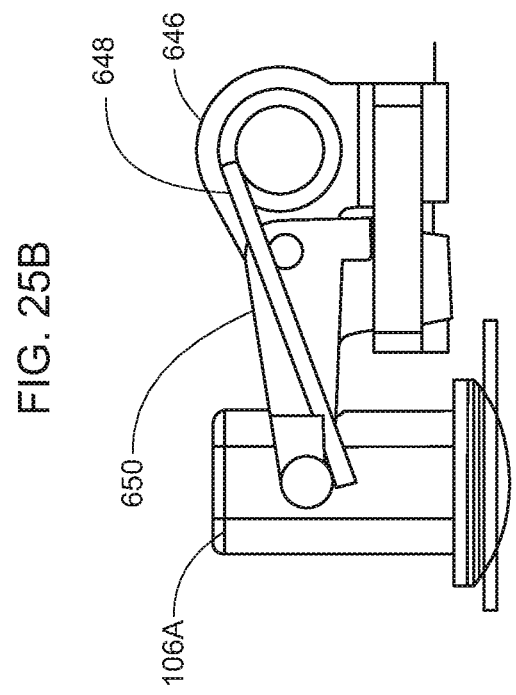
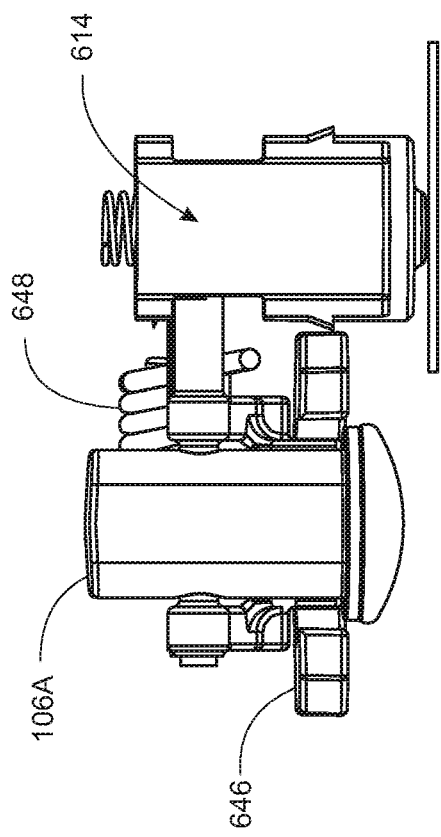
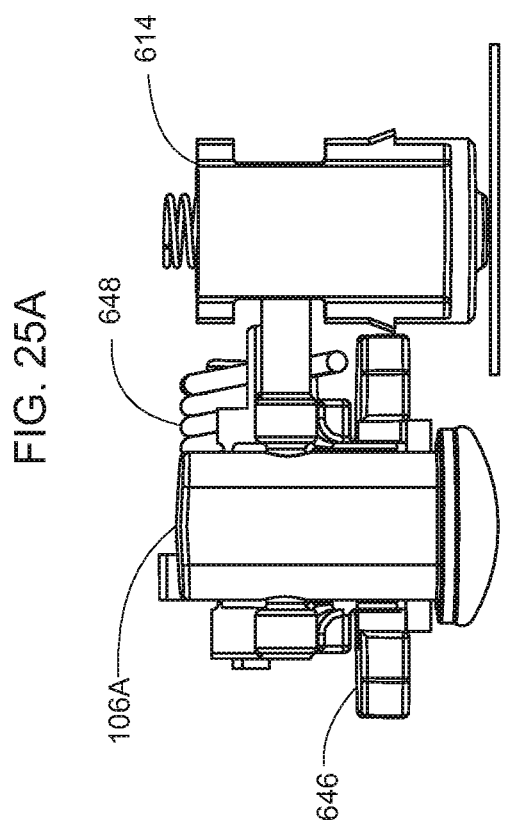

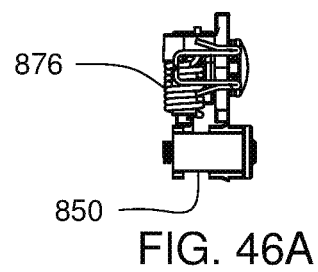
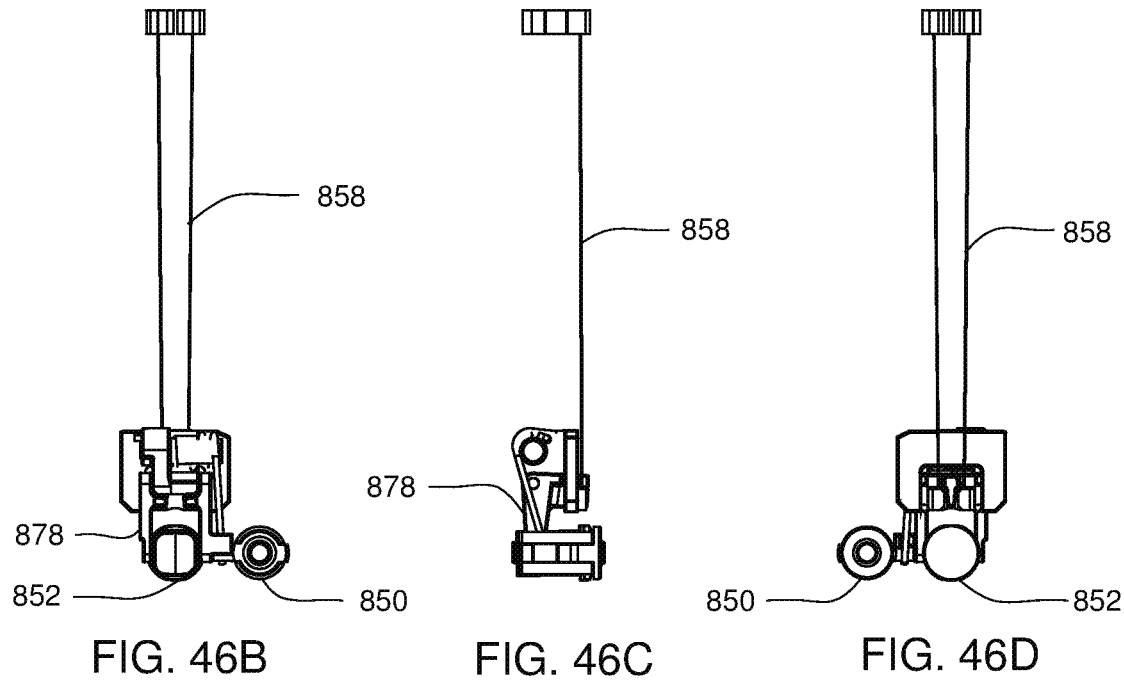
FIG. 46A  FIG. 46B  FIG. 46C  FIG. 46D
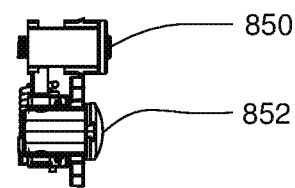
FIG. 46E

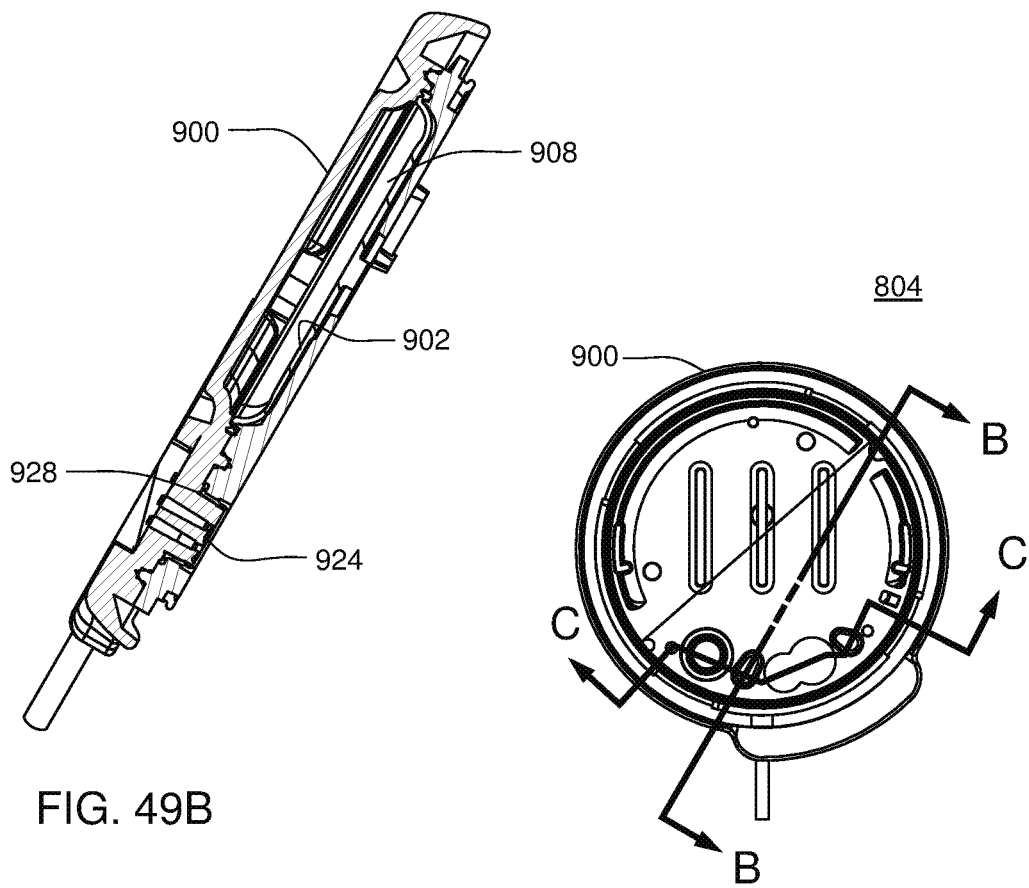
FIG. 49B
FIG. 49A
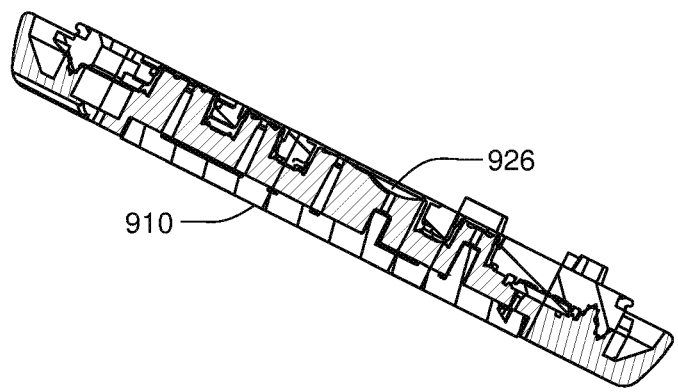
FIG. 49C

924

924

924

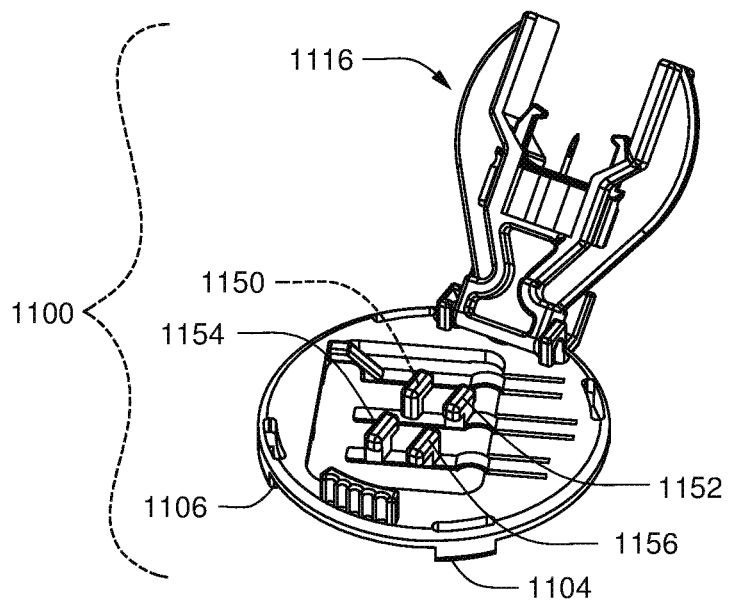
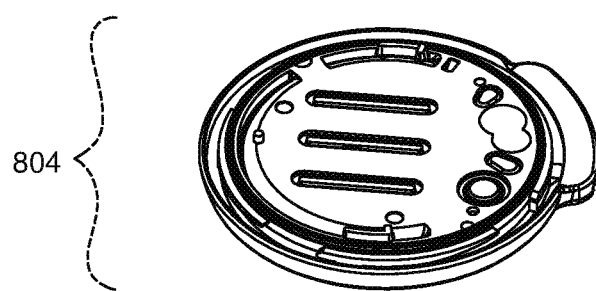
FIG. 68

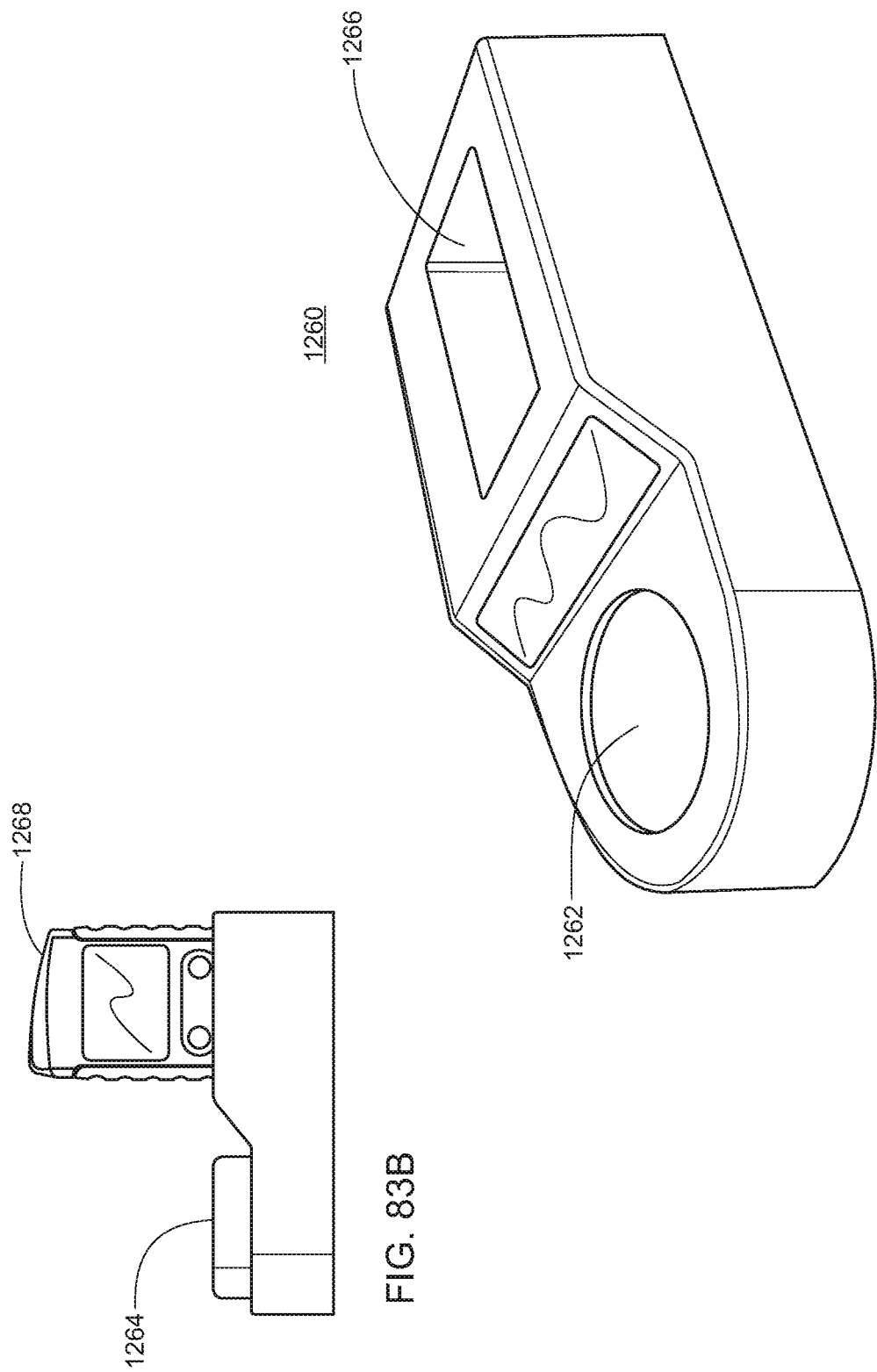

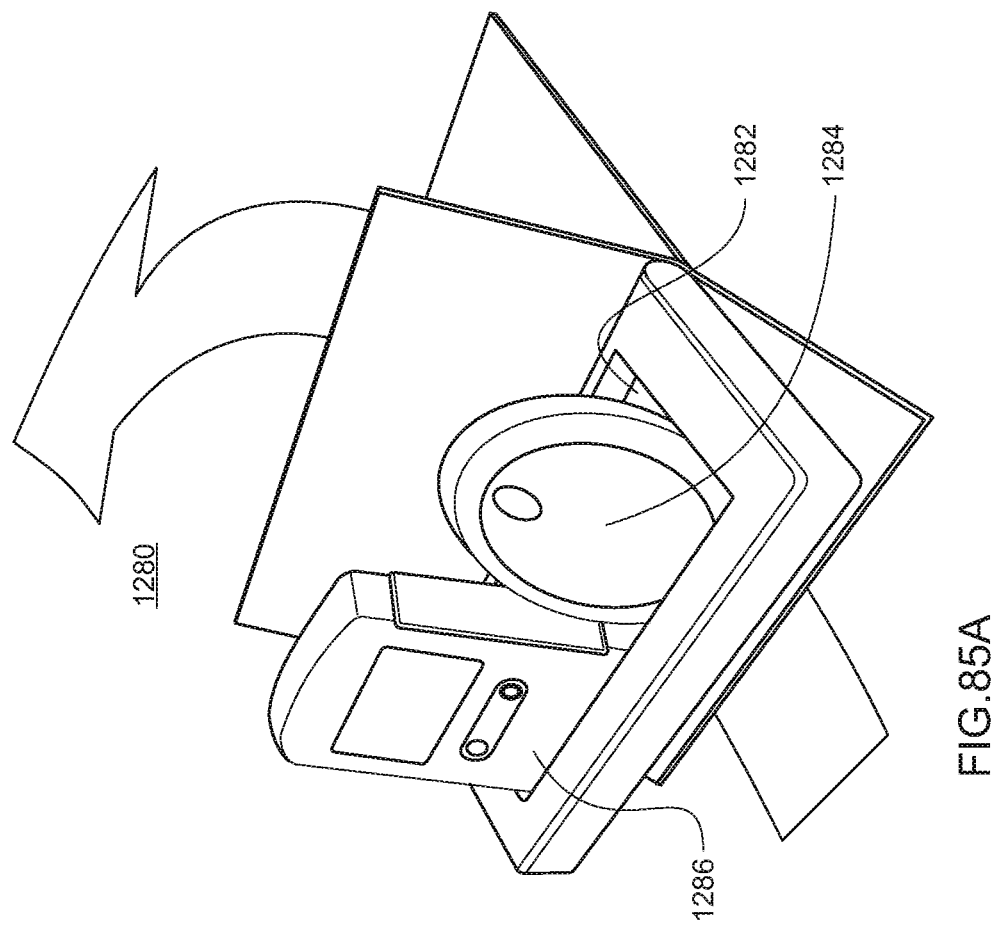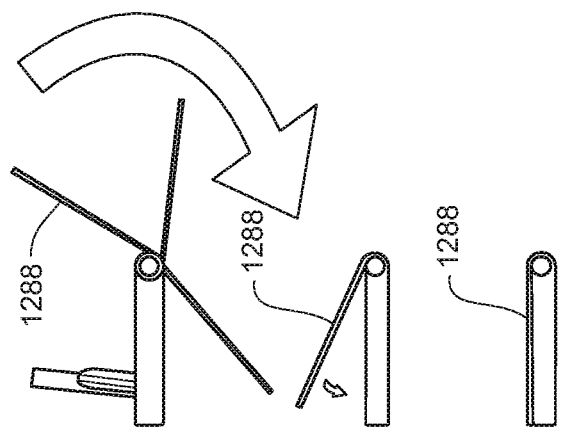

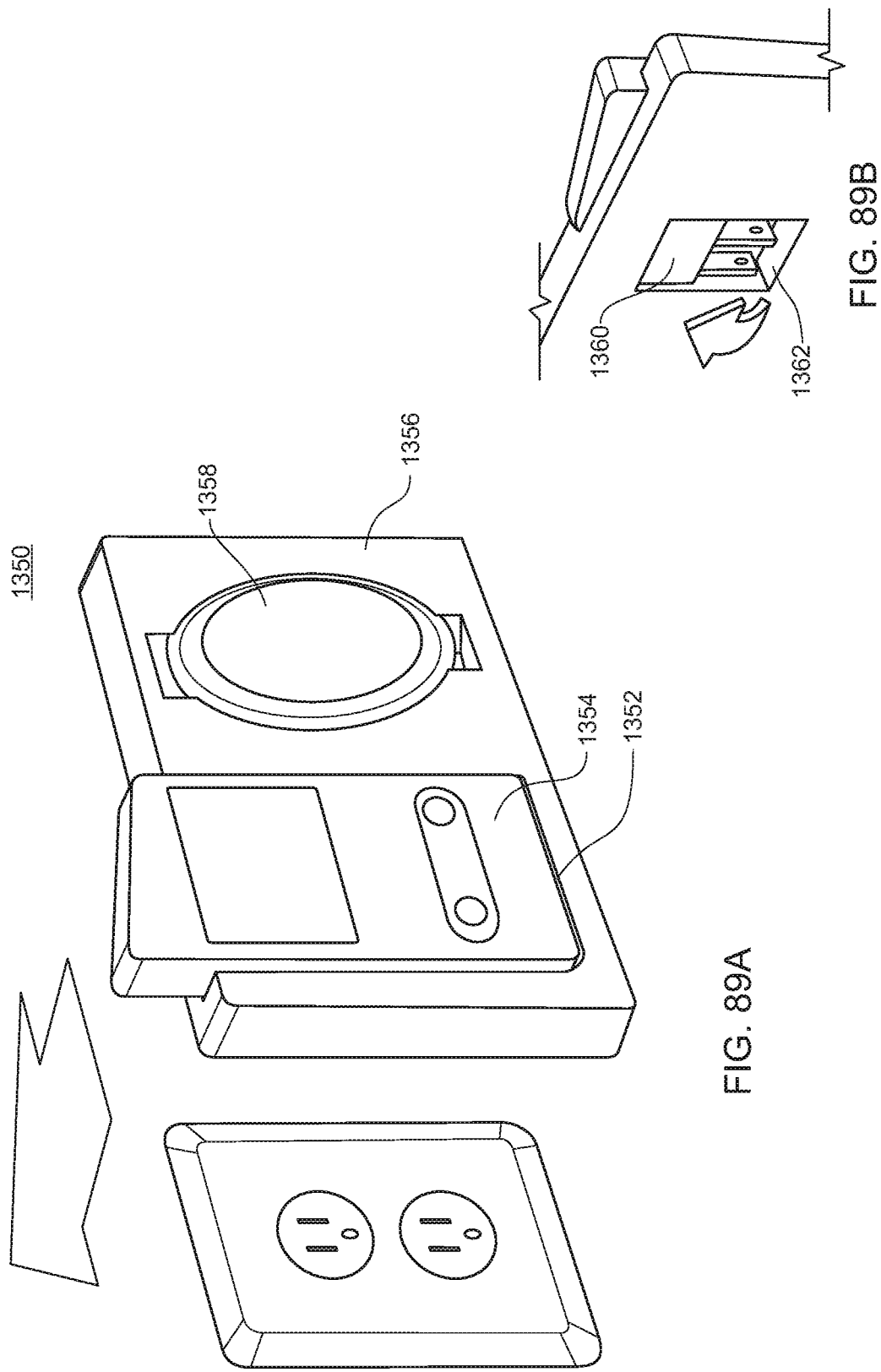

Section A-A

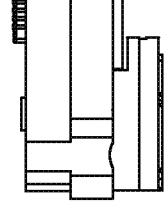
FIG. 91C
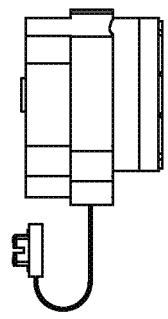
FIG. 91F
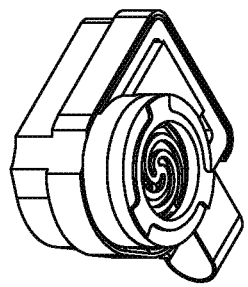
FIG. 91I
FIG. 91B
FIG. 91E
FIG. 91H
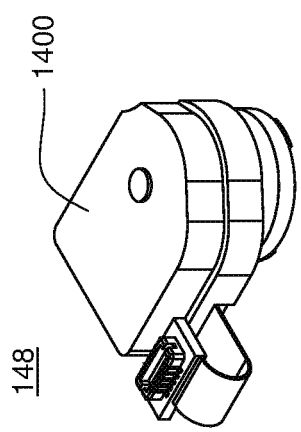
FIG. 91A
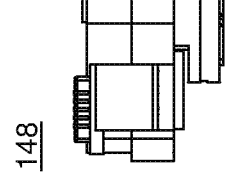
FIG. 91D
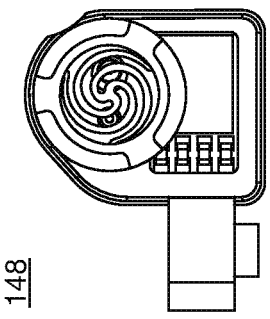
FIG. 91G

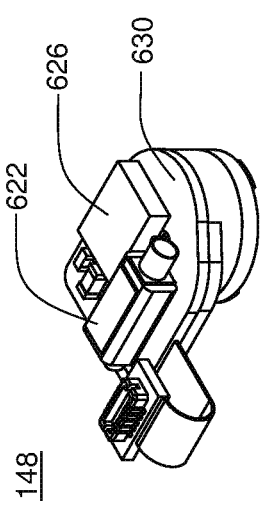
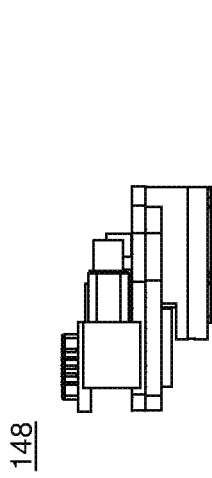
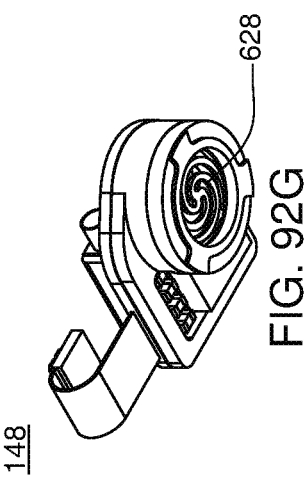
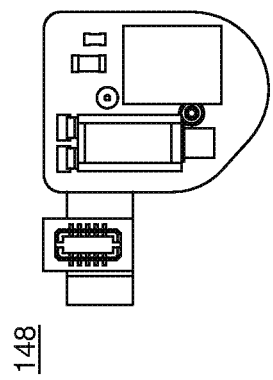
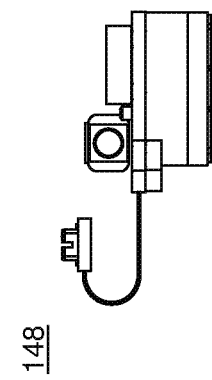
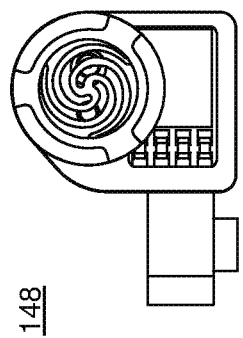
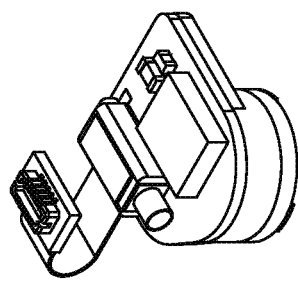
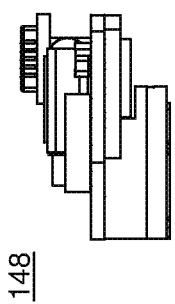
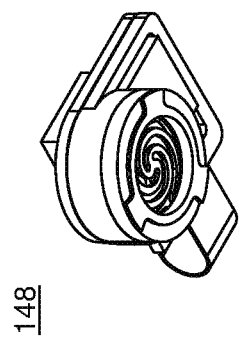

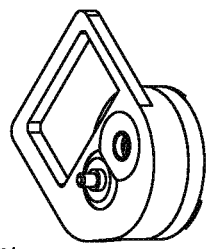
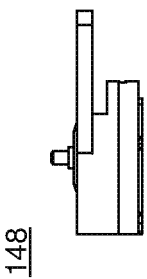
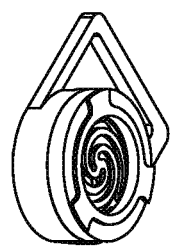
FIG. 93C  FIG. 93F  FIG. 93I
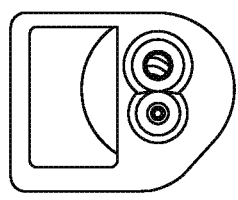
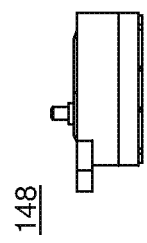
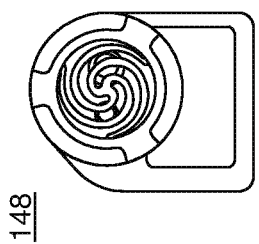
FIG. 93B  FIG. 93E  FIG. 93H
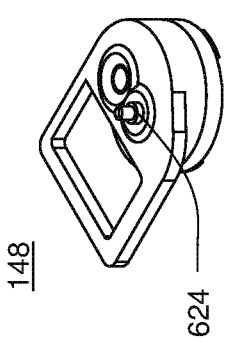
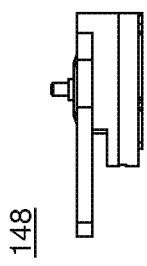
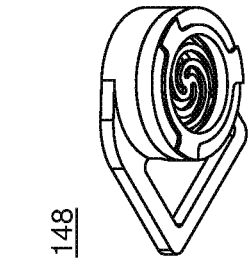
FIG. 93A  FIG. 93D  FIG. 93G

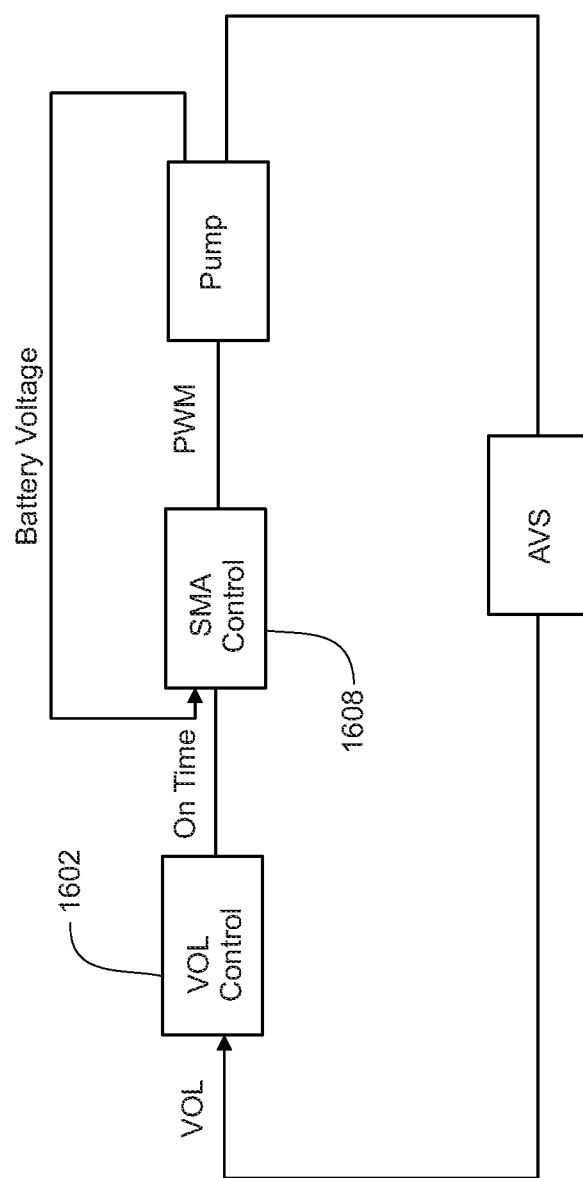

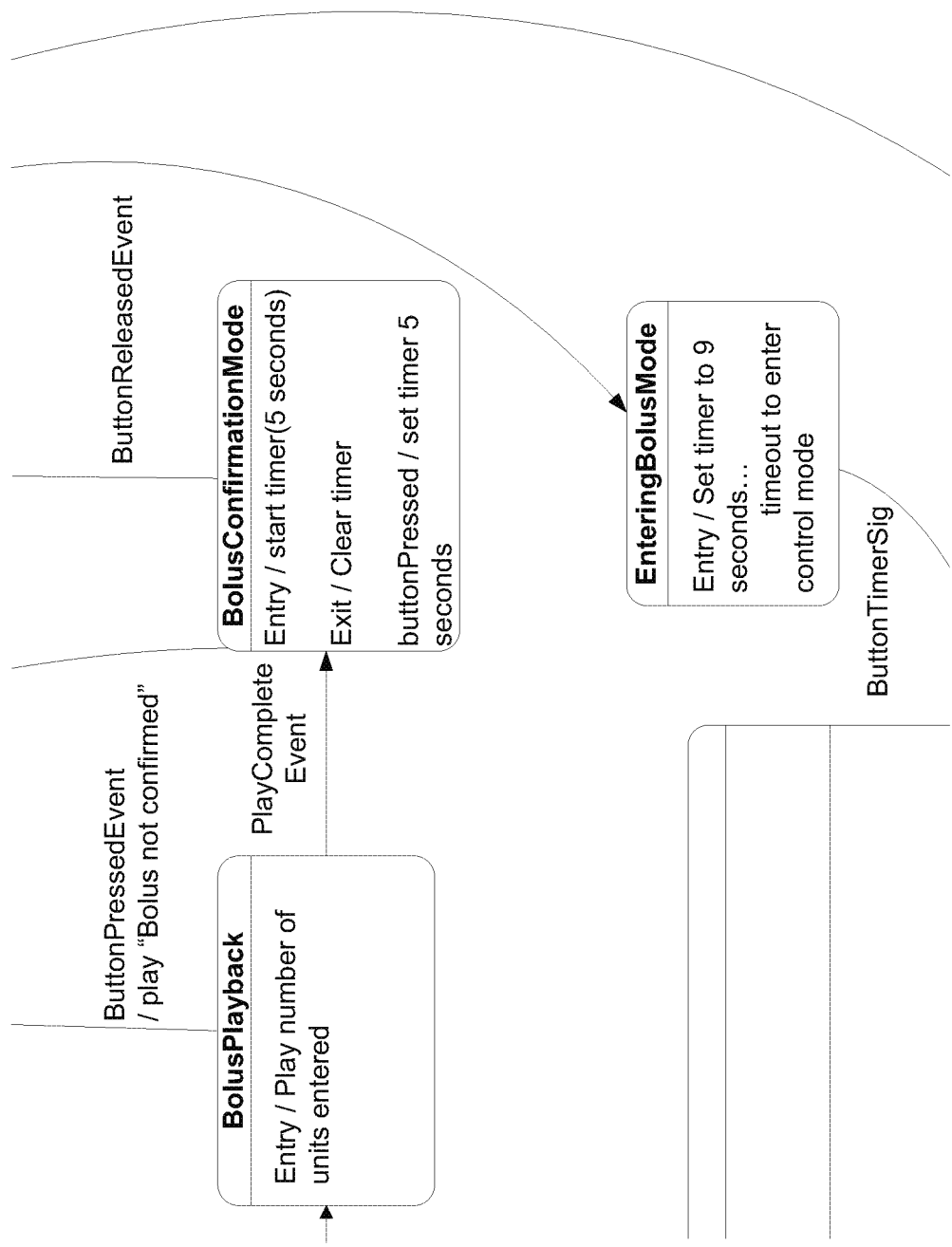

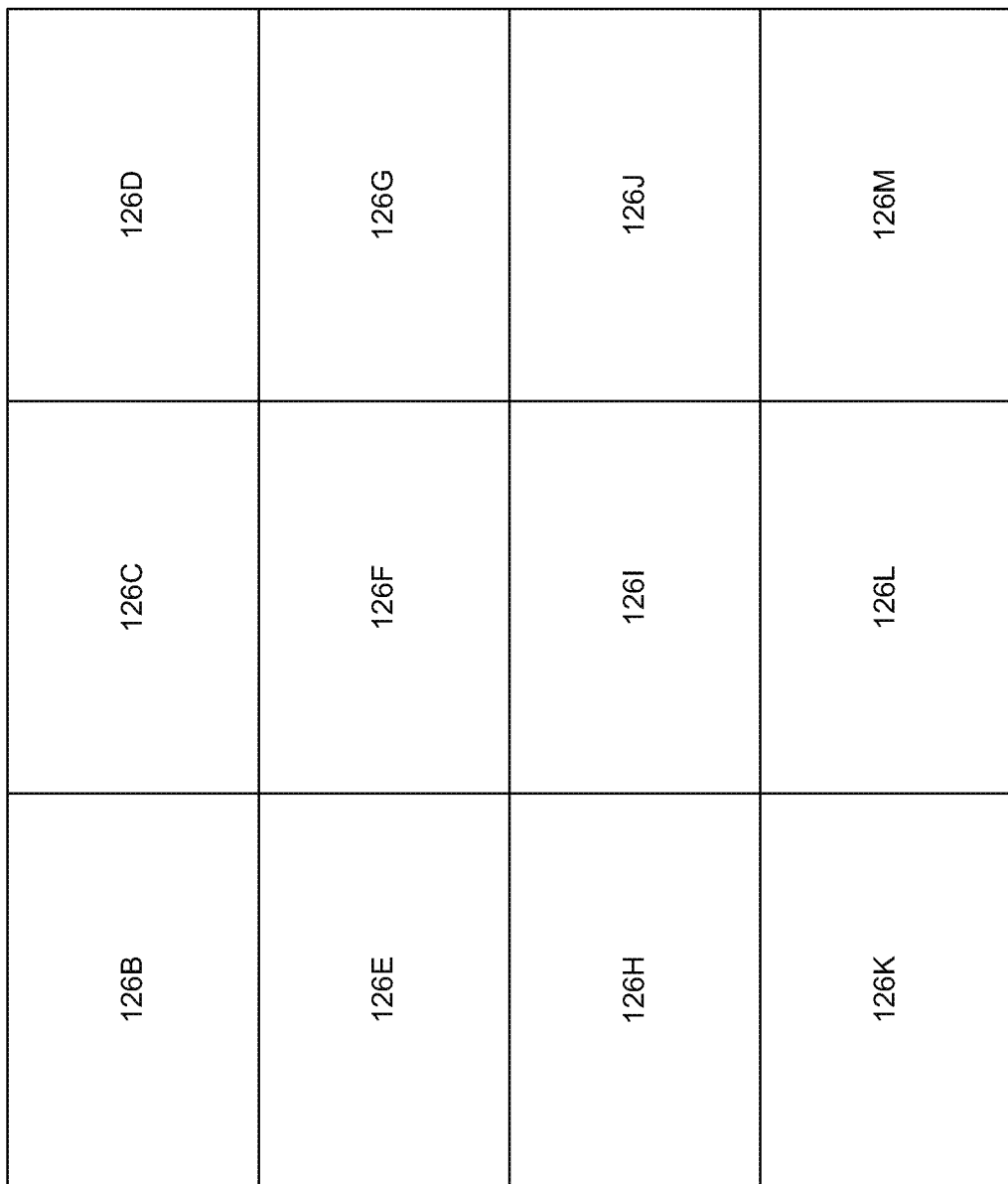

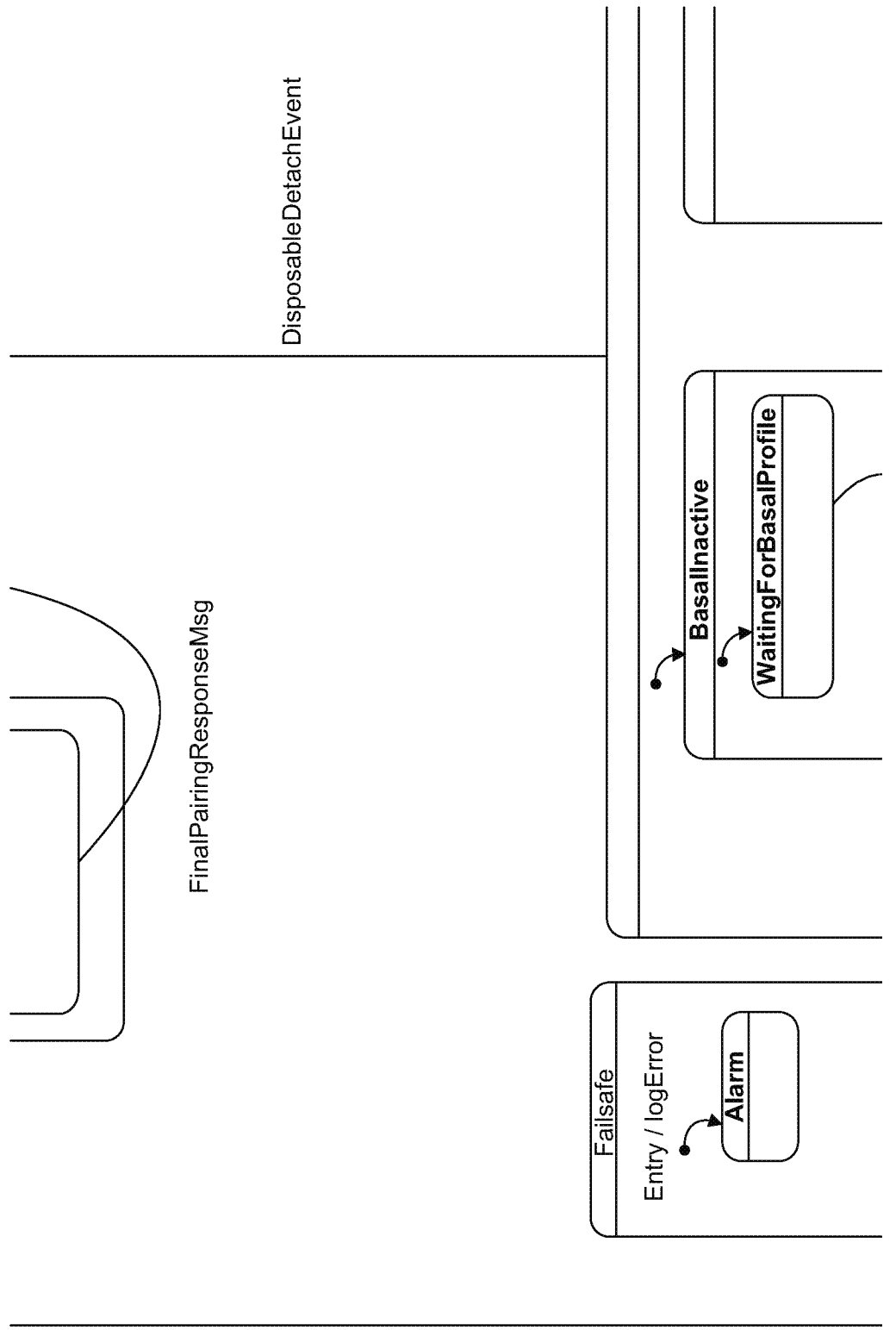

RIS event StartBasalCommand |
RIS event StopBasalCommand |
RIS event TempBasalModifyCommand |
RIS event TempBasalOverrideCommand |
RIS event BolusPrimeStatus
RIS event StopBasalCommand |
RIS event TempBasalModifyCommand |
RIS event TempBasalOverrideCommand |
RIS event NormalBolusCommand |
RIS event ExtendedBolusCommand |
RIS event DualBolusCommand |
RIS event AbortBolusCommand / NACK RIS command

FIG. 126L

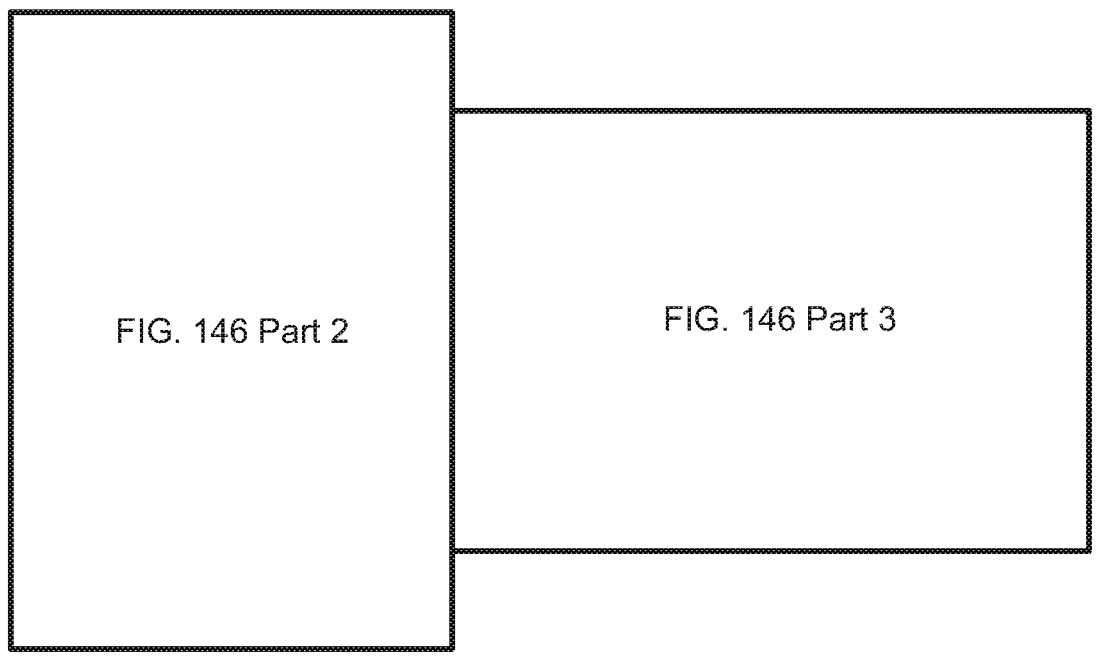
FIG. 146 Part 1

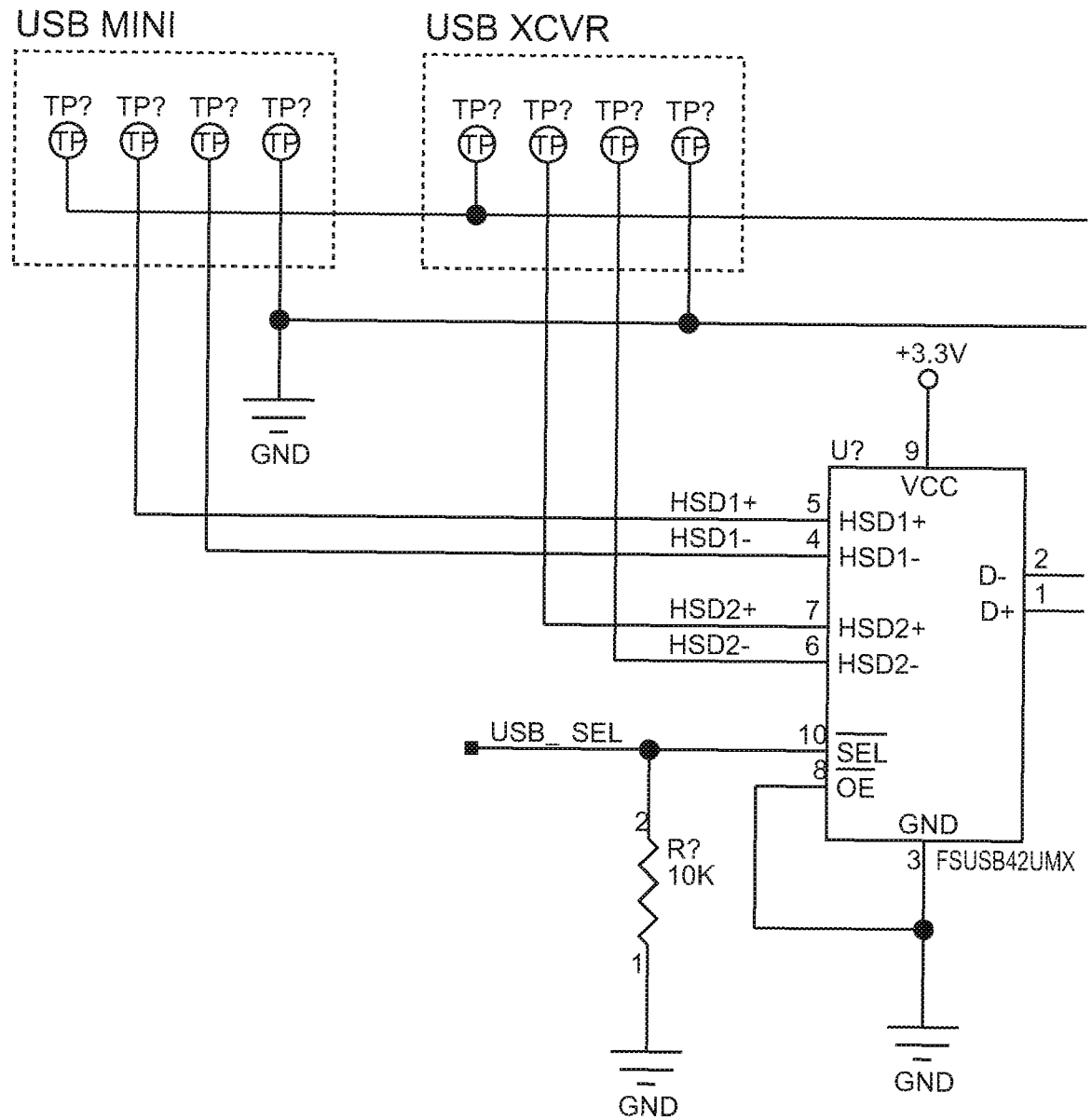
FIG. 146 Part 2

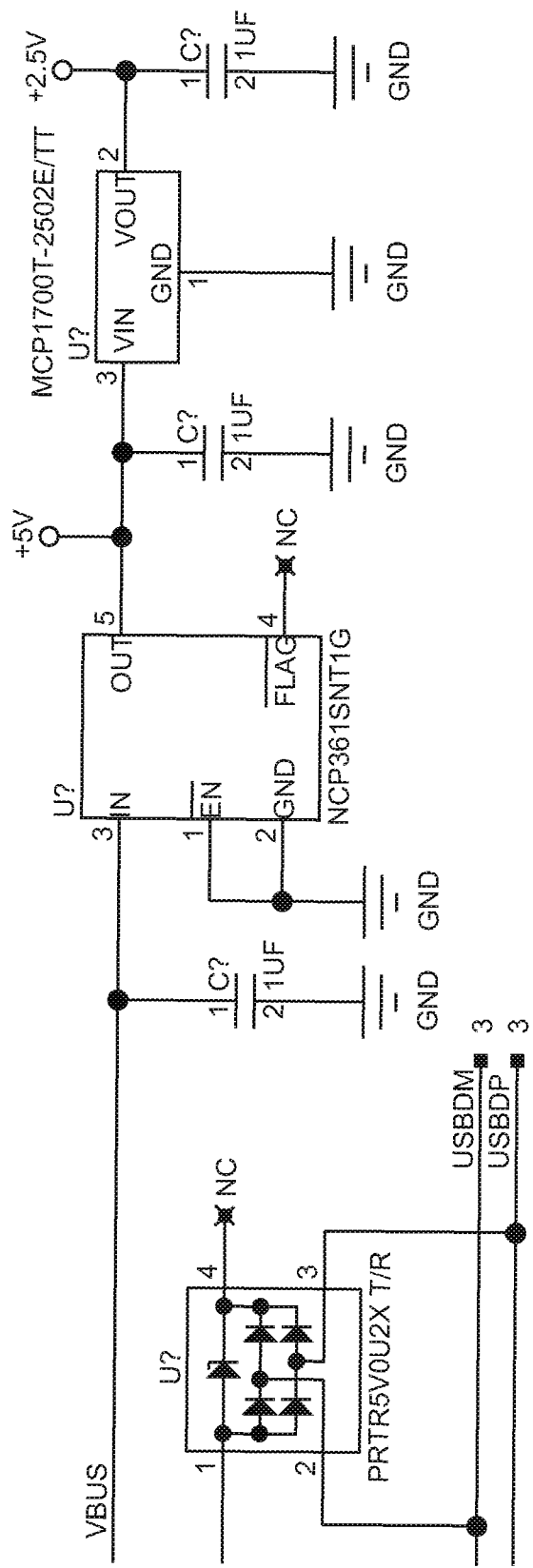
FIG. 146 Part 3

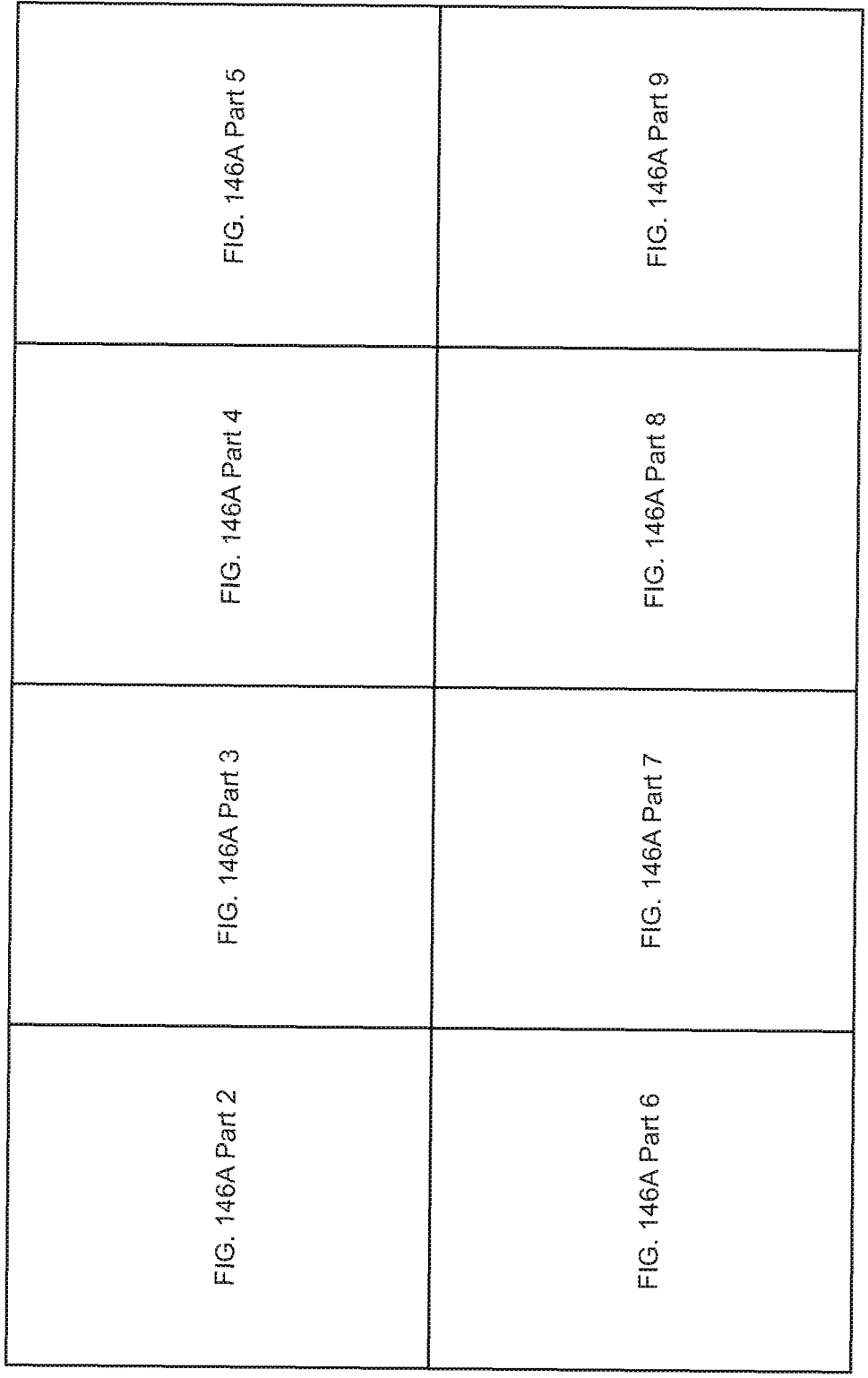

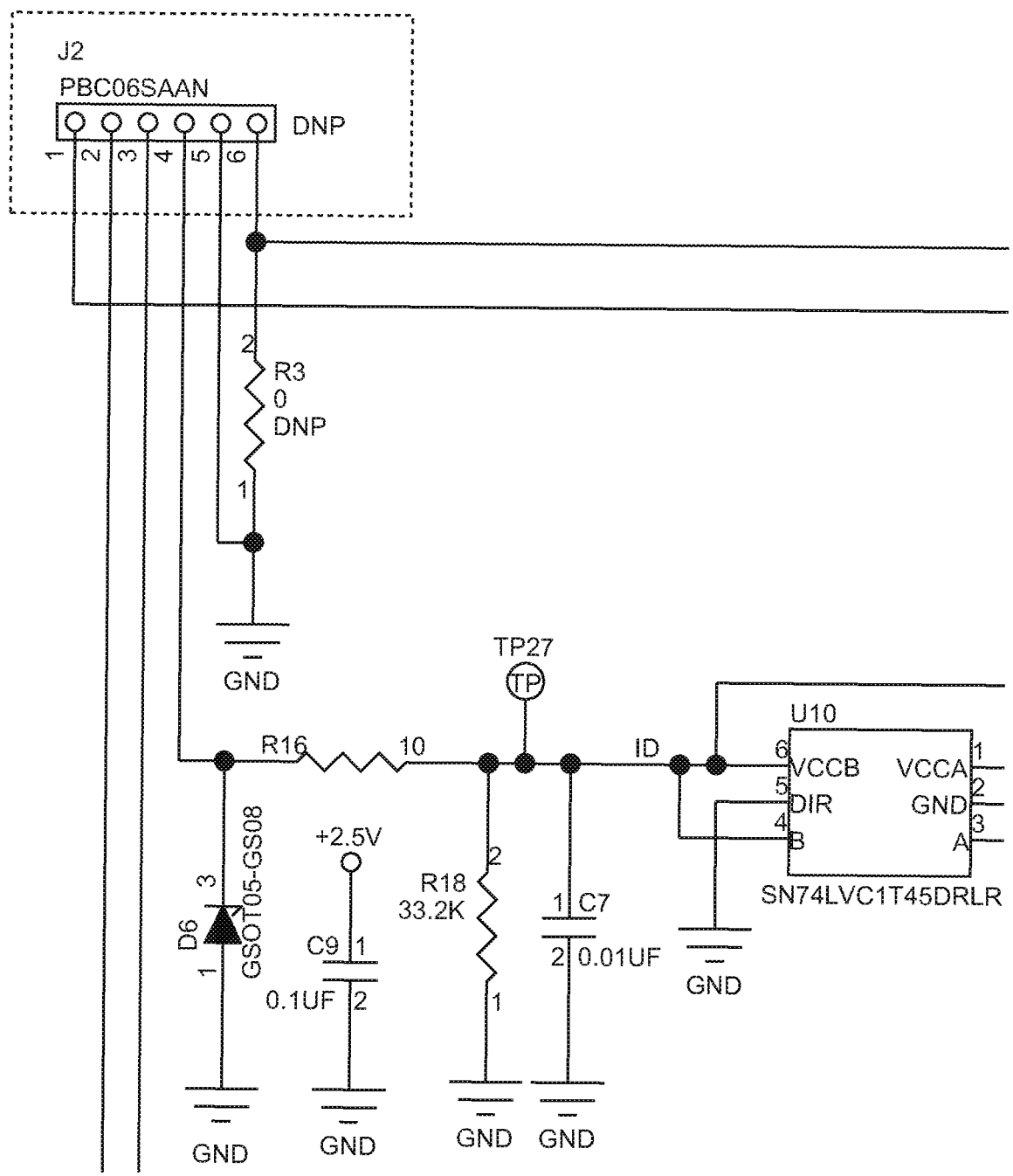
FIG. 146A Part 2

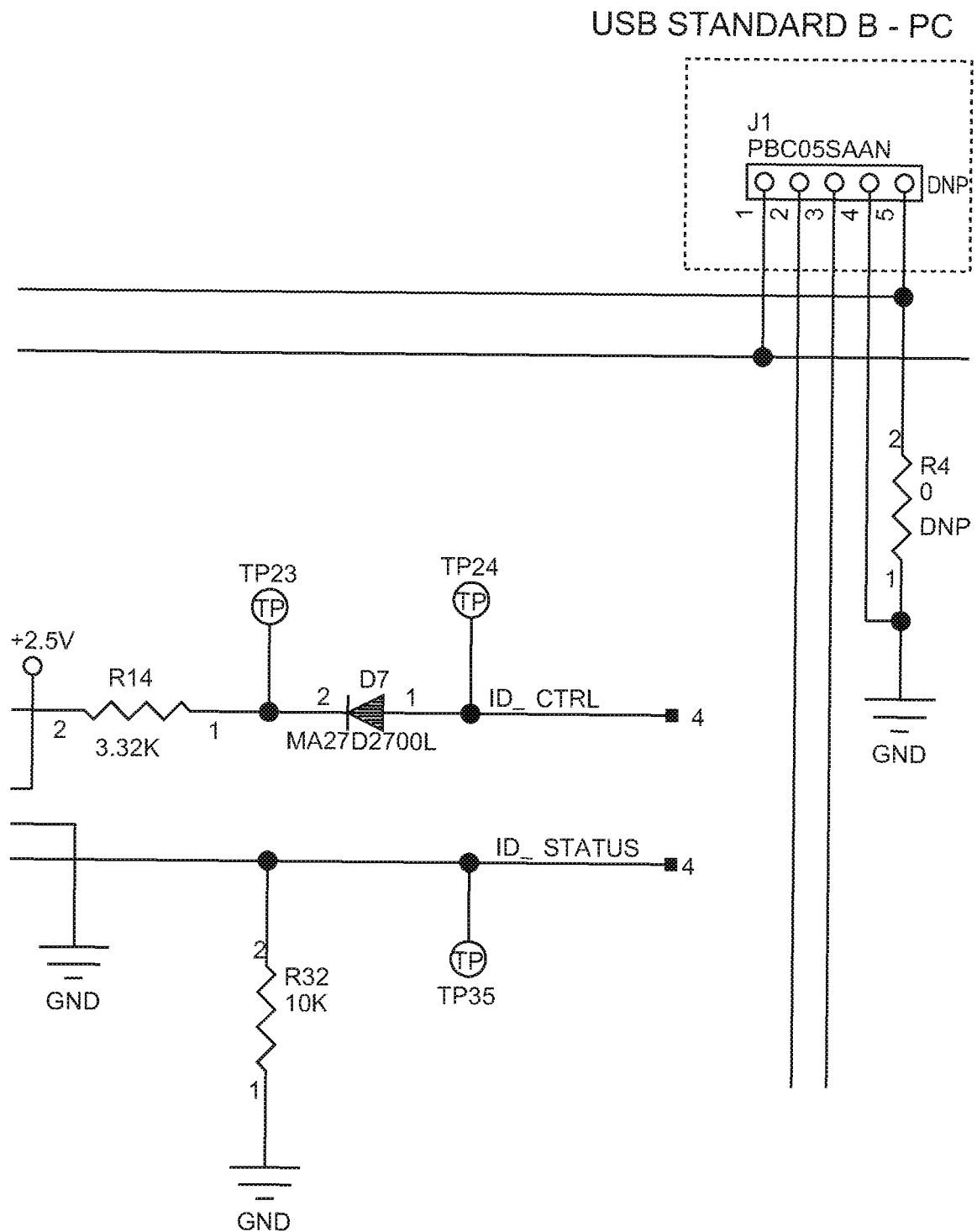
FIG. 146A Part 3

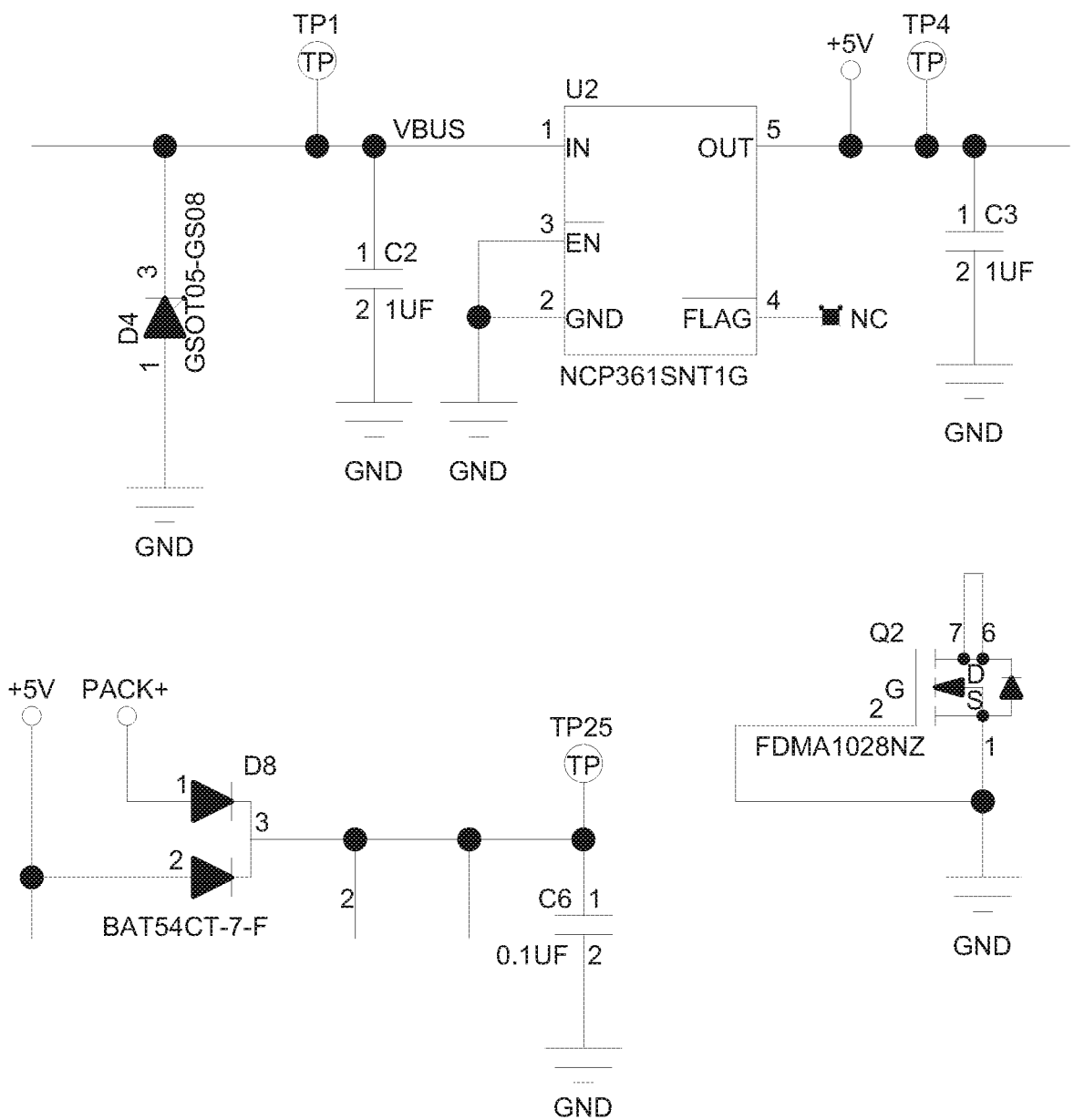
FIG. 146A Part 4

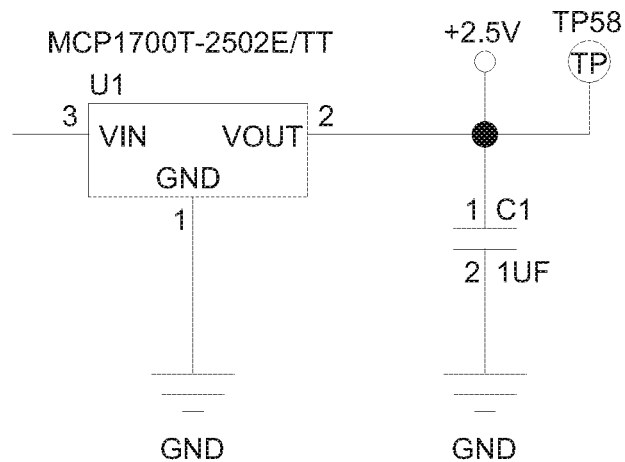
FIG. 146A Part 5

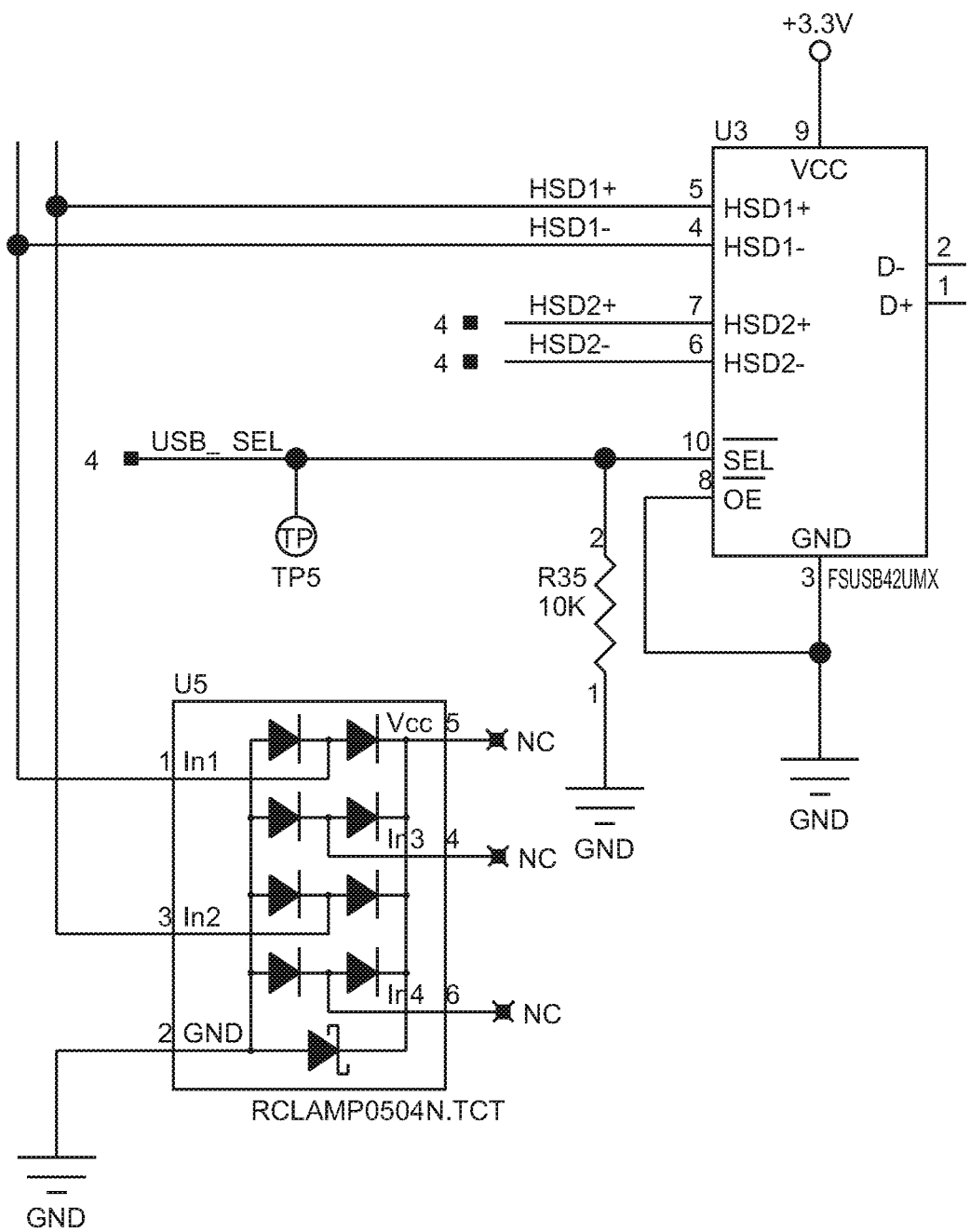
FIG. 146A Part 6

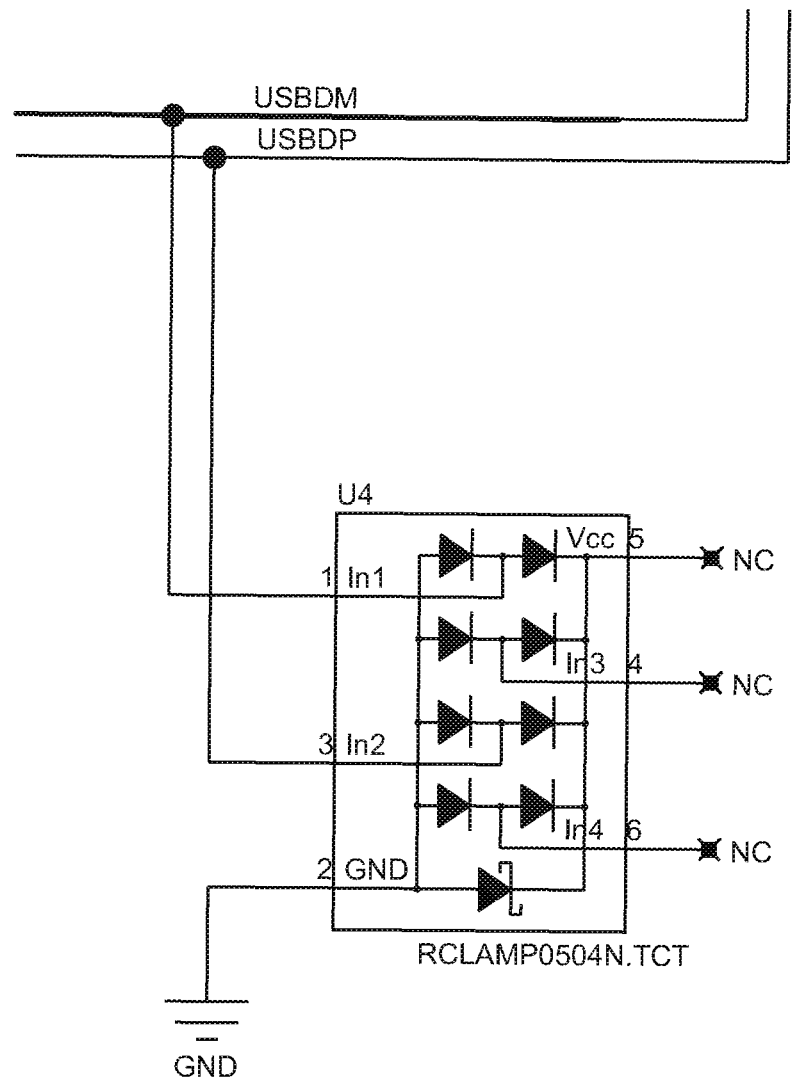
FIG. 146A Part 7

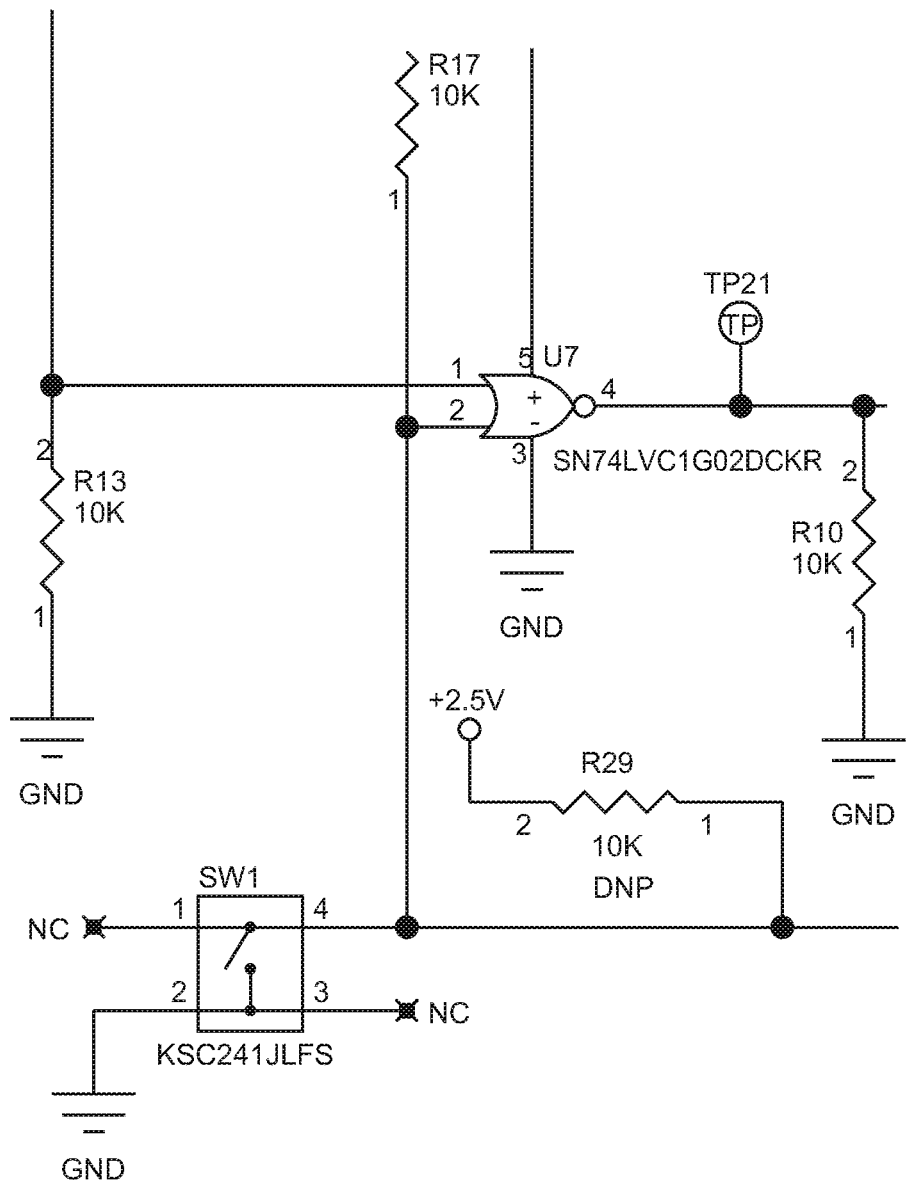
FIG. 146A Part 8

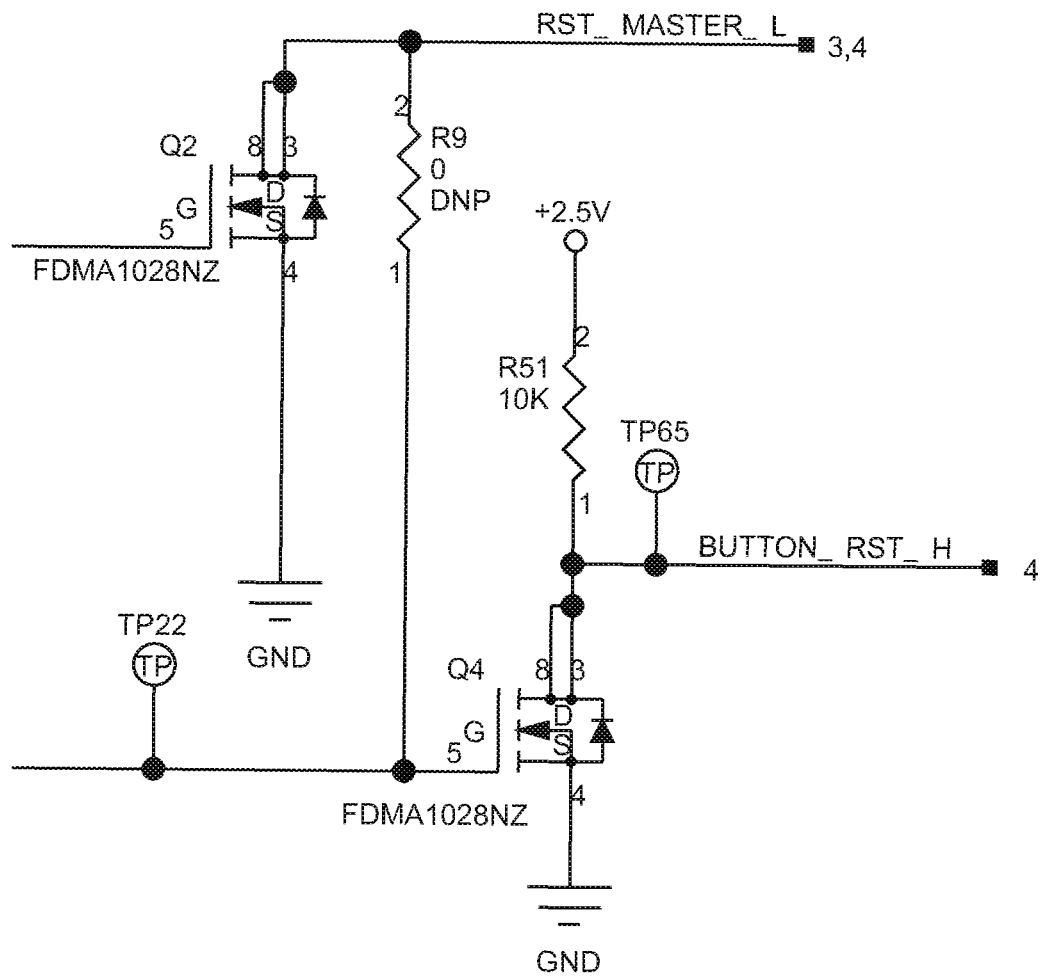
FIG. 146A Part 9

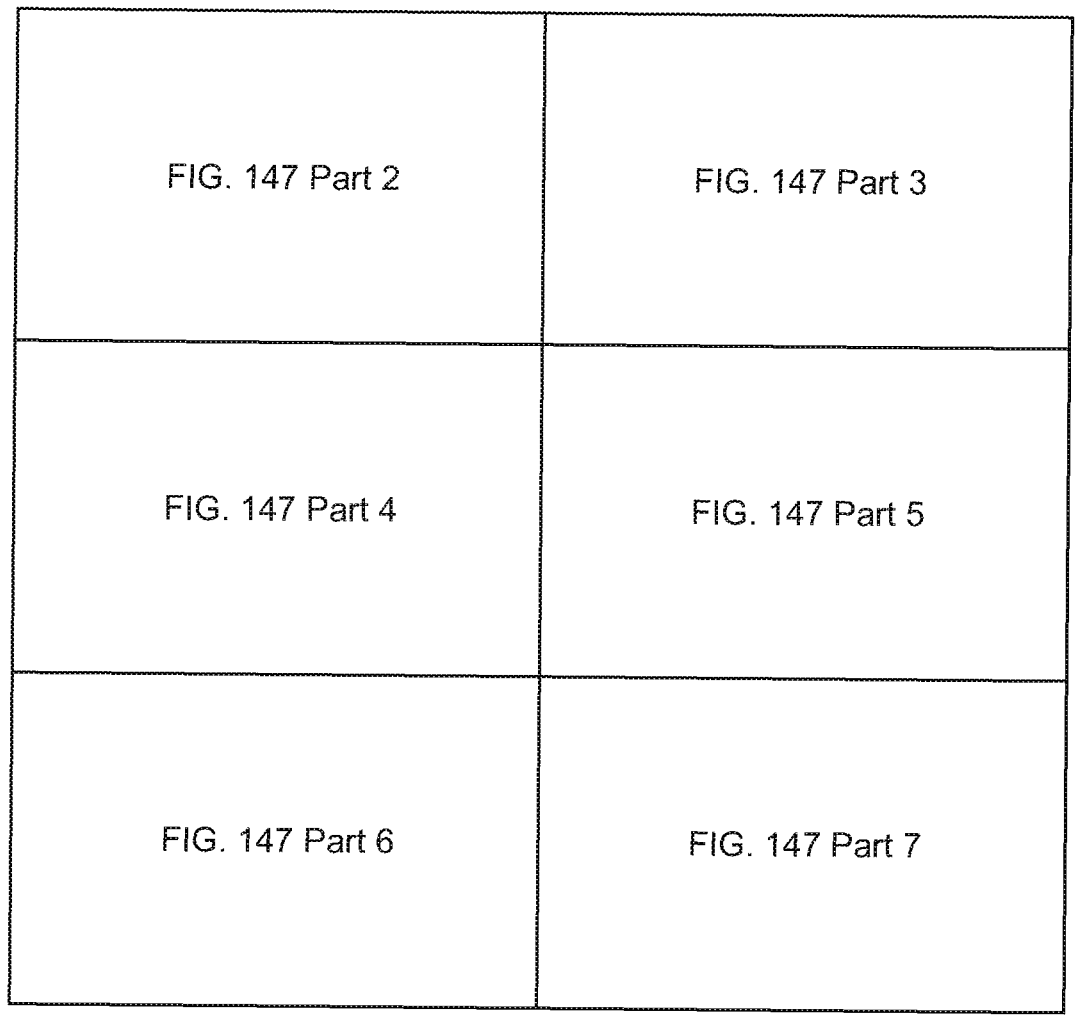
FIG. 147 Part 1

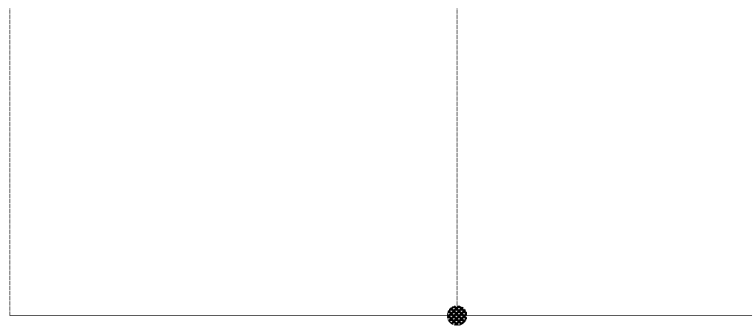
FIG. 147 Part 2

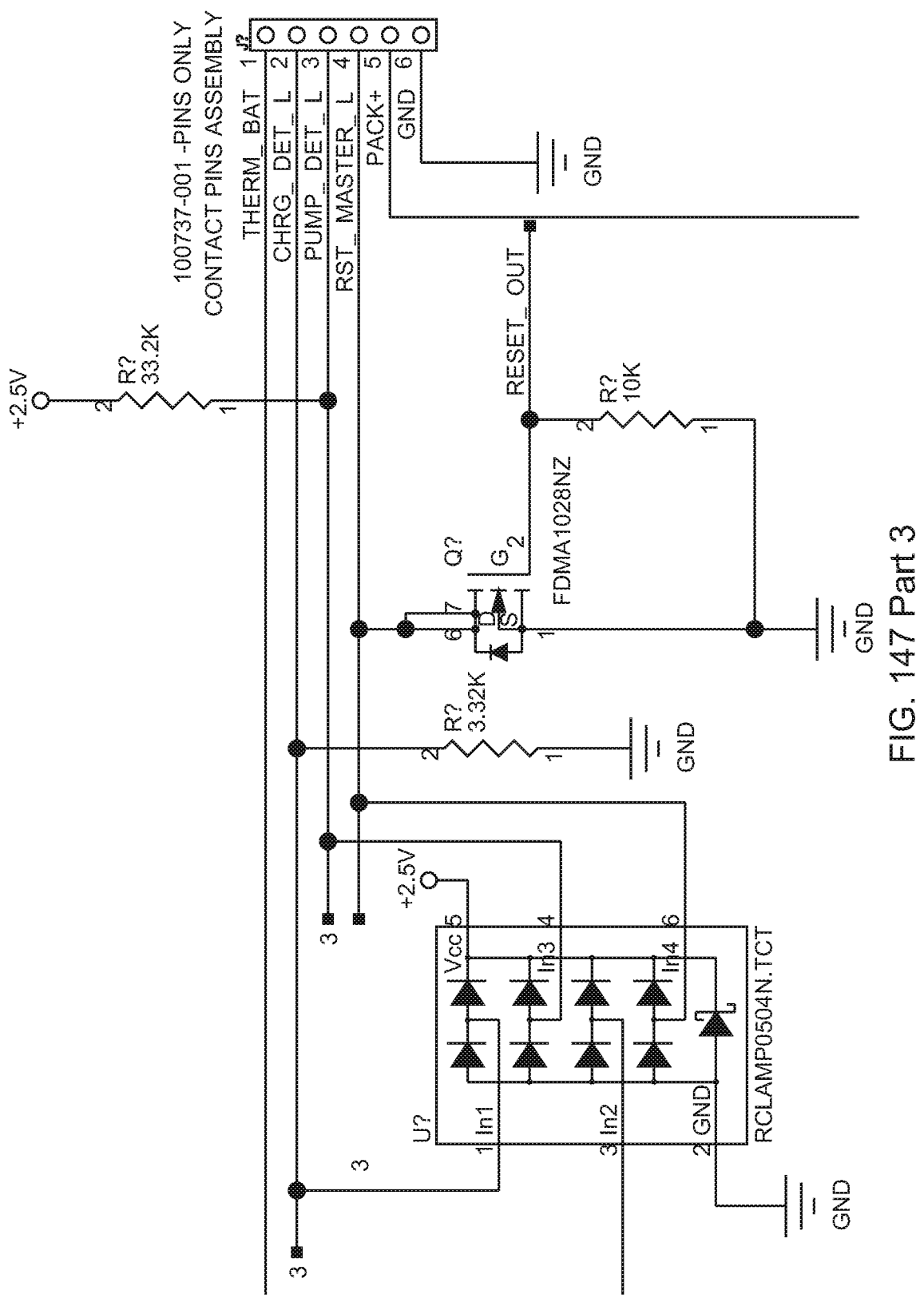
FIG. 147 Part 3

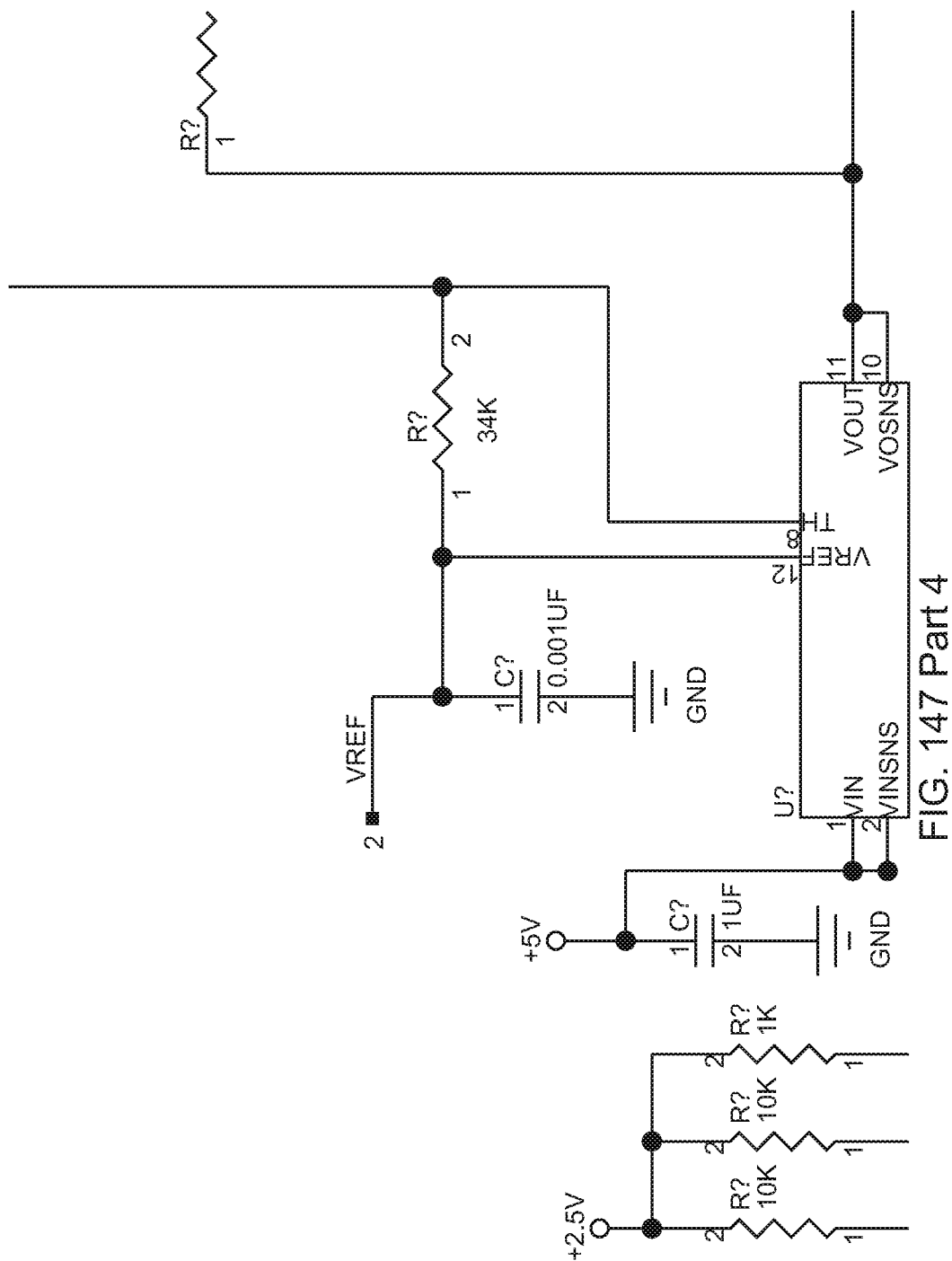
FIG. 147 Part 4

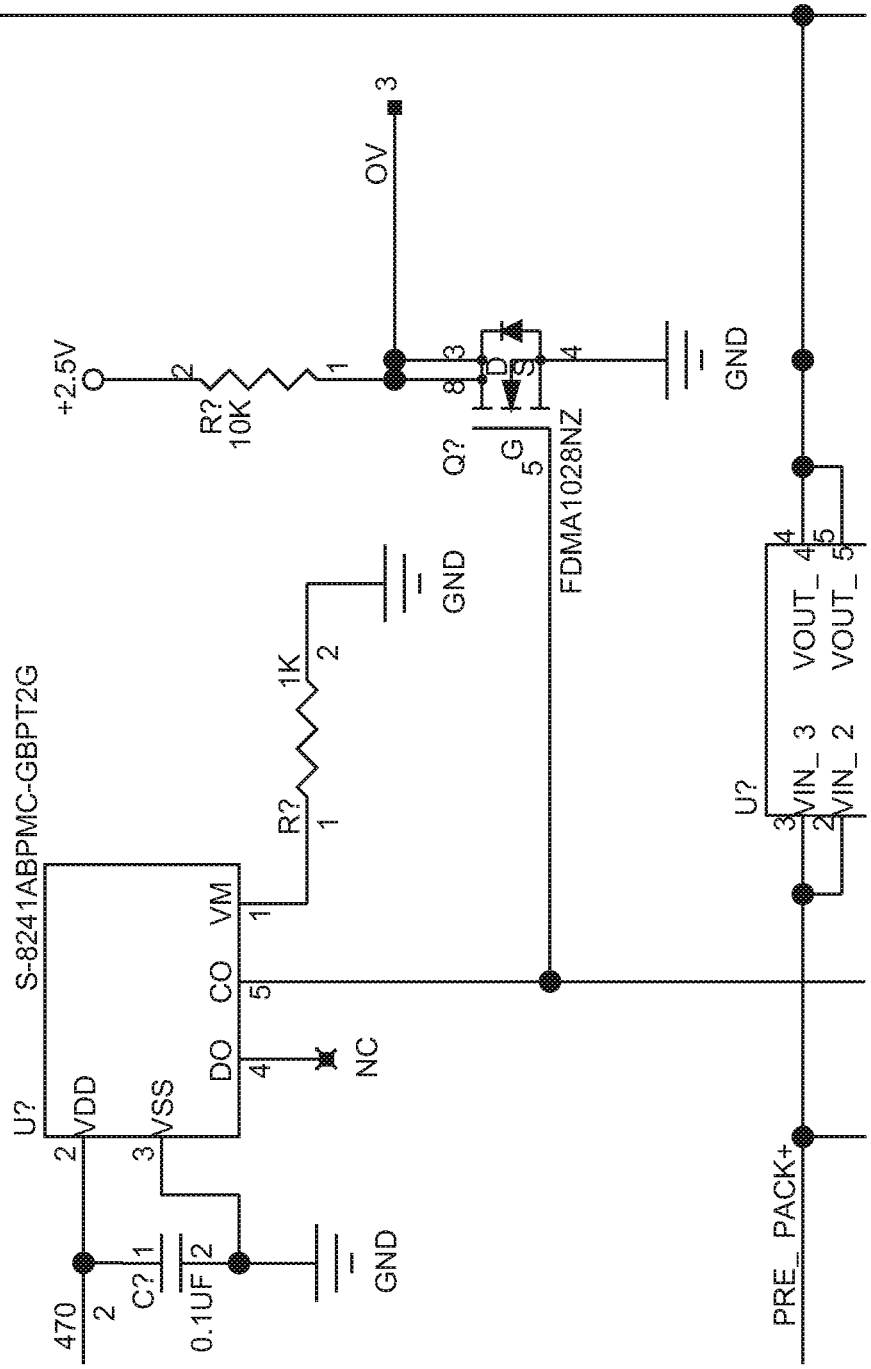
FIG. 147 Part 5

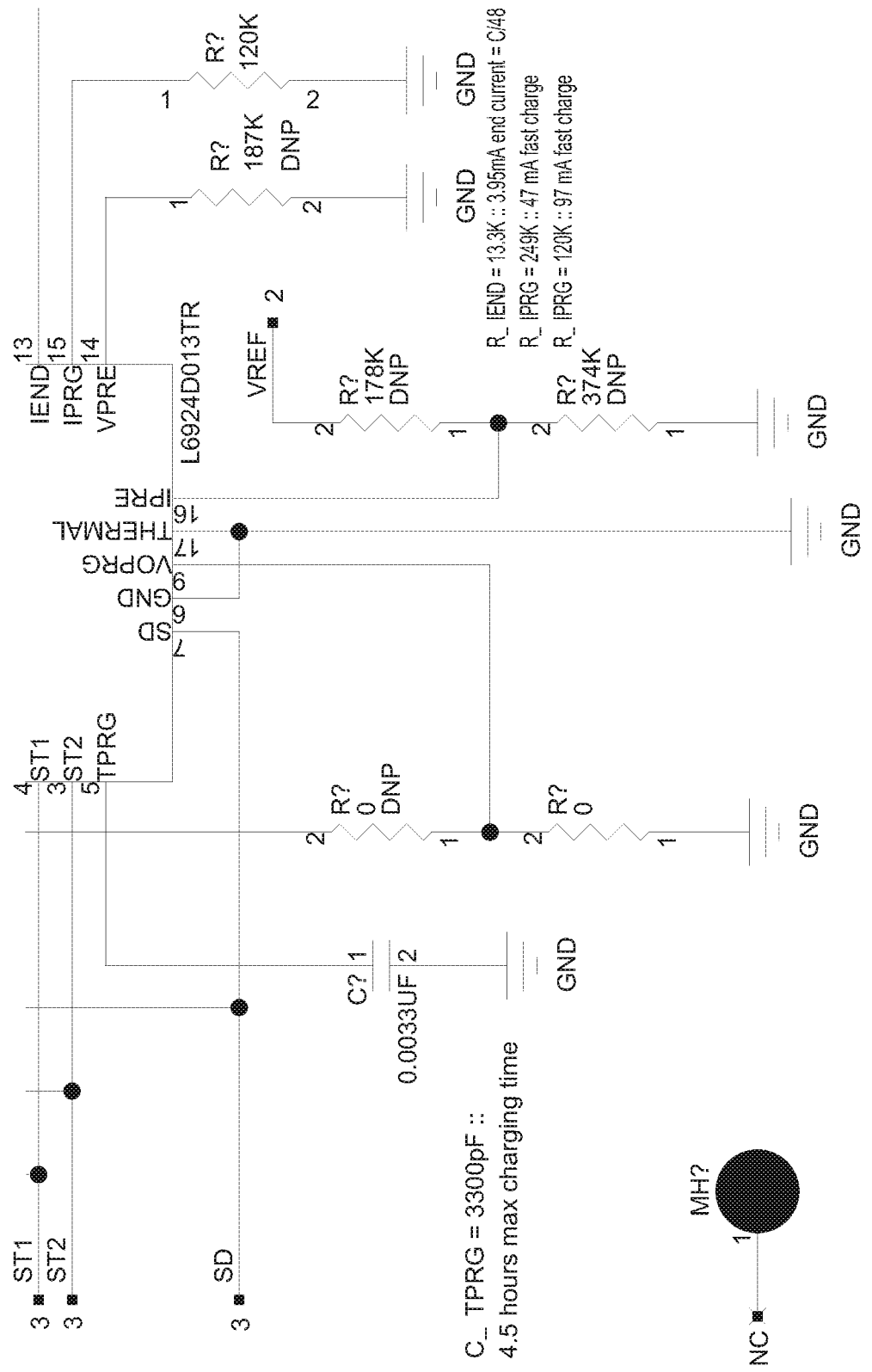
FIG. 147 Part 6

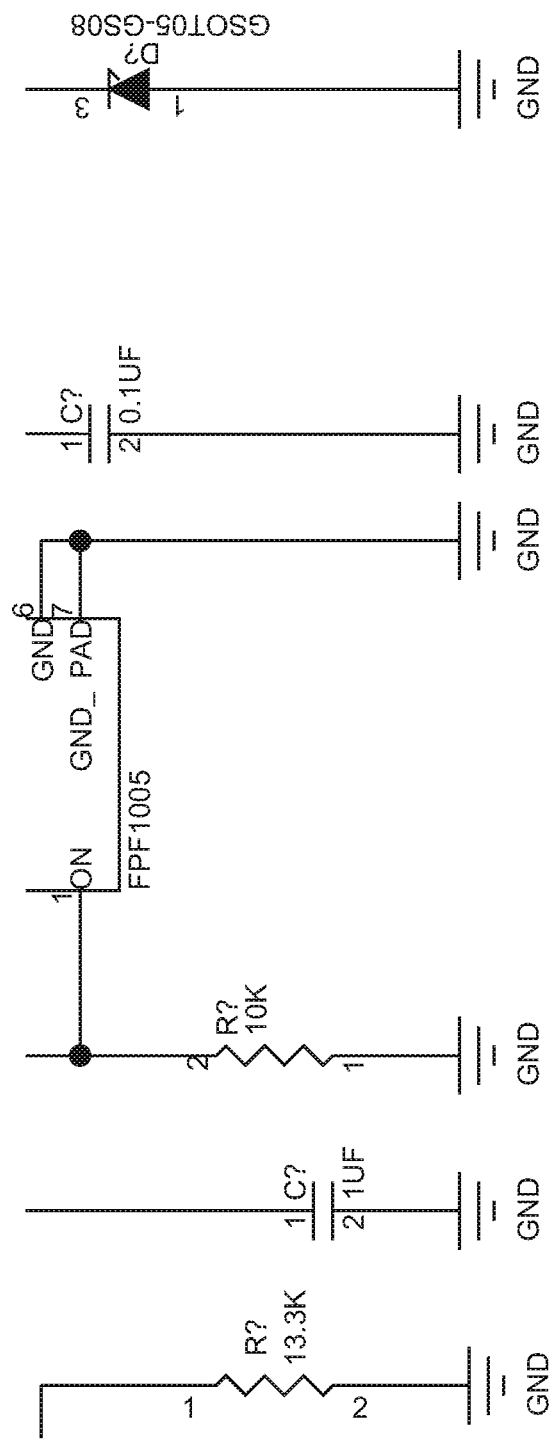
FIG. 147 Part 7

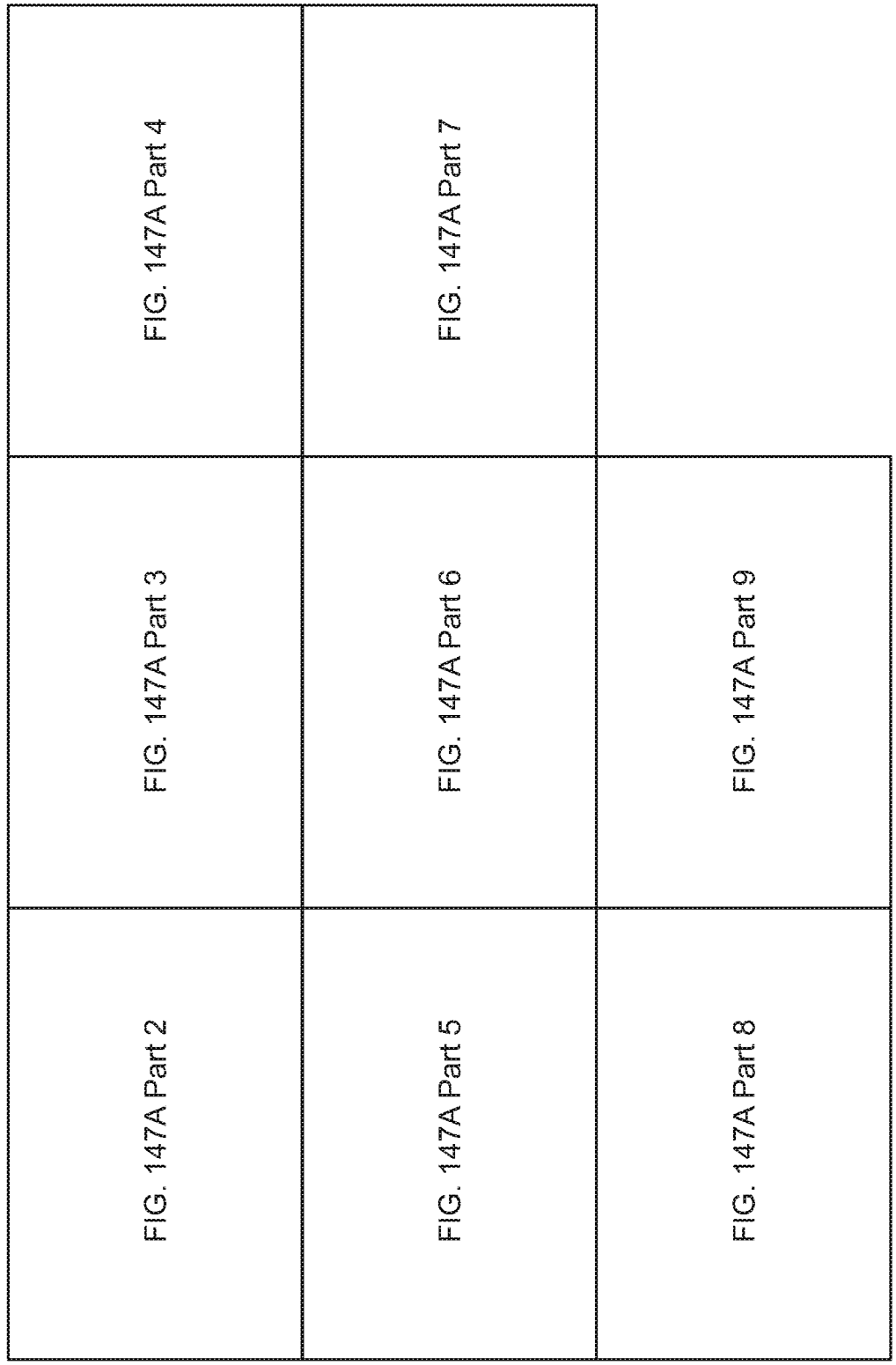

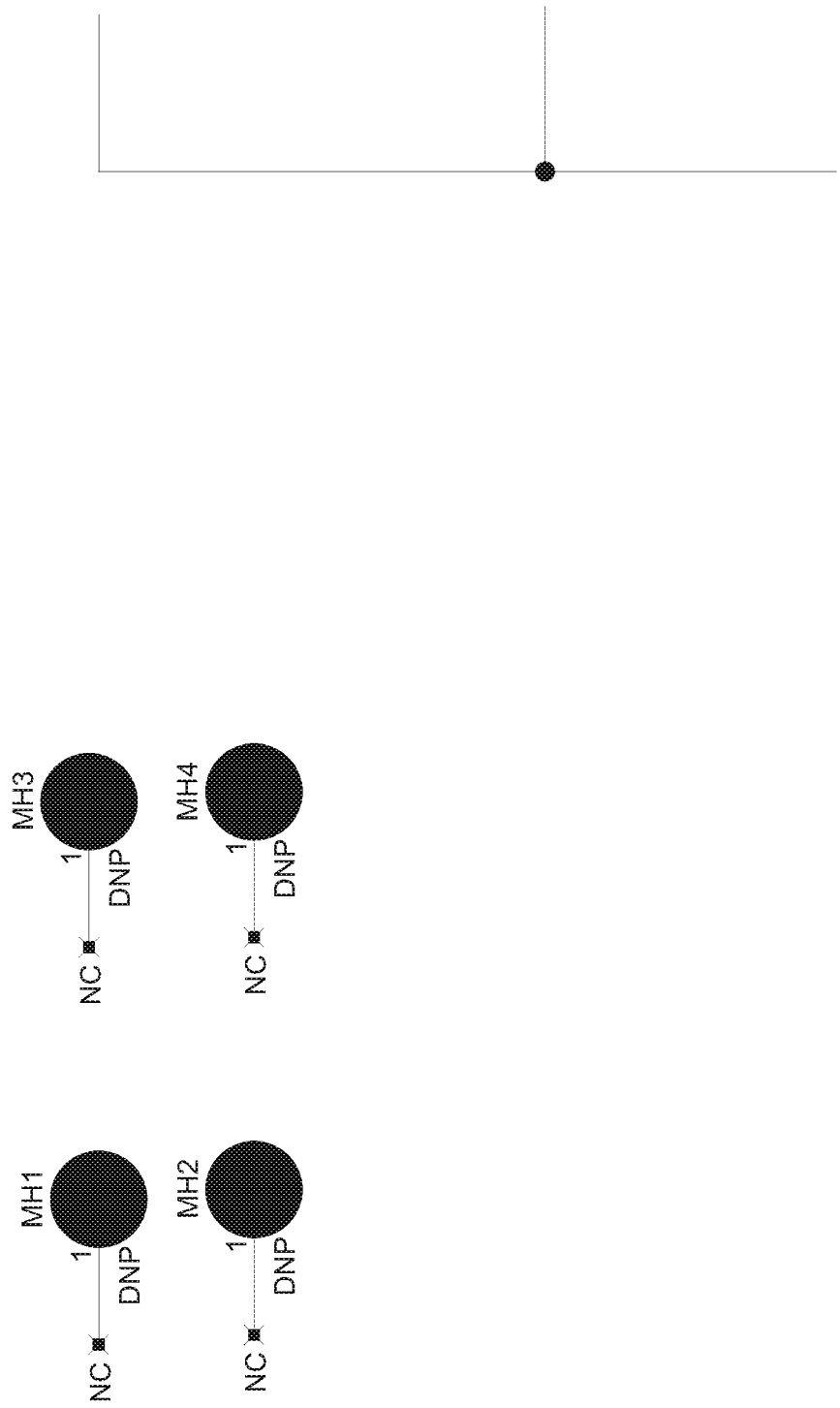
FIG. 147A Part 2

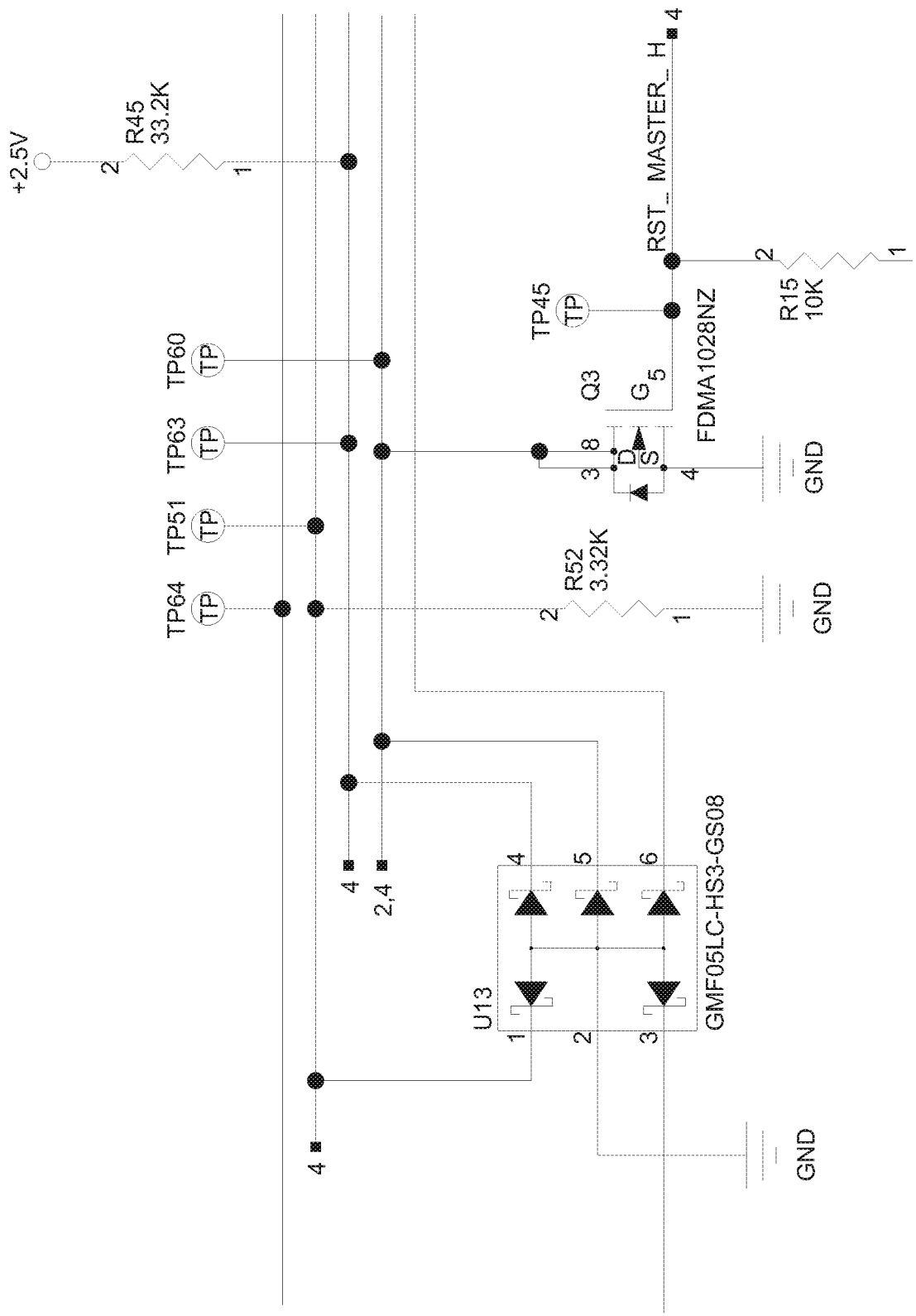
FIG. 147A Part 3

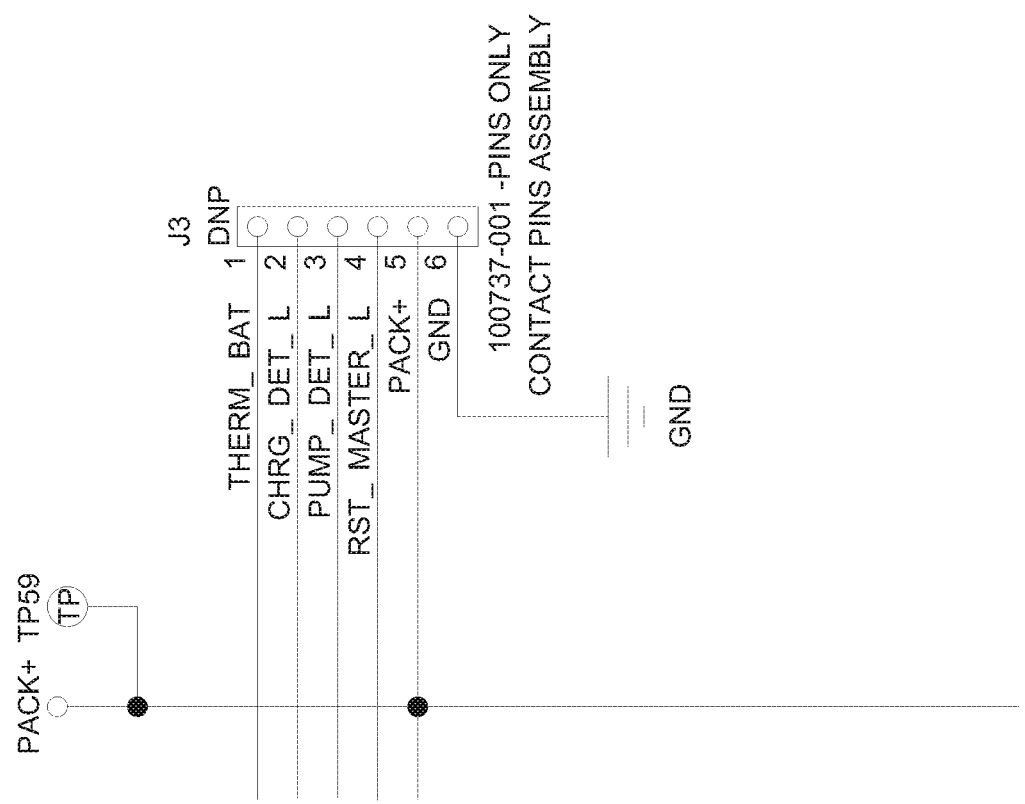
FIG. 147A Part 4

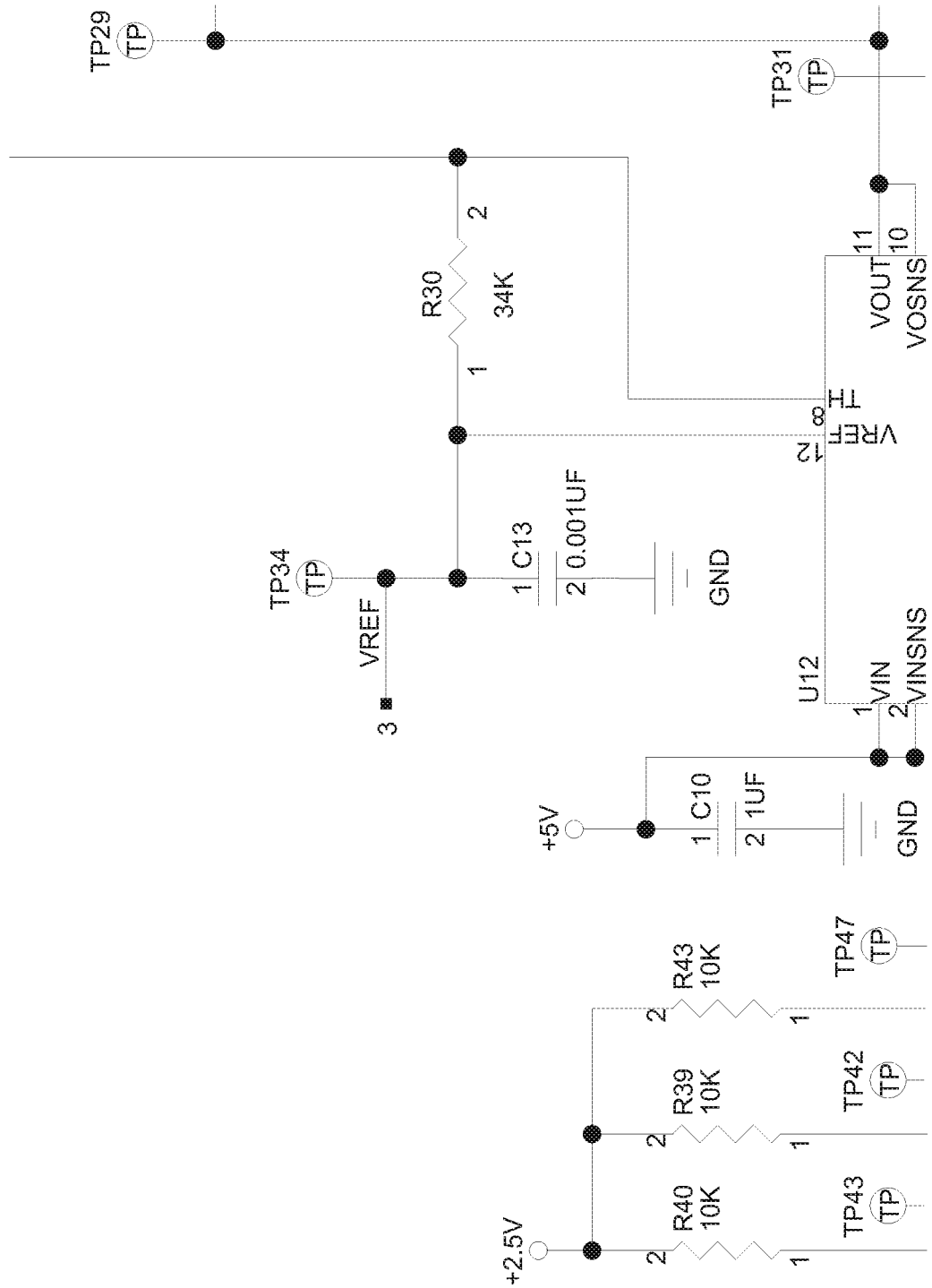
FIG. 147A Part 5

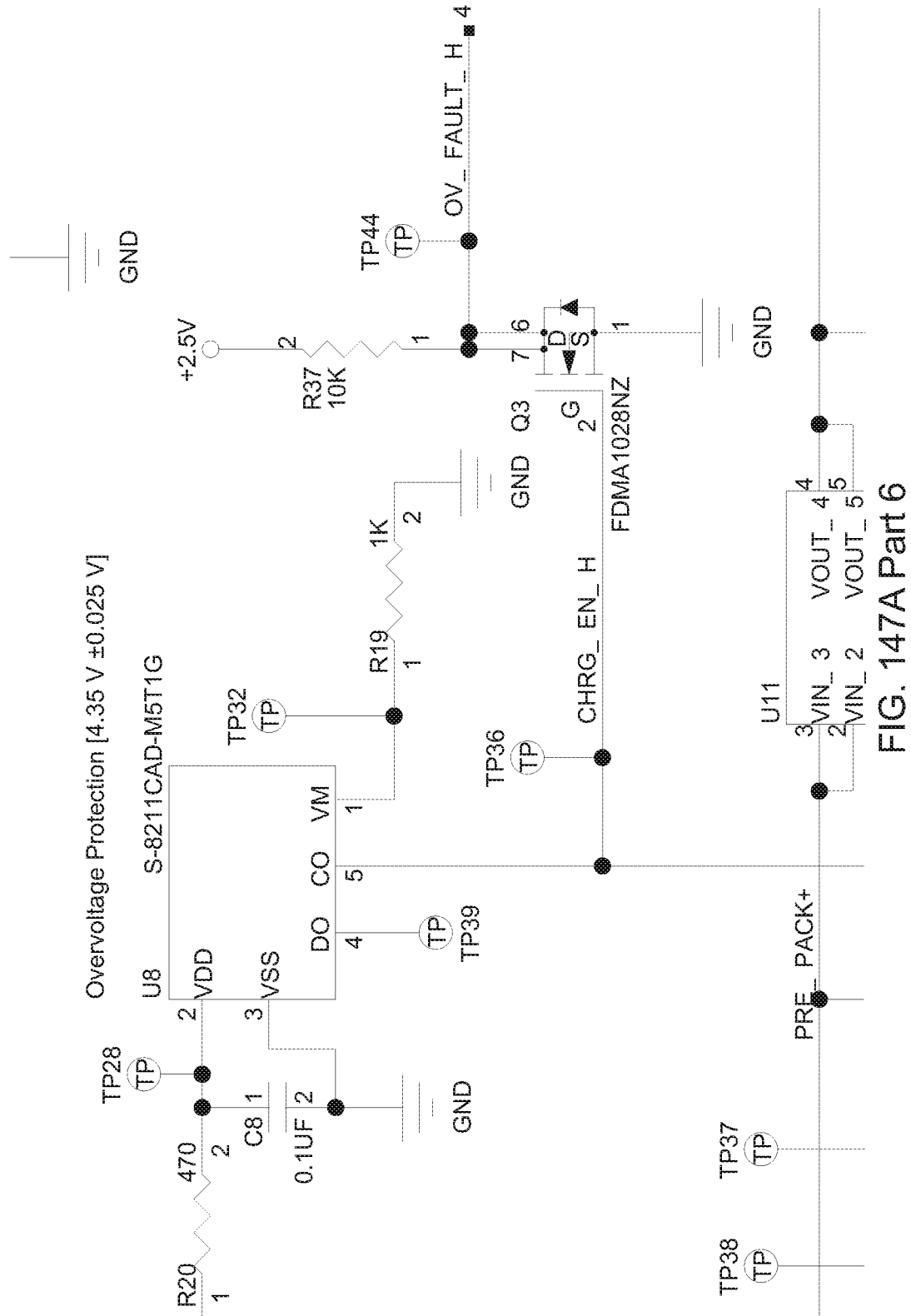
FIG. 147A Part 6

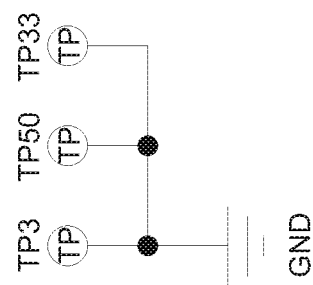
FIG. 147A Part 7

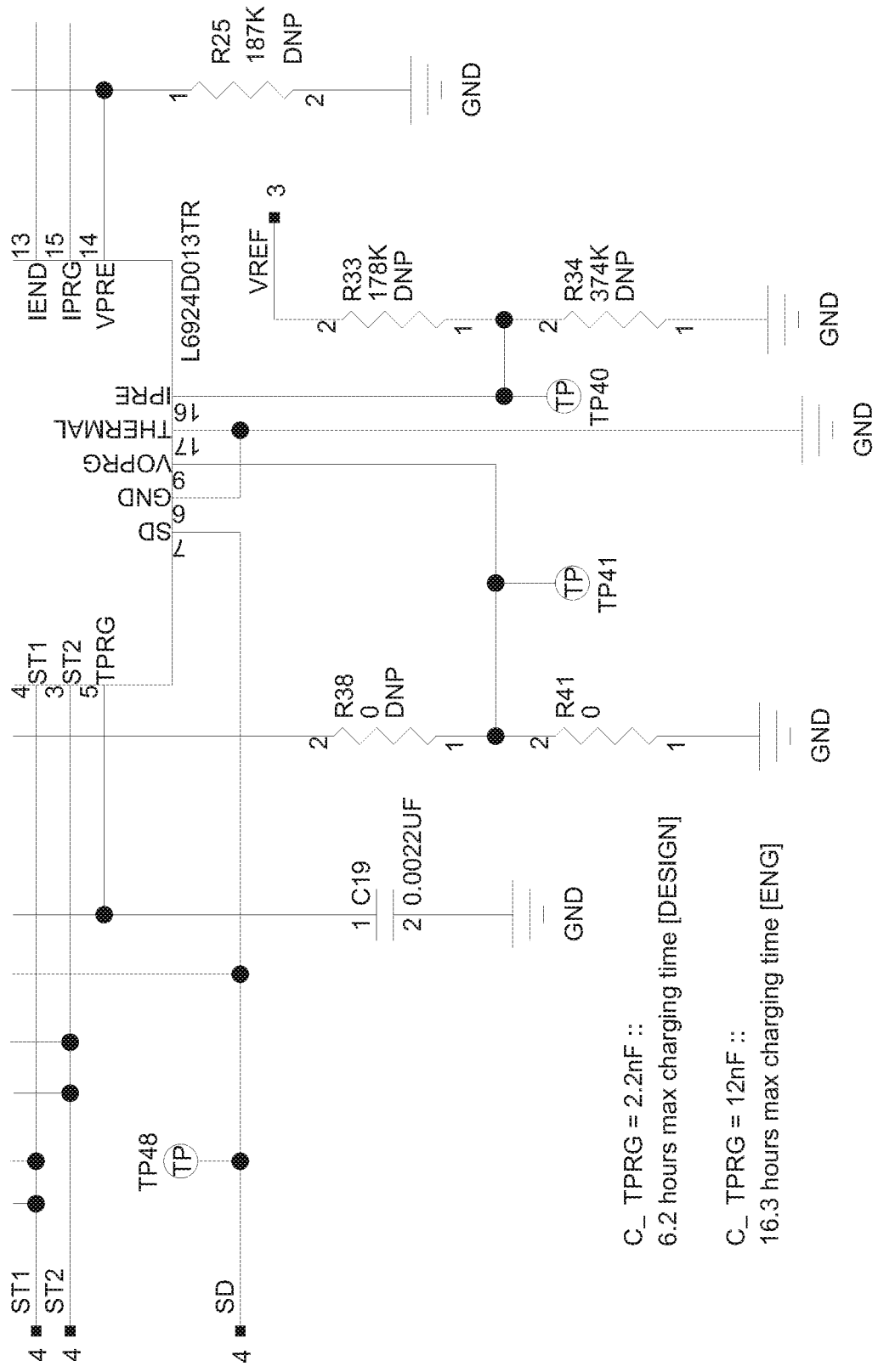
FIG. 147A Part 8

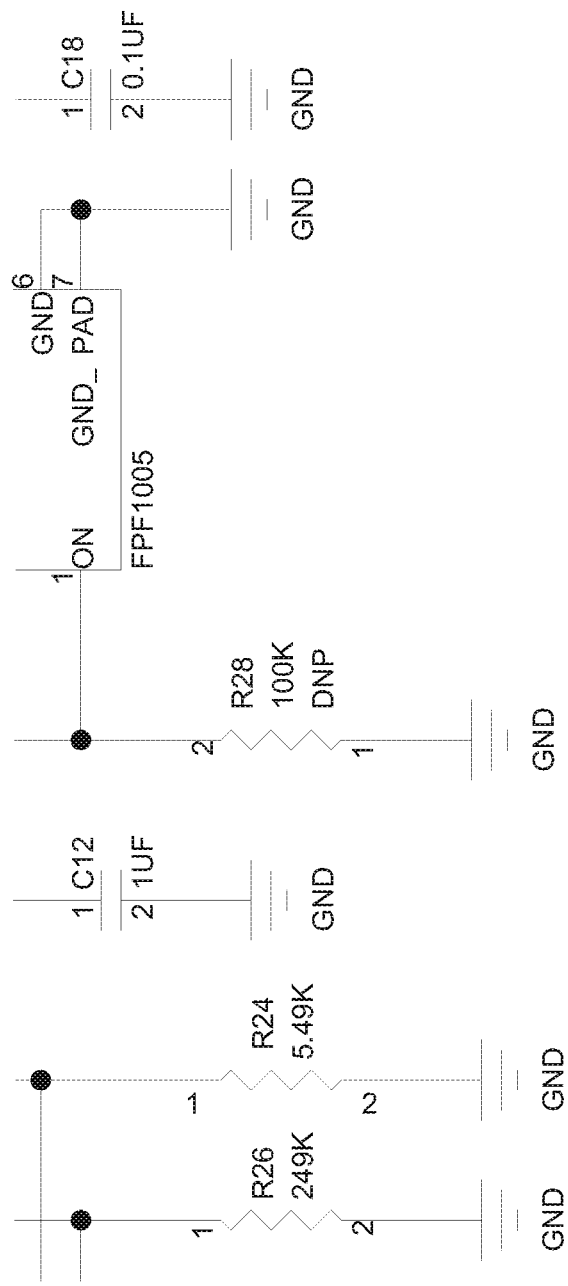
FIG. 147A Part 9

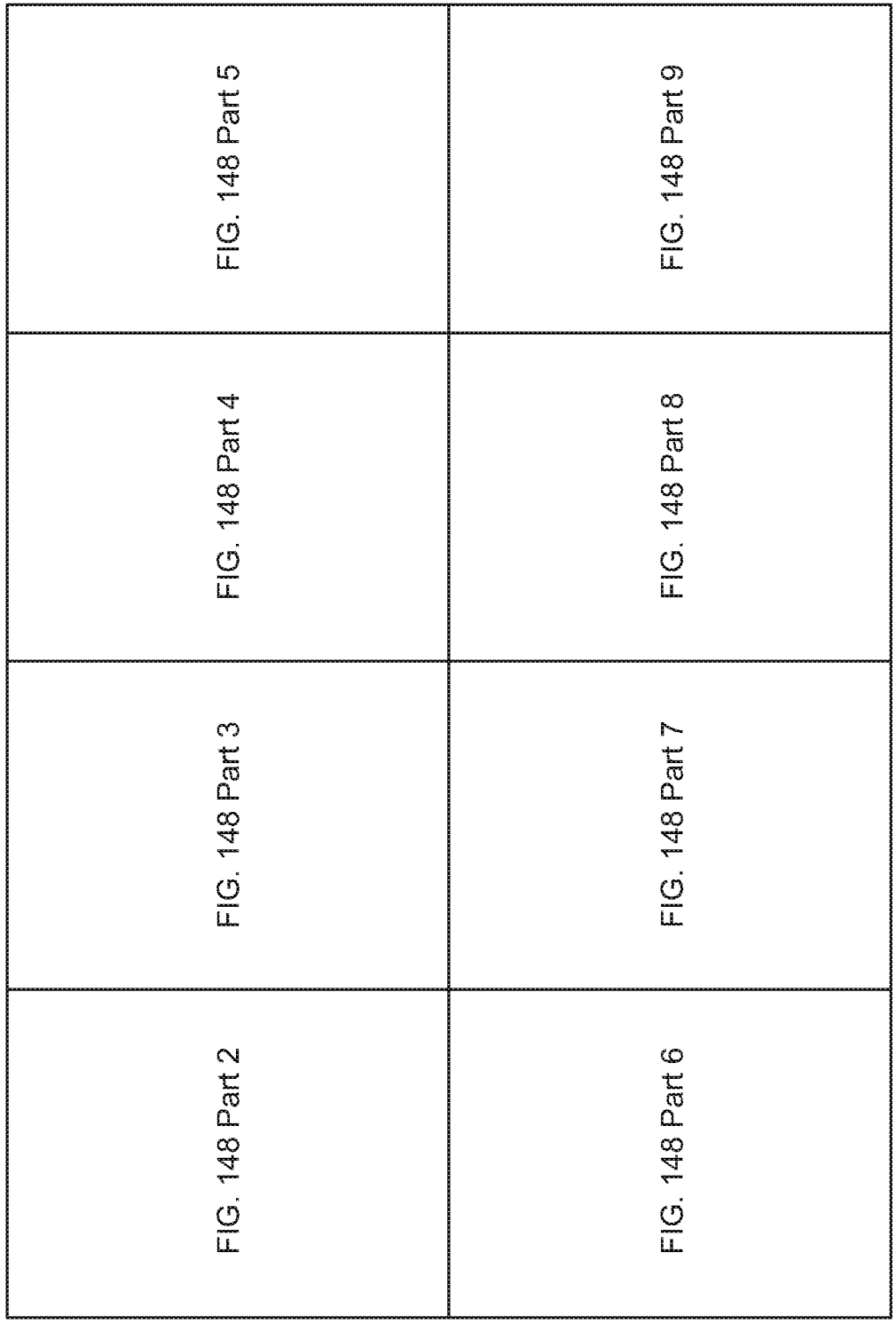

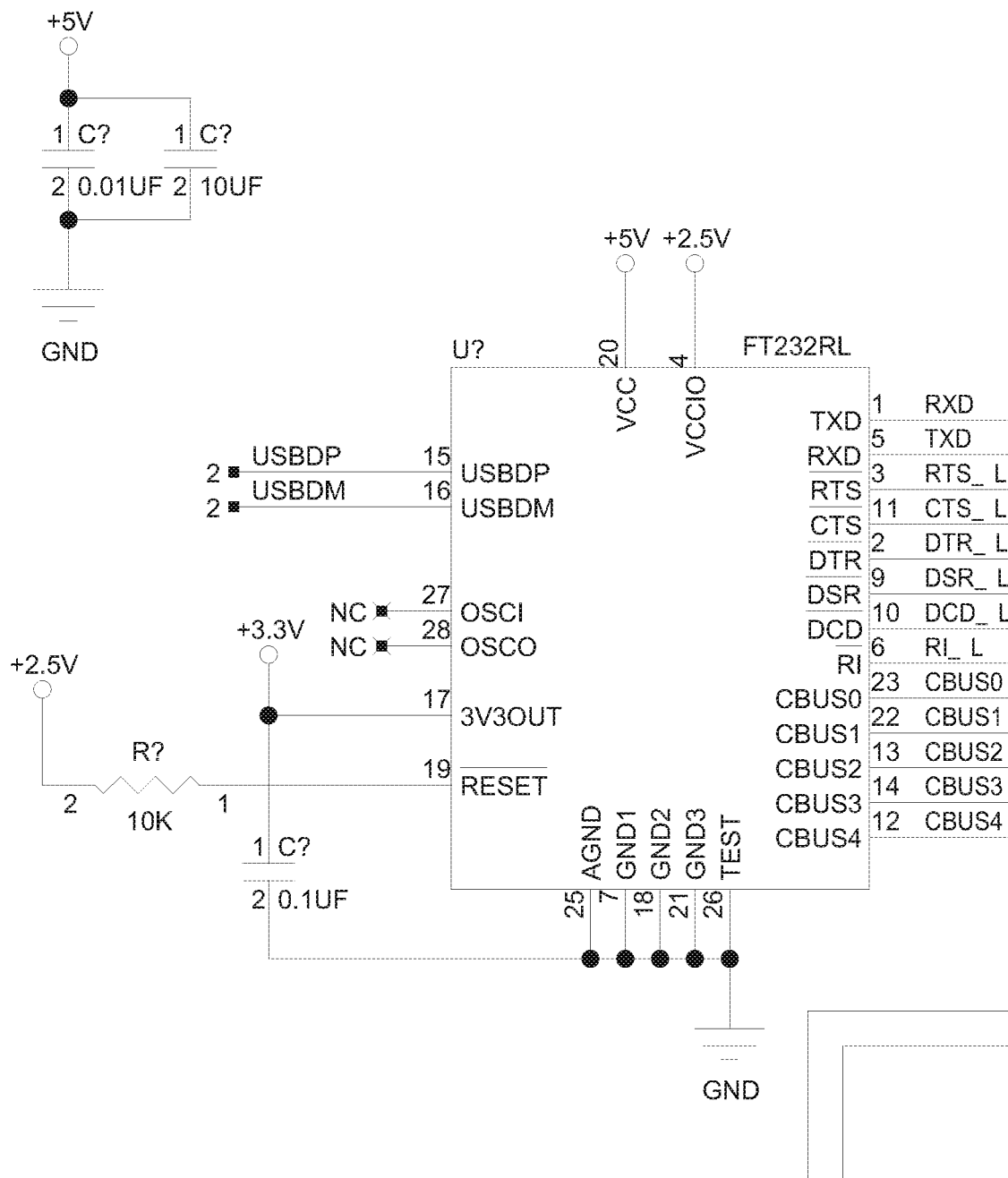
FIG. 148 Part 2

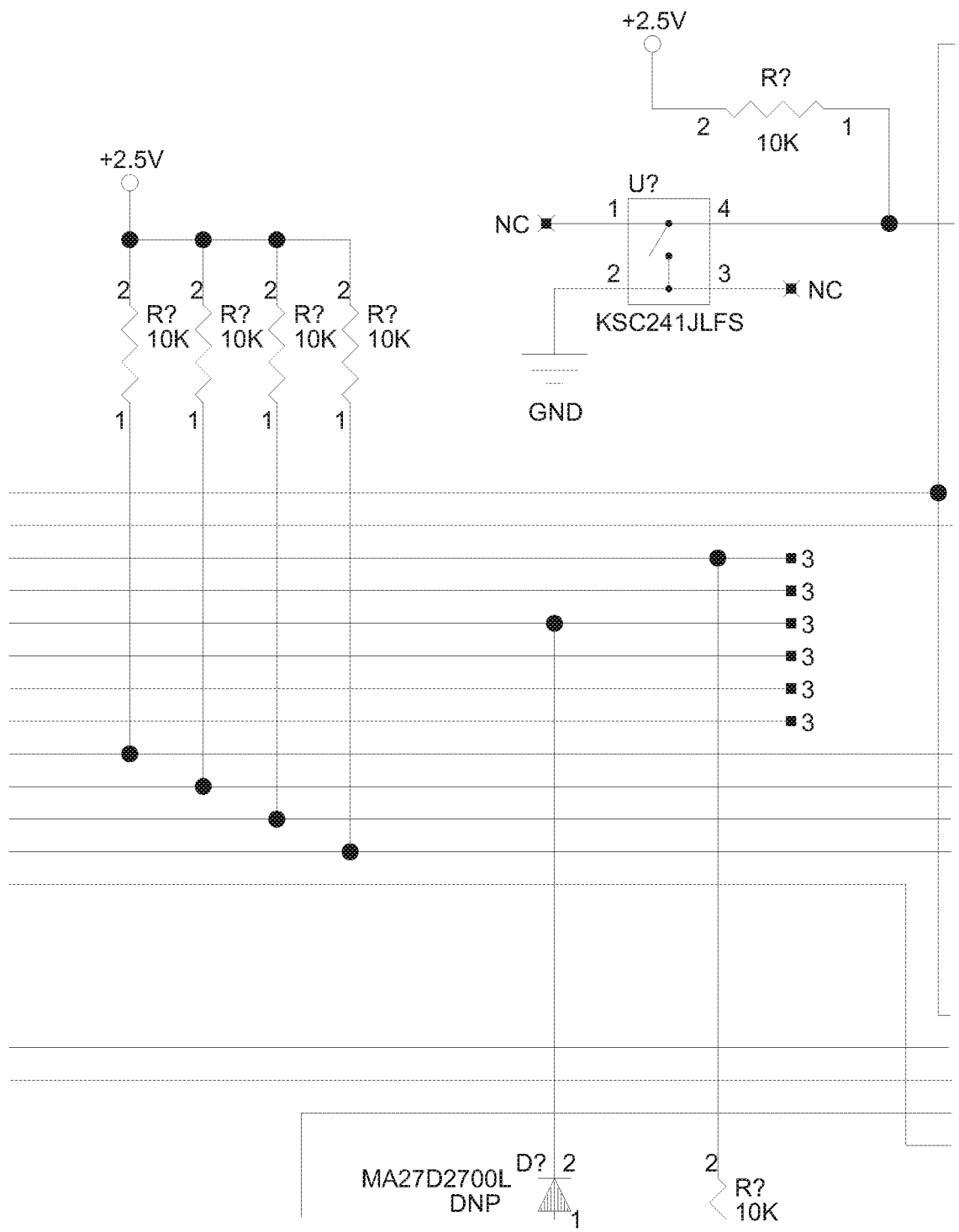
FIG. 148 Part 3

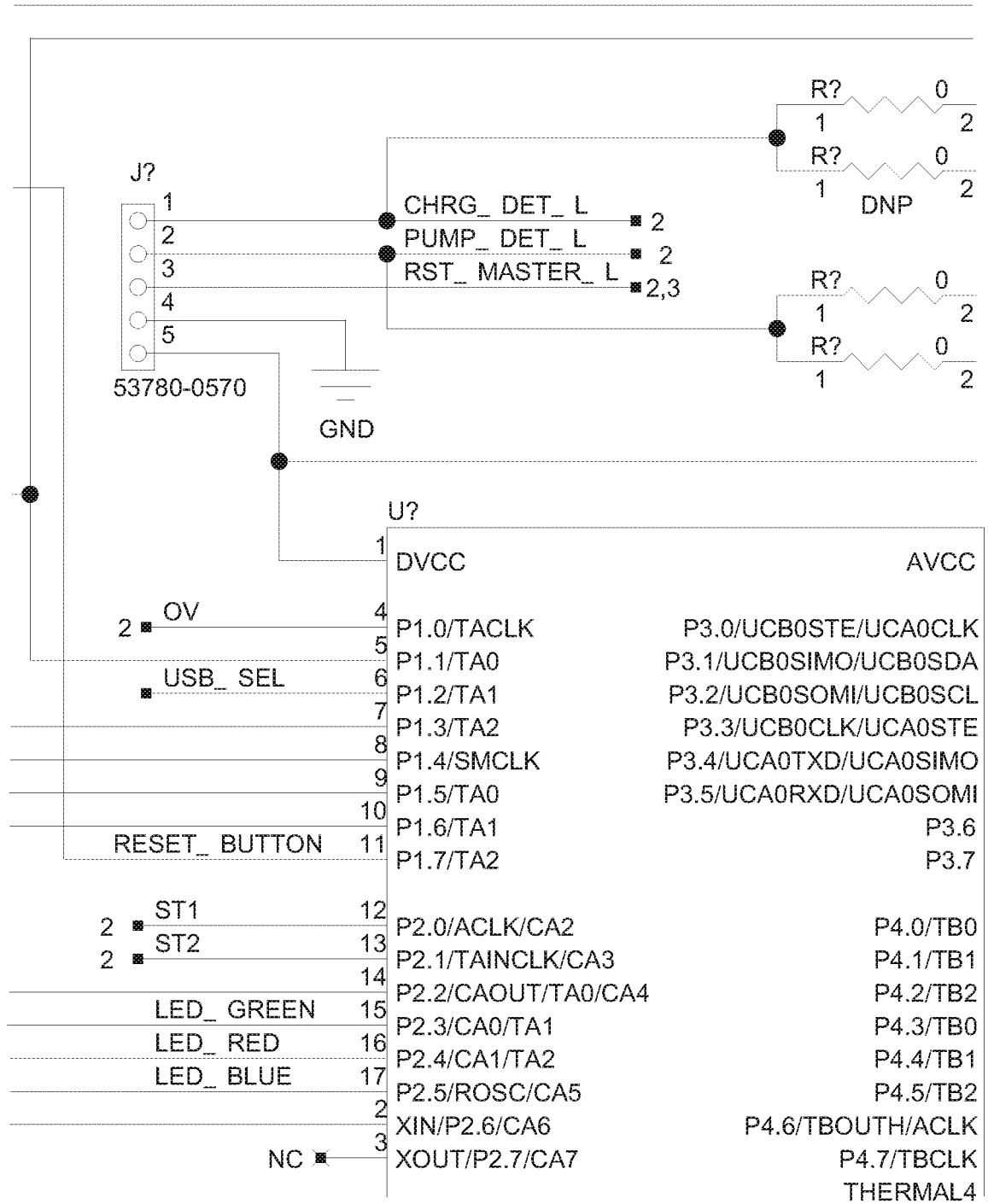
FIG. 148 Part 4

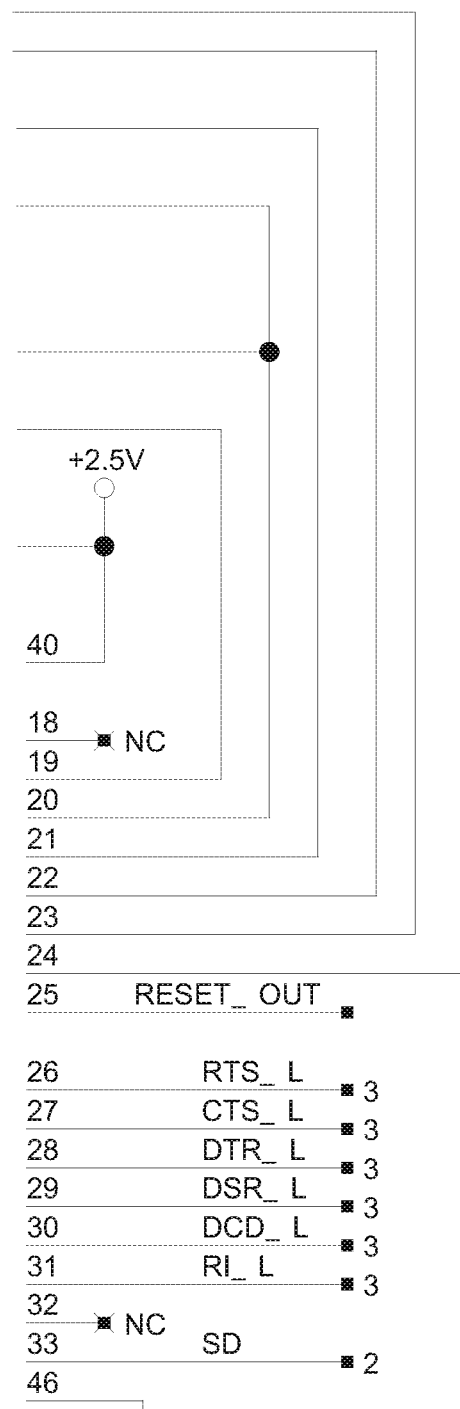
FIG. 148 Part 5

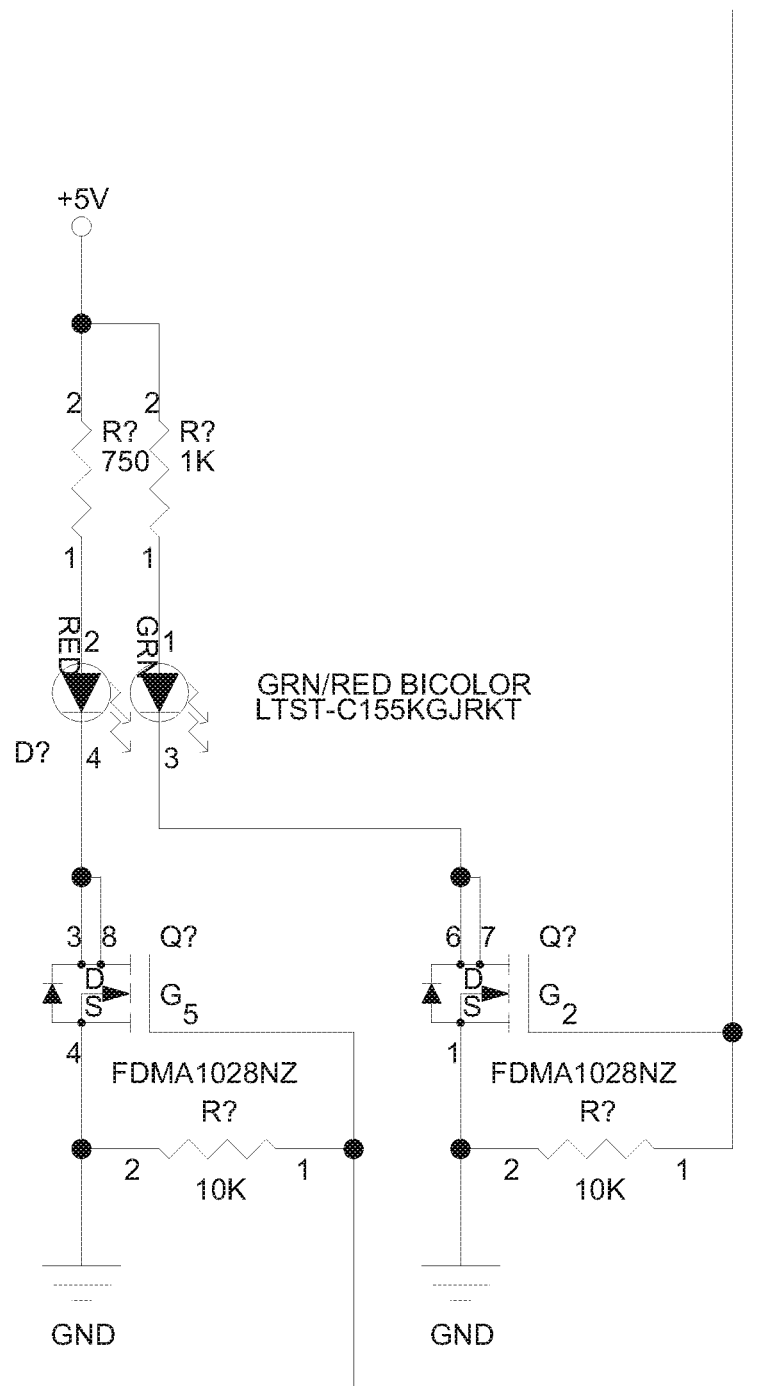
FIG. 148 Part 6

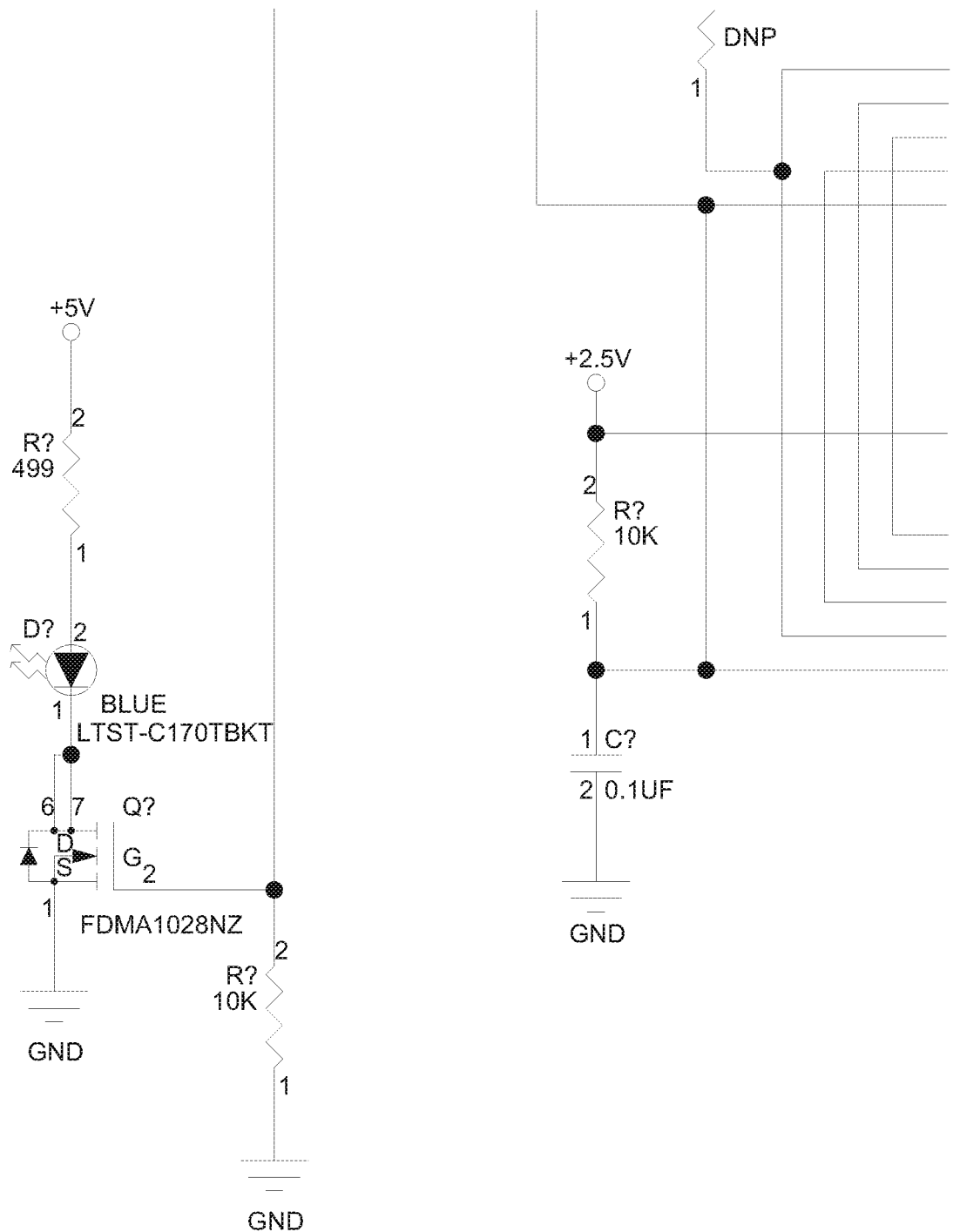
FIG. 148 Part 7

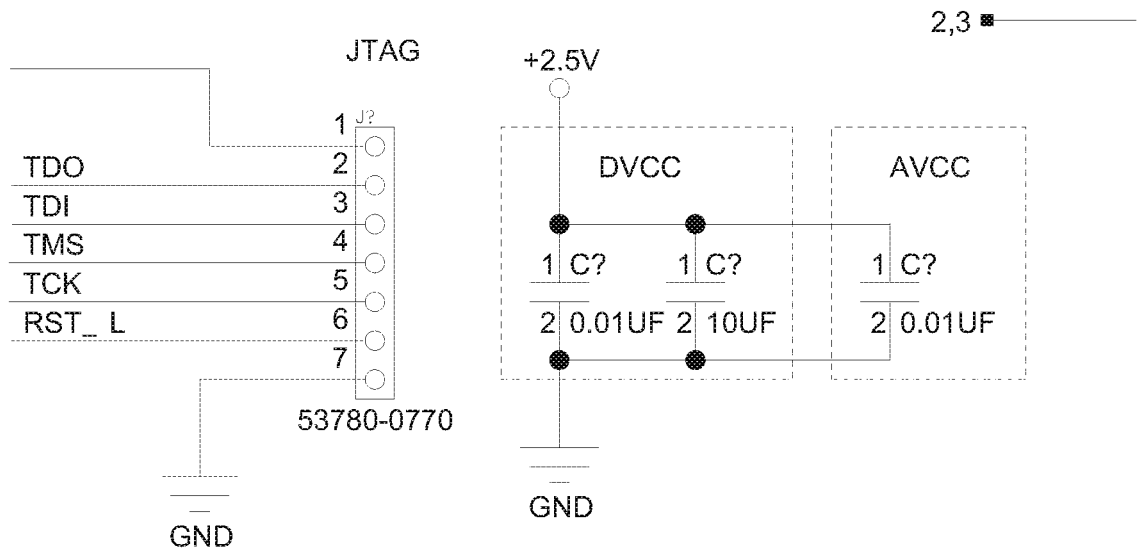
FIG. 148 Part 8

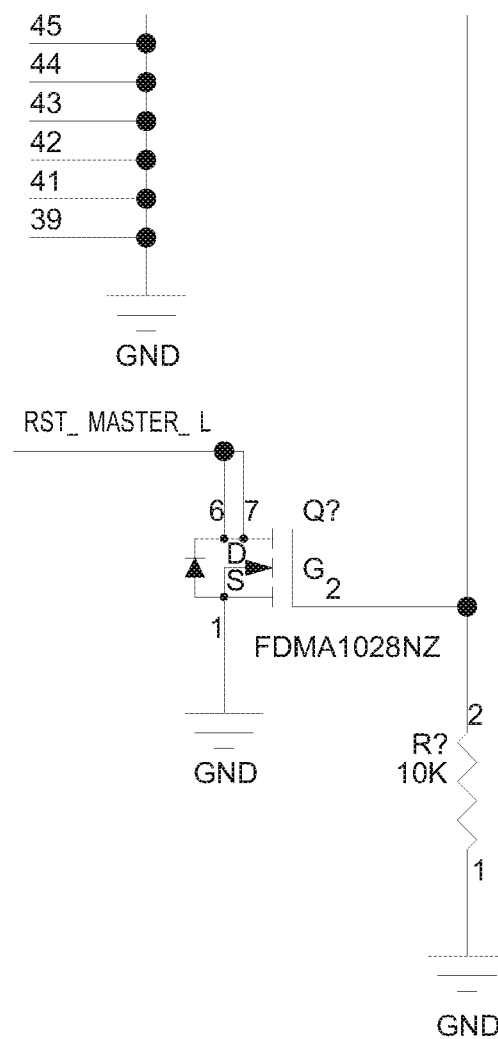
FIG. 148 Part 9

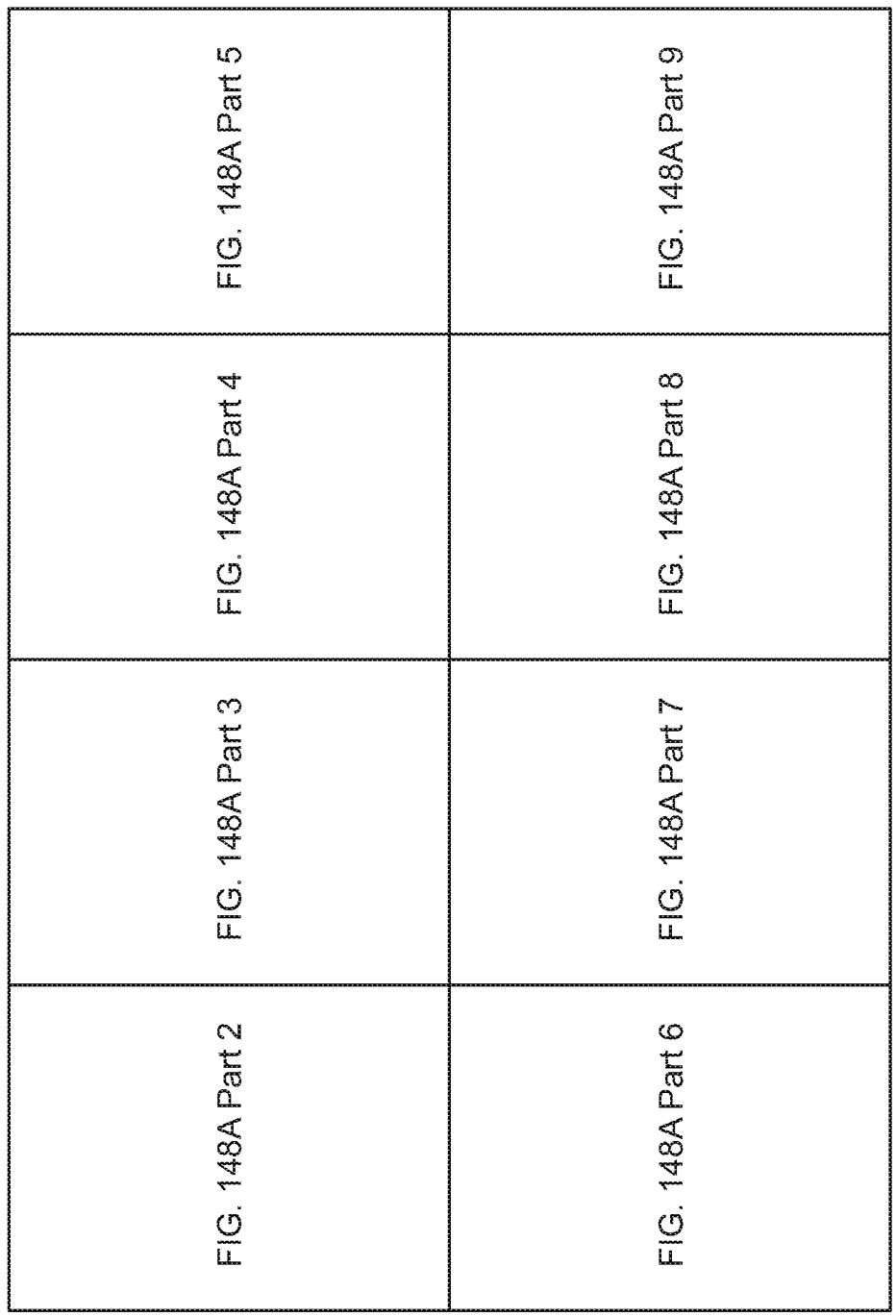
FIG. 148A Part 1

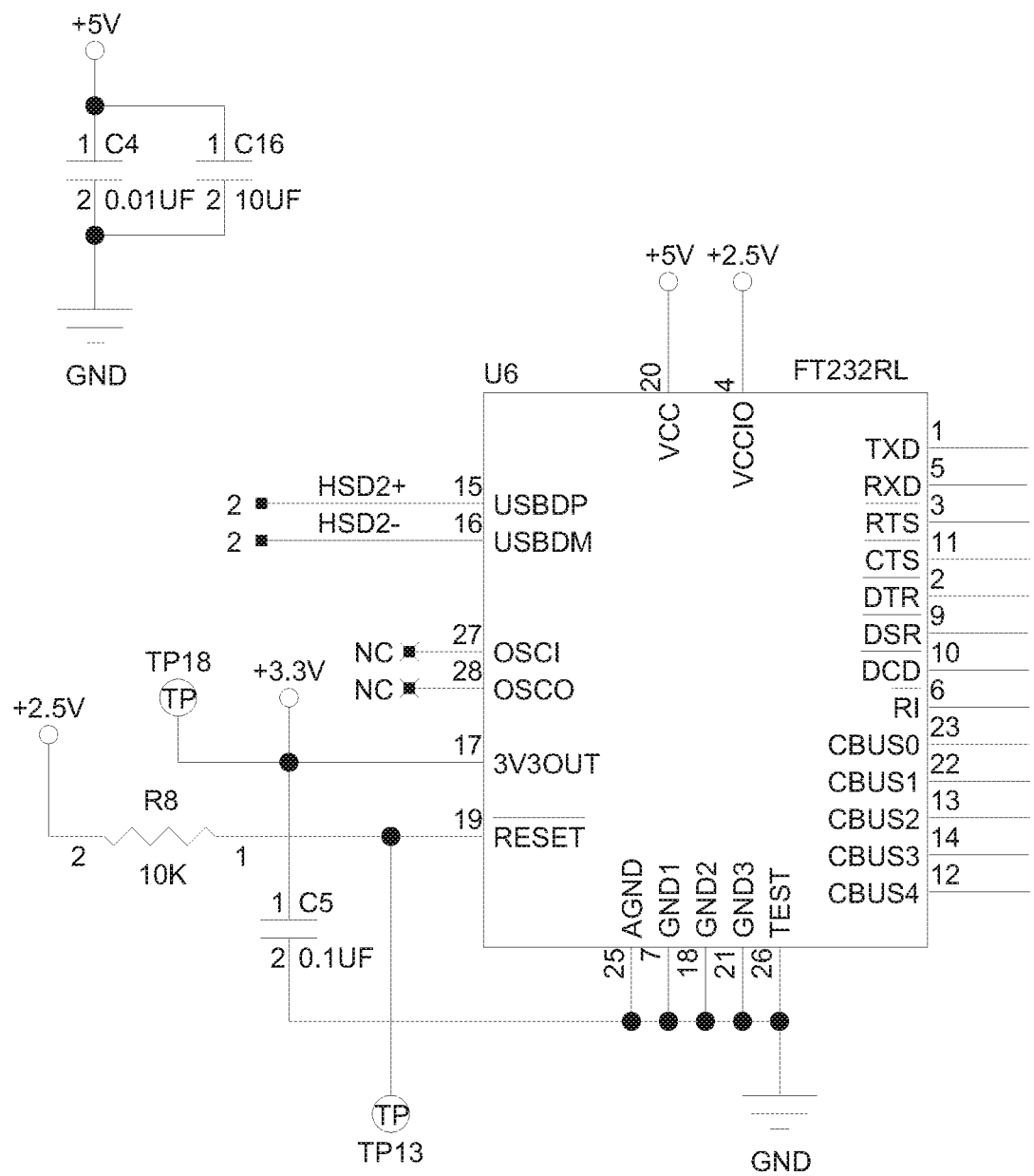
FIG. 148A Part 2

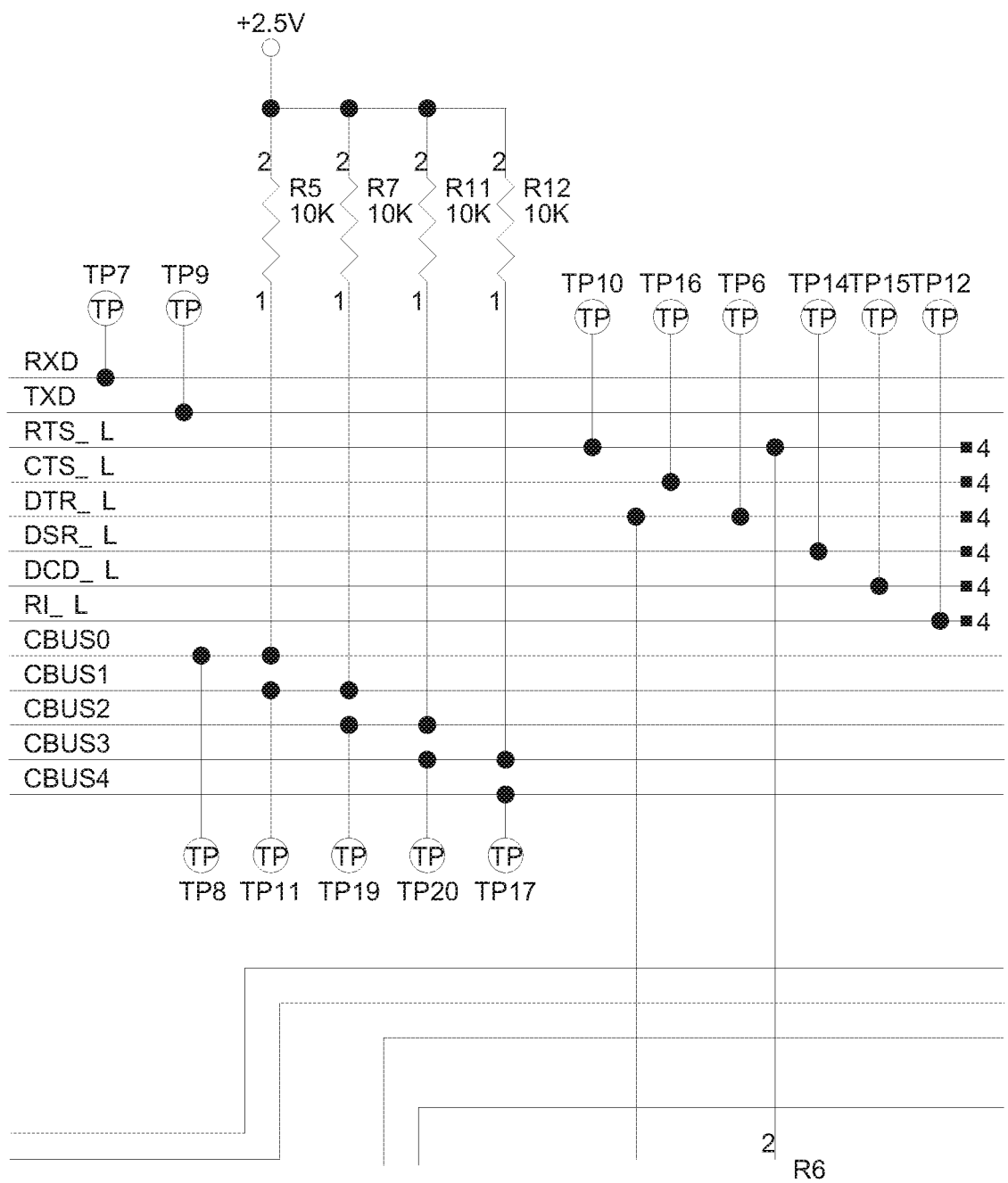
FIG. 148A Part 3

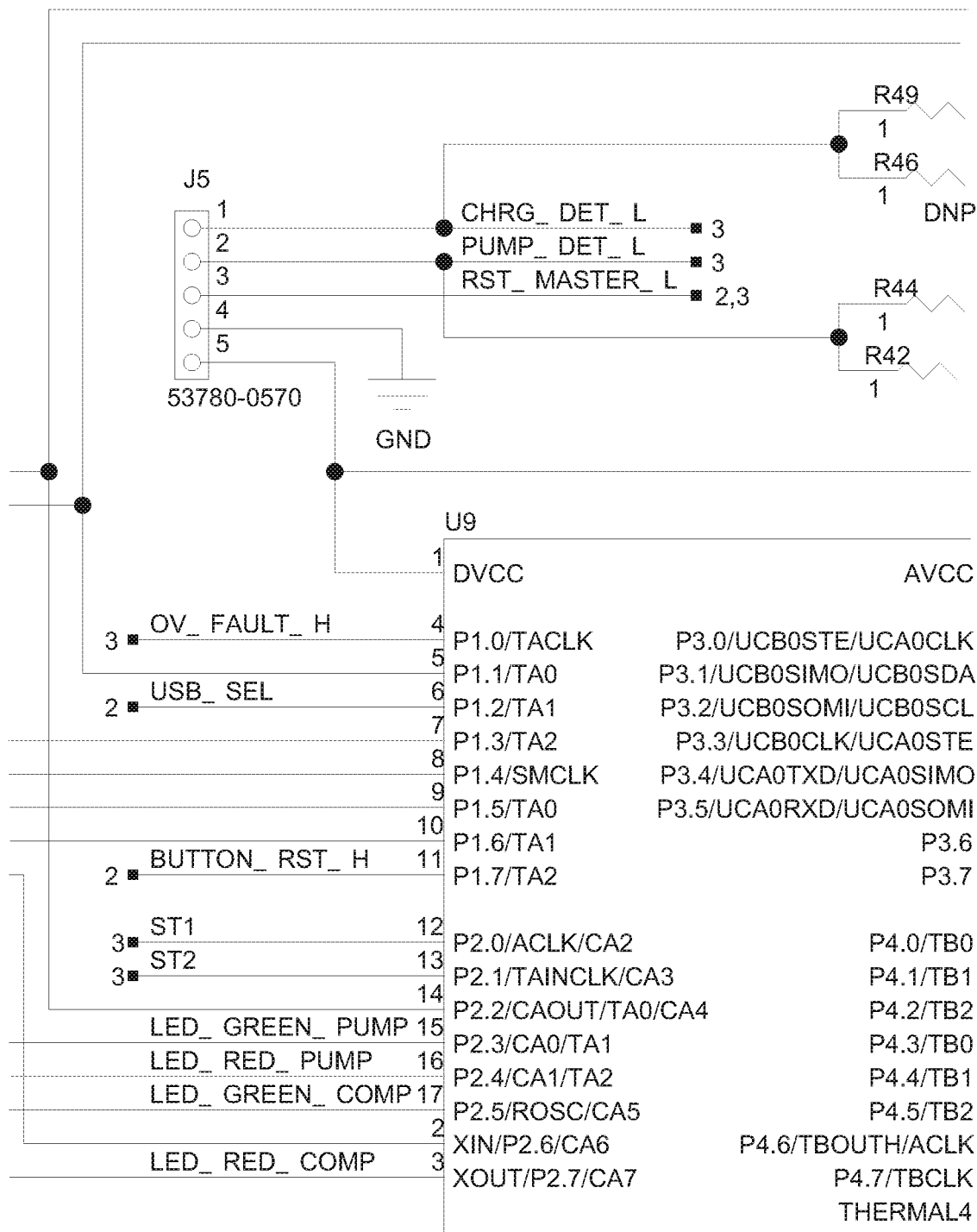
FIG. 148A Part 4

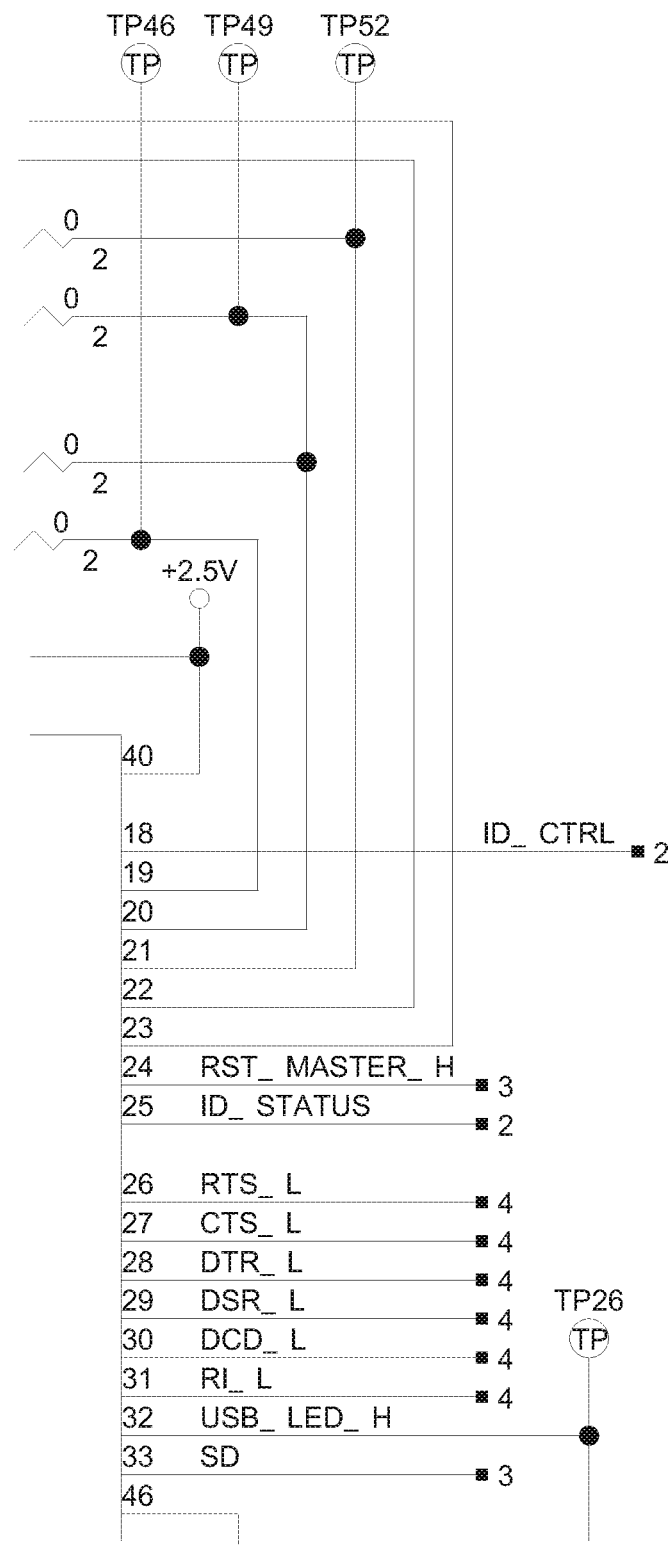
FIG. 148A Part 5

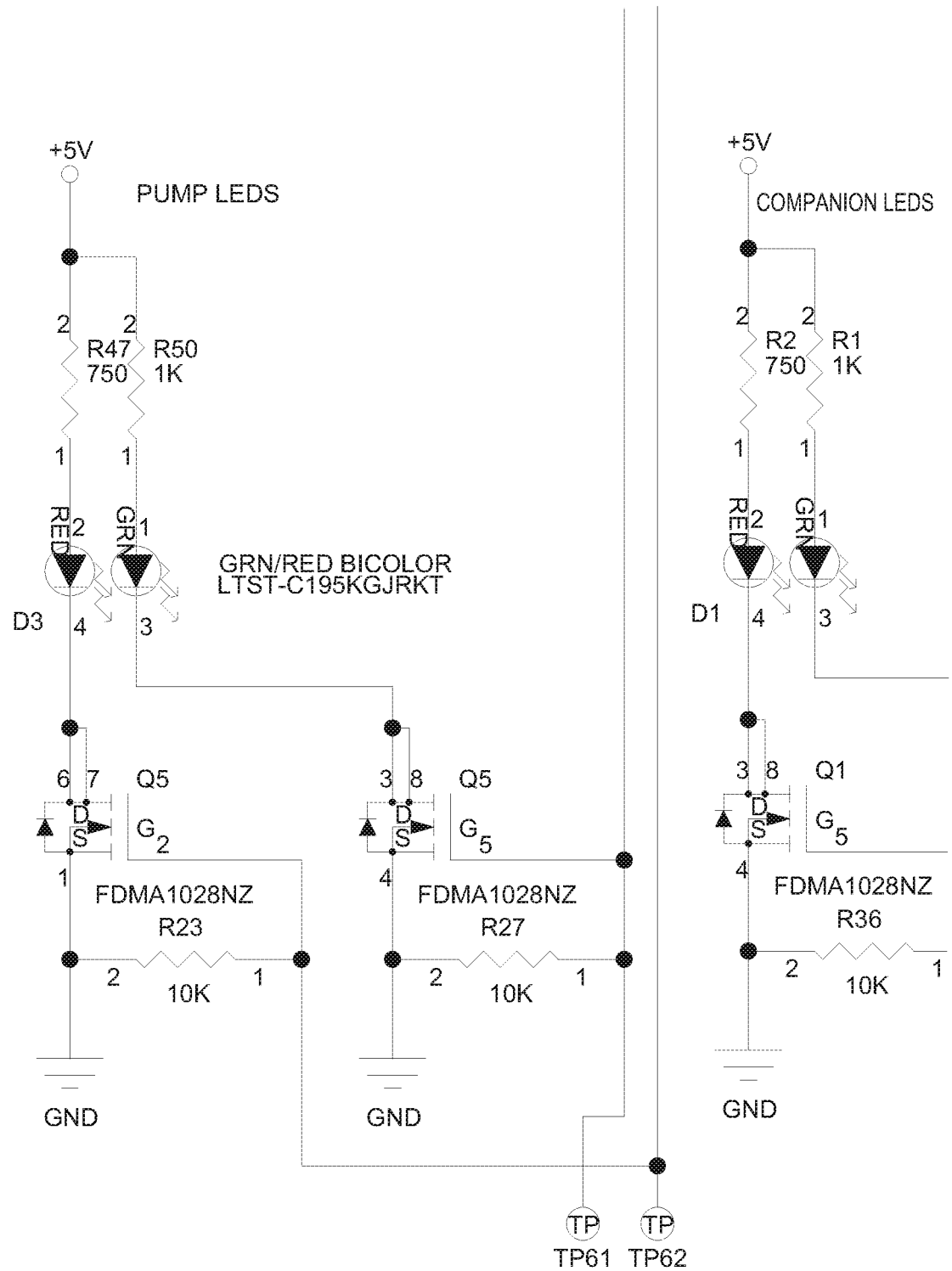
FIG. 148A Part 6

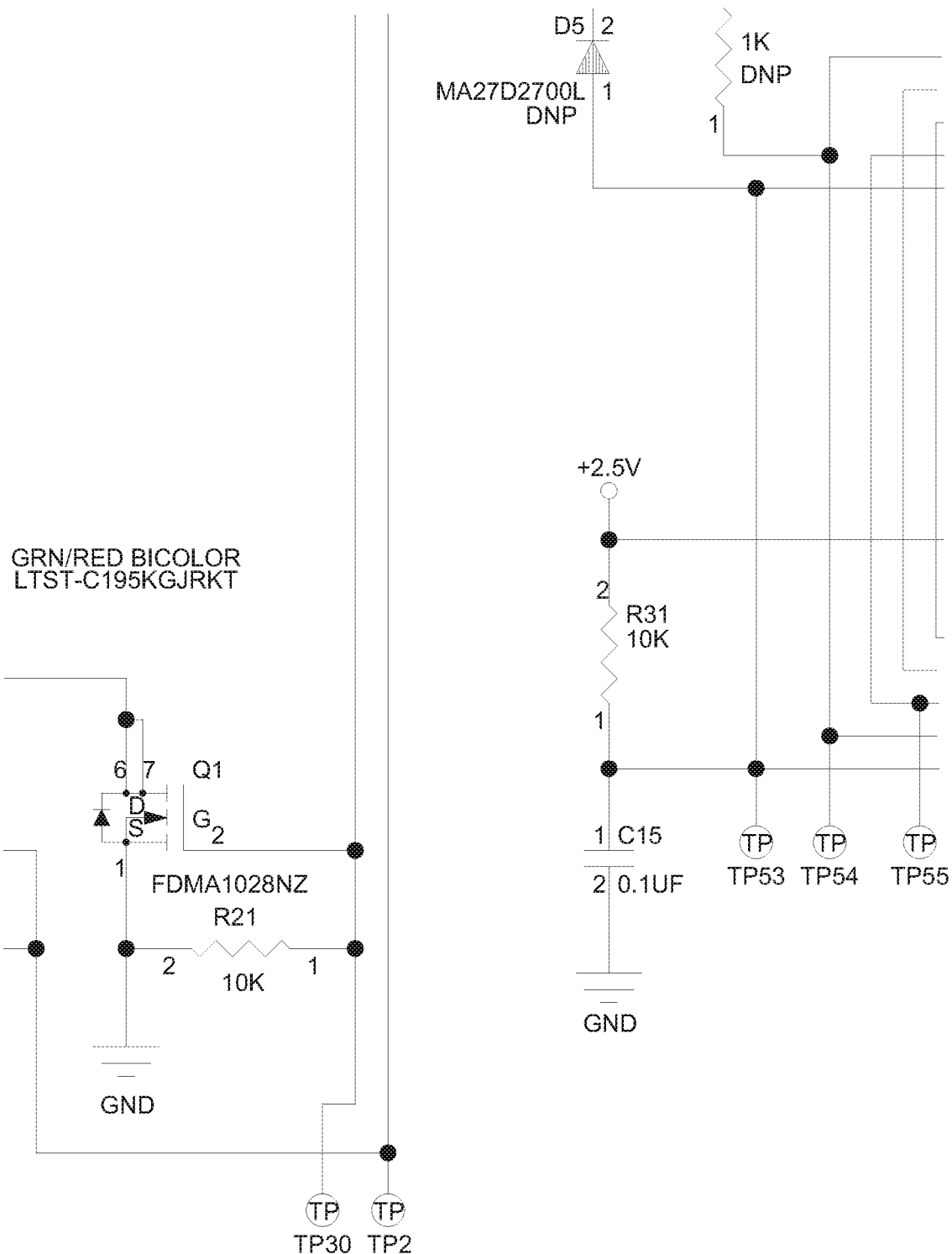
FIG. 148A Part 7

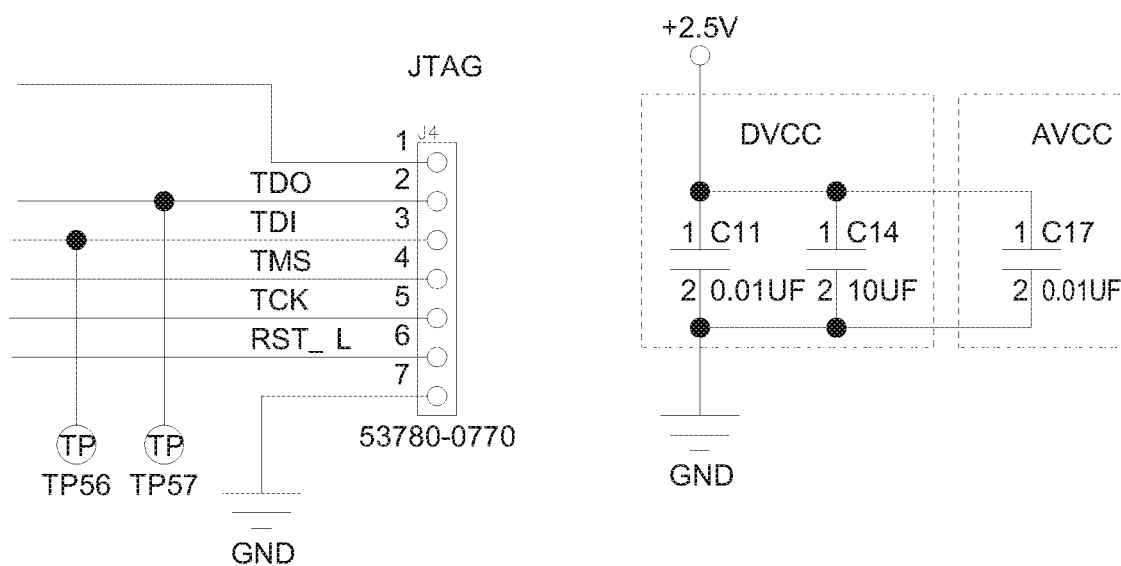
FIG. 148A Part 8

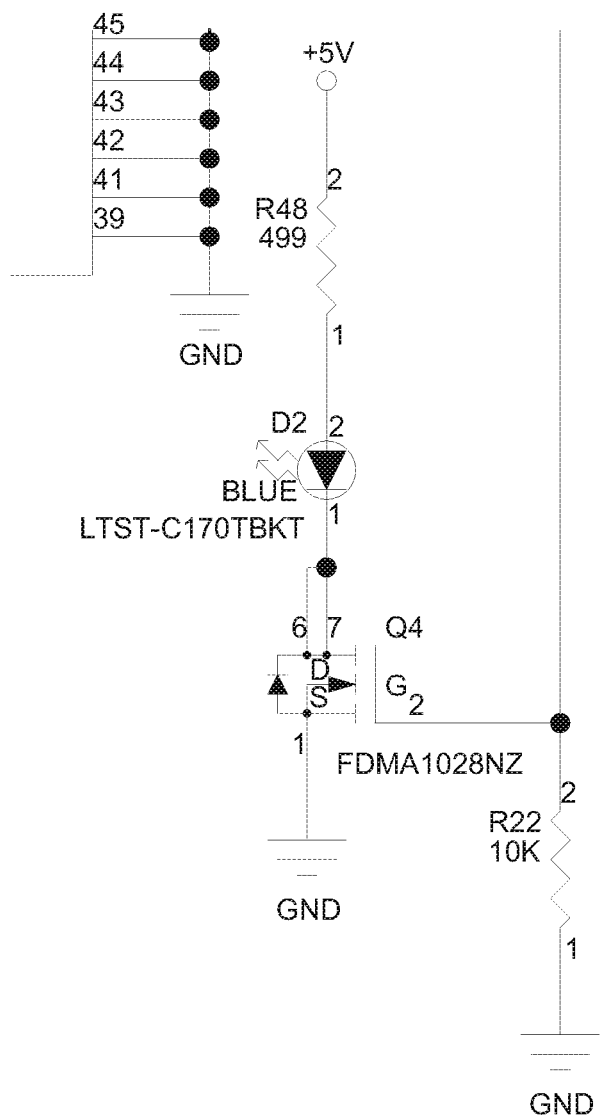
FIG. 148A Part 9

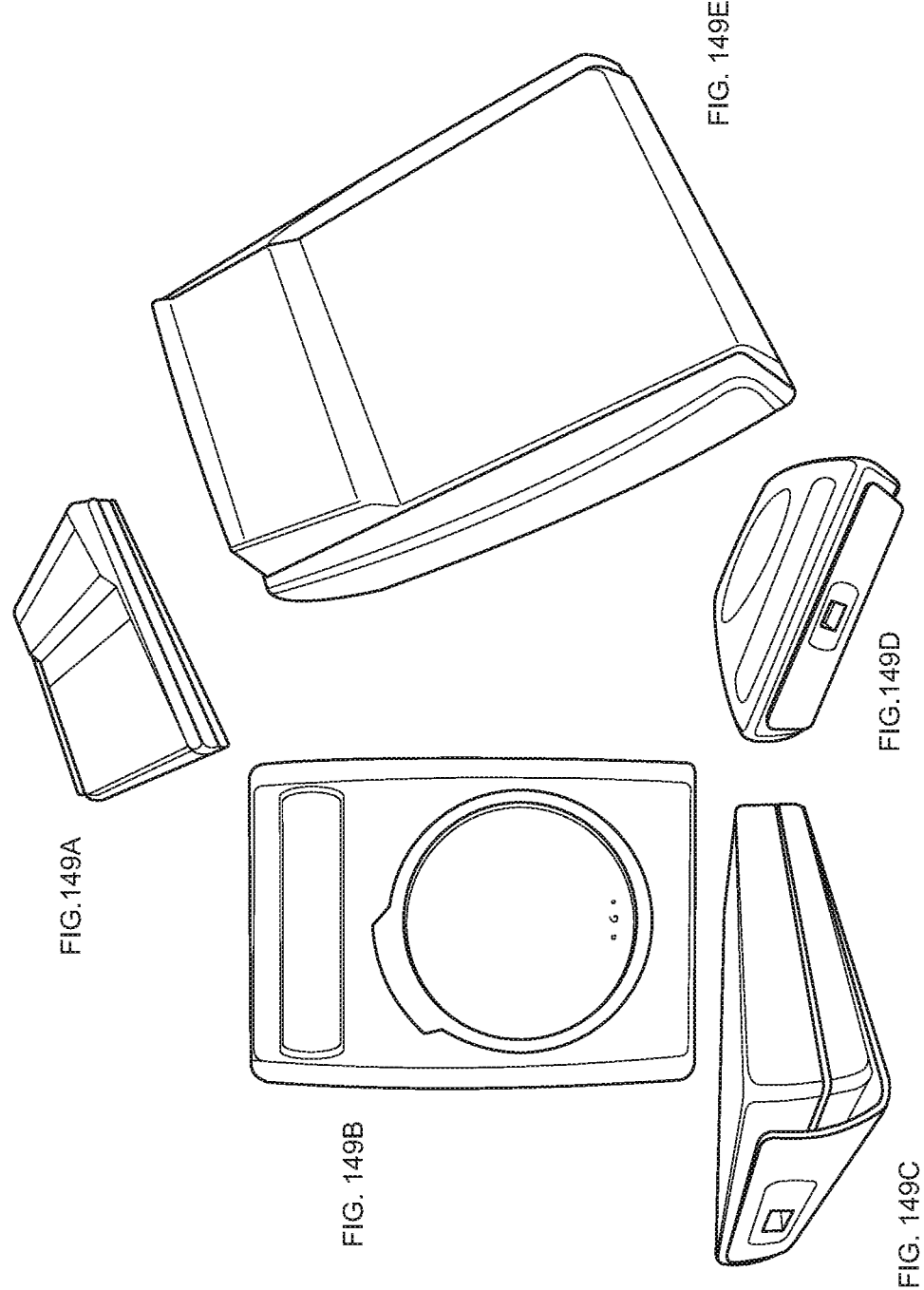

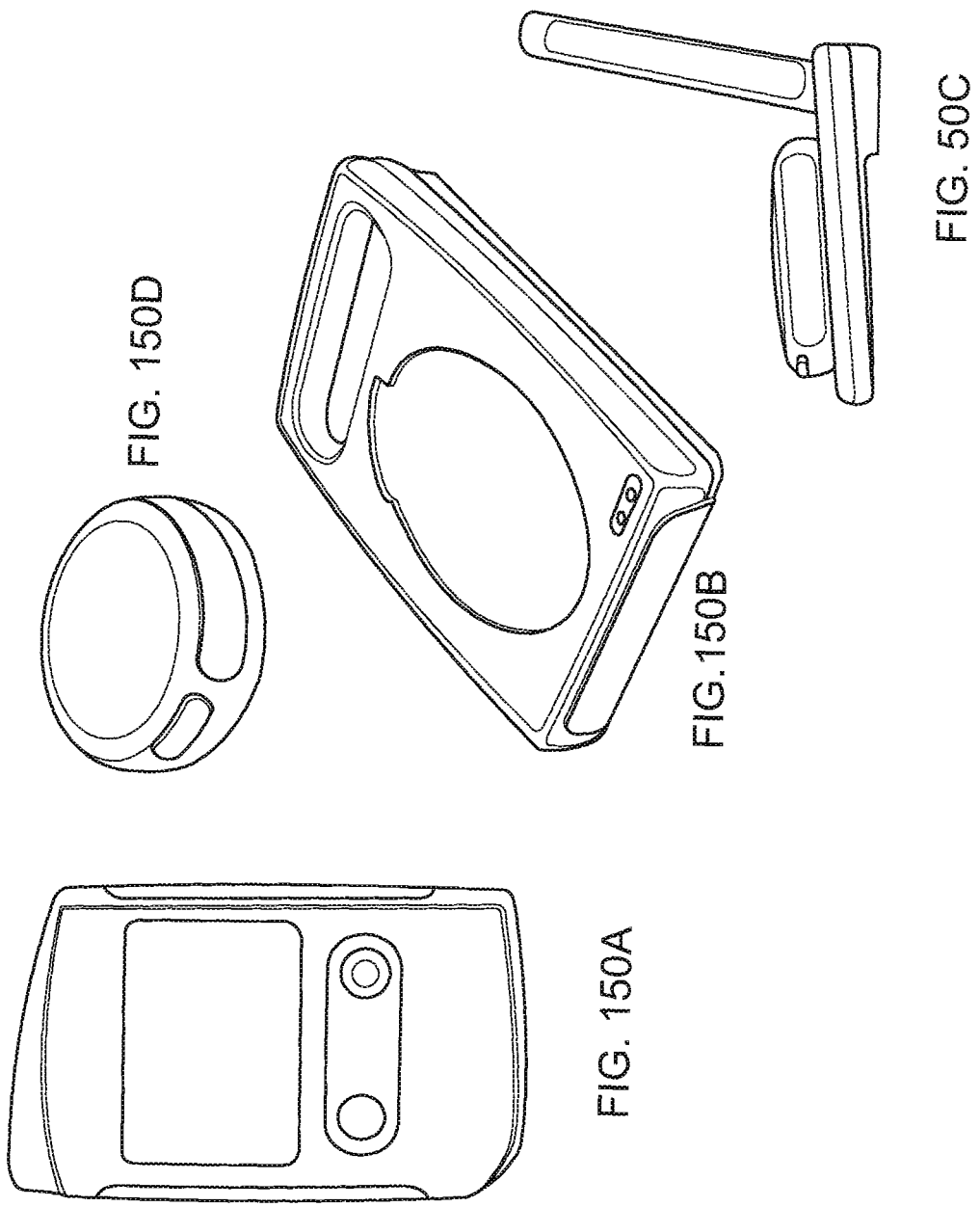

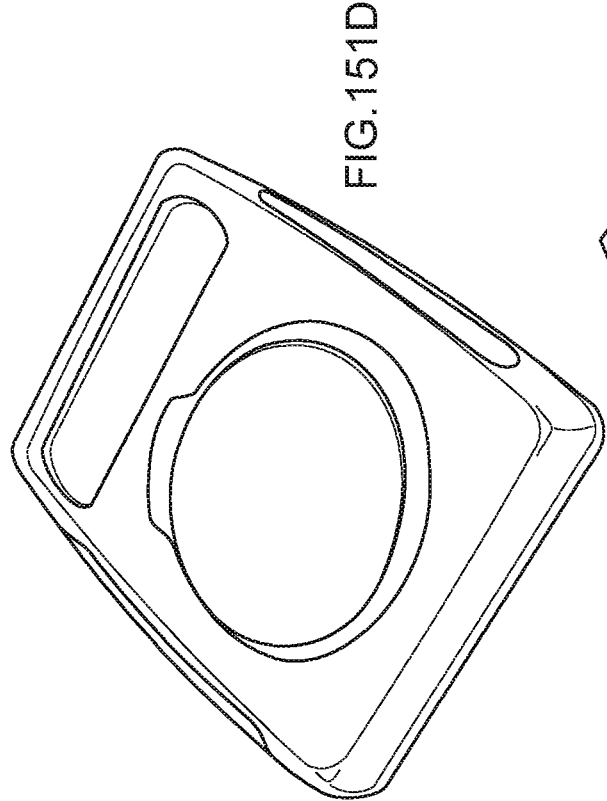
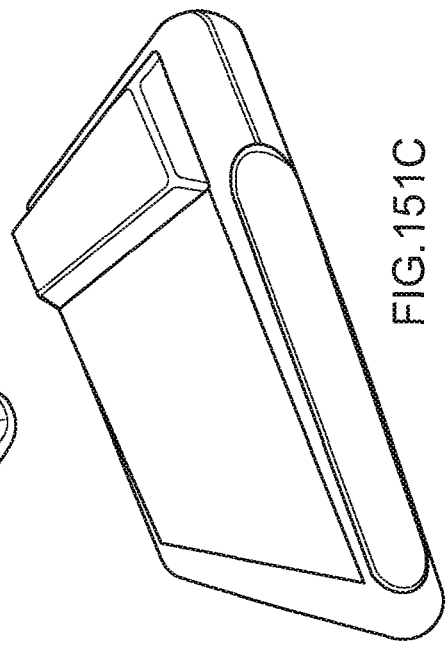
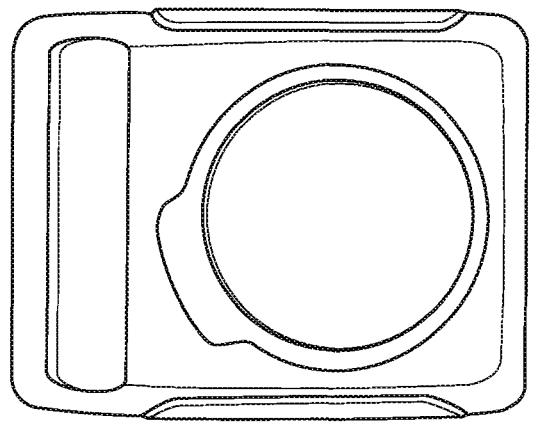
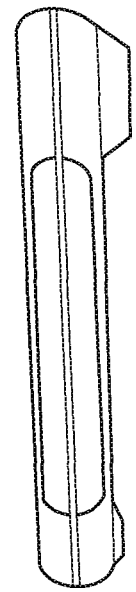
FIG. 151A
FIG. 151B
FIG. 151C
FIG. 151D

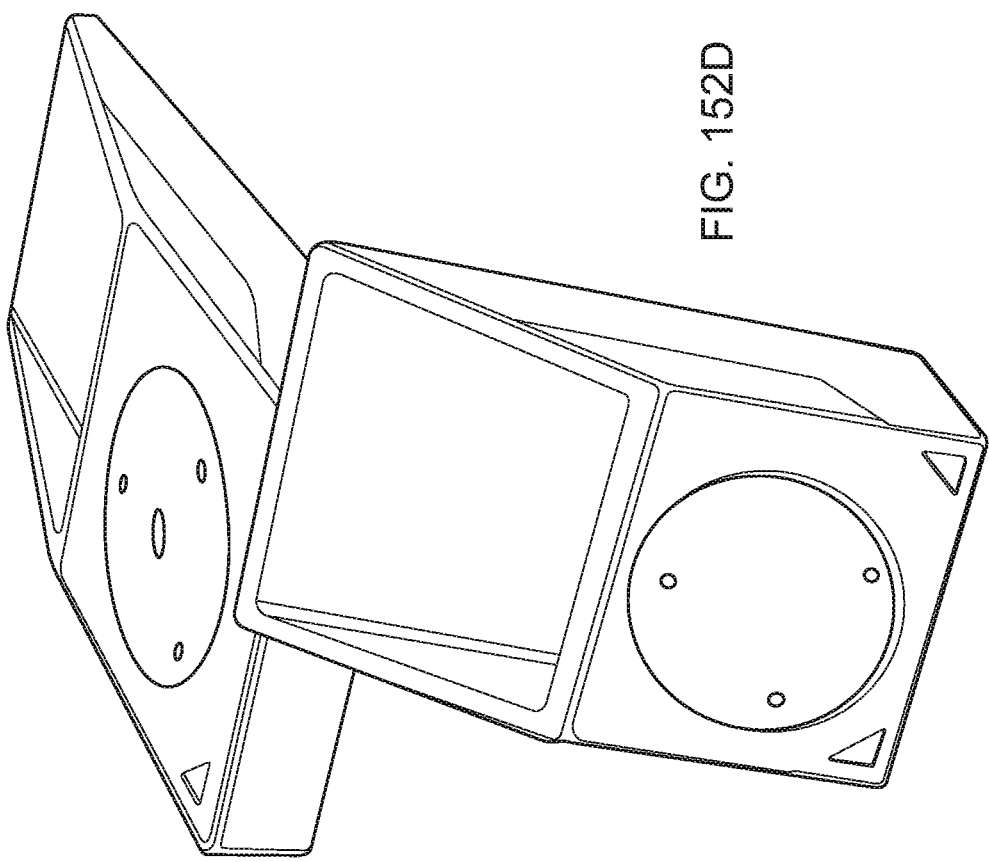
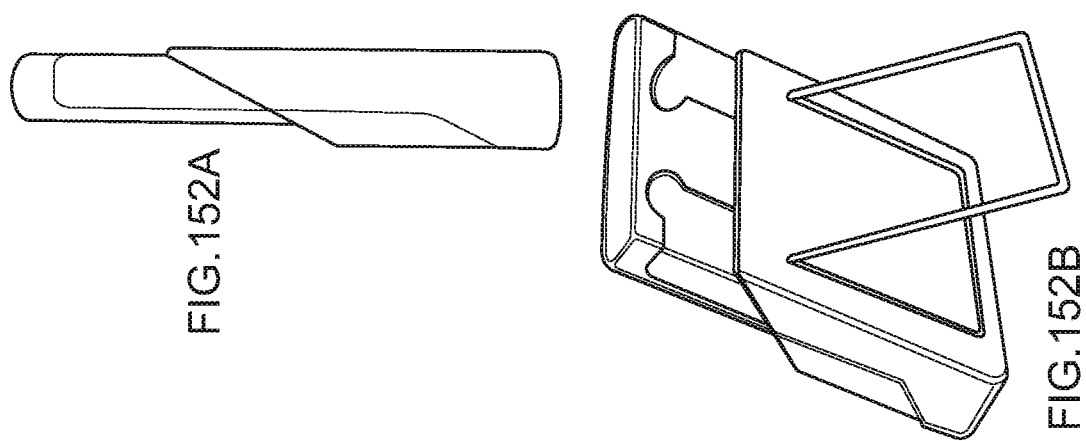

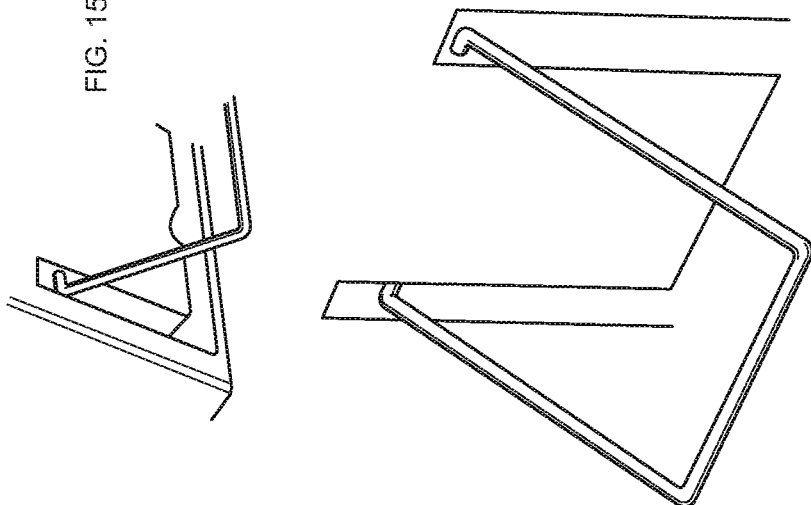
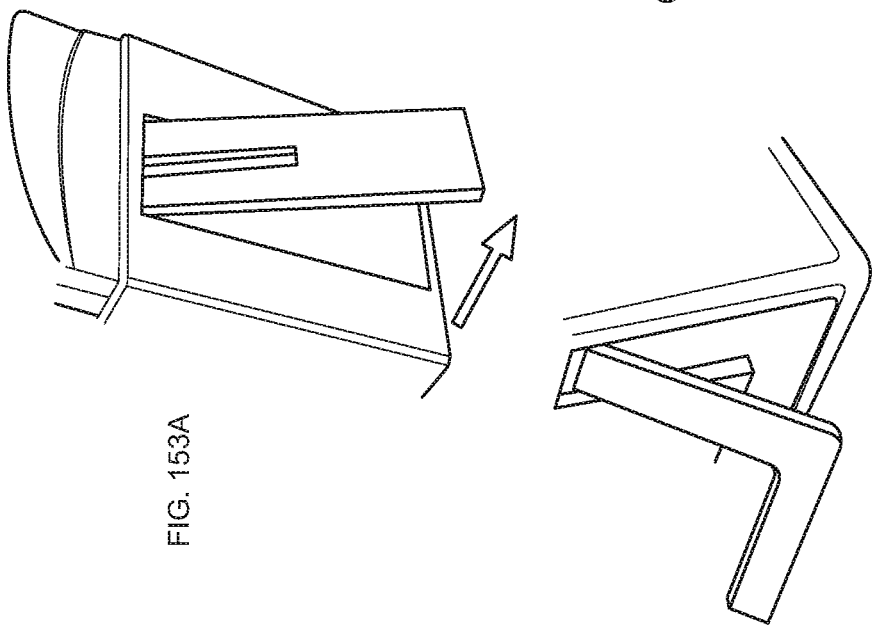
FIG. 153A
FIG. 153B
FIG. 153C
FIG. 153D

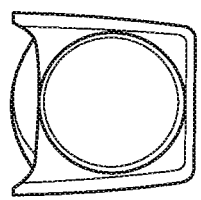
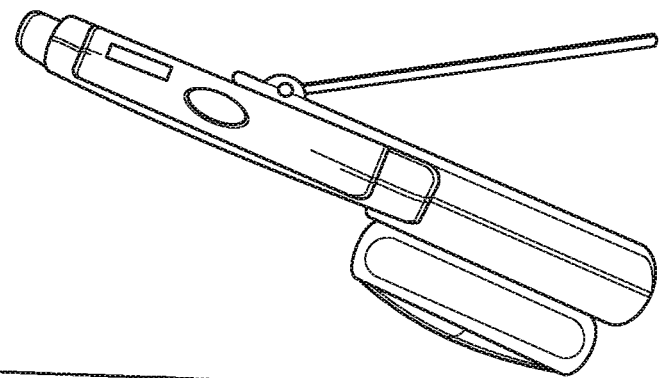
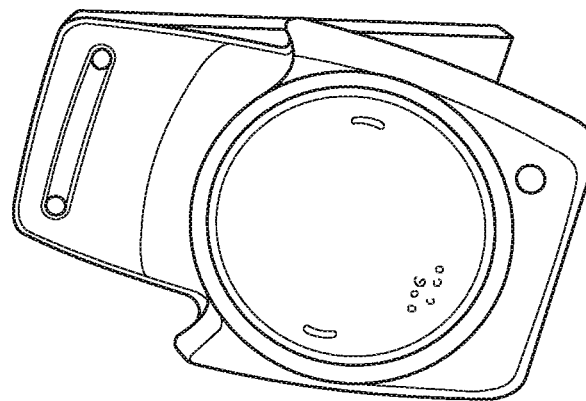
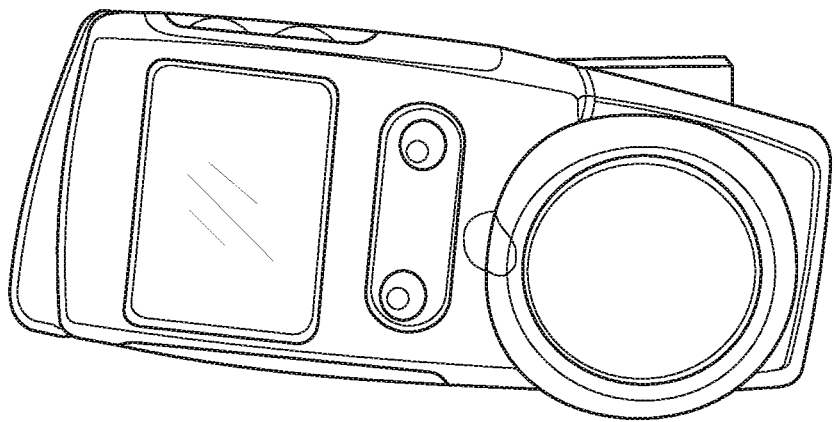
FIG. 154D
FIG. 154C
FIG. 154B
FIG. 154A

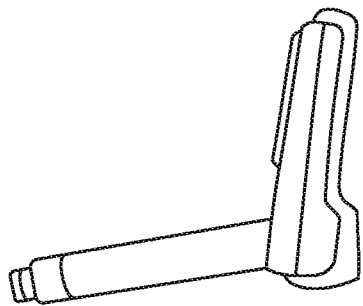
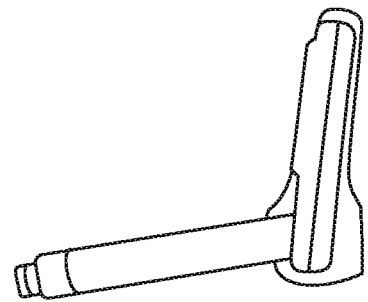
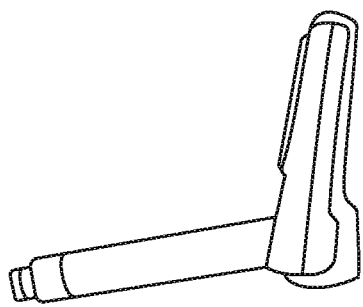
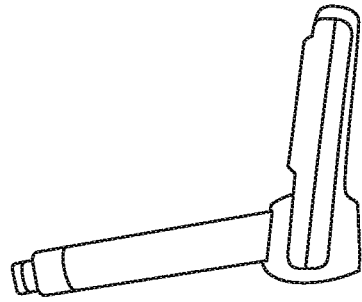
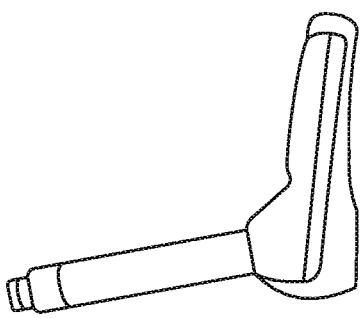
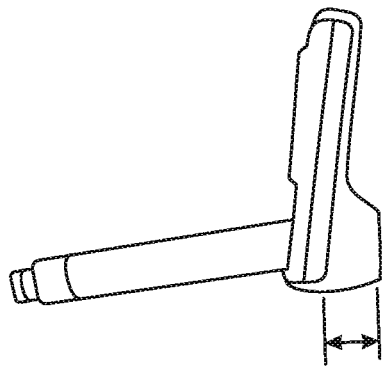

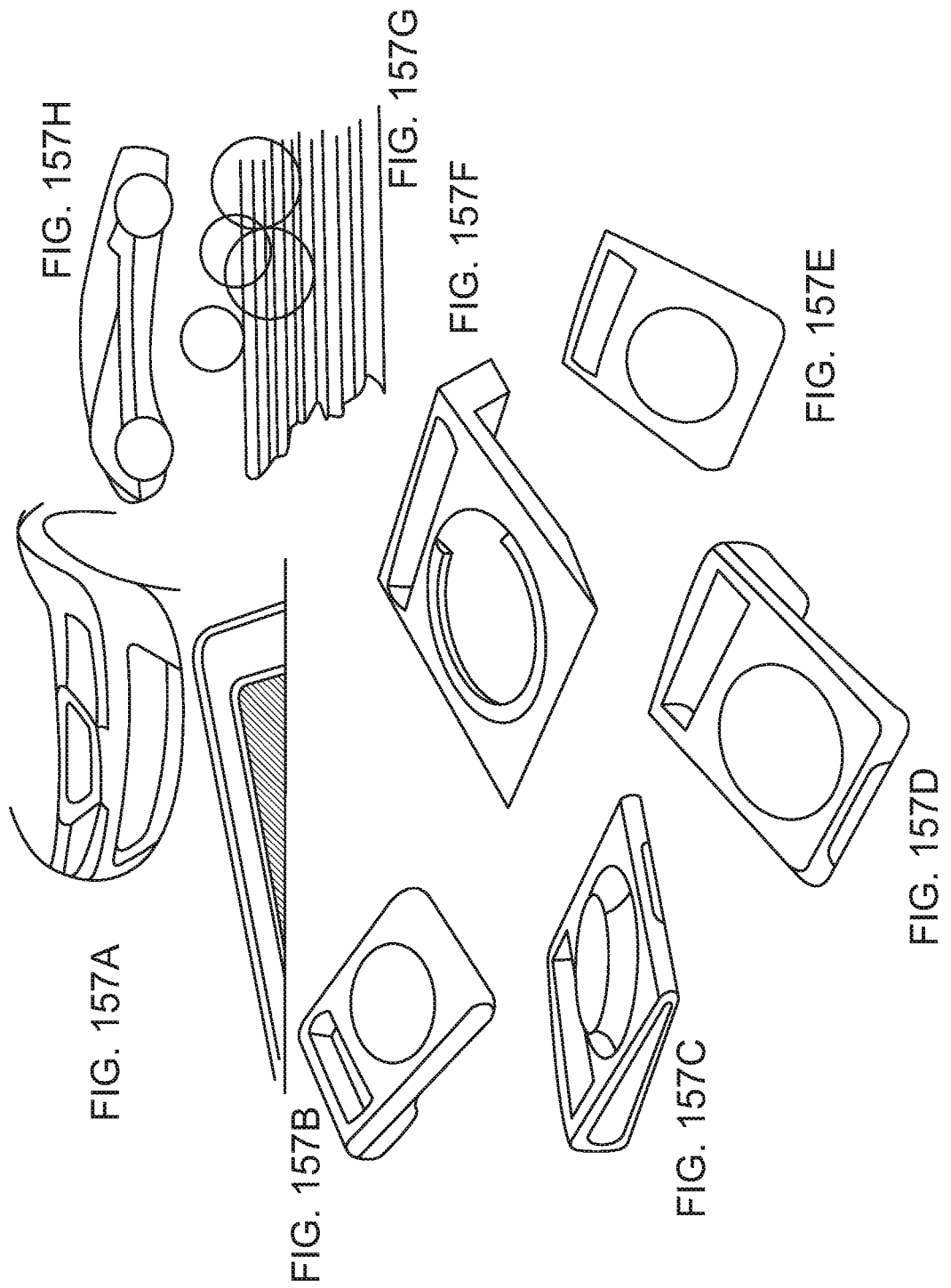

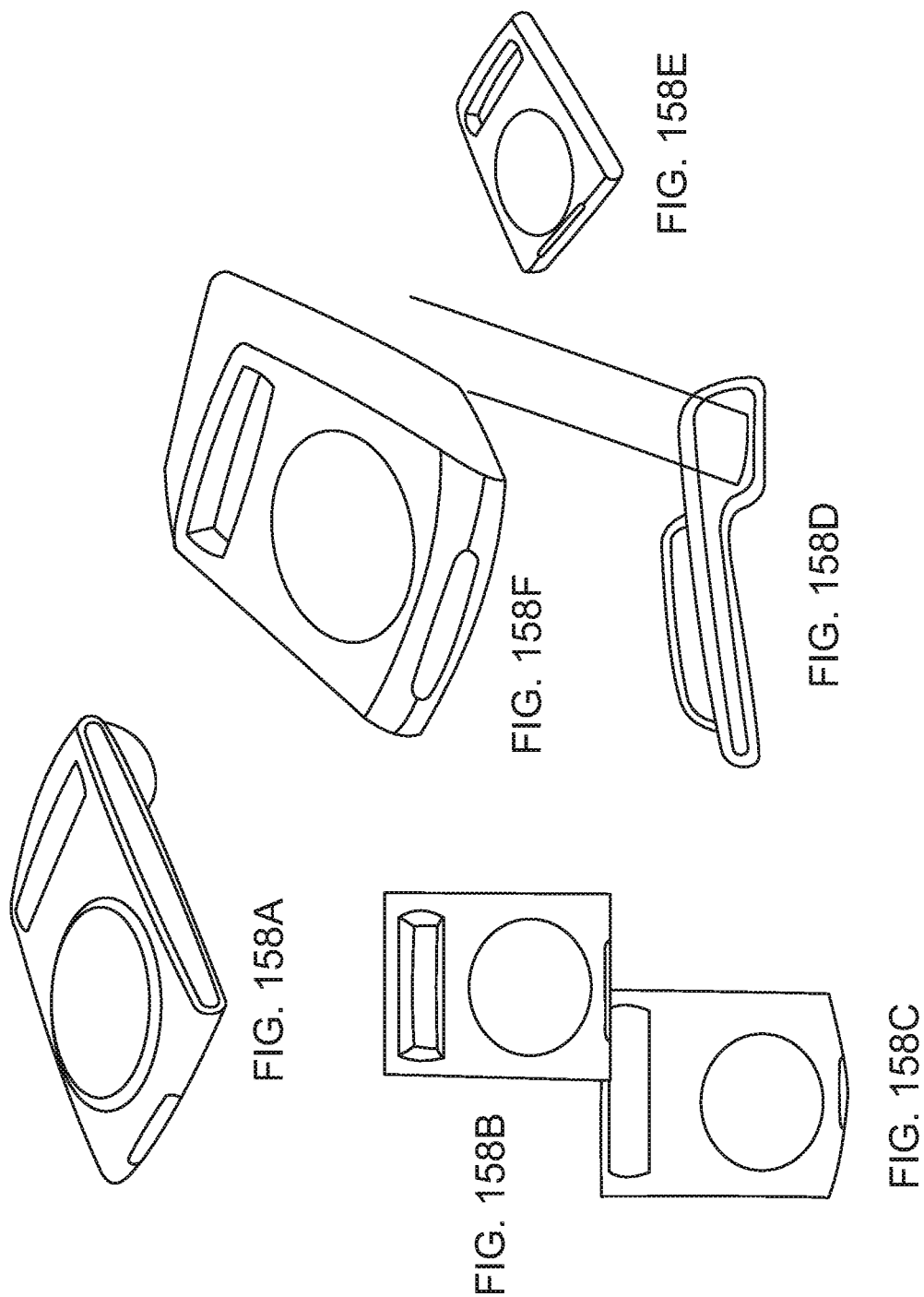

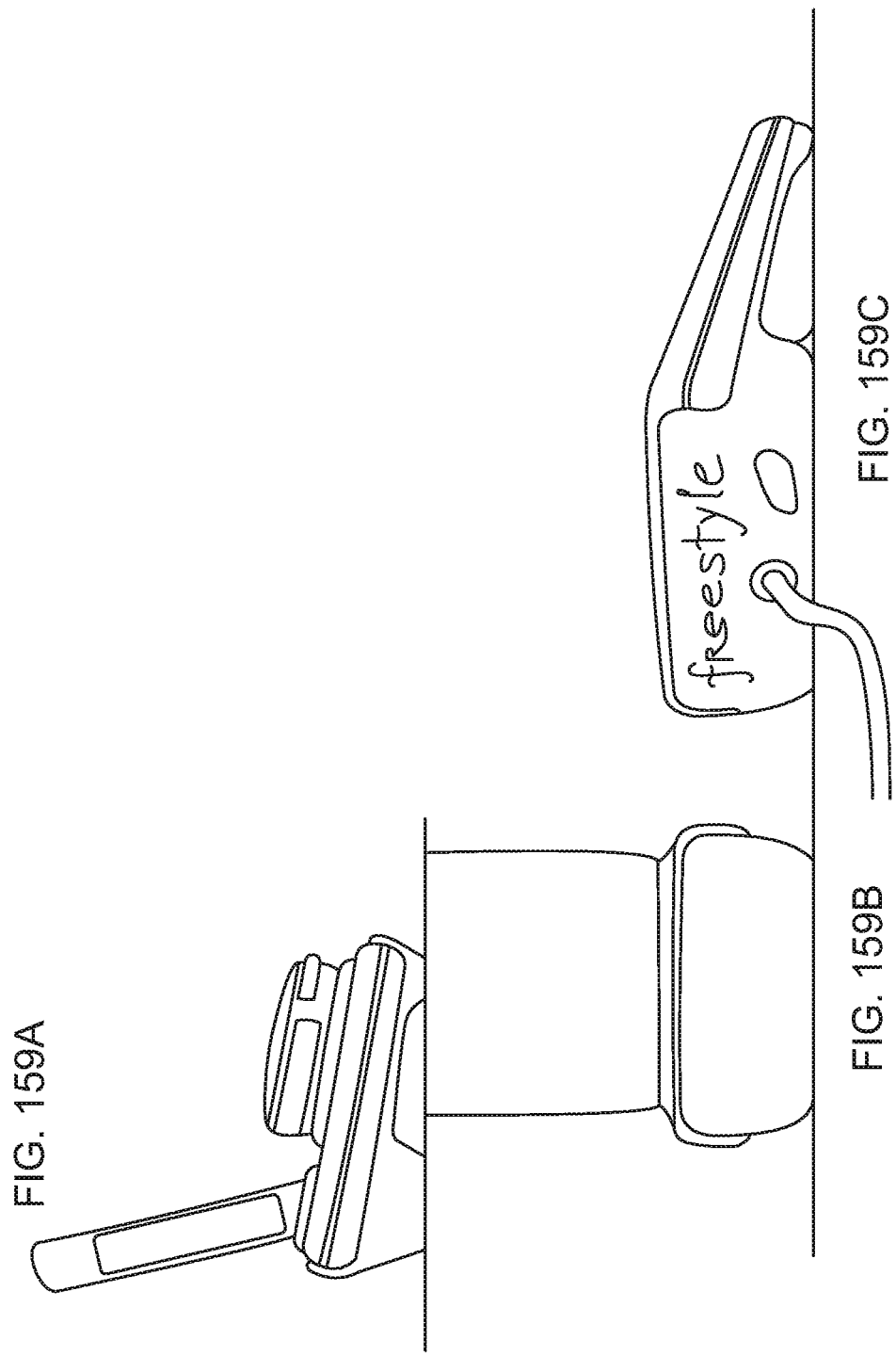

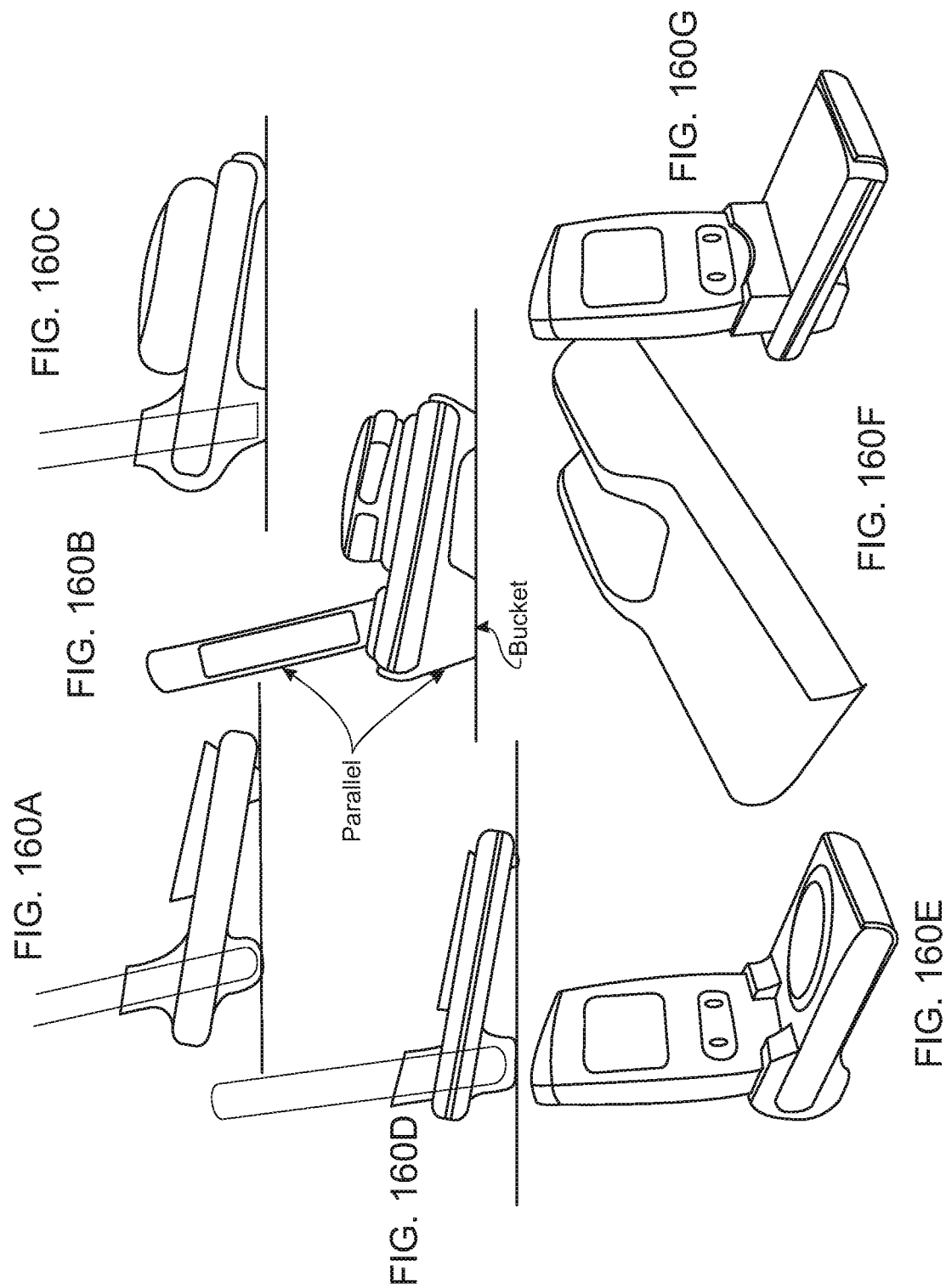

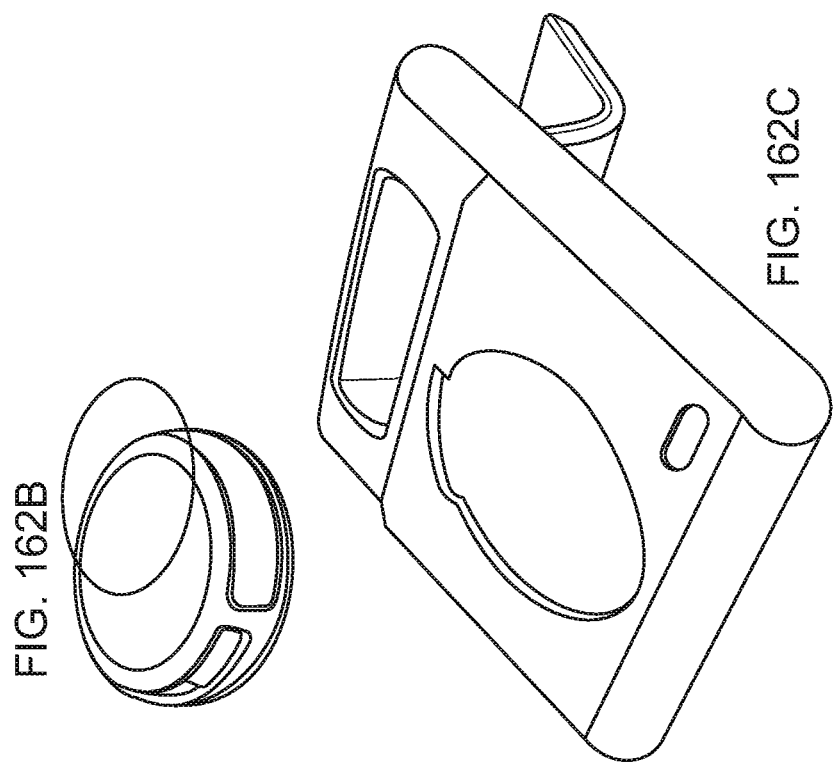
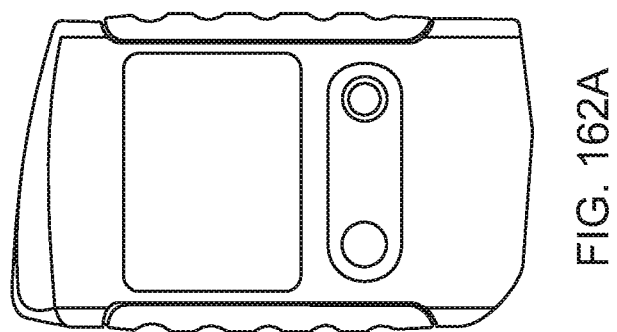
FIG. 162A
FIG. 162B
FIG. 162C

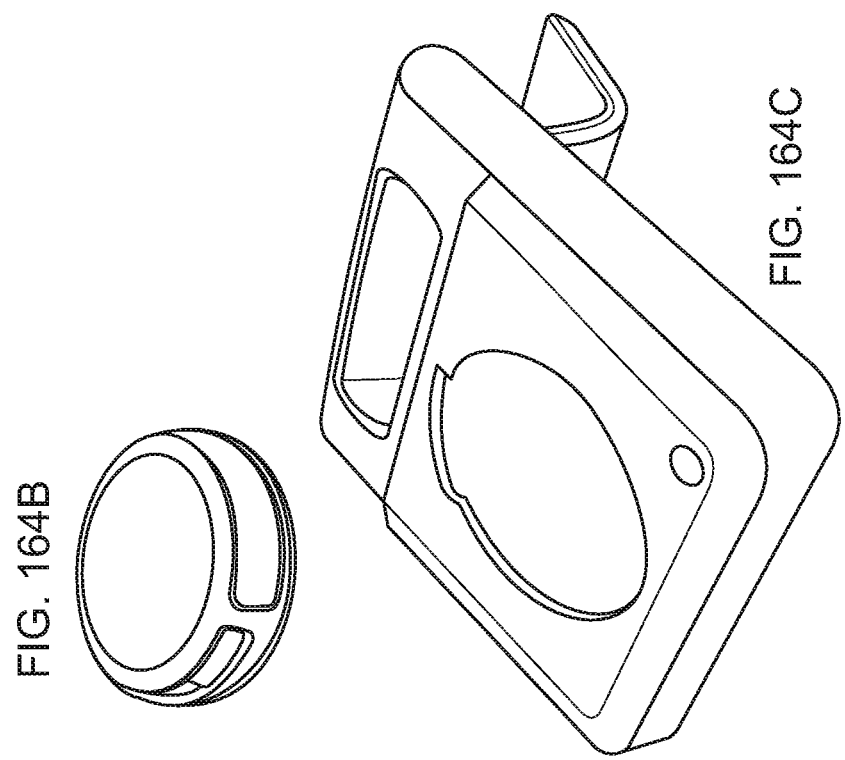
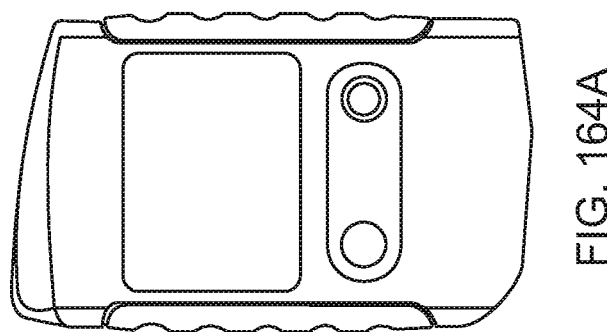

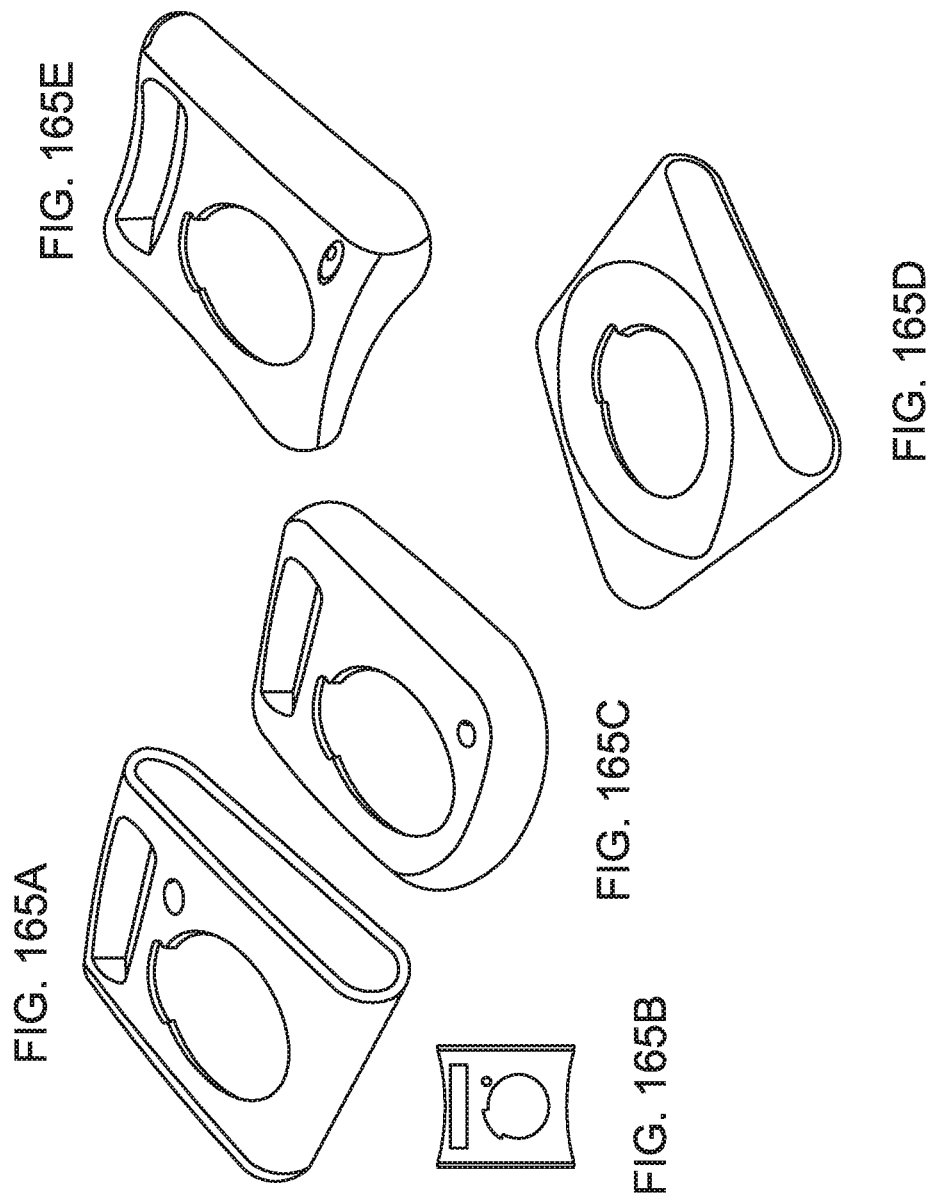

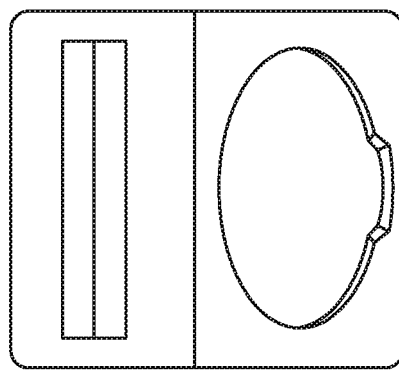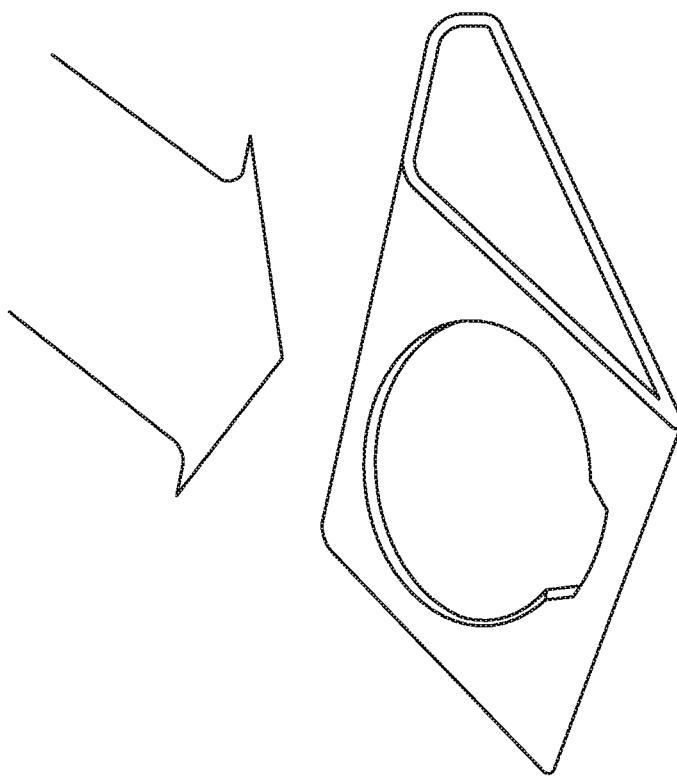

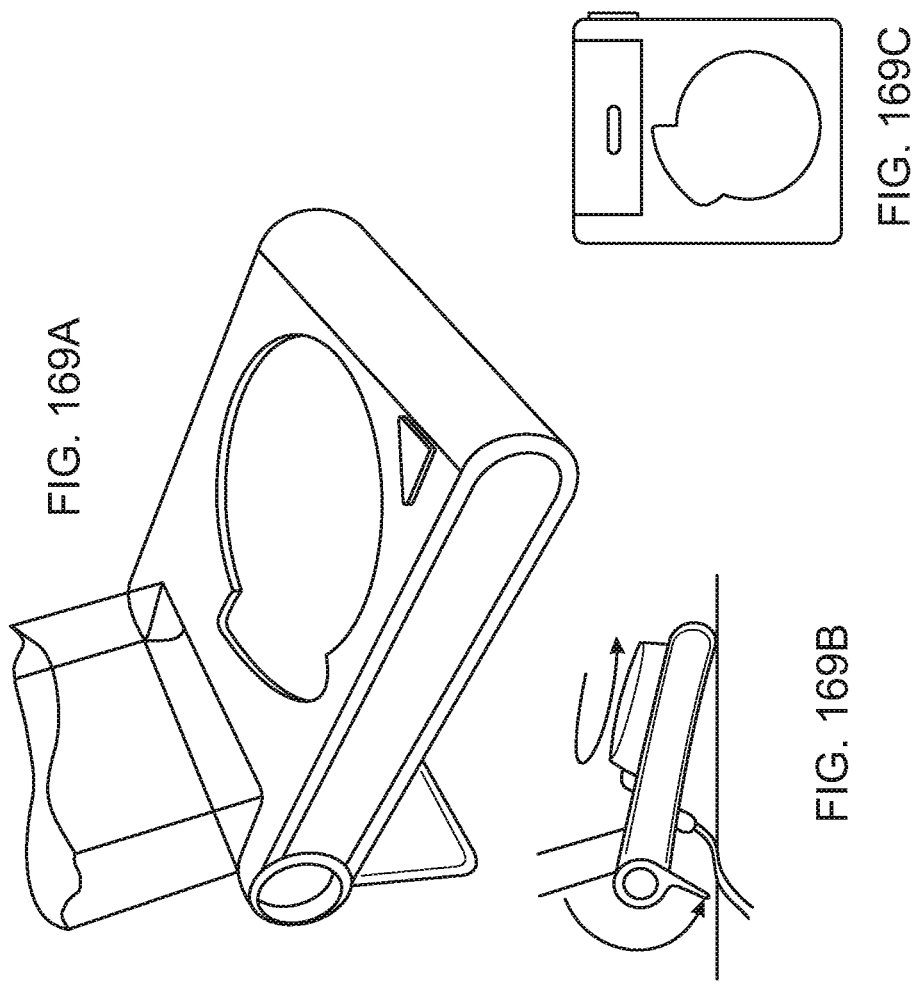

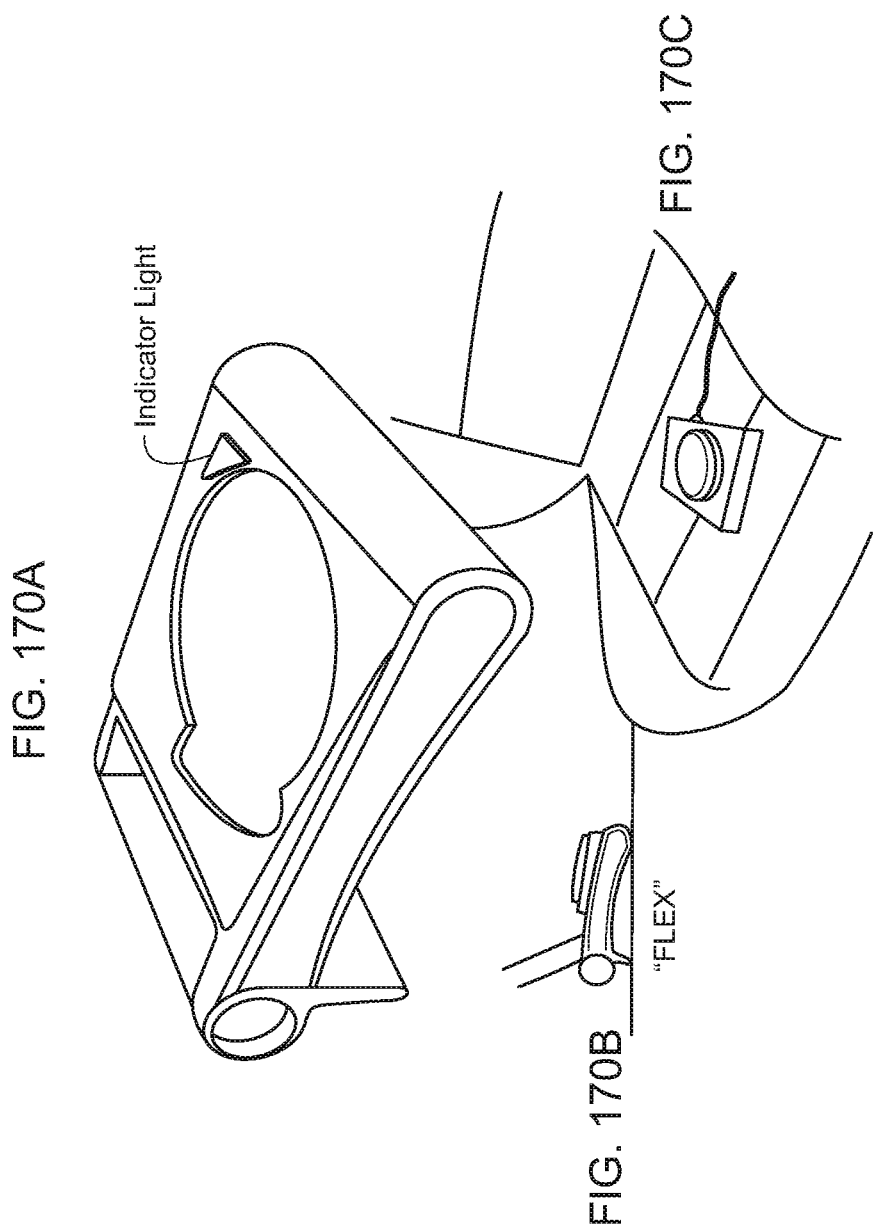

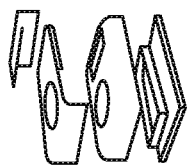
FIG. 172B
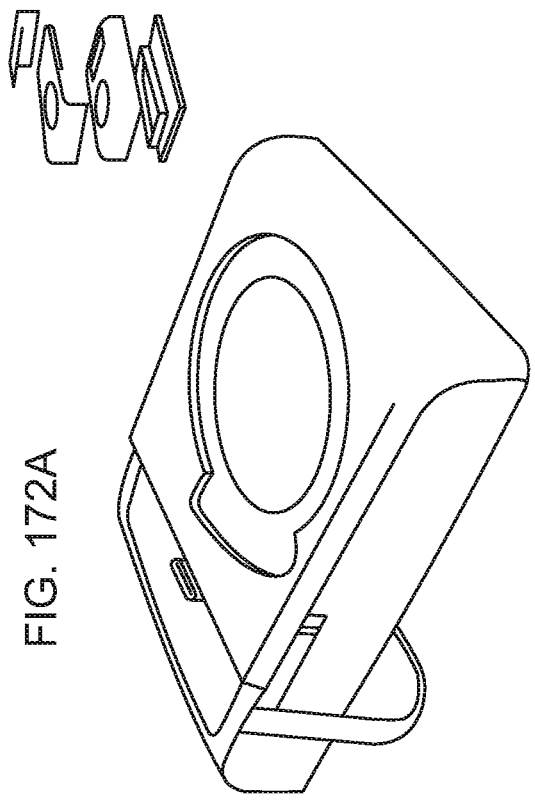
FIG. 172A
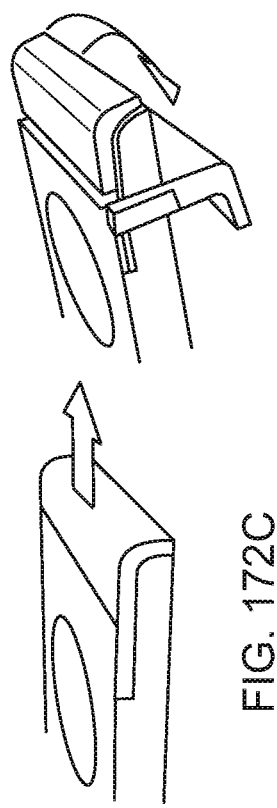
FIG. 172D
FIG. 172C

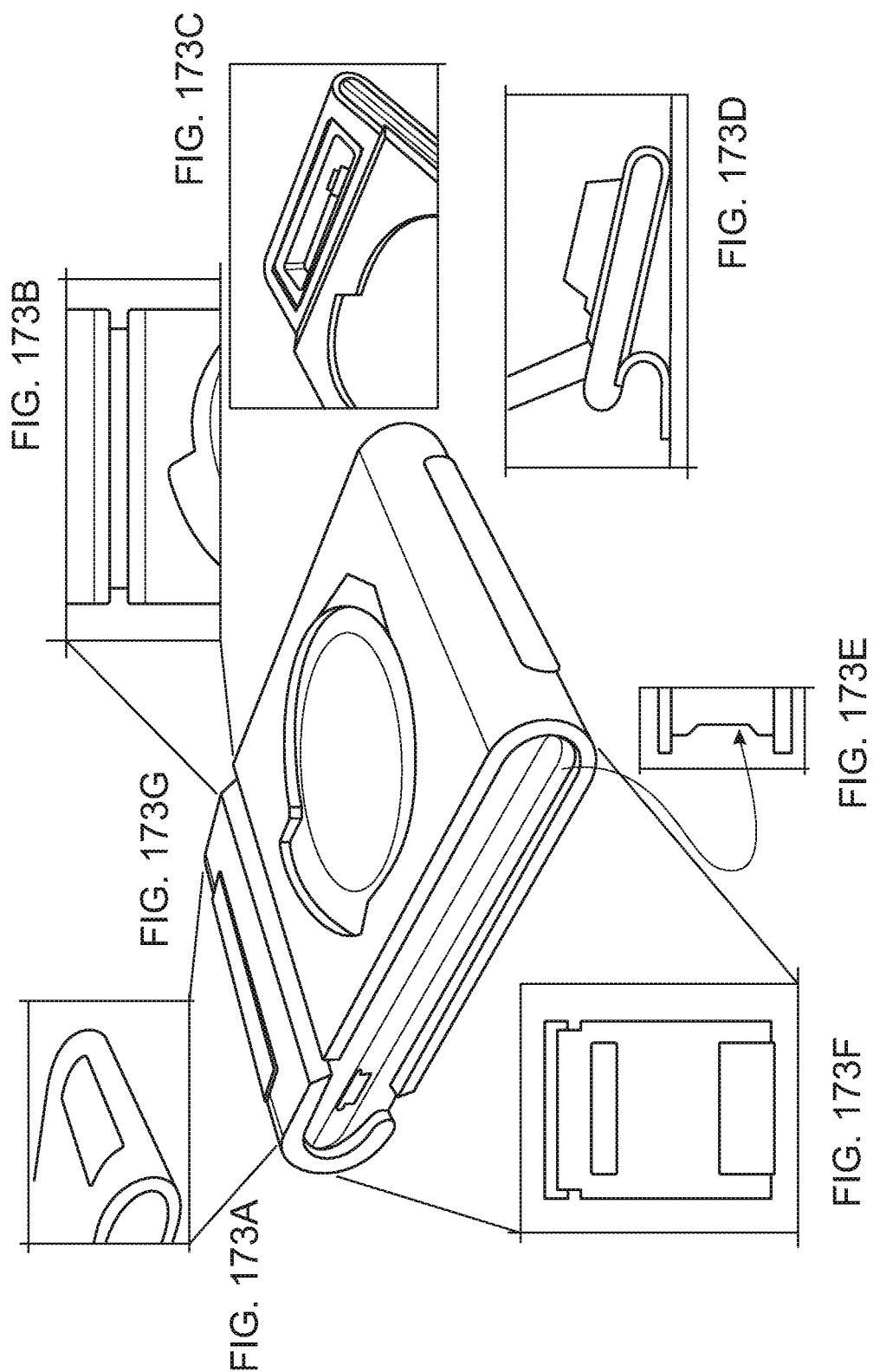

2700

2700

2700

2700

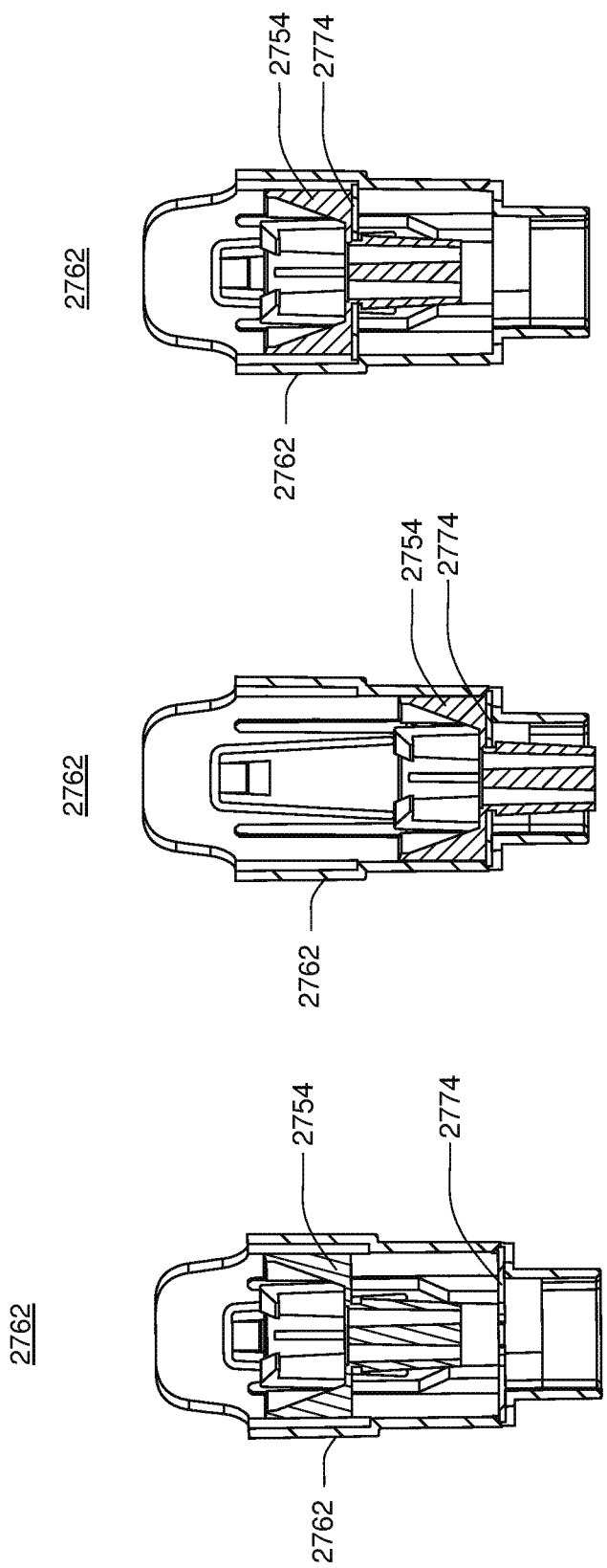

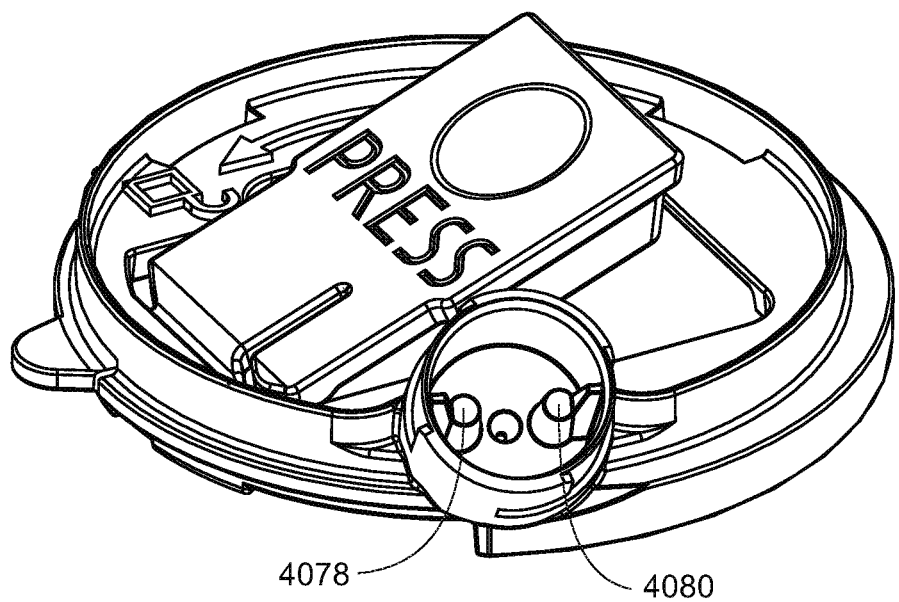
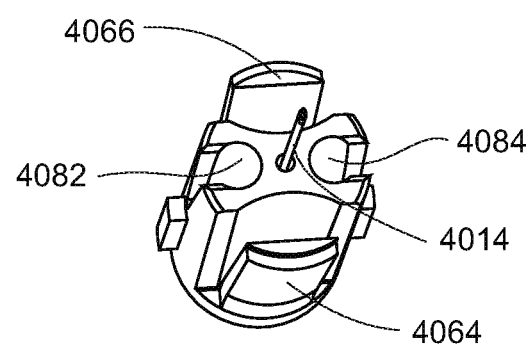
FIG. 218

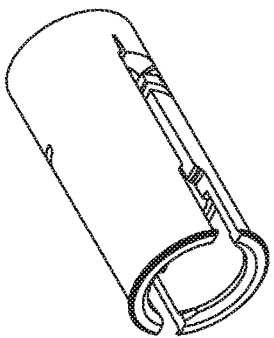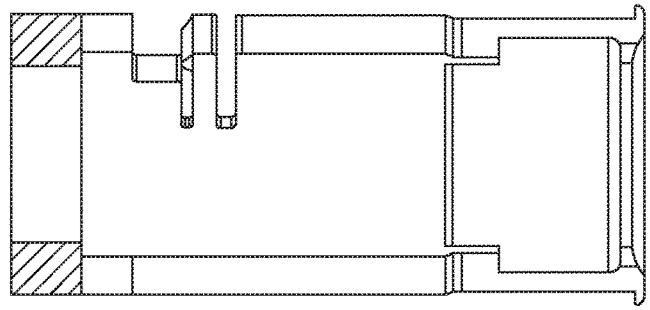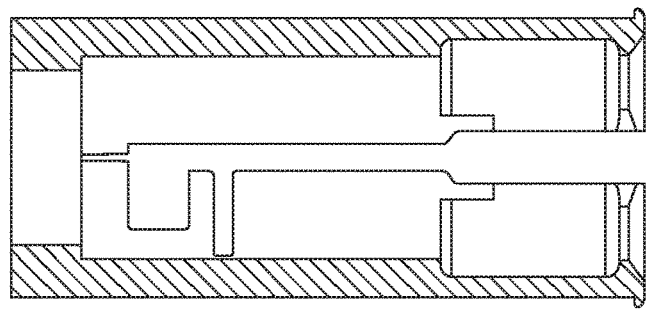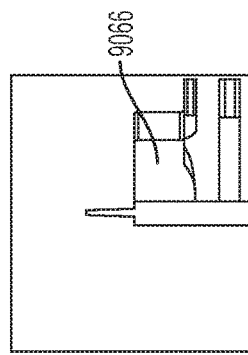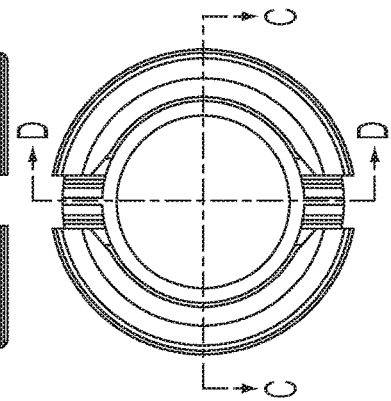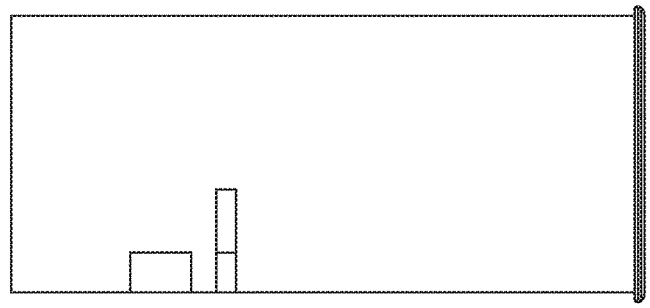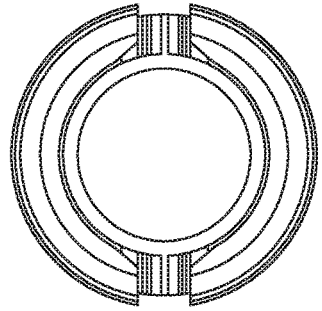
FIG. 244E

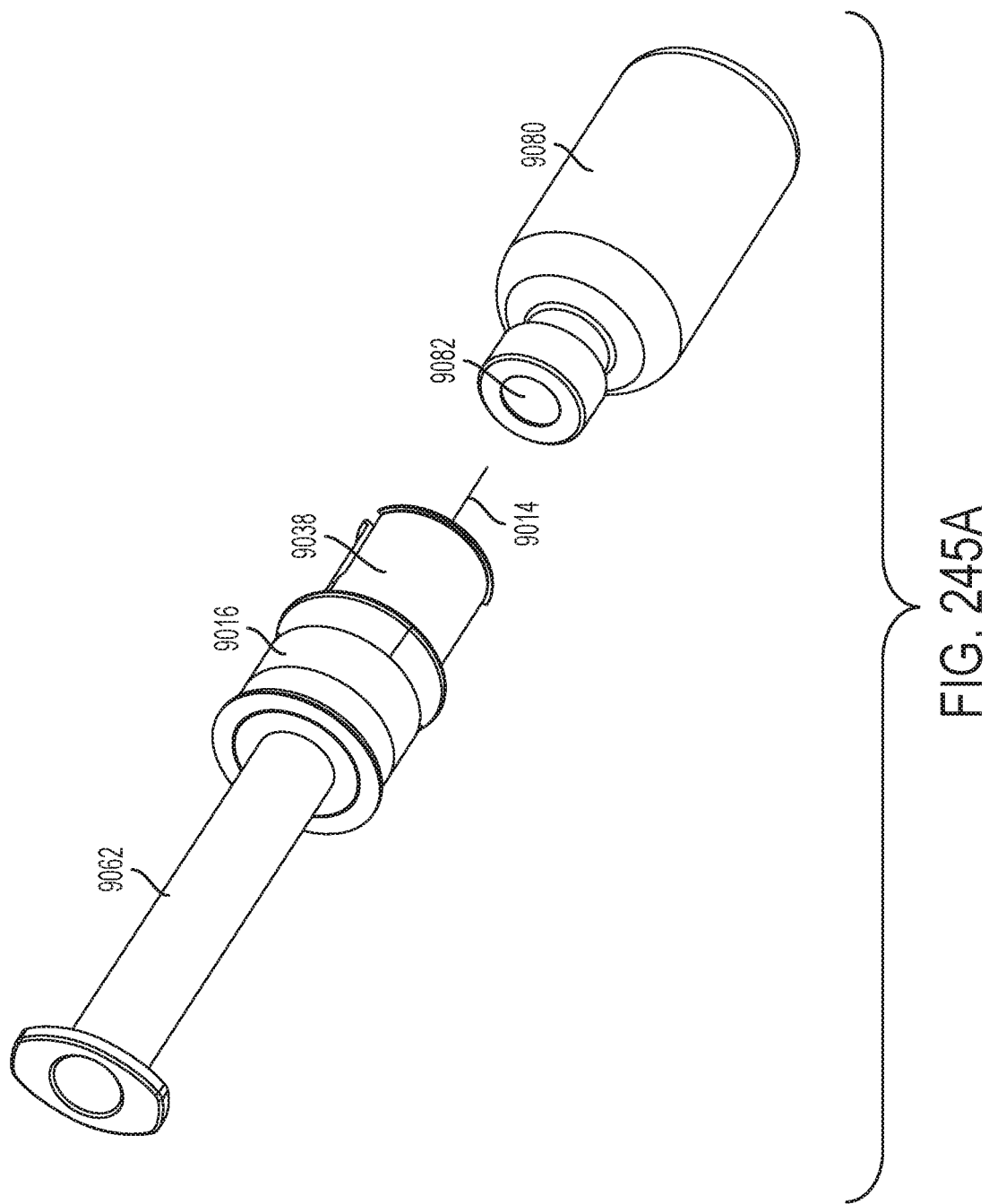

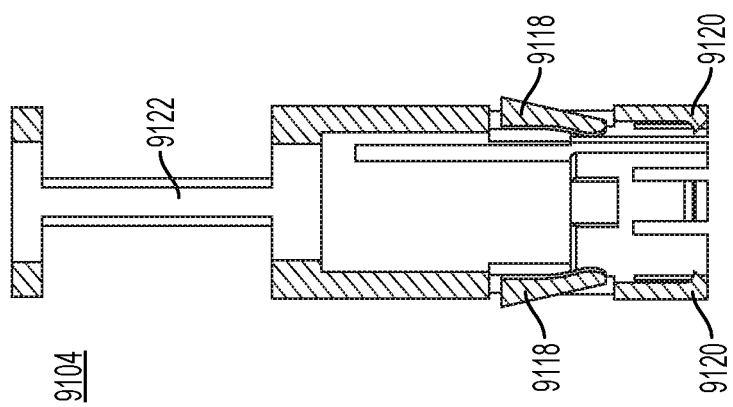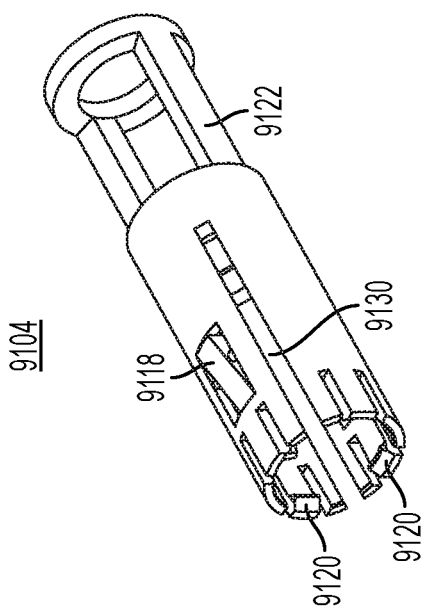

SECTION K-K

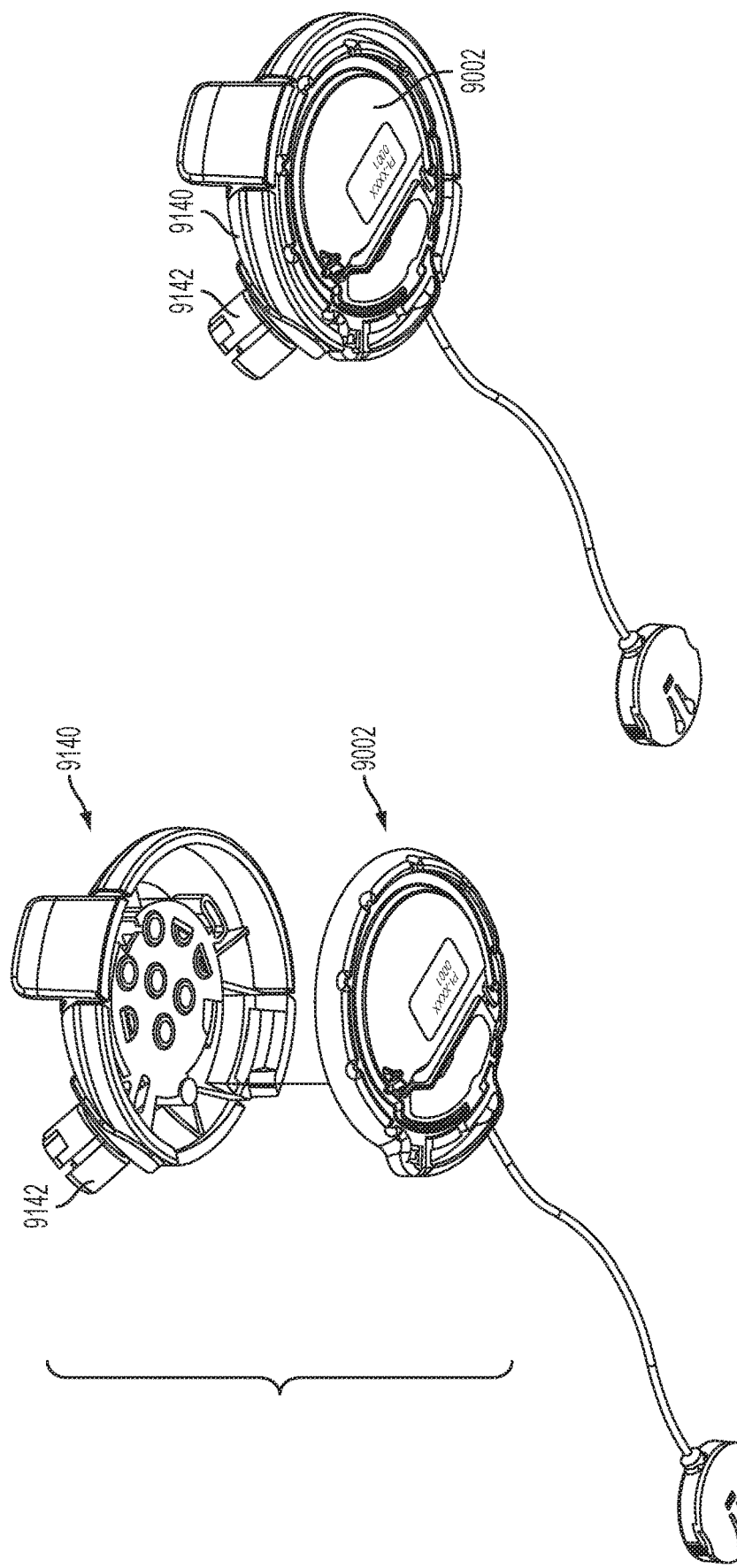

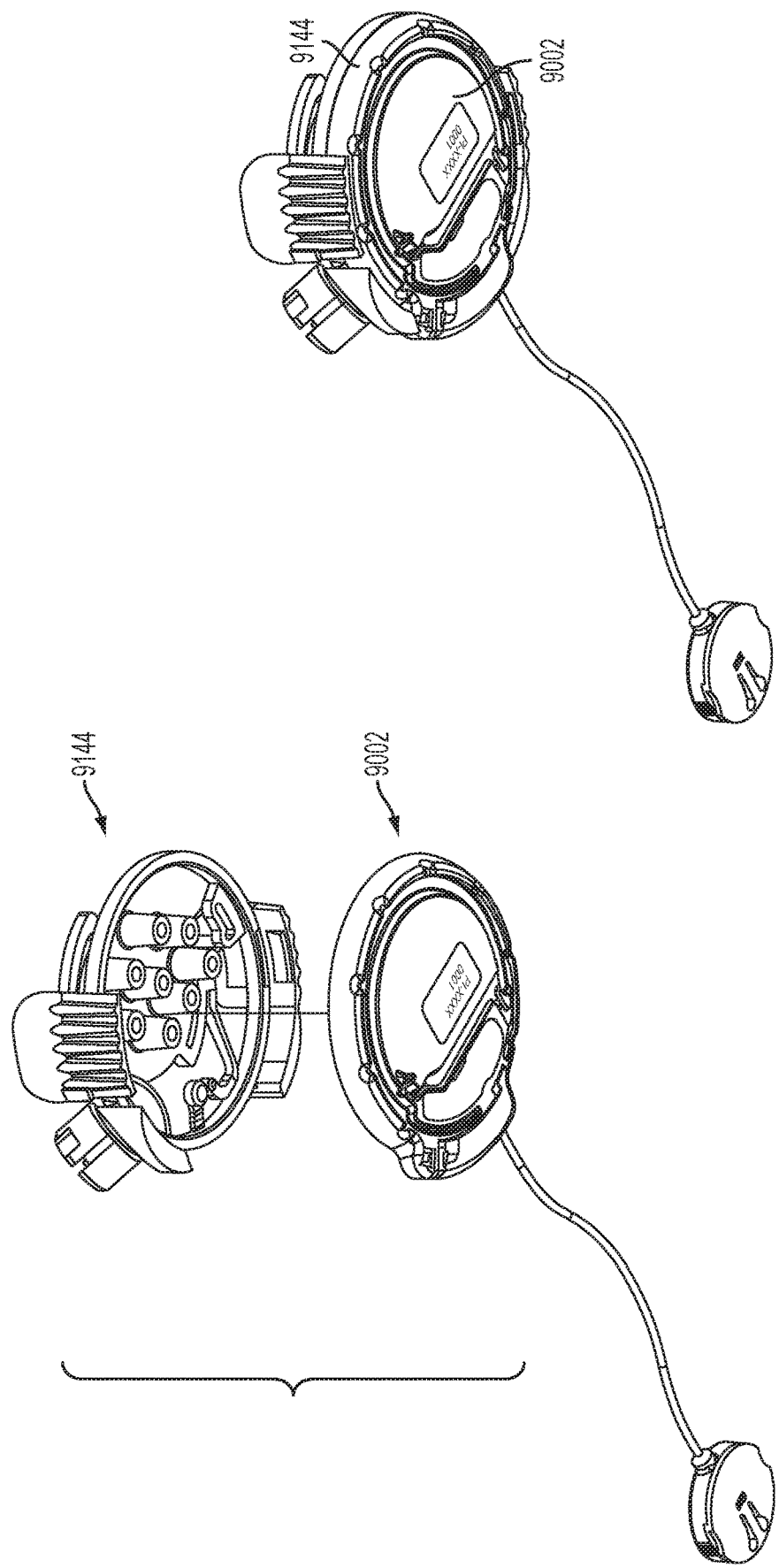

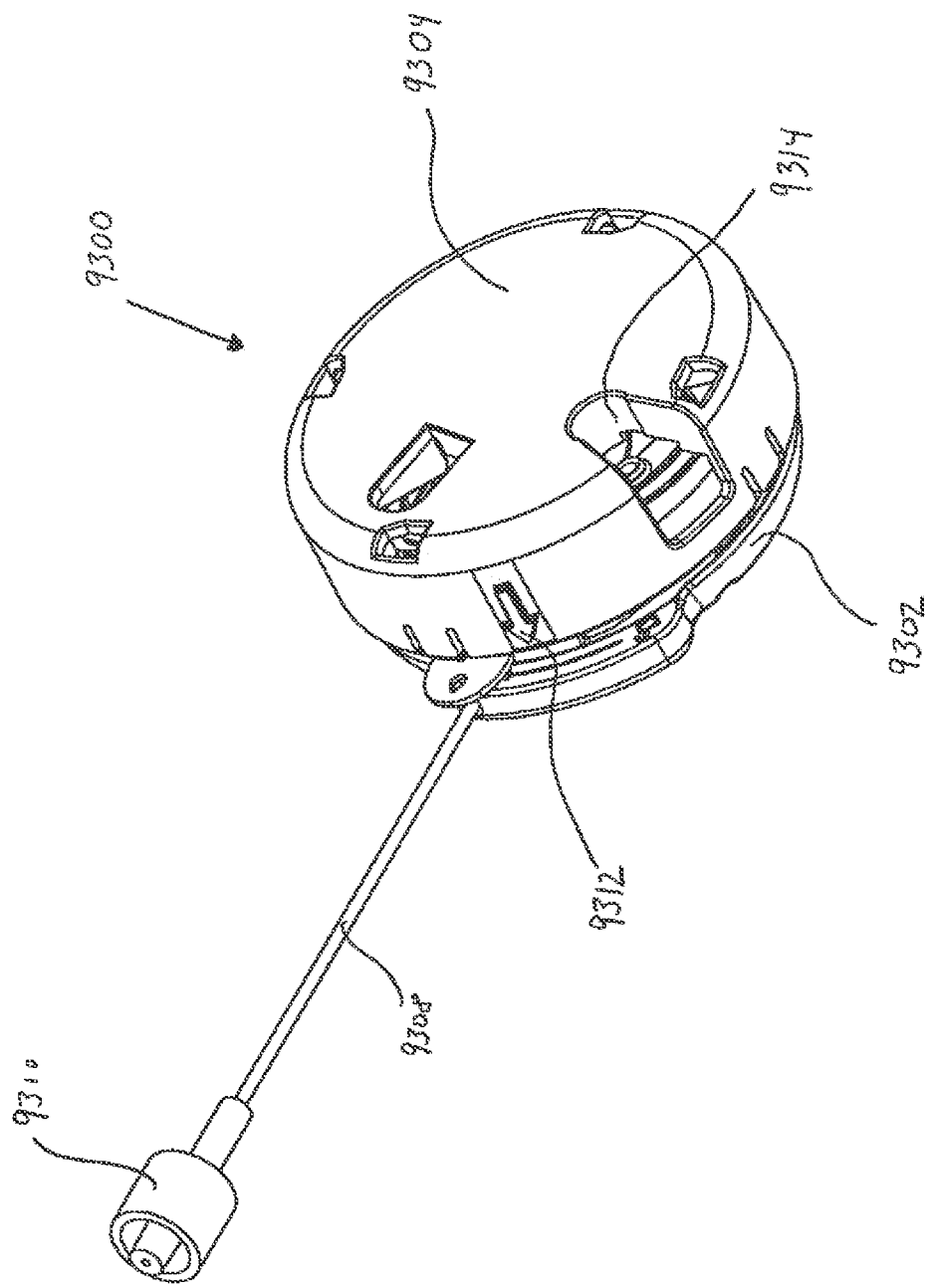

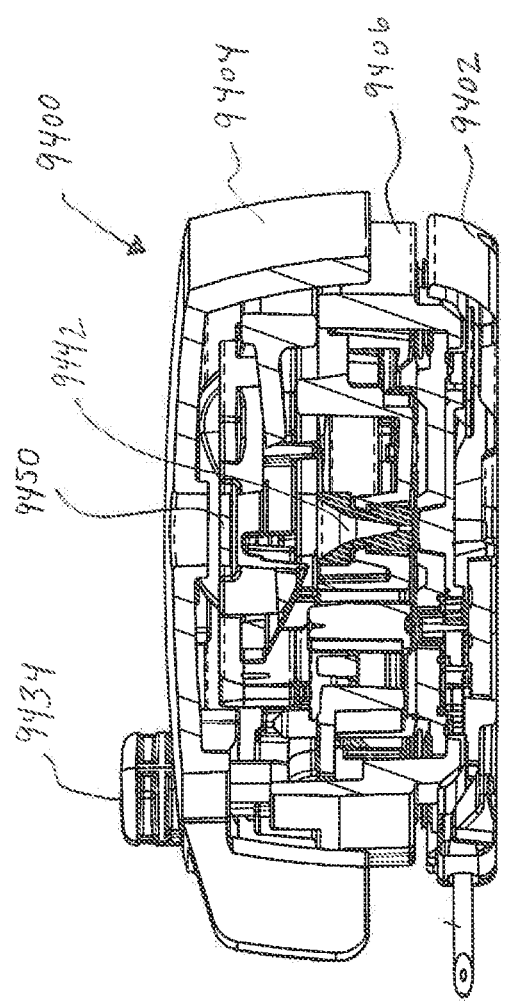

APPARATUS, SYSTEM AND METHOD FOR FLUID DELIVERY

CROSS REFERENCE TO RELATED APPLICATIONS

This application is a Non-Provisional application which claims priority from U.S. Provisional Patent Application Ser. No. 62/662,018, filed Apr. 24, 2018 and entitled Apparatus, System and Method for Fluid Delivery, which is hereby incorporated herein by reference in its entirety.

This application is also a Continuation-in-Part of U.S. patent application Ser. No. 15/961,238 filed Apr. 24, 2018 and entitled Apparatus, System and Method for Fluid Delivery, now U.S. Publication No. US-2018-0237174-A1, issued Aug. 23, 2018, which claims the benefit of U.S. Provisional Application Ser. No. 62/489,154, filed Apr. 24, 2017 and entitled Apparatus, System and Method for Fluid Delivery, each of which is hereby incorporated herein by reference in its entirety.

U.S. patent application Ser. No. 15/961,238 filed Apr. 24, 2018 and entitled Apparatus, System and Method for Fluid Delivery, now U.S. Publication No. US-2018-0237174-A1, issued Aug. 23, 2018 is also a Continuation-in-Part of U.S. patent application Ser. No. 15/483,490 filed Apr. 10, 2017 and entitled Apparatus, System and Method for Fluid Delivery, now U.S. Publication No. US-2017-0210496-A1, issued Jul. 27, 2017, which is a Continuation of U.S. patent application Ser. No. 14/323,672 filed Jul. 3, 2014 and entitled Apparatus, System and Method for Fluid Delivery, now U.S. Pat. No. 9,617,020, issued Apr. 11, 2017, which claims the benefit of U.S. Provisional Application Ser. No. 61/842,553 filed Jul. 3, 2013 and entitled Apparatus, System and Method for Fluid Delivery and U.S. Provisional Application Ser. No. 61/905,533, filed Nov. 18, 2013 and entitled Apparatus, System and Method for Fluid Delivery, each of which is hereby incorporated herein by reference in its entirety.

FIELD OF THE INVENTION

This application relates generally to fluid delivery systems, and more particularly to apparatus, system and method for fluid delivery.

BACKGROUND OF THE INVENTION

Many potentially valuable medicines or compounds, including biologicals, are not orally active due to poor absorption, hepatic metabolism or other pharmacokinetic factors. Additionally, some therapeutic compounds, although they can be orally absorbed, are sometimes required to be administered so often it is difficult for a patient to maintain the desired schedule. In these cases, parenteral delivery is often employed or could be employed.

Effective parenteral routes of drug delivery, as well as other fluids and compounds, such as subcutaneous injection, intramuscular injection, and intravenous (IV) administration include puncture of the skin with a needle or stylet. Insulin is an example of a therapeutic fluid that is self-injected by millions of diabetic patients. Users of parenterally delivered drugs may benefit from a wearable device that would automatically deliver needed drugs/compounds over a period of time.

To this end, there have been efforts to design portable and wearable devices for the controlled release of therapeutics. Such devices are known to have a reservoir such as a cartridge, syringe, or bag, and to be electronically controlled. These devices suffer from a number of drawbacks including the malfunction rate. Reducing the size, weight and cost of these devices is also an ongoing challenge. Additionally, these devices often apply to the skin and pose the challenge of frequent re-location for application.

SUMMARY OF THE INVENTION

In accordance with one aspect of the present invention, a filling aid device for filling a reservoir comprising. The device includes a cover portion comprising a septum window; a slider beam comprising a septum cover; and a first filling aid tab attached to the slider beam, the first filling aid tab in slidable relation to the cover from a first position to a second position, wherein when the filling aid device is in an unlocked position, the septum cover is located below the septum window, wherein when the first filling aid tab is moved from the first position to the second position, the septum cover is moved from below the septum window, and the filling aid device is in the locked position.

Some embodiments of this aspect of the invention include one or more of the following. Wherein the device further comprising a second filling aid tab attached to the cover. Wherein the device further comprising a bottom portion wherein the cover portion slides downward over the bottom portion and wherein when the cover portion slides downward over the bottom portion, the device is in an unlocked configuration. Wherein the cover portion slides downward over the bottom portion and wherein when the cover portion slides downward over the bottom portion, the device is in an unlocked configuration. The device further comprising a first valve beam cover and a first check valve beam, wherein when the cover portion and the bottom portion are in the unlocked position, the first valve beam cover is rotated over the first check valve beam. The device further comprising a first check valve beam, wherein when the cover portion and the bottom portion are in the unlocked position, the first valve beam is actuated. The device further comprising a pump chamber plunger beam and a pump chamber plunger, wherein when the cover portion and the bottom portion are in the unlocked position, the pump chamber plunger beam is rotated over the pump chamber plunger. The device further comprising a pump chamber plunger, wherein when the cover portion and the bottom portion are in the unlocked position, the pump chamber plunger is actuated. The device further comprising a second valve beam cover and a second valve beam, wherein when the cover portion and the bottom portion are in the unlocked position, the second valve beam cover is rotated over the second valve beam. The device further comprising a second valve beam, wherein when the cover portion and the bottom portion are in the unlocked position, the second valve beam is actuated. Wherein when the cover portion and the bottom portion are placed in a priming configuration, the device primes a disposable housing assembly. Wherein when the cover portion and the bottom portion are in a priming configuration, a first valve and a second valve are in their opened positions. Wherein when the cover portion and the bottom portion are in the priming position, the first valve beam is unactuated. Wherein when the cover portion and the bottom portion are in the priming position, the second valve beam is unactuated.

In accordance with one aspect of the present invention, a system for filling a reservoir is disclosed. The system includes a disposable housing assembly comprising the reservoir and a septum; and a filling aid comprising a cover portion comprising a septum window; a slider beam comprising a septum cover; and a first filling aid tab attached to the slider beam, the first filling aid tab in slidable relation to the cover from a first position to a second position, wherein when the filling aid device is in an unlocked position, the septum cover is located below the septum window, wherein when the first filling aid tab is moved from the first position to the second position, the septum cover is moved from below the septum window, and the filling aid device is in the locked position.

Some embodiments of this aspect of the invention include one or more of the following. Wherein the filling aid further comprising a needle guide accessible through the septum window. Wherein the filling aid further comprising a second filling aid tab attached to the cover. Wherein the filling aid comprising a bottom portion wherein the cover portion slides downward over the bottom portion and wherein when the cover portion slides downward over the bottom portion, the device is in an unlocked configuration. Wherein the cover portion slides downward over the bottom portion and wherein when the cover portion slides downward over the bottom portion, the device is in an unlocked configuration. The device further comprising a first valve beam cover and a first check valve beam, wherein when the cover portion and the bottom portion are in the unlocked position, the first valve beam cover is rotated over the first check valve beam. The device further comprising a first check valve beam, wherein when the cover portion and the bottom portion are in the unlocked position, the first valve beam is actuated. The device further comprising a pump chamber plunger beam and a pump chamber plunger, wherein when the cover portion and the bottom portion are in the unlocked position, the pump chamber plunger beam is rotated over the pump chamber plunger. The device further comprising a pump chamber plunger, wherein when the cover portion and the bottom portion are in the unlocked position, the pump chamber plunger is actuated. The device further comprising a second valve beam cover and a second valve beam, wherein when the cover portion and the bottom portion are in the unlocked position, the second valve beam cover is rotated over the second valve beam. The device further comprising a second valve beam, wherein when the cover portion and the bottom portion are in the unlocked position, the second valve beam is actuated. Wherein when the cover portion and the bottom portion are placed in a priming configuration, the device primes a disposable housing assembly. Wherein when the cover portion and the bottom portion are in a priming configuration, a first valve and a second valve are in their opened positions. Wherein when the cover portion and the bottom portion are in the priming position, the first valve beam is unactuated. Wherein when the cover portion and the bottom portion are in the priming position, the second valve beam is unactuated.

The details of one or more embodiments are set forth in the accompanying drawings and the description below. Other features and advantages will become apparent from the description, the drawings, and the claims.

BRIEF DESCRIPTION OF THE DRAWINGS

FIGS. 10A-10E depict a plurality of hook-and-loop fastener configurations;

FIGS. 12A-12F is a plurality of display screens rendered by the remote control assembly of FIG. 11A;

FIG. 13 is an isometric view of an alternative embodiment of the infusion pump assembly of FIG. 1;

FIG. 24 is a cutaway isometric view of a pump assembly of the infusion pump assembly of FIG. 16;

FIGS. 25A-25D are other isometric views of the pump assembly of FIG. 24;

FIGS. 46A-46E depict various views of the plunger pump and reservoir valve of the mechanical control assembly of the reusable housing assembly of FIGS. 35A-35C;

FIG. 49A is a plan view of the disposable housing assembly of FIG. 48;

FIG. 49B is a sectional view of the disposable housing assembly of FIG. 49A taken along line B-B;

FIG. 49C is a sectional view of the disposable housing assembly of FIG. 49A taken along line C-C;

FIGS. 68-74 are various views of the fill adapter of FIG. 66;

FIGS. 81-89B depict various embodiments of battery chargers/docking stations;

FIGS. 91A-91I are various views of a volume sensor assembly included within the infusion pump assembly of FIG. 1;

FIGS. 92A-92I are various views of a volume sensor assembly included within the infusion pump assembly of FIG. 1;

FIGS. 93A-93I are various views of a volume sensor assembly included within the infusion pump assembly of FIG. 1;

FIG. 114A-114B is an alternate implementation of an SMA controller;

FIG. 125A-125G depicts a hierarchal state machine;

FIG. 126A-126M depicts a hierarchal state machine;

FIGS. 146-148A Part 9 are schematics of an exemplary electrical system that may be utilized in connection with the charger of FIGS. 134-145;

FIGS. 149A-173G show various additional embodiments of a charger, as well as various features of such additional embodiments;

FIGS. 174-193 depict various views and aspects of an embodiment of a fill adapter;

FIGS. 194-198 depict various views and aspects of another embodiment of a fill adapter;

FIGS. 199A-199H depicts a sequential cross sectional view of one embodiment of the fill adapter in operation;

FIG. 200 is an exploded view of one embodiment of a fill adapter;

FIG. 201 is an isometric view of a fill adapter base according to one embodiment;

FIG. 202A-202B are isometric views of the vial adapter according to one embodiment;

FIGS. 203A-203K depicts a sequential cross sectional view of one embodiment of the fill adapter in operation;

FIGS. 204A-204C is a cross section view of a sequence of the fill adapter in operation, without a vial, according to one embodiment;

FIG. 205 shows one embodiment of a system for verification of volume and pumping;

FIG. 206A is an isometric top view of one embodiment of the fill adapter;

Figure 206A:
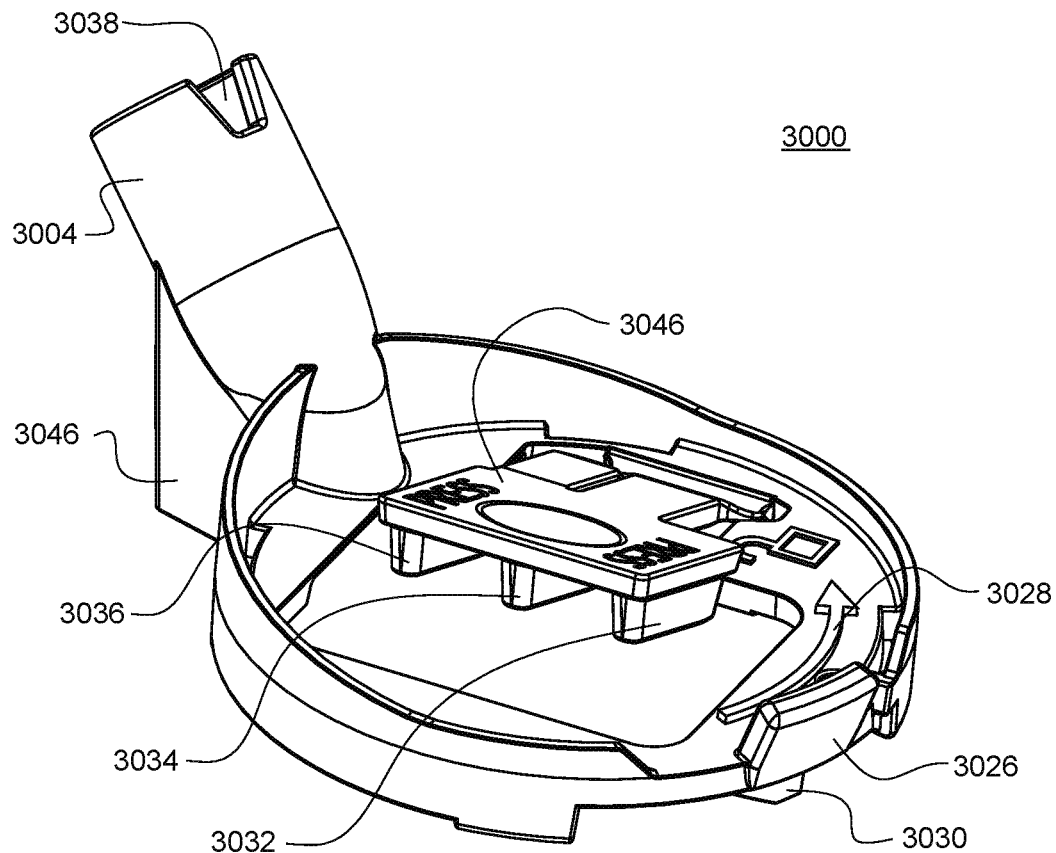
Figure 206B:
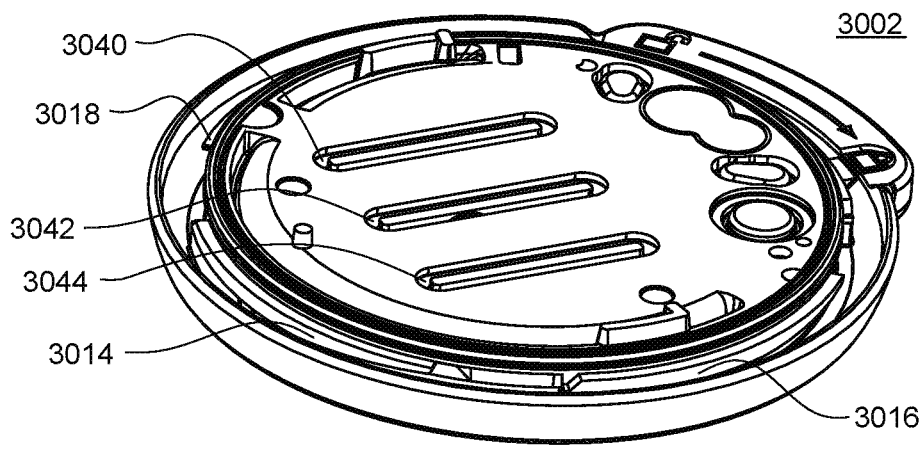
Figure 207A:
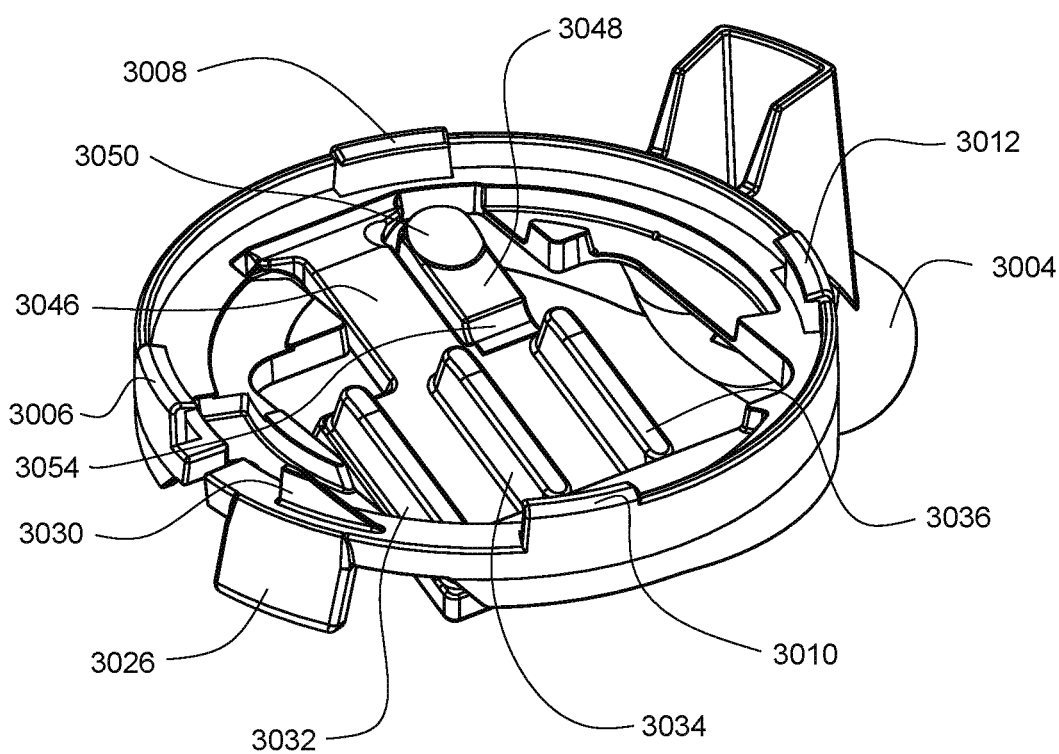
Figure 207B:
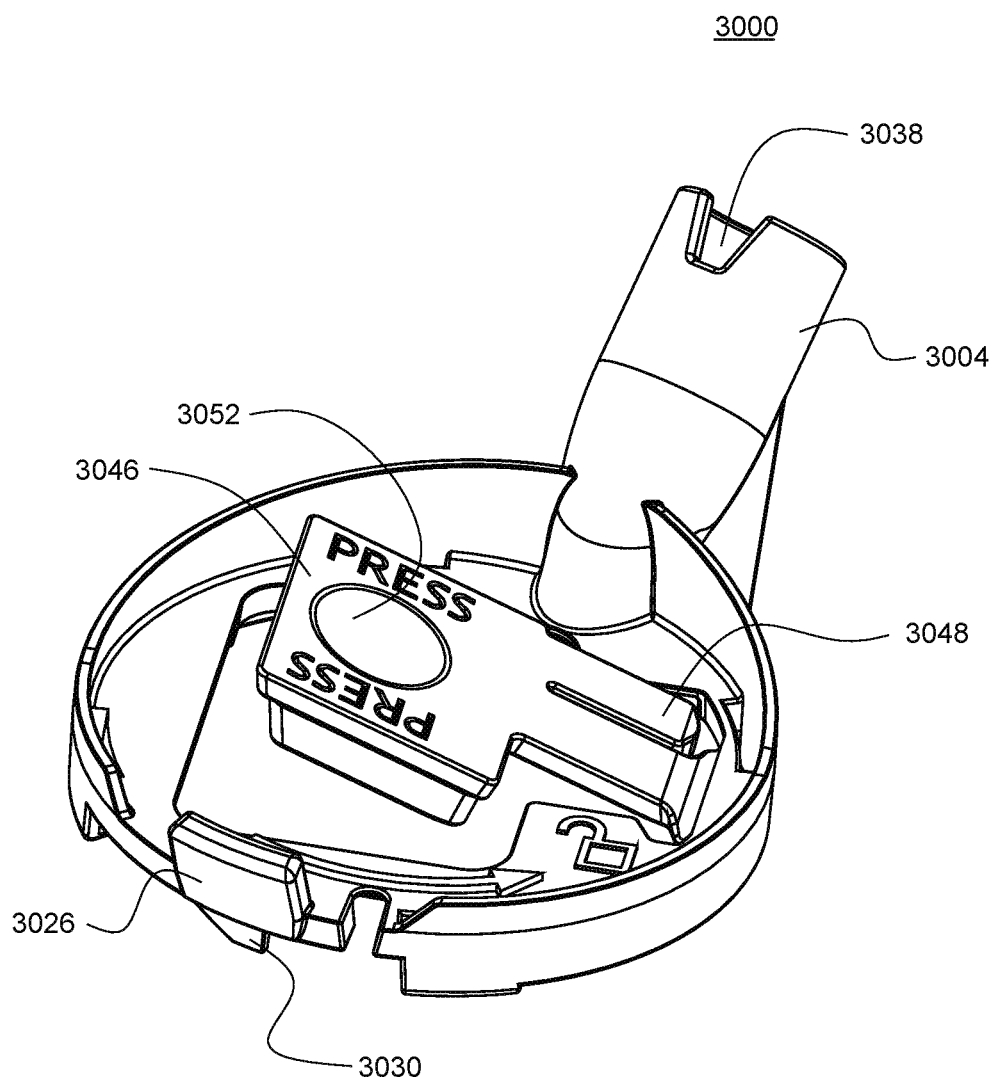
Figure 208B:
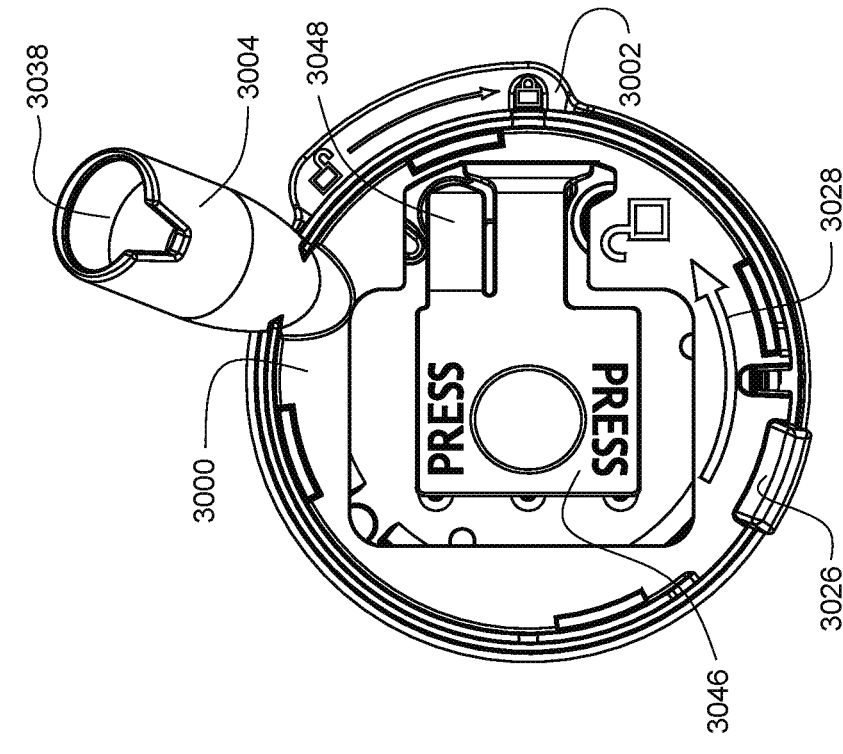
Figure 208A:
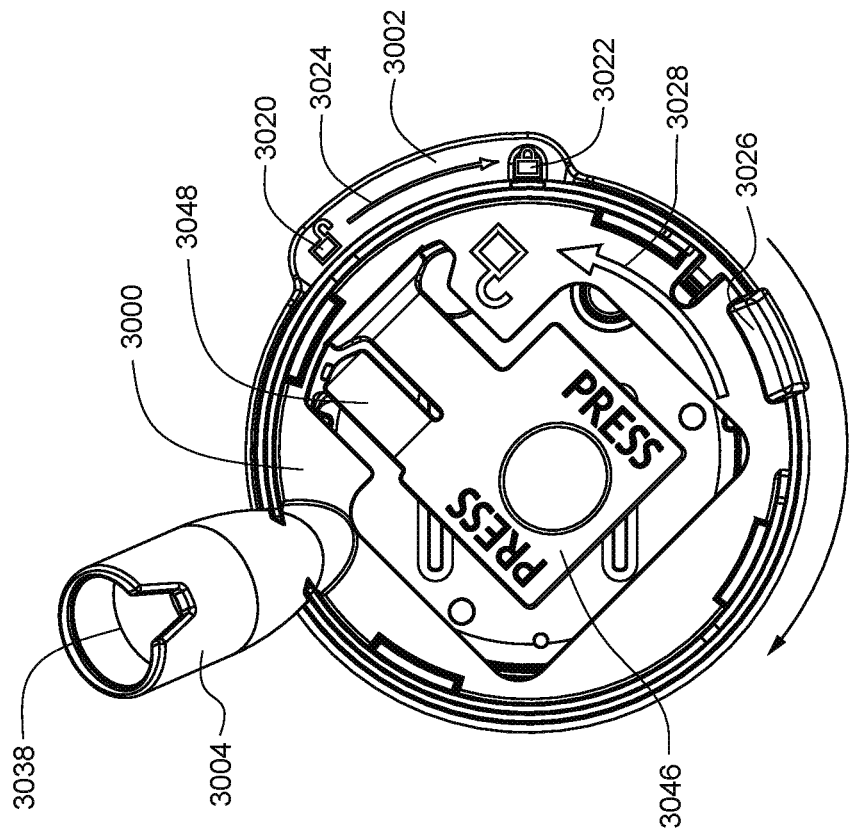
Figure 209A:
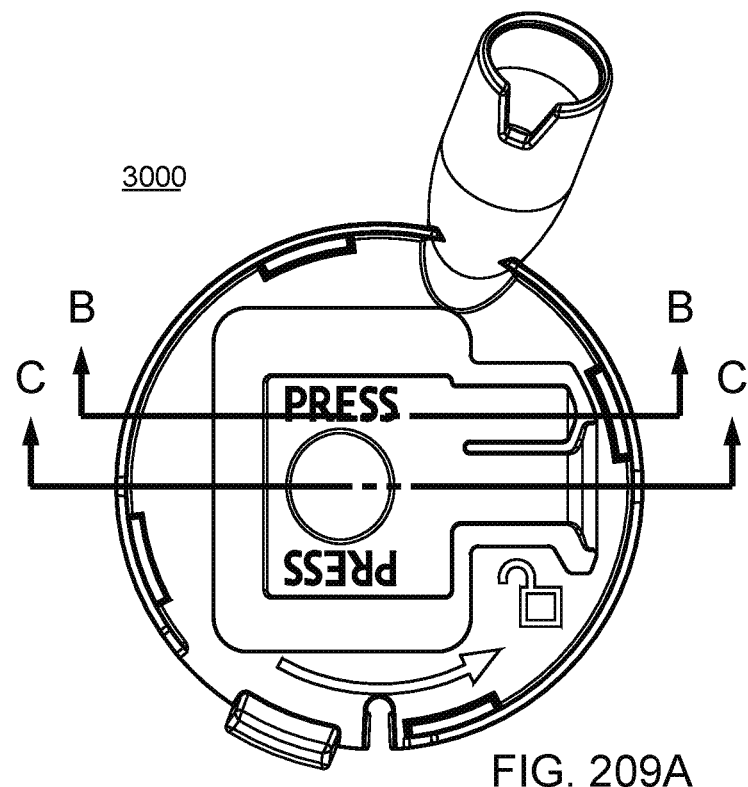
Figure 209B:
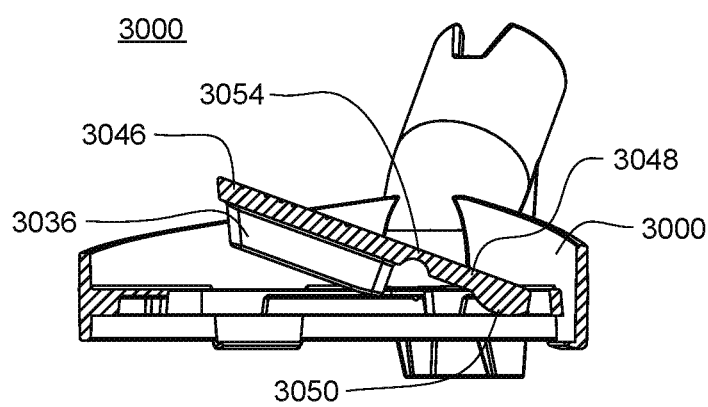
Figure 209C:
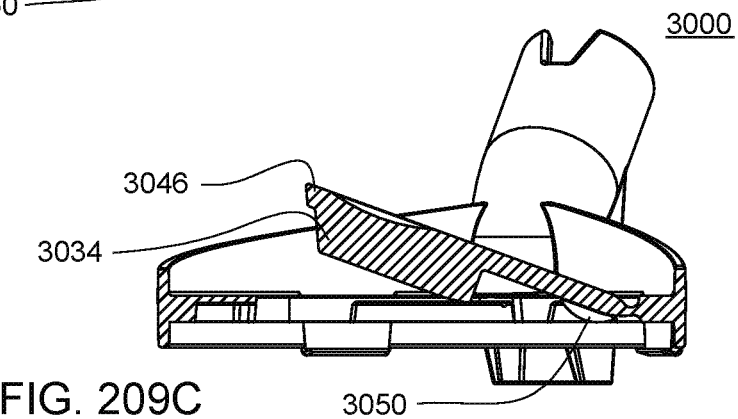
Figure 210A:
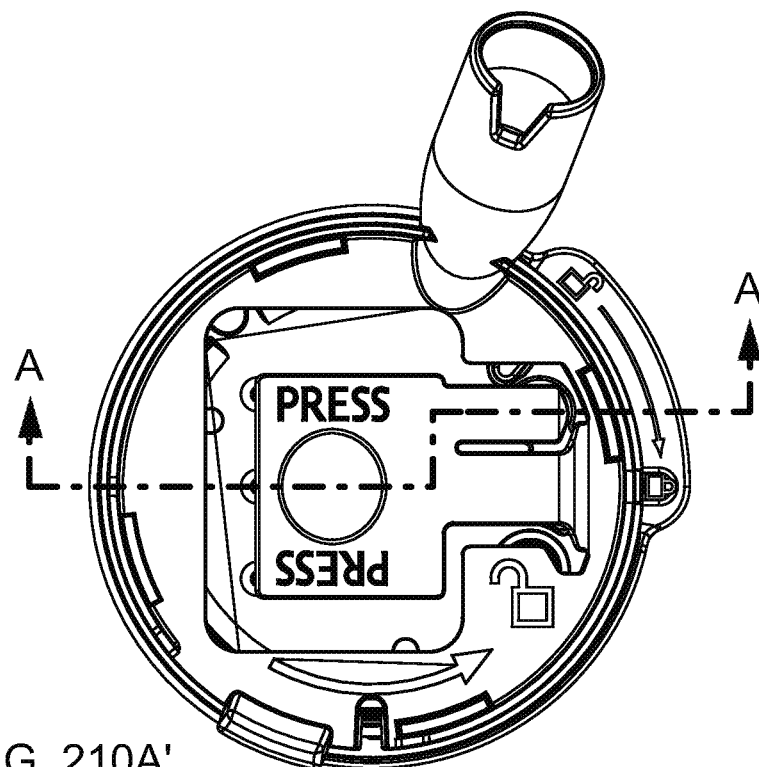
Figure 210A:
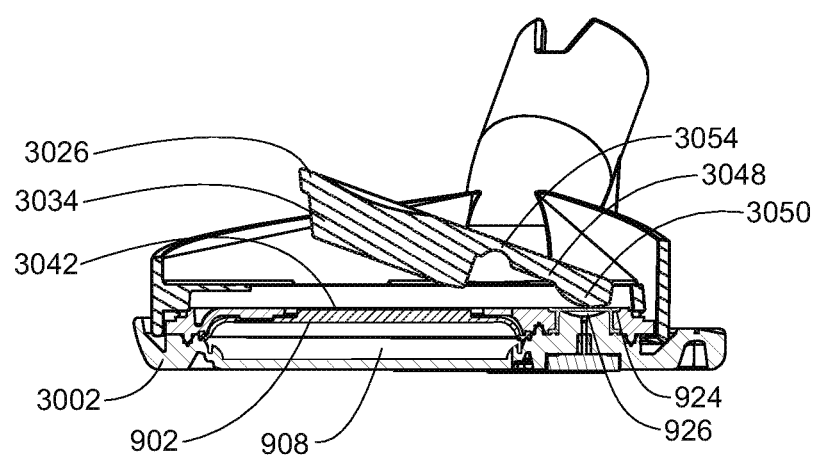
Figure 210B:
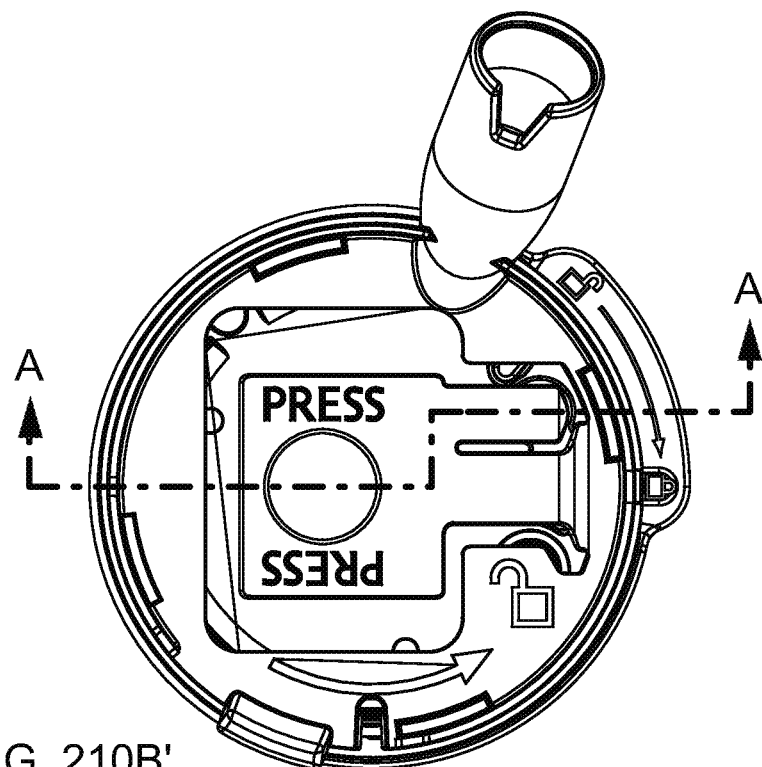
Figure 210B:
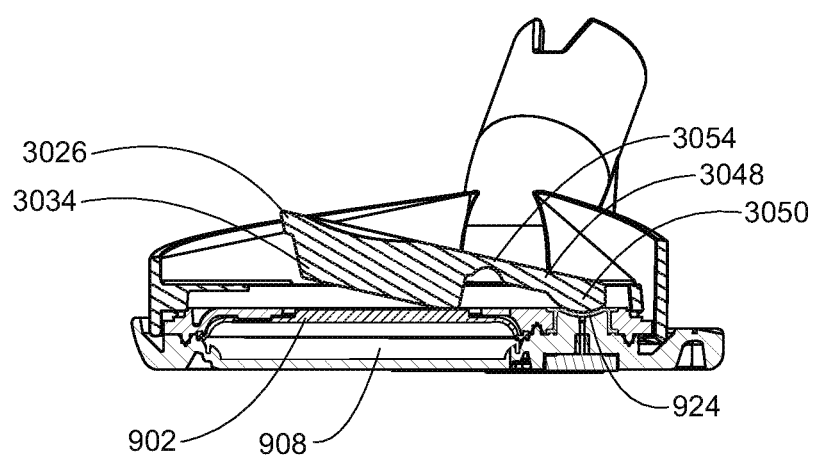
Figure 210C:
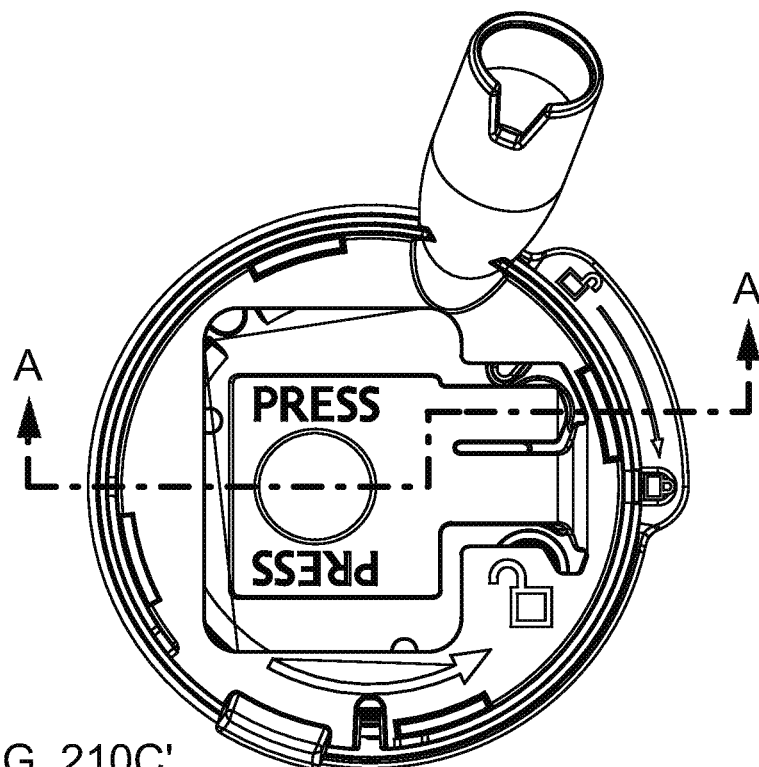
Figure 210C:
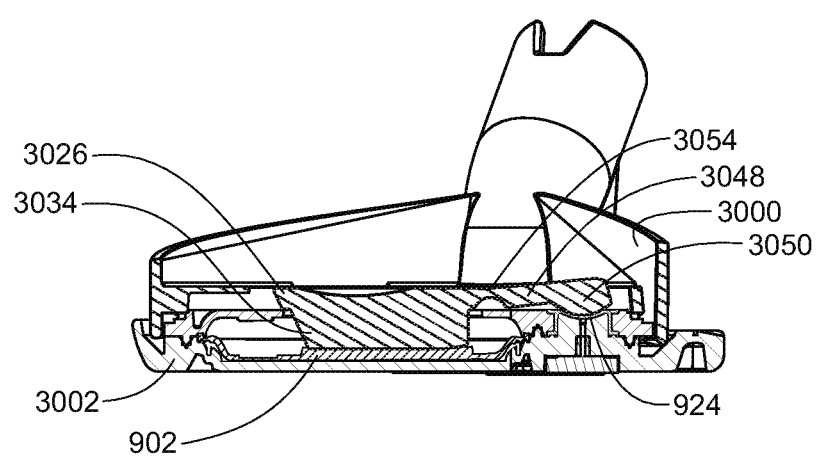
Figure 211A:
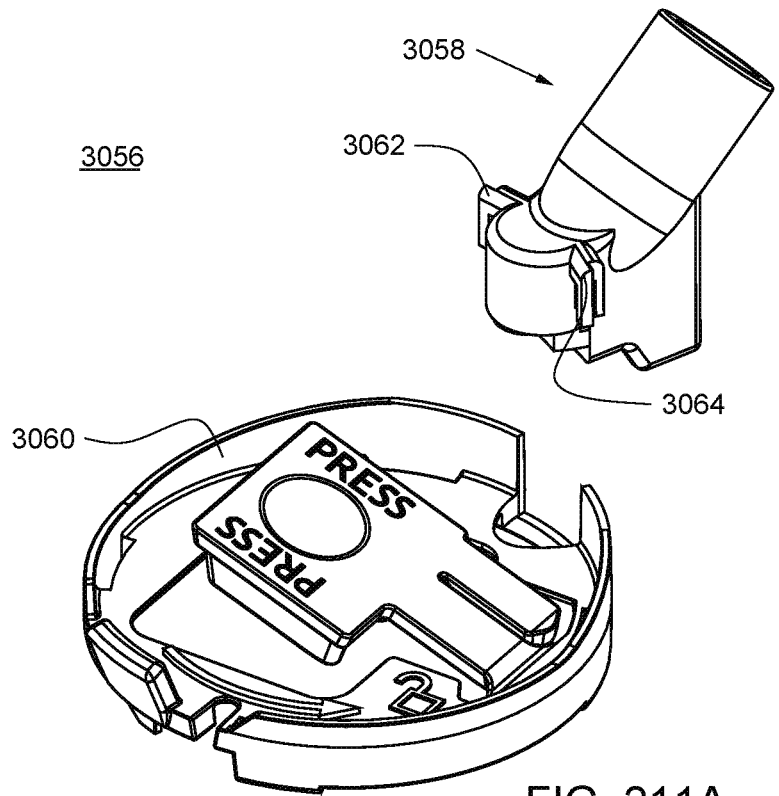
Figure 211B:
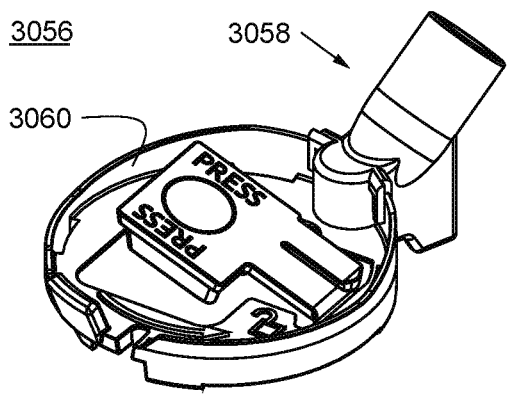
Figure 211C:
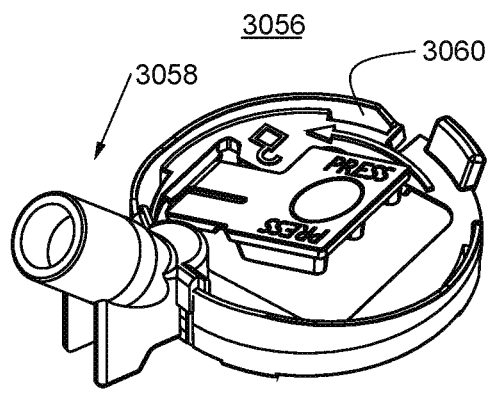
Figure 212A:
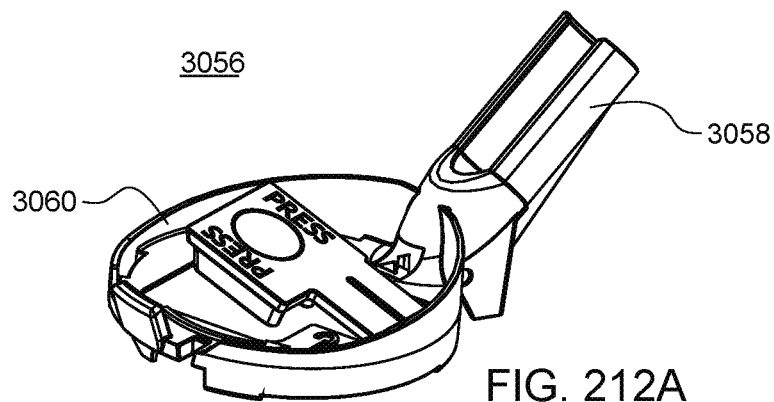
Figure 212B:
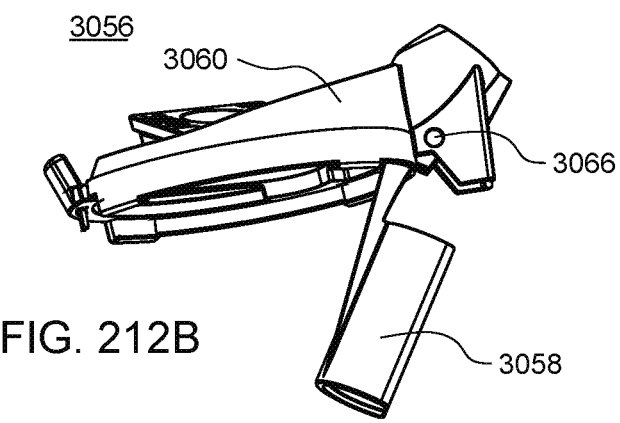
Figure 212C:
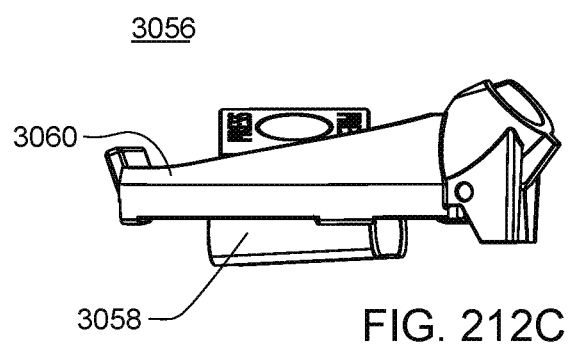
Figure 213A:
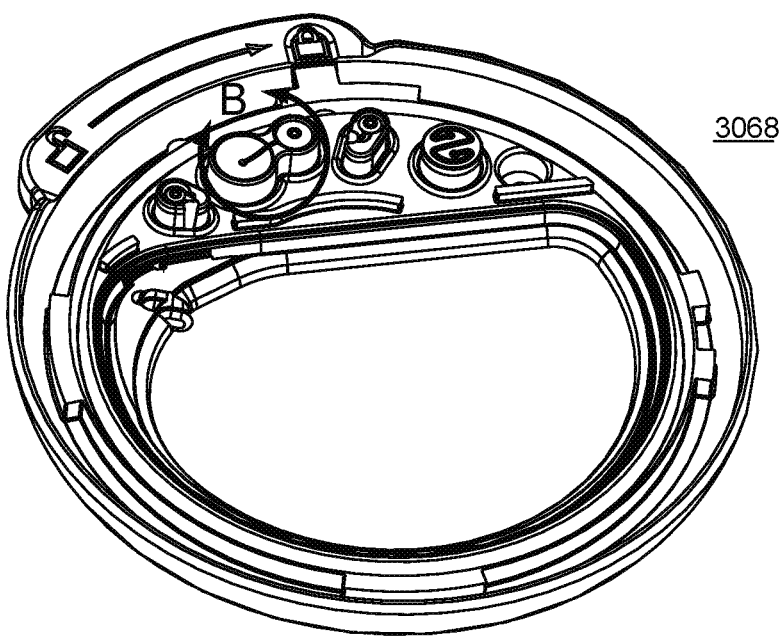
Figure 213B:
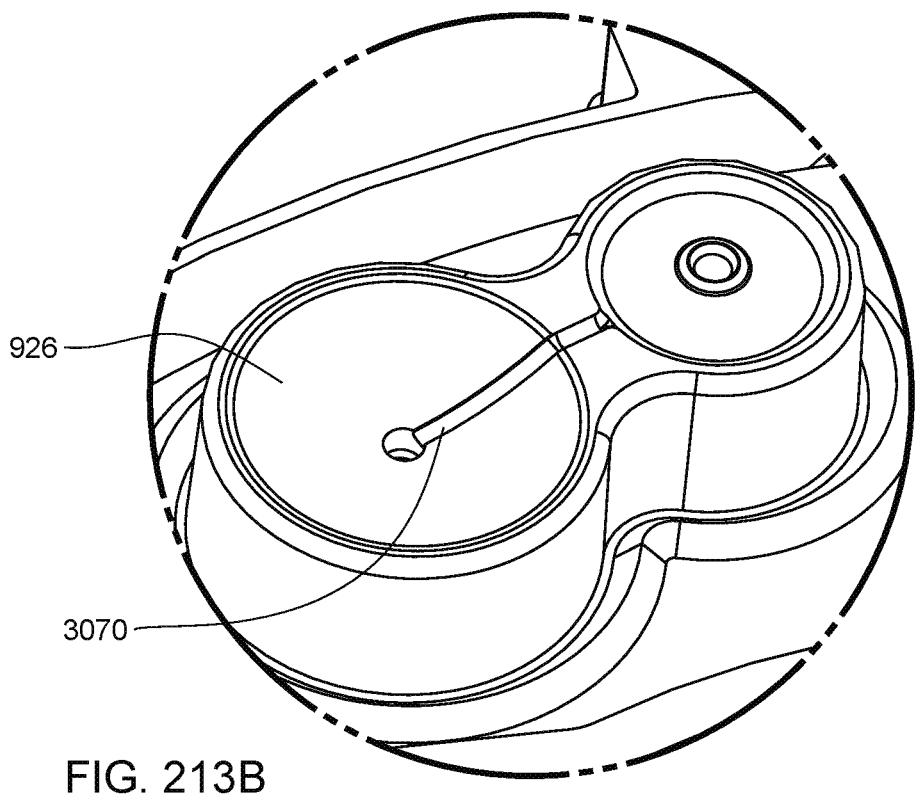
Figure 214:
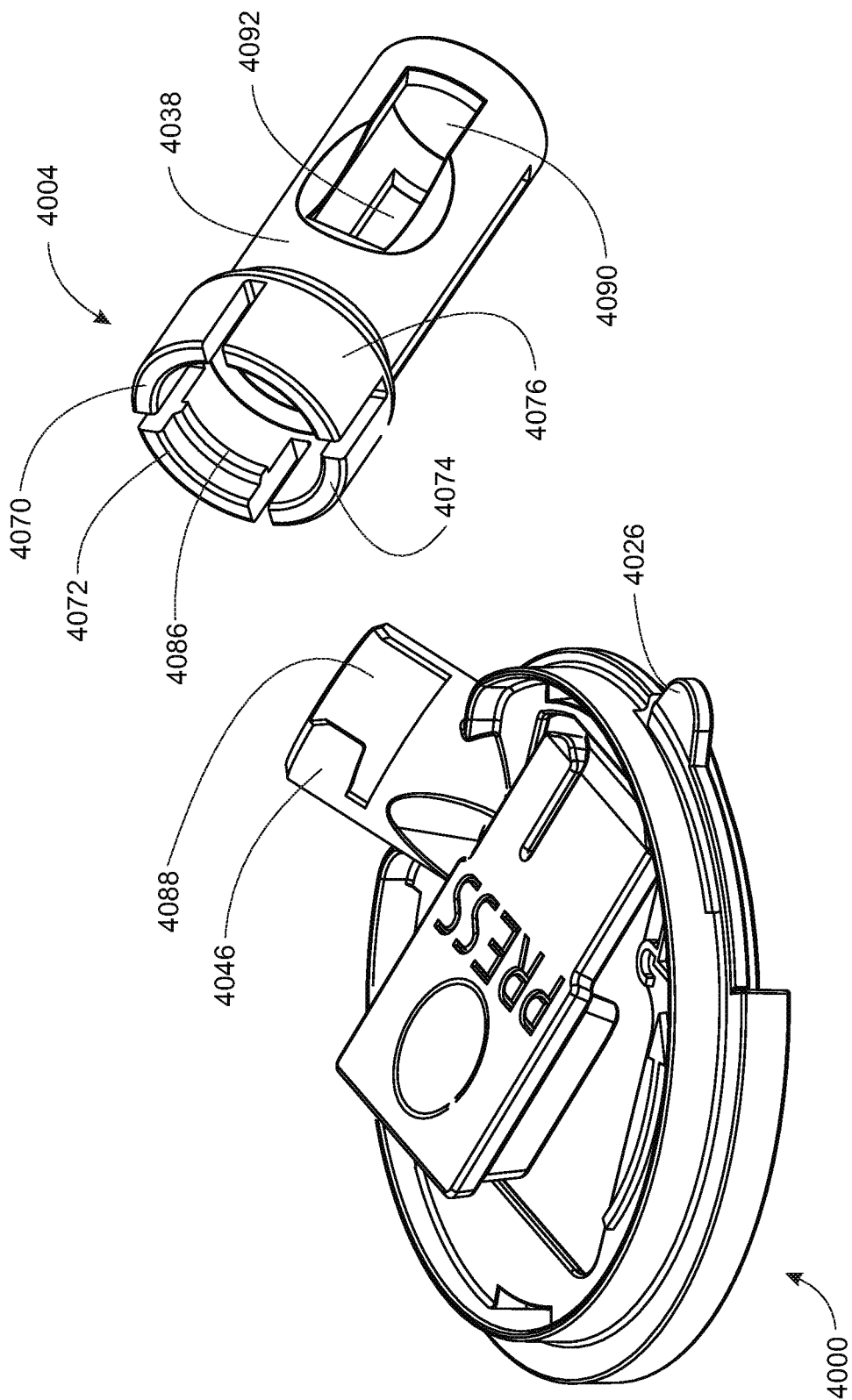
Figure 215:
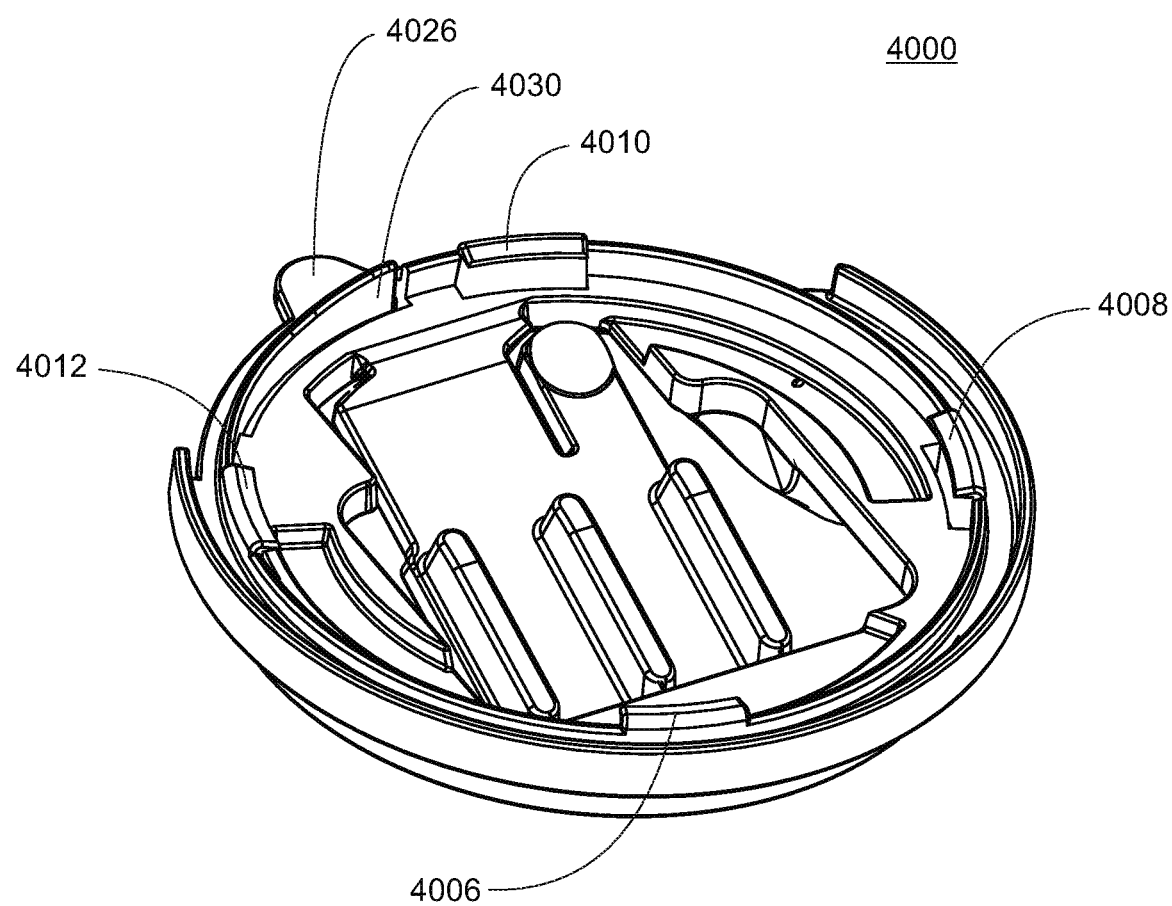
Figure 216:
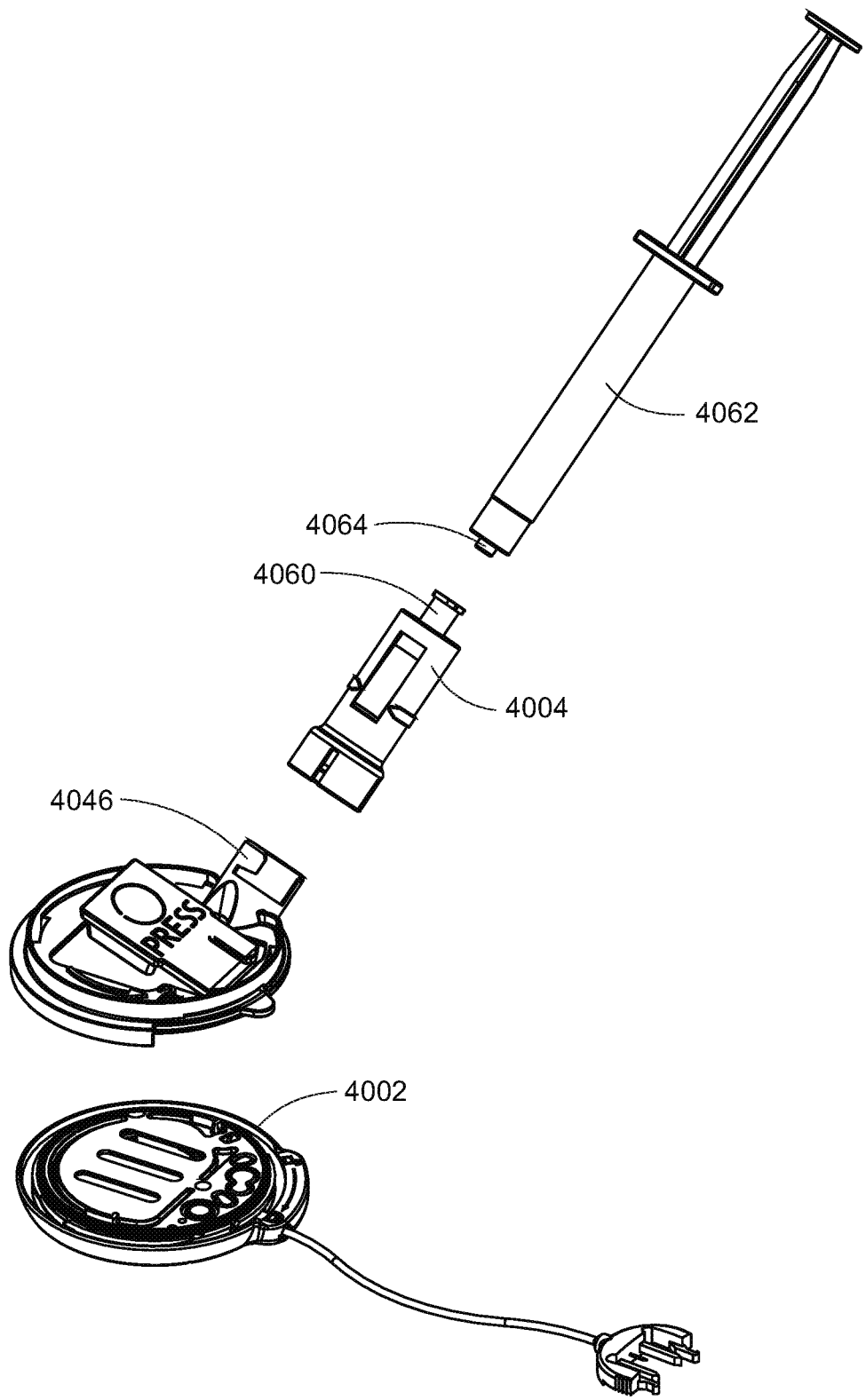
Figure 217:
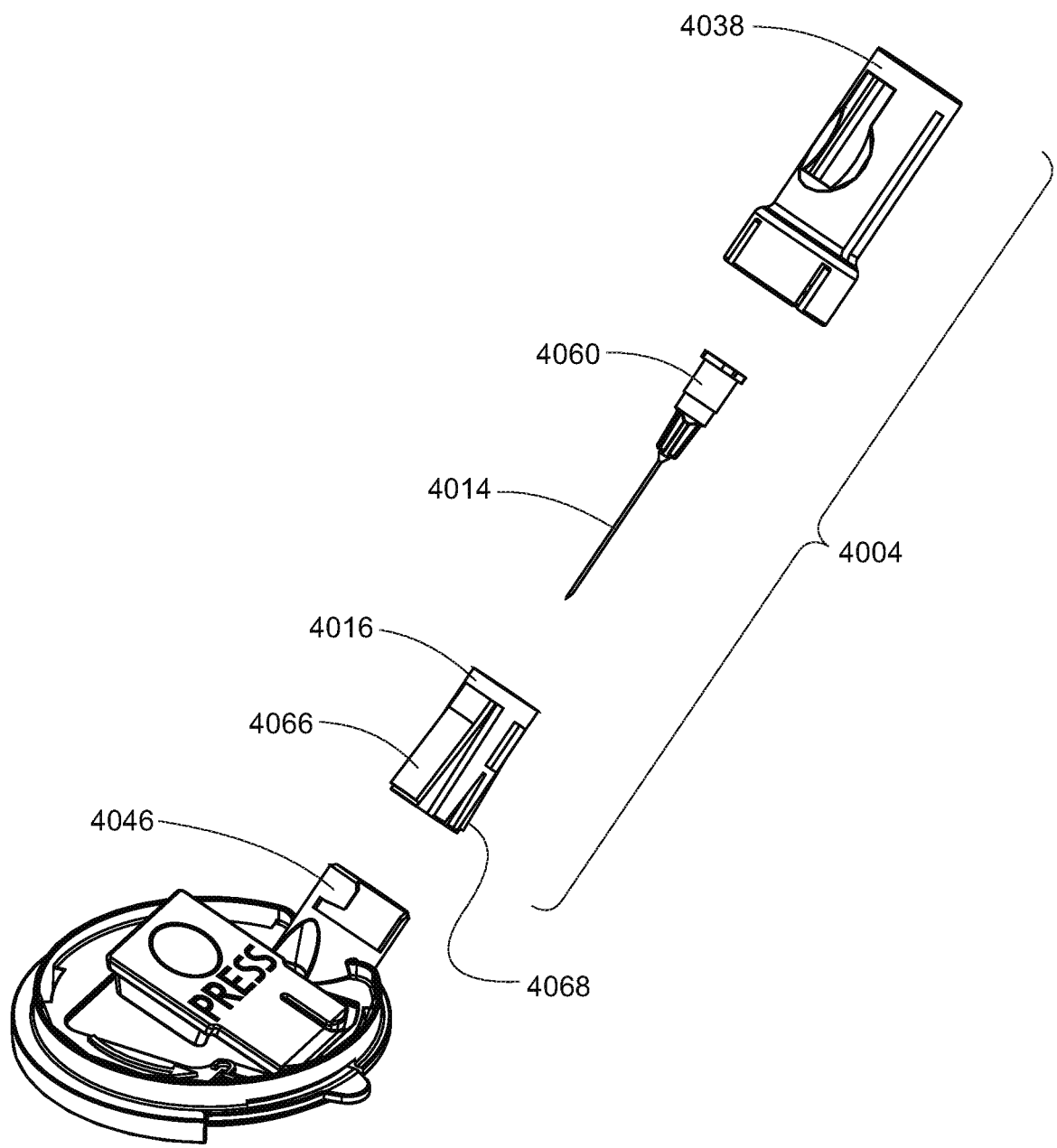
Figure 219:
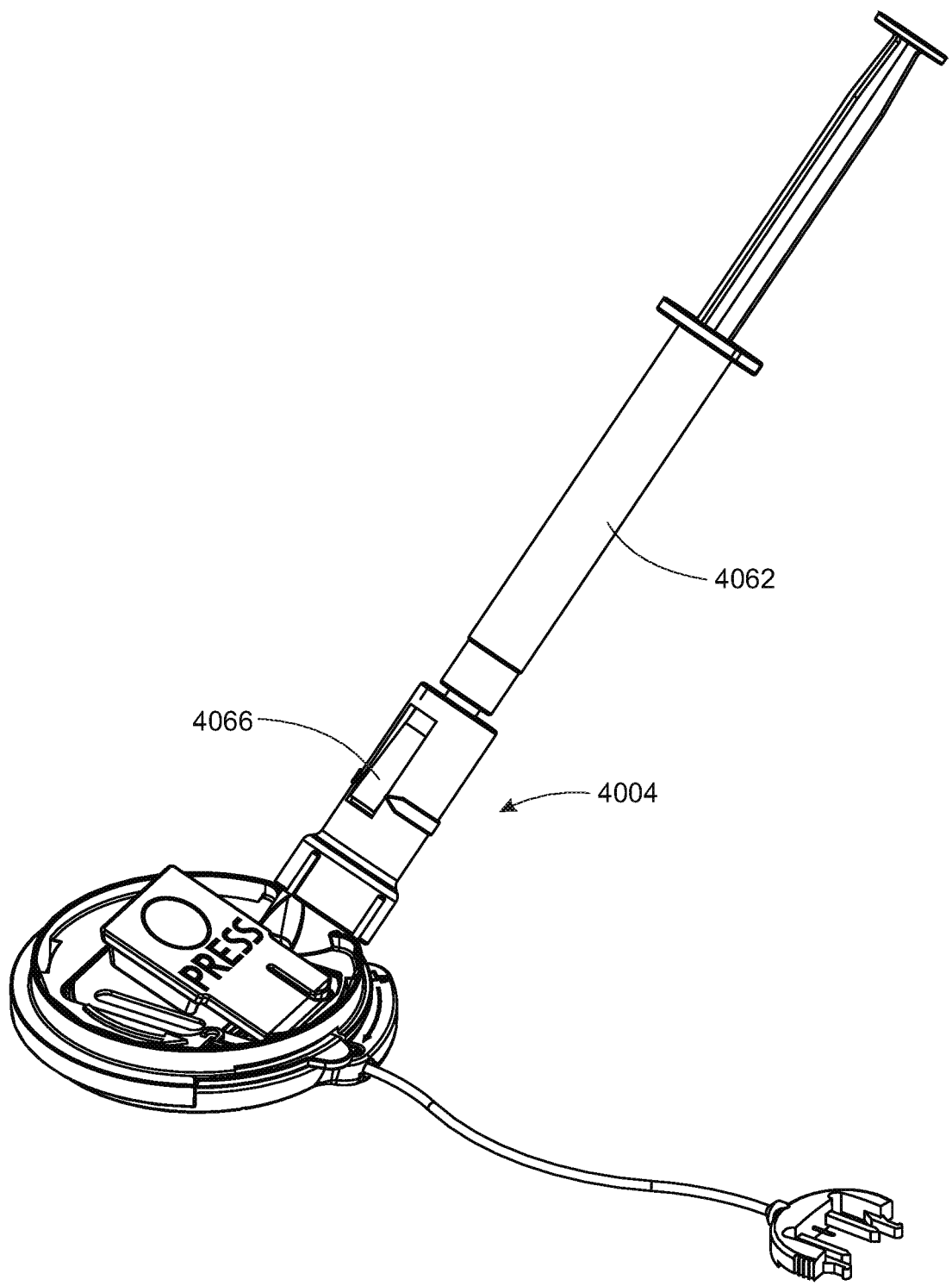
Figure 221:
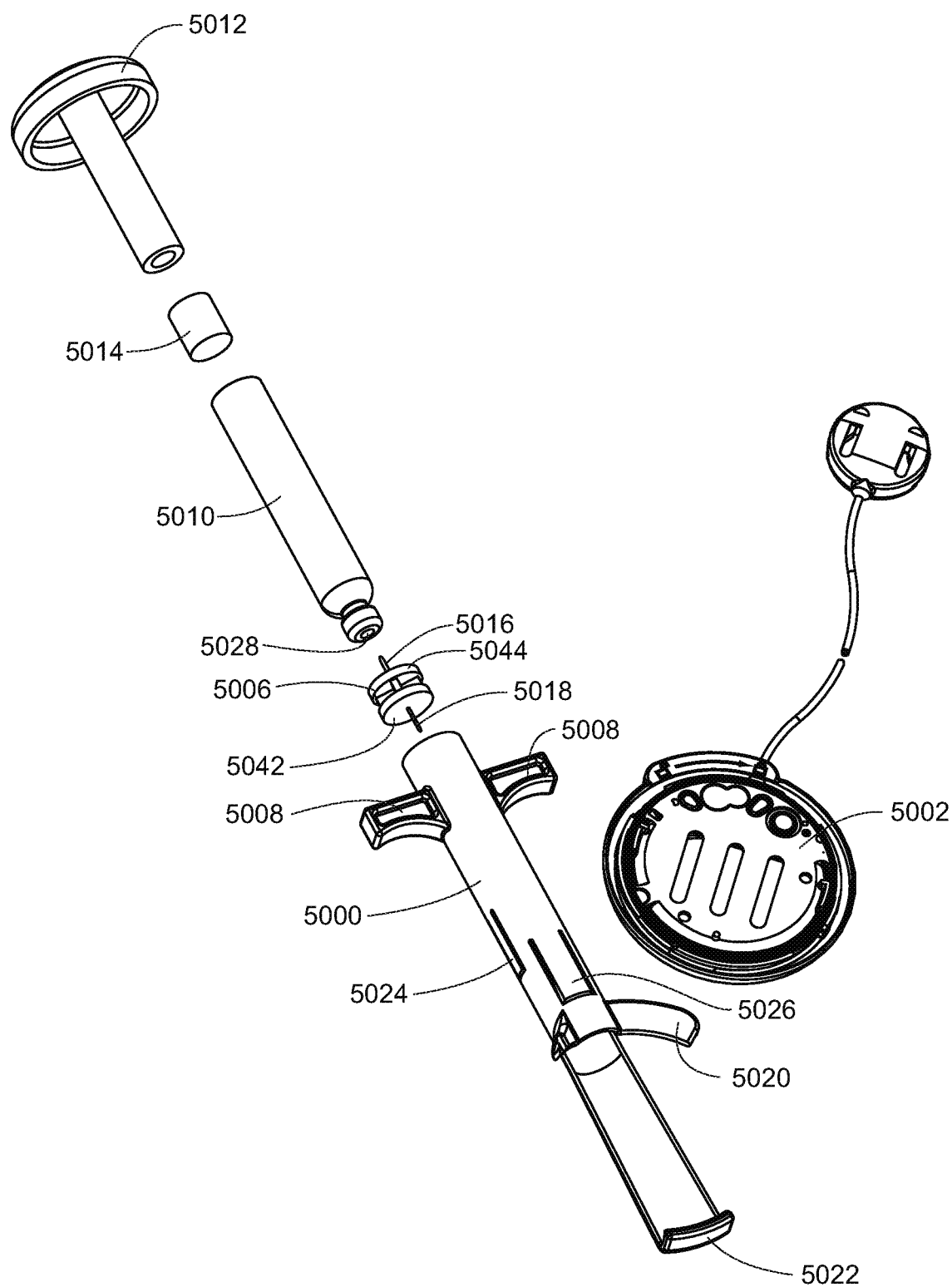
Figure 223:
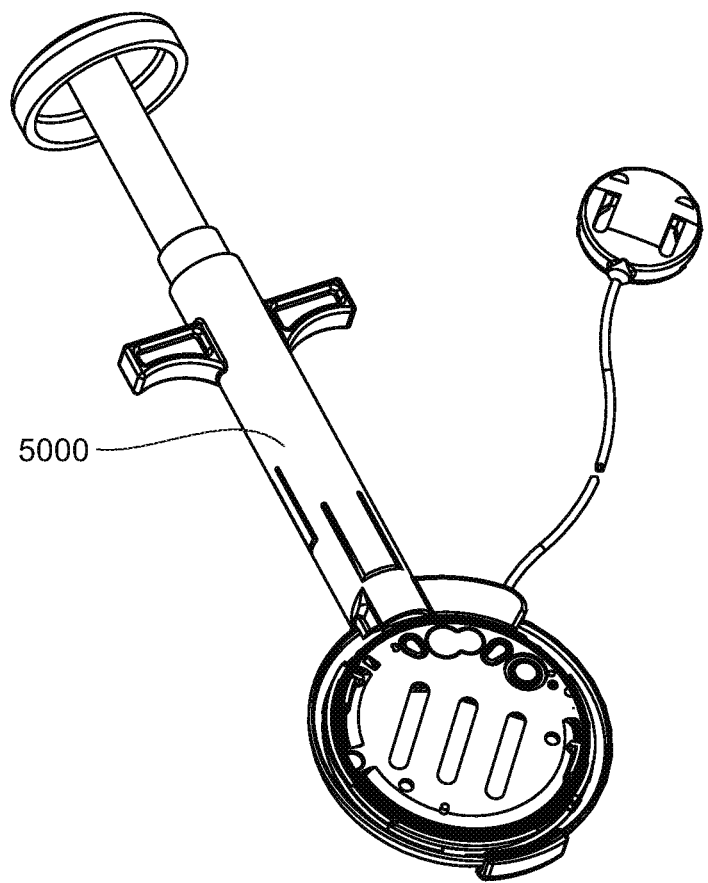
Figure 224:
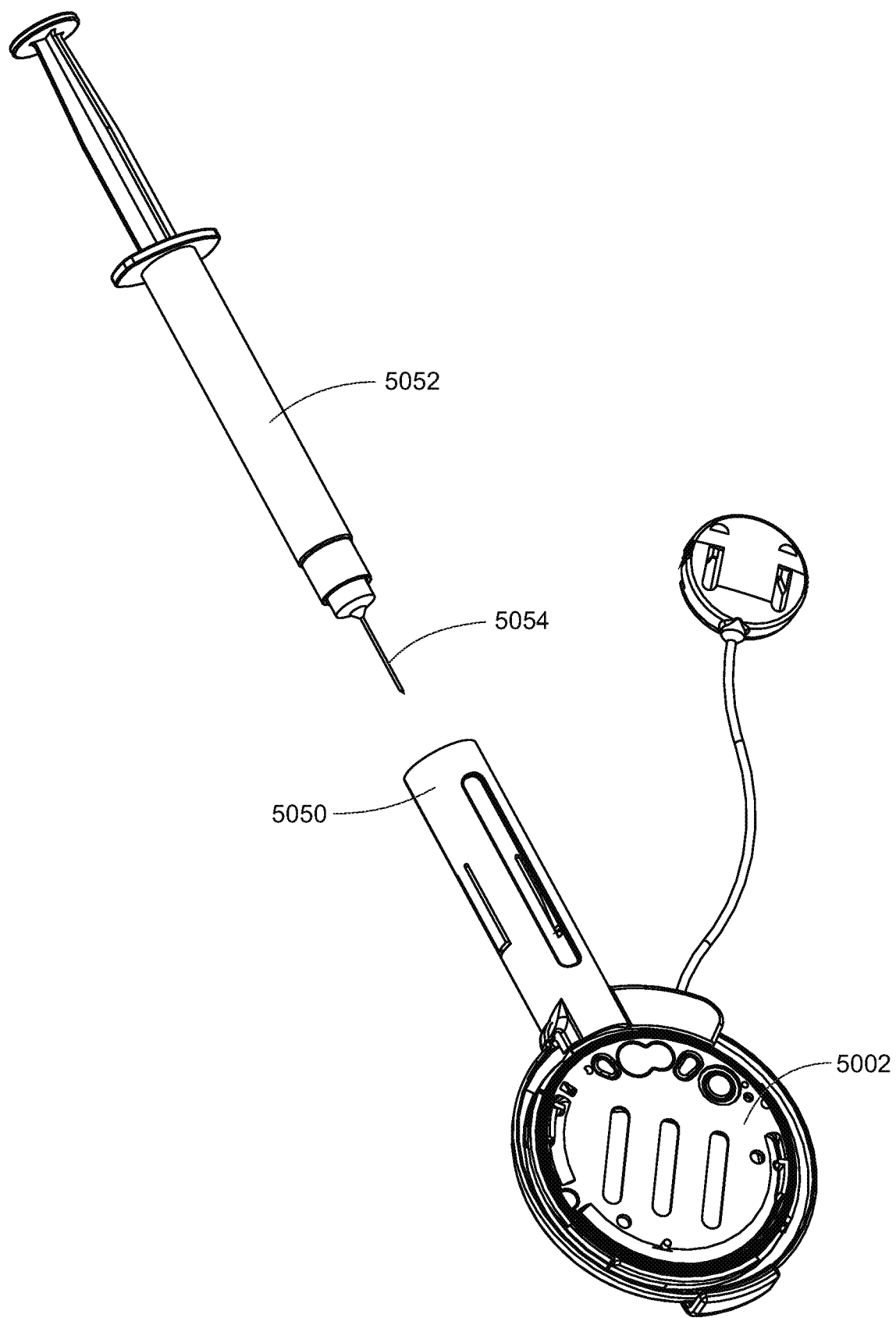
Figure 225:
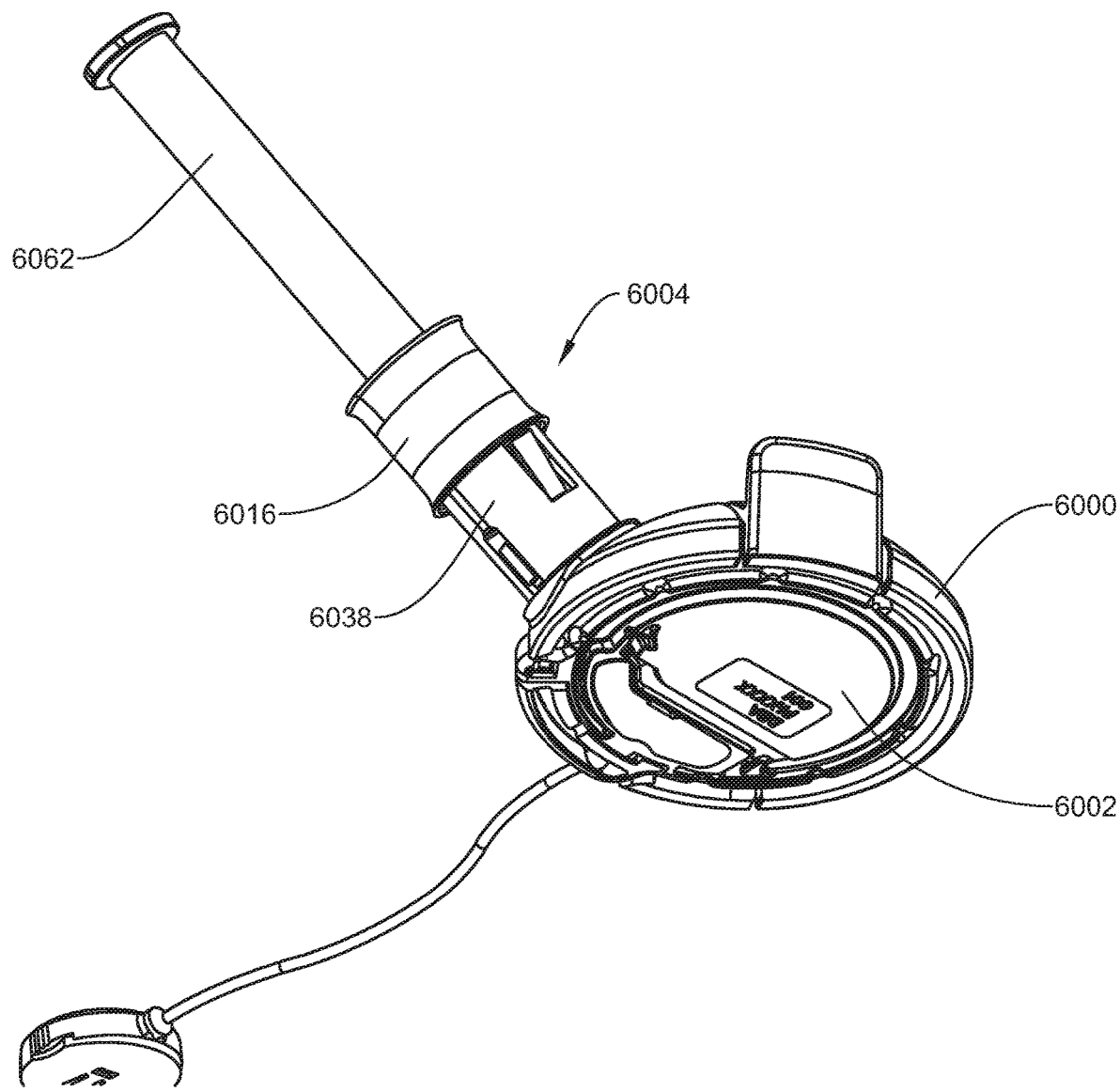
Figure 226A:
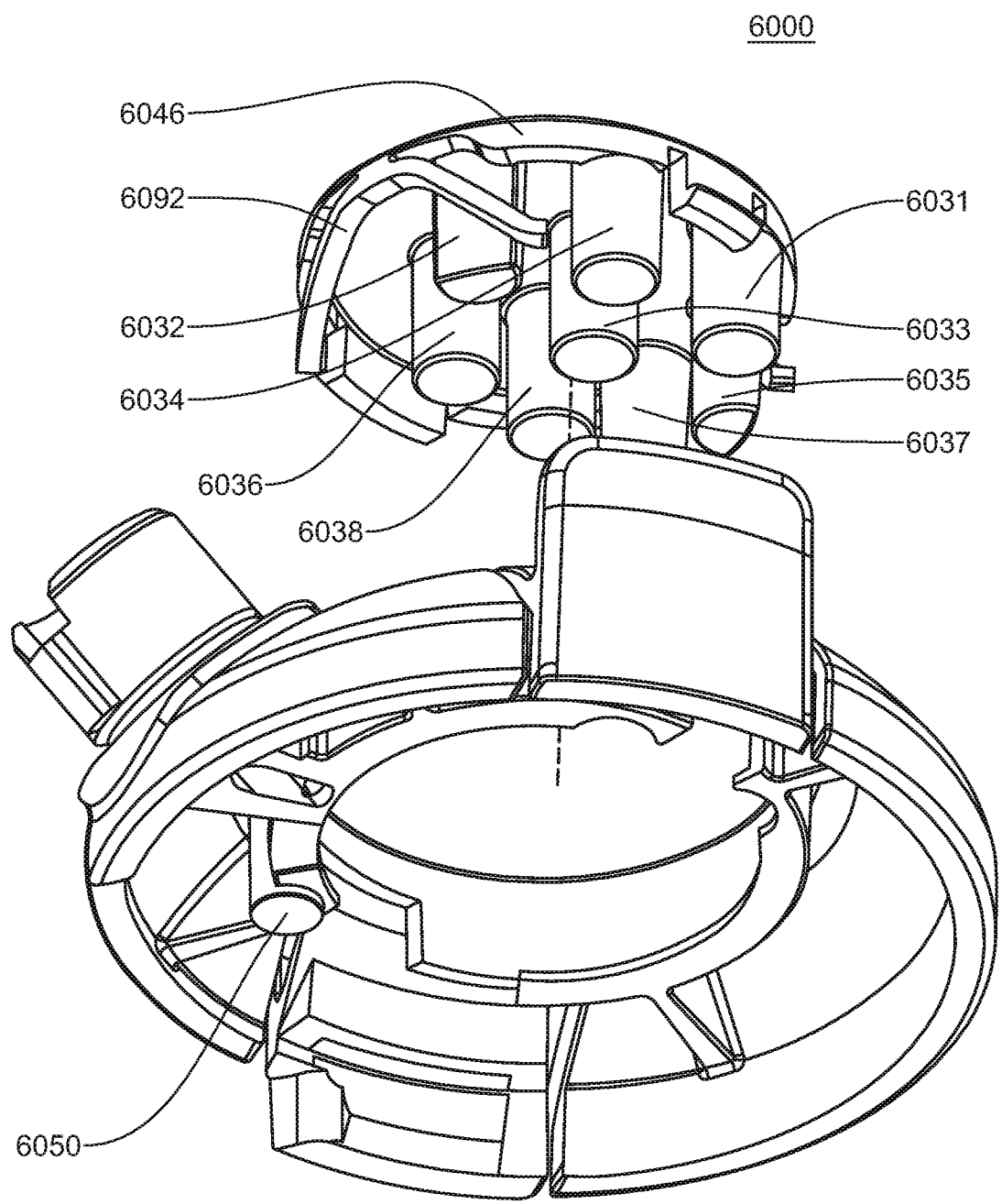
Figure 226B:
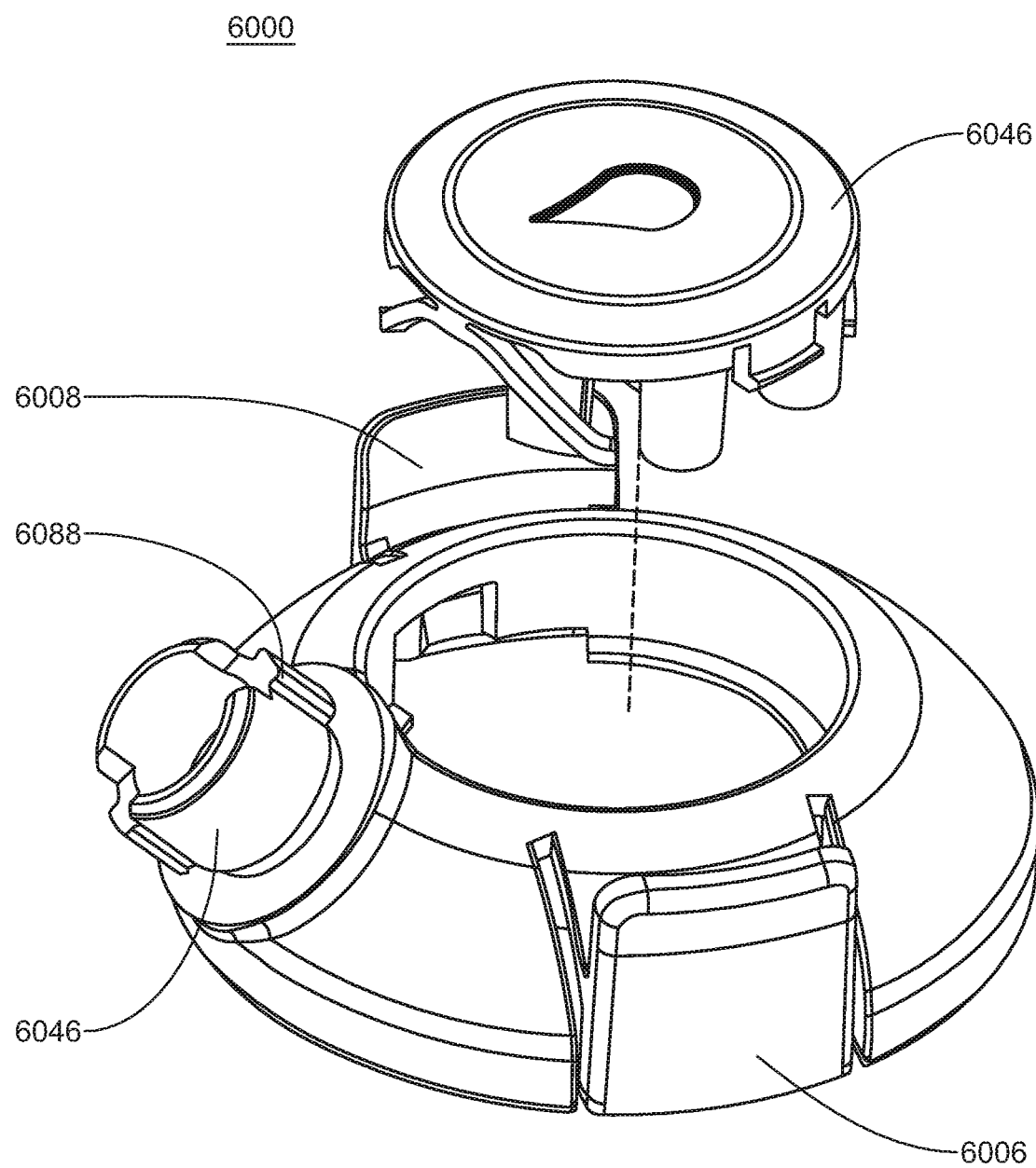
Figure 227:
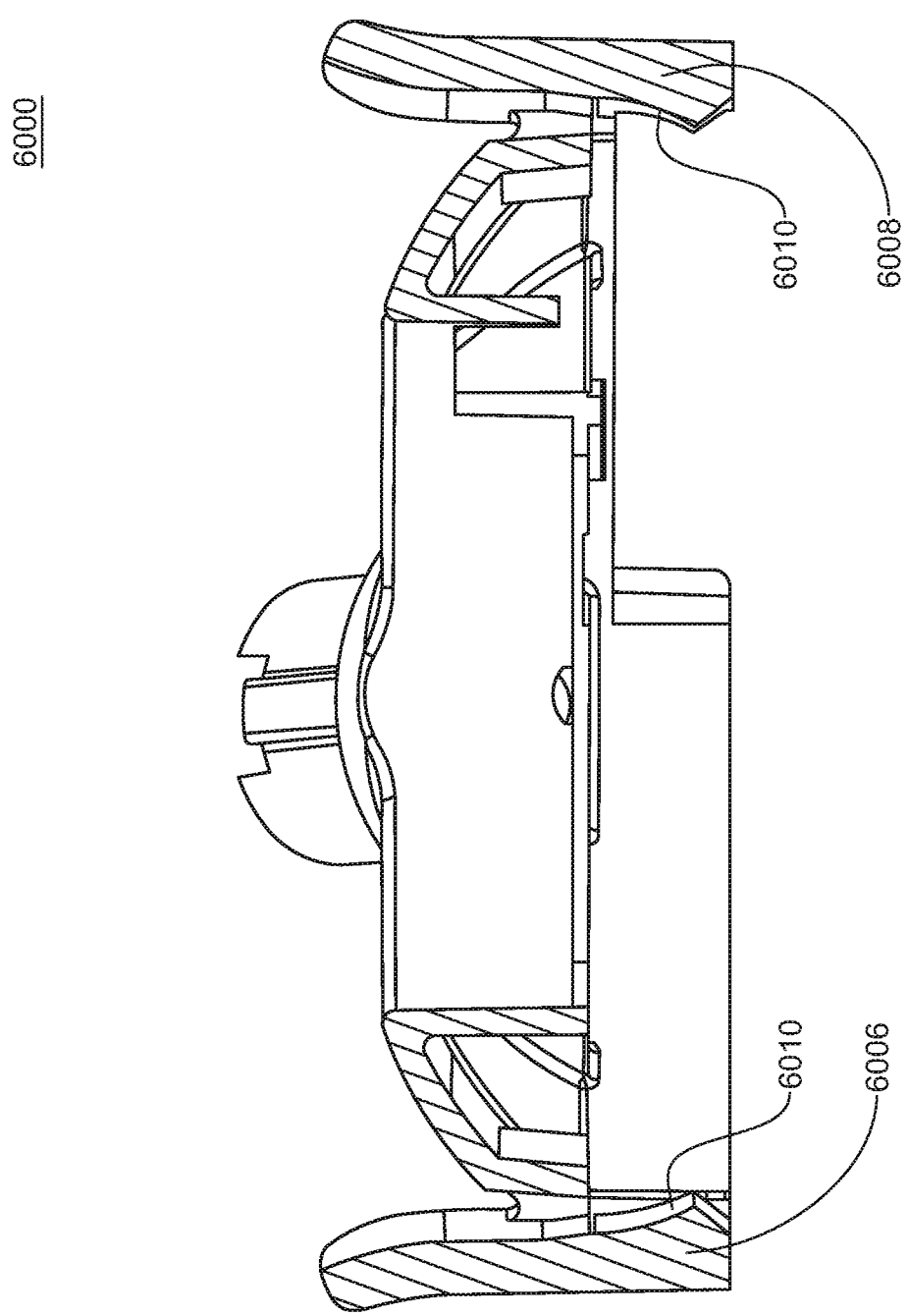
Figure 228:
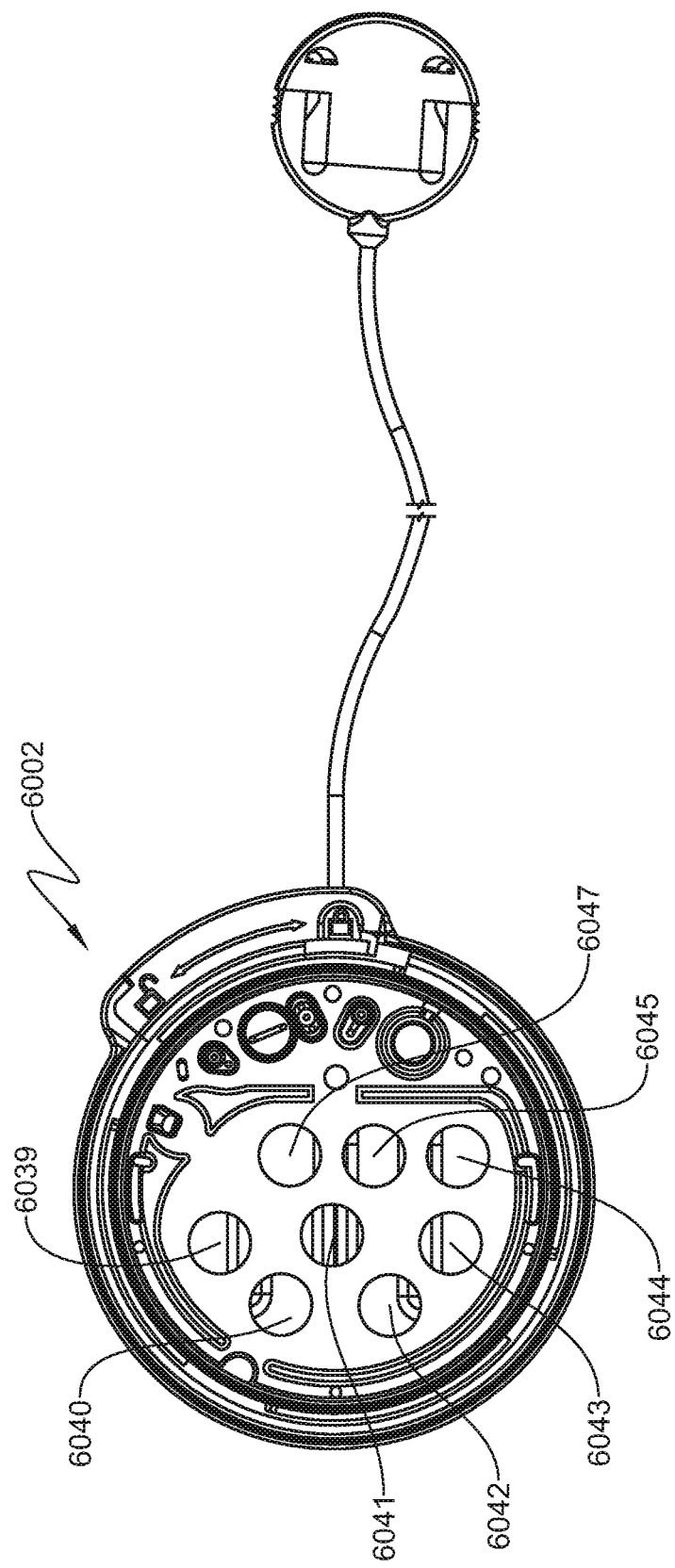
Figure 229:
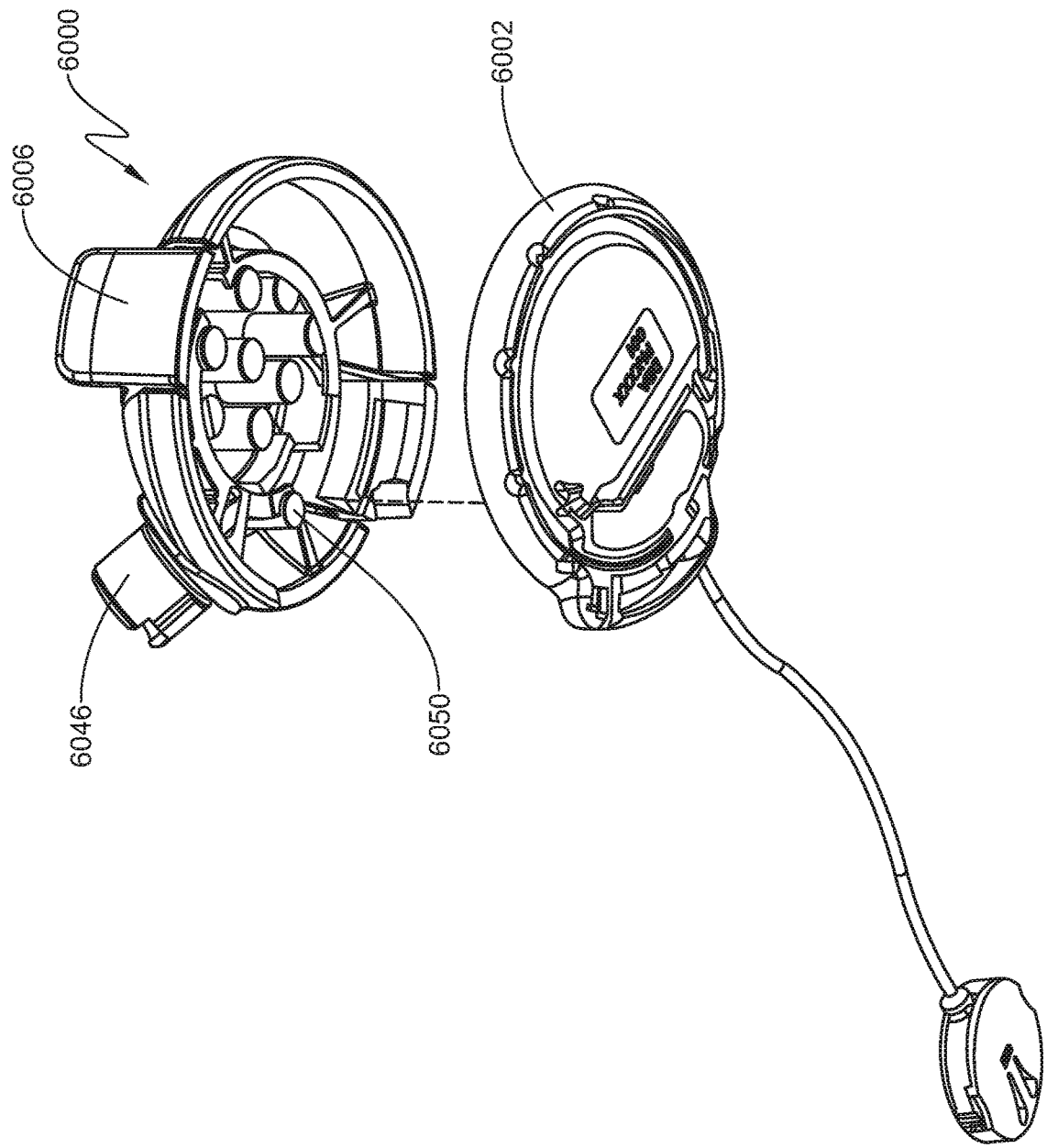
Figure 230:
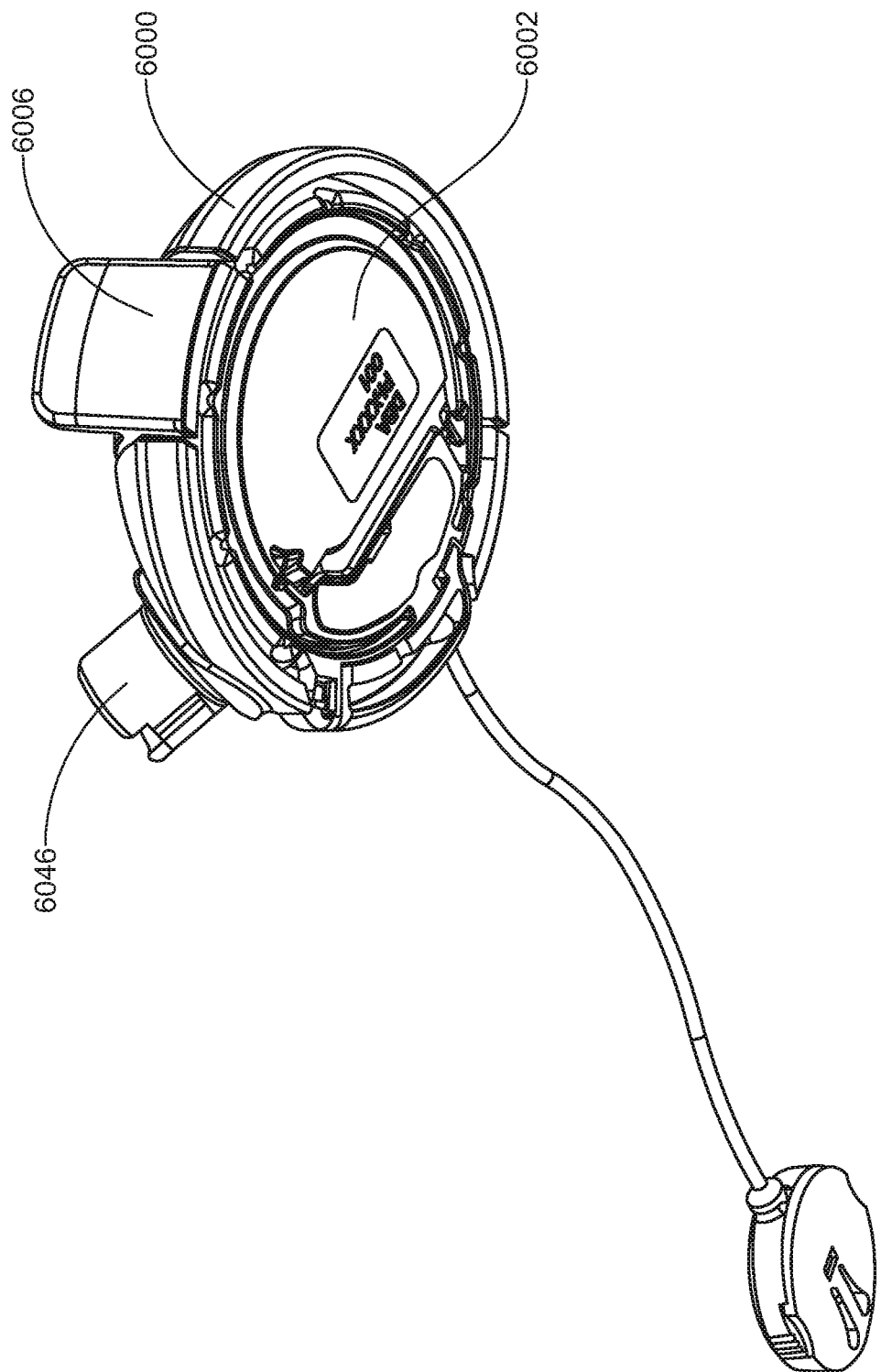
Figure 231A:
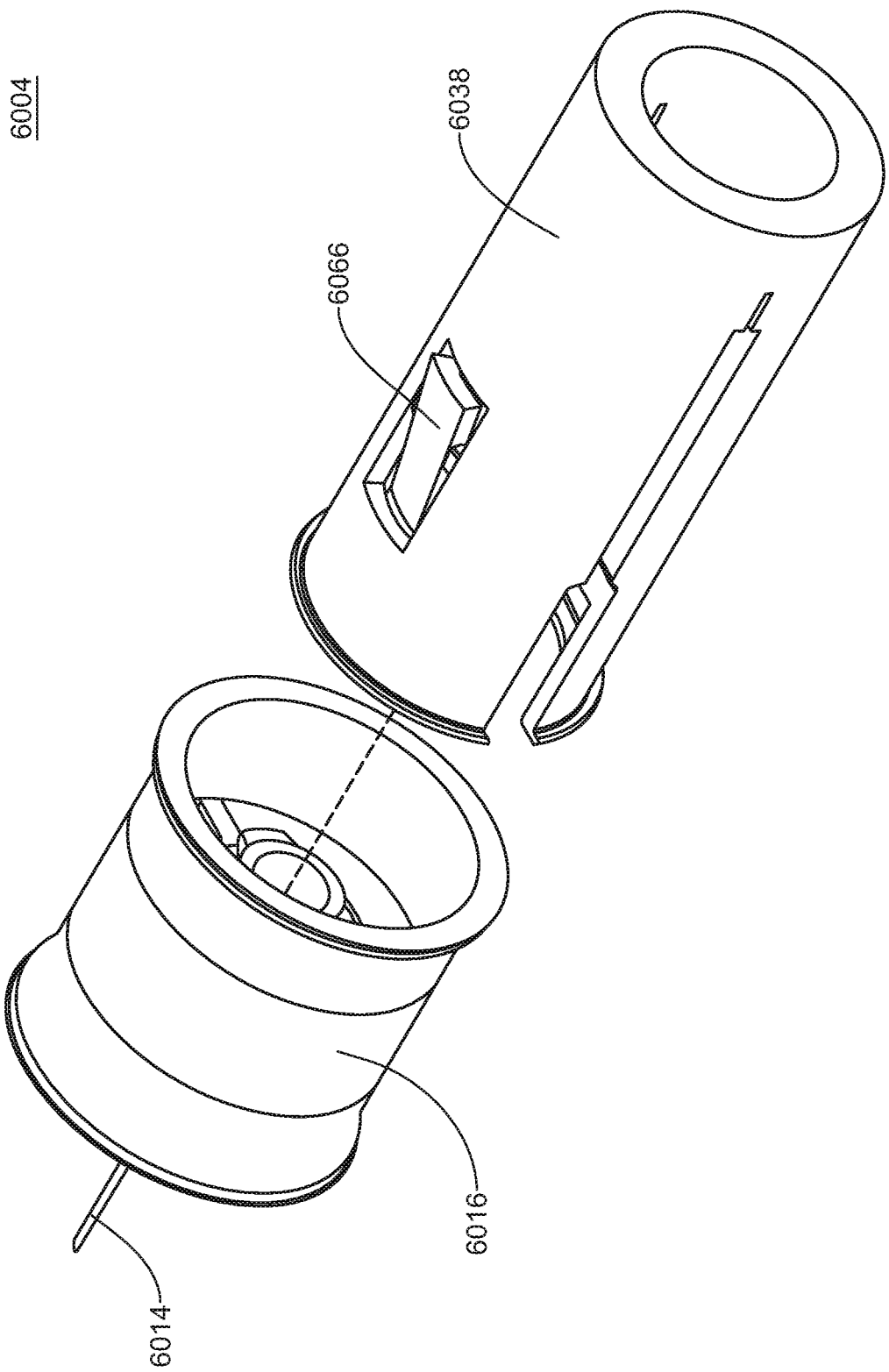
Figure 231B:
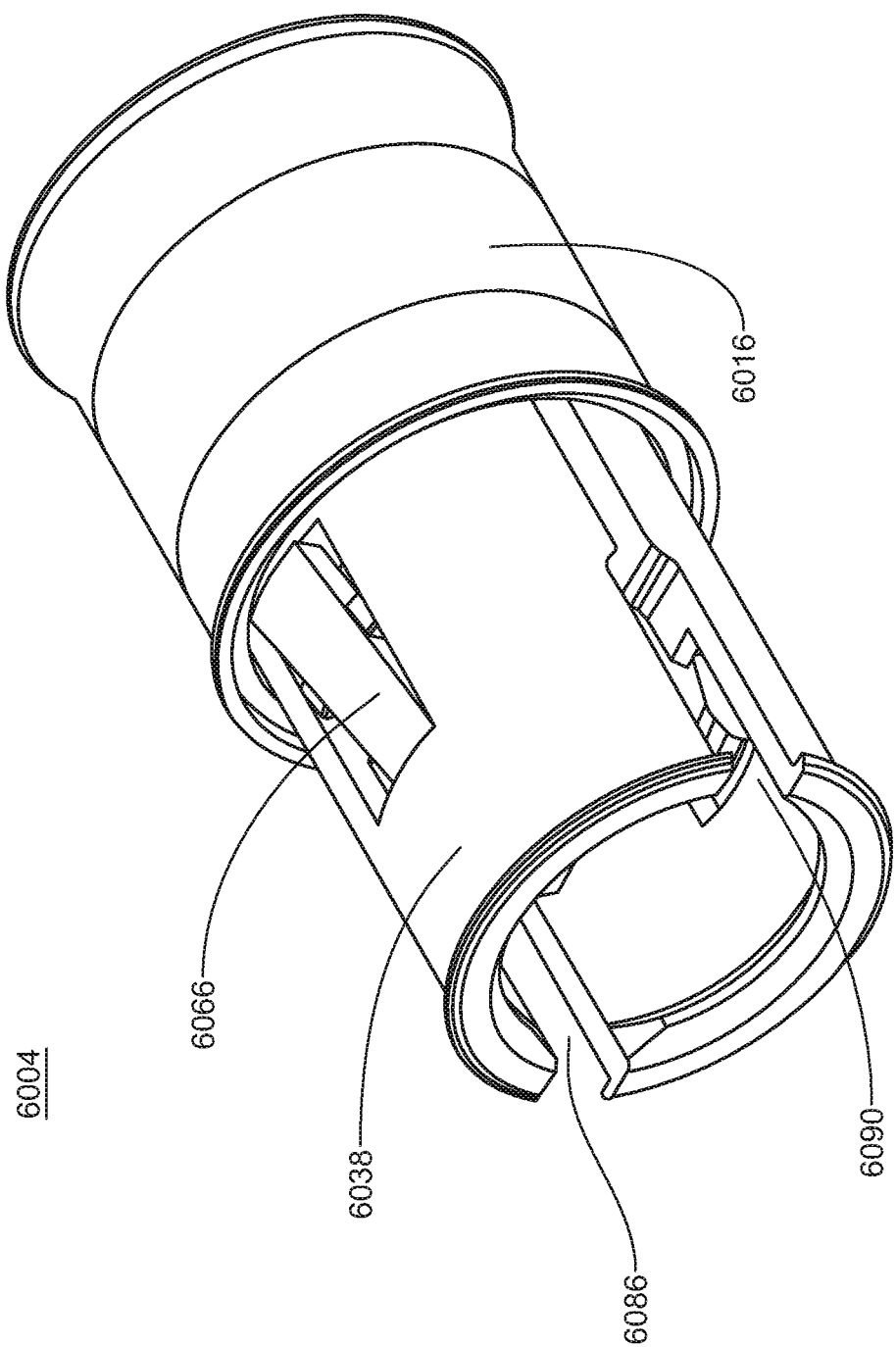
Figure 231C:
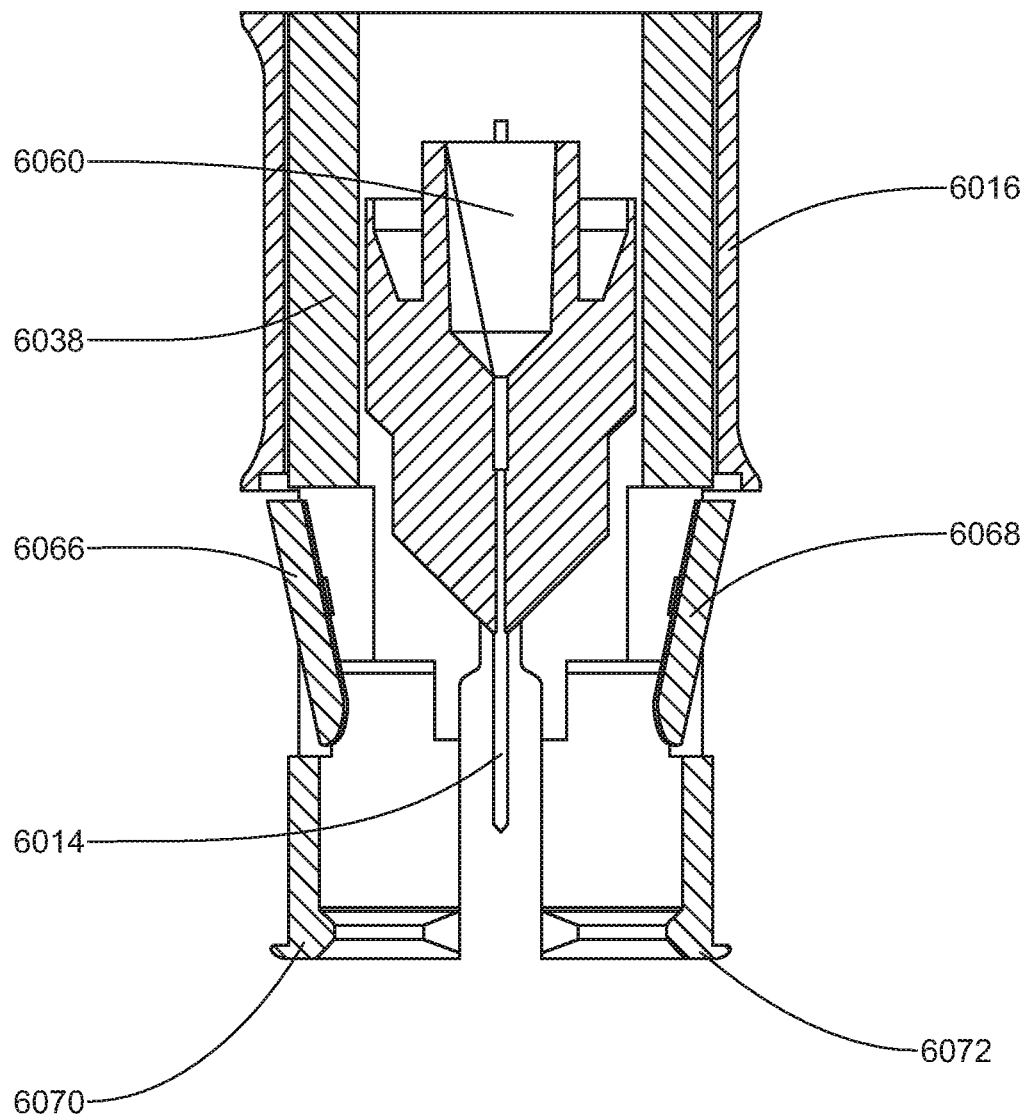
Figure 232A:
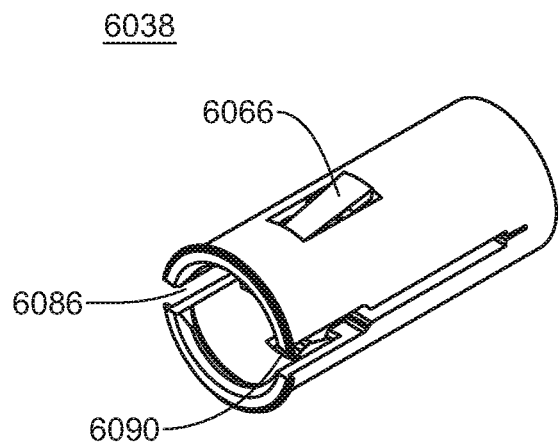
Figure 232B:
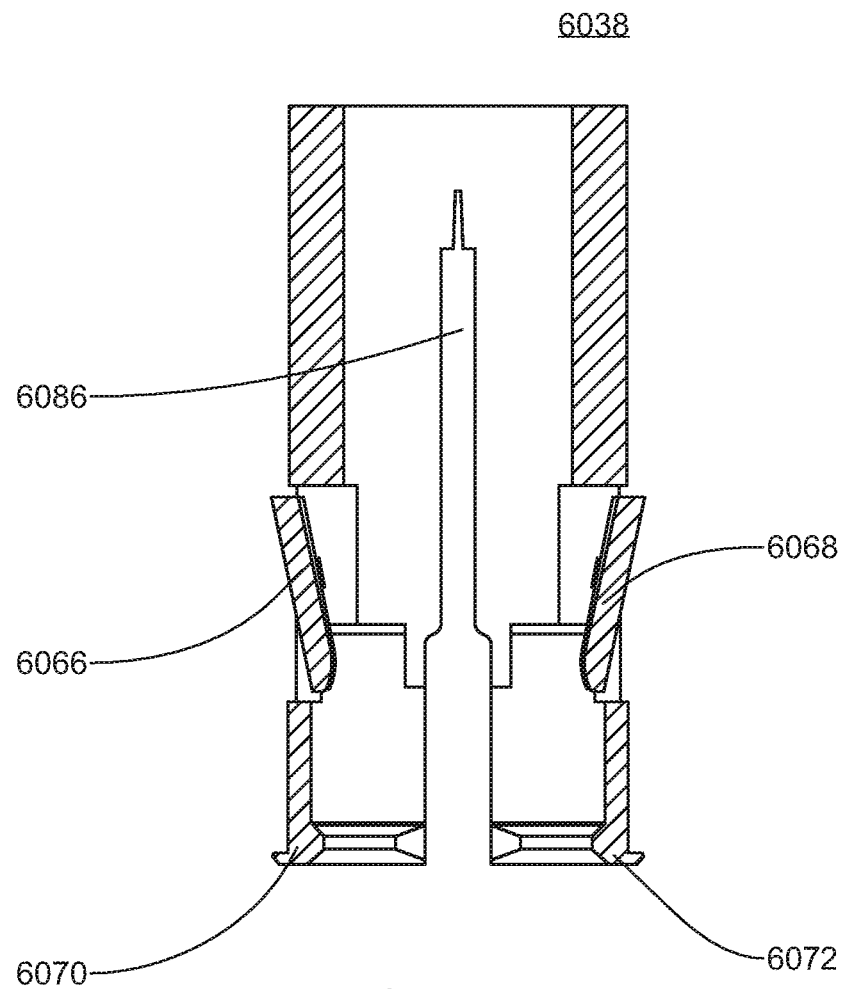
Figure 233C:
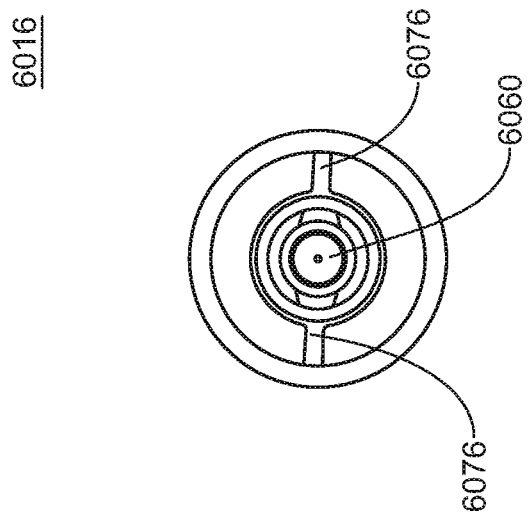
Figure 233B:
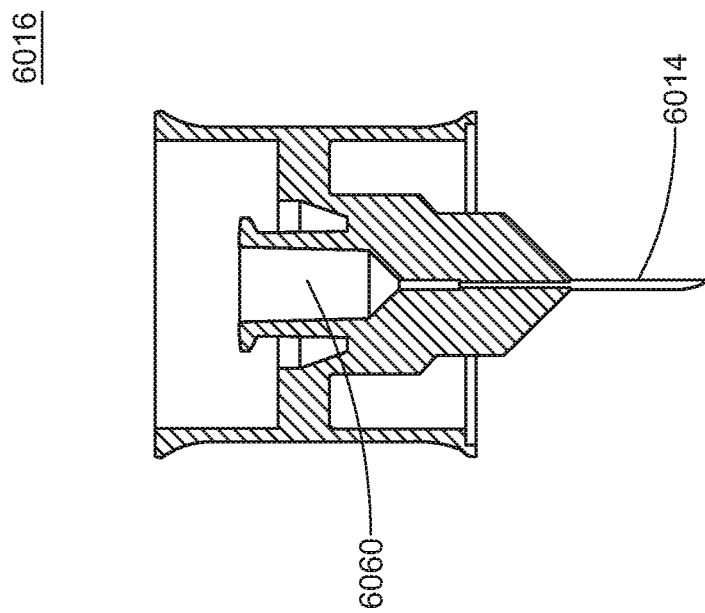
Figure 233A:
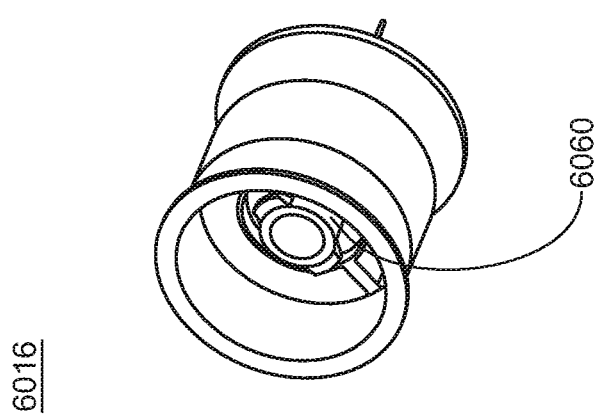
Figure 234:
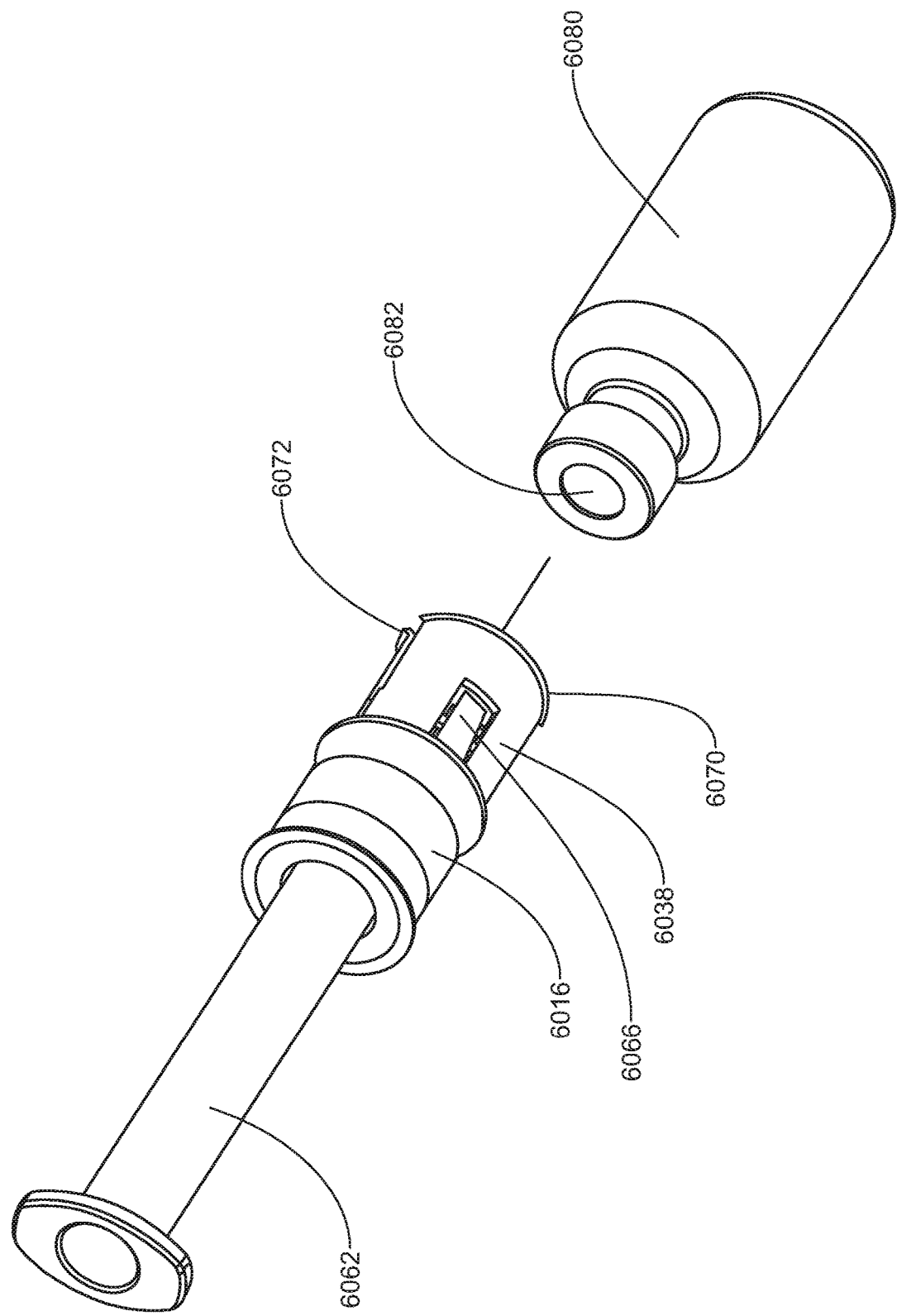
Figure 235A:
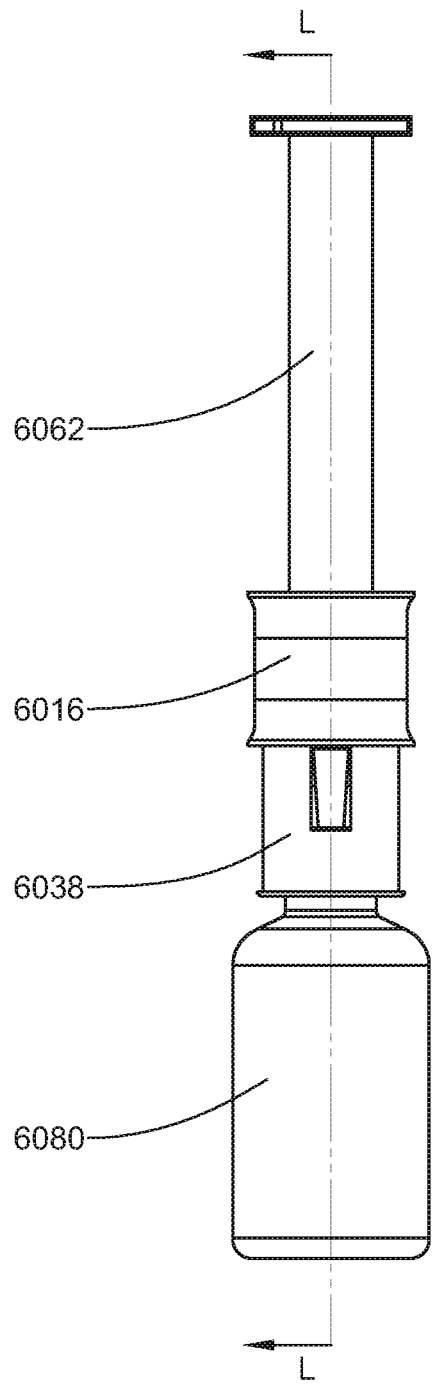
Figure 235B:
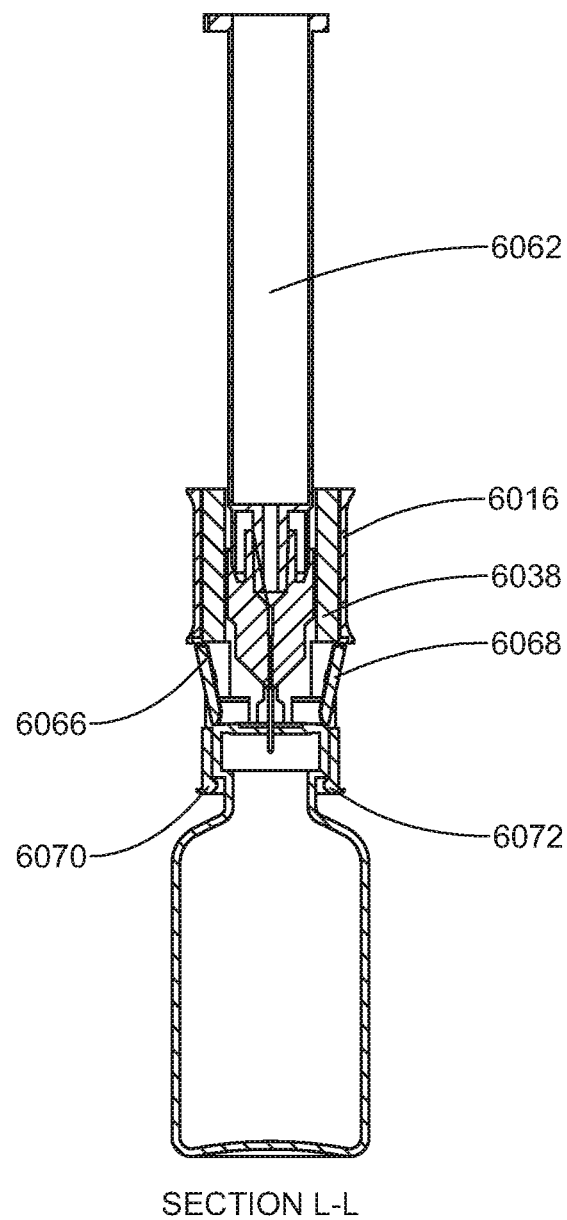
Figure 236:
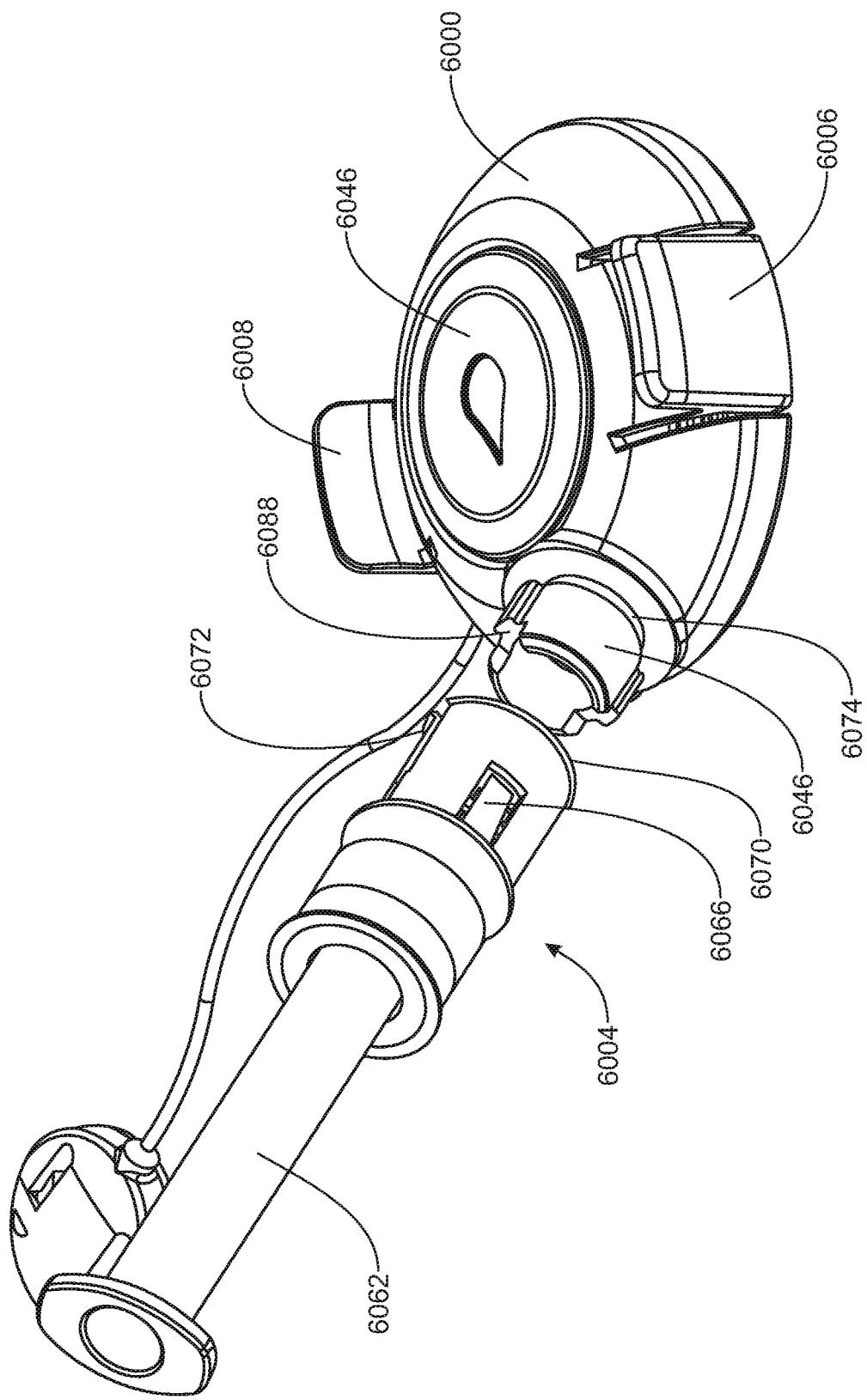
Figure 241A:
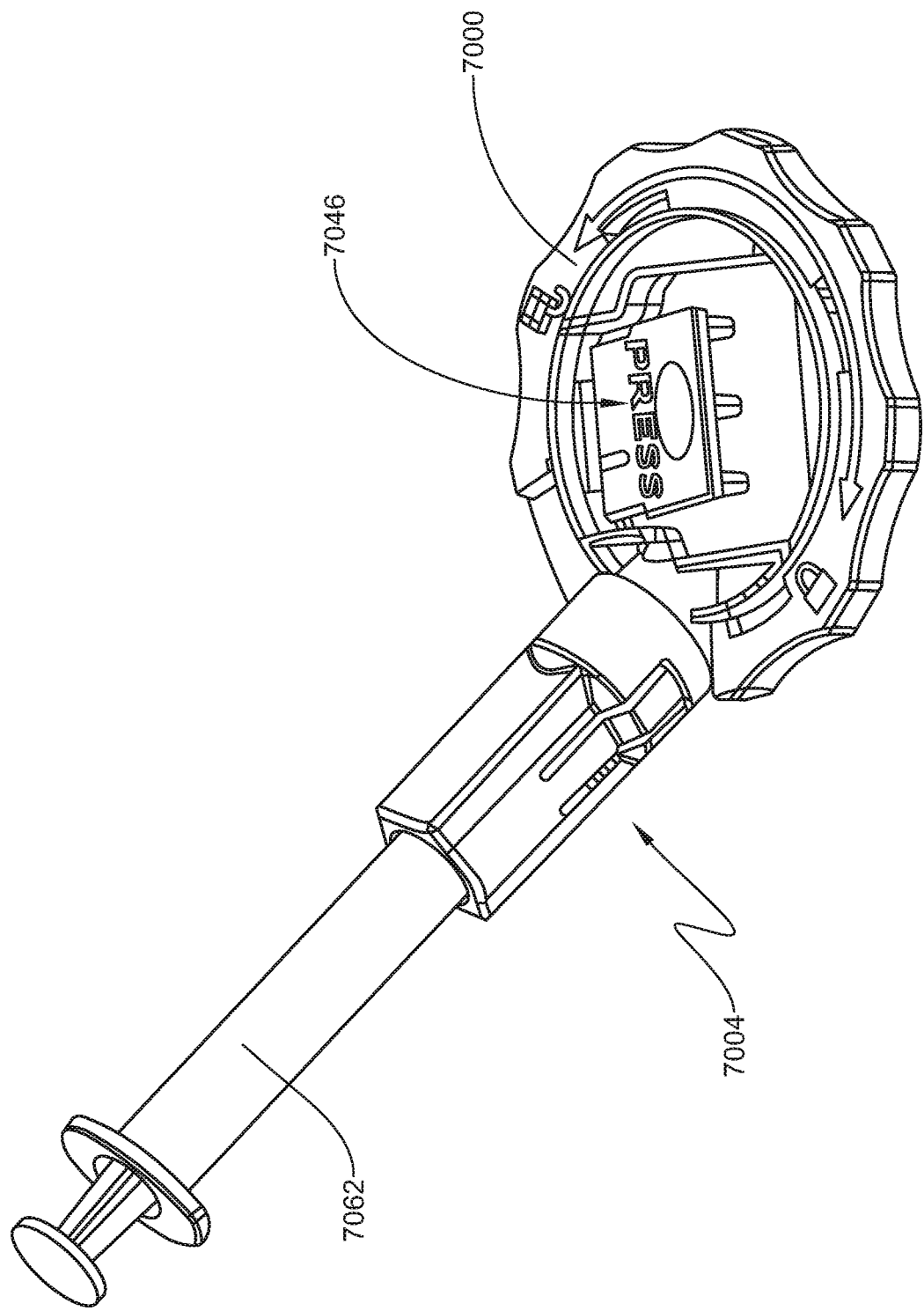
Figure 241B:
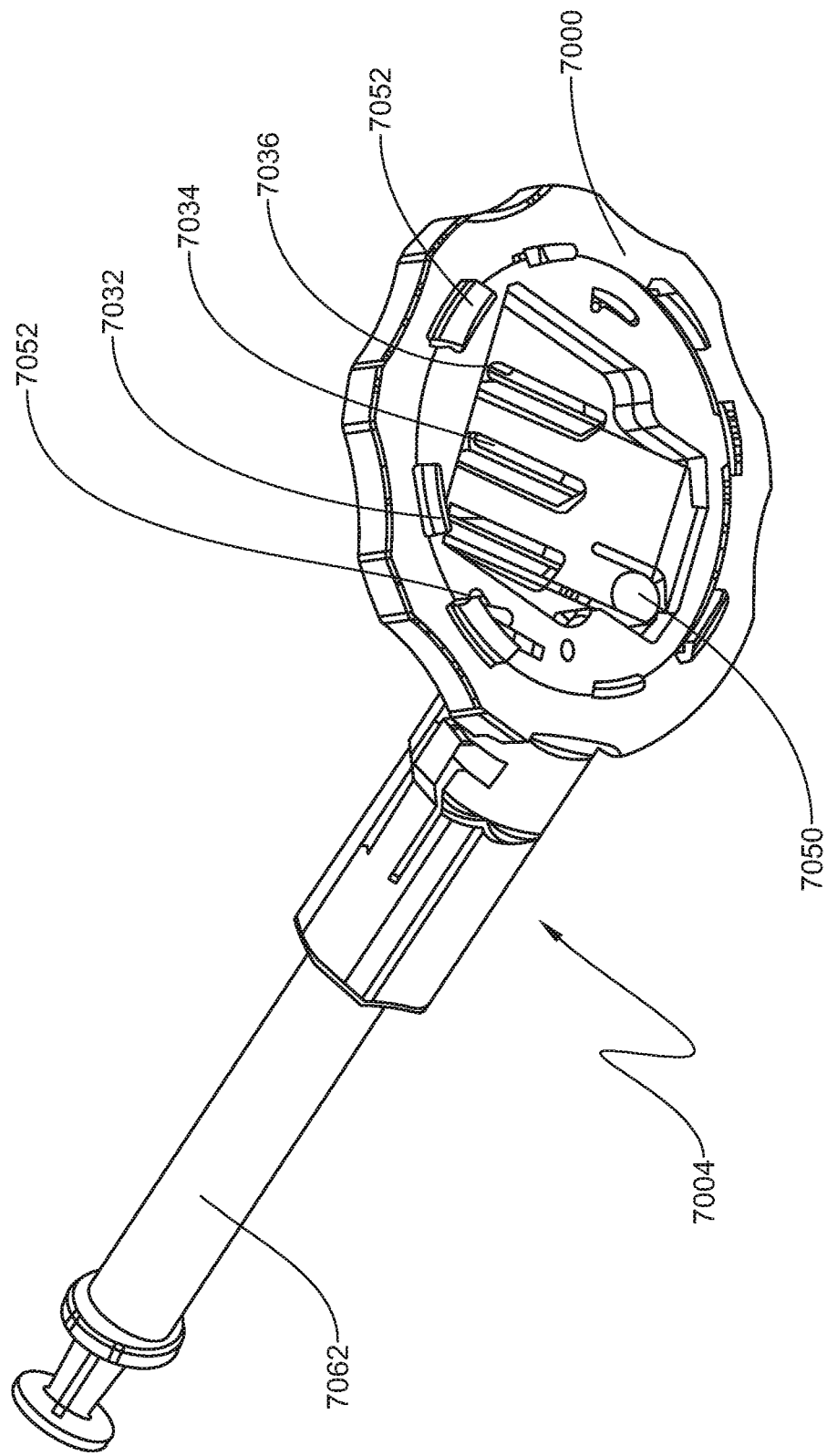
Figure 243B:
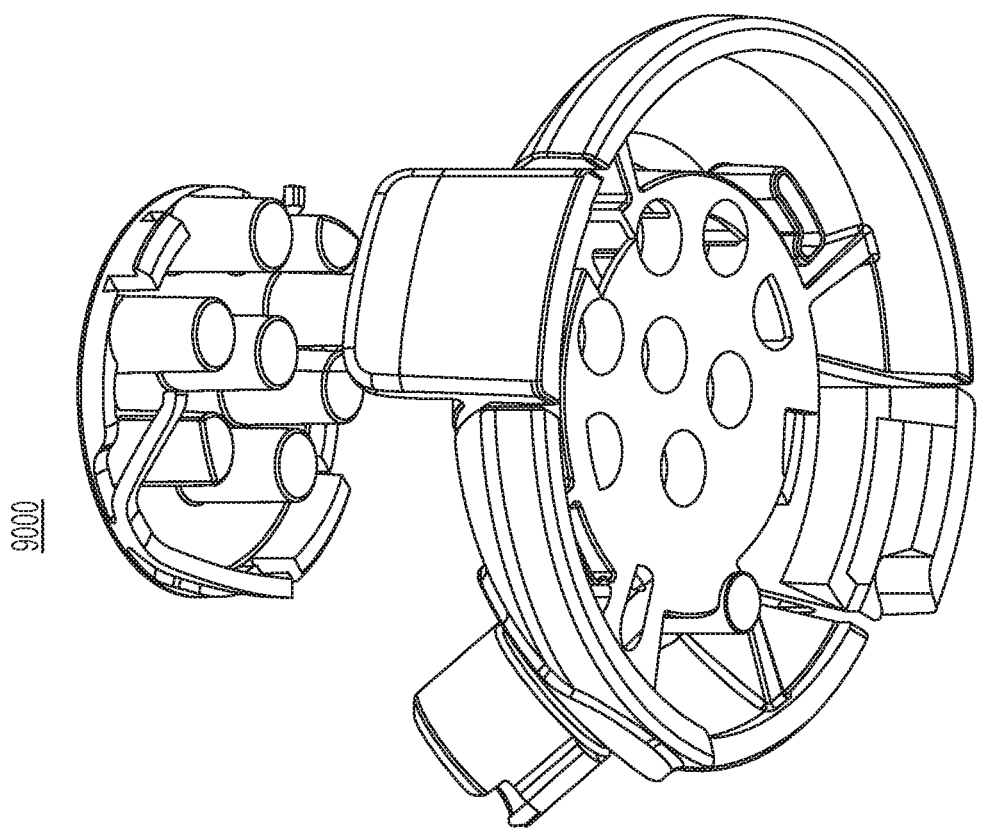
Figure 243A:
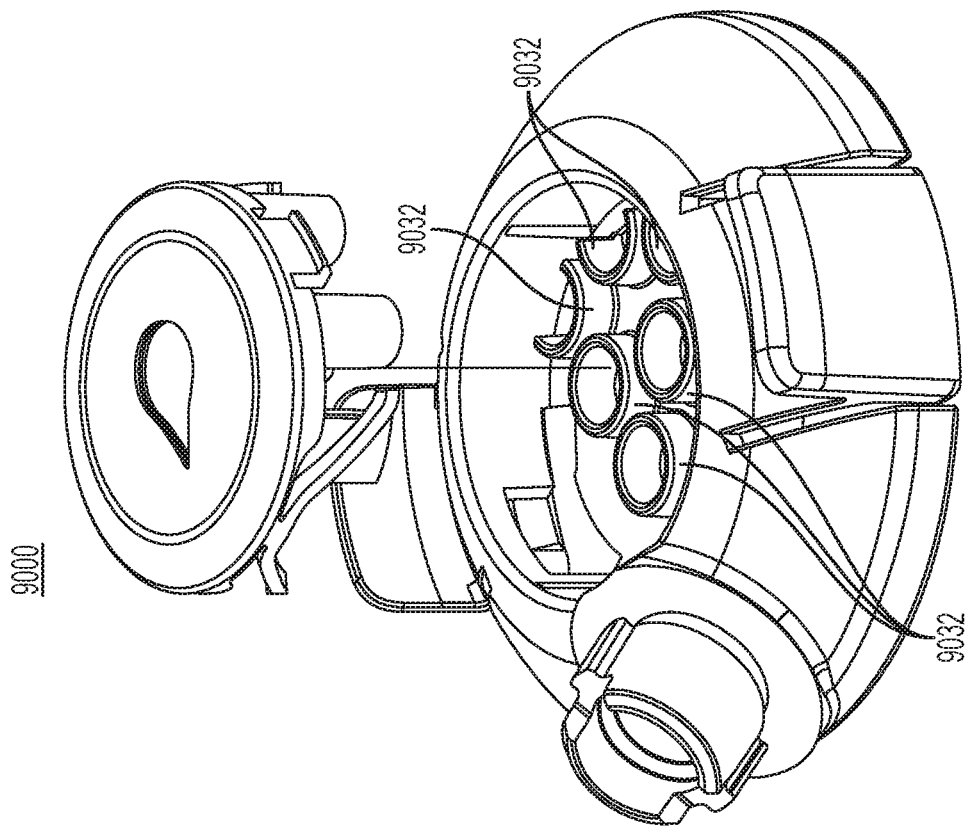
Figure 244A:
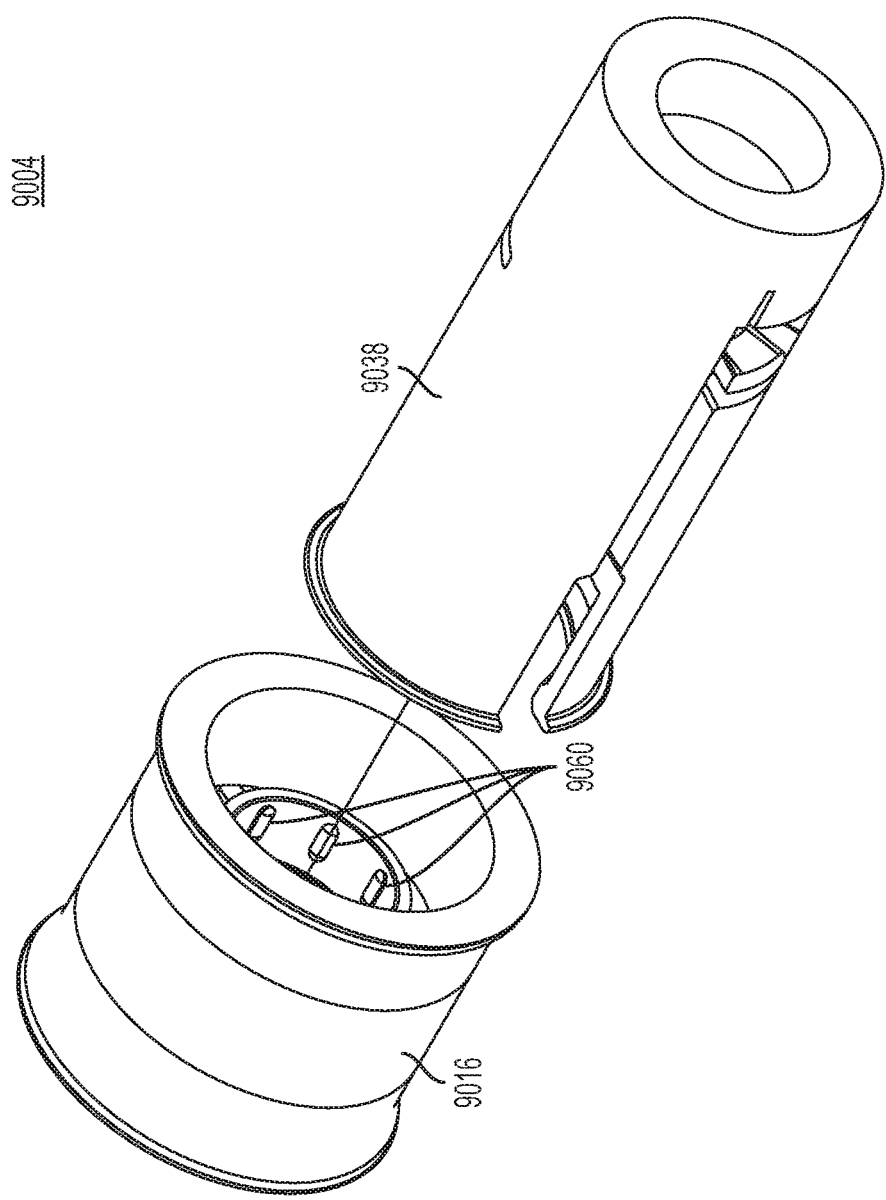
Figure 244C:
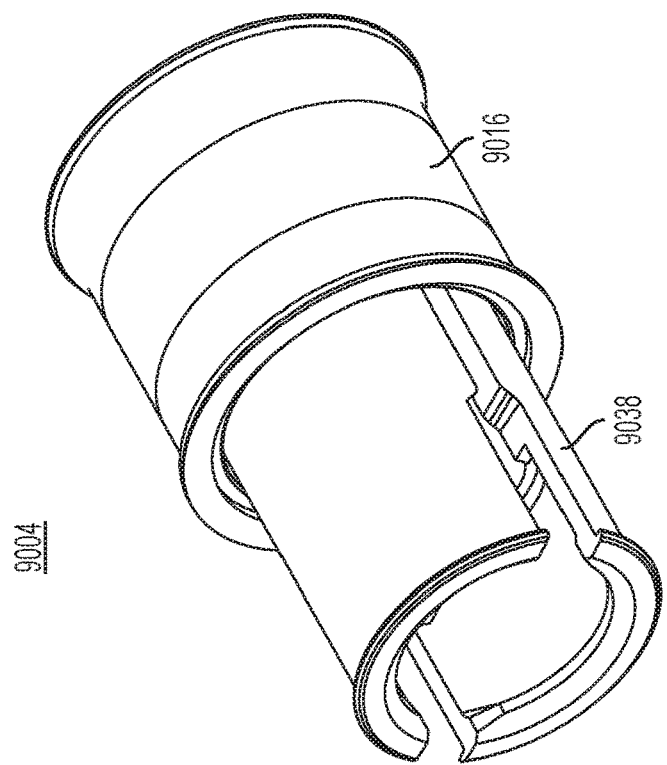
Figure 244B:
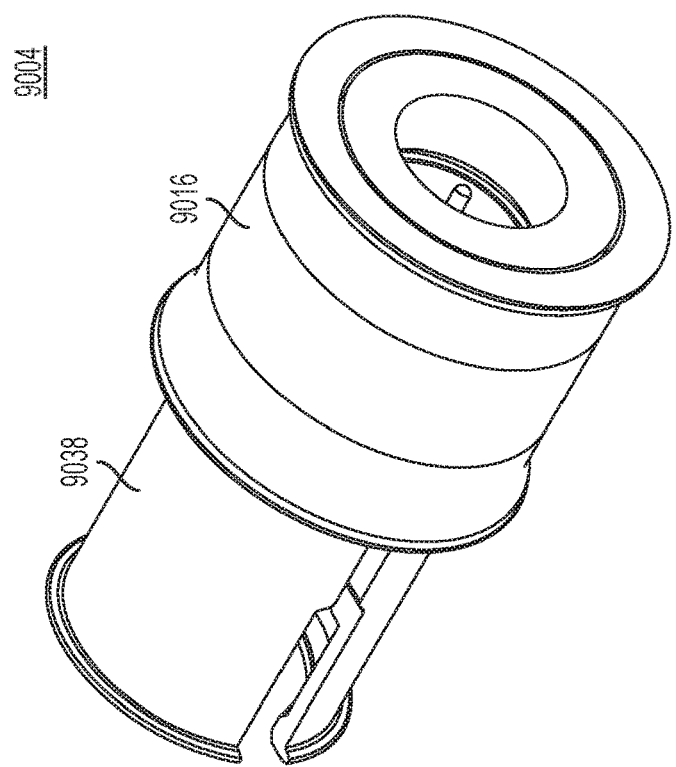
Figure 244D:
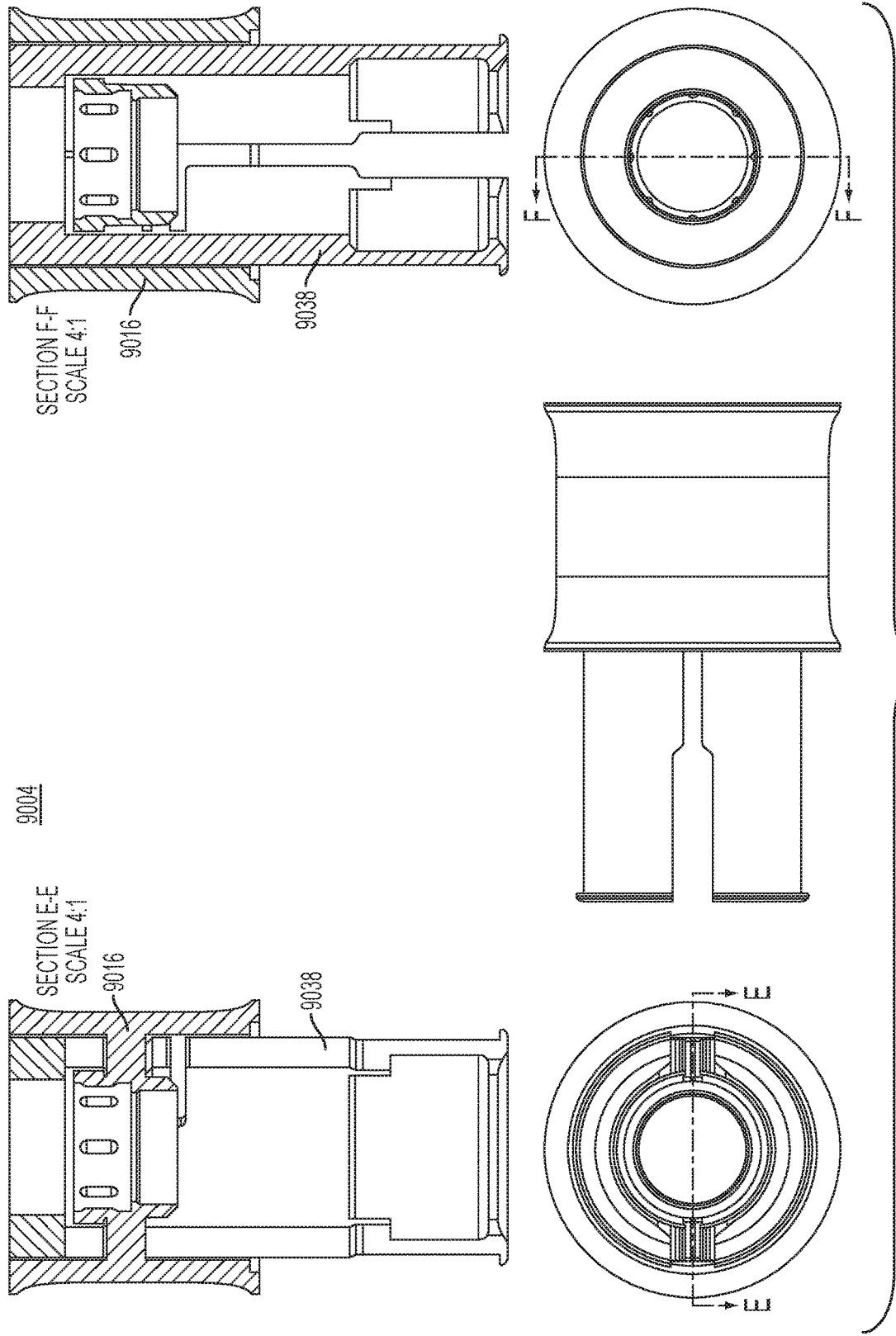
Figure 244F:
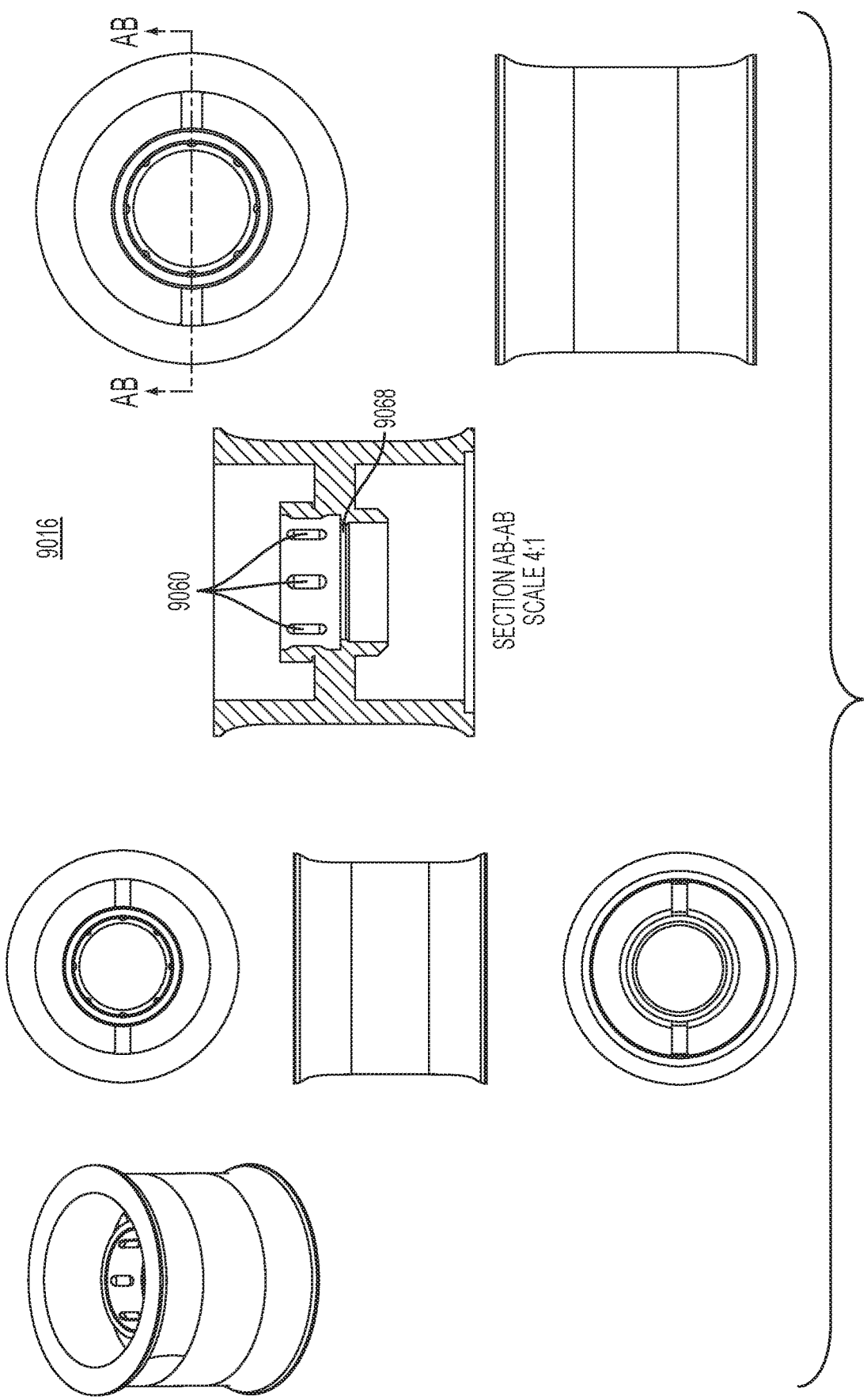
Figure 245B:
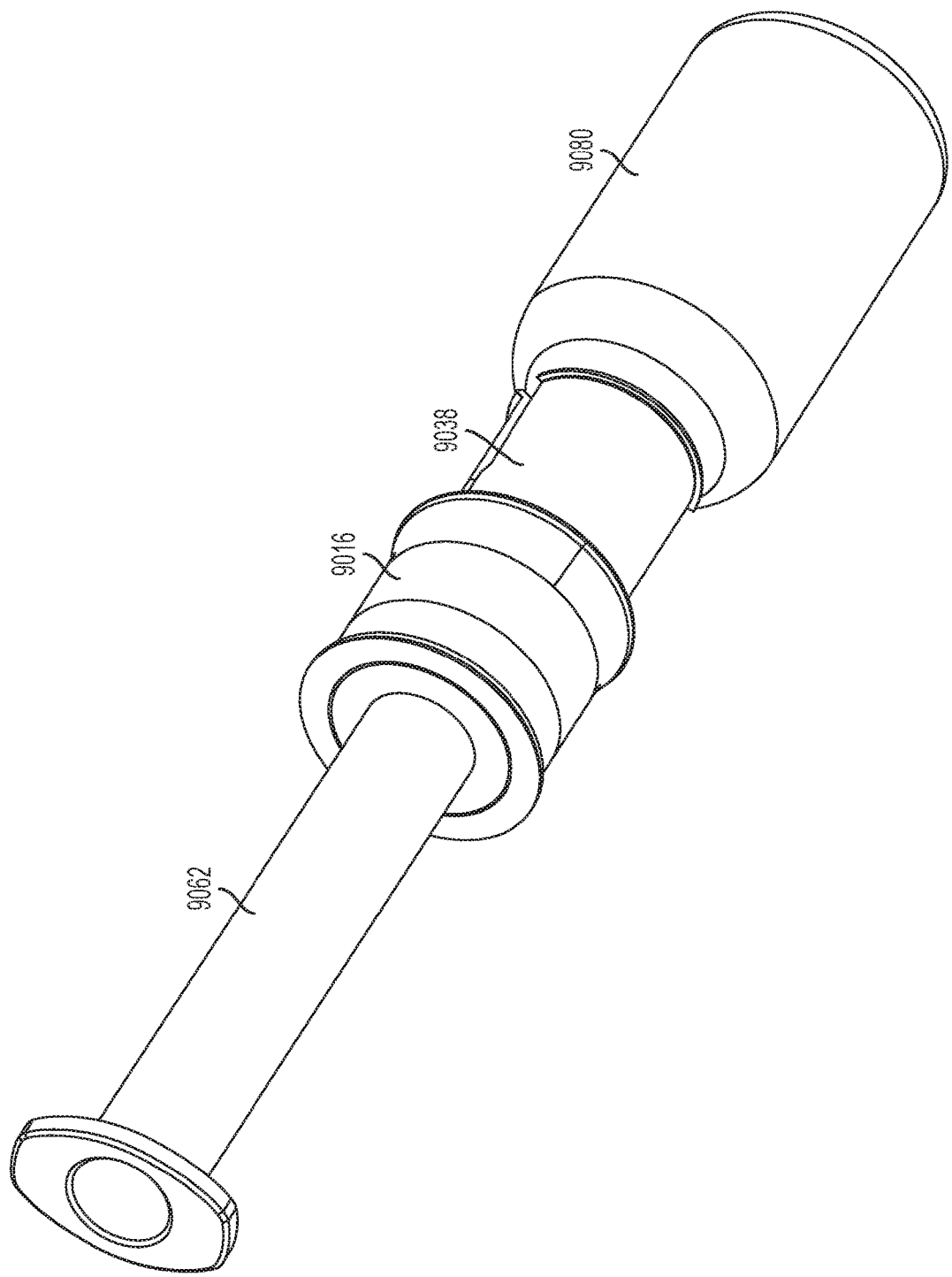
Figure 246:
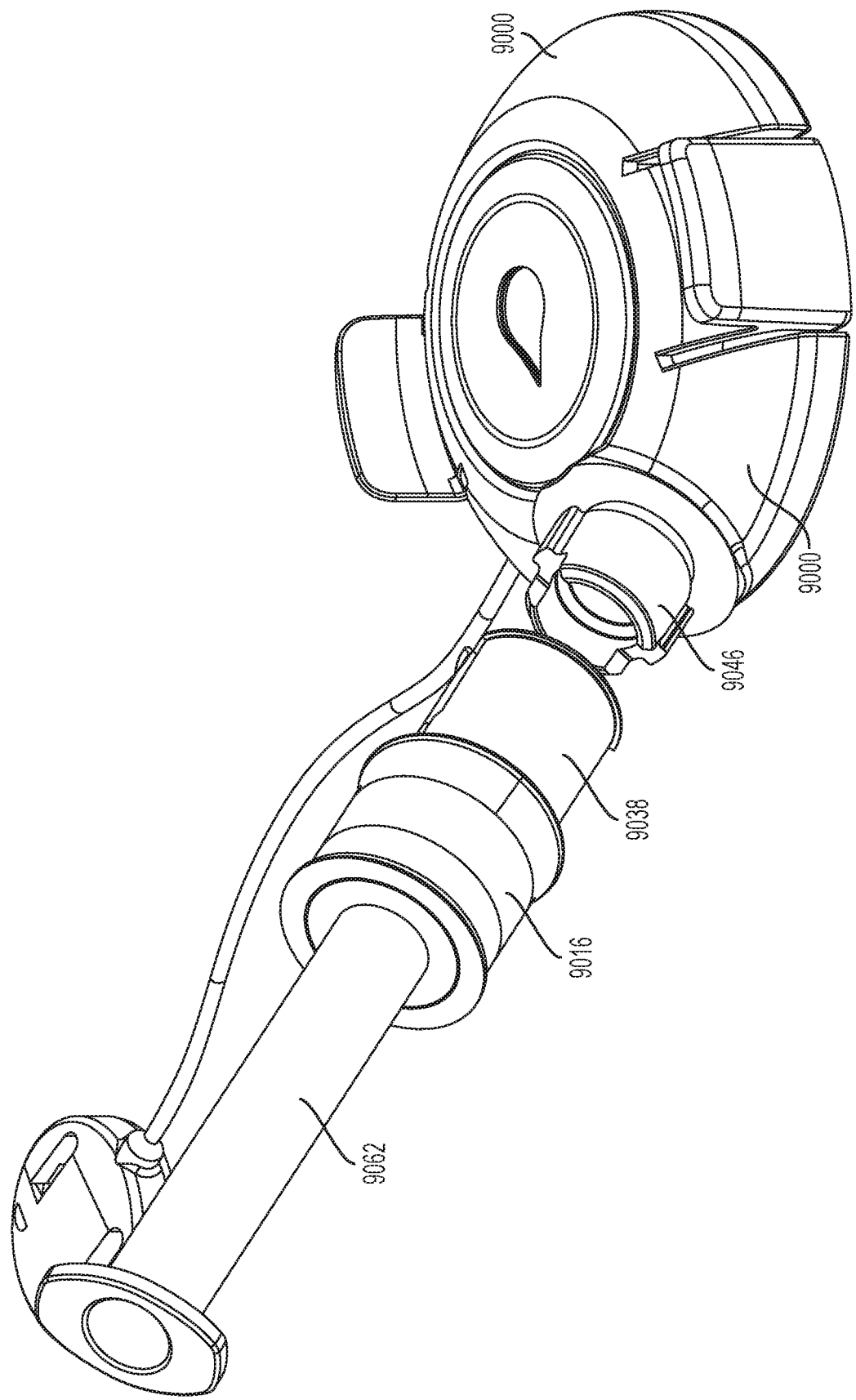
Figure 247:
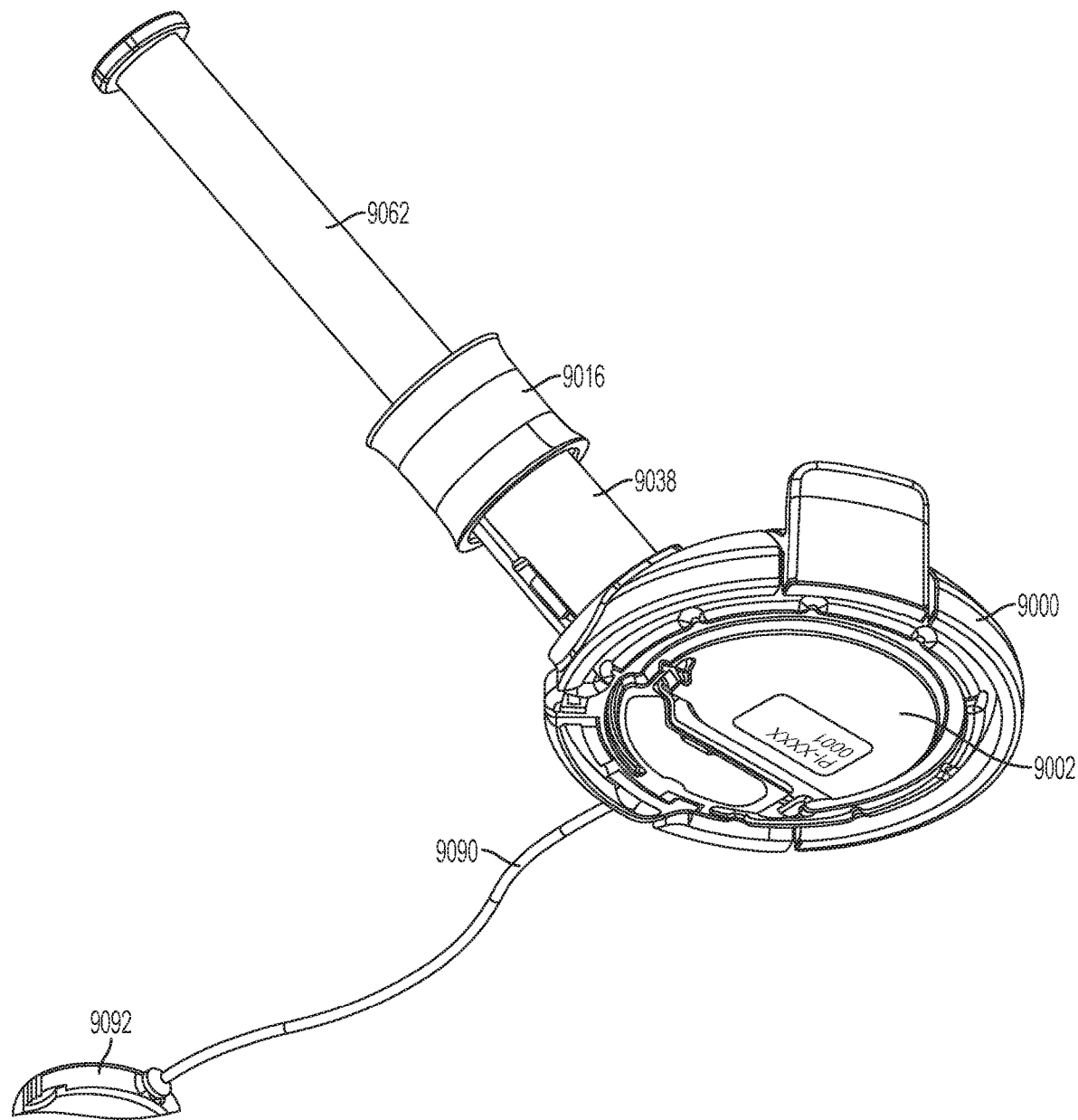
Figure 248:
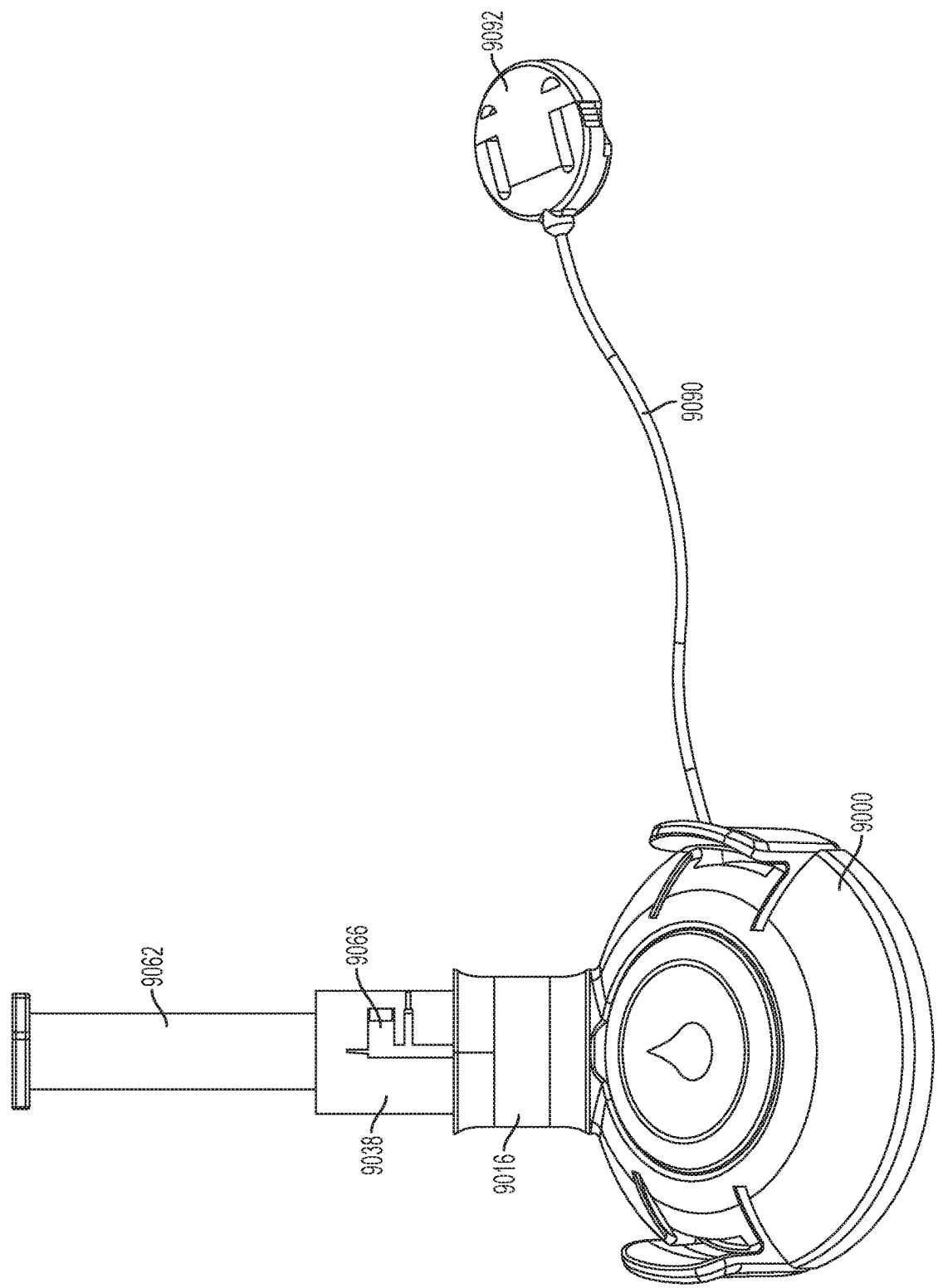
Figure 249B:
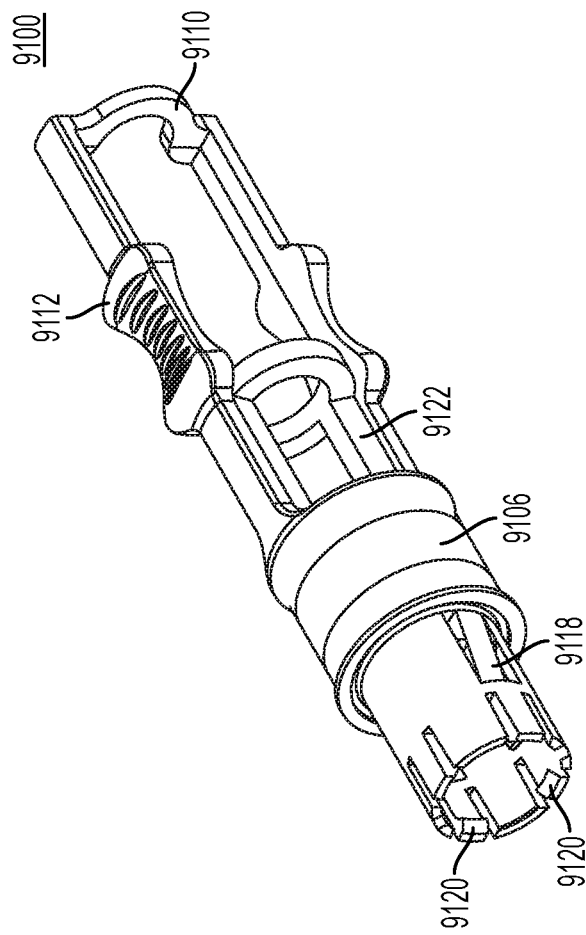
Figure 249A:
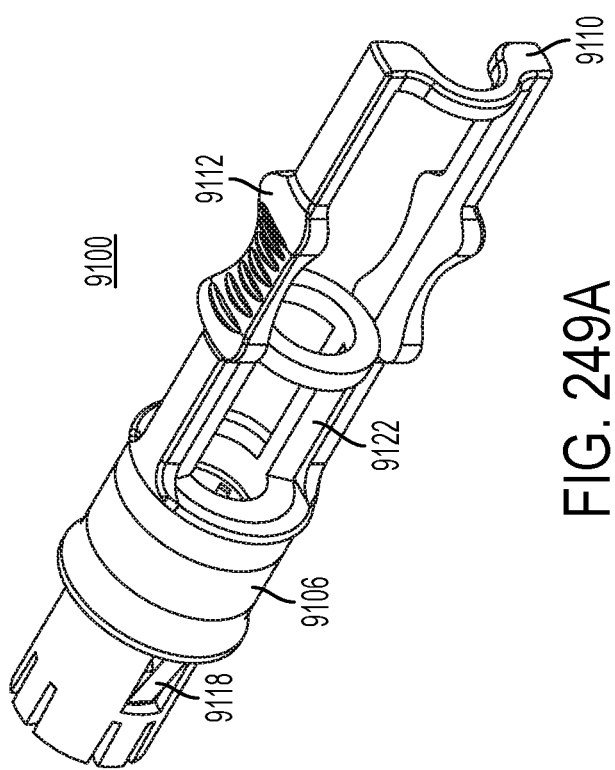
Figure 249C:
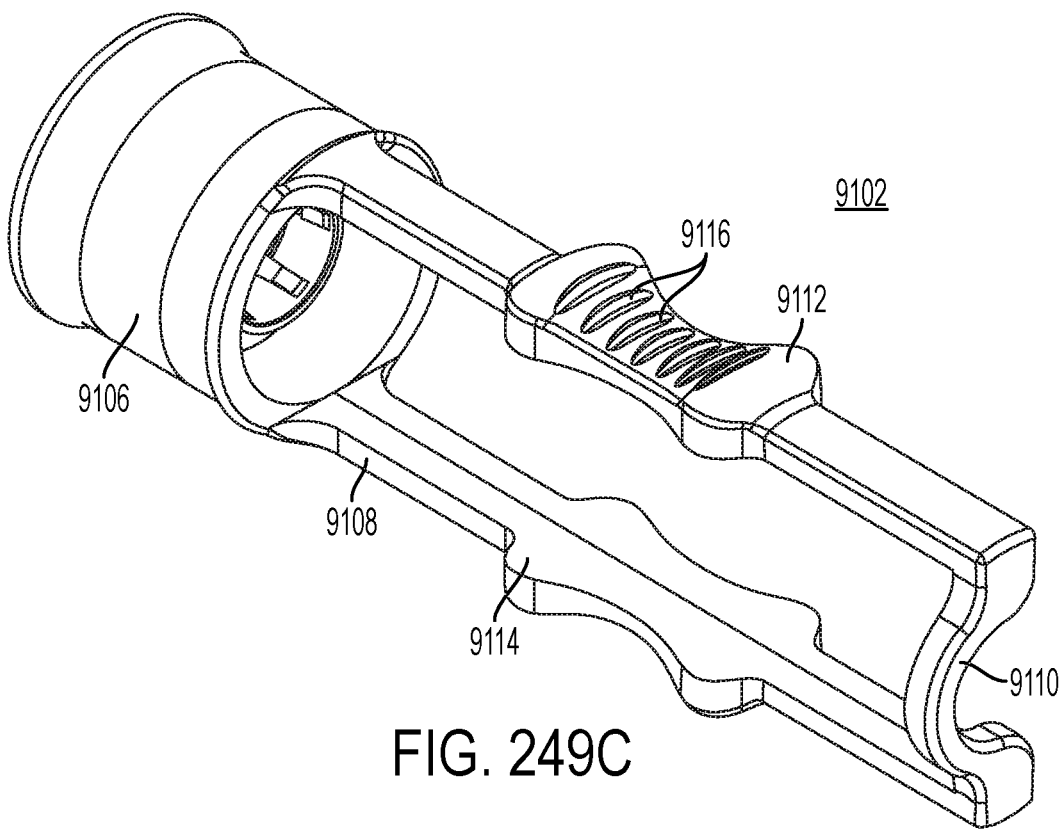
Figure 249D:
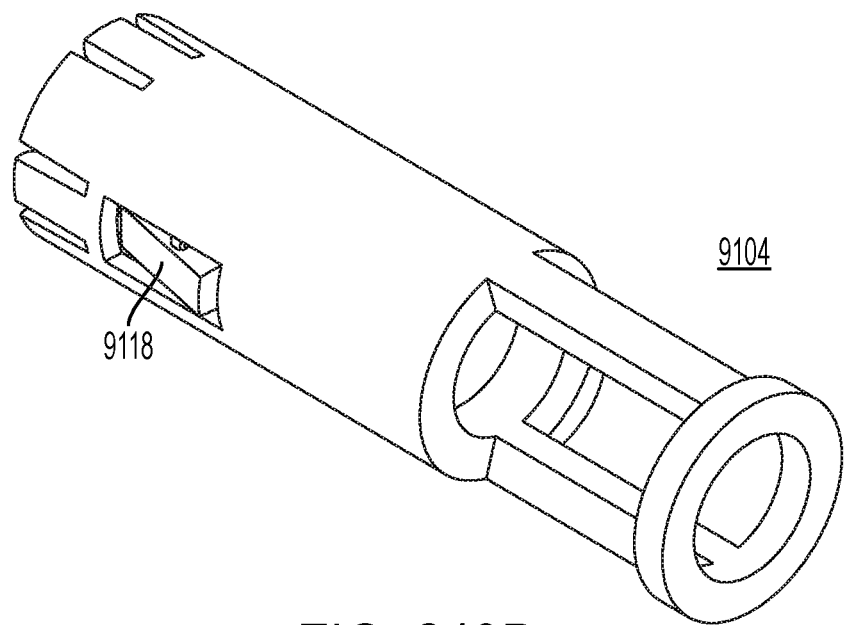
Figure 249E:
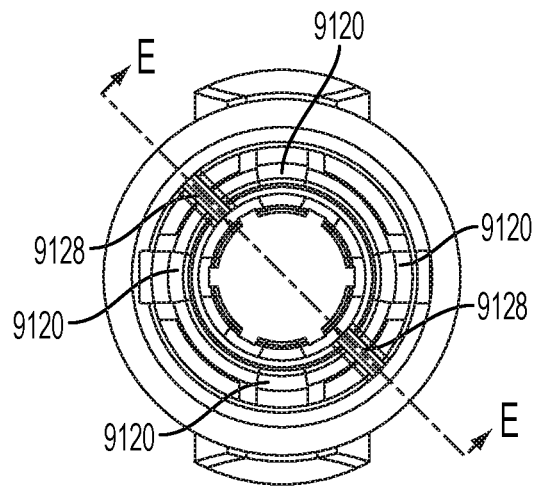
Figure 249F:
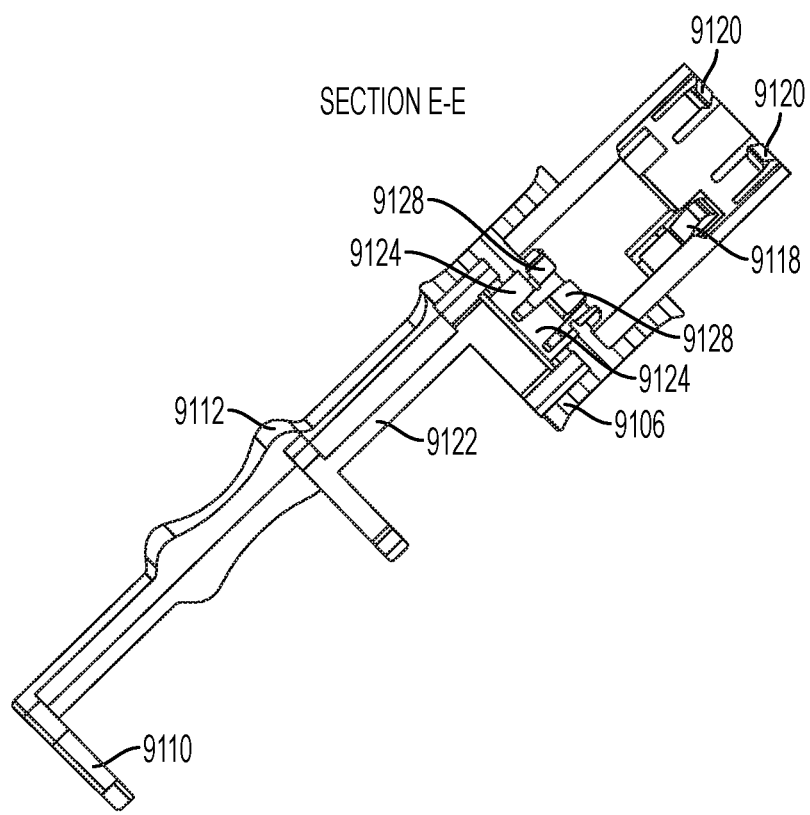
Figure 250A:
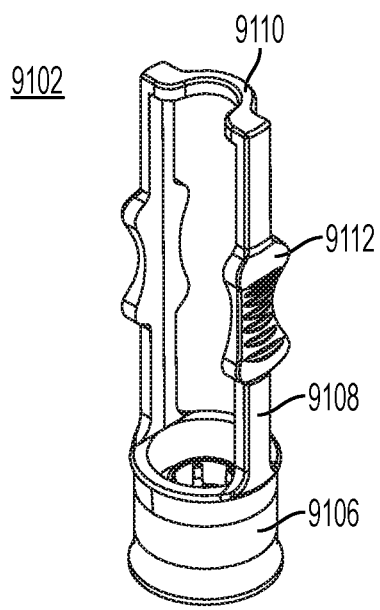
Figure 250B:
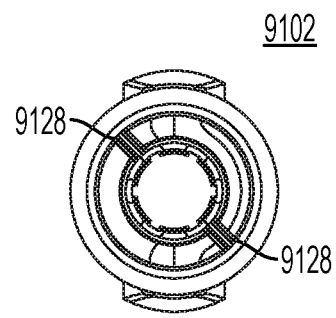
Figure 250C:
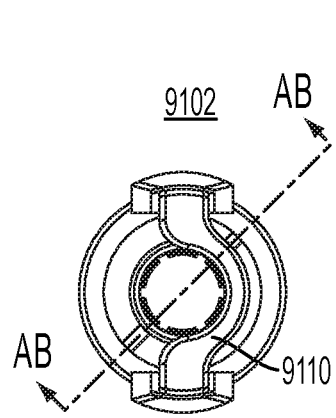
Figure 250D:
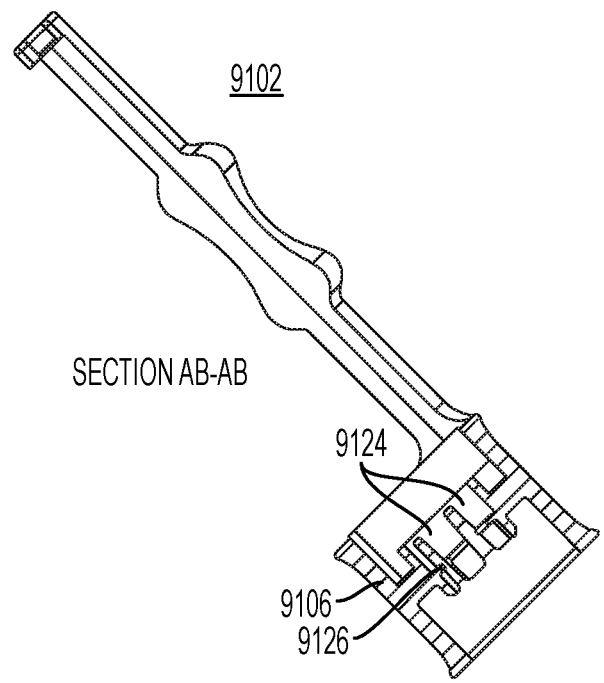
Figure 252A:
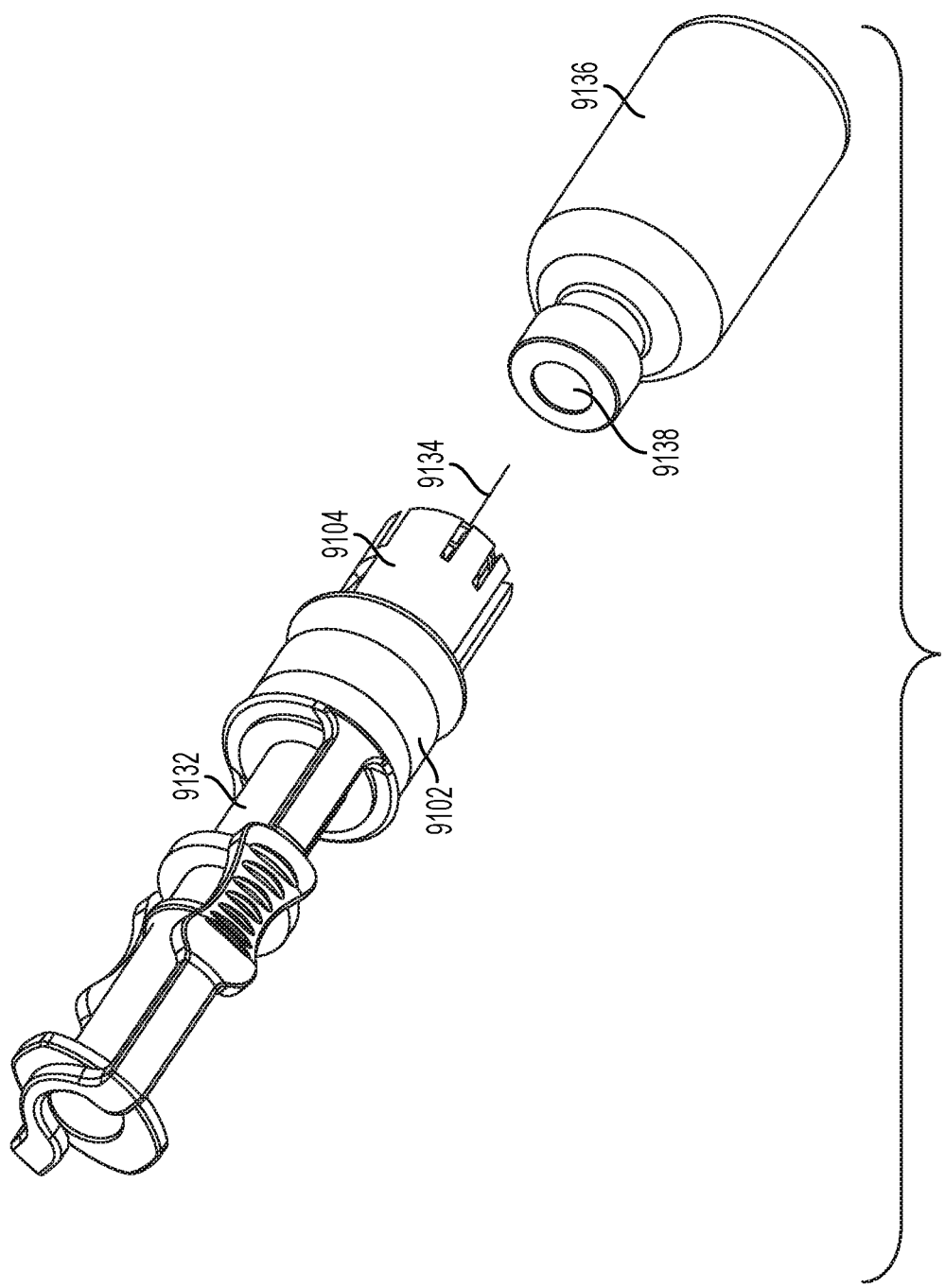
Figure 252B:
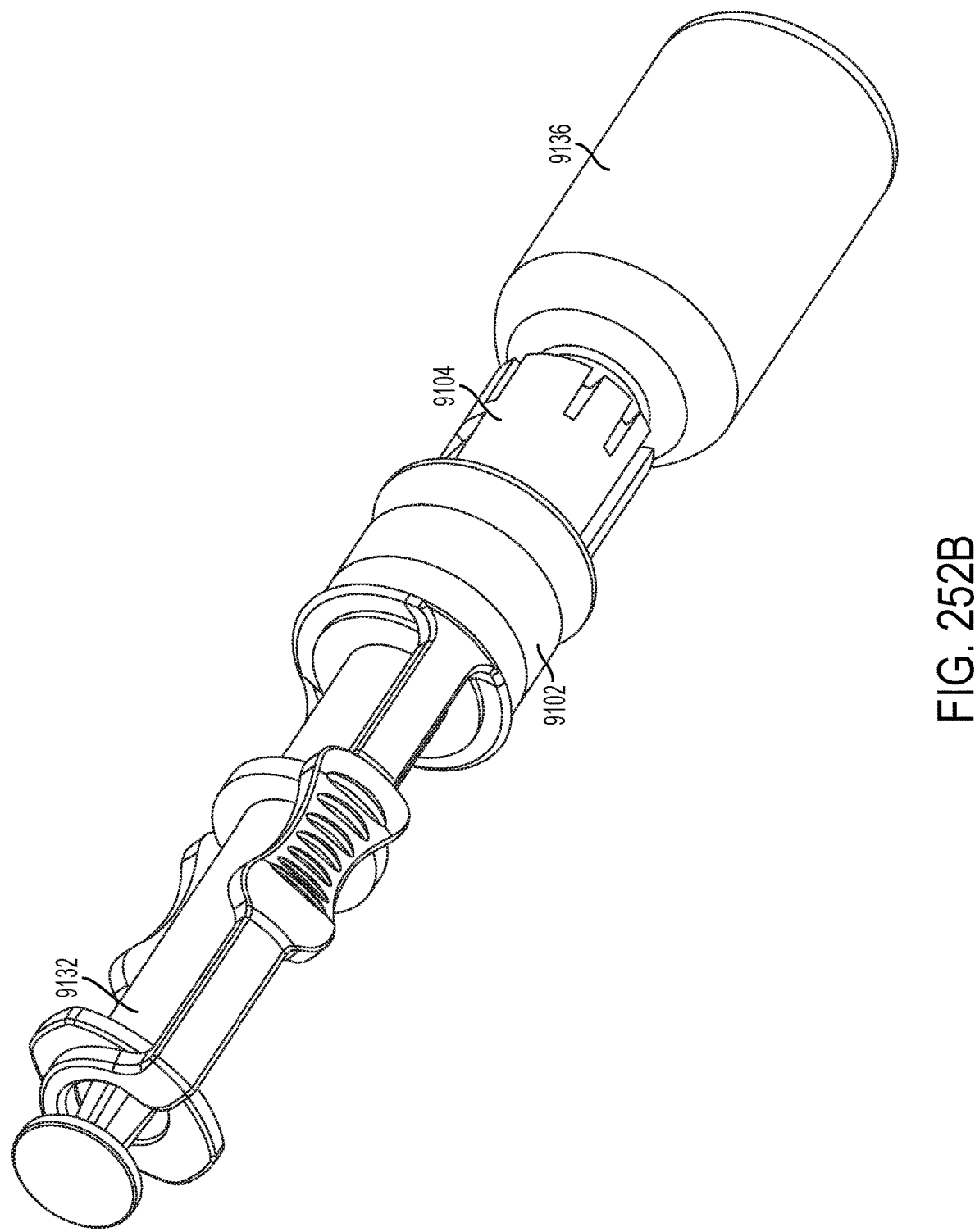
Figure 252C:
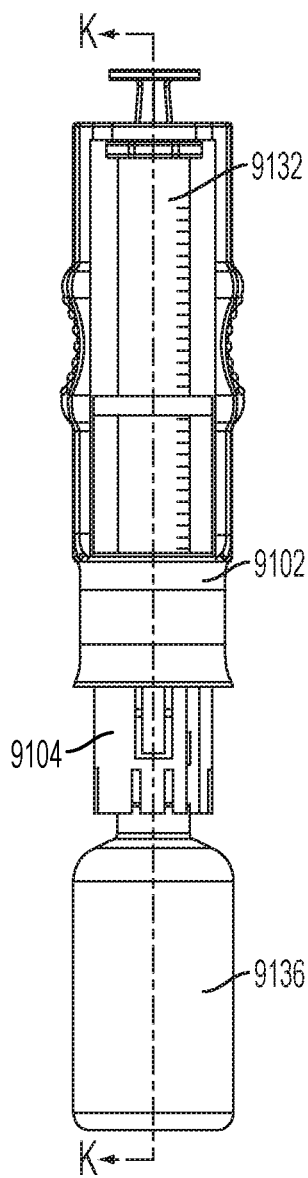
Figure 252D:
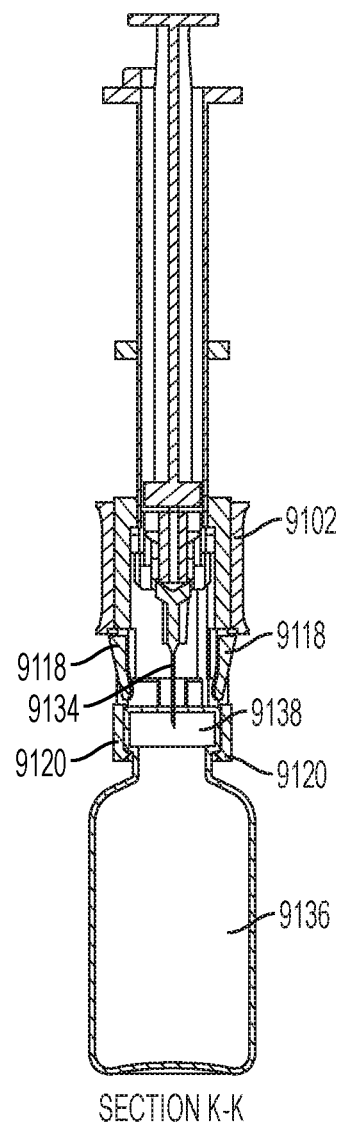
Figure 254A:
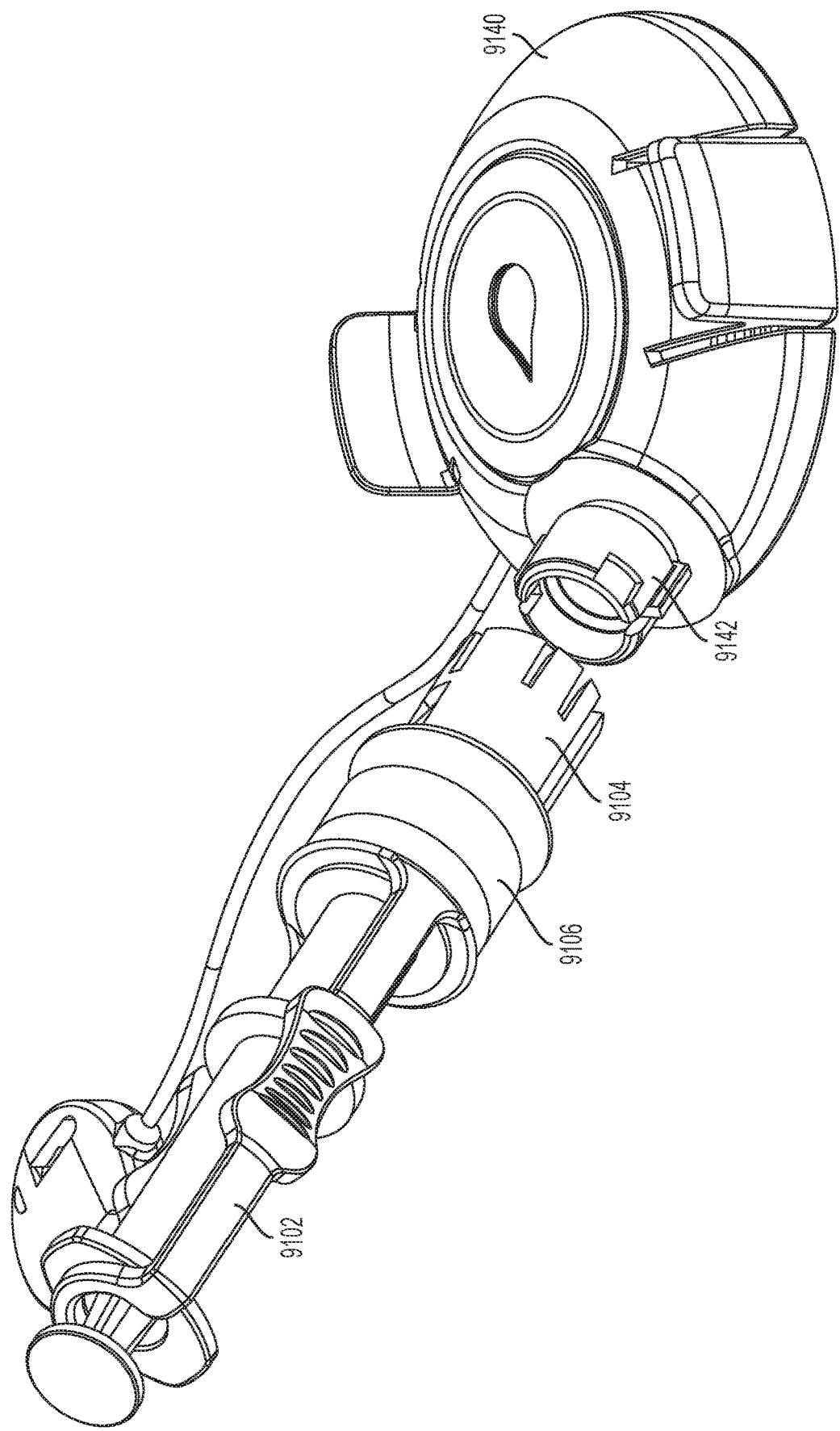
Figure 254B:
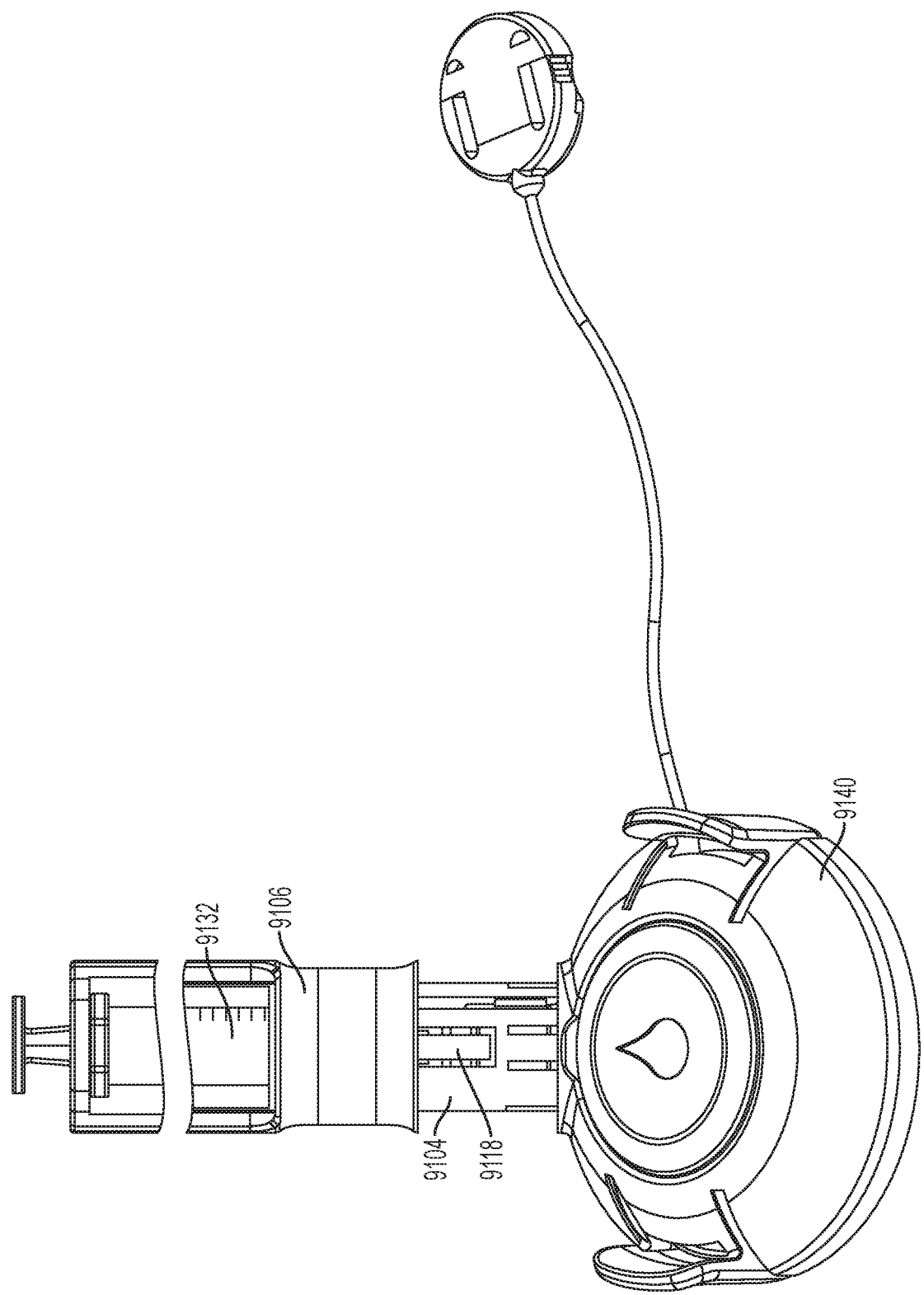
Figure 254C:
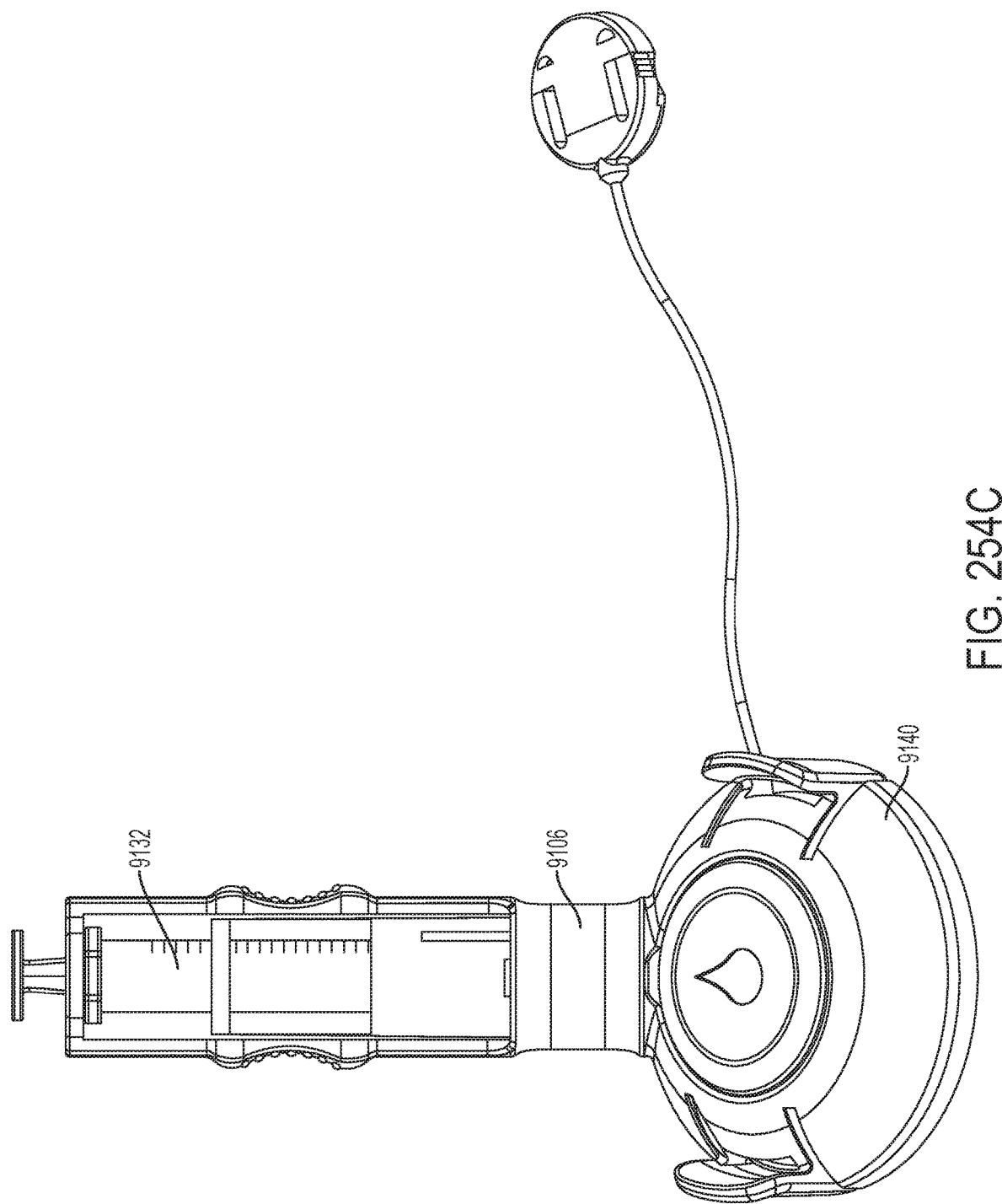
Figure 255A:
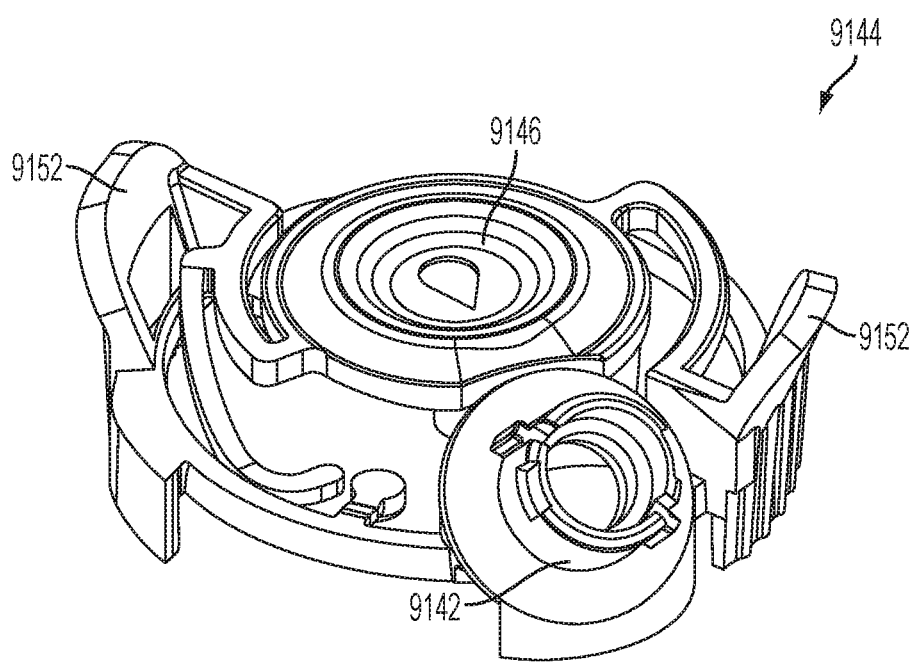
Figure 255B:
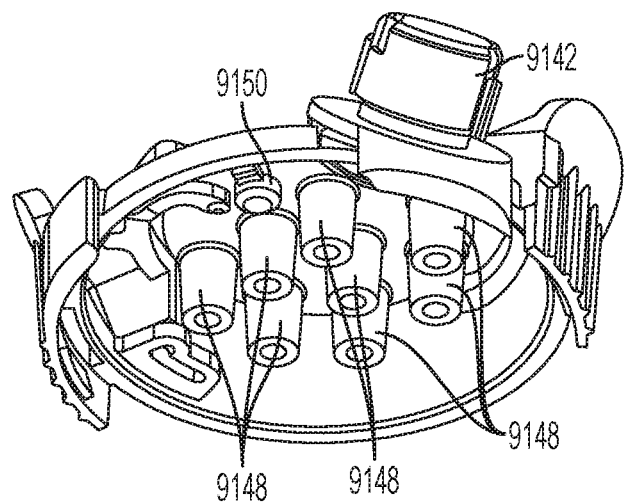
Figure 255C:
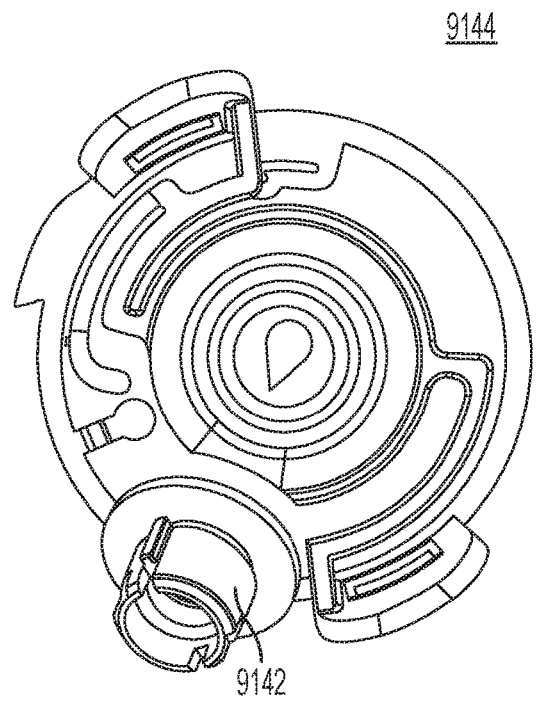
Figure 255D:
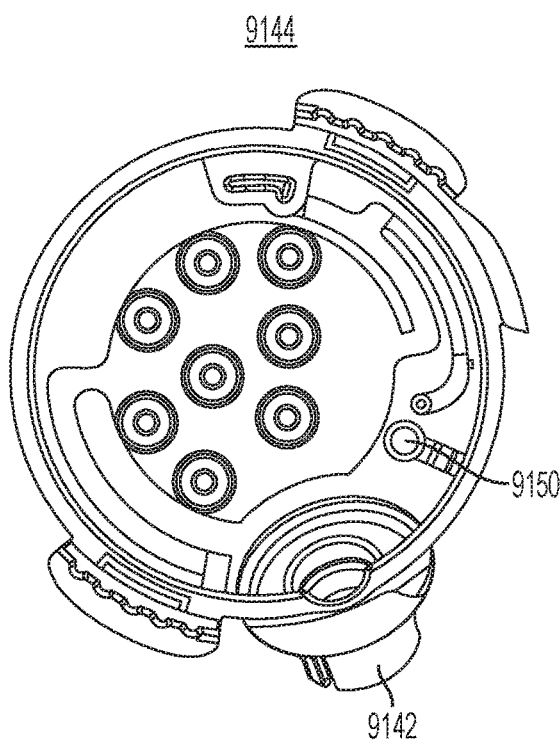
Figure 257A:
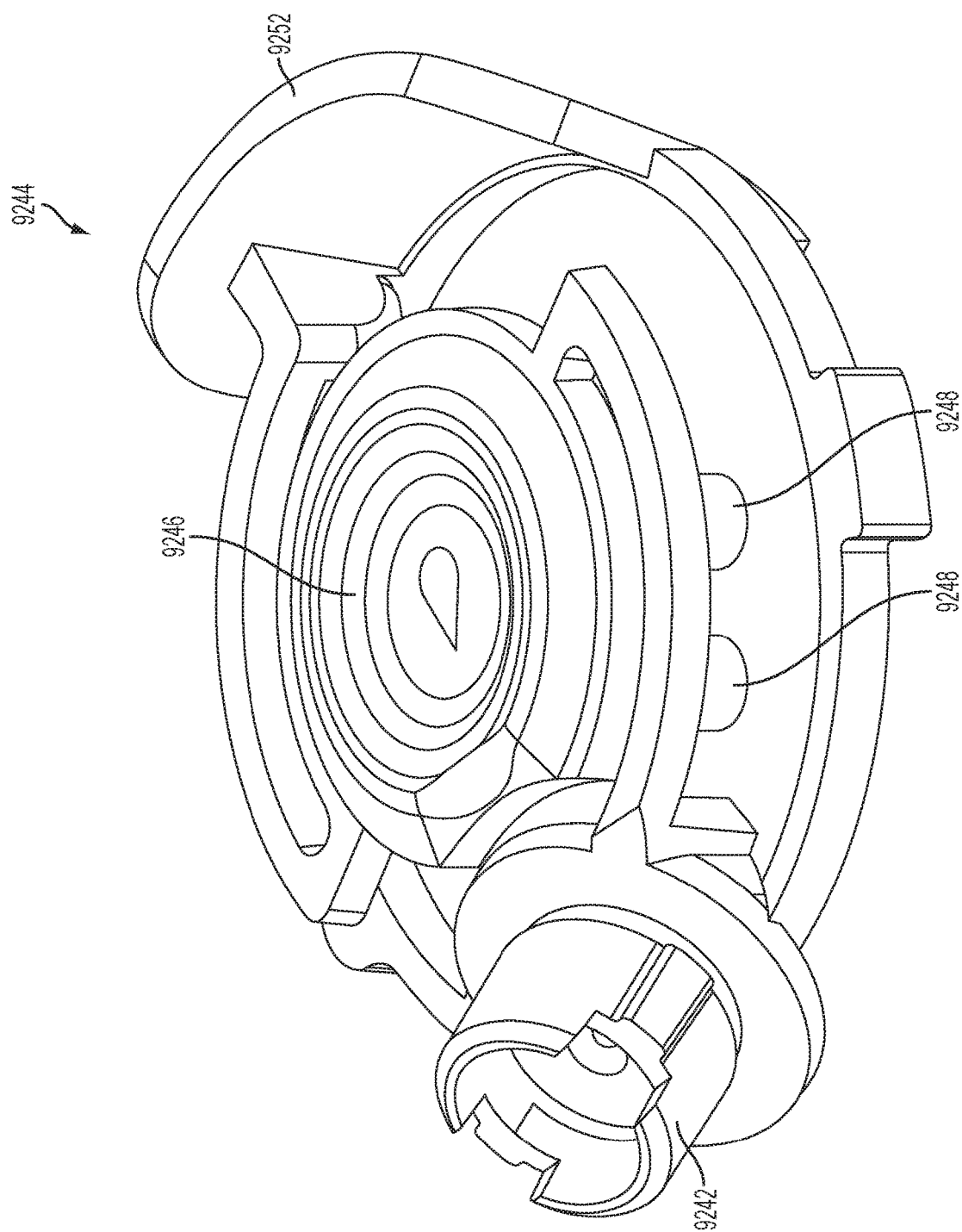
Figure 257B:
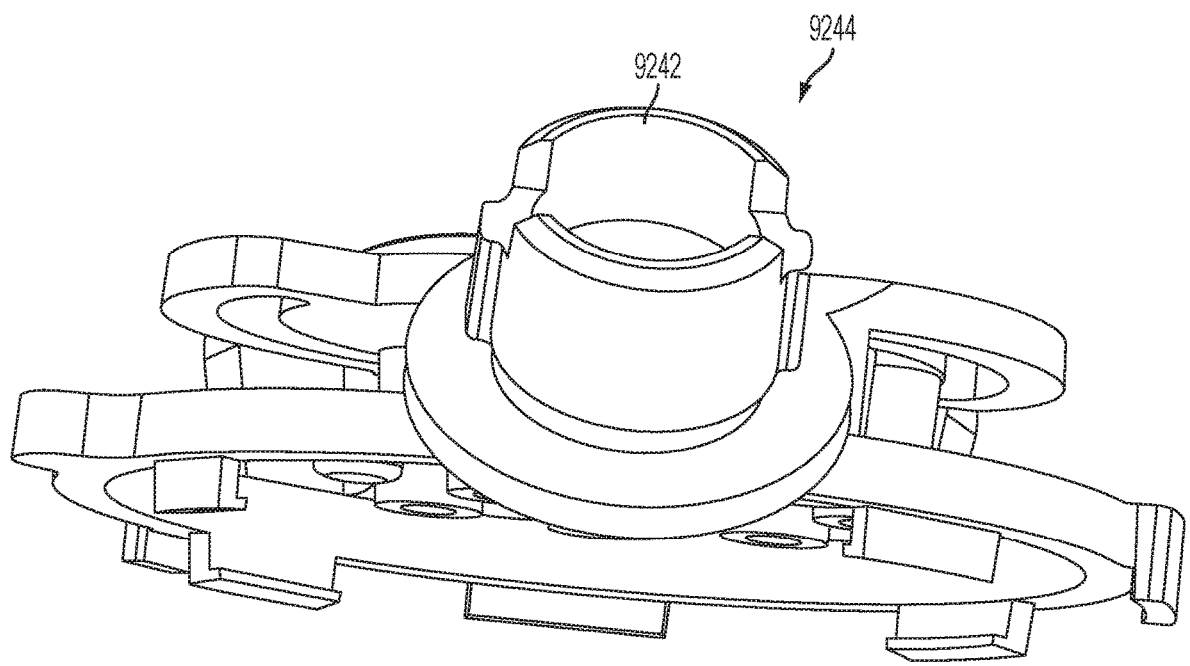
Figure 257C:
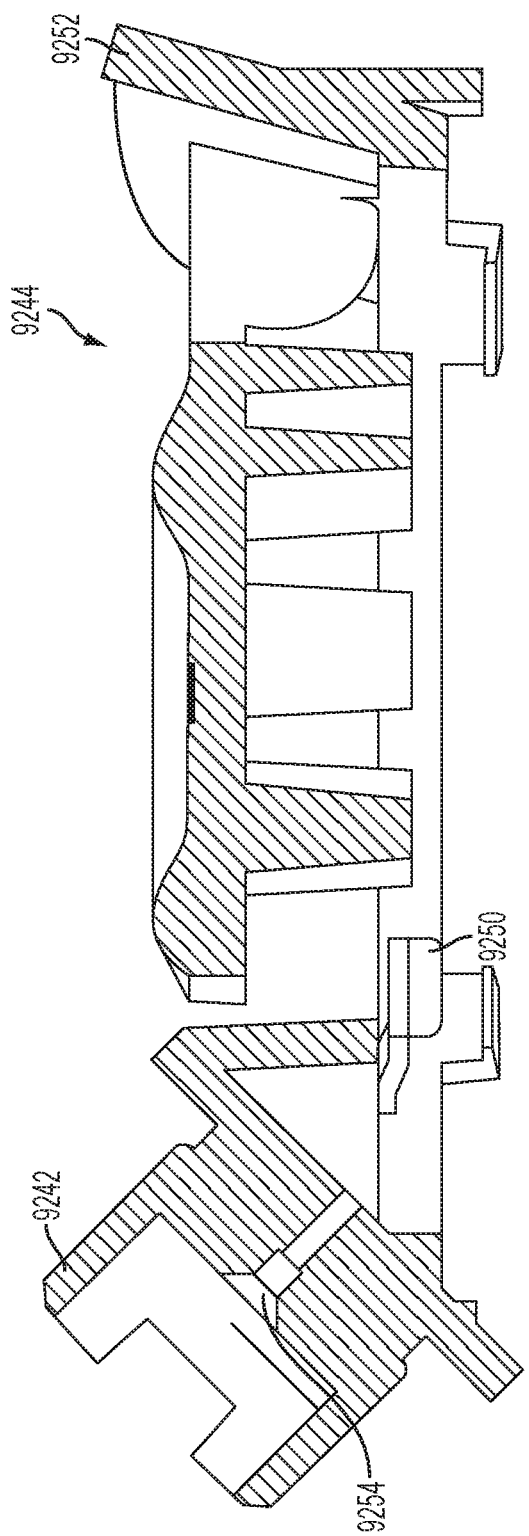
Figure 259:
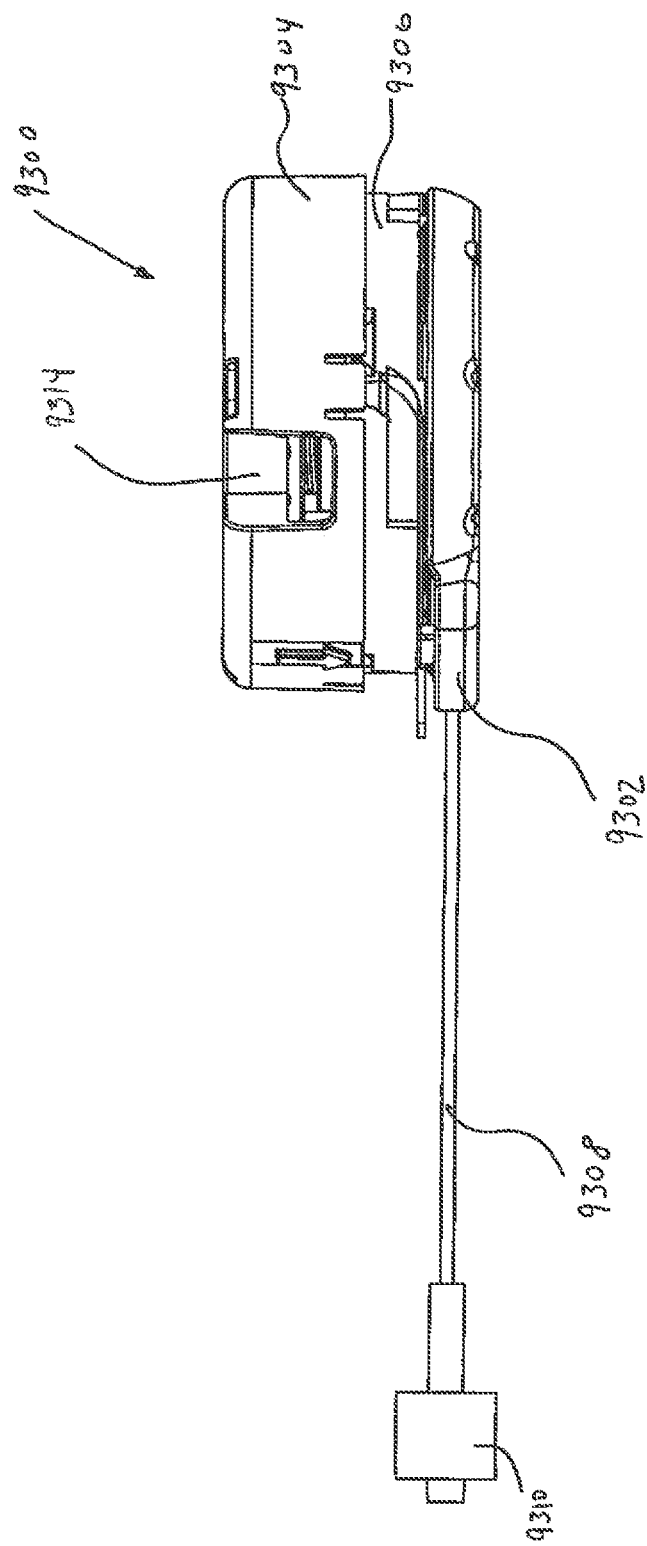
Figure 260:
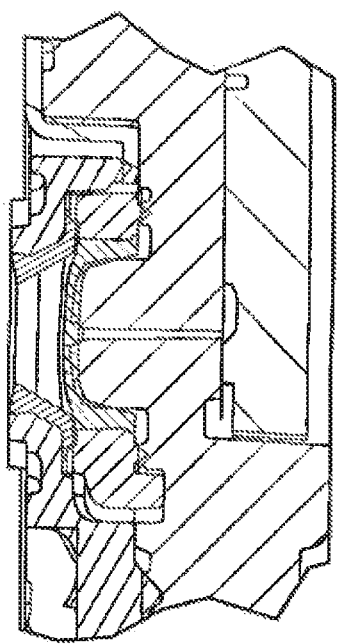
Figure 261:
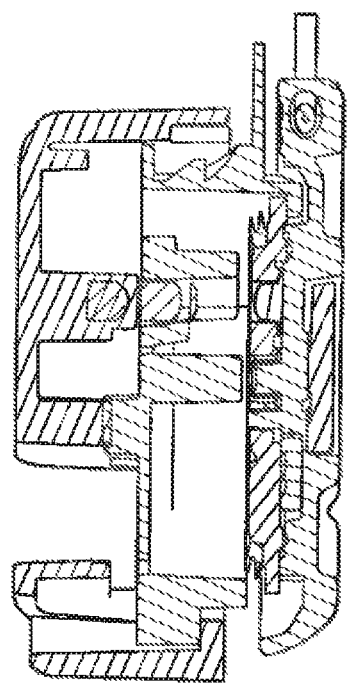
Figure 262:
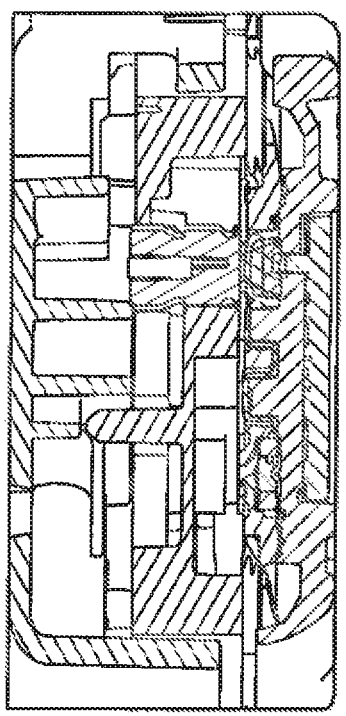
Figure 263:
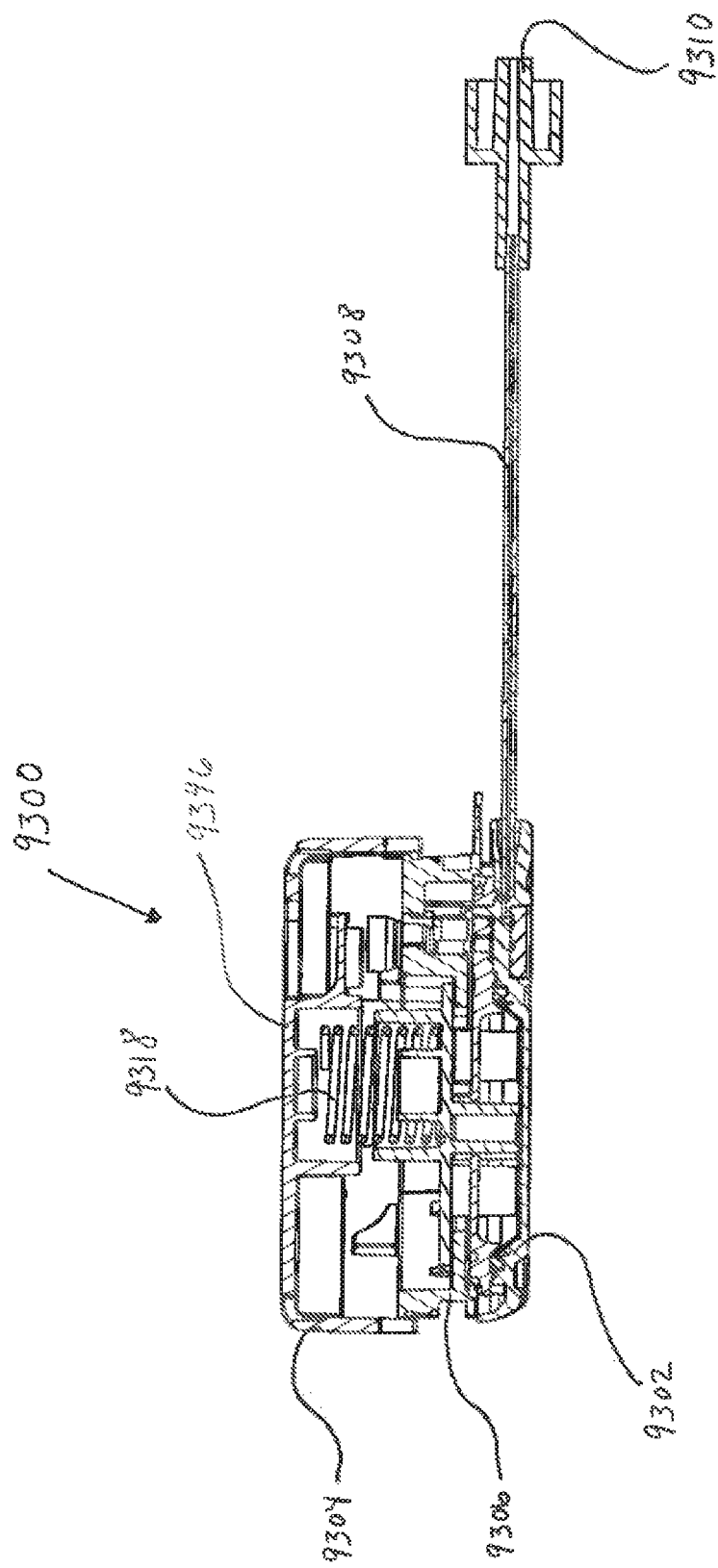
Figure 273:
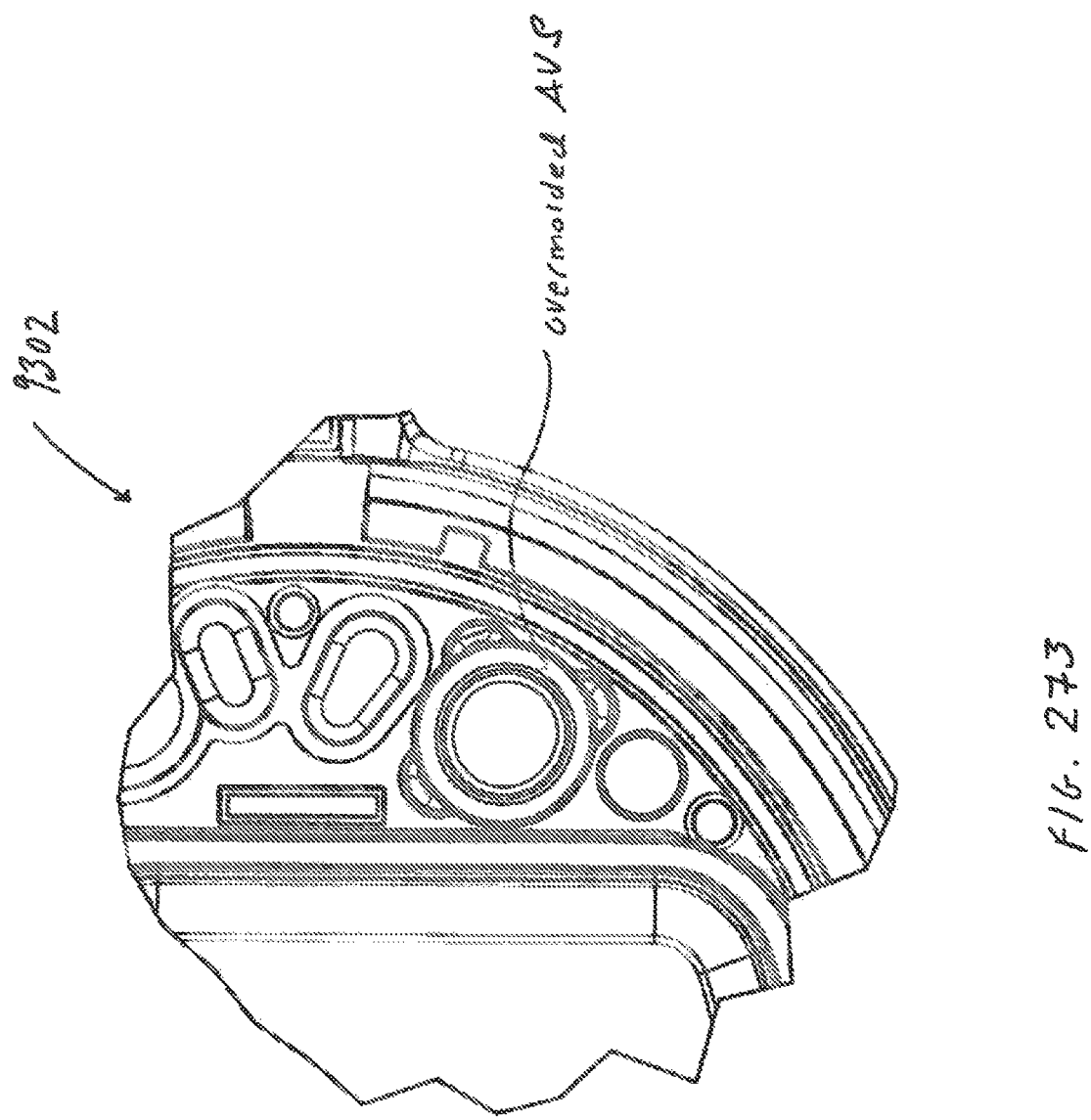
Figure 288:
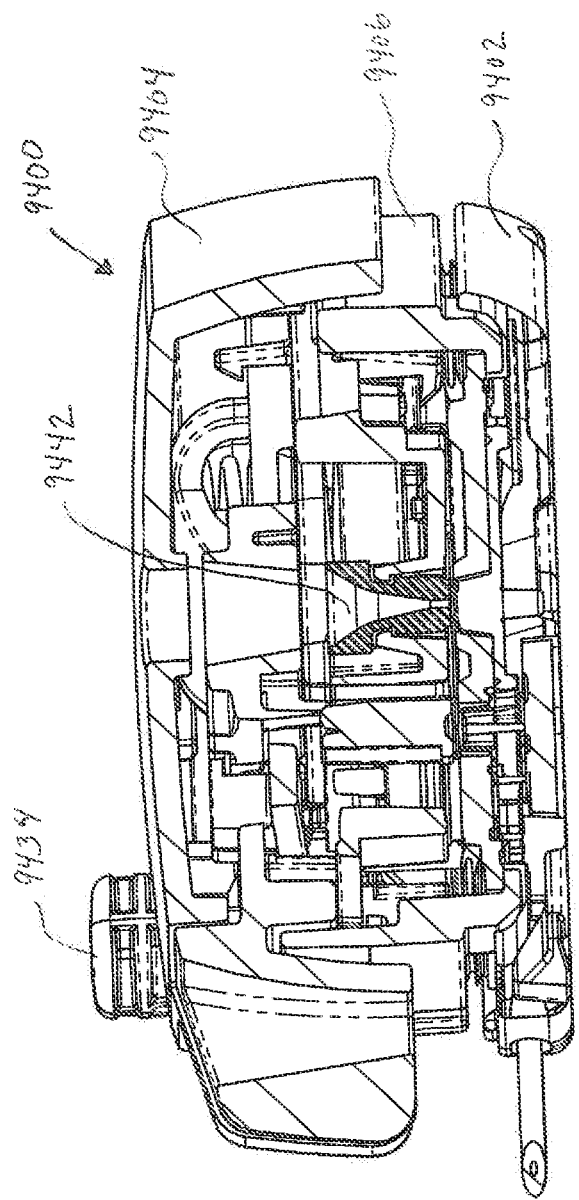

FIG. 206B an isometric top view of one embodiment of the disposable housing assembly;

FIG. 207A an isometric bottom view of one embodiment of the fill adapter;

FIG. 207B is an isometric top view of one embodiment of the fill adapter according to one embodiment;

FIGS. 208A-208B are top views of the fill adapter and disposable housing assembly in two different positions relative to one another according to one embodiment;

FIG. 209A is a top view of one embodiment of the fill adapter;

FIG. 209B is a cross sectional view of FIG. 209A taken at section "B";

FIG. 209C is a cross sectional view of FIG. 209A taken at section "C";

FIG. 210A$^1$ is a top view of one embodiment of the fill adapter and disposable housing assembly in an attached and unlocked position;

FIG. 210A is a cross sectional view of FIG. 210A$^1$ taken at section "A";

FIG. 210B$^1$ is a top view of one embodiment of the fill adapter and disposable housing assembly in an attached and unlocked position;

FIG. 210B is a cross sectional view of FIG. 210B$^1$ taken at section "B";

FIG. 210C$^1$ is a top view of one embodiment of the fill adapter and disposable housing assembly in an attached and unlocked position;

FIG. 210C is a cross sectional view of FIG. 210C$^1$ taken at section "C";

FIG. 211A is an isometric exploded view of one embodiment of the fill adapter base and filling aid;

FIG. 211B is an isometric top view of one embodiment of the of the fill adapter base and filling aid;

FIG. 211C is an isometric top view of one embodiment of the fill adapter base and filling aid, rotated from the view shown in FIG. 211B;

FIG. 212A is an isometric top view of one embodiment of the fill adapter;

FIG. 212B is an isometric top view of the embodiment of the fill adapter shown in FIG. 212A in a partially folded position;

FIG. 212C is an isometric top view of the embodiment of the fill adapter shown in FIG. 212A in a folded position;

FIG. 213A is an isometric top view of one embodiment of a disposable housing assembly without the top portion or membrane;

FIG. 213B is a magnified partial sectional view of FIG. 213A taken at section "B";

FIG. 214 is a view of a fill adapter according to one embodiment;

FIG. 215 is a bottom view of a fill adapter according to one embodiment;

FIG. 216 is a view of a fill adapter with a filling syringe and a disposable housing assembly according to one embodiment;

FIG. 217 is an exploded view of one embodiment of a fill adapter;

FIG. 218 is a view of one embodiment of a fill adapter with a view of one embodiment of a filling needle cradle;

FIG. 219 is a view of a filling syringe attached to a fill adapter according to one embodiment and a disposable housing assembly according to one embodiment;

FIGS. 220A-220F are cross sections views of one embodiment of a filling syringe and a fill adapter during the fill process according to one embodiment;

FIG. 221 is a view of one embodiment of a fill adapter together with a one embodiment of a vial, a pusher and one embodiment of a disposable housing assembly;

FIG. 222A-222G are cross sections views of one embodiment of a vial, a pusher, a fill adapter and a disposable housing assembly during the fill process according to one embodiment;

FIG. 223 is a view of one embodiment of the fill adapter together with one embodiment of the pusher, vial and disposable housing assembly;

FIG. 224 is a view of one embodiment of the fill adapter together with one embodiment of the filling syringe and disposable housing assembly;

FIG. 225 shows an embodiment of a fill adapter together connected to a disposable housing assembly, with a filling aid and filling syringe;

FIG. 226A is an underside exploded view of one embodiment of a fill adapter;

FIG. 226B is a top view exploded view of one embodiment of a fill adapter;

FIG. 227 is a cross sectional view of one embodiment of a fill adapter;

FIG. 228 is a top view of one embodiment of a disposable housing assembly;

FIG. 229 is an isometric underside view of one embodiment of a fill adapter and one embodiment of a disposable housing assembly;

FIG. 230 is an isometric underside view of one embodiment of a fill adapter attached to one embodiment of a disposable housing assembly;

FIG. 231 A is an exploded view of one embodiment of a filling aid;

FIG. 231B is an isometric view of one embodiment of a filling aid;

FIG. 231C is a cross sectional view of one embodiment of a filling aid;

FIG. 232A is an isometric view of one embodiment of a needle housing;

FIG. 232B is a cross sectional view of one embodiment of a needle housing;

FIG. 233A is an isometric view of one embodiment of a filling needle cradle;

FIG. 233B is a cross sectional view of one embodiment of a filling needle cradle;

FIG. 233C is a top view of one embodiment of a filling needle cradle;

FIG. 234 is an isometric view of a filling syringe attached to a filling aid, and a vial, according to one embodiment;

FIG. 235A is a side view of a filling syringe attached to a filling aid and a vial, according to one embodiment;

FIG. 235B is a cross sectional view of the view shown in FIG. 235A;

FIG. 236 is an isometric view of a fill adapter attached to a disposable housing assembly, and a filling syringe attached to a filling aid, according to one embodiment;

FIGS. 237-240B show cross sectional views and isometric views of one embodiment of a filling syringe, a filling aid and a fill adapter during the fill process of filling one embodiments of a disposable housing assembly, according to one embodiment;

FIG. 241A is one embodiment of a fill adapter together with an embodiment of a filling syringe and a filling aid;

FIG. 241B is an underside view of the embodiment shown in FIG. 241A;

FIG. 242A-242E are various views of a fill adapter, together with a filling syringe and a filling aid, according to one embodiment;

FIG. 243A is a top exploded view of one embodiment of a fill adapter;

FIG. 243B is a bottom exploded view of one embodiment of a fill adapter;

FIG. 244A is an exploded view of one embodiment of a filling aid;

FIGS. 244B-244C are isometric views of one embodiment of a filling aid;

FIG. 244D are various views of one embodiment of a filling aid;

FIG. 244E are various views of one embodiment of a needle housing;

FIG. 244F are various views of one embodiment of a filling needle cradle;

FIG. 245A is an isometric view of a filling syringe attached to a filling aid, also, a vial, according to one embodiment;

FIG. 245B is an isometric view of a filling syringe attached to both a filling aid and the filling aid attached to a vial, according to one embodiment;

FIG. 246 is an isometric view of a fill adapter attached to a disposable housing assembly, and a filling syringe attached to a filling aid, according to one embodiment;

FIG. 247 is an isometric view of a fill adapter attached to a disposable housing assembly and to a filling aid, which is also attached to a filling syringe, according to one embodiment;

FIG. 248 is an isometric view of one embodiment of a filling syringe, a filling aid and a fill adapter during the fill process of filling one embodiment of a disposable housing assembly, according to one embodiment;

FIGS. 249A-249B are isometric views of a filling aid according to one embodiment;

FIG. 249C is an isometric view of a filling syringe holder according to one embodiment;

FIG. 249D is an isometric view of a locking portion according to one embodiment;

FIG. 249E is bottom view of a filling aid according to one embodiment;

FIG. 249F is a cross sectional view of one embodiment of a filling aid taken at section "E" shown in FIG. 249E;

FIG. 250A is an isometric view of a filling syringe holder according to one embodiment;

FIG. 250B is a bottom view of filling syringe holder according to one embodiment;

FIG. 250C is a top view filling syringe holder according to one embodiment;

FIG. 250D is a cross sections view of one embodiment of a filling syringe holder taken at section "AB" shown in FIG. 250C;

FIG. 251A is an isometric view of one embodiment of a locking portion;

FIG. 251B is a cross sectional view of one embodiment of a locking portion;

FIG. 252A is an isometric view of a filling syringe attached to a filling aid, also, a vial, according to one embodiment;

FIG. 252B is an isometric view of a filling syringe attached to both a filling aid and the filling aid attached to a vial, according to one embodiment;

FIG. 252C is a view of a filling syringe attached to both a filling aid and the filling aid attached to a vial, according to one embodiment;

FIG. 252D is a cross sectional view of one embodiment of a filling syringe attached to both a filling aid and the filling aid attached to a vial, taken at secion "K" as shown in FIG. 252C;

FIG. 253A is an exploded view of a fill adapter and a disposable housing assembly according to one embodiment;

FIG. 253B is an isometric view of a fill adapter attached to a disposable housing assembly according to one embodiment;

FIG. 254A is an isometric view of a fill adapter attached to a disposable housing assembly, and a filling syringe attached to a filling aid, according to one embodiment;

FIG. 254B is an isometric view of a fill adapter attached to a disposable housing assembly and to a filling aid, in the locked and starting position, which is also attached to a filling syringe, according to one embodiment;

FIG. 254C is an isometric view of one embodiment of a filling syringe, a filling aid in the unlocked and filling position and a fill adapter during the fill process of filling one embodiment of a disposable housing assembly, according to one embodiment;

FIG. 255A is a to isometric view of one embodiment of a fill adapter;

FIG. 255B is a bottom isometric view of one embodiment of a fill adapter;

FIG. 255C is a top view of one embodiment of a fill adapter;

FIG. 255D is a bottom view of one embodiment of a fill adapter;

FIG. 256A is an exploded isometric view of a one embodiment of a fill adapter and one embodiment of a disposable housing assembly;

FIG. 256B is an isometric view of a one embodiment of a fill adapter attached to one embodiment of a disposable housing assembly;

FIGS. 257A-257C show various views of one embodiment of a fill adapter;

FIGS. 258-272 show various views of one embodiment of a filling aid attached to one embodiment of a disposable housing assembly;

FIG. 273 is an enlarged partial view of a disposable housing assembly showing an over molded AVS assembly;

FIGS. 274-287 show various views of one embodiment of a filling aid and a system including a filling aid and a disposable housing assembly;

FIG. 288 is a cross section of one embodiment of a filling aid and system in a fill position; and FIG. 289 is a cross section of one embodiment of a filling aid and system in a closed position.

Like reference symbols in the various drawings indicate like elements.

DETAILED DESCRIPTION OF THE PREFERRED EMBODIMENTS

Figure 1:
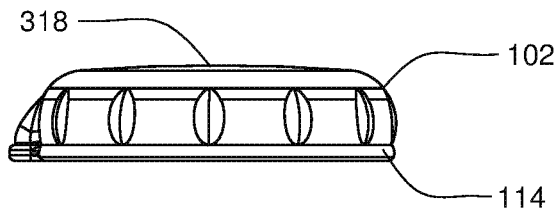
FIG. 1 is a side view of an infusion pump assembly.
Figure 2:
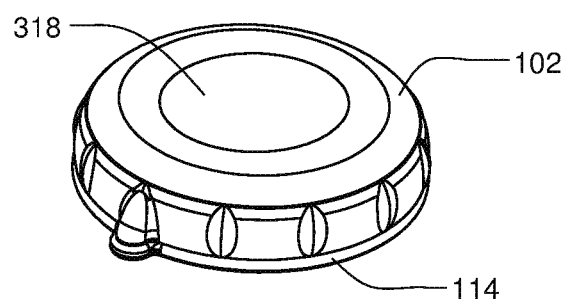
FIG. 2 is a perspective view of the infusion pump assembly of FIG. 1.
Figure 3:
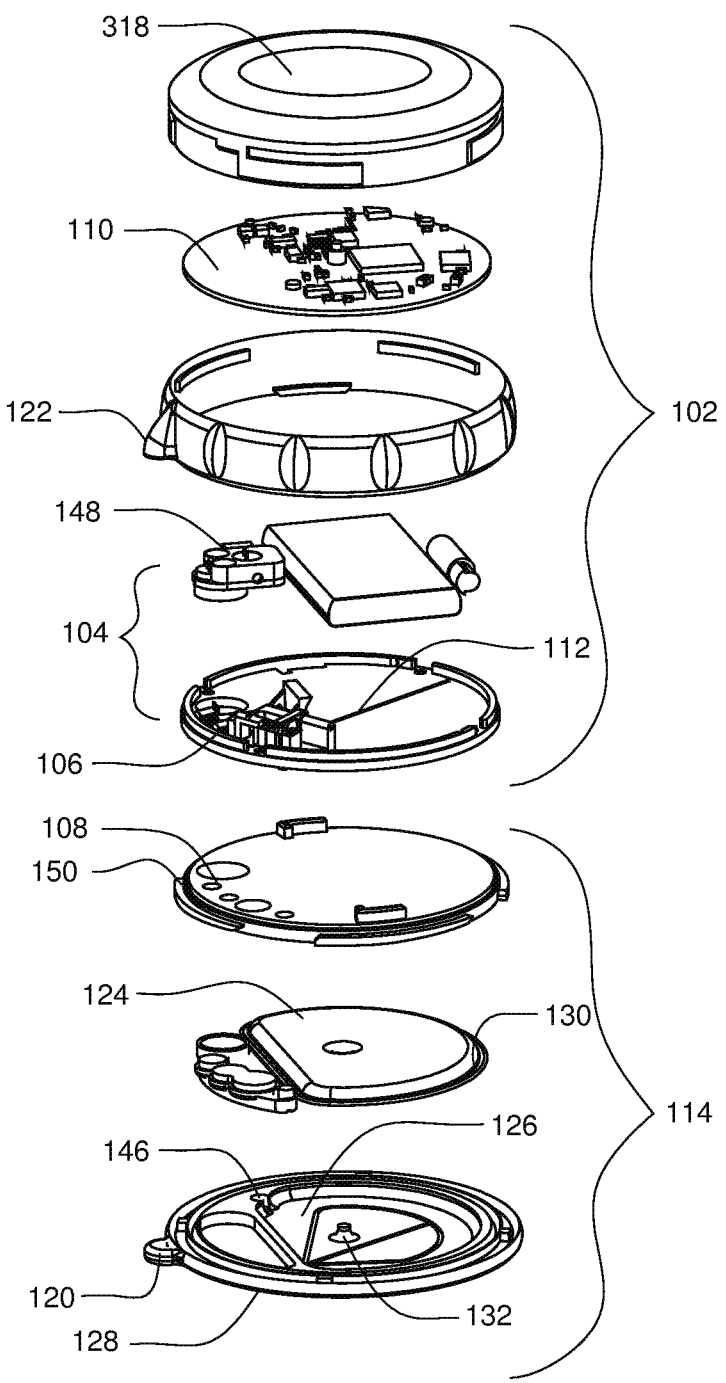
FIG. 3 is an exploded view of various components of the infusion pump assembly of FIG. 1.

Referring to FIGS. 1-3, an infusion pump assembly 100 may include a reusable housing assembly 102. Reusable housing assembly 102 may be constructed from any suitable material, such as a hard or rigid plastic, that will resist compression. For example, use of durable materials and parts may improve quality and reduce costs by providing a reusable portion that lasts longer and is more durable, providing greater protection to components disposed therein.

Reusable housing assembly 102 may include mechanical control assembly 104 having a pump assembly 106 and at least one valve assembly 108. Reusable housing assembly 102 may also include electrical control assembly 110 configured to provide one or more control signals to mechanical control assembly 104 and effectuate the basal and/or bolus delivery of an infusible fluid to a user. Disposable housing assembly 114 may include valve assembly 108 which may be configured to control the flow of the infusible fluid through a fluid path. Reusable housing assembly 102 may also include pump assembly 106 which may be configured to pump the infusible fluid from the fluid path to the user.

Electrical control assembly 110 may monitor and control the amount of infusible fluid that has been and/or is being pumped. For example, electrical control assembly 110 may receive signals from volume sensor assembly 148 and calculate the amount of infusible fluid that has just been dispensed and determine, based upon the dosage required by the user, whether enough infusible fluid has been dispensed. If enough infusible fluid has not been dispensed, electrical control assembly 110 may determine that more infusible fluid should be pumped. Electrical control assembly 110 may provide the appropriate signal to mechanical control assembly 104 so that any additional necessary dosage may be pumped or electrical control assembly 110 may provide the appropriate signal to mechanical control assembly 104 so that the additional dosage may be dispensed with the next dosage. Alternatively, if too much infusible fluid has been dispensed, electrical control assembly 110 may provide the appropriate signal to mechanical control assembly 104 so that less infusible fluid may be dispensed in the next dosage.

Mechanical control assembly 104 may include at least one shape-memory actuator 112. Pump assembly 106 and/or valve assembly 108 of mechanical control assembly 104 may be actuated by at least one shape-memory actuator, e.g., shape-memory actuator 112, which may be a shape-memory wire in wire or spring configuration. Shape memory actuator 112 may be operably connected to and activated by electrical control assembly 110, which may control the timing and the amount of heat and/or electrical energy used to actuate mechanical control assembly 104. Shape memory actuator 112 may be, for example, a conductive shape-memory alloy wire that changes shape with temperature. The temperature of shape-memory actuator 112 may be changed with a heater, or more conveniently, by application of electrical energy. Shape memory actuator 112 may be a shape memory wire constructed of nickel/titanium alloy, such as NITINOL™ or FLEXINOL®.

Infusion pump assembly 100 may include a volume sensor assembly 148 configured to monitor the amount of fluid infused by infusion pump assembly 100. For example, volume sensor assembly 148 may employ, for example, acoustic volume sensing. Acoustic volume measurement technology is the subject of U.S. Pat. Nos. 5,575,310 and 5,755,683 assigned to DEKA Products Limited Partnership, as well as U.S. Patent Application Publication Nos. US 2007/0228071 A1, US 2007/0219496 A1, US 2007/0219480 A1, US 2007/0219597 A1, the entire disclosures of all of which are incorporated herein by reference. Other alternative techniques for measuring fluid flow may also be used;

for example, Doppler-based methods; the use of Hall-effect sensors in combination with a vane or flapper valve; the use of a strain beam (for example, related to a flexible member over a fluid reservoir to sense deflection of the flexible member); the use of capacitive sensing with plates; or thermal time of flight methods. One such alternative technique is disclosed in U.S. patent application Ser. No. 11/704, 899, entitled Fluid Delivery Systems and Methods, filed 9 Feb. 2007, the entire disclosure of which is incorporated herein by reference. Infusion pump assembly 100 may be configured so that the volume measurements produced by volume sensor assembly 148 may be used to control, through a feedback loop, the amount of infusible fluid that is infused into the user.

Infusion pump assembly 100 may further include a disposable housing assembly 114. For example, disposable housing assembly 114 may be configured for a single use or for use for a specified period of time, e.g., three days or any other amount of time. Disposable housing assembly 114 may be configured such that any components in infusion pump assembly 100 that come in contact with the infusible fluid are disposed on and/or within disposable housing assembly 114. For example, a fluid path or channel including a reservoir, may be positioned within disposable housing assembly 114 and may be configured for a single use or for a specified number of uses before disposal. The disposable nature of disposable housing assembly 114 may improve sanitation of infusion pump assembly 100.

Figure 4:
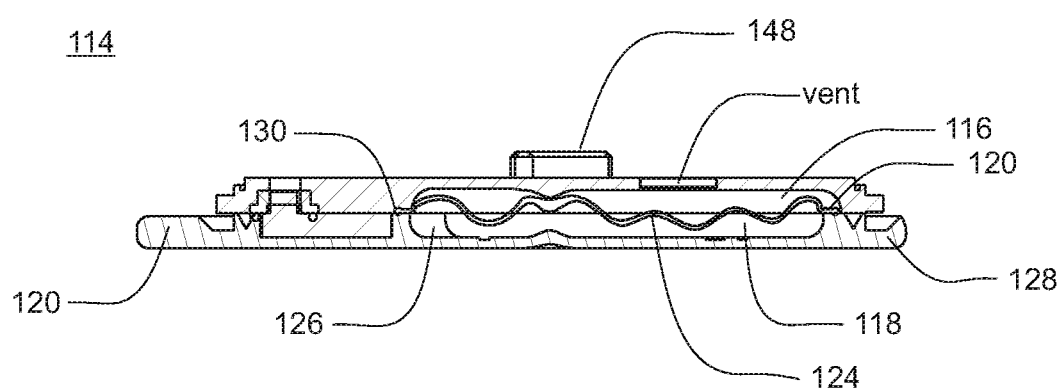
FIG. 4 is a cross-sectional view of the disposable housing assembly of the infusion pump assembly of FIG. 1.

Referring also to FIG. 4, disposable housing assembly 114 may be configured to releasably engage reusable housing assembly 102, and includes a cavity 116 that has a reservoir 118 for receiving an infusible fluid (not shown), e.g., insulin. Such releasable engagement may be accomplished by a screw-on, a twist-lock or a compression fit configuration, for example. Disposable housing assembly 114 and/or reusable housing assembly 102 may include an alignment assembly configured to assist in aligning disposable housing assembly 114 and reusable housing assembly 102 for engagement in a specific orientation. Similarly, base nub 120 and top nub 122 may be used as indicators of alignment and complete engagement.

Cavity 116 may be at least partially formed by and integral to disposable housing assembly 114. Cavity 116 may include a membrane assembly 124 for at least partially defining reservoir 118. Reservoir 118 may be further defined by disposable housing assembly 114, e.g., by a recess 126 formed in base portion 128 of disposable housing assembly 114. For example, membrane assembly 124 may be disposed over recess 126 and attached to base portion 128, thereby forming reservoir 118. Membrane assembly 124 may be attached to base portion 128 by conventional means, such as gluing, heat sealing, and/or compression fitting, such that a seal 130 is formed between membrane assembly 124 and base portion 128. Membrane assembly 124 may be flexible and the space formed between membrane assembly 124 and recess 126 in base portion 128 may define reservoir 118. Reservoir 118 may be non-pressurized and in fluid communication with a fluid path (not shown). Membrane assembly 124 may be at least partially collapsible and cavity 116 may include a vent assembly, thereby advantageously preventing the buildup of a vacuum in reservoir 118 as the infusible fluid is delivered from reservoir 118 to the fluid path. In a preferred embodiment, membrane assembly 124 is fully collapsible, thus allowing for the complete delivery of the infusible fluid. Cavity 116 may be configured to provide sufficient space to ensure there is always some air space even when reservoir 118 is filled with infusible fluid.

The membranes and reservoirs described herein may be made from materials including but not limited to silicone, NITRILE, and any other material having desired resilience and properties for functioning as described herein. Additionally, other structures could serve the same purpose.

The use of a partially collapsible non pressurized reservoir may advantageously prevent the buildup of air in the reservoir as the fluid in the reservoir is depleted. Air buildup in a vented reservoir could prevent fluid egress from the reservoir, especially if the system is tilted so that an air pocket intervenes between the fluid contained in the reservoir and the septum of the reservoir. Tilting of the system is expected during normal operation as a wearable device.

Reservoir 118 may be conveniently sized to hold an insulin supply sufficient for delivery over one or more days. For example, reservoir 118 may hold about 1.00 to 3.00 ml of insulin. A 3.00 ml insulin reservoir may correspond to approximately a three day supply for about 90% of potential users. In other embodiments, reservoir 118 may be any size or shape and may be adapted to hold any amount of insulin or other infusible fluid. In some embodiments, the size and shape of cavity 116 and reservoir 118 is related to the type of infusible fluid that cavity 116 and reservoir 118 are adapted to hold.

Disposable housing assembly 114 may include a support member 132 (FIG. 3) configured to prevent accidental compression of reservoir 118. Compression of reservoir 118 may result in an unintentional dosage of infusible fluid being forced through the fluid path to the user. In a preferred embodiment, reusable housing assembly 102 and disposable housing assembly 114 may be constructed of a rigid material that is not easily compressible. However, as an added precaution, support member 132 may be included within disposable housing assembly 114 to prevent compression of infusion pump assembly 100 and cavity 116 therein. Support member 132 may be a rigid projection from base portion 128. For example, support member 132 may be disposed within cavity 116 and may prevent compression of reservoir 118.

As discussed above, cavity 116 may be configured to provide sufficient space to ensure there is always some air space even when reservoir 118 is filled with infusible fluid. Accordingly, in the event that infusion pump assembly 100 is accidentally compressed, the infusible fluid may not be forced through cannula assembly 136 (e.g., shown in FIG. 9).

Cavity 116 may include a septum assembly 146 (FIG. 3) configured to allow reservoir 118 to be filled with the infusible fluid. Septum assembly 146 may be a conventional septum made from rubber or plastic and have a one-way fluid valve configured to allow a user to fill reservoir 118 from a syringe or other filling device. In some embodiments, septum 146 may be located on the top of membrane assembly 124. In these embodiments, cavity 116 may include a support structure (e.g., support member 132 in FIG. 3) for supporting the area about the back side of the septum so as to maintain the integrity of the septum seal when a needle is introducing infusible fluid into cavity 116. The support structure may be configured to support the septum while still allowing the introduction of the needle for introducing infusible fluid into cavity 116.

Infusion pump assembly 100 may include an overfill prevention assembly (not shown) that may e.g., protrude into cavity 116 and may e.g., prevent the overfilling of reservoir 118.

In some embodiments, reservoir 118 may be configured to be filled a plurality of times. For example, reservoir 118 may be refillable through septum assembly 146. As infusible fluid may be dispensed to a user, electronic control assembly 110 may monitor the fluid level of the infusible fluid in reservoir 118. When the fluid level reaches a low point, electronic control assembly 110 may provide a signal, such as a light or a vibration, to the user that reservoir 118 needs to be refilled. A syringe, or other filling device, may be used to fill reservoir 118 through septum 146.

Reservoir 118 may be configured to be filled a single time. For example, a refill prevention assembly (not shown) may be utilized to prevent the refilling of reservoir 118, such that disposable housing assembly 114 may only be used once. The refill prevention assembly (not shown) may be a mechanical device or an electro-mechanical device. For example, insertion of a syringe into septum assembly 146 for filling reservoir 118 may trigger a shutter to close over septum 146 after a single filling, thus preventing future access to septum 146. Similarly, a sensor may indicate to electronic control assembly 110 that reservoir 118 has been filled once and may trigger a shutter to close over septum 146 after a single filling, thus preventing future access to septum 146. Other means of preventing refilling may be utilized and are considered to be within the scope of this disclosure.

As discussed above, disposable housing assembly 114 may include septum assembly 146 that may be configured to allow reservoir 118 to be filled with the infusible fluid. Septum assembly 146 may be a conventional septum made from rubber or any other material that may function as a septum, or, in other embodiments, septum assembly 146 may be, but is not limited to, a plastic, or other material, one-way fluid valve. In various embodiments, including the exemplary embodiment, septum assembly 146 is configured to allow a user to fill reservoir 118 from a syringe or other filling device. Disposable housing assembly 114 may include a septum access assembly that may be configured to limit the number of times that the user may refill reservoir 118.

Figure 5A:
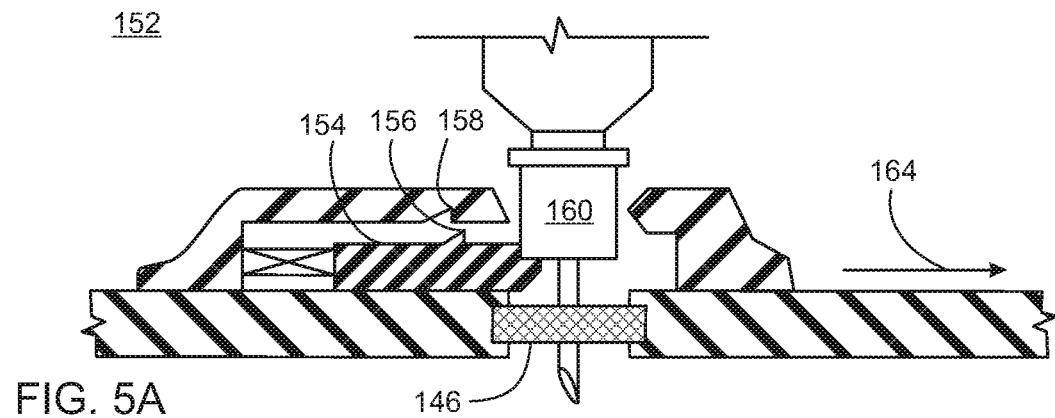
FIGS. 5A-5C are cross-sectional views of an embodiment of a septum access assembly.
Figure 5B:
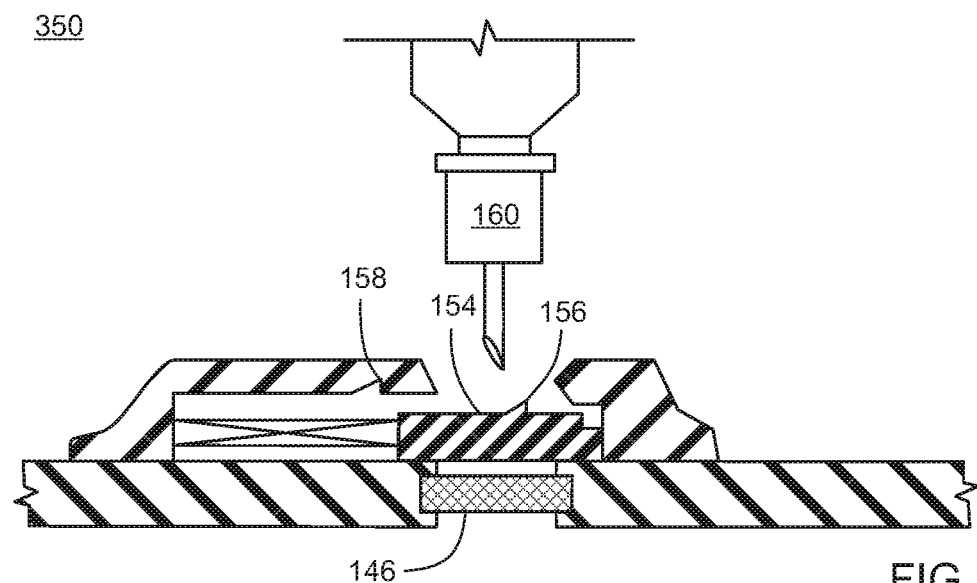
Figure 5C:
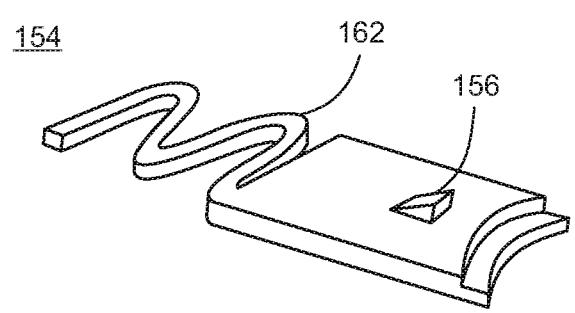

For example and referring also to FIGS. 5A-5C, septum access assembly 152 may include shutter assembly 154 that may be held in an "open" position by a tab assembly 156 that is configured to fit within a slot assembly 158. Upon penetrating septum 146 with filling syringe 160, shutter assembly 154 may be displaced downward, resulting in tab assembly 156 disengaging from slot assembly 158. Once disengaged, spring assembly 162 may displace shutter assembly 154 in the direction of arrow 164, resulting in septum 146 no longer being accessible to the user.

Figure 6A:
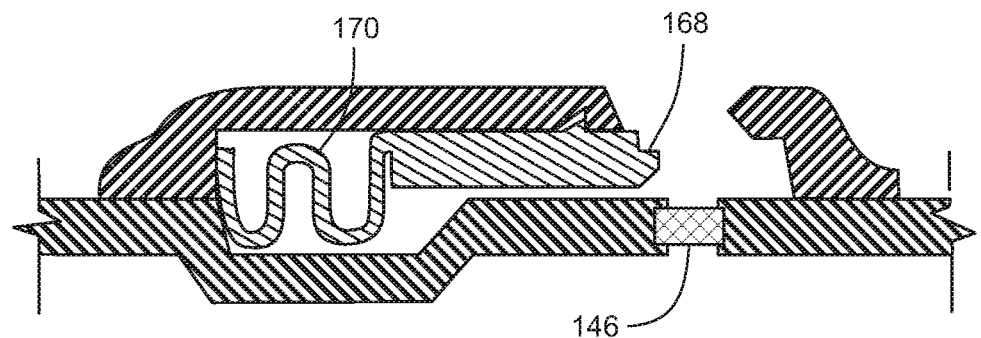
FIGS. 6A-6B are cross-sectional views of another embodiment of a septum access assembly.

Referring also to FIG. 6A, an alternative-embodiment septum access assembly 166 is shown in the "open" position. In a fashion similar to that of septum access assembly 152, septum access assembly 166 includes shutter assembly 168 and spring assembly 170.

Figure 6B:
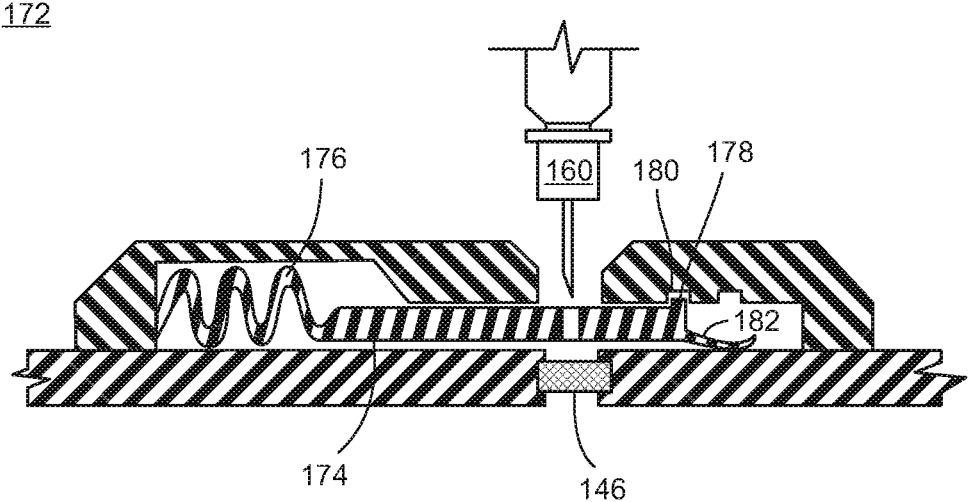

Referring also to FIG. 6B, an alternative-embodiment of septum access assembly 172 is shown in the "open" position where tab 178 may engage slot 180. In a fashion similar to that of septum access assembly 166, septum access assembly 172 may include shutter assembly 174 and spring assembly 176. Once shutter assembly 172 moves to the "closed" position (e.g., which may prevent further access of septum 146 by the user), tab 178 may at least partially engage slot 180a. Engagement between tab 178 and slot 180a may lock shutter assembly 172 in the "closed" position to inhibit tampering and reopening of shutter assembly 172. Spring tab 182 of shutter assembly 172 may bias tab 178 into engagement with slot 180a.

Figure 7A:
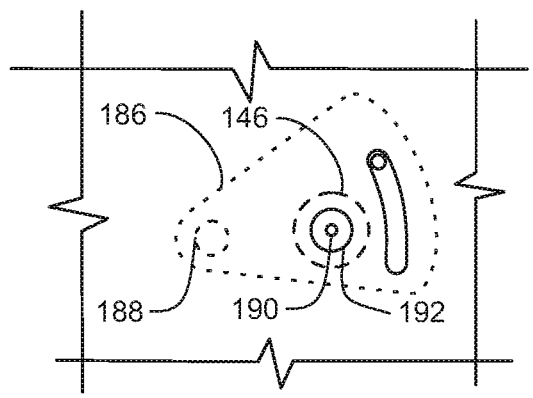
FIGS. 7A-7B are partial top views of another embodiment of a septum access assembly.
Figure 7B:
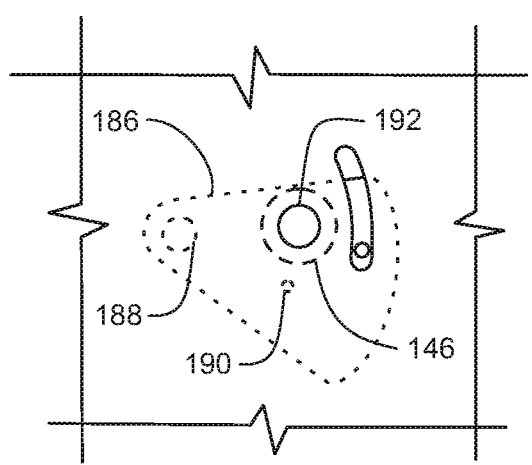

However, in various embodiments, septum access assemblies may not be actuated linearly. For example and referring also to FIGS. 7A-7B, there is shown alternative embodiment septum access assembly 184 that includes shutter assembly 186 that is configured to pivot about axis 188. When positioned in the open position (as shown in FIG. 7A), septum 146 may be accessible due to passage 190 (in shutter assembly 186) being aligned with passage 192 in e.g., a surface of disposable housing assembly 114. However, in a fashion similar to septum access assemblies 166, 172, upon penetrating septum 146 with filling syringe 160 (See FIG. 6B), shutter assembly 186 may be displaced in a clockwise fashion, resulting in passage 190 (in shutter assembly 186) no longer being aligned with passage 192 in e.g., a surface of disposable housing assembly 114, thus preventing access to septum 146.

Figure 8A:
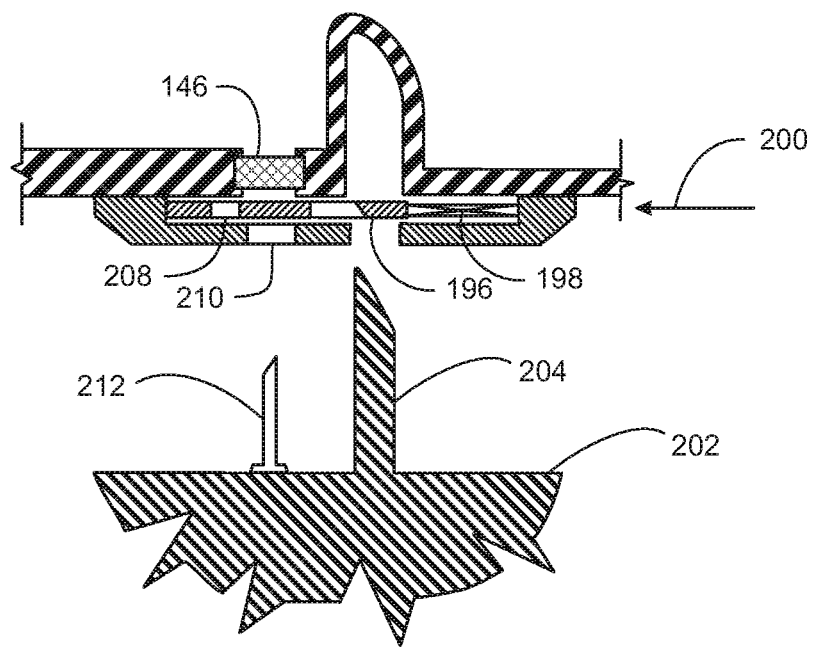
FIGS. 8A-8B are cross-sectional views of another embodiment of a septum access assembly.
Figure 8B:
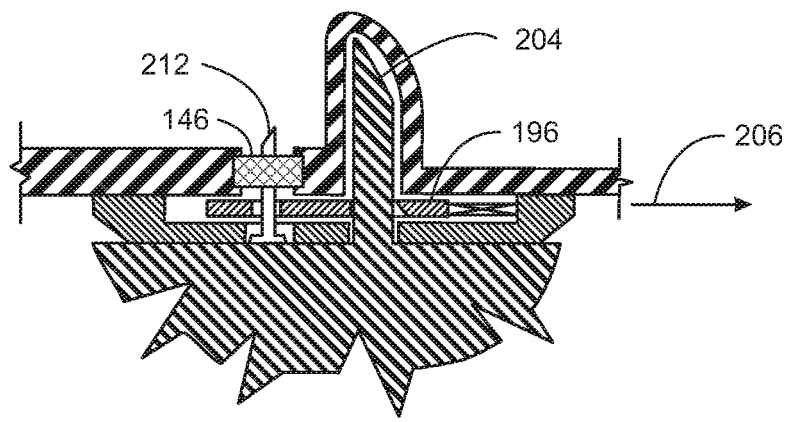

Referring also to FIGS. 8A-8B, an alternative-embodiment septum access assembly 194 is shown. In a fashion similar to that of septum access assemblies 166, 172, septum access assembly 194 includes shutter assembly 196 and spring assembly 198 that is configured to bias shutter assembly 196 in the direction of arrow 200. Filling assembly 202 may be used to fill reservoir 118. Filling assembly 202 may include shutter displacement assembly 204 that may be configured to displace shutter assembly 196 in the direction of arrow 206, which in turn aligns passage 208 in shutter assembly 196 with septum 146 and passage 210 in septum access assembly 194, thus allowing filling syringe assembly 212 to penetrate septum 146 and fill reservoir 118.

Infusion pump assembly 100 may include a sealing assembly 150 (FIG. 3) configured to provide a seal between reusable housing assembly 102 and disposable housing assembly 114. For example, when reusable housing assembly 102 and disposable housing assembly 114 are engaged by e.g. rotational screw-on engagement, twist-lock engagement or compression engagement, reusable housing assembly 102 and disposable housing assembly 114 may fit together snuggly, thus forming a seal. In some embodiments, it may be desirable for the seal to be more secure. Accordingly, sealing assembly 150 may include an o-ring assembly (not shown). Alternatively, sealing assembly 150 may include an over molded seal assembly (not shown). The use of an o-ring assembly or an over molded seal assembly may make the seal more secure by providing a compressible rubber or plastic layer between reusable housing assembly 102 and disposable housing assembly 114 when engaged thus preventing penetration by outside fluids. In some instances, the o-ring assembly may prevent inadvertent disengagement. For example, sealing assembly 150 may be a watertight seal assembly and, thus, enable a user to wear infusion pump assembly 100 while swimming, bathing or exercising.

Figure 9:
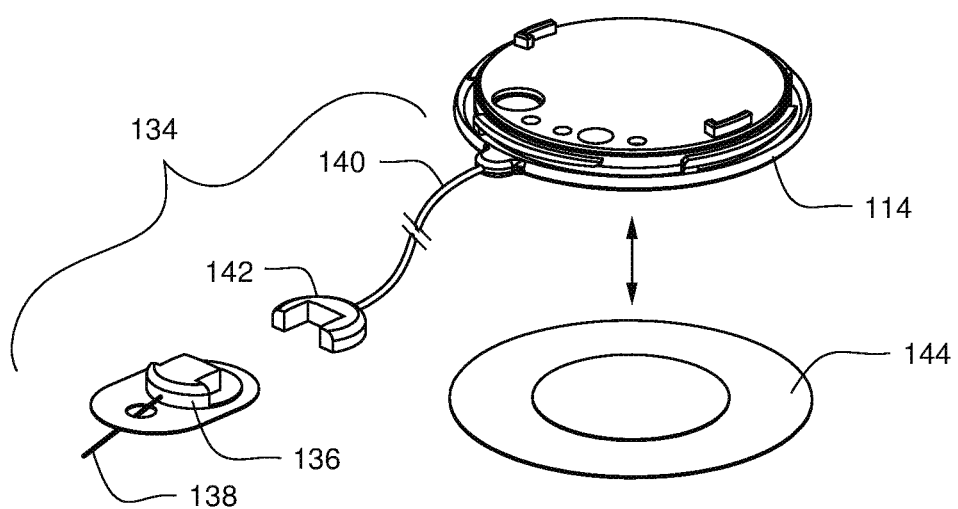
FIG. 9 is a perspective view of the infusion pump assembly of FIG. 1 showing an external infusion set.

Referring also to FIG. 9, infusion pump assembly 100 may include an external infusion set 134 configured to deliver the infusible fluid to a user. External infusion set 134 may be in fluid communication with cavity 118, e.g. by way of the fluid path. External infusion set 134 may be disposed adjacent to infusion pump assembly 100. Alternatively, external infusion set 134 may be configured for application remote from infusion pump assembly 100, as discussed in greater detail below. External infusion set 134 may include a cannula assembly 136, which may include a needle or a disposable cannula 138, and tubing assembly 140. Tubing assembly 140 may be in fluid communication with reservoir 118, for example, by way of the fluid path, and with cannula assembly 138 for example, either directly or by way of a cannula interface 142.

External infusion set 134 may be a tethered infusion set, as discussed above regarding application remote from infusion pump assembly 100. For example, external infusion set 134 may be in fluid communication with infusion pump assembly 100 through tubing assembly 140, which may be of any length desired by the user (e.g., 3-18 inches). Though infusion pump assembly 100 may be worn on the skin of a user with the use of adhesive patch 144, the length of tubing assembly 140 may enable the user to alternatively wear infusion pump assembly 100 in a pocket. This may be beneficial to users whose skin is easily irritated by application of adhesive patch 144. Similarly, wearing and/or securing infusion pump assembly 100 in a pocket may be preferable for users engaged in physical activity.

In addition to/as an alternative to adhesive patch 144, a hook and loop fastener system (e.g. such as hook and loop fastener systems offered by Velcro USA Inc. of Manchester, N.H.) may be utilized to allow for easy attachment/removal of an infusion pump assembly (e.g., infusion pump assembly 100) from the user. Accordingly, adhesive patch 144 may be attached to the skin of the user and may include an outward facing hook or loop surface. Additionally, the lower surface of disposable housing assembly 114 may include a complementary hook or loop surface. Depending upon the separation resistance of the particular type of hook and loop fastener system employed, it may be possible for the strength of the hook and loop connection to be stronger than the strength of the adhesive to skin connection. Accordingly, various hook and loop surface patterns may be utilized to regulate the strength of the hook and loop connection.

Referring also to FIGS. 10A-10E, five examples of such hook and loop surface patterns are shown. Assume for illustrative purposes that the entire lower surface of disposable housing assembly 114 is covered in a "loop" material. Accordingly, the strength of the hook and loop connection may be regulated by varying the pattern (i.e., amount) of the "hook" material present on the surface of adhesive patch 144. Examples of such patterns may include but are not limited to: a singular outer circle 220 of "hook" material (as shown in FIG. 10A); a plurality of concentric circles 222, 224 of "hook" material (as shown in FIG. 10B); a plurality of radial spokes 226 of "hook" material (as shown in FIG. 10C); a plurality of radial spokes 228 of "hook" material in combination with a single outer circle 230 of "hook" material (as shown in FIG. 10D); and a plurality of radial spokes 232 of "hook" material in combination with a plurality of concentric circles 234, 236 of "hook" material (as shown in FIG. 10E).

Figure 11A:
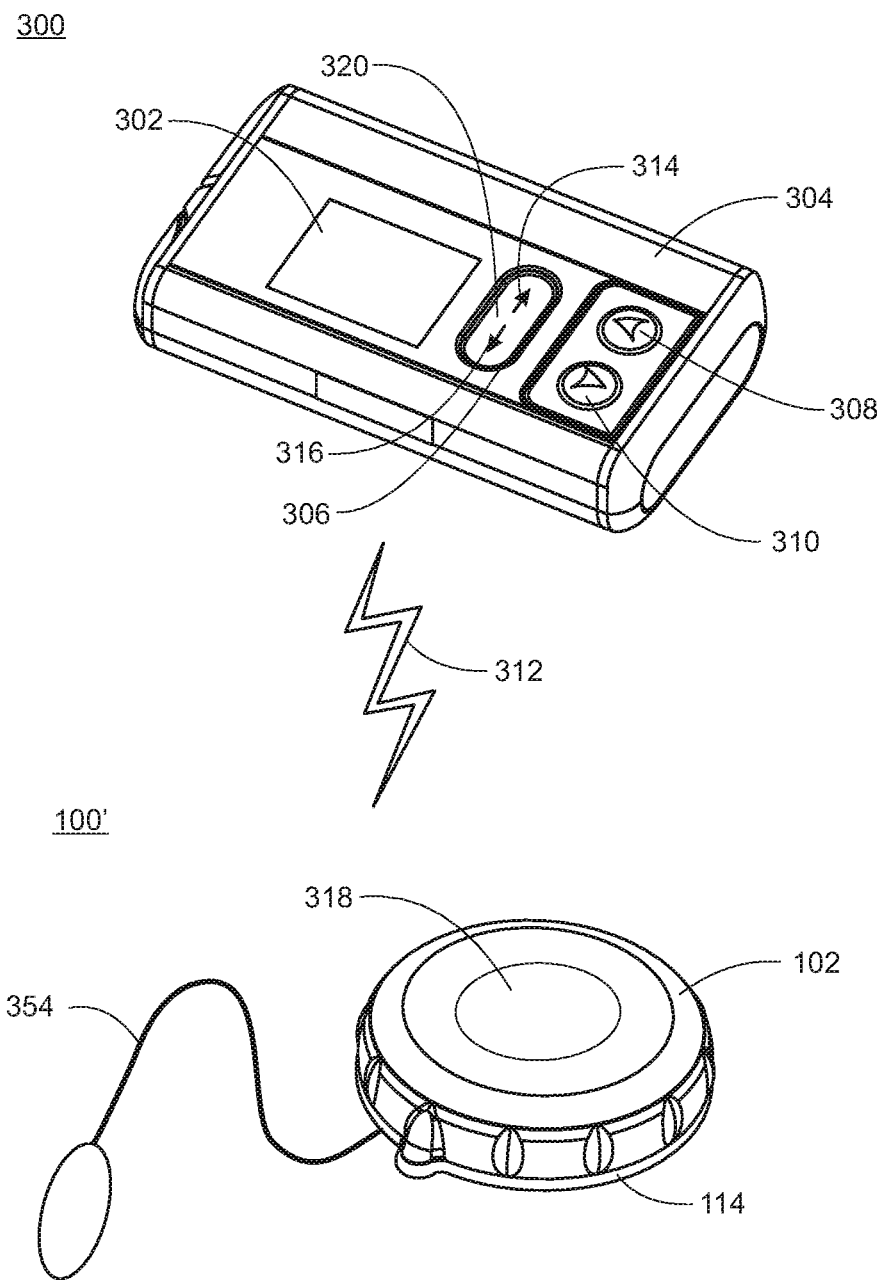
FIG. 11A is an isometric view of a remote control assembly and an alternative embodiment of the infusion pump assembly of FIG. 1.

Additionally and referring also to FIG. 11A, in one exemplary embodiment of the above-described infusion pump assembly, infusion pump assembly 100' may be configured via a remote control assembly 300. In this particular embodiment, infusion pump assembly 100' may include telemetry circuitry (not shown) that allows for communication (e.g., wired or wireless) between infusion pump assembly 100' and e.g., remote control assembly 300, thus allowing remote control assembly 300 to remotely control infusion pump assembly 100'. Remote control assembly 300 (which may also include telemetry circuitry (not shown) and may be capable of communicating with infusion pump assembly 100') may include display assembly 302 and input assembly 304. Input assembly 304 may include slider assembly 306 and switch assemblies 308, 310. In other embodiments, the input assembly may include a jog wheel, a plurality of switch assemblies, or the like.

Remote control assembly 300 may include the ability to pre-program basal rates, bolus alarms, delivery limitations, and allow the user to view history and to establish user preferences. Remote control assembly 300 may also include a glucose strip reader.

During use, remote control assembly 300 may provide instructions to infusion pump assembly 100' via wireless communication channel 312 established between remote control assembly 300 and infusion pump assembly 100'. Accordingly, the user may use remote control assembly 300 to program/configure infusion pump assembly 100'. Some or all of the communication between remote control assembly 300 and infusion pump assembly 100' may be encrypted to provide an enhanced level of security.

Figure 11B:
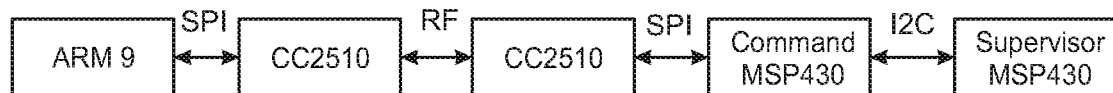
FIGS. 11B-11R depicts various views of high level schematics and flow charts of the infusion pump assembly of FIG. 1.

Communication between remote control assembly 300 and infusion pump assembly 100' may be accomplished utilizing a standardized communication protocol. Further, communication between the various components included within infusion pump assembly 100, 100' may be accomplished using the same protocol. One example of such a communication protocol is the Packet Communication Gateway Protocol (PCGP) developed by DEKA Research & Development of Manchester, N.H. As discussed above, infusion pump assembly 100, 100' may include electrical control assembly 110 that may include one or more electrical components. For example, electrical control assembly 110 may include a plurality of data processors (e.g. a supervisor processor and a command processor) and a radio processor for allowing infusion pump assembly 100, 100' to communicate with remote control assembly 300. Further, remote control assembly 300 may include one or more electrical components, examples of which may include but are not limited to a command processor and a radio processor for allowing remote control assembly 300 to communicate with infusion pump assembly 100, 100'. A high-level diagrammatic view of one example of such a system is shown in FIG. 11B.

Each of these electrical components may be manufactured from a different component provider and, therefore, may utilize native (i.e. unique) communication commands. Accordingly, through the use of a standardized communication protocol, efficient communication between such disparate components may be accomplished.

Figure 11C:
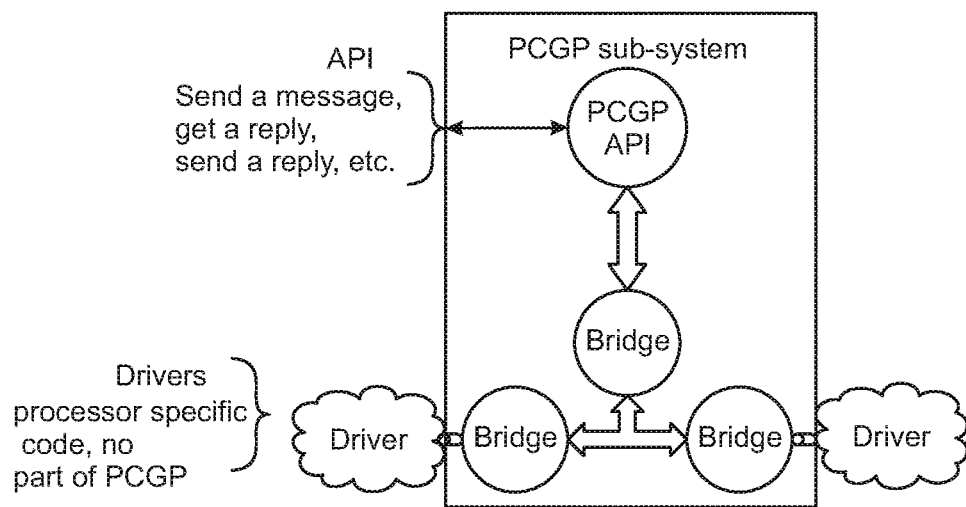

PCGP may be a flexible extendable software module that may be used on the processors within infusion pump assembly 100, 100' and remote control assembly 300 to build and route packets. PCGP may abstract the various interfaces and may provide a unified application programming interface (API) to the various applications being executed on each processor. PCGP may also provide an adaptable interface to the various drivers. For illustrative purposes only, PCGP may have the conceptual structure illustrated in FIG. 11C for any given processor.

PCGP may ensure data integrity by utilizing cyclic redundancy checks (CRCs). PCGP may also provide guaranteed delivery status. For example, all new messages should have a reply. If such a reply isn't sent back in time, the message may time out and PCGP may generate a negative acknowledge reply message for the application (i.e., a NACK). Accordingly, the message-reply protocol may let the application know whether the application should retry sending a message.

PCGP may also limit the number of messages in-flight from a given node, and may be coupled with a flow-control mechanism at the driver level to provide a deterministic approach to message delivery and may let individual nodes have different quantities of buffers without dropping packets. As a node runs out of buffers, drivers may provide back pressure to other nodes and prevent sending of new messages.

PCGP may use a shared buffer pool strategy to minimize data copies, and may avoid mutual exclusions, which may have a small affect on the API used to send/receive messages to the application, and a larger affect on the drivers. PCGP may use a "Bridge" base class that provides routing and buffer ownership. The main PCGP class may be sub-classed from the bridge base class. Drivers may either be derived from a bridge class, or talk to or own a derived bridge class.

Figure 11D:
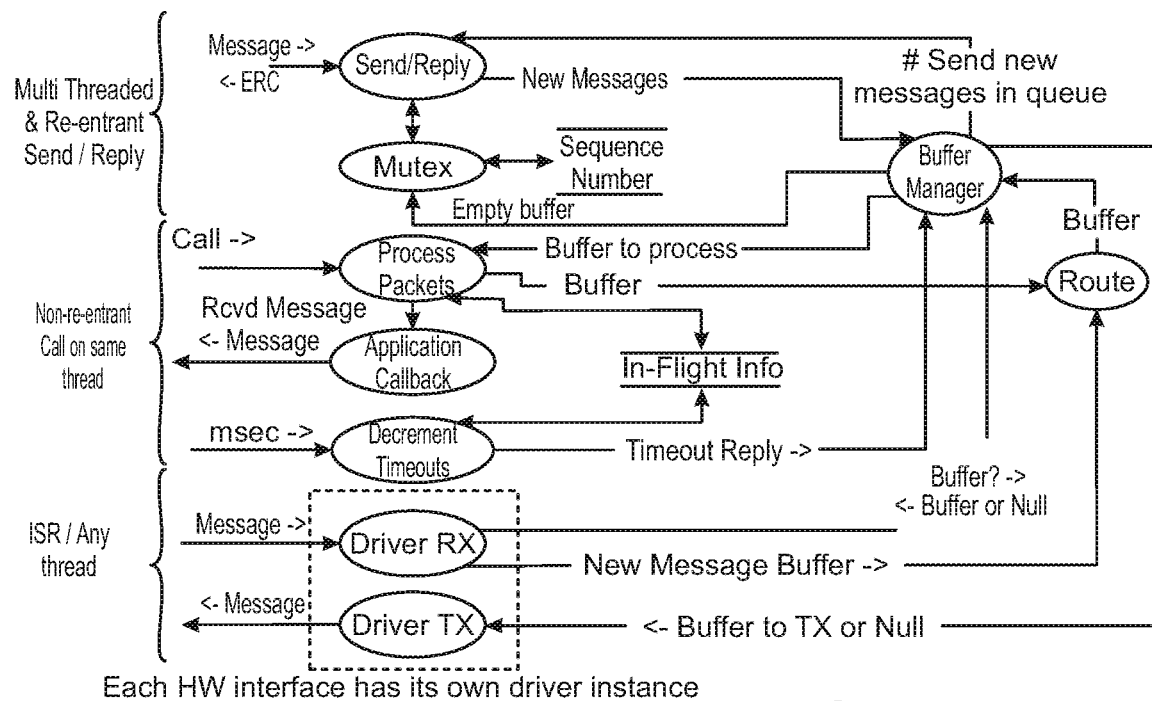

PCGP may be designed to work in an embedded environment with or without an operating system by using a semaphore to protect shared data such that some calls can be re-entrant and run on a multiple threads. One illustrative example of such an implementation is shown in FIG. 11D. PCGP may operate the same way in both environments, but there may be versions of the call for specific processor types (e.g., the ARM 9/OS version). So while the functionality may be the same, there may be an operating system abstraction layer with slightly different calls tailored for e.g., the ARM 9 Nucleus OS environment.

Figure 11E:
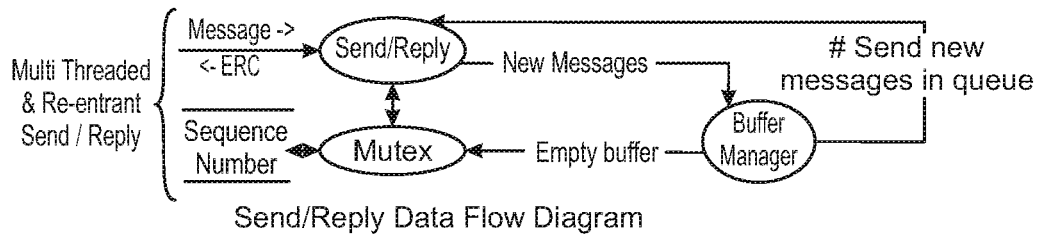

Referring also to FIG. 11E, PCGP may:
allow multiple Send/Reply calls to occur (on Pilot's ARM 9 on multiple tasks re-entrant);
have multiple drivers running asynchronously for RX and TX on different interfaces; and
provide packet ordering for send/receive, and deterministic timeout on message send.

Each software object may ask the buffer manager for the next buffer to use, and may then give that buffer to another object. Buffers may pass from one exclusive owner to another autonomicly, and queues may occur automatically by ordering buffers by sequence number. When a buffer is no longer in use, the buffer may be recycled (e.g., object attempts to give the buffer to itself, or frees it for the buffer manager to re-allocate later). Accordingly, data generally doesn't need to be copied, and routing simply writes over the buffer ownership byte.

Such an implementation of PCGP may provide various benefits, examples of which may include but are not limited to:
dropping a message due to lack of buffers may be impossible, as once a message is put into a buffer, the message may live there until it is transferred or received by the application;
data may not need to be copied, as offsets are used to access driver, PCGP and payload sections of a buffer;
drivers may exchange ownership of message data by writing over one byte (i.e., the buffer ownership byte);
there may be no need for multiple exclusions except for re-entrant calls, as a mutual exclusion may be needed only when a single buffer owner could simultaneously want to use a buffer or get a new sequence number;
there may be fewer rules for application writers to follow to implement a reliable system;
drivers may use ISR/push/pull and polled data models, as there are a set of calls provided to push/pull data out of the buffer management system from the drivers;
drivers may not do much work beyond TX and RX, as drivers may not copy, CRC or check anything but the destination byte and CRC and other checks may be done off of the ISR hot path later;
as the buffer manager may order access by sequence number, queue ordering may automatically occur; and
a small code/variable foot print may be utilized; hot path code may be small and overhead may be low.

Figure 11F:
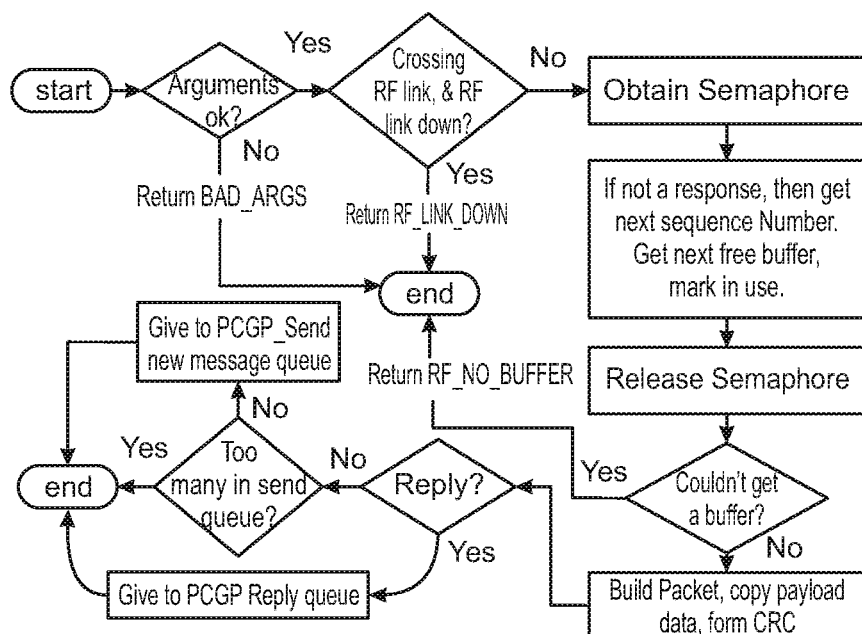

As shown in FIG. 11F, when a message needs to be sent, the PCGP may build the packet quickly and may insert it into the buffer management system. Once in the buffer management system, a call to "packetProcessor" may apply protocol rules and may give the messages to the drivers/application.

To send a new message or send a reply, PCGP may:
check the call arguments to e.g., make sure the packet length is legal, destination is ok, etc.;
avoid trying to send a message across a link that is down unless the down link is the radio node, which may allow PCGP to be used by the radio processors to establish a link, pair, etc. and may notify the application when PCGP is trying to talk across a link that is not functional (instead of timing out);
obtain a sequence number for a new message or utilize an existing sequence number for an existing message;
build the packet, copy the payload data and write in the CRC, wherein (from this point forward) the packet integrity may be protected by the CRC; and
either give the message to the buffer manager as a reply or as a new message, and check to see if putting this buffer into the buffer manager would exceed the maximum number of en-queued send messages.

Figure 11G:
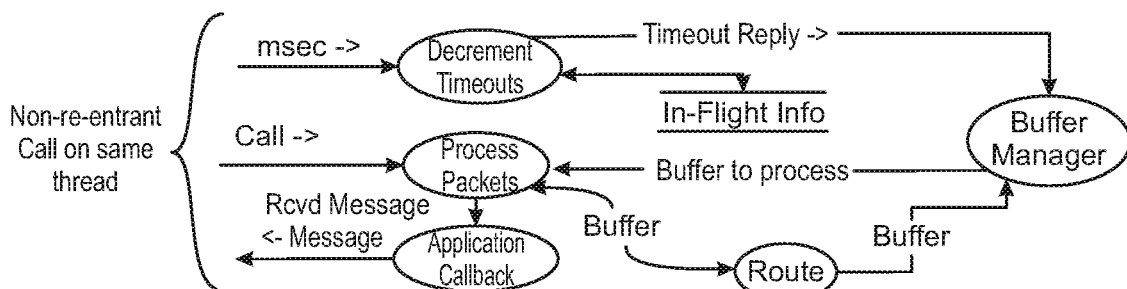
Figure 11H:
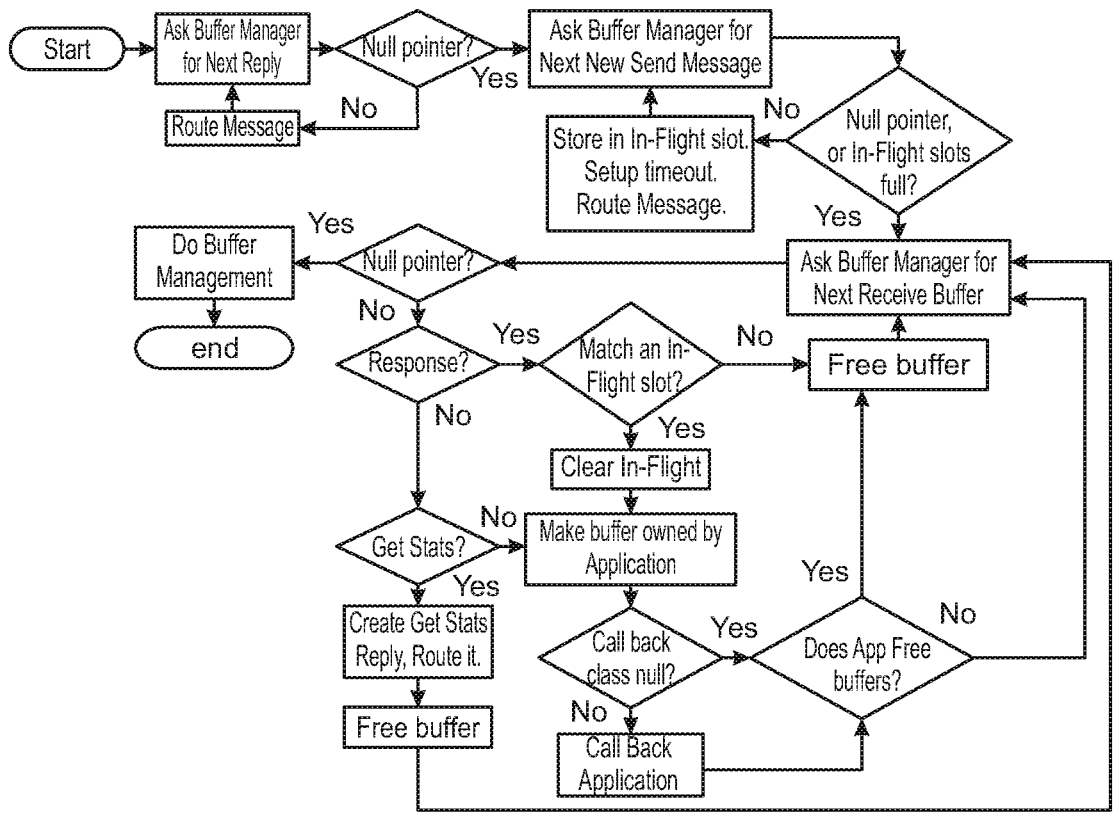

Referring also to FIGS. 11G-11H, PCGP may work by doing all of the main work on one thread to avoid mutual exclusions, and to avoid doing considerable work on the send/reply or driver calls. The "packetProcessor" call may have to apply protocol rules to replies, new sent messages, and received messages. Reply messages may simply get routed, but new messages and received messages may have rules for routing the messages. In each case, the software may loop while a message of the right type is available to apply protocol rules until it cannot process the packets.

Sending a new message may conform to the following rules:
only two messages may be allowed "in-flight" on the network; and
enough data about an in-flight message may be stored to match the response and handle timeout.

Receiving a message may conform to the following rules:
responses that match may clear out the "in-flight" information slot so a new packet can be sent;
responses that do not match may be dropped;
new messages may be for the protocol (e.g., getting/clearing network statistics for this node);
to receive a message, the buffer may be given up to the application and may use a call back; and
the buffer may be freed or left owned by the application.

Accordingly, PCGP may be configured such that:
the call back function may copy the payload data out or may use it completely before returning;
the call back function owns the buffer and may reference the buffer and the buffer's payload by the payload address, wherein the message may be processed later;
applications may poll the PCGP system for received messages; and
applications may use the call back to set an event and then poll for received messages.

The communication system may have a limited number of buffers. When PCGP runs out of buffers, drivers may stop receiving new packets and the application may be told that the application cannot send new packets. To avoid this and maintain optimal performance, the application may try to perform one or more procedures, examples of which may include but are not limited to:
a) The application should keep PCGP up to date with radio status: Specifically, if the link goes down and PCGP doesn't know, PCGP may accept and queue new messages to send (or not timeout messages optimally), which may jam the send queue and delay the application from using the link optimally.

b) The application should call "decrement timeouts" regularly: Optimally, every 20-100 milliseconds unless the processor is asleep. In general, a message moves fast (milliseconds) slow (seconds) or not at all. Timeouts are an attempt to remove "in-flight" messages that should be dropped to free up buffers and bandwidth. Doing this less often may delay when a new message gets sent, or when the application can queue a new message.

c) The application should ask PCGP if it has work to do that is pending before going to sleep: If PCGP has nothing to do, driver activity may wake up the system and thus PCGP, and then PCGP won't need a call to "packetProcessor" or "decrement timeouts" until new packets enter the system. Failure to do this may cause messages that could have been sent/forwarded/received successfully to be dropped due to a timeout condition.

d) The application should not hold onto received messages indefinitely: The message system relies on prompt replies. If the application is sharing PCGP buffers, then holding onto a message means holding onto a PCGP buffer. The receiving node doesn't know if the sending node has timeout configured for slow or fast radio. This means when a node receives a message it should assume the network's fast timeout speed.

e) The application should call the "packetProcessor" often: The call may cause new messages queued by the application to get sent and may handle receipt of new messages. The call may also cause buffers to re-allocate and calling it infrequently may delay message traffic.

Figure 11I:
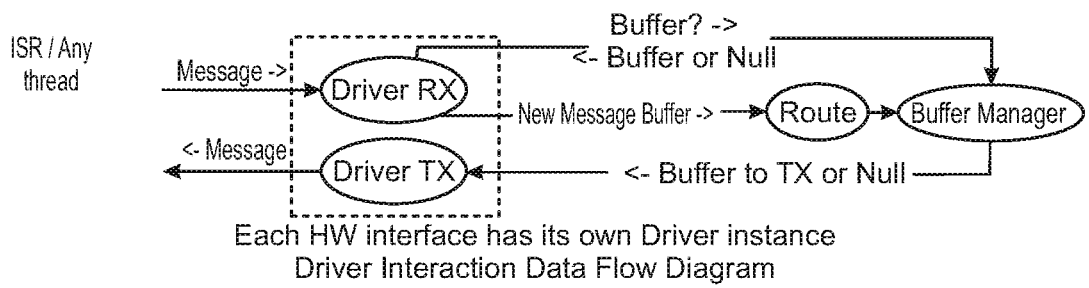

As shown in FIG. 11I, at some point the RX driver may be asked to receive a message from the other side of the interface. To ensure a message does not get dropped, the RX driver may ask the buffer manager if there is an available buffer for storing a new message. The driver may then ask for a buffer pointer and may start filling the buffer with received data. When a complete message is received, the RX driver may call a function to route the packet. The route function may examine the destination byte in the packet header and may change the owner to either the other driver, or the application, or may detect that the packet is bad and may drop the packet by freeing the buffer.

PCGP RX overhead may consist of asking for the next available buffer and calling the route function. An example of code that performs such a function is as follows:

```
@ Receive request
uint8 i=0, *p;
if (Bridge::canReceiveFlowControl( ))
{
   p = Bridge::nextBufferRX( );
   while (not done) { p[i] = the next byte; }
   Bridge::route(p);
}
```

A driver may perform a TX by asking the buffer manager for the pointer to the next buffer to send. The TX driver may then ask the other side of the interface if it can accept a packet. If the other side denies the packet, the TX driver may do nothing to the buffer, as its status has not changed. Otherwise, the driver may send the packet and may recycle/free the buffer. An example of code that performs such a function is as follows:

```
uint8 *p = Bridge::nextBufferTX( );
if (p != (uint8 *)0)
{
   send the buffer p;
   Bridge::recycle(p);
}
```

To avoid forwarding packets that are past the maximum message system timeout time, asking for the nextBuffer may call the BufferManager::first(uint8 owner) function that may scan for buffers to free. Accordingly, full TX buffers with no hope of making a timeout may be freed on the thread that owns the buffer. A bridge that is doing TX (i.e., while looking for the next TX buffer) may free all of the TX buffers that are expired before receiving the next TX buffer for processing.

Figure 11J:
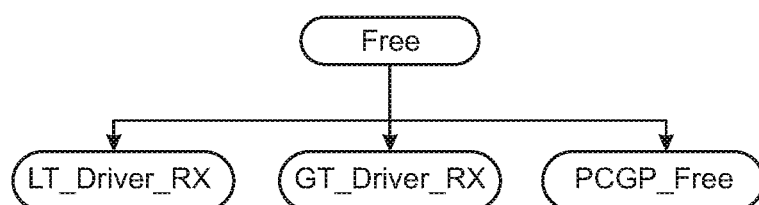
Figure 11K:
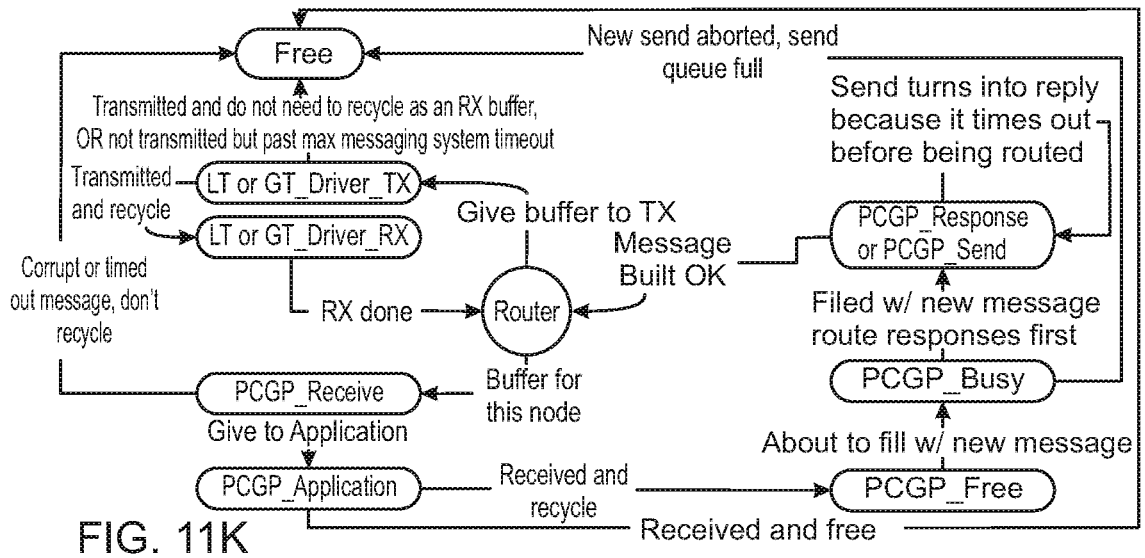
Figure 11L:
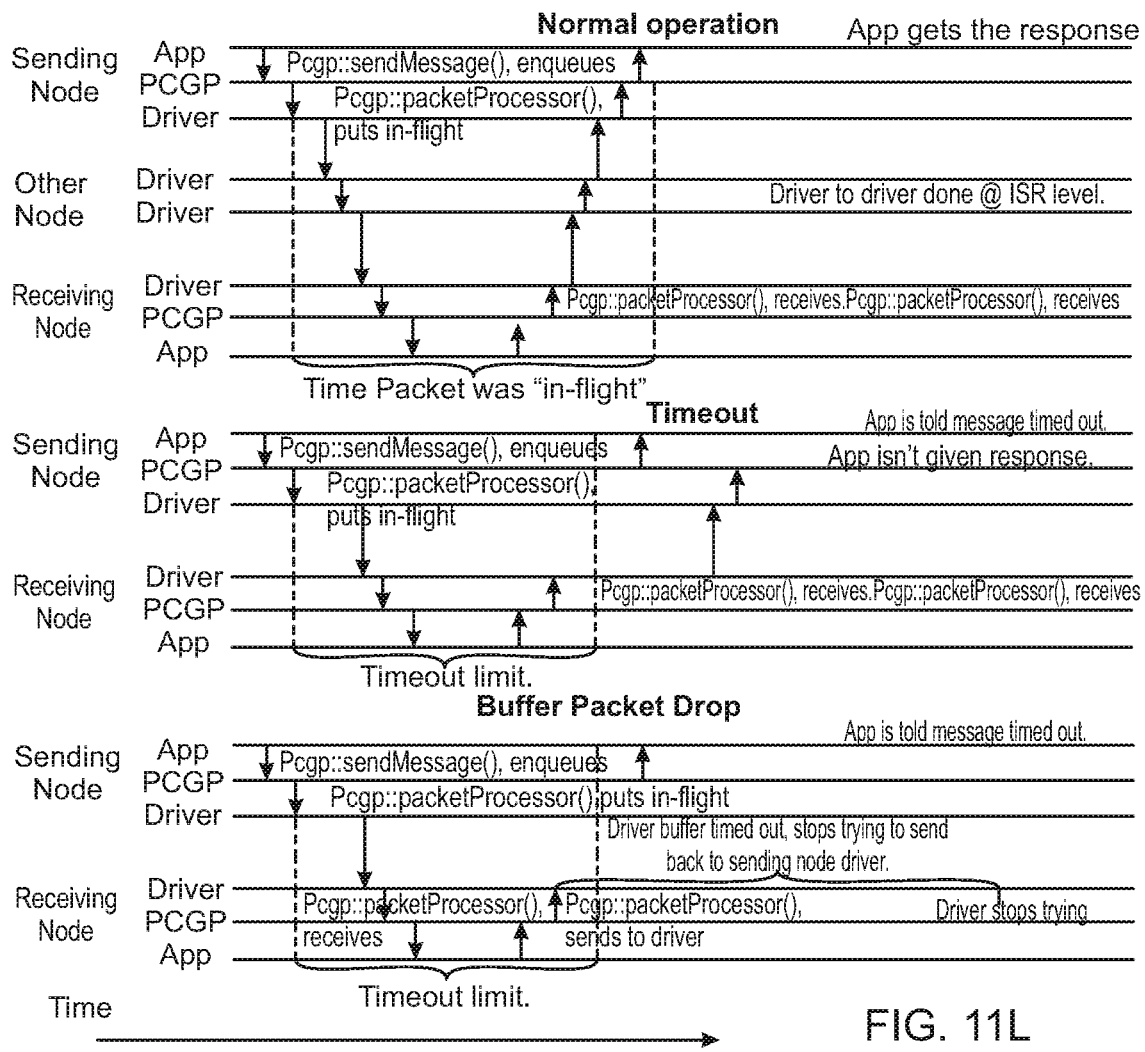

As shown in FIG. 11J-11L, during the buffer allocation process, buffers marked free may be transferred to the drivers to receive new packets, or to PCGP to receive new payloads for TX. Allocation from "free" may be done by the "packetProcessor" function. The number of sends and receives between "packetProcessor" calls may dictate how many LT_Driver_RX, GT_Driver_RX and PCGP_Free buffers need to be allocated. LT_Driver may represent drivers that handle addresses that are less than the node address. GT_Driver may represent drivers that handle addresses that are greater than the node address.

When a driver receives a packet, the driver may put the data into an RX buffer that gets handed to the router. The router may then reassign the buffer to PCGP_Receive or to the other driver's TX (not shown). If the buffer contains obviously invalid data, the buffer may transition to free.

After a router marks a buffer for TX, the driver may discover the buffer is TX and may send the message. After sending the message, the buffer may immediately become an RX buffer if the driver was low in RX buffers, or the buffer may be freed for re-allocation.

During the "packetProcessor" call, PCGP may process all buffers that the router marked as PCGP_Receive. At this point, data may be acted upon, so the CRC and other data items may be checked. If the data is corrupted, a statistic may be incremented and the buffer may be freed. Otherwise, the buffer may be marked as owned by the application. Buffers marked as owned by the application may be either recycled for the use of PCGP or freed for reallocation by the buffer manager.

When the application wants to send a new message, it may be done in a re-entrant friendly/mutual exclusion manner. If the buffer may be allocated, PCGP may mark the buffer as busy. Once marked busy, no other thread calling the send or reply functions may grab this buffer, as it is owned by this function call's invocation. The remainder of the process of error checking and building the message may be done outside the isolated race condition mutual exclusion guarded code. The buffer may either transition to free or may become a valid filled CRC-checked buffer and passed to the router. These buffers may not be routed immediately and may be queued so that messages can be sent later (assuming that protocol rules allow). Reply messages may be marked differently than new send messages because reply messages may be routed with a higher priority than regular send messages and reply messages may have no rules limiting how many/when they can be sent.

PCGP was designed to work with flow control, and flow control may negotiate the transfer of messages from one node to another node so that a buffer is never dropped because the other side of an interface lacks a buffer (which may cause back pressure on the sending node).

Flow control may be apart of the shared buffer format. The first two bytes may be reserved for the driver so that the driver never needs to shift the packet bytes. Two bytes may be used so that one byte is the DMA length −1, and the second byte is to control the flow of messages. These same two bytes may be synchronizing bytes if a PCGP message is transmitted over RS232.

When a packet is "in-flight", the packet may be in the process of being sent by a driver on the way to its destination, being processed by the destination, or being sent back as a response.

Typical delays are as follows:

| Interface/Delay cause | Delay (seconds) | Notes |
|---|---|---|
| SPI | <3 | Roughly 400 kbps |
| I2C | <1 | |
| Waking a CC2510 | <6 ? | Clock calibration, min. sleep time. |
| Flow control | <0.2 | |
| RF link | 20 to 2000 | |
| Interference/separation | Minutes, never | |

Accordingly, messages tend to complete the round trip either: quickly (e.g., <50 ms); slowly (e.g., one or more seconds); or not at all.

PCGP may use two different times (set at initialization) for all timeouts, one for when the RF link is in fast heartbeat mode, and another for when the RF link is in slow mode. If a message is in-flight and the link status changes from fast to slow, the timeout may be adjusted and the difference between fast and slow may be added to the time-to-live counter for the packet. No additional transitions back and forth may affect the time-to-live time for the message.

There is a second timeout that may be twice as long as the slow timeout that is used to monitor buffer allocation inside PCGP. Accordingly, if a message is "stuck" inside a driver and hasn't been sent due to e.g., flow control or hardware damage, the buffer may be freed by the buffer manager, resulting in the buffer being dropped. For a "new" message, this may mean that the packet already timed out and the application was already given a reply saying the message wasn't delivered, resulting in the buffer being freed. Since the driver polls the buffer manager for buffers that need to be sent, the buffer is freed up so that a message that could be sent is handed to the driver the next time that it unblocks. For a reply message, the reply may simply get dropped and the sending node may time out.

The PCGP messaging system may pass messages that contain header information and payload. Outside of PCGP, the header may be a set of data items in a call signature. However, internal to PCGP, there may be a consistent, driver friendly byte layout. Drivers may insert bytes either into the PCGP packet or before the PCGP packet such:

- DE, CA: Synch bytes for use with RS232, nominal value of 0xDE, 0xCA or 0x5A, 0xA5.
- LD: Driver DMA length byte, equals amount driver is pushing in this DMA transfer, which is the total size, not including the size byte or synch bytes.
- Cmd: Driver command and control byte used for flow control.
- LP: PCGP packet length, always the total header+payload size in bytes+CRC size. LD=LP+1.
- Dst: Destination address.
- Src: Source address
- Cmd: Command byte
- Scd: Sub command byte
- AT: Application Tag is defined by the application and has no significance to PCGP.
  It allows the application to attach more information to a message e.g., the thread from which the message originated.
- SeqNum: thirty-two bit sequence number is incremented by PCGP for a new message sent, guarantees the number will not wrap, acts as a token, endianess isn't relevant.
- CRC16: A sixteen bit CRC of the PCGP header and payload.

An example of a message with no payload, cmd=1, subcmd=2 is as follows:

0xDE, 0xCA, 0xC, 0x5, 0x14, 1, 2, 0, 0, 0, 0, 0x1, crchigh, crclow.

0x0D, cmd, 0xC, 0x5, 0x14, 1, 2, 0, 0, 0, 0, 0x1, crchigh, crclow.

There may be several advantages to this methodology, examples of which may include but are not limited to:

- Most of our hardware DMA engines may use the first byte to define how many additional bytes to move, so in this methodology, drivers and PCGP may share buffers.
- A byte may be provided right after the DMA length to pass flow control information between drivers.
- Driver length and "Cmd" byte may be outside the CRC region so they may be altered by the driver, may be owned by the driver transport mechanism, and the driver may guard for invalid lengths.
- There may be a separate PGCP packet length byte that is CRC protected. Accordingly, the application may trust that the payload length is correct.
- The endianess of the sequence number may not be relevant, as it is just a byte pattern that may be matched that happens to also be a thirty-two bit integer.
- The sequence number may be four bytes aligned to the edge of the shared buffer pool length.
- There may be optional RS232 synchronizing bytes so that users may move cables around while debugging a message stream and both sides of the interface may resynchronize.
- The application, driver and PCGP may share buffers and may release them by pointer.

Figure 11M:
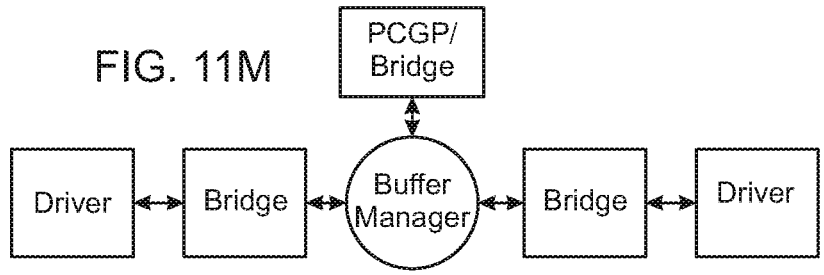
Figure 11N:
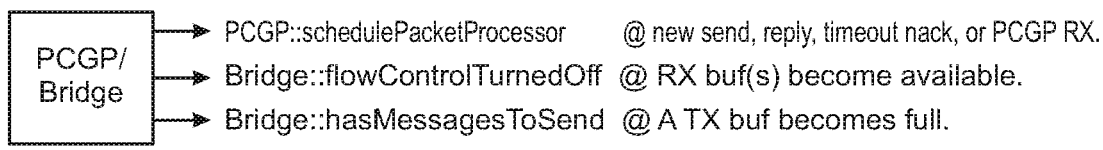
Figure 11O:
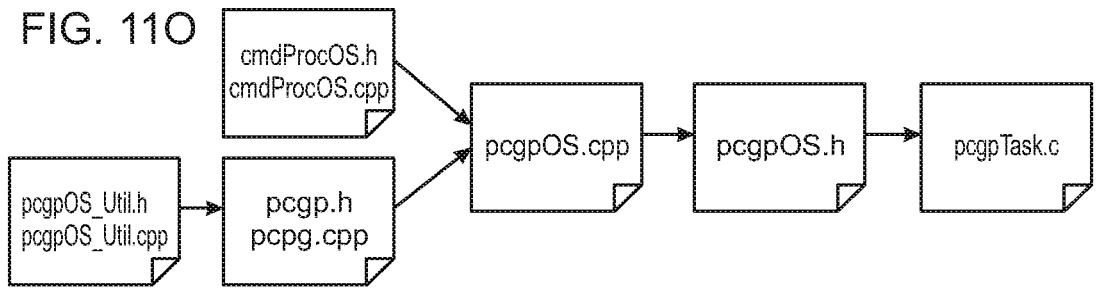

PCGP may not be an event driven software design, but may be used in event driven architectures by how the sub-classes are written. Data may be exchanged between the classes conceptually (as shown in FIG. 11M-11N).

Some event model in the driver may wake the driver, may receive a message and may pass the message through the bridge into the buffer manager that routes the message to new owner of the new message (through a bridge to either a driver or PCGP).

The following summarizes some exemplary events:

| Event: | Possible use: | Where this occurs: |
|---|---|---|
| When a new send or reply is queued, or decTimeouts generates a timeout reply. | Decide to run packetProcessor. | Inside PCGP::sendInternal |
| When a messages is received for PCGP. | Decide to run packetProcessor. | BufferManager::give |
| When a driver has something new to send. | Wake driver for TX. | BufferManager::give |

| Event: | Possible use: | Where this occurs: |
|---|---|---|
| When a Driver RX buffer becomes available. | Turn off flow control. | BufferManager::give |

The following illustrative example shows how the PCUP event model may work with Nucleus to wakeup the PCGP task after every message send, reply, or decTimeout that generated a NACK:

```
class PcgpOS : public Pcgp
{
  virtual void schedulePacketProcessor(void)
  {
    OS_EventGrp_Set(g_RCVEvGrps[EVG_RF_TASK].pEvgHandle,
      RfRadioTxEvent, OS_EV_OR_NO_CLEAR);
  }
}
```

The following is a pseudo code driver that is event based, illustrating how driver events work. The Driver subclasses Bridge and overrides hasMessagesToSend and flowControl-TurnedOff to schedule the TX and RX functions to run if they aren't already running.

```
class SPI_Driver : public Bridge
{
  virtual void hasMessagesToSend( )
  {
    Trigger_ISR(TX_ISR, this);
  }
  virtual void flowControlTurnedOff( )
  {
    Trigger_ISR(RX_ISR, this);
  }
  static void TX_RetryTimer( )
  {
    Trigger_ISR(TX_ISR, this);
  }
  static void TX_ISR(Bridge *b)
  {
    DisableISRs( );
    do
    {
      uint8 *p = b->nextBufferTX( );
      if (p == null) break;
      if (b->_bufferManager->bufferTimedOut(p)==false)
      {
        if (OtherSideSPI_FlowControl( ) == false)
        {
          Trigger TX_RetryTimer in 20 msec.
          break;
        }
        send(p);
      }
      free (p);
    } while (true) ;
    EnableISRs( );
  }
  static void RX_ISR(Bridge *b)
  {
    DisableISRs( );
    do
    {
      uint8* p = b->nextBufferRX( );
      if (p == null) break;
      uint i;
      while (not done receiving)
        p[i++] = getChar( );
      b->route(p);
    } while (true) ;
    EnableISRs( );
  }
}
```

The following statistics may be supported by PCGP:
Number of packets sent;
Number of packets received;
CRC errors;
Timeouts; and
Buffer unavailable (ran out of buffers)

PCGP may be designed to run in multiple processing environments. Most parameters may be run time configured because it facilitates testing, and any run time fine tuning for performance. Other parameters may be compile time e.g., anything that alters memory allocation must be done statically at compile time.

The following may be compile time configuration #defines that may vary where PCGP is implemented:
  # driver bytes: may be two bytes reserved in the common buffer scheme for the driver, but this may be a compile time option to accommodate other drivers such as RF protocol.
  # RX driver buffers: may be tuned to how many buffers would be good for that processor/traffic flow, etc.
  # PCGP RX buffers: may be tuned to how many buffers would be good for that processor/traffic flow, etc.
  Total # of buffers: may be tuned to how many buffers should be at that processor.

The CRC may be used to ensure data integrity. If a CRC is invalid, it may not be delivered to the application and the CRC error may be tracked. The message may eventually timeout and may be retried by the originator.

Likewise, if the messaging system informs the application that a message was delivered when it was not, this may be a hazard to the system. The Stop Bolus Command is an example of such a command. This may be mitigated by the Request/Action sequence of messages which may be required by the application to change therapy. The Controller may receive a matching command from the Pump application to consider the message delivered.

Figure 110:
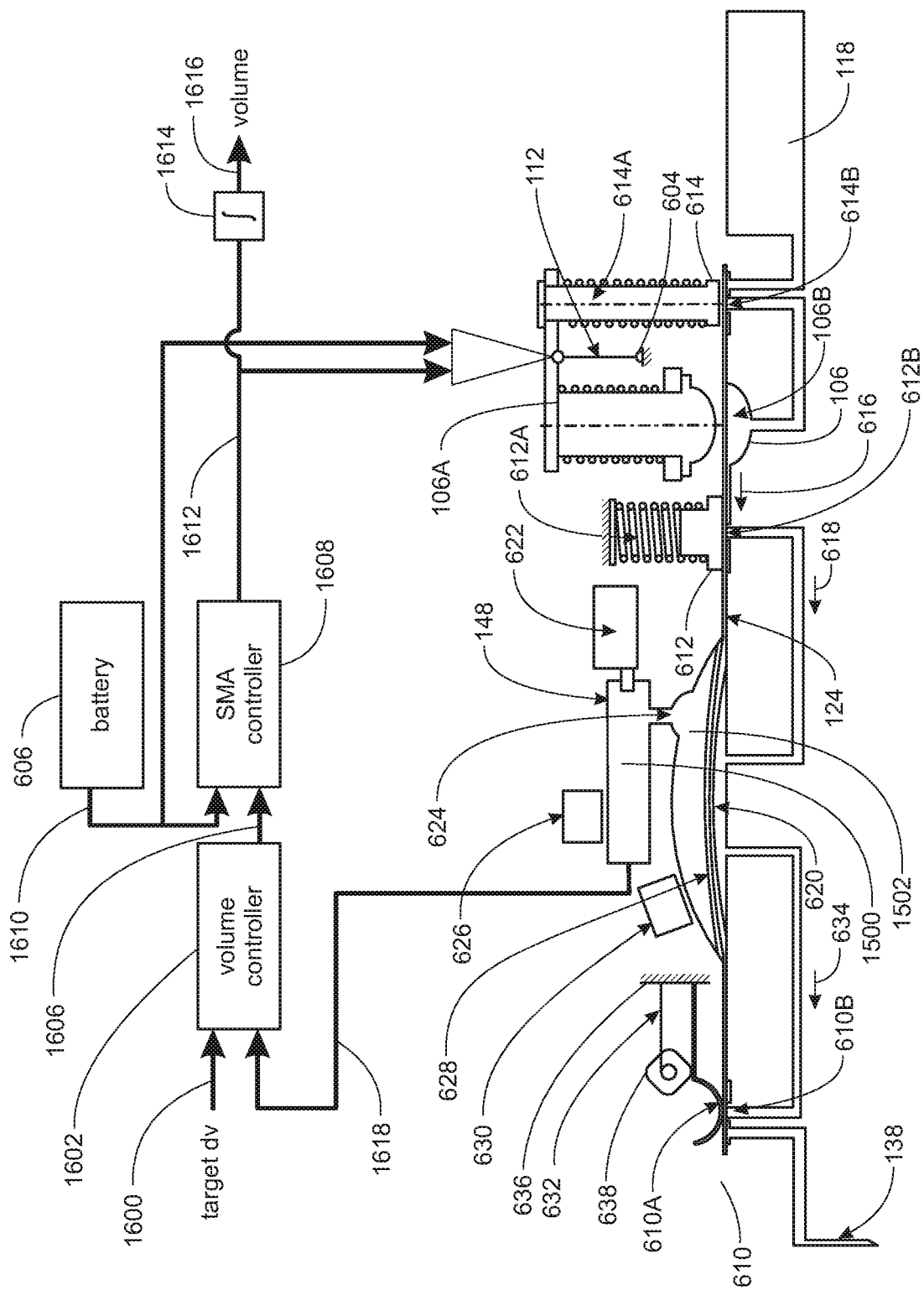
FIG. 110 is a diagrammatic view of an electrical control assembly for the volume sensor assembly included within the infusion pump assembly of FIG. 1.

DEKA may provide a reference way of interfacing PCGP into the Nucleus OS system on the ARM 9 (as shown in FIG. 110).

Figure 11P:
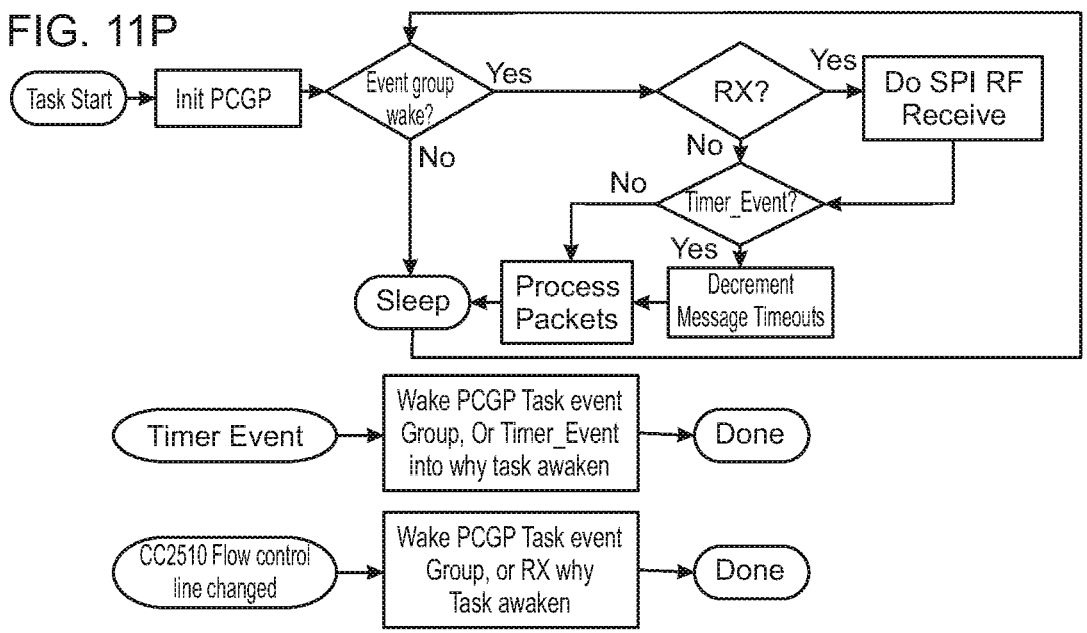

As shown in FIG. 11P, the pcgpOS.cpp file may instantiate a PCGP node instance (Pcgp, a Bridge, etc.) and may provide through pcgpOS.h a 'C' linkable set of function calls that provide a 'C' language interface to the C++ code. This may simplify the 'C' code as the objects acted upon are implicit.

The following general rules may be applied:
  PCGP may run on all nodes: any driver may support a generic driver interface.
  Race conditions may not be permitted.
  May support half duplex on the SPI port between slave processor and master processor.
  Data transfer may not be attempted; as it either succeeds or returns fail/false.
  May require low overhead (time, processing, bandwidth wasted).
  May support CC2510 operating at DMA (fast) SPI clock rates.

SPI flow control may prevent data from being sent if the receiving side does not currently have an empty buffer to place the packet. This may be accomplished by asking for permission to send and waiting for a response indicating that you have been cleared to do so. There may also be a way to tell the other side that there are currently no free buffers and the transfer should be attempted at a later time.

All transmission may begin with a length byte that indicates the number of bytes to be sent, not including the length byte itself. Following the length may be a single byte indicating the command being sent.

The actual transmission of a packet may be the length of packet plus one for the command byte, followed by the command byte for a message appended and finally the packet itself.

In addition to the command bytes that will be sent, an additional hardware line called the FlowControl line may be added to the traditional four SPI signals. The purpose of this line is to allow the protocol to run as quickly as possible without a need for preset delays. It also allows the slave processor to tell the master processor that it has a packet waiting to be sent, thus eliminating the need for the master processor to poll the slave processor for status.

The following exemplary command values may be used:
Commands to be Sent by the Master Processor:

| Command | Value | Description |
| --- | --- | --- |
| M_RTS | 0xC1 | Master is requesting to send a packet |
| M_MSG_APPENDED | 0xC2 | Master is sending a packet |
| M_CTS | 0xC3 | Master is tell slave it is Cleared to Send |
| M_ERROR | 0xC4 | An Error condition has been encountered |

Commands to be Sent by the Slave Processor:

| Command | Value | Description |
| --- | --- | --- |
| S_PREPARING_FOR_RX | 0xA1 | Slave is prepare the dma to receive a packet |
| S_RX_BUFF_FULL | 0xA2 | Slave is currently out of RX buffers, retry later |
| S_MSG_APPENDED | 0xA3 | Slave is sending a packet |
| S_ERROR | 0xA4 | An Error condition has been encountered |

As illustrated in FIG. 11Q, when the slave processor has a packet to send to the master processor, the slave processor may notify the master processor (by asserting the FlowControl line) that it has a pending packet that is waiting to be sent. Doing so may result in an IRQ on the master processor at which time the master processor may decide when to go retrieve the message from the slave processor. Retrieving the packet may be delayed at the discretion of the master processor, and the master processor may even decide to attempt to send a packet to the slave processor before retrieving from the slave processor.

The master processor may begin the retrieval by sending the slave processor M_CTS commands; this shall be repeated until the slave processor responds by sending the S_MSG_APPENDED command along with the packet itself. The FlowControl line may be cleared after the packet has been sent. If a M_CTS command is received by the slave processor when one is not expected, the M_CTS command may be ignored.

As illustrated in FIG. 11R, when the master processor has a packet to send to the slave processor, the master processor may initiate the transfer by sending a M_RTS command. Upon receiving the M_RTS command, if the slave processor currently has a send packet pending, the slave processor will lower the FlowControl line so that it may be re-used as a Cleared To Send signal. The slave processor may then tell the master processor that it is in the process of preparing the SPI DMA to receive the packet, during which time the master processor may stop clocking bytes onto the bus and may allow the slave processor to finish preparing for the receive.

The slave processor may then indicate it is ready to receive the full packet by raising the FlowControl line (which is now used as the CTS signal). Upon receiving the CTS signal, the master processor may proceed to send the M_MSG_APPENDED command along with the packet itself.

After the completion of the transfer, the slave processor may lower the FlowControl line. If a packet was pending at the start of the transfer, or a send occurred on the slave processor when the packet was being received, the slave processor may reassert the FlowControl line now indicating that it has a pending packet.

Referring again to FIG. 11A, infusion pump assembly 100, 100' may include switch assembly 318 coupled to electrical control assembly 110 (FIG. 3) that may allow a user (not shown) to perform at least one, and in some embodiments, a plurality of tasks. One illustrative example of such a task is the administration of a bolus dose of the infusible fluid (e.g., insulin) without the use of a display assembly. Remote control assembly 300 may allow the user to enable/disable/configure infusion pump assembly 100, 100' to administer the bolus dose of insulin.

Referring also to FIG. 12A, slider assembly 306 may be configured, at least in part, to enable the user to manipulate the menu-based information rendered on display assembly 302. An example of slider assembly 306 may include a capacitive slider assembly, which may be implemented using a CY8C21434-24LFXI PSOC offered by Cypress Semiconductor of San Jose, Calif., the design an operation of which are described within the "CSD User Module" published by Cypress Semiconductor. For example, via slider assembly 306, the user may slide their finger in the direction of arrow 314, resulting in the highlighted portion of the information included within main menu 350 (shown in FIG. 12A) rendered on display assembly 302 scrolling upward. Alternatively, the user may slide their finger in the direction of arrow 316, resulting in the highlighted portion of the information included within main menu 350 rendered on display assembly 302 scrolling downward.

Slider assembly 306 may be configured so that the rate at which e.g. the highlighted portion of main menu 350 scrolls "upward" or "downward" varies depending upon the displacement of the finger of the user with respect to point of origin 320. Therefore, if the user wishes to quickly scroll "upward", the user may position their finger near the top of slider assembly 306. Likewise, if the user wishes to quickly scroll "downward", the user may position their finger near the bottom of slider assembly 306. Additionally, if the user wishes to slowly scroll "upward", the user may position their finger slightly "upward" with respect to point of origin 320 Further, if the user wishes to slowly scroll "downward", the user may position their finger slightly "downward" with respect to point of origin 320. Once the appropriate menu item is highlighted, the user may select the highlighted menu item via one or more switch assemblies 308, 310.

Referring also to FIGS. 12B-12F, assume for illustrative purposes that infusion pump assembly 100, 100' is an insulin pump and the user wishes to configure infusion pump assembly 100, 100' so that when switch assembly 318 is depressed by the user, a 0.20 unit bolus dose of insulin is administered. Accordingly, the user may use slider assembly 306 to highlight "Bolus" within main menu 350 rendered on display assembly 302. The user may then use switch assembly 308 to select "Bolus". Once selected, processing logic (not shown) within remote control assembly 300 may then render submenu 352 on display assembly 302 (as shown in FIG. 12B).

The user may then use slider assembly 306 to highlight "Manual Bolus" within submenu 352, which may be selected using switch assembly 308. Processing logic (not shown) within remote control assembly 300 may then render submenu 354 on display assembly 302 (as shown in FIG. 12C).

The user may then use slider assembly 306 to highlight "Bolus: 0.0 Units" within submenu 354, which may be selected using switch assembly 308. Processing logic (not shown) within remote control assembly 300 may then render submenu 356 on display assembly 302 (as shown in FIG. 12D).

The user may then use slider assembly 306 to adjust the "Bolus" insulin amount to "0.20 units", which may be selected using switch assembly 308. Processing logic (not shown) within remote control assembly 300 may then render submenu 358 on display assembly 302 (as shown in FIG. 12E).

The user 14 may then use slider assembly 306 to highlight "Confirm", which may be selected using switch assembly 308. Processing logic (not shown) within remote control assembly 300 may then generate the appropriate signals that may be sent to the above-described telemetry circuitry (not shown) included within remote control assembly 300. The telemetry circuitry (not shown) included within the remote control assembly may then transmit, via wireless communication channel 312 established between remote control assembly 300 and infusion pump assembly 100', the appropriate configuration commands to configure infusion pump assembly 100' so that whenever switch assembly 318 is depressed by the user, a 0.20 unit bolus dose of insulin is administered.

Once the appropriate commands are successfully transmitted, processing logic (not shown) within remote control assembly 300 may once again render submenu 350 on display assembly 302 (as shown in FIG. 12F).

Specifically and once programmed via remote control assembly 300, the user may depress switch assembly 318 of infusion pump assembly 100' to administer the above-described 0.20 unit bolus dose of insulin. Via the above-described menuing system included within remote control assembly 300, the user may define a quantity of insulin to be administered each time that the user depresses switch assembly 318. While this particular example specifies that a single depression of switch assembly 318 is equivalent to 0.20 units of insulin, this is for illustrative purposes only and is not intended to be a limitation of this disclosure, as other values (e.g. 1.00 units of insulin per depression) are equally applicable.

Assume for illustrative purposes that the user wishes to administer a 2.00 unit bolus dose of insulin. To activate the above-describe bolus dose administration system, the user may be required to press and hold switch assembly 318 for a defined period of time (e.g. five seconds), at which point infusion pump assembly 100, 100' may generate an audible signal indicating to the user that infusion pump assembly 100, 100' is ready to administer a bolus does of insulin via switch assembly 318. Accordingly, the user may depress switch assembly 318 ten times (i.e., 2.00 units is ten 0.20 unit doses). After each time that switch assembly 318 is depressed, infusion pump assembly 100, 100' may provide on audible response to the user via an internal speaker/sound generation device (not shown). Accordingly, the user may depress switch assembly 318 the first time and infusion pump assembly 100, 100' may generate a confirmation beep in response, thus indicating to the user that infusion pump assembly 100, 100' received the command for (in this particular example) 0.20 units of insulin. As the desired bolus dose is 2.00 units of insulin, the user may repeat this procedure nine more times in order to effectuate a bolus dose of 2.00 units, wherein infusion pump assembly 100, 100' generates a confirmation beep after each depression of switch assembly 318.

While in this particular example, infusion pump assemblies 100, 100' are described as providing one beep after each time the user depresses switch assembly 318, this is for illustrative purposes only and is not intended to be a limitation of this disclosure. Specifically, infusion pump assembly 100, 100' may be configured to provide a single beep for each defined quantity of insulin. As discussed above, a single depression of switch assembly 318 may be equivalent to 0.20 units of insulin. Accordingly, infusion pump assembly 100, 100' may be configured to provide a single beep for each 0.10 units of insulin. Accordingly, if infusion pump assembly 100, 100' is configured such that a single depression of switch assembly 318 is equivalent to 0.20 units of insulin, each time switch assembly 318 is depressed, infusion pump assembly 100, 100' may provide the user with two beeps (i.e. one for each 0.10 units of insulin).

Once the user has depressed switch assembly 318 on infusion pump assembly 100' a total of ten times, the user may simply wait for infusion pump assembly 100, 100' to acknowledge receipt of the instructions to administer a 2.00 unit bolus dose of insulin (as opposed to the confirmation beep received at each depression of switch assembly 318). Once a defined period of time (e.g., two seconds) passes, infusion pump assembly 100, 100' may provide an audible confirmation to the user concerning the quantity of units to be administered via the bolus insulin dose that the user just requested. For example, as (in this example) infusion pump assembly 100, 100' was programmed by the user so that a single depression of switch assembly 318 is equivalent to 0.20 units of insulin, infusion pump assembly 100, 100' may beep ten times (i.e., 2.00 units is ten 0.20 unit doses).

When providing feedback to the user concerning the quantity of units to be administered via the bolus insulin dose, infusion pump assembly 100, 100' may provide a multifrequency audible confirmation. For example and continuing with the above-stated example in which ten beeps are to be provided to the user, infusion pump assembly 100, 100' may group the beeps into groups of five (to facilitate easier counting by the user) and the beeps within each group of five may be rendered by infusion pump assembly 100, 100' so that each subsequent beep has a higher frequency than the preceding beep (in a manner similar to a musical scale). Accordingly and continuing with the above-stated example, infusion pump assembly 100, 100' may render a 1,000 Hz beep, followed by an 1,100 Hz beep, followed by a 1,200 Hz beep, followed by a 1,300 Hz beep, followed by a 1,400 Hz beep (thus completing a group of five beeps), followed by a short pause, and then a 1,000 Hz beep, followed by an 1,100 Hz beep, followed by a 1,200 Hz beep, followed by a 1,300 Hz beep, followed by a 1,400 Hz beep (thus completing the second group of five beeps). According to various additional/alternative embodiments the multifrequency audible confirmation may utilize various numbers of tones incrementing in frequency. For example, an embodiment may utilize twenty different tones incrementing in frequency. However, the number of tones should not be construed as a limitation of the present disclosure as number of tones may vary according to design criteria and user need.

Once infusion pump assembly 100, 100' completes the rendering of the multifrequency audible confirmation (i.e. the ten beeps described above), the user may, within a defined period of time (e.g. two seconds), depress switch assembly 318 to provide a confirmation signal to infusion pump assembly 100, 100', indicating that the multifrequency audible confirmation was accurate and indicative of the size of the bolus dose of insulin to be administered (i.e. 2.00 units). Upon receiving this confirmation signal, infusion pump assembly 100, 100' may render a "confirmation received" audible tone and effectuate the delivery of (in this particular example) the 2.00 unit bolus dose of insulin. In the event that infusion pump assembly 100, 100' fails to receive the above-described confirmation signal, infusion pump assembly 100, 100' may render a "confirmation failed" audible tone and will not effectuate the delivery of the bolus dose of insulin. Accordingly, if the multifrequency audible confirmation was not accurate/indicative of the size of the bolus dose of insulin to be administered, the user may simply not provide the above-described confirmation signal, thereby canceling the delivery of the bolus dose of insulin.

As discussed above, in one exemplary embodiment of the above-described infusion pump assembly, infusion pump assembly 100' may be used to communicate with a remote control assembly 300. When such a remote control assembly 300 is utilized, infusion pump assembly 100' and remote control assembly 300 may routinely contact each other to ensure that the two devices are still in communication with each other. For example, infusion pump assembly 100' may "ping" remote control assembly 300 to ensure that remote control assembly 300 is present and active. Further, remote control assembly 300 may "ping" infusion pump assembly 100' to ensure that infusion pump assembly 100' is still present and active. In the event that one of infusion pump assembly 100' and remote control assembly 300 fails to establish communication with the other assembly, the assembly that is unable to establish communication may sound a "separation" alarm. For example, assume that remote control assembly 300 is left in the car of the user, while infusion pump assembly 100' is in the pocket of the user. Accordingly and after a defined period of time, infusion pump assembly 100' may begin sounding the "separation" alarm, indicating that communication with remote control assembly 300 cannot be established. Using switch assembly 318, the user may acknowledge/silence this "separation" alarm.

As the user may define and administer a bolus insulin dose via switch assembly 318 of infusion pump assembly 100' while remote control assembly 300 is not in communication with infusion pump assembly 100', infusion pump assembly 100' may store information concerning the administered bolus insulin dose within a log file (not shown) stored within infusion pump assembly 100'. This log file (not shown) may be stored within nonvolatile memory (not shown) included within infusion pump assembly 100'. Upon communication being reestablished between infusion pump assembly 100' and remote control assembly 300, infusion pump assembly 100' may provide the information concerning the administered bolus insulin dose stored within the log file (not shown) of infusion pump assembly 100' to remote control assembly 300.

Further, if the user anticipates separating remote control assembly 300 from infusion pump assembly 100', the user (via the above-described menuing system) may configure infusion pump assembly 100' and remote control assembly 300 to be in "separation" mode, thus eliminating the occurrence of the above-described "separation" alarms. However, the devices may continue to "ping" each other so that when they come back into communication with each other, infusion pump assembly 100' and remote control assembly 300 may automatically exit "separation" mode.

Further, if the user anticipates traveling in an airplane, the user (via the above-described menuing system of remote control assembly 300) may configure infusion pump assembly 100' and remote control assembly 300 to be in "airplane" mode, in which each of infusion pump assembly 100' and remote control assembly 300 suspend any and all data transmissions. While in "airplane" mode, infusion pump assembly 100' and remote control assembly 300 may or may not continue to receive data.

Switch assembly 318 may be used to perform additional functions, such as: checking the battery life of reusable housing assembly 102; pairing reusable housing assembly 102 with remote control assembly 300; and aborting the administration of a bolus does of infusible fluid.

Checking Battery Life:

Reusable housing assembly 102 may include a rechargeable battery assembly that may be capable of powering infusion pump assembly 100, 100' for approximately three days (when fully charged). Such a rechargeable battery assembly may have a usable life of a predetermined number of usable hours, for example, or years, or other predetermined length of usage. However, the predetermined life may depend on many factors, including but not limited to, one or more of the following: climate, daily usage, and number of recharges. Whenever reusable housing assembly 102 is disconnected from disposable housing assembly 114, infusion pump assembly 100, 100' may perform a battery check on the above-described rechargeable battery assembly whenever switch assembly 318 is depressed for a defined period of time (e.g. in excess of two seconds). In the event that the above-described rechargeable battery assembly is determined to be charged above a desired threshold, infusion pump assembly 100, 100' may render a "battery pass" tone. Alternatively, in the event that the above-described rechargeable battery assembly is determined to be charged below a desired threshold, infusion pump assembly 100, 100' may render a "battery fail" tone. Infusion pump assembly 100, 100' may include components and/or circuitry to determine whether reusable housing assembly 102 is disconnected from disposable housing assembly 114.

Pairing:

As discussed above and in one exemplary embodiment of the above-described infusion pump assembly, infusion pump assembly 100' may be used to communicate with remote control assembly 300. In order to effectuate communication between infusion pump assembly 100' and remote control assembly 300, a paring process may be performed. During such a pairing process, one or more infusion pump assemblies (e.g. infusion pump assembly 100') may be configured to communicate with remote control assembly 300 and (conversely) remote control assembly 300 may be configured to communicate with one or more infusion pump assemblies (e.g. infusion pump assembly 100'). Specifically, the serial numbers of the infusion pump assemblies (e.g. infusion pump assembly 100') may be recorded within a pairing file (not shown) included within remote control assembly 300 and the serial number of remote control assembly 300 may be recorded within a pairing file (not shown) included within the infusion pump assemblies (e.g. infusion pump assembly 100').

According to an embodiment, in order to effectuate such a pairing procedure, the user may simultaneously hold down one or more switch assemblies on both remote control assembly 300 and infusion pump assembly 100'. For example, the user may simultaneously hold down switch assembly 310 included within remote control assembly 300 and switch assembly 318 included within infusion pump assembly 100' for a defined period exceeding e.g. five seconds. Once this defined period is reached, one or more of remote control assembly 300 and infusion pump assembly 100' may generate an audible signal indicating that the above-described pairing procedure has been effectuated.

According to another embodiment, prior to performing the pairing process, the user may uncouple reusable housing assembly 102 from disposable housing assembly 114. By requiring this initial step, further assurance is provided that an infusion pump assembly being worn by a user may not be surreptitiously paired with a remote control assembly.

Once uncoupled, the user may enter pairing mode via input assembly 304 of remote control assembly 300. For example, the user may enter pairing mode on remote control assembly 300 via the above-described menuing system in combination with e.g., switch assembly 310. The user may be prompted on display assembly 302 of remote control assembly 300 to depress and hold switch assembly 318 on infusion pump assembly 100'. Additionally, remote control assembly 304 may switch to a low power mode to e.g., avoid trying to pair with distant infusion pump assemblies. The user may then depress and hold switch assembly 318 on infusion pump assembly 100' so that infusion pump assembly 100' enters a receive mode and waits for a pairing command from remote control assembly 300.

Remote control assembly 300 may then transmit a pairing request to infusion pump assembly 100', which may be acknowledged by infusion pump assembly 100'. Infusion pump assembly 100' may perform a security check on the pairing request received from remote control assembly 300 and (if the security check passes) infusion pump assembly 100' may activate a pump pairing signal (i.e., enter active pairing mode). Remote control assembly 300 may perform a security check on the acknowledgment received from infusion pump assembly 100'.

The acknowledgment received from infusion pump assembly 100' may define the serial number of infusion pump assembly 100' and remote control assembly 300 may display that serial number on display assembly 302 of remote control assembly 300. The user may be asked if they wish to pair with the pump found. If the user declines, the pairing process may be aborted. If the user agrees to the pairing process, remote control assembly 300 may prompt the user (via display assembly 302) to depress and hold switch assembly 318 on infusion pump assembly 100'.

The user may then depress and hold switch assembly 318 on infusion pump assembly 100' and depress and hold e.g. switch assembly 310 on remote control assembly 300.

Remote control assembly 300 may confirm that remote switch assembly 310 was held (which may be reported to infusion pump assembly 100'). Infusion pump assembly 100' may perform a security check on the confirmation received from remote control assembly 300 to confirm the integrity of same. If the integrity of the confirmation received is not verified, the pairing process is aborted. If the integrity of the confirmation received is verified, any existing remote pair configuration file is overwritten to reflect newly-paired remote control assembly 300, the pump pairing completed signal is activated, and the pairing process is completed.

Additionally, infusion pump assembly 100' may confirm that switch assembly 318 was held (which may be reported to remote control assembly 300). Remote control assembly 300 may perform a security check on the confirmation received from infusion pump assembly 100' to confirm the integrity of same. If the integrity of the confirmation received is not verified, the pairing process is aborted. If the integrity of the confirmation received is verified, a pair list file within remote control assembly 300 may be modified to add infusion pump assembly 100'. Typically, remote control assembly 300 may be capable of pairing with multiple infusion pump assemblies, while infusion pump assembly 100' may be capable of only pairing with a single remote control assembly. The pairing completed signal may be activated and the pairing process may be completed.

When the pairing process is completed, one or more of remote control assembly 300 and infusion pump assembly 100' may generate an audible signal indicating that the above-described pairing procedure has been successfully effectuated.

Aborting Bolus Dose:

in the event that the user wishes to cancel a bolus dose of e.g. insulin being administered by infusion pump assembly 100', the user may depress switch assembly 318 (e.g., shown in FIGS. 1 & 2) for a defined period exceeding e.g. five seconds. Once this defined period is reached, infusion pump assembly 100' may render an audible signal indicating that the above-described cancellation procedure has been effectuated.

While switch assembly 318 is shown as being positioned on the top of infusion pump assembly 100, 100', this is for illustrative purposes only and is not intended to be a limitation of this disclosure, as other configurations are possible. For example, switch assembly 318 may be positioned about the periphery of infusion pump assembly 100, 100'.

Figure 14:
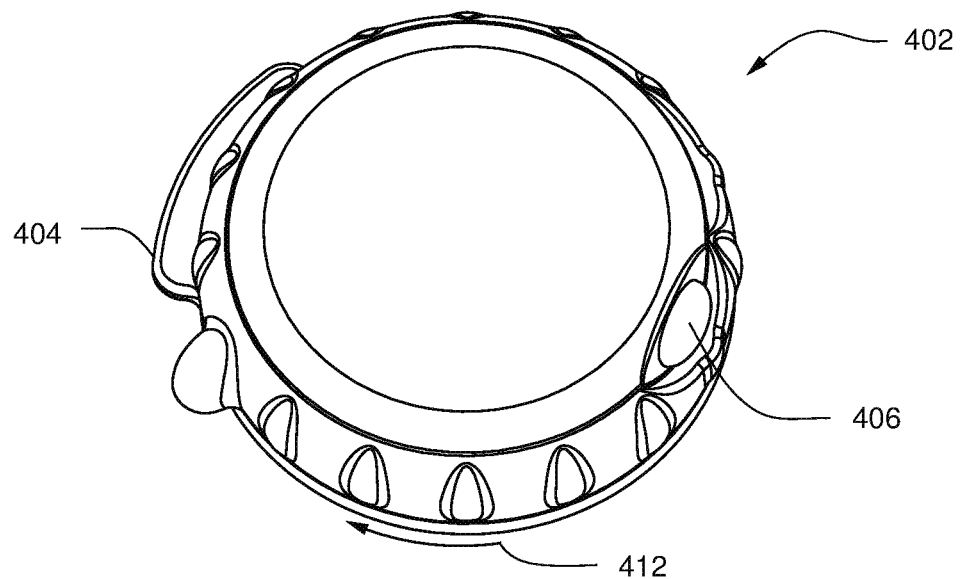
FIG. 14 is an isometric view of the infusion pump assembly of FIG. 13.
Figure 15:
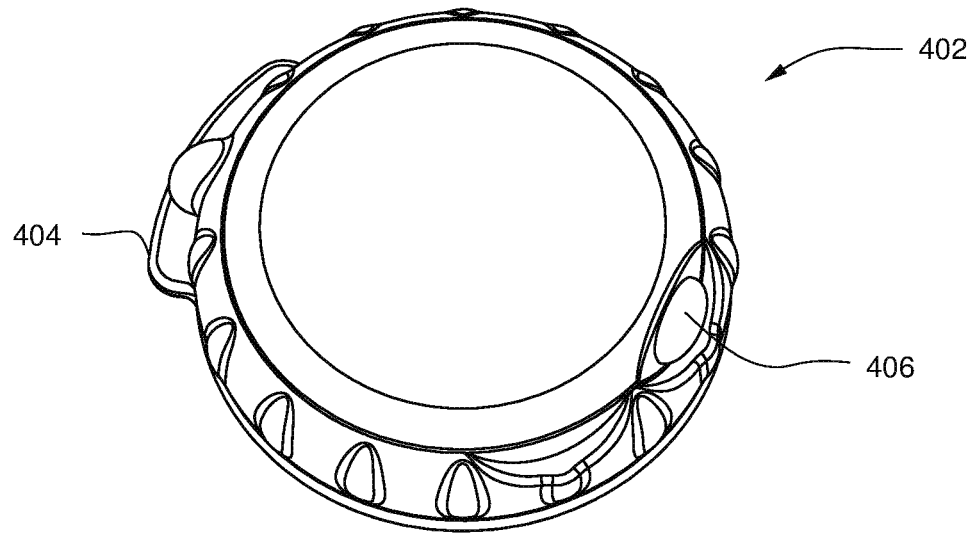
FIG. 15 is an isometric view of the infusion pump assembly of FIG. 13.

Referring also to FIGS. 13-15, there is shown an alternative-embodiment infusion pump assembly 400. As with pump assembly 100, 100', infusion pump assembly 400 may include reusable housing assembly 402 and disposable housing assembly 404.

In a fashion similar to reusable housing assembly 102, reusable housing assembly 402 may include a mechanical control assembly (that includes at least one pump assembly and at least one valve assembly). Reusable housing assembly 402 may also include an electrical control assembly that is configured to provide control signals to the mechanical control assembly and effectuate the delivery of an infusible fluid to a user. The valve assembly may be configured to control the flow of the infusible fluid through a fluid path and the pump assembly may be configured to pump the infusible fluid from the fluid path to the user In a fashion similar to disposable housing assembly 114, disposable housing assembly 404 may be configured for a single use or for use for a specified period of time, e.g., e.g., three days or any other amount of time. Disposable housing assembly 404 may be configured such that any components in infusion pump assembly 400 that come in contact with the infusible fluid are disposed on and/or within disposable housing assembly 404.

In this particular embodiment of the infusion pump assembly, infusion pump assembly 400 may include switch assembly 406 positioned about the periphery of infusion pump assembly 400. For example, switch assembly 406 may be positioned along a radial edge of infusion pump assembly 400, which may allow for easier use by a user. Switch assembly 406 may be covered with a waterproof membrane configured to prevent the infiltration of water into infusion pump assembly 400. Reusable housing assembly 402 may include main body portion 408 (housing the above-described mechanical and electrical control assemblies) and locking ring assembly 410 that may be configured to rotate about main body portion 408 (in the direction of arrow 412).

In a fashion similar to reusable housing assembly 102 and disposable housing assembly 114, reusable housing assembly 402 may be configured to releasably engage disposable housing assembly 404. Such releasable engagement may be accomplished by a screw-on, a twist-lock or a compression fit configuration, for example. In an embodiment in which a twist-lock configuration is utilized, the user of infusion pump assembly 400 may first properly position reusable housing assembly 402 with respect to disposable housing assembly 404 and may then rotate locking ring assembly 410 (in the direction of arrow 412) to releasably engage reusable housing assembly 402 with disposable housing assembly 404.

Through the use of locking ring assembly 410, reusable housing assembly 402 may be properly positioned with respect to disposable housing assembly 404 and then releasably engaged by rotating locking ring assembly 410, thus eliminating the need to rotate reusable housing assembly 402 with respect to disposable housing assembly 404. Accordingly, reusable housing assembly 402 may be properly aligned with disposable housing assembly 404 prior to engagement, and such alignment may not be disturbed during the engagement process. Locking ring assembly 410 may include a latching mechanism (not shown) that may prevent the rotation of locking ring assembly 410 until reusable housing assembly 402 and disposable housing assembly 404 are properly positioned with respect to each other.

Figure 16:
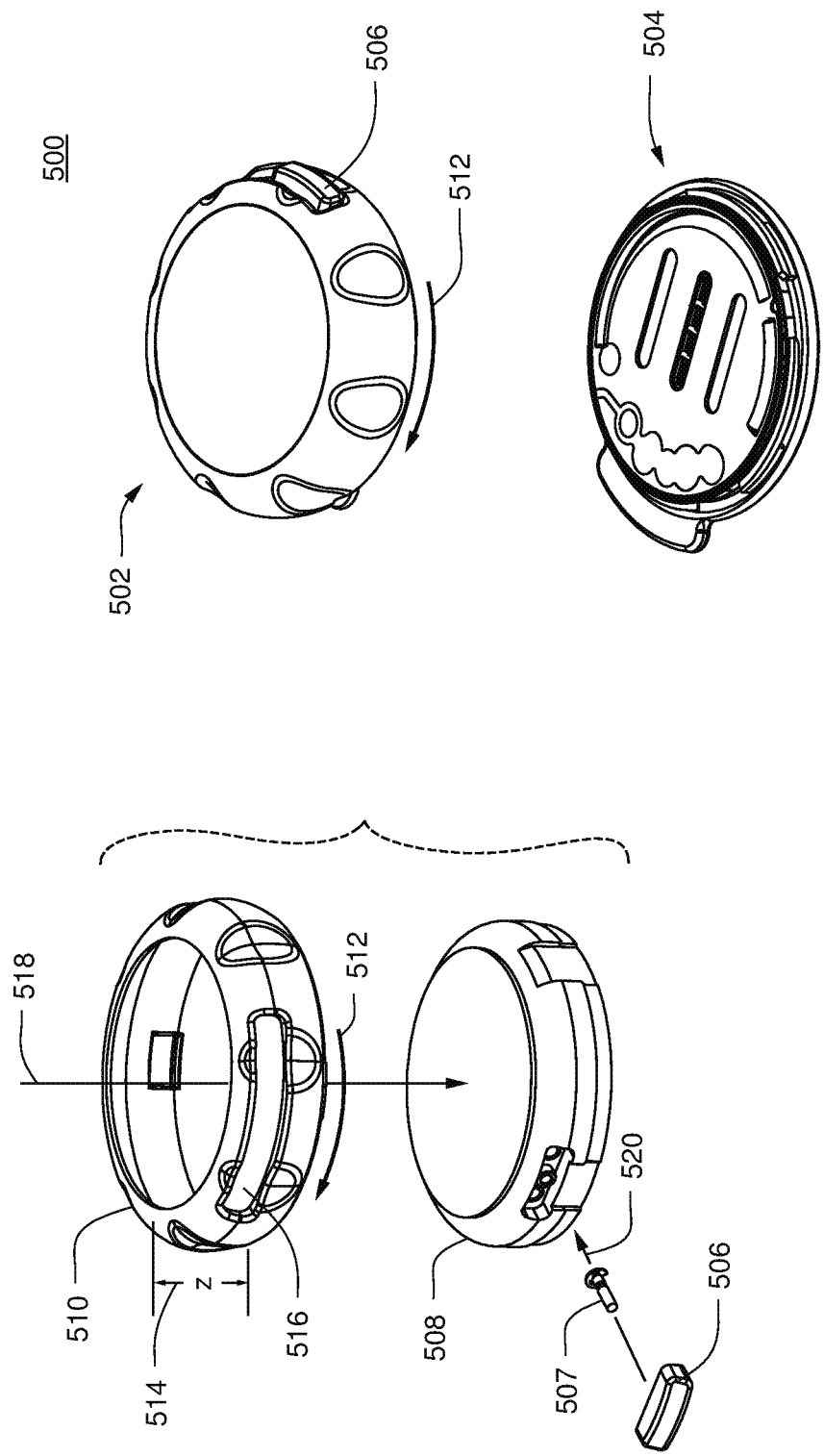
FIG. 16 is an isometric view of an alternative embodiment of the infusion pump assembly of FIG. 1.
Figure 17:
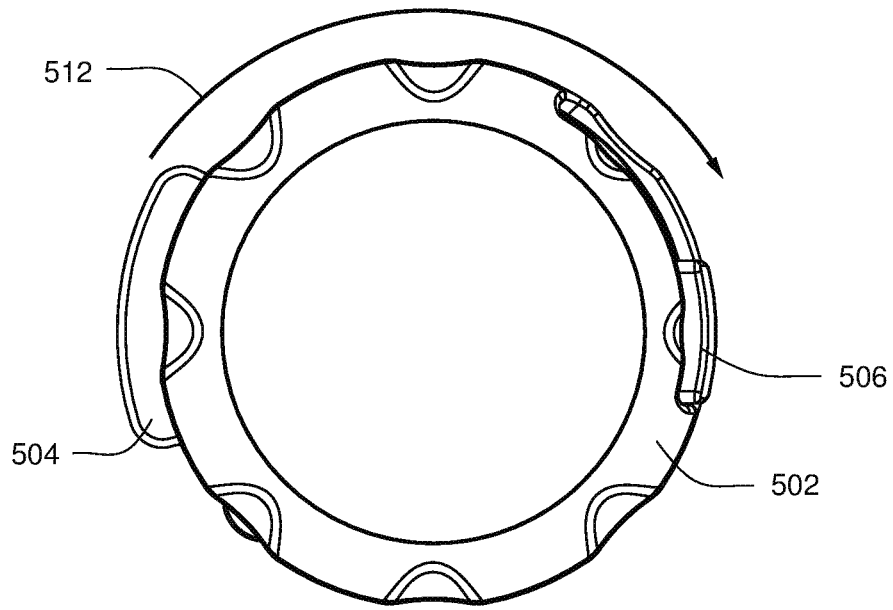
FIG. 17 is a plan view of the infusion pump assembly of FIG. 16.
Figure 18:
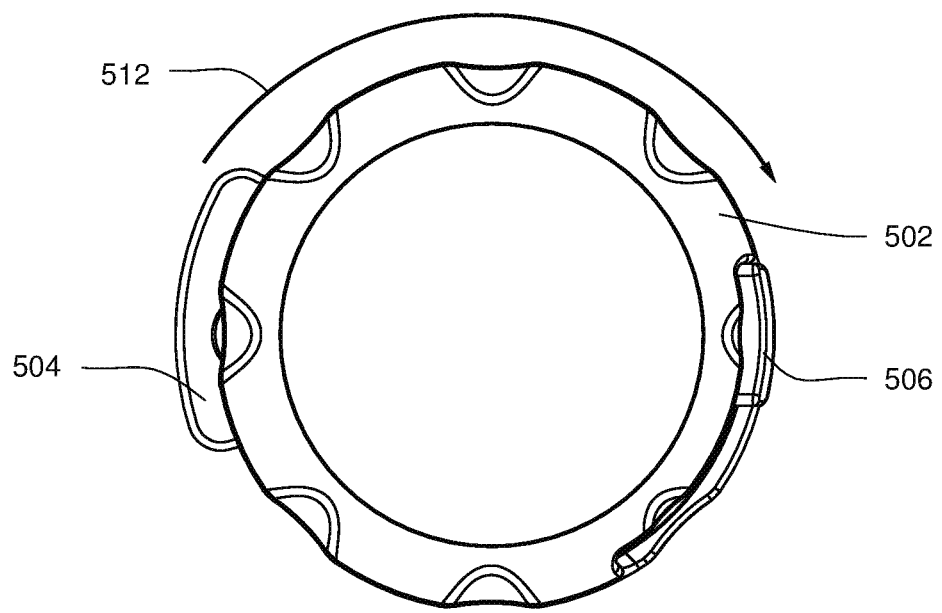
FIG. 18 is a plan view of the infusion pump assembly of FIG. 16.
Figure 19:
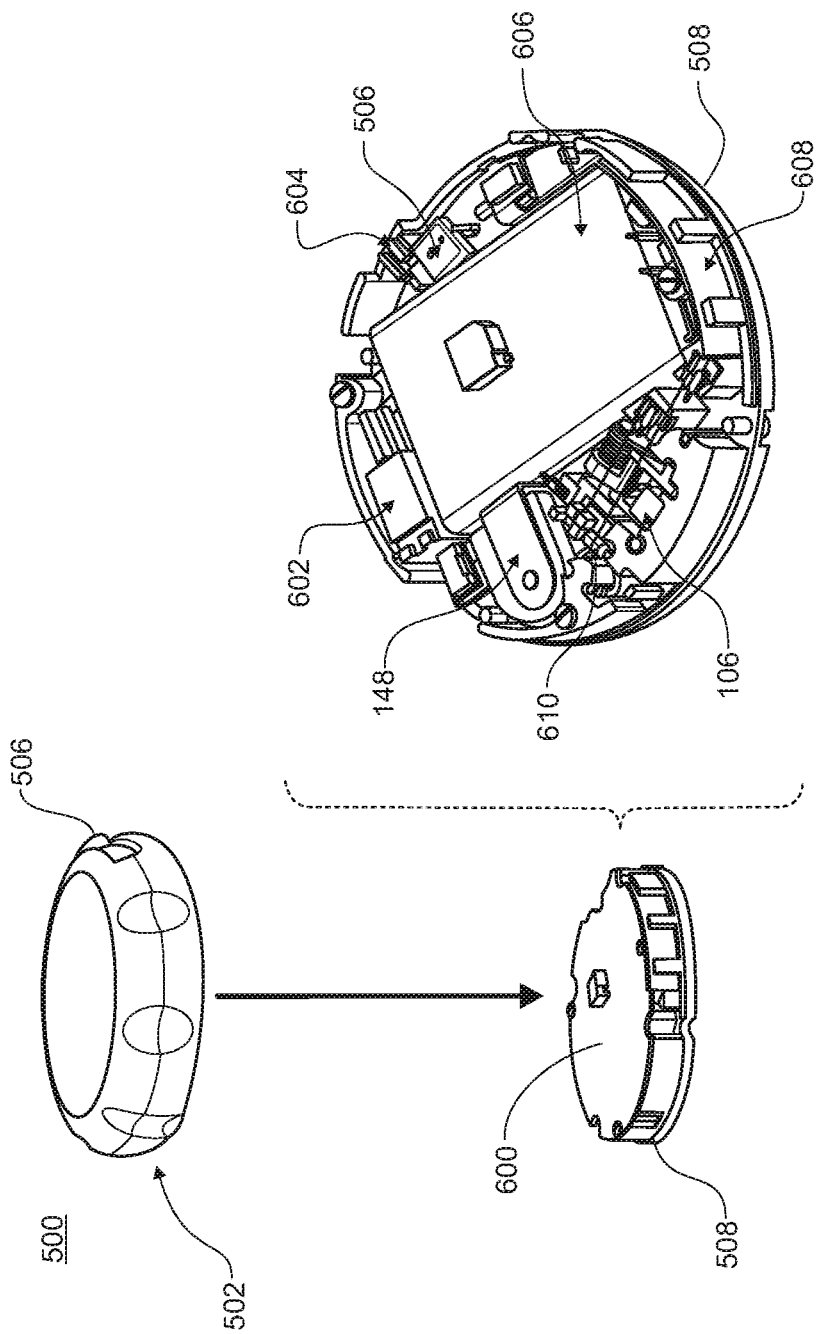
FIG. 19A is an exploded view of various components of the infusion pump assembly of FIG. 16.
FIG. 19B is an isometric view of a portion of the infusion pump assembly of FIG. 16.
Figure 20:
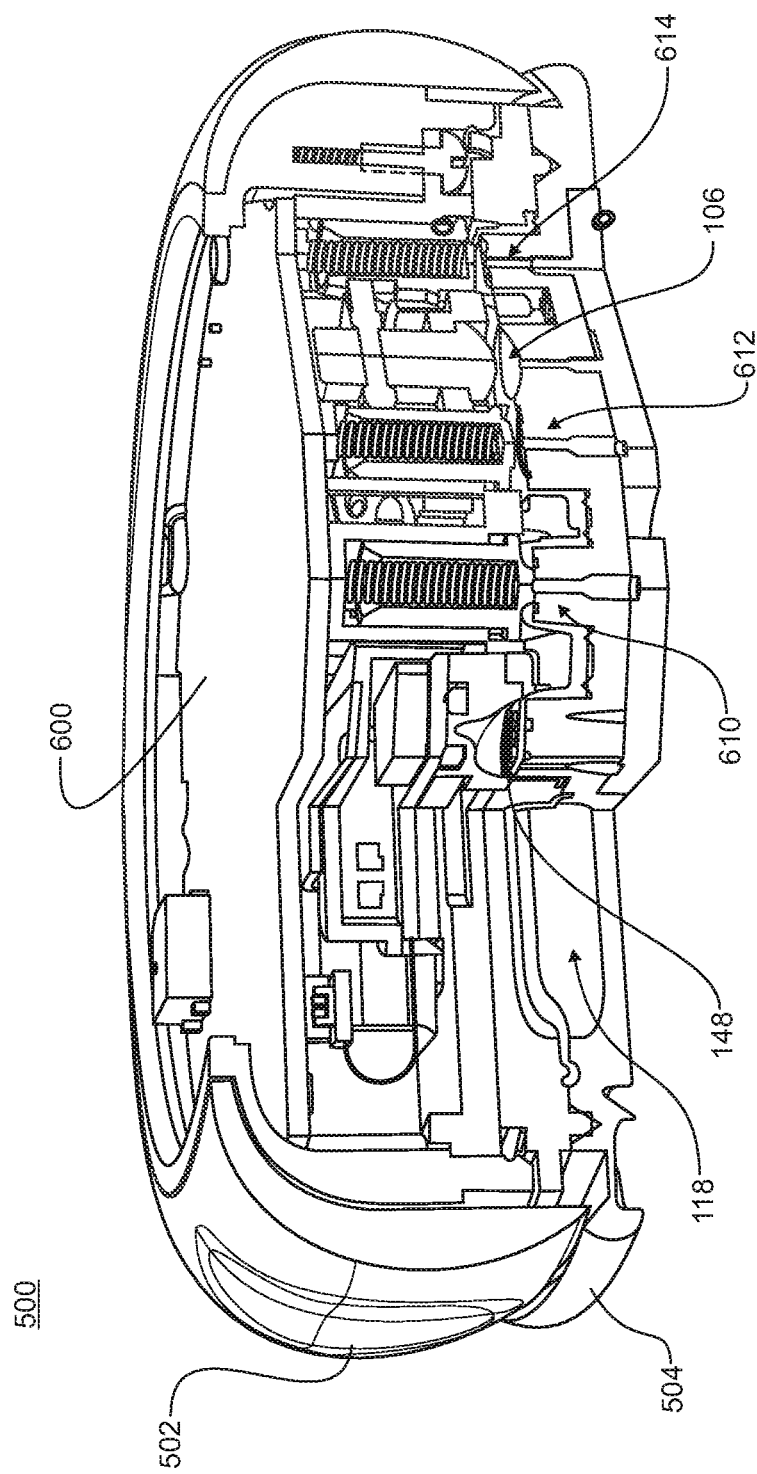
FIG. 20 is a cross-sectional view of the disposable housing assembly of the infusion pump assembly of FIG. 16.
Figure 21:
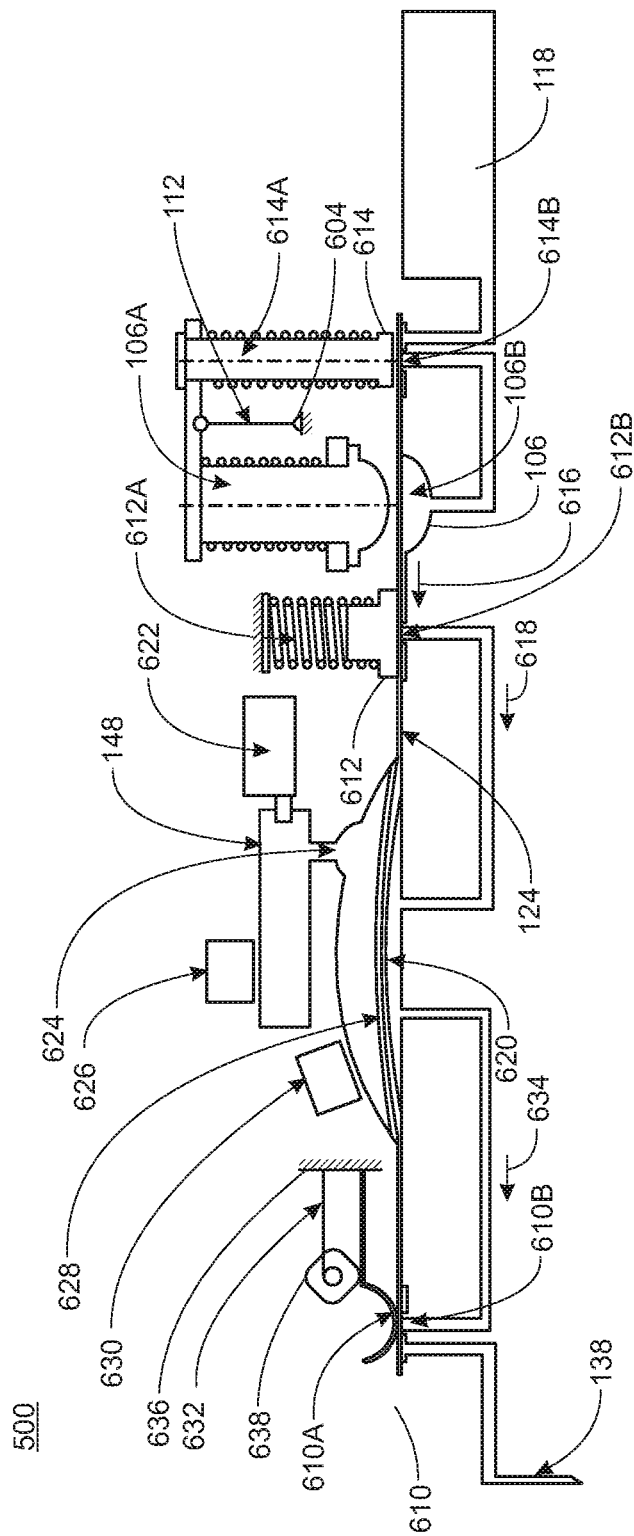
FIG. 21 is a diagrammatic view of a fluid path within the infusion pump assembly of FIG. 16.

Referring also to FIGS. 16-18, there is shown an alternative-embodiment infusion pump assembly 500. As with pump assembly 100, 100', infusion pump assembly 500 may include reusable housing assembly 502 and disposable housing assembly 504.

In a fashion similar to reusable housing assembly 402, reusable housing assembly 502 may include a mechanical control assembly (that includes at least one pump assembly and at least one valve assembly). Reusable housing assembly 502 may also include an electrical control assembly that is configured to provide control signals to the mechanical control assembly and effectuate the delivery of an infusible fluid to a user. The valve assembly may be configured to control the flow of the infusible fluid through a fluid path and the pump assembly may be configured to pump the infusible fluid from the fluid path to the user.

In a fashion similar to disposable housing assembly 404, disposable housing assembly 504 may be configured for a single use or for use for a specified period of time, e.g., e.g., three days or any other amount of time. Disposable housing assembly 504 may be configured such that any components in infusion pump assembly 500 that come in contact with the infusible fluid are disposed on and/or within disposable housing assembly 504.

In this particular embodiment of the infusion pump assembly, infusion pump assembly 500 may include switch assembly 506 positioned about the periphery of infusion pump assembly 500. For example, switch assembly 506 may be positioned along a radial edge of infusion pump assembly 500, which may allow for easier use by a user. Switch assembly 506 may be covered with a waterproof membrane and/or an o-ring or other sealing mechanism may be included on the stem 507 of the switch assembly 506 configured to prevent the infiltration of water into infusion pump assembly 500. However, in some embodiments, switch assembly 506 may include an overmolded rubber button, thus providing functionality as a waterproof seal without the use of a waterproof membrane or an o-ring. However, in still other embodiments, the overmolded rubber button may additionally be covered by a waterproof membrane and/or include an o-ring. Reusable housing assembly 502 may include main body portion 508 (housing the above-described mechanical and electrical control assemblies) and locking ring assembly 510 that may be configured to rotate about main body portion 508 (in the direction of arrow 512).

In a fashion similar to reusable housing assembly 402 and disposable housing assembly 404, reusable housing assembly 502 may be configured to releasably engage disposable housing assembly 504. Such releasable engagement may be accomplished by a screw-on, a twist-lock or a compression fit configuration, for example. In an embodiment in which a twist-lock configuration is utilized, the user of infusion pump assembly 500 may first properly position reusable housing assembly 502 with respect to disposable housing assembly 504 and may then rotate locking ring assembly 510 (in the direction of arrow 512) to releasably engage reusable housing assembly 502 with disposable housing assembly 404.

As locking ring assembly 510 included within infusion pump assembly 500 may be taller (i.e., as indicated by arrow 514) than locking ring assembly 410, locking ring assembly 510 may include a passage 516 through which button 506 may pass. Accordingly, when assembling reusable housing assembly 502, locking ring assembly 510 may be installed onto main body portion 508 (in the direction of arrow 518). Once locking ring assembly 510 is installed onto main body portion 508, one or more locking tabs (not shown) may prevent locking ring assembly 510 from being removed from main body portion 508. The portion of switch assembly 506 that protrudes through passage 516 may then be pressed into main body portion 508 (in the direction of arrow 520), thus completing the installation of switch assembly 506.

Although button 506 is shown in various locations on infusion pump assembly 500, button 506, in other embodiments, may be located anywhere desirable on infusion pump assembly 500.

Through the use of locking ring assembly 510, reusable housing assembly 502 may be properly positioned with respect to disposable housing assembly 504 and then releasably engaged by rotating locking ring assembly 510, thus eliminating the need to rotate reusable housing assembly 502 with respect to disposable housing assembly 504. Accordingly, reusable housing assembly 502 may be properly aligned with disposable housing assembly 504 prior to engagement, and such alignment may not be disturbed during the engagement process. Locking ring assembly 510 may include a latching mechanism (not shown) that prevents the rotation of locking ring assembly 510 until reusable housing assembly 502 and disposable housing assembly 504 are properly positioned with respect to each other. Passage 516 may be elongated to allow for the movement of locking ring 510 about switch assembly 506.

Referring also to FIGS. 19A-19B & 20-21, there are shown various views of infusion pump assembly 500, which is shown to include reusable housing assembly 502, switch assembly 506, and main body portion 508. As discussed above, main body portion 508 may include a plurality of components, examples of which may include but are not limited to volume sensor assembly 148, printed circuit board 600, vibration motor assembly 602, shape memory actuator anchor 604, switch assembly 506, battery 606, antenna assembly 608, pump assembly 106, measurement valve assembly 610, volume sensor valve assembly 612 and reservoir valve assembly 614. To enhance clarity, printed circuit board 600 has been removed from FIG. 19B to allow for viewing of the various components positioned beneath printed circuit board 600.

The various electrical components that may be electrically coupled with printed circuit board 600 may utilize spring-biased terminals that allow for electrical coupling without the need for soldering the connections. For example, vibration motor assembly 602 may utilize a pair of spring-biased terminals (one positive terminal and one negative terminal) that are configured to press against corresponding conductive pads on printed circuit board 600 when vibration motor assembly 602 is positioned on printed circuit board 600. However, in the exemplary embodiment, vibration motor assembly 602 is soldered directly to the printed circuit board.

As discussed above, volume sensor assembly 148 may be configured to monitor the amount of fluid infused by infusion pump assembly 500. For example, volume sensor assembly 148 may employ acoustic volume sensing, which is the subject of U.S. Pat. Nos. 5,575,310 and 5,755,683 assigned to DEKA Products Limited Partnership, as well as the U.S. patent application Publication Nos. US 2007/0228071 A1, US 2007/0219496 A1, US 2007/0219480 A1, US 2007/0219597 A1, the entire disclosures of all of which are incorporated herein by reference.

Vibration motor assembly 602 may be configured to provide a vibration-based signal to the user of infusion pump assembly 500. For example, in the event that the voltage of battery 606 (which powers infusion pump assembly 500) is below the minimum acceptable voltage, vibration motor assembly 602 may vibrate infusion pump assembly 500 to provide a vibration-based signal to the user of infusion pump assembly 500. Shape memory actuator anchor 604 may provide a mounting point for the above-described shape memory actuator (e.g. shape memory actuator 112). As discussed above, shape memory actuator 112 may be, for example, a conductive shape-memory alloy wire that changes shape with temperature. The temperature of shape-memory actuator 112 may be changed with a heater, or more conveniently, by application of electrical energy. Accordingly, one end of shape memory actuator 112 may be rigidly affixed (i.e., anchored) to shape memory actuator anchor 604 and the other end of shape memory actuator 112 may be applied to e.g. a valve assembly and/or a pump actuator. Therefore, by applying electrical energy to shape memory actuator 112, the length of shape memory actuator 112 may be controlled and, therefore, the valve assembly and/or the pump actuator to which it is attached may be manipulated.

Antenna assembly 608 may be configured to allow for wireless communication between e.g. infusion pump assembly 500 and remote control assembly 300 (FIG. 11). As discussed above, remote control assembly 300 may allow the user to program infusion pump assembly 500 and e.g. configure bolus infusion events. As discussed above, infusion pump assembly 500 may include one or more valve assemblies configured to control the flow of the infusible fluid through a fluid path (within infusion pump assembly 500) and pump assembly 106 may be configured to pump the infusible fluid from the fluid path to the user. In this particular embodiment of infusion pump assembly 500, infusion pump assembly 500 is shown to include three valve assemblies, namely measurement valve assembly 610, volume sensor valve assembly 612, and reservoir valve assembly 614.

Figure 22A:
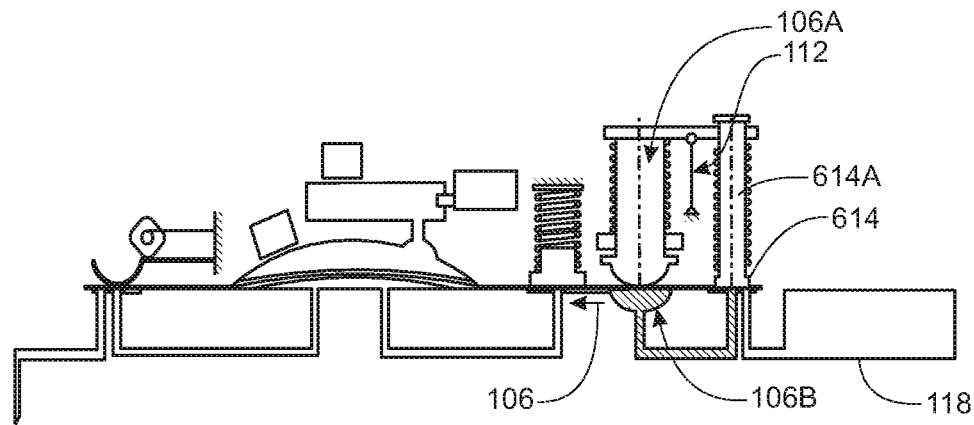
FIGS. 22A-22C are diagrammatic views of a fluid path within the infusion pump assembly of FIG. 16.

As discussed above and referring also to FIG. 21, the infusible fluid may be stored within reservoir 118. In order to effectuate the delivery of the infusible fluid to the user, the processing logic (not shown) included within infusion pump assembly 500 may energize shape memory actuator 112, which may be anchored on one end using shape memory actuator anchor 604. Referring also to FIG. 22A, shape memory actuator 112 may result in the activation of pump assembly 106 and reservoir valve assembly 614. Reservoir valve assembly 614 may include reservoir valve actuator 614A and reservoir valve 614B, and the activation of reservoir valve assembly 614 may result in the downward displacement of reservoir valve actuator 614A and the closing of reservoir valve 614B, resulting in the effective isolation of reservoir 118. Further, pump assembly 106 may include pump plunger 106A and pump chamber 106B and the activation of pump assembly 106 may result in pump plunger 106A being displaced in a downward fashion into pump chamber 106B and the displacement of the infusible fluid (in the direction of arrow 616).

Figure 22B:
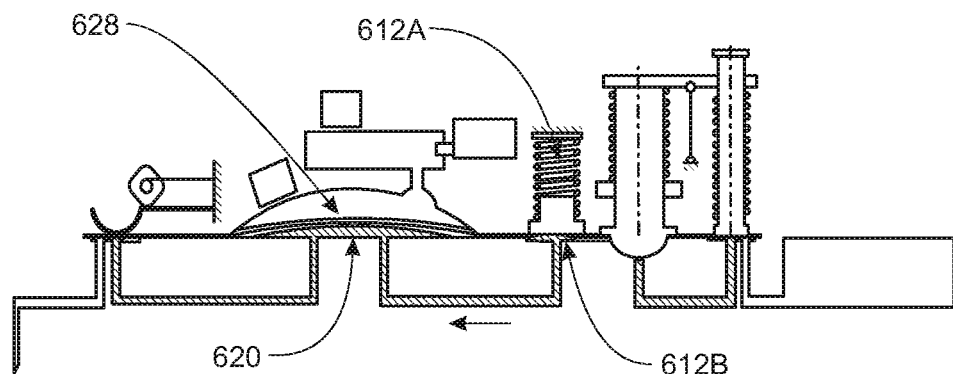

Volume sensor valve assembly 612 may include volume sensor valve actuator 612A and volume sensor valve 612B. Referring also to FIG. 22B, volume sensor valve actuator 612A may be closed via a spring assembly that provides mechanical force to seal volume sensor valve 612B. However, when pump assembly 106 is activated, if the displaced infusible fluid is of sufficient pressure to overcome the mechanical sealing force of volume sensor valve assembly 612, the displacement of the infusible fluid occurs in the direction of arrow 618. This may result in the filling of volume sensor chamber 620 included within volume sensor assembly 148. Through the use of speaker assembly 622, port assembly 624, reference microphone 626, spring diaphragm 628, invariable volume microphone 630, volume sensor assembly 148 may determine the volume of infusible fluid included within volume sensor chamber 620.

Figure 22C:
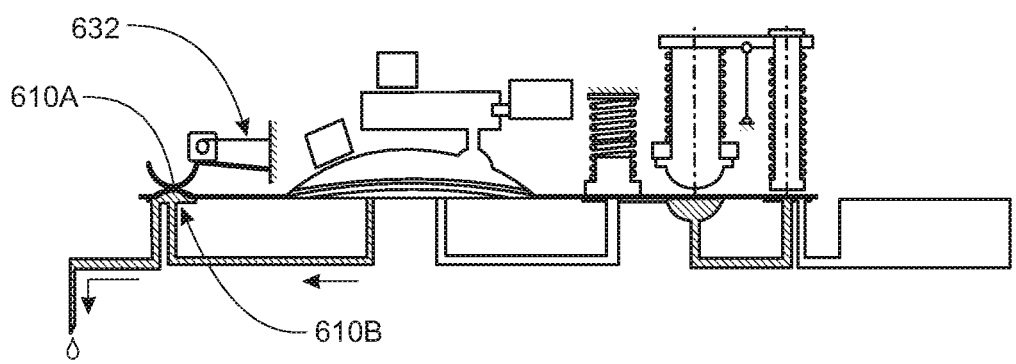

Referring also to FIG. 22C, once the volume of infusible fluid included within volume sensor chamber 620 is calculated, shape memory actuator 632 may be energized, resulting in the activation of measurement valve assembly 610, which may include measurement valve actuator 610A and measurement valve 610B. Once activated and due to the mechanical energy asserted on the infusible fluid within volume sensor chamber 620 by spring diaphragm 628, the infusible fluid within volume sensor chamber 620 may be displaced (in the direction of arrow 634) through disposable cannula 138 and into the body of the user.

Figure 23:
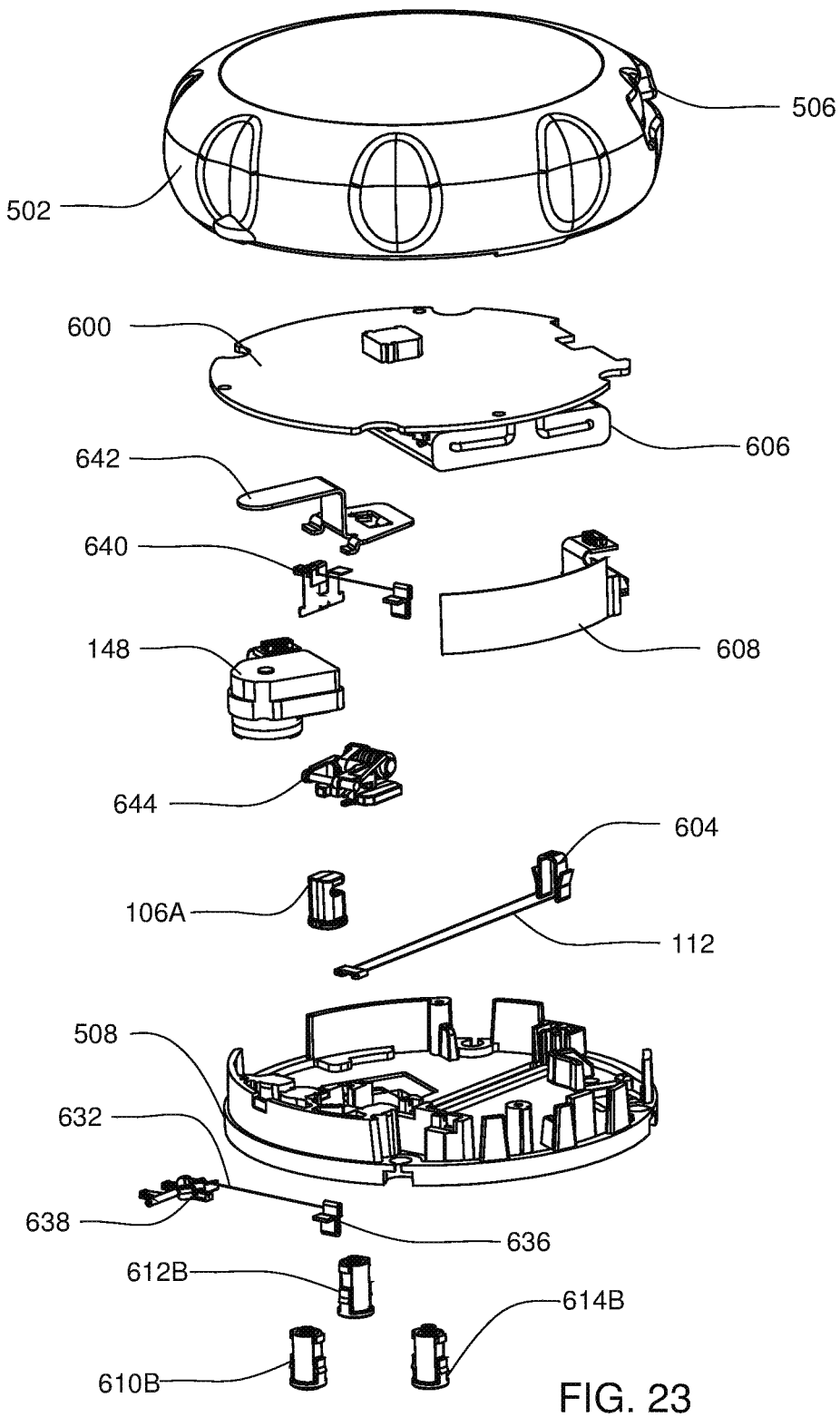
FIG. 23 is an exploded view of various components of the infusion pump assembly of FIG. 16.
Figure 26B:
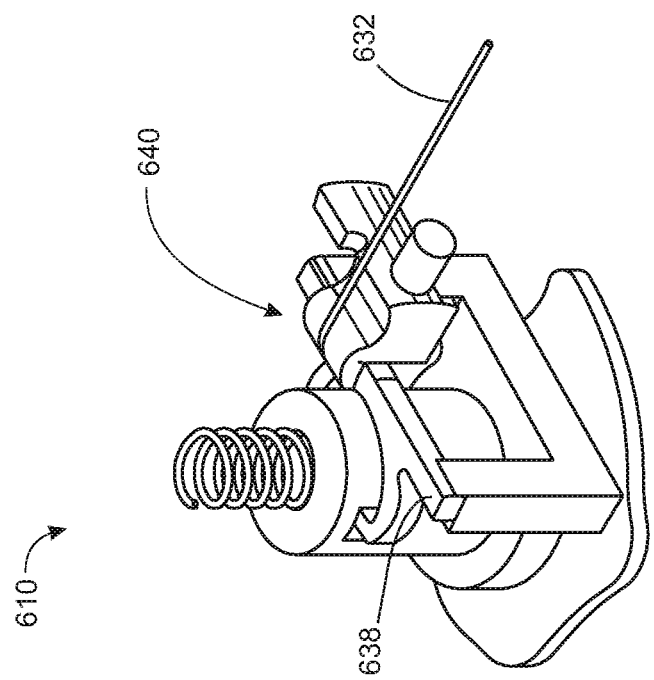
FIG. 26A-26B are isometric views of a measurement valve assembly of the infusion pump assembly of FIG. 16.
Figure 26A:
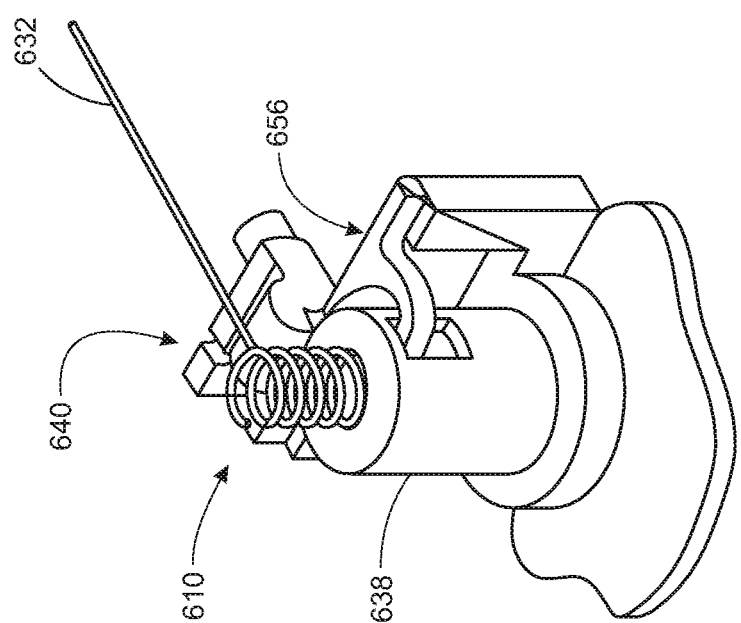
Figure 27B:
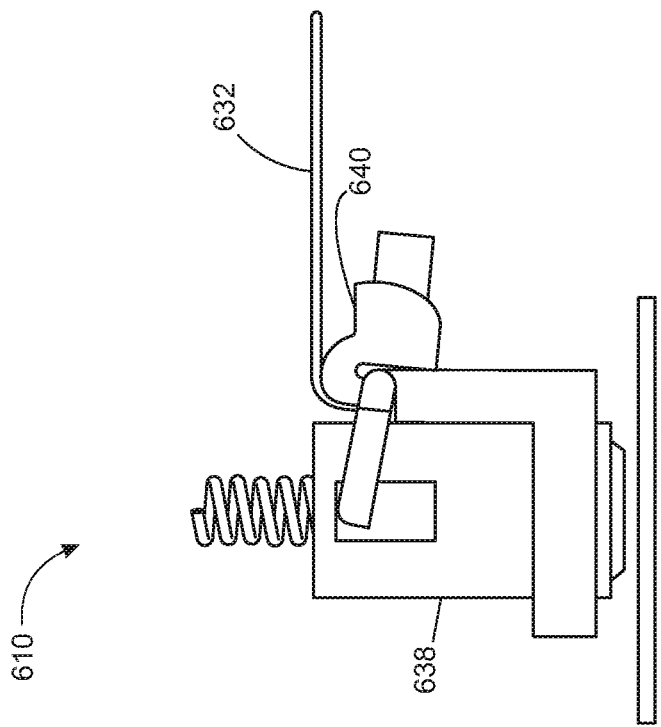
FIG. 27A-27B are side views of the measurement valve assembly of FIGS. 26A-26B.
Figure 27A:
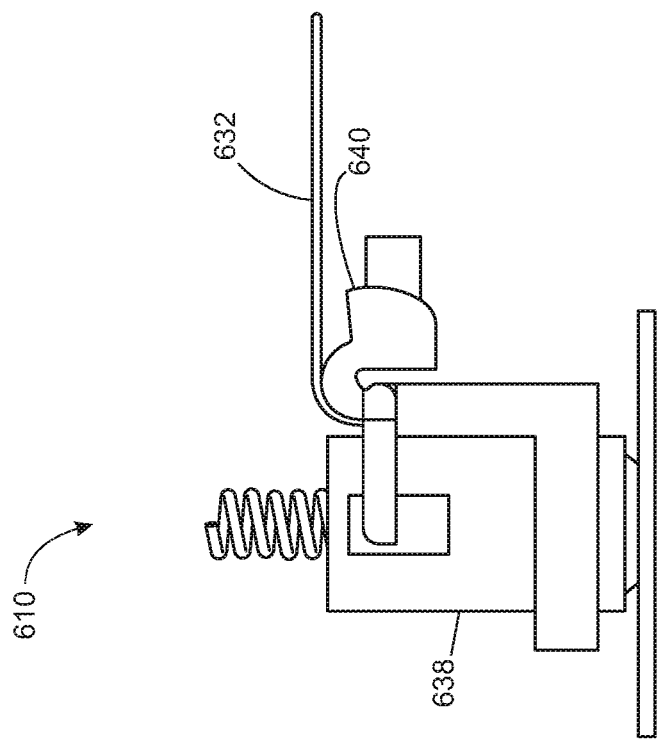
Figure 28A:
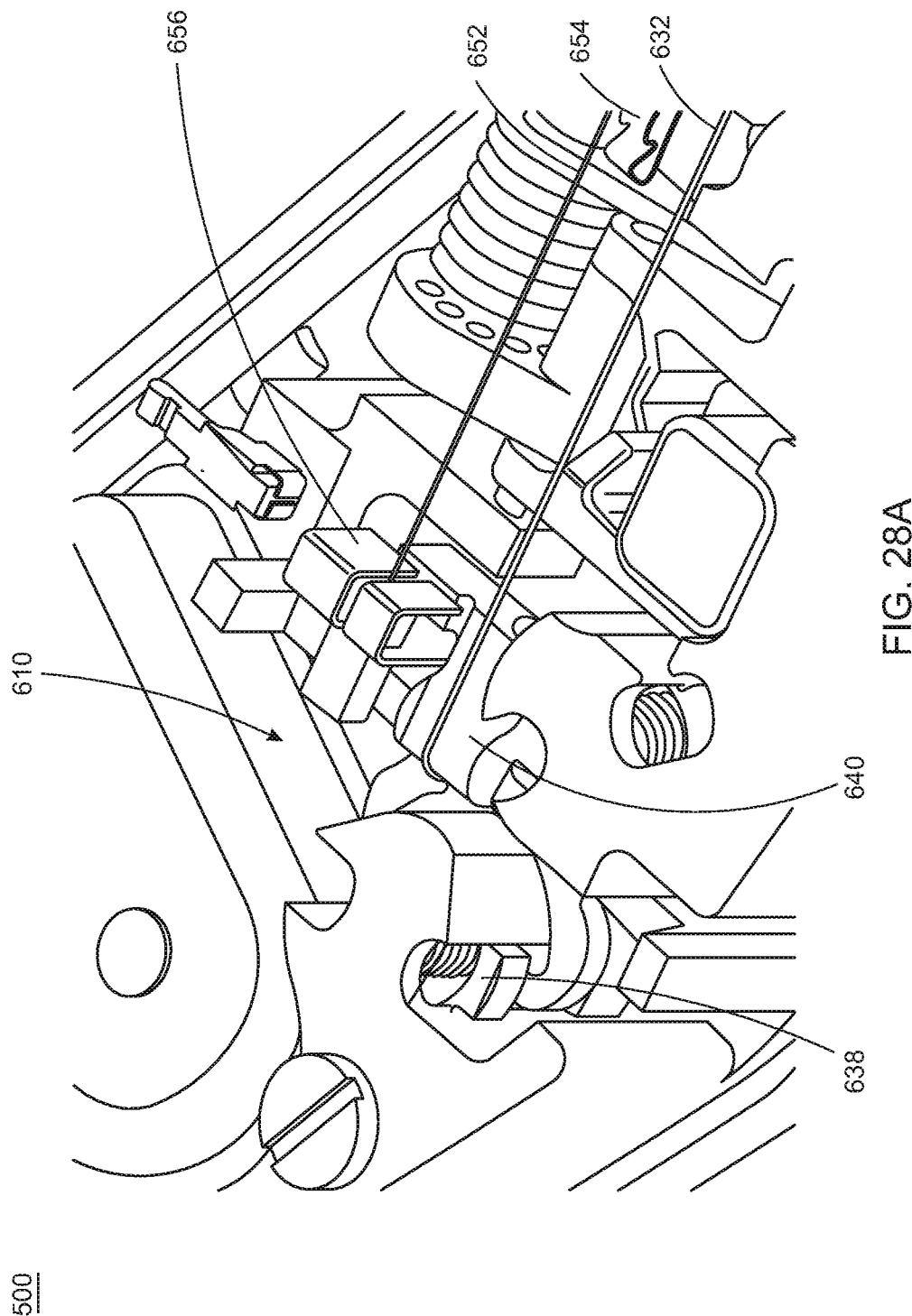
FIGS. 28A-28D are views of a measurement valve assembly of the infusion pump assembly of FIG. 16.
Figure 28B:
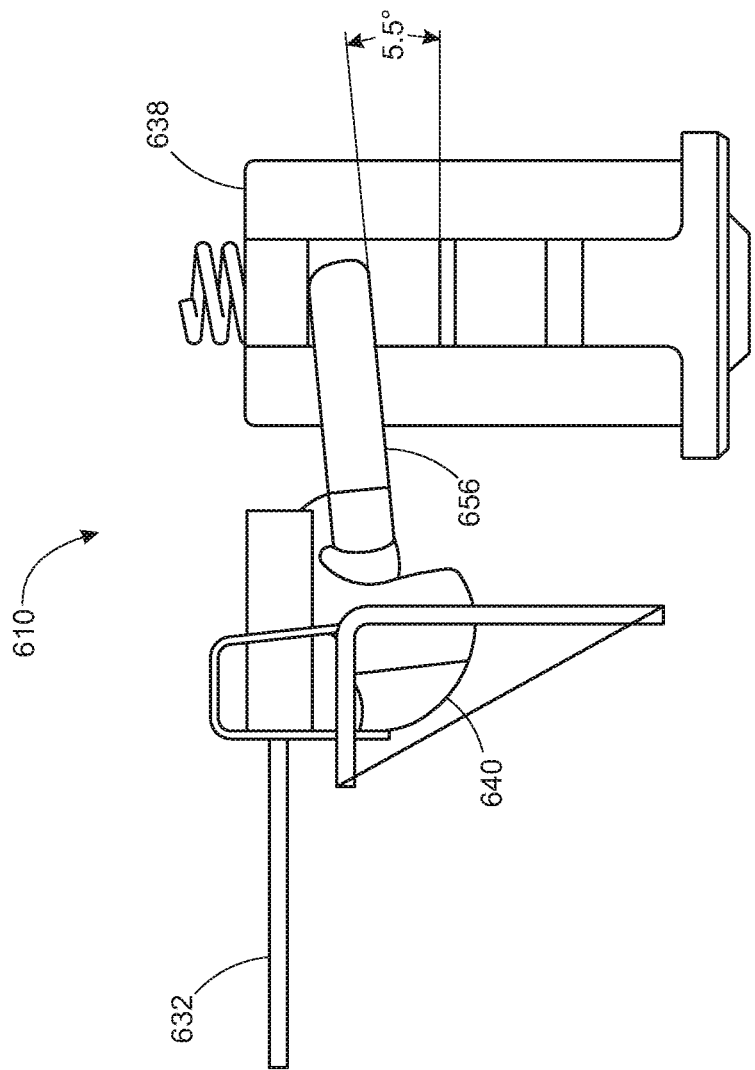
Figure 28C:
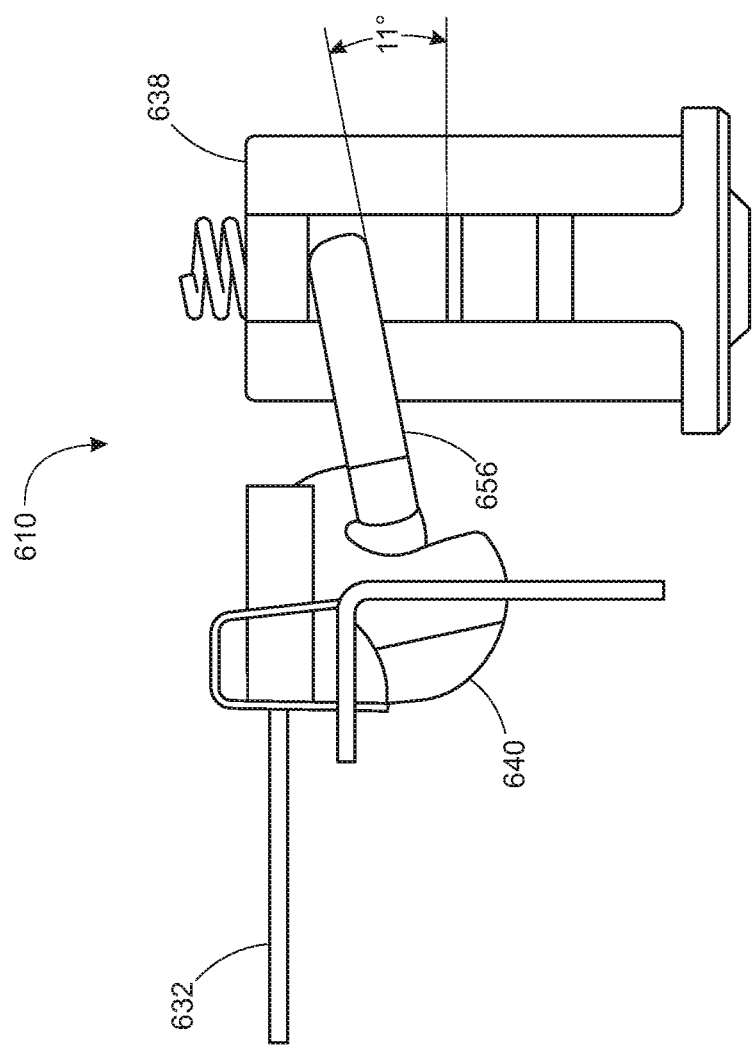
Figure 28D:
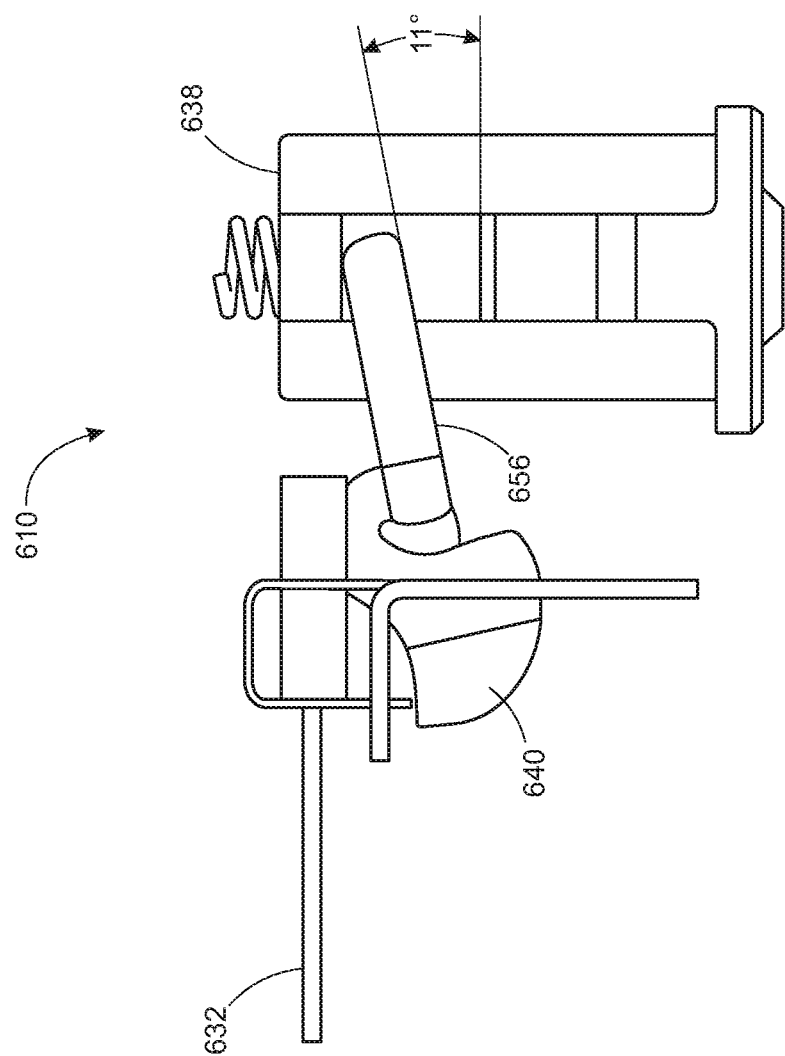

Referring also to FIG. 23, there is shown an exploded view of infusion pump assembly 500. Shape memory actuator 632 may be anchored (on a first end) to shape memory actuator anchor 636. Additionally, the other end of shape memory actuator 632 may be used to provide mechanical energy to valve assembly 638, which may activate measurement valve assembly 610. Volume sensor assembly spring retainer 642 may properly position volume sensor assembly 148 with respect to the various other components of infusion pump assembly 500. Valve assembly 638 may be used in conjunction with shape memory actuator 112 to activate pump plunger 106A. Measurement valve 610B, volume sensor valve 612B and/or reservoir valve 614B may be self-contained valves that are configured to allow for installation during assembly of infusion pump assembly 500 by pressing the valves upward into the lower surface of main body portion 508.

Referring also to FIG. 24 & FIGS. 25A-25D, there is shown a more-detailed view of pump assembly 106. Pump actuator assembly 644 may include pump actuator support structure 646, bias spring 648, and lever assembly 650.

Referring also to FIGS. 26A-26B & FIGS. 27A-27B, there is shown a more-detailed view of measurement valve assembly 610. As discussed above, valve assembly 638 may activate measurement valve assembly 610.

Referring also to FIGS. 28A-28D, infusion pump assembly 500 may include measurement valve assembly 610. As discussed above, valve assembly 638 may be activated via shape memory actuator 632 and actuator assembly 640. Accordingly, to infuse the quantity of infusible fluid stored within volume sensor chamber 620, shape memory actuator 632 may need to activate valve assembly 638 for a considerable period of time (e.g. one minute or more). As this would consume a considerable amount of power from battery 606, measurement valve assembly 610 may allow for the temporary activation of valve assembly 638, at which point measurement valve latch 656 may prevent valve assembly 638 from returning to its non-activated position. Shape memory actuator 652 may be anchored on a first end using electrical contact 654. The other end of shape memory actuator 652 may be connected to a valve latch 656. When shape memory actuator 652 is activated, shape memory actuator 652 may pull valve latch 656 forward and release valve assembly 638. As such, measurement valve assembly 610 may be activated via shape memory actuator 632. Once measurement valve assembly 610 has been activated, valve latch 656 may automatically latch valve assembly 638 in the activated position. Actuating shape memory actuator 652 may pull valve latch 656 forward and release valve assembly 638. Assuming shape memory actuator 632 is no longer activated, measurement valve assembly 610 may move to a de-activated state once valve latch 656 has released valve assembly 638. Accordingly, through the use of measurement valve assembly 610, shape memory actuator 632 does not need to be activated during the entire time that it takes to infuse the quantity of infusible fluid stored within volume sensor chamber 620.

As discussed above, the above-described infusion pump assemblies (e.g., infusion pumps assemblies 100, 100', 400, 500) may include an external infusion set 134 configured to deliver the infusible fluid to a user. External infusion set 134 may include a cannula assembly 136, which may include a needle or a disposable cannula 138, and tubing assembly 140. Tubing assembly 140 may be in fluid communication with reservoir 118, for example, by way of the fluid path, and with cannula assembly 138 for example, either directly or by way of a cannula interface 142.

Figure 29:
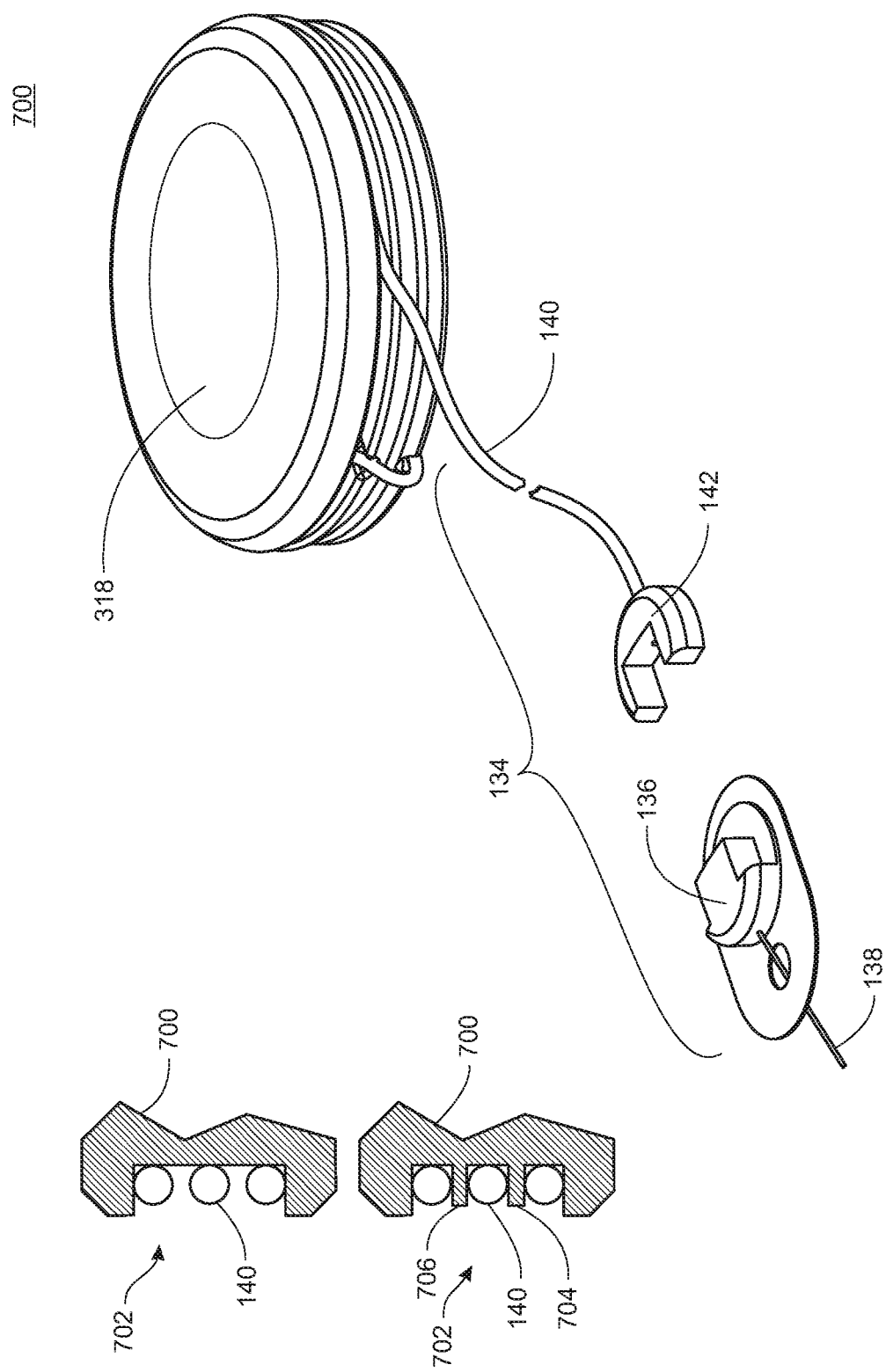
FIG. 29 is an isometric view of an alternative embodiment of the infusion pump assembly of FIG. 1.

Referring also to FIG. 29, there is shown an alternative embodiment infusion pump assembly 700 that is configured to store a portion of tubing assembly 140. Specifically, infusion pump assembly 700 may include peripheral tubing storage assembly 702 that is configured to allow the user to wind a portion of tubing assembly 140 about the periphery of infusion pump assembly 700 (in a manner similar to that of a yoyo). Peripheral tubing storage assembly 702 may be positioned about the periphery of infusion pump assembly 700. Peripheral tubing storage assembly 702 may be configured as an open trough into which a portion of tubing assembly 140 may be wound. Alternatively, peripheral tubing storage assembly 702 may include one or more divider portions 704, 706 that form a plurality of narrower troughs that may be sized to generate an interference fit between the walls of the narrower trough and the exterior surface of the portion of tubing 140. When peripheral tubing storage assembly 705 includes plurality of divider portions 704, 706, the resulting narrower troughs may be wound in a spiral fashion about the periphery of infusion pump assembly 700 (in a manner similar to the thread of a screw).

Figure 30:
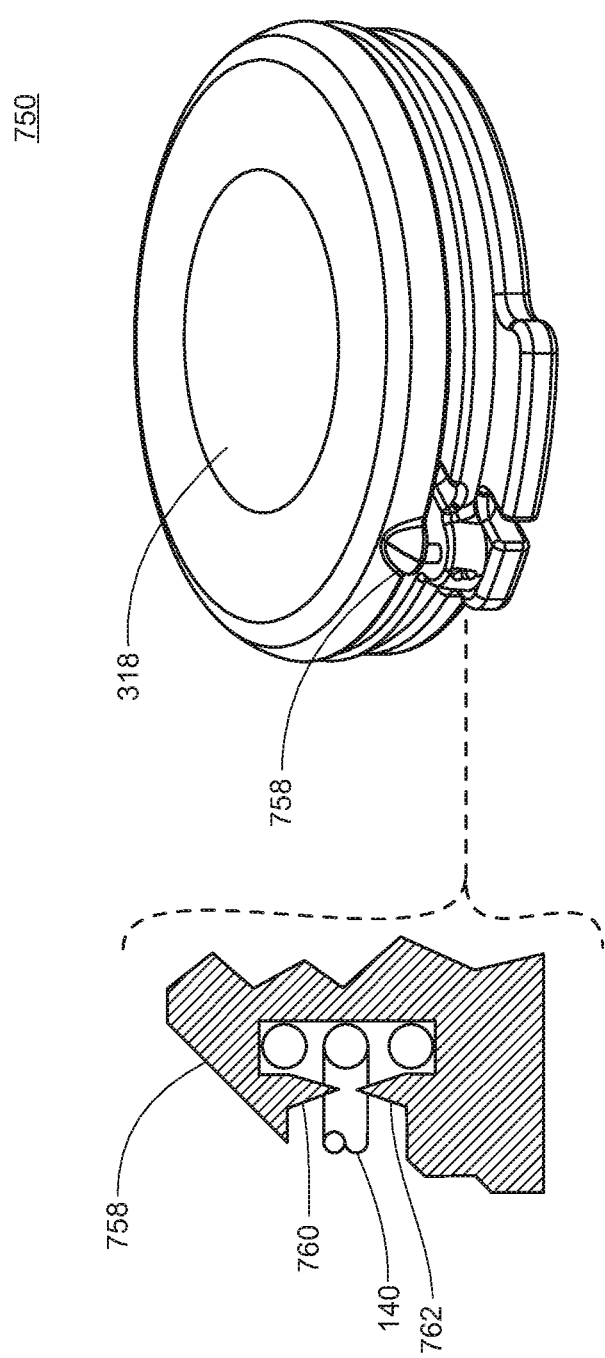
FIG. 30 is an isometric view of an alternative embodiment of the infusion pump assembly of FIG. 1.
Figure 31:
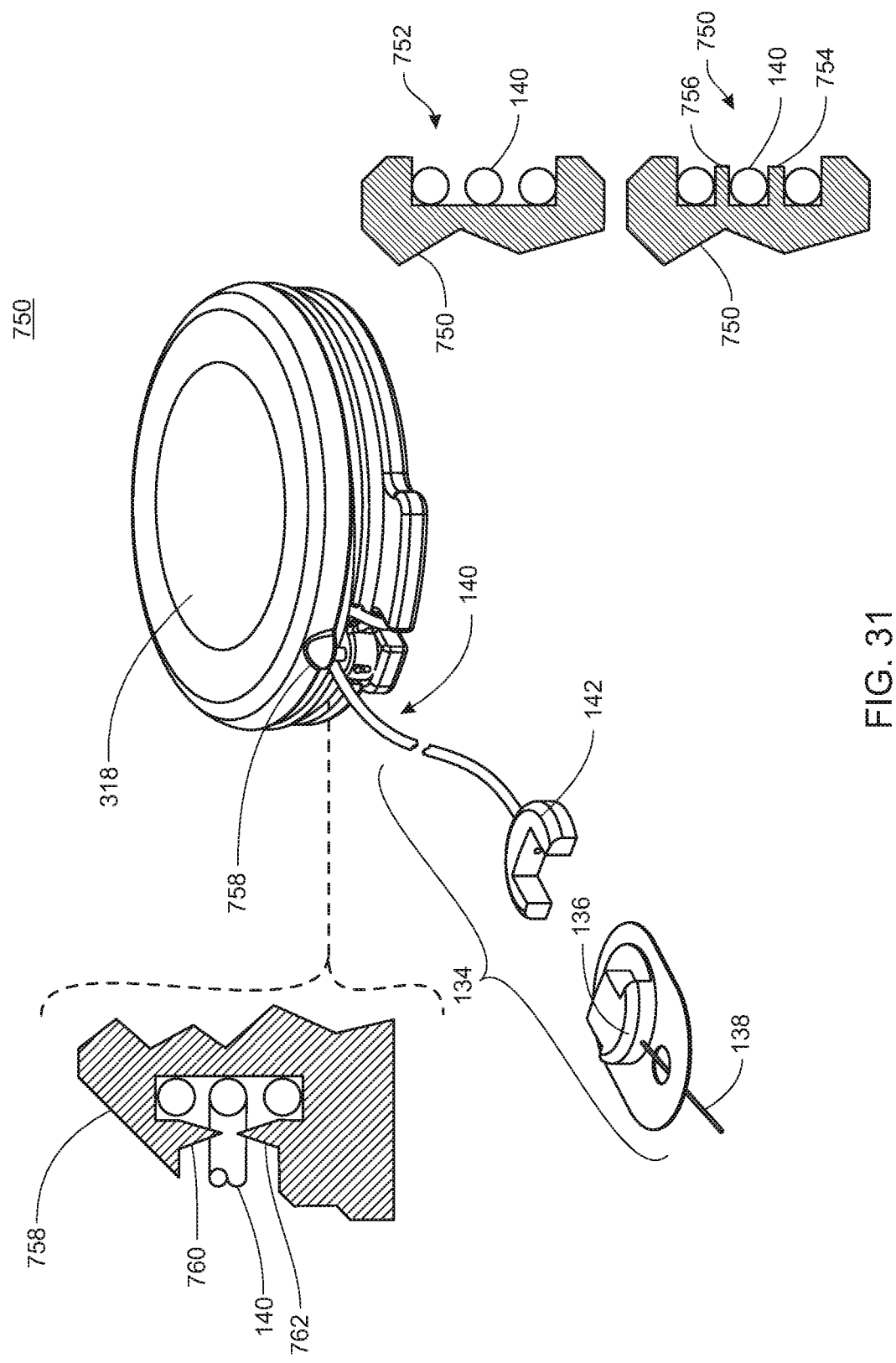
FIG. 31 is another view of the alternative embodiment infusion pump assembly of FIG. 9.

Referring also to FIGS. 30-31, there is shown an alternative embodiment infusion pump assembly 750 that is configured to store a portion of tubing assembly 140. Specifically, infusion pump assembly 750 may include peripheral tubing storage assembly 752 that is configured to allow the user to wind a portion of tubing assembly 140 about the periphery of infusion pump assembly 750 (again, in a manner similar to that of a yoyo). Peripheral tubing storage assembly 752 may be positioned about the periphery of infusion pump assembly 750. Peripheral tubing storage assembly 752 may be configured as an open trough into which a portion of tubing assembly 140 is wound. Alternatively, peripheral tubing storage assembly 752 may include one or more divider portions 754, 756 that form a plurality of narrower troughs that may be sized to generate an interference fit between the walls of the narrower trough and the exterior surface of the portion of tubing 140. When peripheral tubing storage assembly 752 includes plurality of divider portions 754, 756, the resulting narrower trough may be wound in a spiral fashion about the periphery of infusion pump assembly 750 (again, in a manner similar to the thread of a screw).

Infusion pump assembly 750 may include tubing retainer assembly 758. Tubing retainer assembly 758 may be configured to releasably secure tubing assembly 140 so as to prevent tubing assembly 140 from unraveling from around infusion pump assembly 750. In one embodiment of tubing retainer assembly 758, tubing retainer assembly 758 may include downward facing pin assembly 760 positioned above upward facing pin assembly 762. The combination of pin assemblies 760, 762 may define a "pinch point" through which tubing assembly 140 may be pushed. Accordingly, the user may wrap tubing assembly 140 around the periphery of infusion pump assembly 750, wherein each loop of tubing assembly 140 is secured within peripheral tubing storage assembly 752 via tubing retainer assembly 758. In the event that the user wishes to lengthen the unsecured portion of tubing assembly 140, the user may release one loop of tubing assembly 140 from tubing retainer assembly 758. Conversely, in the event that the user wishes to shorten the unsecured portion of tubing assembly 140, the user may secure one additional loop of tubing assembly 140 within tubing retainer assembly 758.

Figure 33:
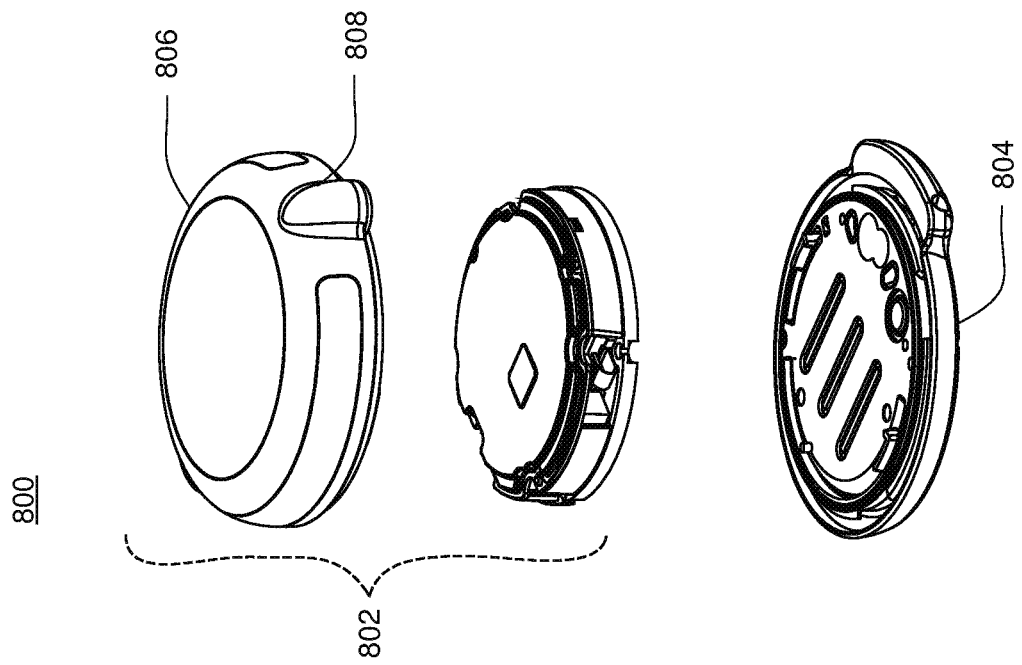
FIG. 33 is another exploded view of the infusion pump assembly of FIG. 32.
Figure 32:
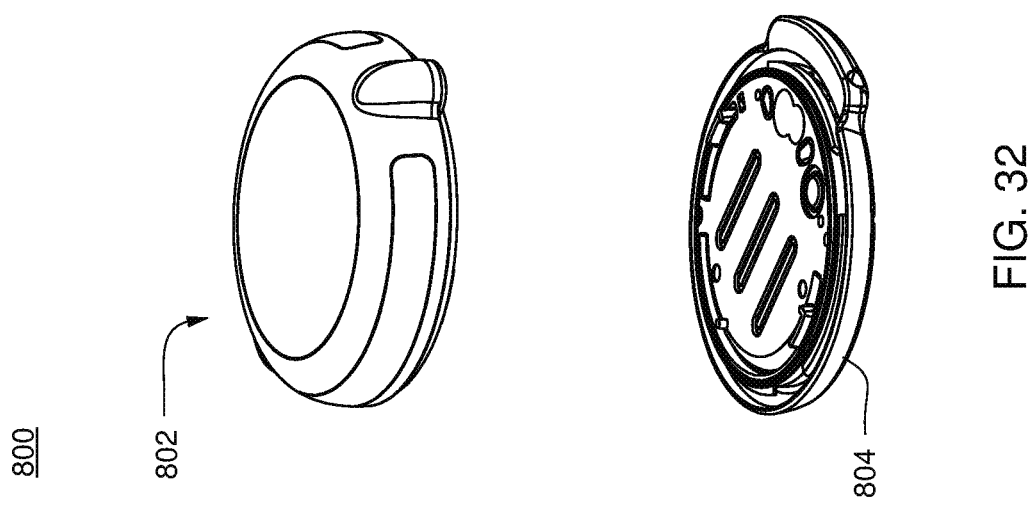
FIG. 32 is an exploded view of another embodiment of an infusion pump assembly.

Referring also to FIGS. 32-33, there is shown an exemplary embodiment of infusion pump assembly 800. As with infusion pump assemblies 100, 100', 400, and 500, infusion pump assembly 800 may include reusable housing assembly 802 and disposable housing assembly 804.

Figure 34A:
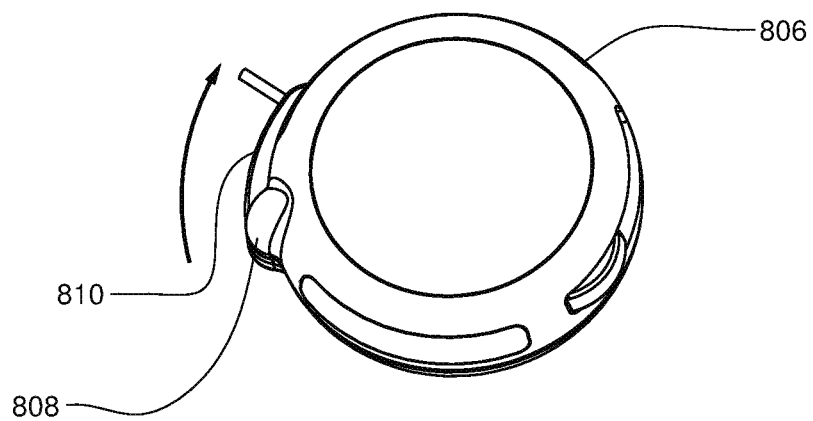
FIGS. 34A-34B depict another embodiment of an infusion pump assembly.
Figure 34B:
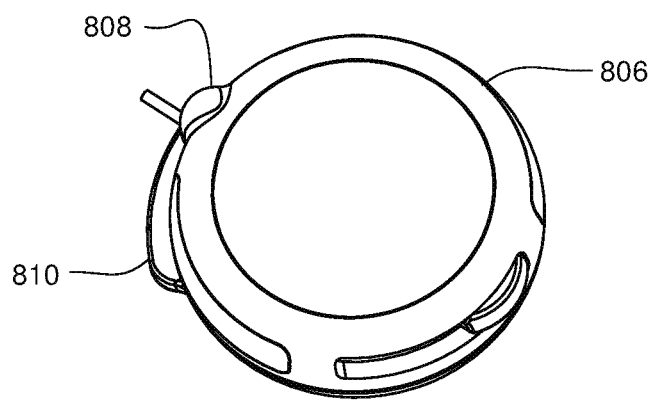

With reference also to FIGS. 34A-34B, in a fashion similar to infusion pump assembly 100, reusable housing assembly 802 may be configured to releasably engage disposable housing assembly 804. Such releasable engagement may be effectuated by a screw-on, twist-lock, or compression fit configuration, for example. Infusion pump assembly 800 may include locking ring assembly 806. For example, reusable housing assembly 802 may be properly positioned relative to disposable housing assembly, and locking ring assembly 806 may be rotated to releasable engage reusable housing assembly 802 and disposable housing assembly 804.

Locking ring assembly 806 may include nub 808 that may facilitate rotation of locking ring assembly 806. Additionally, the position of nub 808, e.g., relative to tab 810 of disposable housing assembly 804, may provide verification that reusable housing assembly 802 is fully engaged with disposable housing assembly 804. For example, as shown in FIG. 34A, when reusable housing assembly 802 is properly aligned with disposable housing assembly 804, nub 808 may be aligned in a first position relative to tab 810. Upon achieving a fully engaged condition, by rotation locking ring assembly 806, nub 808 may be aligned in a second position relative to tab 810, as shown in FIG. 34B.

Figure 35A:
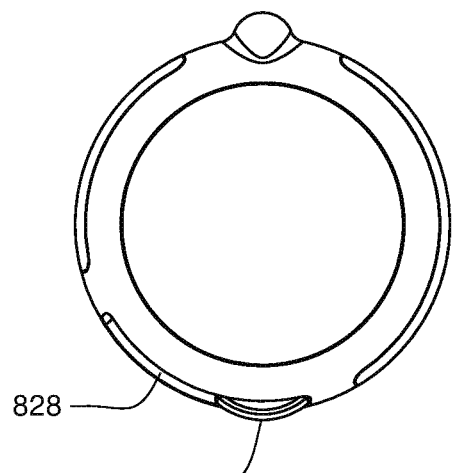
FIGS. 35A-35C are a top view, side view, and bottom view of a reusable housing assembly of the infusion pump assembly of FIG. 32.
Figure 35B:
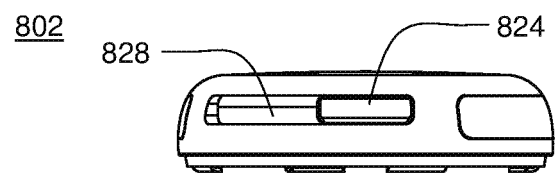
Figure 35C:
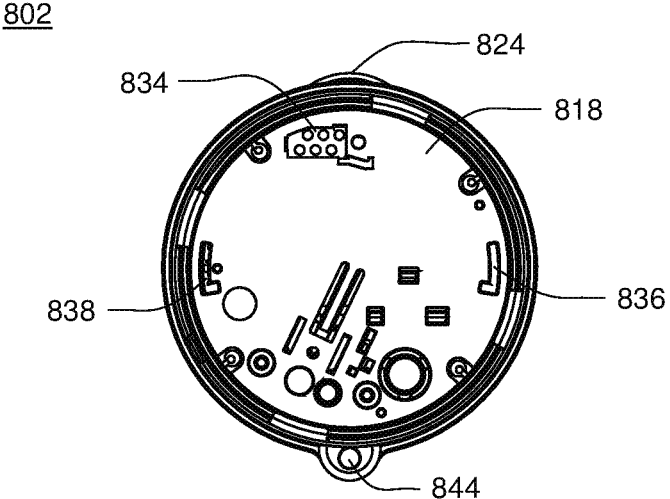
Figure 36:
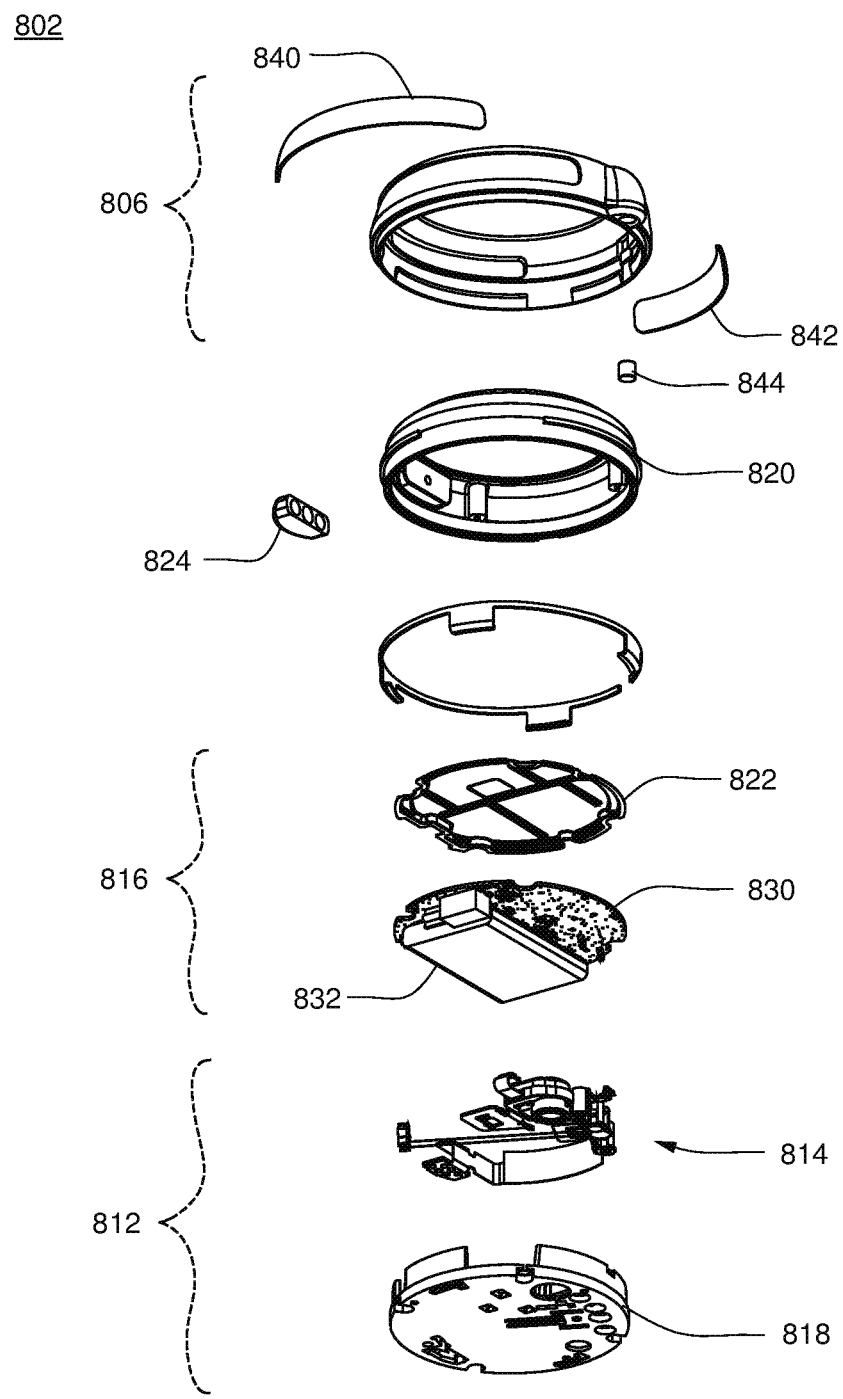
FIG. 36 is an exploded view of the reusable housing assembly of FIGS. 35A-35C.

Referring also to FIGS. 35A-35C and FIGS. 36-38A, in a fashion similar to reusable housing assembly 102, reusable housing assembly 802 may include mechanical control assembly 812 (e.g., which may include valve assembly 814, shown in FIG. 36, including one or more valves and one or more pumps for pumping and controlling the flow of the infusible fluid). Reusable housing assembly 802 may also include an electrical control assembly 816 that may be configured to provide control signals to the mechanical control assembly 812 to effectuate the delivery of an infusible fluid to the user. Valve assembly 814 may be configured to control the flow of the infusible fluid through a fluid path and the pump assembly may be configured to pump the infusible fluid from the fluid path to the user.

Figure 37:
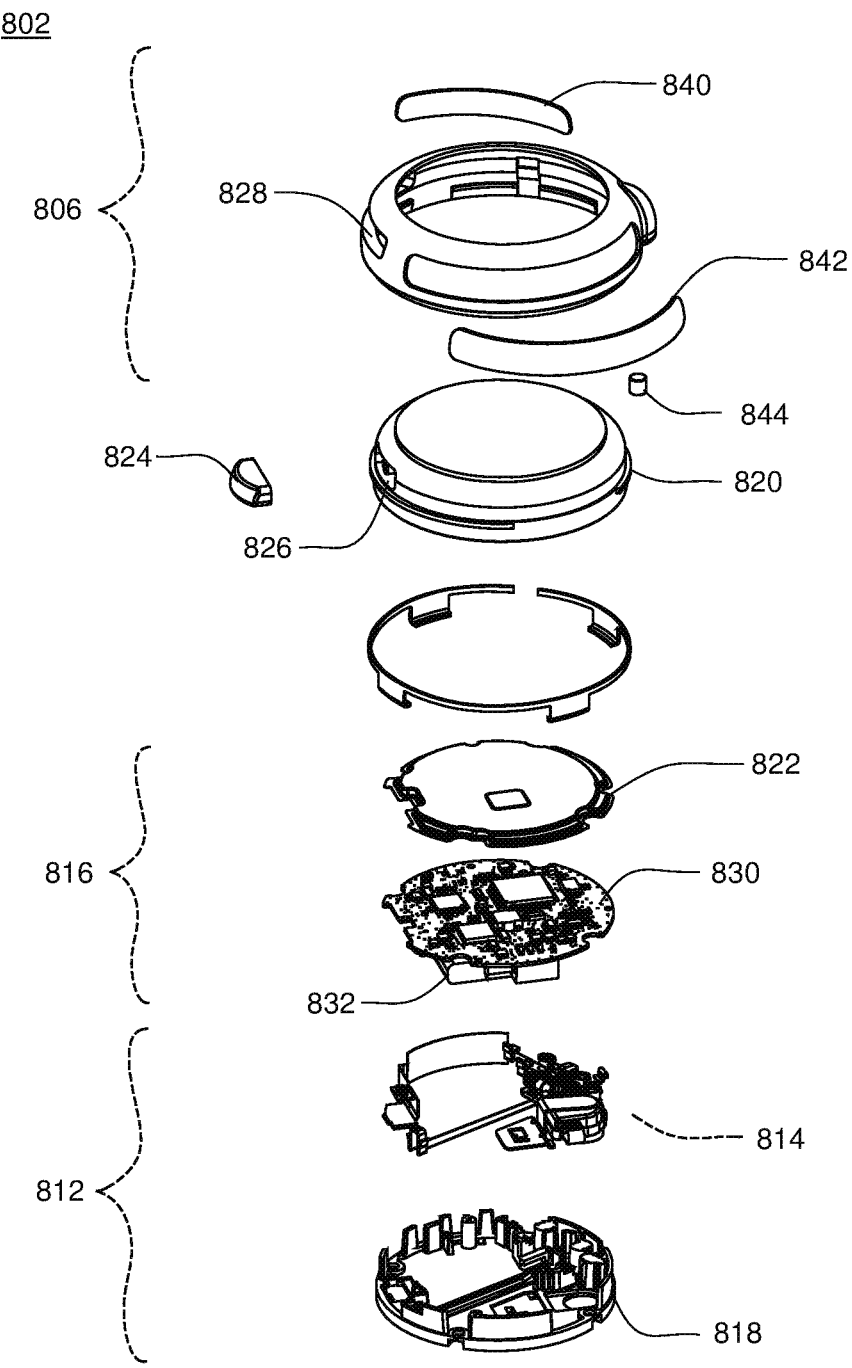
FIG. 37 is an exploded view of the reusable housing assembly of FIGS. 35A-35C.

Mechanical control assembly 812 and electrical control assembly 816 may be contained within a housing defined by base plate 818, body 820. In some embodiments one or more of base plate 818 and body 820 may provide electromagnetic shielding. In such an embodiment, the electromagnetic shielding may prevent and/or reduce electromagnetic interference received by electrical control assembly 816 and/or created by electrical control assembly 816. Additionally/alternatively, EMI shield 822 may be included, as shown in FIG. 36 and FIG. 37. EMI shield 822 may provide shielding against generated and/or received electromagnetic interference.

Reusable housing assembly 802 may include a switch assembly that may be configured to receive user commands (e.g., for bolus delivery, pairing with a remote control assembly, or the like). The switch assembly may include button 824 that may be disposed in opening 826 of body 820. As shown, e.g., in FIG. 35B, locking ring assembly 806 may include radial slot 828 that may be configured to allow locking ring assembly 806 to be rotated relative to body 820 while still providing facile access to button 824.

Figure 39A:
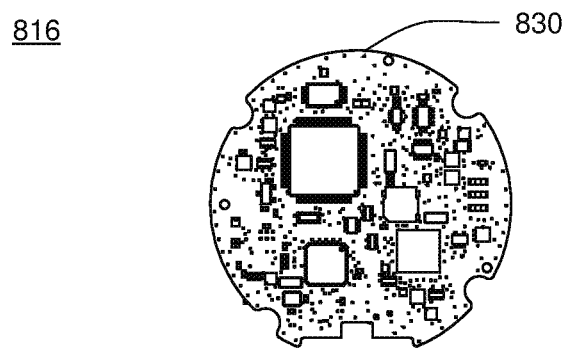
FIGS. 39A-39C are a top view, side view, and bottom view of an electrical control assembly of the reusable housing assembly of FIGS. 35A-35C.
Figure 39B:
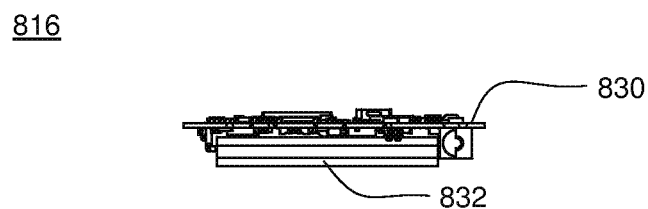
Figure 39C:
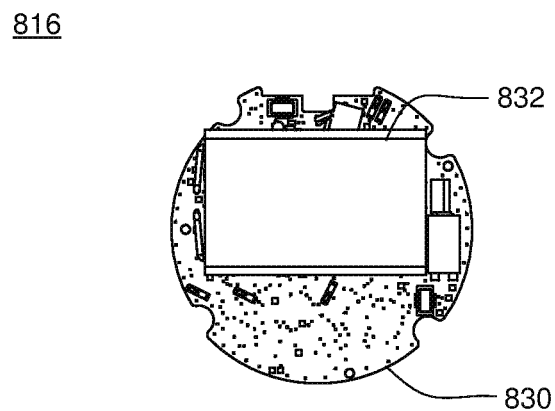
Figure 40A:
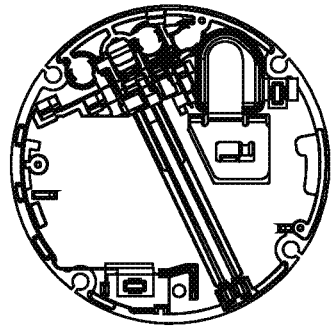
FIGS. 40A-40C are a top view, side view, and bottom view of a base plate of the reusable housing assembly of FIGS. 35A-35C.
Figure 40B:
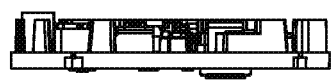
Figure 40C:
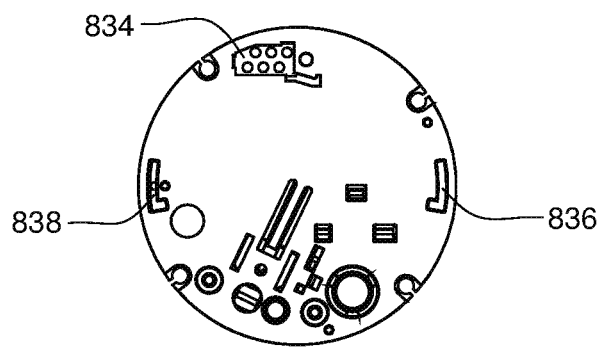
Figure 41A:
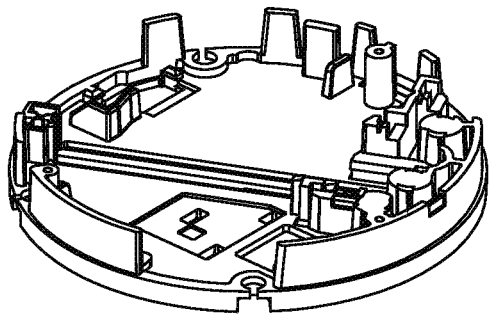
FIGS. 41A-41B are a perspective top view and a perspective bottom view of the base plate of FIGS. 40A-40C.
Figure 41B:
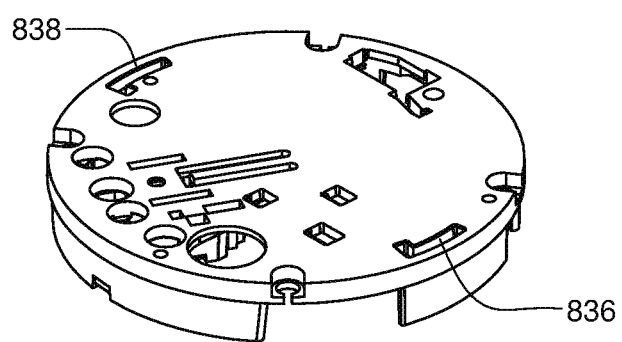
Figure 42A:
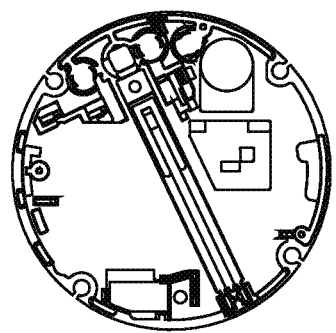
FIGS. 42A-42C are a top view, side view, and bottom view of a base plate of the reusable housing assembly of FIGS. 35A-35C.
Figure 42B:
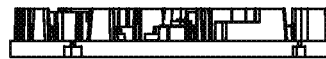
Figure 42C:
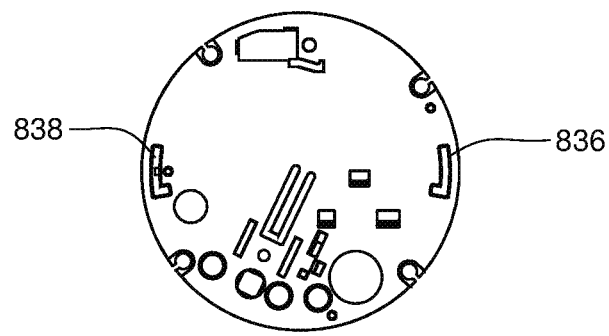
Figure 43A:
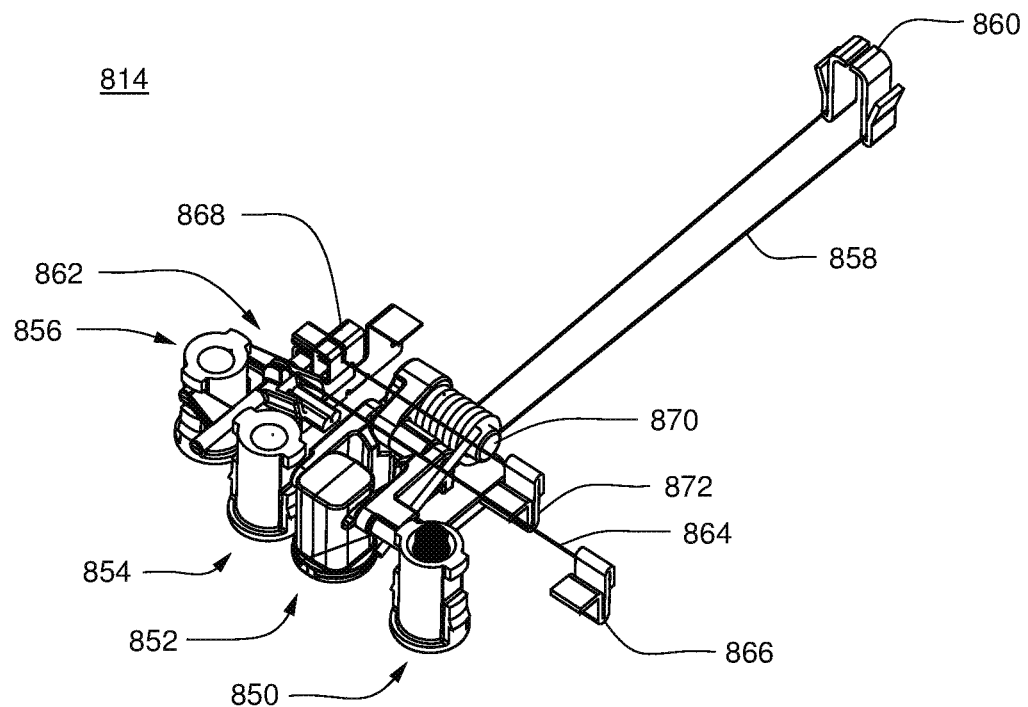
FIGS. 43A-43B depict a mechanical control assembly of the reusable housing assembly of FIGS. 35A-35C.
Figure 43B:
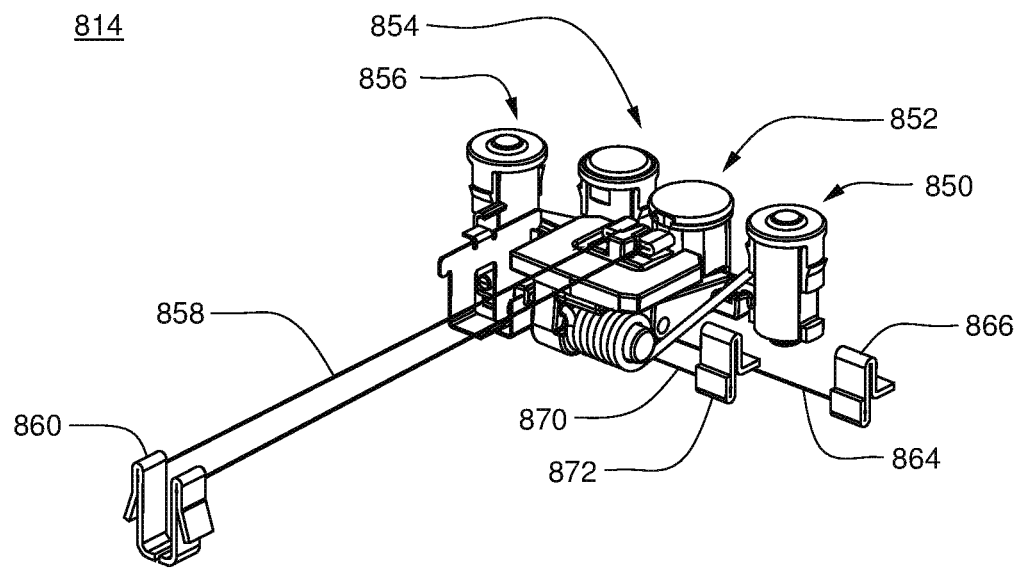
Figure 44A:
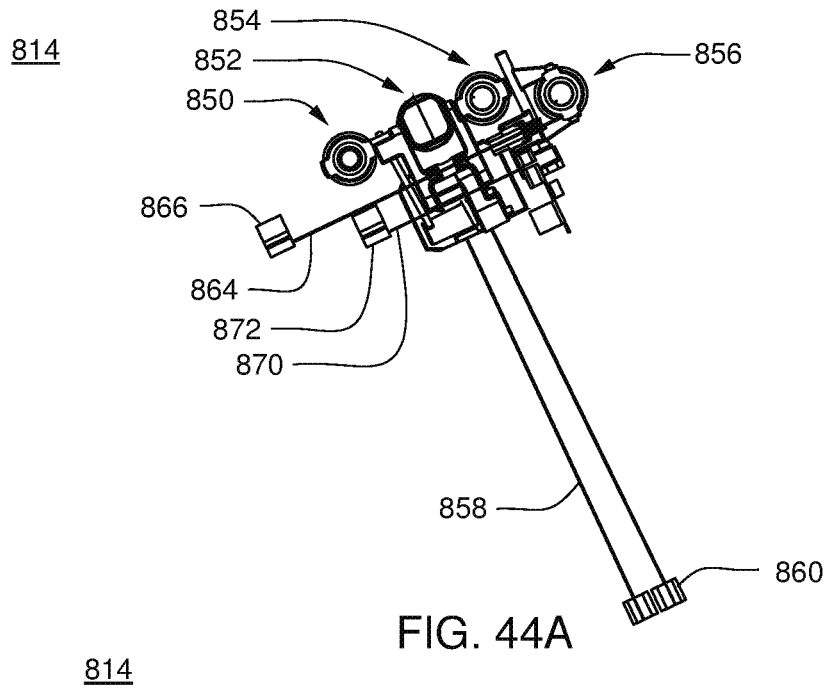
FIGS. 44A-44C depict the mechanical control assembly of the reusable housing assembly of FIGS. 35A-35C.
Figure 44B:
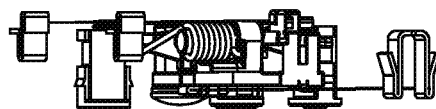
Figure 44C:
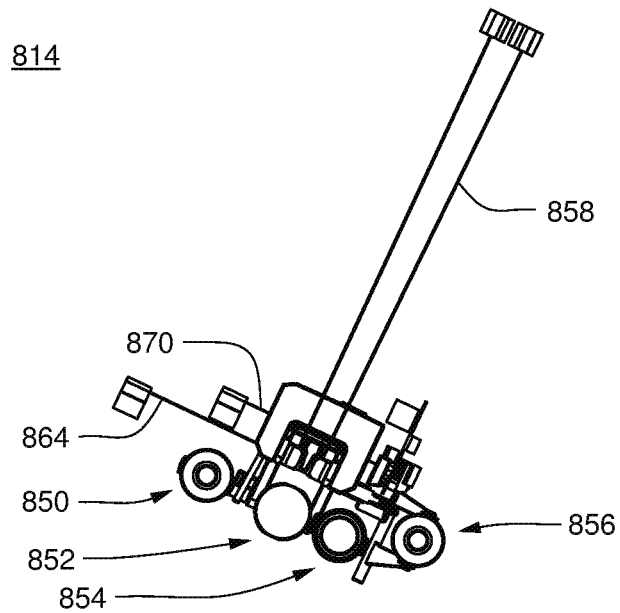
Figure 45A:
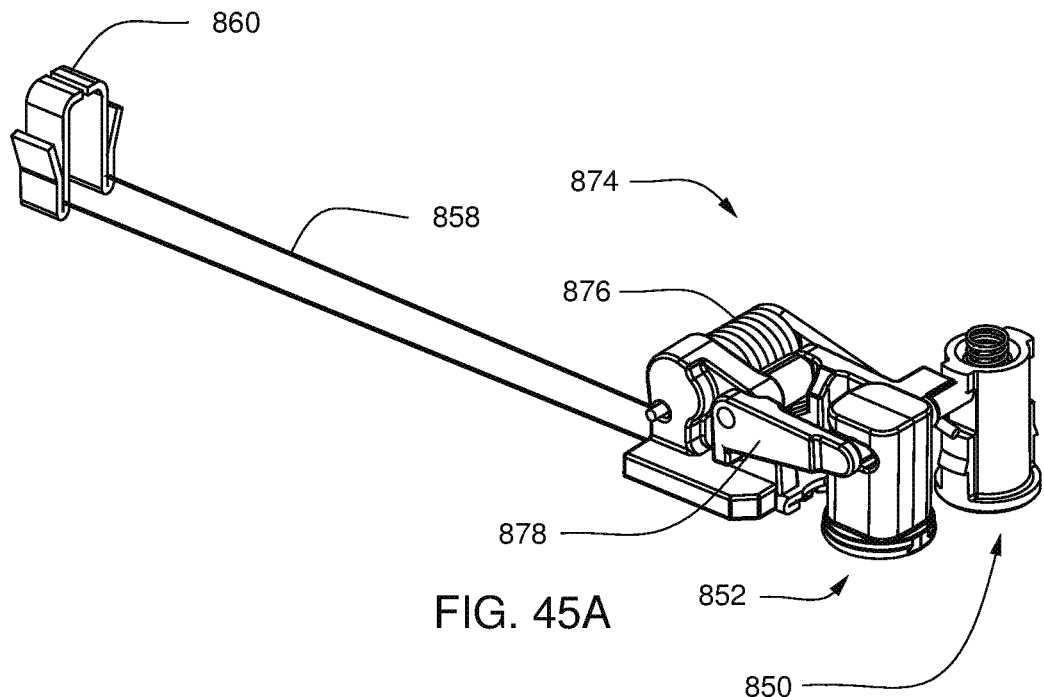
FIGS. 45A-45B depict the pump plunger and reservoir valve of the mechanical control assembly of the reusable housing assembly of FIGS. 35A-35C.
Figure 45B:
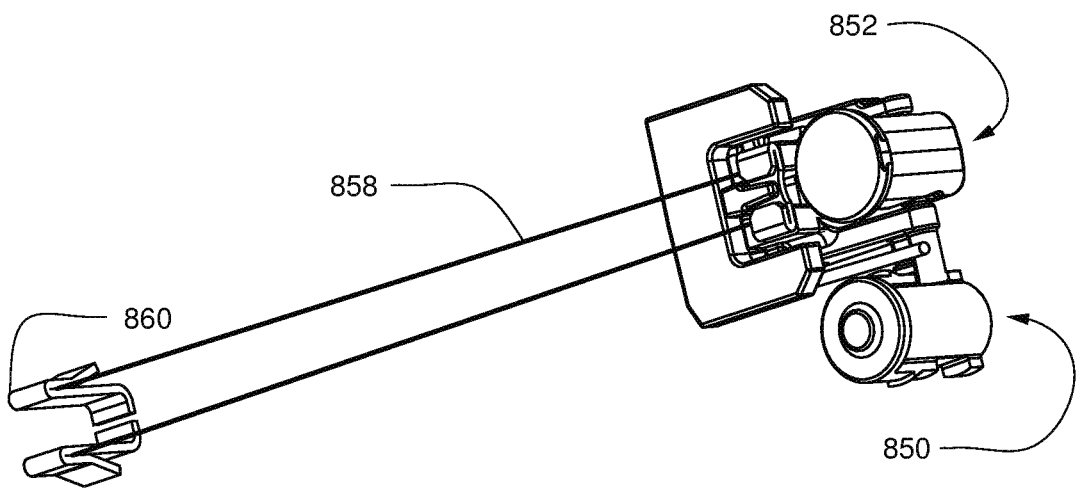

Referring also to FIGS. 39A-39C, electrical control assembly 816 may include printed circuit board 830 as well as battery 832. Printed circuit board 830 may include the various control electronics for monitoring and controlling the amount of infusible fluid that has been and/or is being pumped. For example, electrical control assembly 816 may measure the amount of infusible fluid that has just been dispensed, and determine, based upon the dosage required by the user, whether enough infusible fluid has been dispensed. If not enough infusible fluid has been dispensed, electrical control assembly 816 may determine that more infusible fluid should be pumped. Electrical control assembly 816 may provide the appropriate signal to mechanical control assembly 812 so that any additional necessary dosage may be pumped or electrical control assembly 816 may provide the appropriate signal to mechanical control assembly 812 so that the additional dosage may be dispensed with the next dosage. Alternatively, if too much infusible fluid has been dispensed, electrical control assembly 816 may provide the appropriate signal to mechanical control assembly 812 so that less infusible fluid may be dispensed in the next dosage. Electrical control assembly 816 may include one or more microprocessors. In an exemplary embodiment, electrical control assembly 816 may include three microprocessors. One processor (e.g., which may include, but is not limited to a CC2510 microcontroller/RF transceiver, available from Chipcon AS, of Oslo, Norway) may be dedicated to radio communication, e.g., for communicating with a remote control assembly. Two additional microprocessors (example of which may include, but is not limited to an MSP430 microcontroller, available from Texas Instruments Inc. of Dallas, Tex.) may be dedicated to issuing and carrying out commands (e.g., to dispense a dosage of infusible fluid, process feedback signals from a volume measurement device, and the like).

As shown in FIG. 35C, base plate 818 may provide access to electrical contacts 834, e.g., which may be electrically coupled to electrical control assembly 816 for recharging battery 832. Base plate 818 may include one or more features (e.g., openings 836, 838) which may be configured to facilitate proper alignment with disposable housing assembly 804 by way of cooperating features (e.g., tabs) of disposable housing assembly 804. Additionally, as shown in FIGS. 40A-40C, 41A-41B, and 42A-42C, base plate 818 may include various features for mounting valve assembly 814 and electrical control assembly 816, as well as providing access to disposable housing assembly 804 by valve assembly 814.

Locking ring assembly 806 may include grip inserts 840, 842, e.g., which may include an elastomeric or textured material that may facilitate gripping and twisting locking ring assembly 806, e.g., for engaging/disengaging reusable housing assembly 802 and disposable housing assembly 804. Additionally, locking ring assembly 806 may include a sensing component (e.g., magnet 844) that may interact with a component of reusable housing assembly 802 (e.g., a Hall Effect sensor), e.g., to provide an indication of the nature of a mating component (e.g., which in some embodiments may include, but is not limited to, one or more of disposable housing assembly 804, a charging station, or a filling station) and/or of whether reusable housing assembly 802 is properly engaged with the mating component. In the exemplary embodiment, a Hall Effect sensor (not shown) may be located on the pump printed circuit board. The Hall Effect sensor may detect when the locking ring has been rotated to a closed position. Thus, the Hall Effect sensor together with magnet 844 may provide a system for determining whether the locking ring has been rotated to a closed position.

The sensing component (magnet) 844 together with the reusable housing assembly components, i.e., in the exemplary embodiment, the Hall Effect sensor, may work to provide for a determination of whether the reusable housing assembly is properly attached to the intended component or device. Locking ring assembly 806 may not turn without being attached to a component, i.e., disposable housing assembly 804, a dust cover or a charger. Thus, the sensing component together with the reusable housing assembly component may function to provide many advantageous safety features to the infusion pump system. These features may include, but are not limited to, one or more of the following. Where the system does not detect being attached to a disposable assembly, a dust cover or a charger, the system may notify, alert or alarm the user as the reusable portion, e.g., the valves and pumping components, may be vulnerable to contamination or destruction which may compromise the integrity of the reusable assembly. Thus, the system may provide for an integrity alarm to alert the user of potential reusable integrity threats. Also, where the system senses the reusable assembly is attached to a dust cover, the system may power off or reduce power to conserve power. This may provide for more efficient use of power where the reusable assembly is not connecting to a component in which it needs to interact.

Figure 38A:
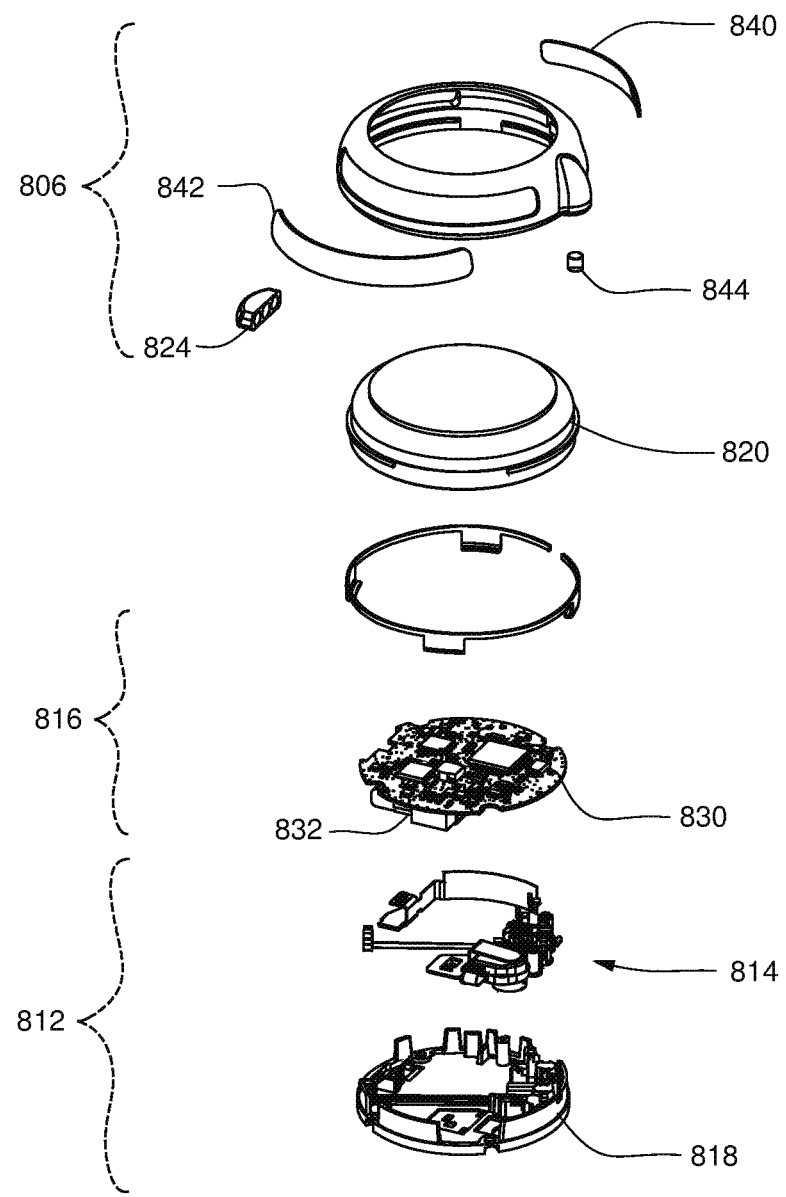
FIG. 38A is an exploded view of the reusable housing assembly of FIGS. 35A-35C.
Figure 38D:
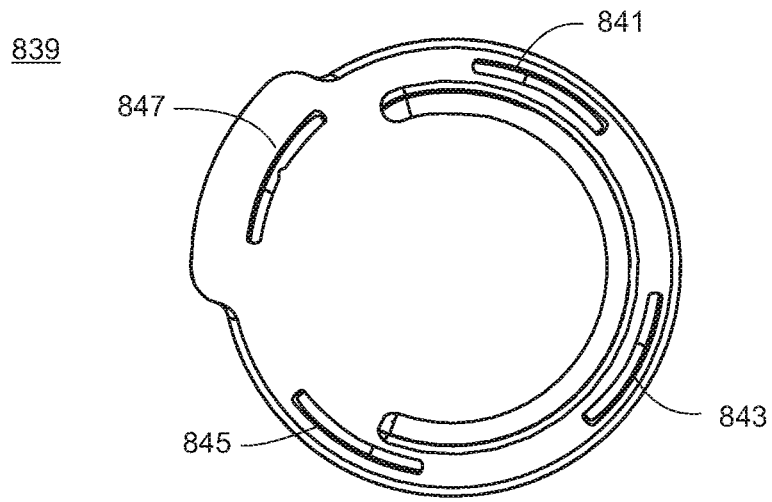
FIG. 38B-38D are top, side and bottom views of one embodiment of a dust cover.
Figure 38C:
Figure 38B:
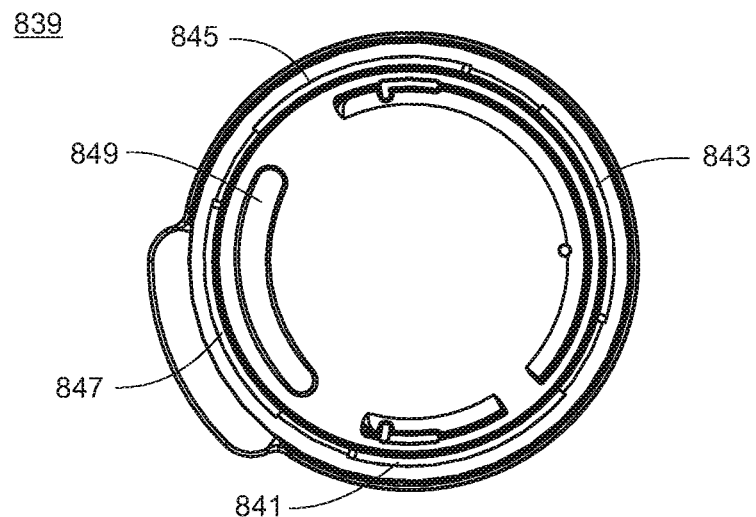

Reusable housing assembly 802 may attach to a number of different components, including but not limited to, a disposable housing assembly, a dust cover or a battery charger/battery charging station. In each case, the Hall Effect sensor may detect that the locking ring is in the closed position, and therefore, that reusable housing assembly 802 is releasably engaged to a disposable housing assembly, a dust cover, or a battery charger/battery charging station (or, another component). The infusion pump system may determine the component to which it is attached by using the AVS system described in more detail below or by an electronic contact. Referring now also to FIGS. 38B-38D, one embodiment of a dust cover (e.g., dust cover 839) is shown. In the exemplary embodiment, dust cover 839 may include features 841, 843, 845, 847 such that the locking ring of reusable housing assembly 802 may releasably engage dust cover 839. In addition, dust cover 839 may further include recess region 849 for accommodating the valving and pumping features of reusable housing assembly 804. For example, with respect to the dust cover, the AVS system may determine that a dust cover, and not a disposable housing assembly, is connected to the reusable housing assembly. The AVS system may distinguish using a look-up table or other comparative data and comparing the measurement data with characteristic dust cover or empty disposable housing assembly data. With respect to the battery charger, the battery charger, in the exemplary embodiments, may include electric contacts. When the reusable housing assembly is attached to the battery charger, the infusion pump assembly electronic system may sense that the contacts have been made, and will thus indicate that the reusable housing assembly is attached to a battery charger.

Referring also to FIGS. 43A-45B and FIGS. 44A-44C an embodiment of valve assembly 814, which may include one or more valves and one or more pumps, is shown. As with infusion pump assemblies 100, 100', 400, and 500, valve assembly 814 may generally include reservoir valve 850, plunger pump 852, volume sensor valve 854, and measurement valve 856. Similar to the previous description, reservoir valve 850 and plunger pump 852 may be actuated by shape memory actuator 858, which may be anchored (on a first end) to shape memory actuator anchor 860. Additionally, measurement valve 856 may be actuated, via valve actuator 862, by shape memory actuator 864, which may be anchored (on a first end) to shape memory actuator anchor 866. In a similar manner as discussed above, measurement valve may be maintained in an open position via measurement valve latch assembly 868. Measurement valve 856 may be released via actuation of shape memory actuator 870, which may be anchored (on a first end) by shape memory actuator anchor 872. In some embodiments, shape memory actuator anchor 860 may be potted onto the reusable housing assembly. Using this process during manufacture ensures shape memory length actuator 858 is installed and maintains the desired length and tension/strain.

Referring also to FIGS. 45A-45B and FIGS. 46A-46E, shape memory actuator 858 (e.g., which may include one or more shape memory wires) may actuate plunger pump 852 via actuator assembly 874. Actuator assembly 874 may include bias spring 876 and lever assembly 878. Actuator assembly 874 may actuate both plunger pump 852 and measurement valve 850.

Figure 47A:
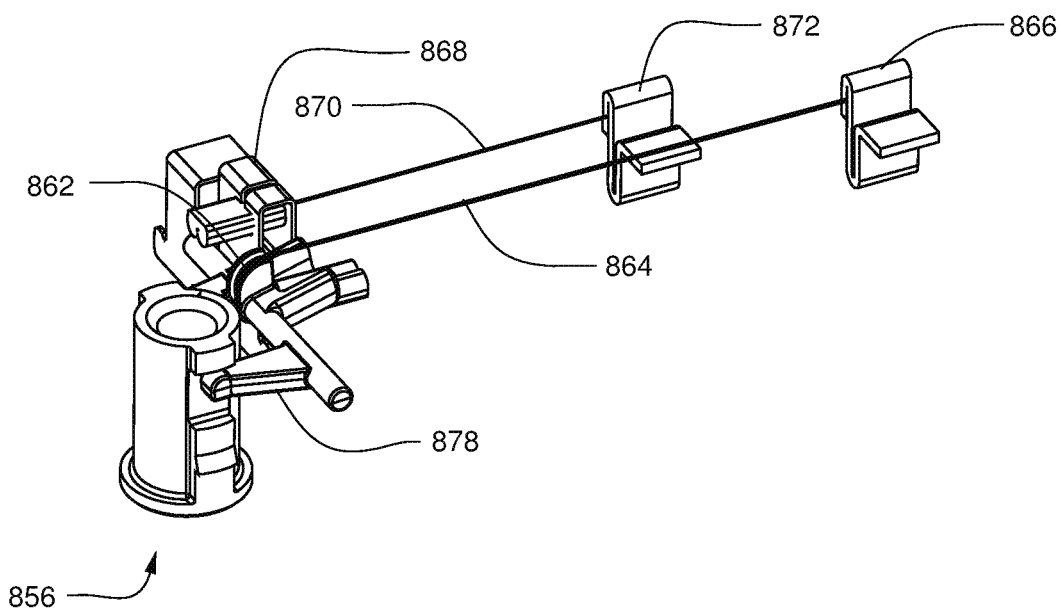
FIGS. 47A-47B depict the measurement valve of the mechanical control assembly of the reusable housing assembly of FIGS. 35A-35C.
Figure 47B:
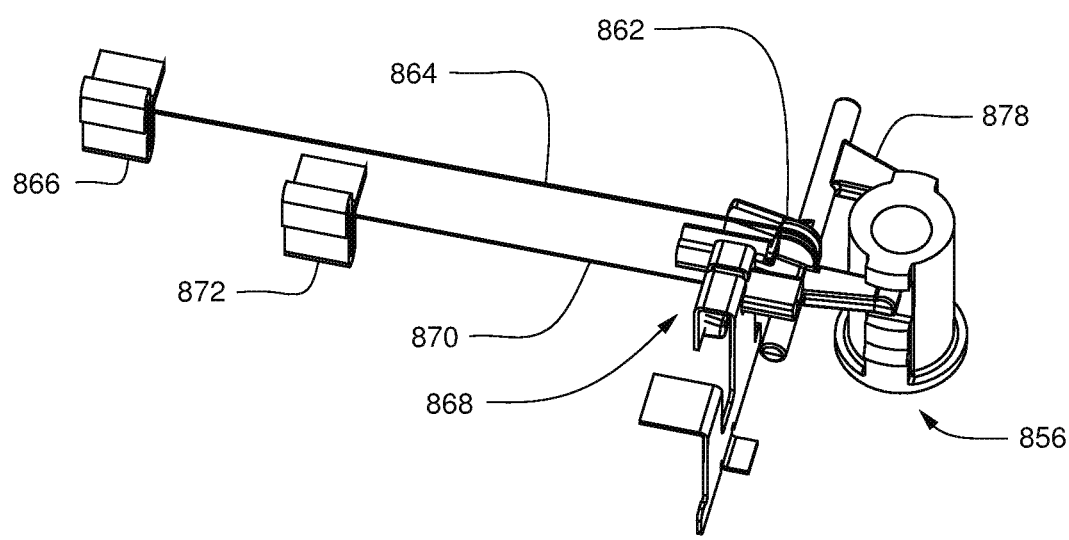

Referring also to FIGS. 47A-47B, measurement valve 856 may be actuated by shape memory actuator 864, via valve actuator 862 and lever assembly 878. Once actuated, measurement valve latch assembly 868 may maintain measurement valve 856 in an open position. Measurement valve latch assembly 868 actuated by shape memory actuator 870 to release measurement valve 856, allowing it to return to a closed position.

Disposable housing assembly 804 may be configured for a single use or for use for a specified period of time, e.g., e.g., three days or any other amount of time. Disposable housing assembly 804 may be configured such that any of the component of infusion pump assembly 800 that come in contact with the infusible fluid may be disposed on and/or within disposable housing assembly 804. As such, the risk of contaminating the infusible fluid may be reduced.

Figure 50A:
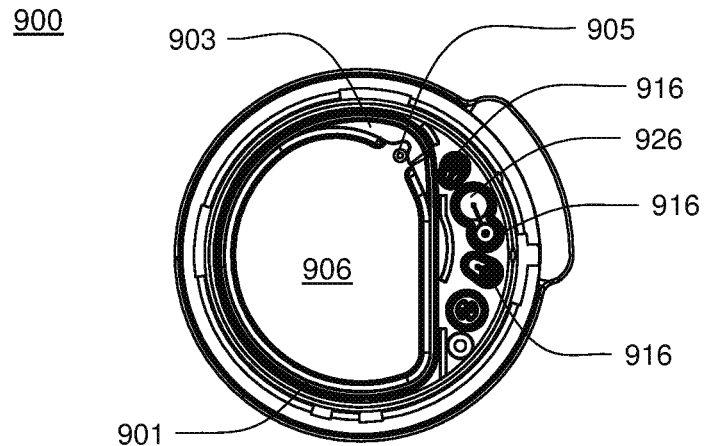
FIGS. 50A-50C depict the base portion of the disposable housing assembly of FIG. 48.
Figure 50B:
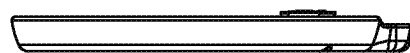
Figure 50C:
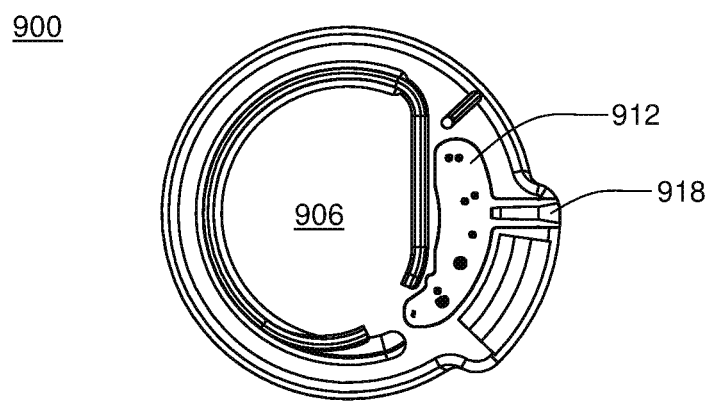

Referring also to FIG. 48 and FIGS. 49A-49C, disposable housing assembly 804 may include base portion 900, membrane assembly 902, and top portion 904. Base portion 900 may include recess 906 that together with membrane assembly 902 defines reservoir 908 for receiving an infusible fluid (not shown), e.g., insulin. Referring also to FIGS. 50A-50C, recess 906 may be at least partially formed by and integral with base portion 900. Membrane assembly 902 may be sealingly engaged with base portion 900, e.g., by being compressively pinched between base portion 900 and top portion 904. Top portion 904 may be attached to base portion 900 by conventional means, such as gluing, heat sealing, ultrasonic welding, and compression fitting. Additionally/alternatively, membrane assembly 902 may be attached to base portion 900, e.g., via gluing, ultrasonic welding, heat sealing, and the like, to provide a seal between membrane assembly 902 and base portion 900.

Figure 48:
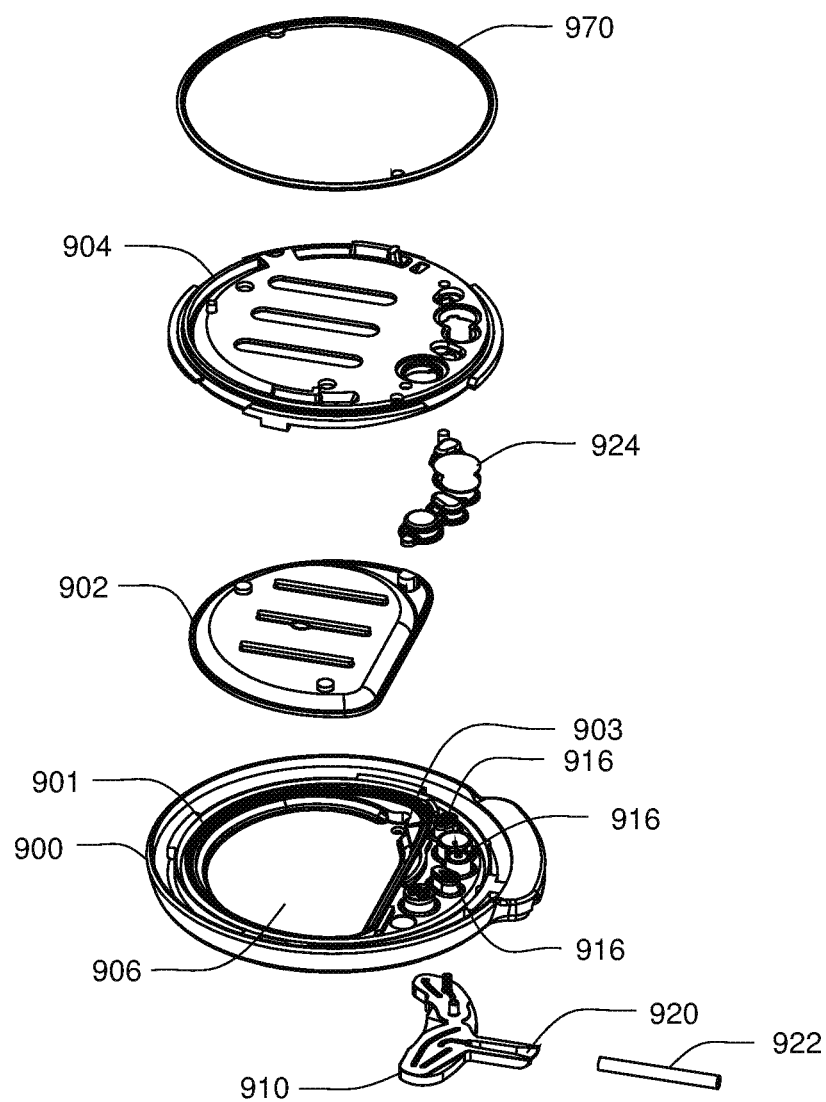
FIG. 48 is an exploded view of the disposable housing assembly of the infusion pump assembly of FIG. 32.

Still referring to FIGS. 48 and 50A, recess 906, in the exemplary embodiment, includes raised portion 901 which includes area 903 about fluid openings 905 leading to the fluid line. Raised portion 901, in the exemplary embodiment, extends about the perimeter of recess 906. However, in other embodiments, raised portion 901 may not extend the entire perimeter, but may be partially about the perimeter. Area 903 about fluid openings 905 may be shaped as shown in the exemplary embodiment, including an angled portion, which in some embodiments, includes 45 degree angles, however in other embodiments, the angle may be greater or lesser. In some embodiments, the pump may not generate a sufficient enough vacuum to collapse the reservoir so as to eliminate the entire volume of fluid that may be stored in the reservoir. Raised portion 901 may act to minimize wasted fluid.

Fluid openings 905, which, in the exemplary embodiment, may include three openings, however, in other embodiments may include more openings or fewer openings, may be surrounded by area 903 of the raised portion. In the exemplary embodiment, fluid openings 905 may be narrow in the center, thus creating a surface tension that may prevent the air from being drawn into the opening. In the exemplary embodiment, this area may be designed to encourage any air that is present in the reservoir to be drawn above one of fluid openings 905 rather than be pulled through fluid openings 905 and into the fluid line. Additionally, because there may be more than one fluid opening 905, where an air bubble is caught above one, the air may not prevent fluid from flowing through the other two openings.

Figure 51A:
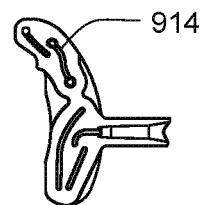
FIGS. 51A-51C depict the fluid pathway cover of the disposable housing assembly of FIG. 48.
Figure 51B:
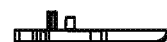
Figure 51C:
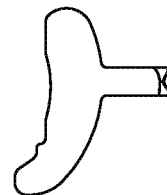

Referring also to FIGS. 51A-51C, disposable housing assembly 804 may also include fluid pathway cover 910. Fluid pathway cover 910 may be received in cavity 912 formed on/within base portion 900. Fluid pathway cover 910 may, in some embodiments, include at least a portion of one or more channels (e.g., channel 914). The channels included in fluid pathway cover 910 may fluidly couple one or more volcano valve features (e.g. volcano valves 916) included on base portion 900. Volcano valves 916 may include a protrusion having an opening extending through it. Additionally, fluid pathway cover 910 and base portion 900 may each define a portion of recess (e.g., recess portions 918, 920 included in base portion 900 and fluid pathway cover 910 respectively) for fluidly coupling to an infusion set (e.g., including cannula 922). Cannula 922 may be coupled to disposable housing assembly 804 by conventional means (e.g., gluing, heat sealing, compression fit, or the like). The fluid pathways defined by fluid pathway cover 910 and the volcano valves (e.g., volcano valves 916) of base portion 900 may define a fluid pathway between reservoir 908 and cannula 922 for the delivery of the infusible fluid to the user via the infusion set. However, in some embodiments, fluid path cover 910 may include at least a portion of the fluid path, and in some embodiments, fluid path cover 910 may not include at least a portion of the fluid path. In the exemplary embodiment, fluid pathway cover 910 may be laser welded to base portion 900. However, in other embodiments, fluid pathway cover 910 may also be connected to base portion 900 by conventional means (e.g., gluing, heat sealing, ultrasonic welding, compression fit, or the like) to achieve a generally fluid tight seal between fluid pathway cover 910 and base portion 900.

Figure 54A:
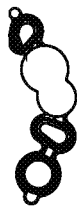
FIGS. 54A-54C depict the valve membrane insert of the disposable housing assembly of FIG. 48.
Figure 54B:
Figure 54C:
Figure 55A:
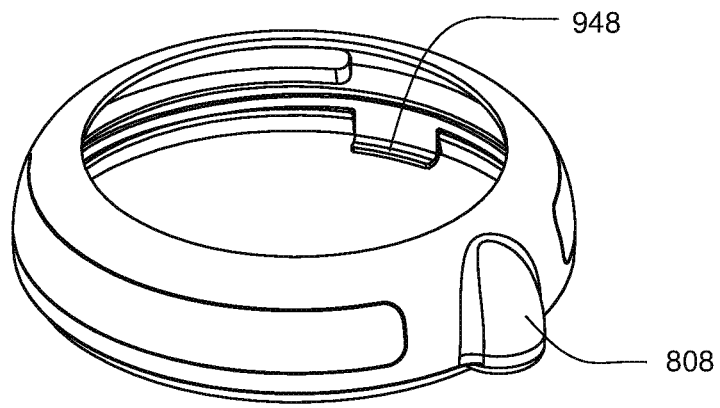
FIGS. 55A-55B depict the locking ring assembly of the infusion pump assembly of FIG. 32.
Figure 55B:
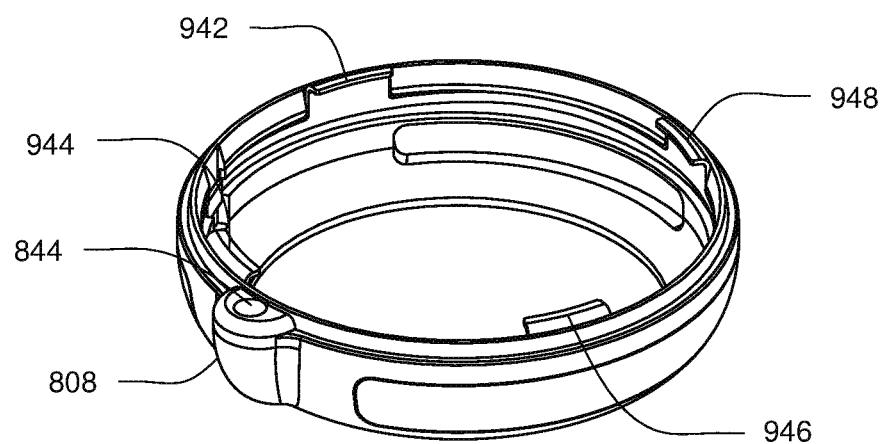
Figure 56A:
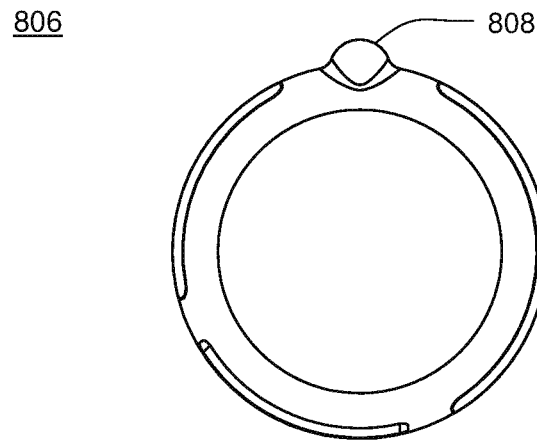
FIG. 56A-56C depict the locking ring assembly of the infusion pump assembly of FIG. 32.
Figure 56B:
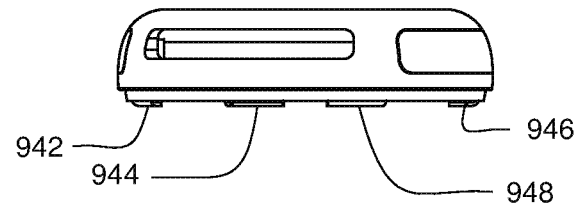
Figure 56C:
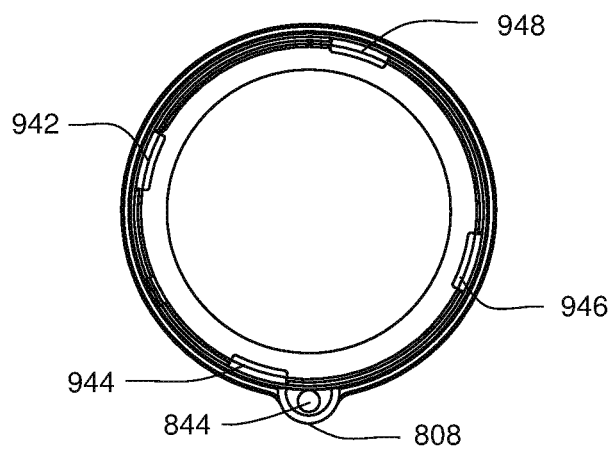
Figure 57:
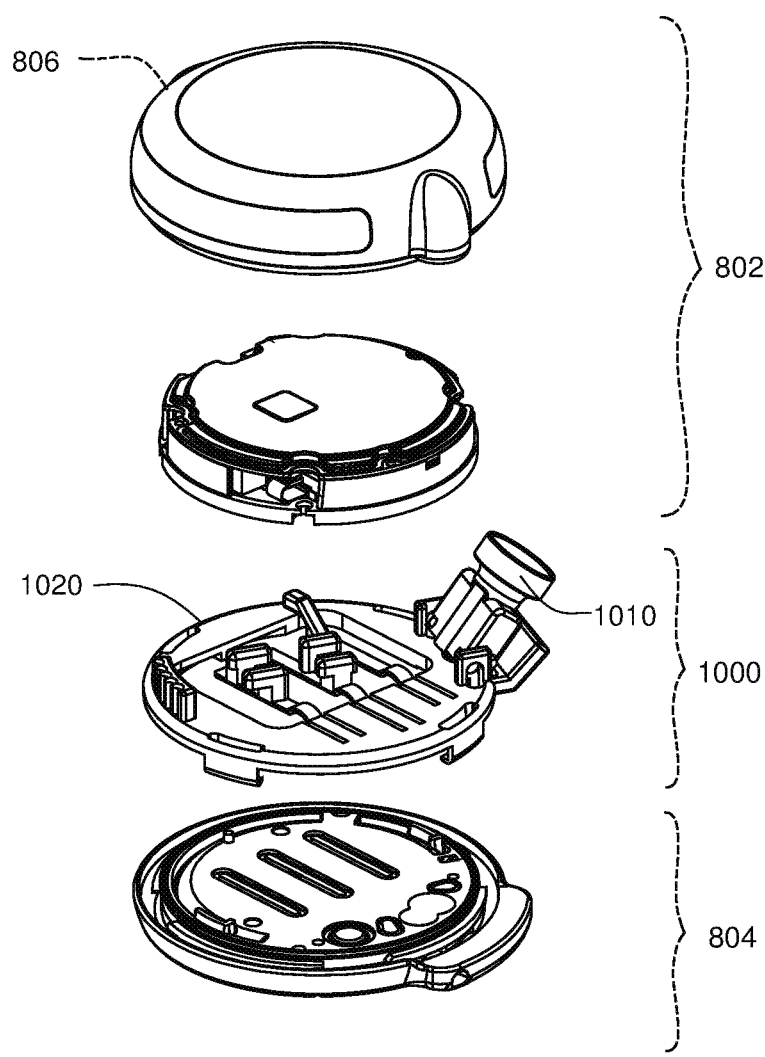
FIGS. 57-58 is an isometric view of an infusion pump assembly and a fill adapter.
Figure 58:
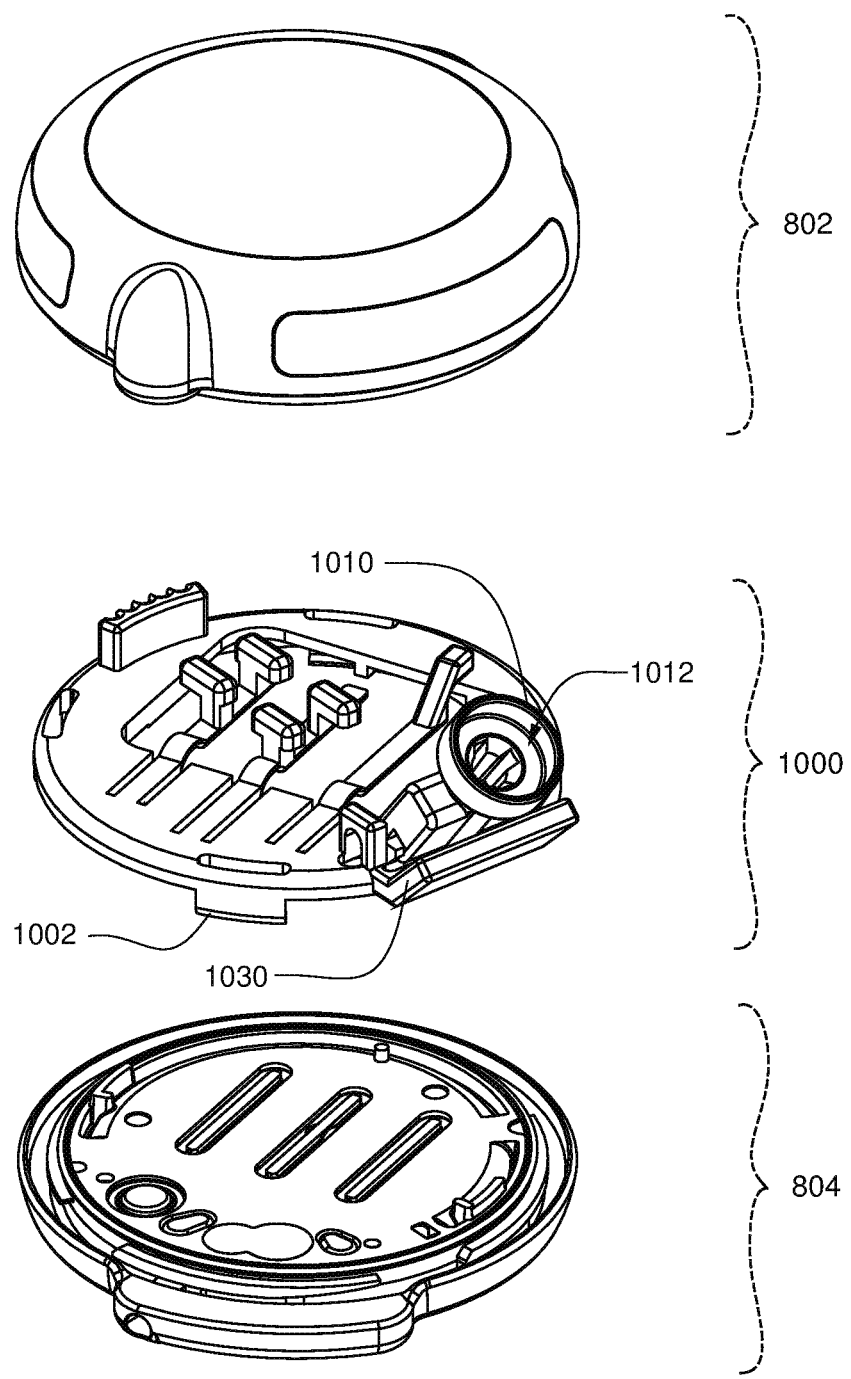
Figure 59:
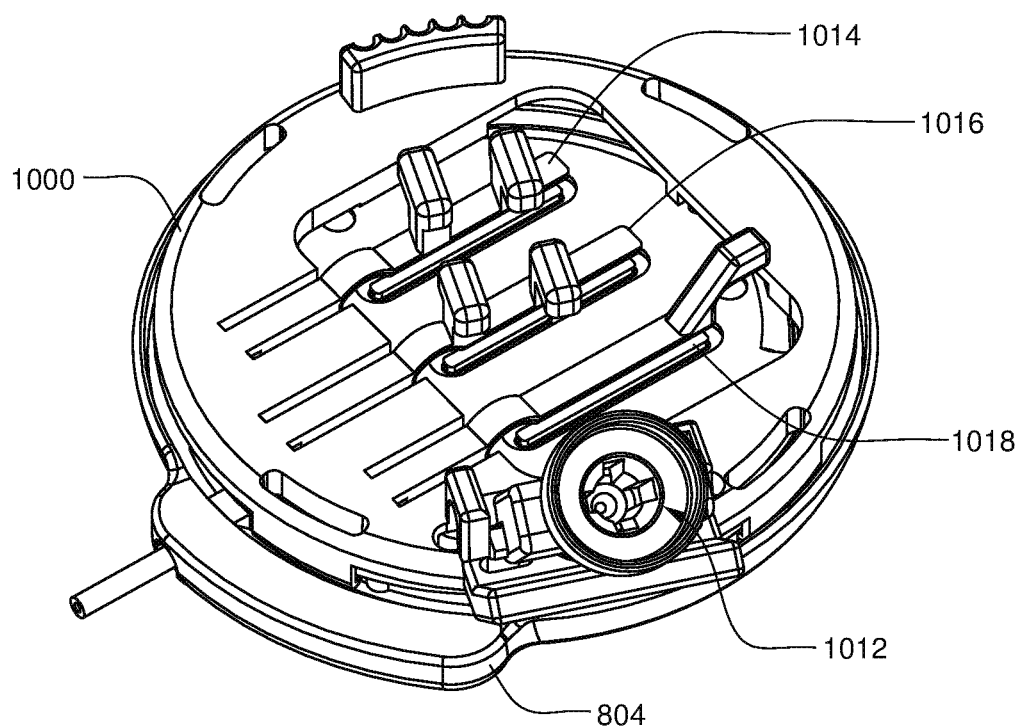
FIGS. 59-64 are various views of the fill adapter of FIG. 57.
Figure 60:
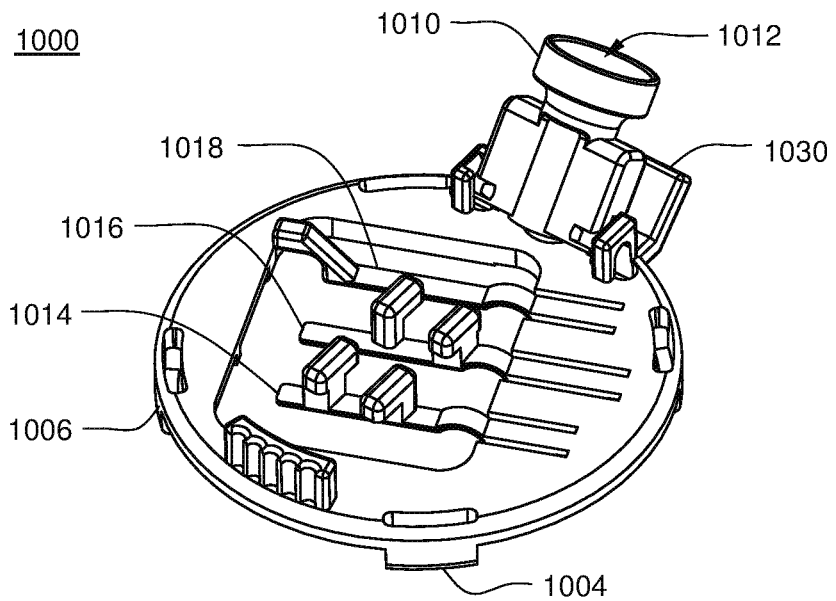
Figure 61:
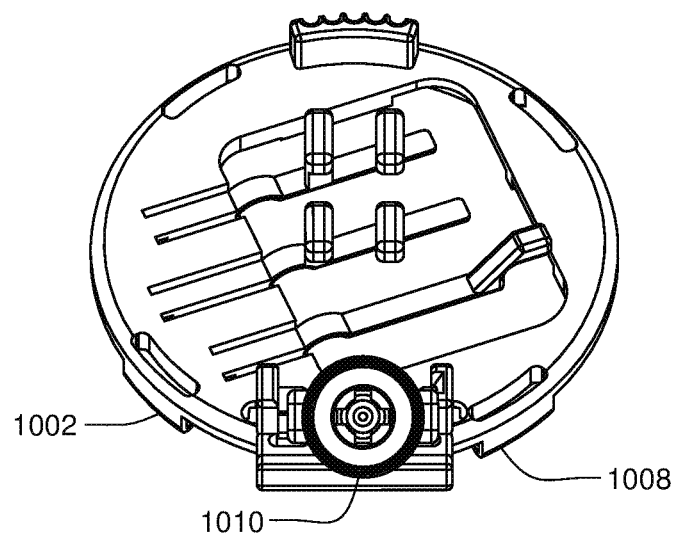

With reference also to FIGS. 54A-54C, disposable housing assembly 804 may further include valve membrane cover 924. Valve membrane cover 924 may be at least partially disposed over the volcano valves (e.g., volcano valve 916) and pumping recess 926 included on/within base portion 900. Valve membrane cover 924 may include a flexible material, e.g., which may be selectively engaged against the volcano valves by reservoir valve 850, volume sensor valve 854, and measurement valve 856 of reusable housing assembly 802, e.g., for controlling the flow of the infusible fluid. Additionally, valve membrane cover 924 may be resiliently deformed into pumping recess 926 by plunger pump 852 to effectuate pumping of the infusible fluid. Valve membrane cover 924 may be engaged between base portion 900 and top portion 904 of disposable housing assembly 804 to form seal 928 between valve membrane cover 924 and base portion 900. For example, in the exemplary embodiment, valve membrane cover 924 may be overmolded onto base portion 900. In other embodiment, valve membrane cover 924 may be compressively pinched between base portion 900 and top portion 904 to form seal 928. Additionally/alternatively, valve membrane insert may be connected to one or more of base portion 900 and top portion 904, e.g., by gluing, heat sealing, or the like.

Figure 53A:
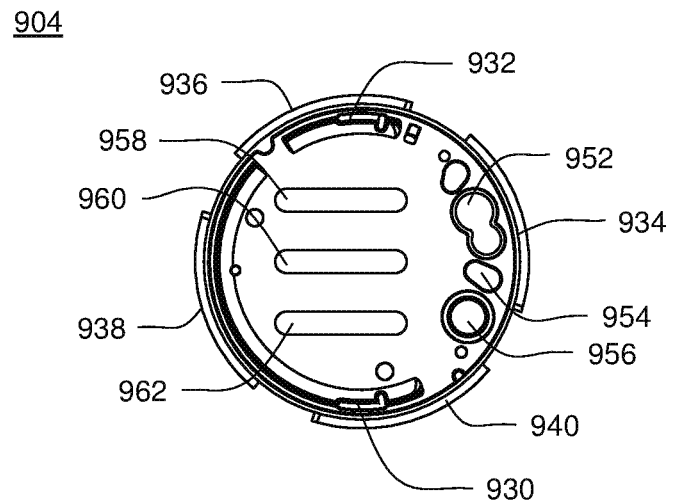
FIGS. 53A-53C depict the top portion of the disposable housing assembly of FIG. 48.
Figure 53B:
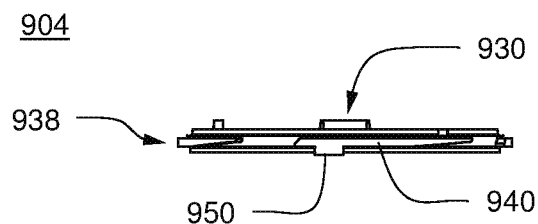
Figure 53C:
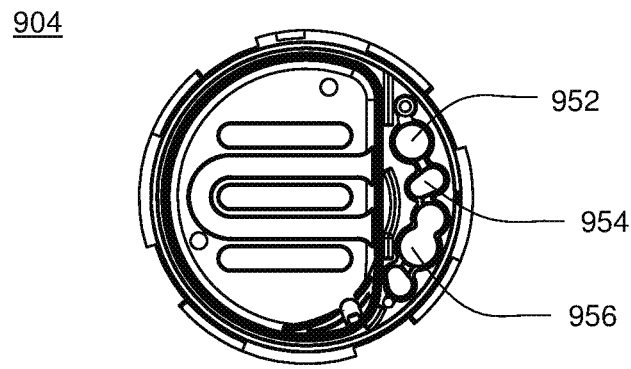

Referring also to FIGS. 53A-C, top portion 904 may include alignment tabs 930, 932 that may be configured to be at least partially received in openings 836, 838 of base plate 818 of reusable housing assembly 802 to ensure proper alignment between reusable housing assembly 802 and disposable housing assembly 804. Additionally, top portion 904 may include one or more radial tabs 934, 936, 938, 940 configured to be engaged by cooperating tabs 942, 944, 946, 948 of locking ring assembly 806. The one or more radial tabs (e.g., radial tab 940) may include stops (e.g., alignment tab stop 950, which may be used for welding, it's the tab that fits in the recess to locate and ultrasonically weld), e.g., which may prevent further rotation of locking ring assembly 806 once reusable housing assembly 802 and disposable housing assembly 804 are fully engaged.

Figure 52A:
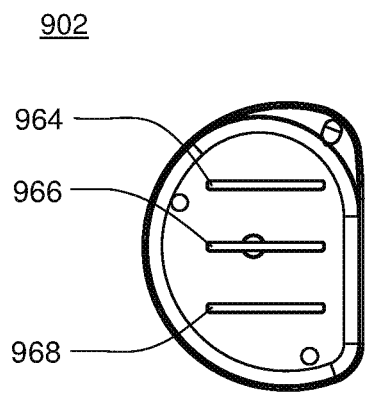
FIGS. 52A-52C depict the membrane assembly of the disposable housing assembly of FIG. 48.
Figure 52B:
Figure 52C:
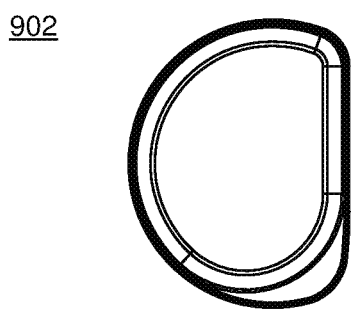

As discussed above, valve membrane insert 924 may allow for pumping and flow of the infusible fluid by reservoir valve 850, plunger pump 852, volume sensor valve 854, and measurement valve 856. Accordingly, top portion 904 may include one or more openings (e.g., openings 952, 954, 956) that may expose at least a portion of valve membrane insert 924 for actuation by reservoir valve 850, plunger pump 852, volume sensor valve 854, and measurement valve 856. Additionally, top portion 904 may include one or more openings 958, 960, 962 which may be configured to allow the fill volume to be controlled during filling of reservoir 908, as will be discussed in greater detail below. Reservoir assembly 902 may include ribs 964, 966, 968 (e.g., as shown in FIG. 52A), which may be at least partially received in respective openings 958, 960, 962. As will be described in greater detail below, a force may be applied to one or more of ribs 964, 966, 968 to, at least temporarily, reduce the volume of reservoir 908.

In some embodiments, it may be desirable to provide a seal between reusable housing assembly 802 and disposable housing assembly 804. Accordingly, disposable housing assembly 804 may include sealing assembly 970. Sealing assembly 970 may include, for example, an elastomeric member that may provide a compressible rubber or plastic layer between reusable housing assembly 802 and disposable housing assembly 804 when engaged, thus preventing inadvertent disengagement and penetration by outside fluids. For example, sealing assembly 970 may be a watertight seal assembly and, thus, enable a user to wear infusion pump assembly 800 while swimming, bathing or exercising.

In a fashion similar to, e.g., disposable housing assembly 114, disposable housing assembly 802 may, in some embodiments, be configured to have reservoir 908 filled a plurality of times. However, in some embodiments, disposable housing assembly 114 may be configured such that reservoir 908 may not be refilled. Referring also to FIGS. 57-64, fill adapter 1000 may be configured to be coupled to disposable housing assembly 804 for refilling reservoir 908 using a syringe (not shown). Fill adapter 1000 may include locking tabs 1002, 1004, 1006, 1008 that may be configured to engage radial tabs 934, 936, 938, 940 of disposable housing assembly 804 in a manner generally similar to tabs 942, 944, 946, 948 of locking ring assembly 806. Accordingly, fill adapter 1000 may be releasably engaged with disposable housing assembly 804 by aligning fill adapter 1000 with disposable housing assembly 804 and rotating fill adapter 1000 and disposable housing assembly 804 relative to one another to releasably engage locking tabs 1002, 1004, 1006, 1008 with radial tabs 934, 936, 938, 940.

Fill adapter 1000 may further include filling aid 1010, which may include guide passage 1012, e.g., which may be configured to guide a needle of a syringe (not shown) to a septum of disposable housing assembly 804 to allow reservoir 908 of disposable housing assembly 804 to be filled by the syringe. In some embodiments, guide passage 1012 may be an angled bevel or other gradual angled bevel to further guide a syringe to a septum. Fill adapter 1000 may facilitate filling reservoir 908 by providing a relatively large insertion area, e.g., at the distal opening of guide passage 1012. Guide passage 1012 may generally taper to a smaller proximal opening that may be properly aligned with the septum of disposable housing assembly 804, when fill adapter 1000 is engaged with disposable housing assembly 804. Accordingly, fill adapter 1000 may reduce the dexterity and aim necessary to properly insert a needle through the septum of disposable housing assembly 804 for the purpose of filling reservoir 908.

As discussed above, disposable housing assembly 804 may configured to facilitate controlling the quantity of infusible fluid delivered to reservoir 908 during filling. For example, membrane assembly 902 of disposable housing assembly 804 may include ribs 964, 966, 968 that may be depressed and at least partially displaced into reservoir 908, thereby reducing the volume of reservoir 908. Accordingly, when infusible fluid is delivered to reservoir 908, the volume of fluid that may be accommodated by reservoir 908 may be correspondingly reduced. Ribs 964, 966, 968 may be accessible via openings 958, 960, 962 in top portion 904 of disposable housing assembly 804.

Fill adapter 1000 may include one or more button assemblies (e.g., button assemblies 1014, 1016, 1018) corresponding to ribs 964, 966, 968. That is, when fill adapter 1000 is releasably engaged with disposable housing assembly 804, buttons 1014, 1016, 1018 may be aligned with ribs 964, 966, 968. Button assemblies 1014, 1016, 1018 may be, for example, cantilever members capable of being depressed. When fill adapter 1000 is releasably engaged with disposable housing assembly 804, one or more of button assemblies 1014, 1016, 1018 may be depressed, and may correspondingly displace a respective one of ribs 964, 966, 698 into reservoir 908, causing an attendant reduction in the volume of reservoir 908.

For example, assume for illustrative purposes that reservoir 908 has a maximum capacity of 3.00 mL. Further, assume that button assembly 1014 is configured to displace rib 964 into disposable housing assembly 804, resulting in a 0.5 mL reduction in the 3.00 mL capacity of disposable housing assembly 804. Further, assume that button assembly 1016 is configured to displace rib 966 into disposable housing assembly 804, also resulting in a 0.5 mL reduction in the 3.00 mL capacity of disposable housing assembly 804. Further, assume that button assembly 1018 is configured to displace slot assembly 968 into disposable housing assembly 804, also resulting in a 0.5 mL reduction in the 3.00 mL capacity of disposable housing assembly 804. Therefore, if the user wishes to fill reservoir 908 within disposable housing assembly 804 with 2.00 mL of infusible fluid, in some embodiments, the user may first fill the reservoir to the 3.00 mL capacity and then depresses button assemblies 1016 and 1014 (resulting in the displacement of rib 966 into disposable housing assembly 804), effectively reducing the 3.00 mL capacity of reservoir 908 within disposable housing assembly 804 to 2.00 mL. In some embodiments, the user may first depress a respective number of button assemblies, effectively reducing the capacity of reservoir 908, and then fill reservoir 908. Although a particular number of button assemblies are shown, representing the exemplary embodiment, in other embodiments, the number of button assemblies may vary from a minimum of 1 to as many as is desired. Additionally, although for descriptive purposes, and in the exemplary embodiment, each button assembly may displace 0.5 mL, in other embodiments, the volume of displacement per button may vary. Additionally, the reservoir may be, in various embodiments, include a larger or smaller volume than described in the exemplary embodiment.

According to the above-described configuration, the button assemblies (e.g., button assemblies 1014, 1016, 108) may be employed, at least in part, to control the fill volume of reservoir 908. By not depressing any of the button assemblies, the greatest fill volume of reservoir 908 may be achieved. Depressing one button assembly (e.g., button assembly 1014) may allow the second greatest fill volume to be achieved. Depressing two button assemblies (e.g., button assemblies 1014, 1016) may achieve the third greatest fill volume. Depressing all three button assemblies (e.g., button assemblies 1014, 1016, 1018) may allow the smallest fill volume to be achieve.

Further, in an embodiment button assemblies 1014, 1016, 1018 may be utilized, at least in part, to facilitate filling of reservoir 908. For example, once a filling needle (e.g., which may be fluidly coupled to a vial of infusible fluid) has been inserted into reservoir 908, button assemblies 1014, 1016, 1018 may be depressed to pump at least a portion of any air that may be contained within reservoir into the vial of infusible fluid. Button assemblies 1014, 1016, 1018 may subsequently be released to allow infusible fluid to flow from the vial into reservoir 908. Once reservoir 908 has been filled with the infusible fluid, one or more button assemblies (e.g., one or more of button assemblies 1014, 1016, 1018) may be depressed, thereby squeezing at least a portion of the infusible fluid from reservoir 908 (e.g., via a needle used to fill reservoir 908 and back into the vial of infusible fluid). As discussed above, the volume of infusible fluid contained within reservoir 908 may be controlled, e.g., depending upon how many button assemblies are depressed (e.g., which may control how much infusible fluid is squeezed back into the vial of infusible fluid).

Figure 62:
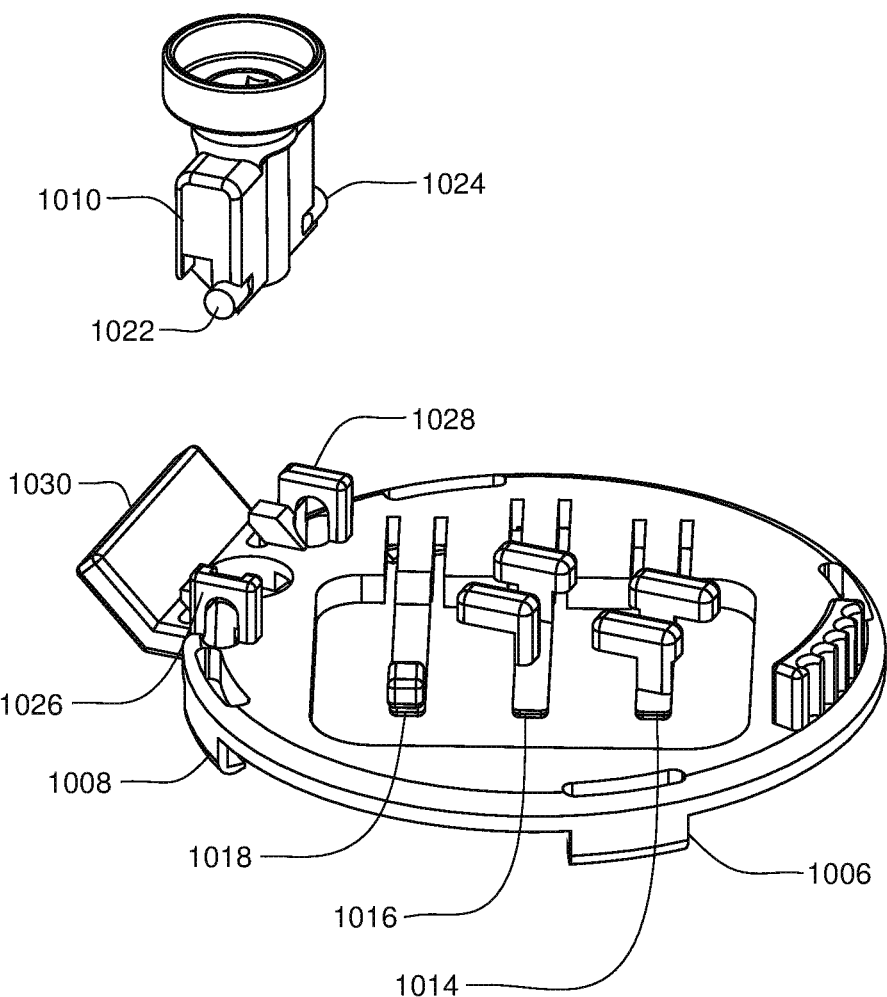
Figure 63:
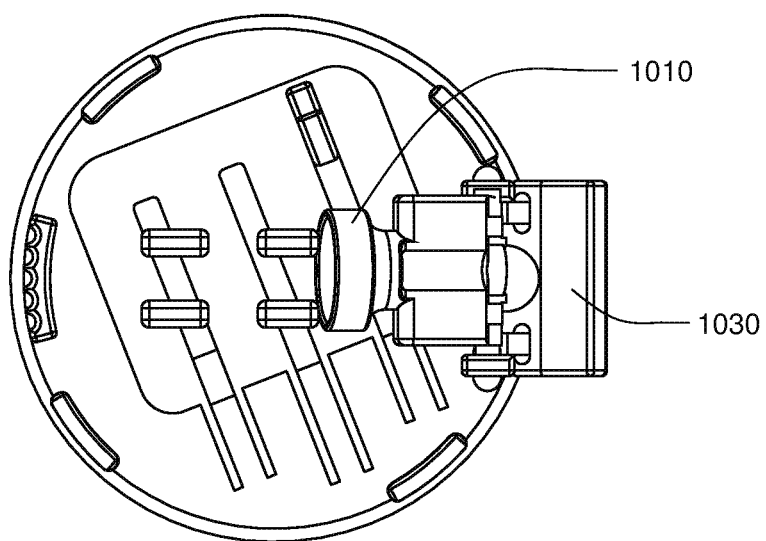
Figure 64:
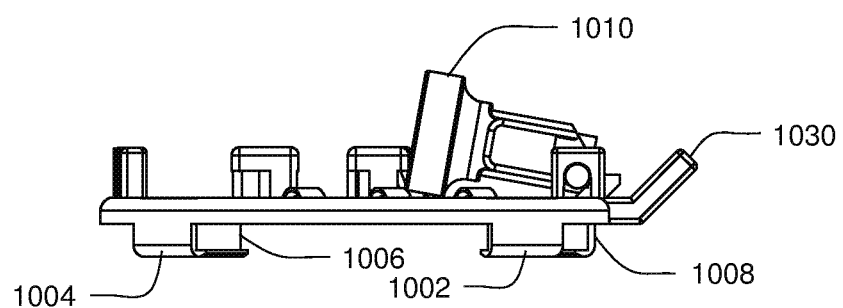

With particular reference to FIGS. 62-64, filling aid 1010 may be pivotally coupled to fill adapter base plate 1020. For example, filling aid 1010 may include pivot members 1022, 1024 that may be configured to be received in pivot supports 1026, 1028, thereby allowing filling aid to pivot between an open position (e.g., as shown in FIGS. 57-61) and a closed position (e.g., as shown in FIGS. 63-64). The closed position may be suitable, e.g., for packaging fill adapter 1000, storage of fill adapter 1000, or the like. In order to ensure that filling aid 1010 is properly oriented for filling reservoir 908, fill adapter 1000 may include support member 1030. To properly orient filling aid 1010, a user may pivot filling aid 1010 to a fully open position, wherein filling aid 1010 may contact support member 1030.

Figure 65:
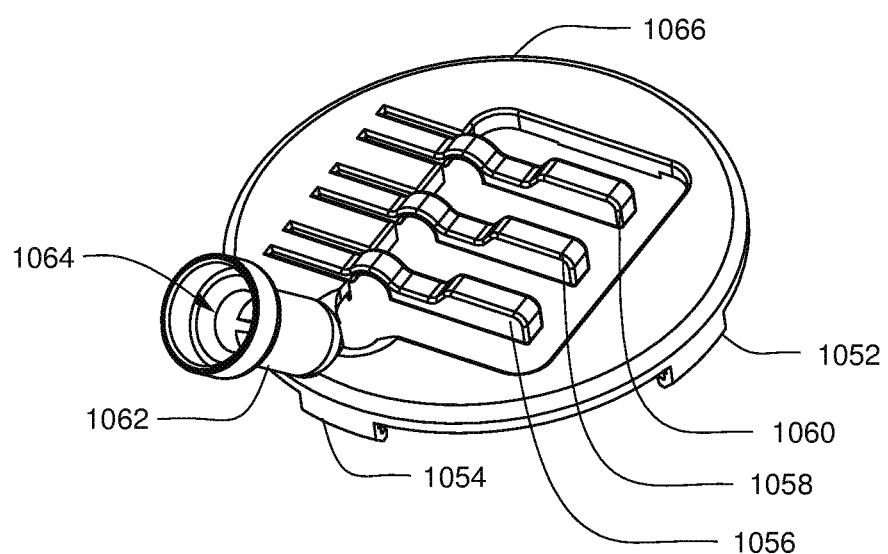
FIG. 65 is an isometric view of another embodiment of a fill adapter.
Figure 66:
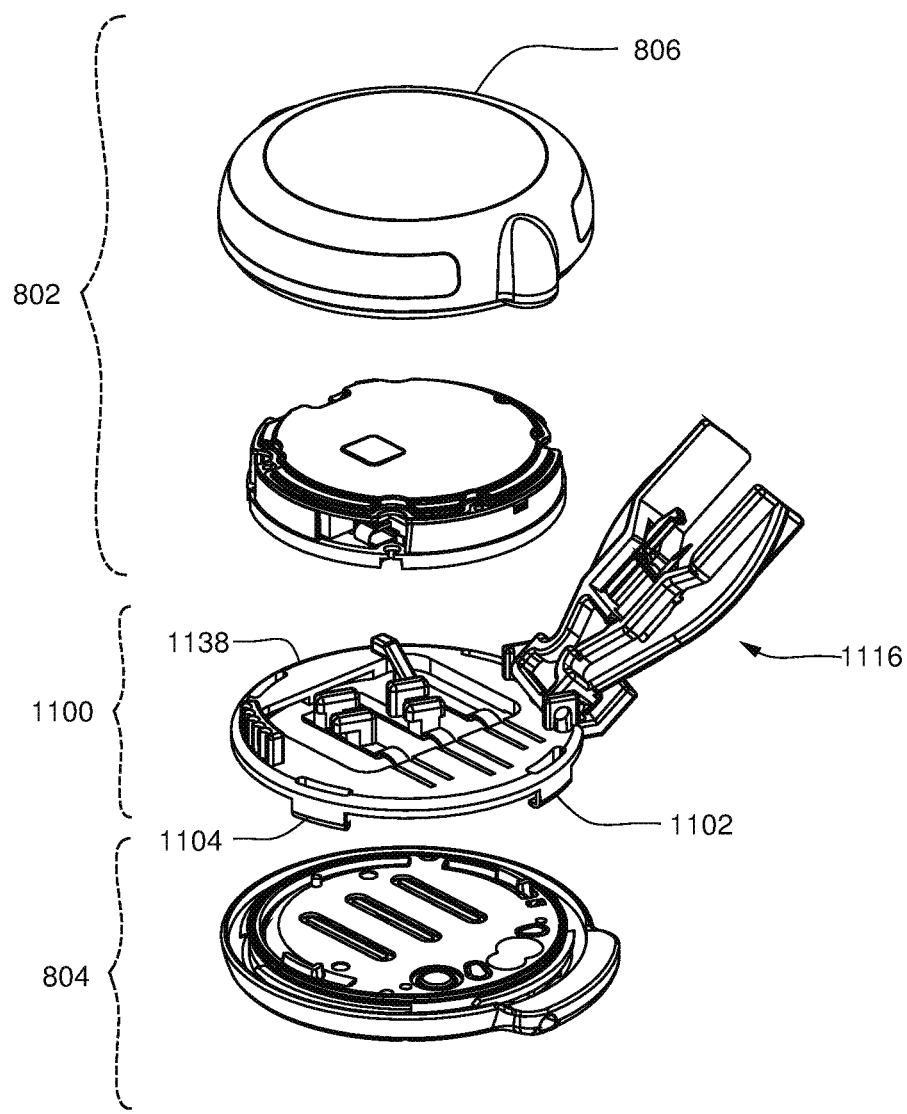
FIGS. 66-67 depict an infusion pump assembly and another embodiment of a fill adapter.
Figure 67:
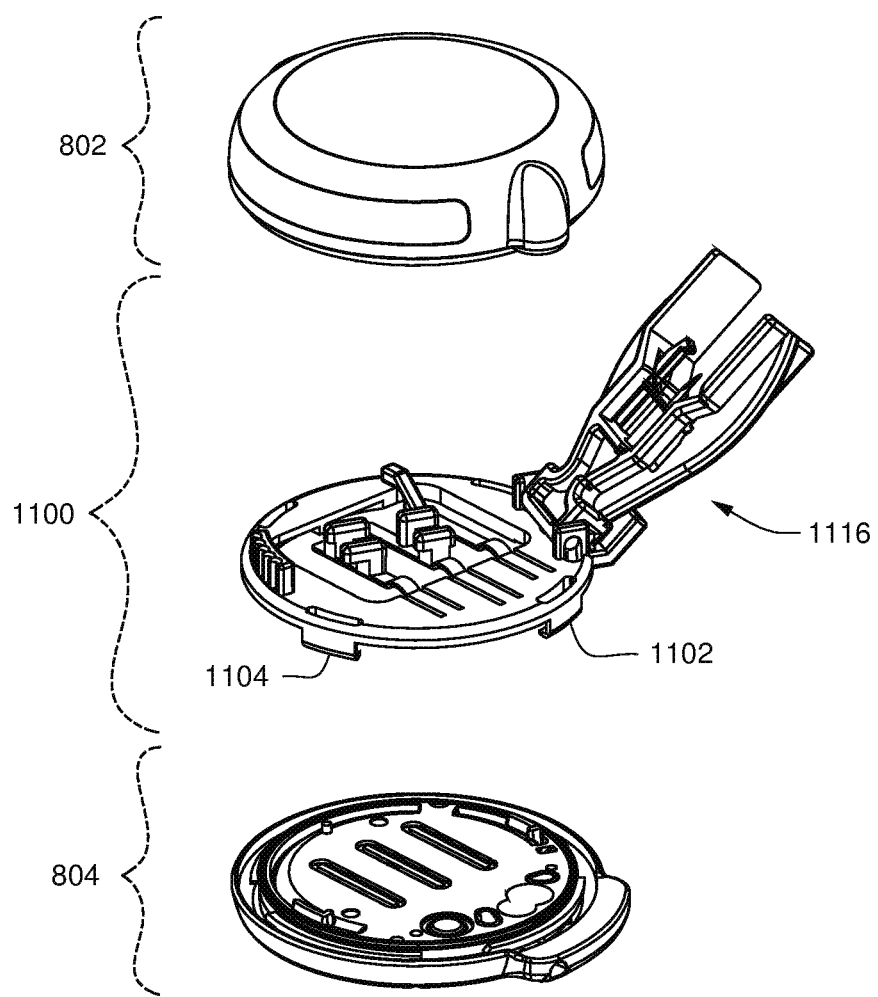
Figure 69:
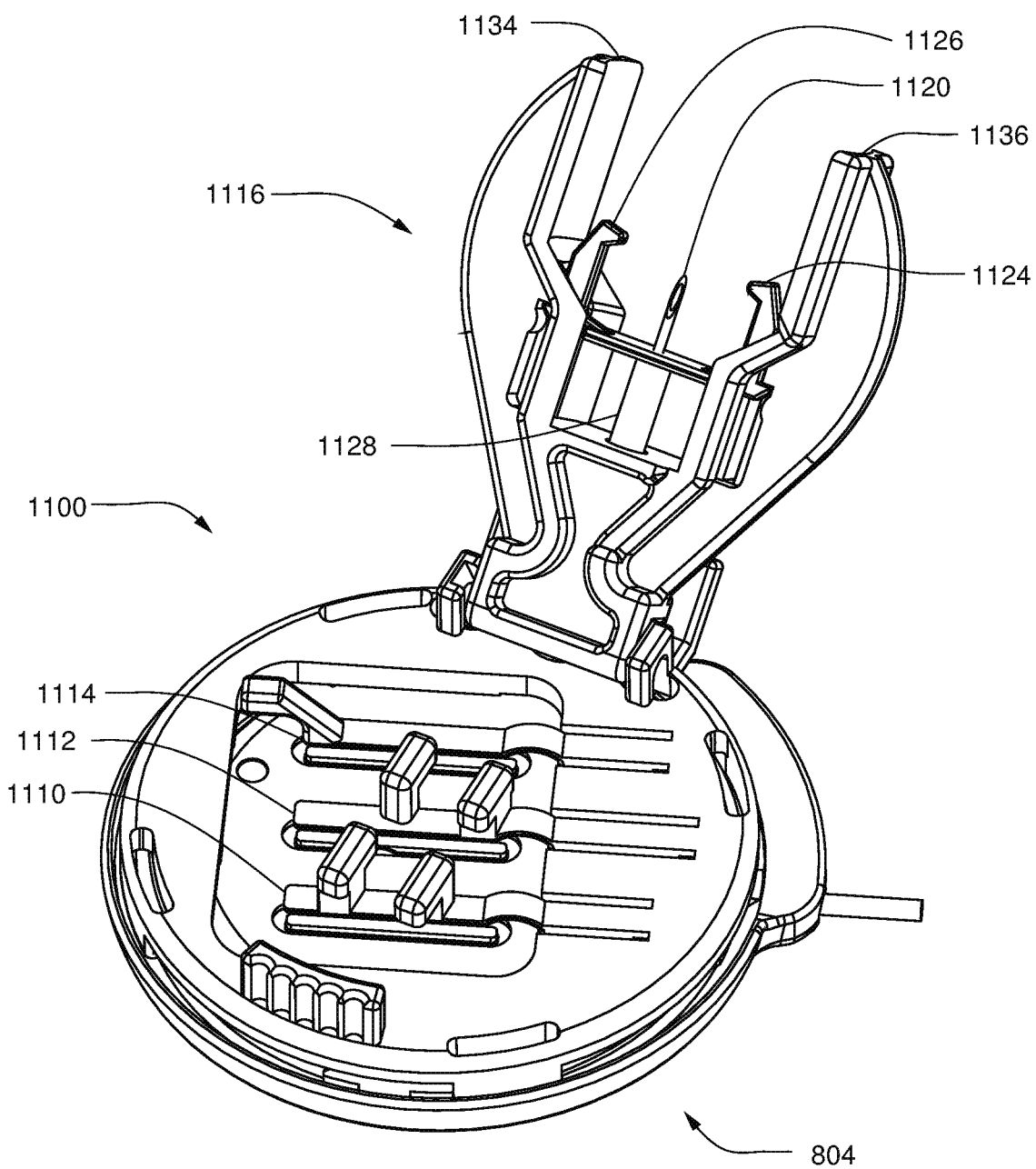

According to an alternative embodiment, and referring also to FIG. 65, fill adapter 1050 may be configured to releasably engage disposable housing assembly 804 via a plurality of locking tabs (e.g., locking tabs 1052, 1054). Additionally, fill adapter 1050 may include a plurality of button assemblies (e.g., button assemblies 1056, 1058, 1060) that may interact with ribs 964, 966, 968 of disposable housing assembly 804 to adjust a fill volume of reservoir 908. Fill adapter 1050 may further include filling aid 1062, having guide passage 1064 configured to align a needle of a syringe with the septum of disposable housing 804, e.g., for accessing reservoir 908 for the purpose of filling reservoir 908 with an infusible fluid. Filling aid 1062 may be connected to base plate 1066, e.g., as an integral component therewith, by gluing, heat sealing, compression fit, or the like.

Referring also to FIGS. 66-74, vial fill adapter 1100 may be configured to facilitate filling reservoir 908 of disposable housing assembly 804 directly from a vial. Similar to fill adapter 1000, vial fill adapter 1100 may include locking tabs 1102, 1104, 1106, 1108 that may be configured to engage radial tabs 934, 936, 938, 940 of disposable housing assembly in a manner generally similar to tabs 942, 944, 946, 948 of locking ring assembly 806. Accordingly, vial fill adapter 1100 may be releasably engaged with disposable housing assembly 804 by aligning vial fill adapter 1100 with disposable housing assembly 804 and rotating vial fill adapter 1100 and disposable housing assembly 804 relative to one another to releasably engage locking tabs 1102, 1104, 1106, 1108 with radial tabs 934, 936, 938, 940.

As discussed above, disposable housing assembly 804 may be configured to facilitate controlling the quantity of infusible fluid delivered to reservoir 908 during filling. For example, membrane assembly 902 of disposable housing assembly 804 may include ribs 964, 966, 968 that may be depressed and at least partially displaced into reservoir 908, thereby reducing the volume of reservoir 908. Accordingly, when infusible fluid is delivered to reservoir 908, the volume of fluid that may be accommodated by reservoir 908 may be correspondingly reduced. Ribs 964, 966, 968 may be accessible via openings 958, 960, 962 in top portion 904 of disposable housing assembly 804.

Vial fill adapter 1100 may include one or more button assemblies (e.g., button assemblies 1110, 1112, 1114) corresponding to ribs 964, 966, 968 (e.g., shown in FIG. 52A). That is, when vial fill adapter 1100 is releasably engaged with disposable housing assembly 804, buttons 1110, 1112, 1114 may be aligned with ribs 964, 966, 968. Button assemblies 1110, 1112, 1114 may be, for example, cantilever members capable of being depressed. When vial fill adapter 1100 is releasably engaged with disposable housing assembly 804, one or more of button assemblies 1110, 1112, 1114 may be depressed, and may correspondingly displace a respective one of ribs 964, 966, 698 into reservoir 908, thereby reducing the volume of reservoir 908.

For example, assume for illustrative purposes that reservoir 908 has a maximum capacity of 3.00 mL. Further, assume that button assembly 1110 is configured to displace rib 964 into disposable housing assembly 804, resulting in a 0.5 mL reduction in the 3.00 mL capacity of disposable housing assembly 804. Further, assume that button assembly 1112 is configured to displace rib 966 into disposable housing assembly 804, also resulting in a 0.5 mL reduction in the 3.00 mL capacity of disposable housing assembly 804. Further, assume that button assembly 1114 is configured to displace rib 968 into disposable housing assembly 804, also resulting in a 0.50 mL reduction in the 3.00 mL capacity of disposable housing assembly 804. Therefore, if the user wishes to fill reservoir 908 within disposable housing assembly 804 with 2.00 mL of infusible fluid, the user may depress button assemblies 1112 and 1114 (resulting in the displacement of ribs 966 and 968 into disposable housing assembly 804), effectively reducing the 3.00 mL capacity of reservoir 908 within disposable housing assembly 804 to 2.0 mL.

Figure 71:
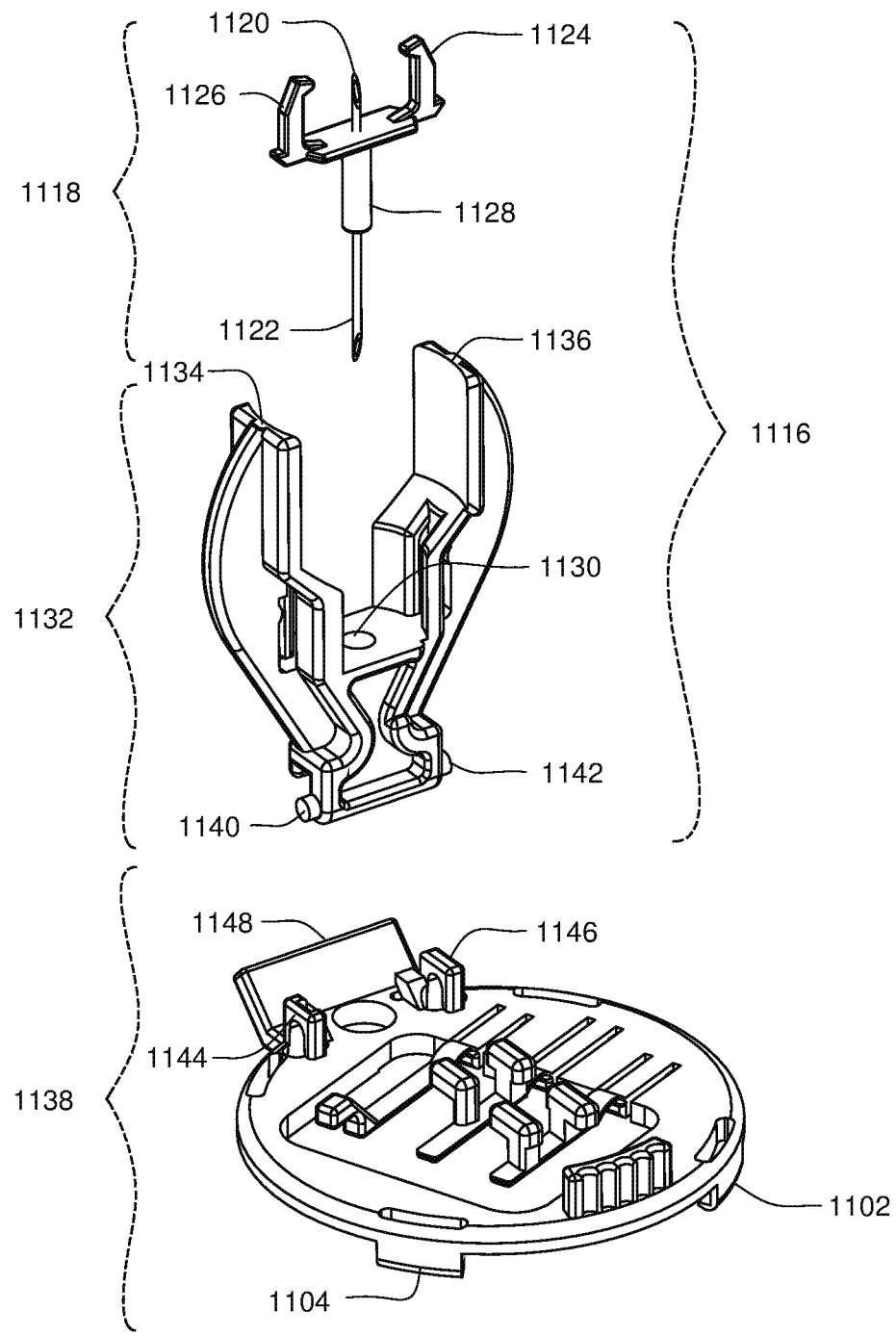

Vial fill adapter 1100 may further include vial filling aid assembly 1116 that may be configured to fluidly couple a vial of infusible fluid to reservoir 908 of disposable housing assembly 804 via a septum. With particular reference to FIG. 71, vial filling aid assembly may include double ended needle assembly 1118. Double ended needle assembly 1118 may include first needle end 1120 configured to penetrate the septum of a vial (not shown) and second needle end 1122 configured to penetrate the septum of disposable housing assembly 804. As such, the vial and reservoir 908 may be fluidly coupled allowing infusible fluid to be transferred from the vial to reservoir 908. Double ended needle assembly 1118 may include vial engagement portion 1124 adjacent first end 1120. Vial engagement arms 1124, 1126 may be configured to releasably engage, e.g., a vial cap, to assist in maintaining the fluid connection between double ended needle assembly 1118 and the vial. Additionally, double ended needle assembly 1118 may include body 1128 that may be slidably received in opening 1130 of vial filling aid body 1132. Vial filling aid body 1132 may include stabilizer arms 1134, 1136, e.g., which may be configured to stabilize the vial during filling of disposable housing assembly 804. In one embodiment, the vial may be engaged with double ended needle assembly 1118 e.g., such that first end 1120 may penetrate the septum of the vial and the cap of the vial may be engaged by engagement arms 1124, 1126. Body 1128 may be slidably inserted into opening 1130 such that second end 1122 of double ended needle assembly 1118 may penetrate the septum of disposable body assembly 804.

Figure 72:
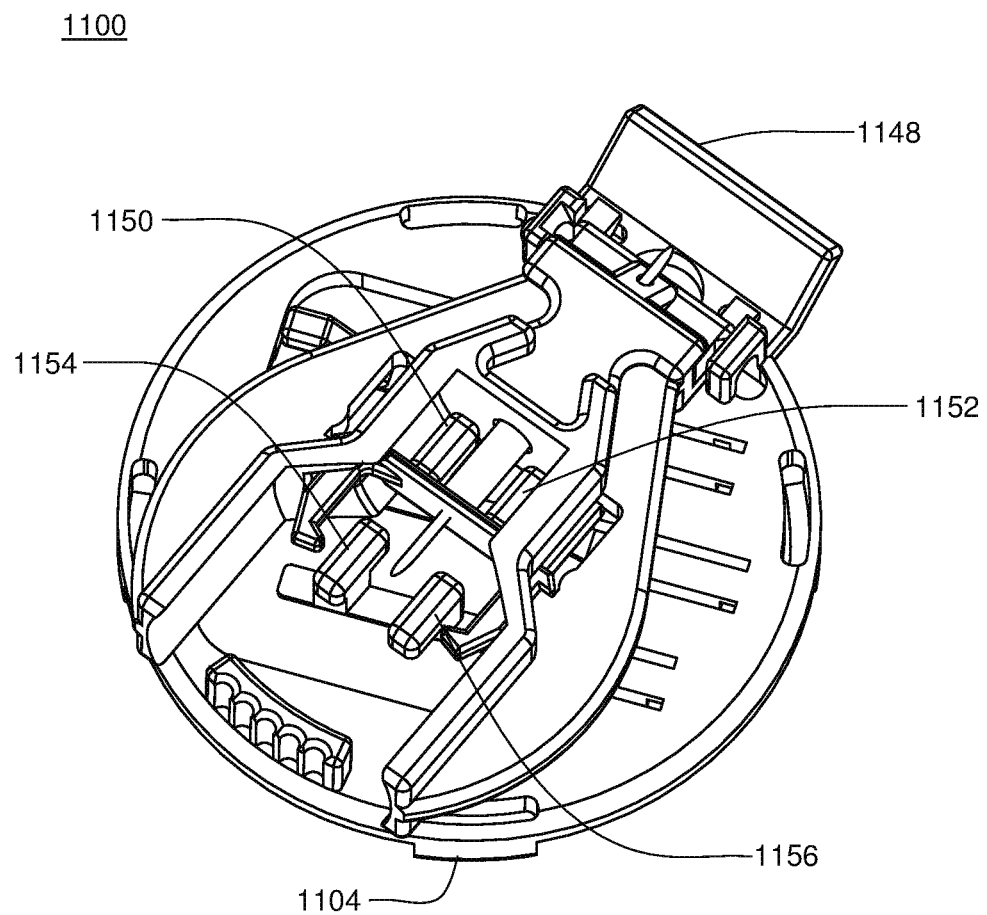
Figure 73:
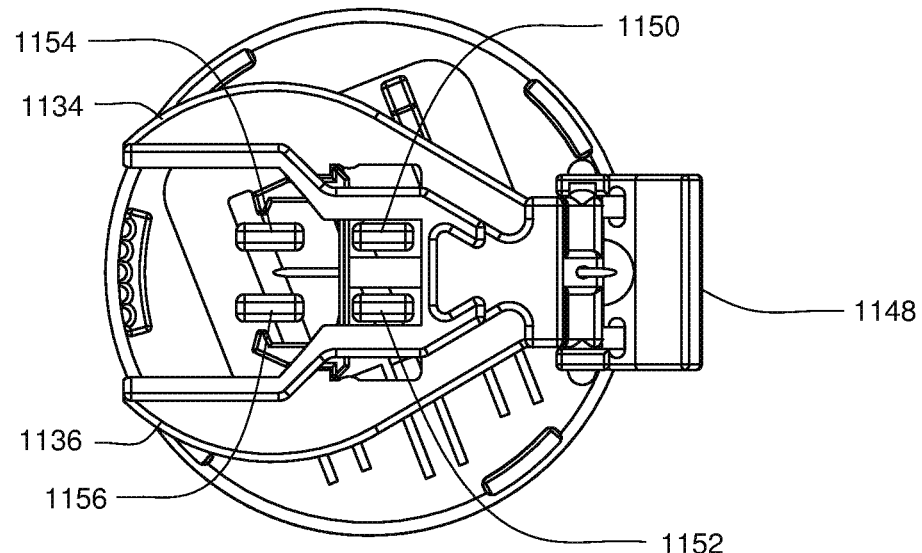
Figure 74:
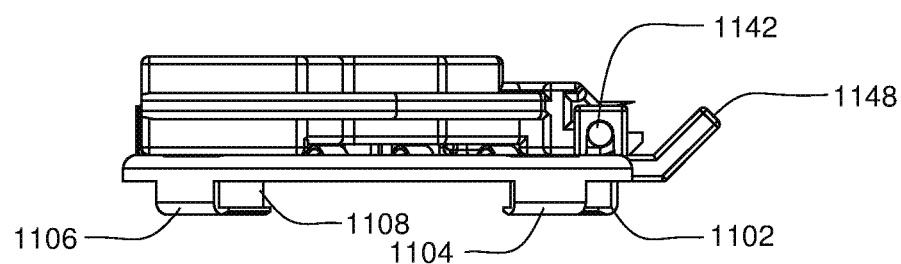
Figure 75:
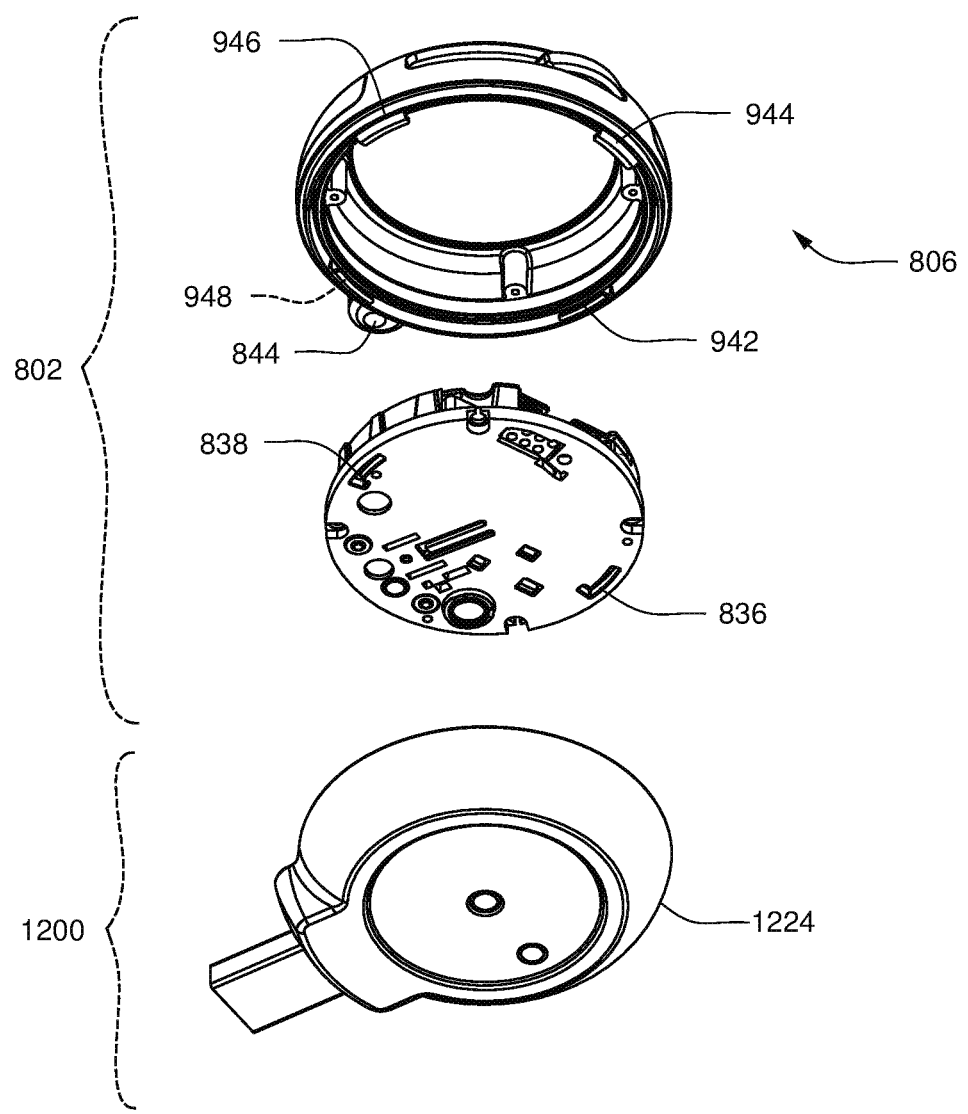
FIGS. 75-80 depict various views of an embodiment of a battery charger.
Figure 76:
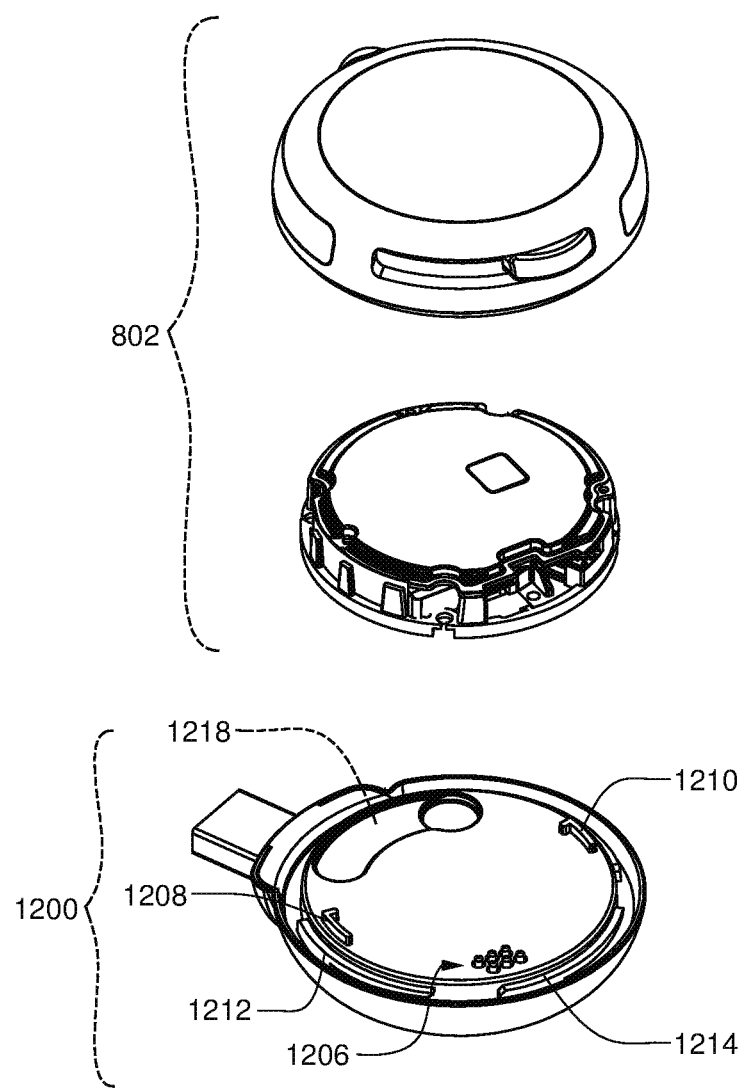

Similar to fill adapter 1000, vial filling aid assembly 1116 may be configured to be pivotally coupled to vial fill adapter base plate 1138. For example, vial filling aid 1116 may include pivot members 1140, 1142 that may be configured to be received in pivot supports 1144, 1146 (e.g., shown in FIG. 71), thereby allowing vial filling aid 1116 to pivot between an open position (e.g., as shown in FIGS. 66-70) and a closed position (e.g., as shown in FIGS. 72-74). The closed position may be suitable, e.g., for packaging vial fill adapter 1100, storage of vial fill adapter 1100, or the like. In order to ensure that vial filling aid 1116 is properly oriented for filling reservoir 908, vial fill adapter 1100 may include support member 1148. To properly orient vial filling aid 1116, a user may pivot vial filling aid 1116 to a fully open position, wherein vial filling aid 1116 may contact support member 1148. Additionally, vial fill adapter base plate 1138 may include one or more locking features (e.g., locking tabs 1150, 1152) that may engage vial filing aid 1116, and may maintain vial filling aid 1116 in the closed position. Vial fill adapter base plate 1138 may also include features (e.g., tabs 1154, 1156) that may be configured to assist in retaining double ended needle assembly 1118, e.g., by preventing slidable separation of double ended needle assembly 1118 from vial filling aid body 1132.

Figure 70:
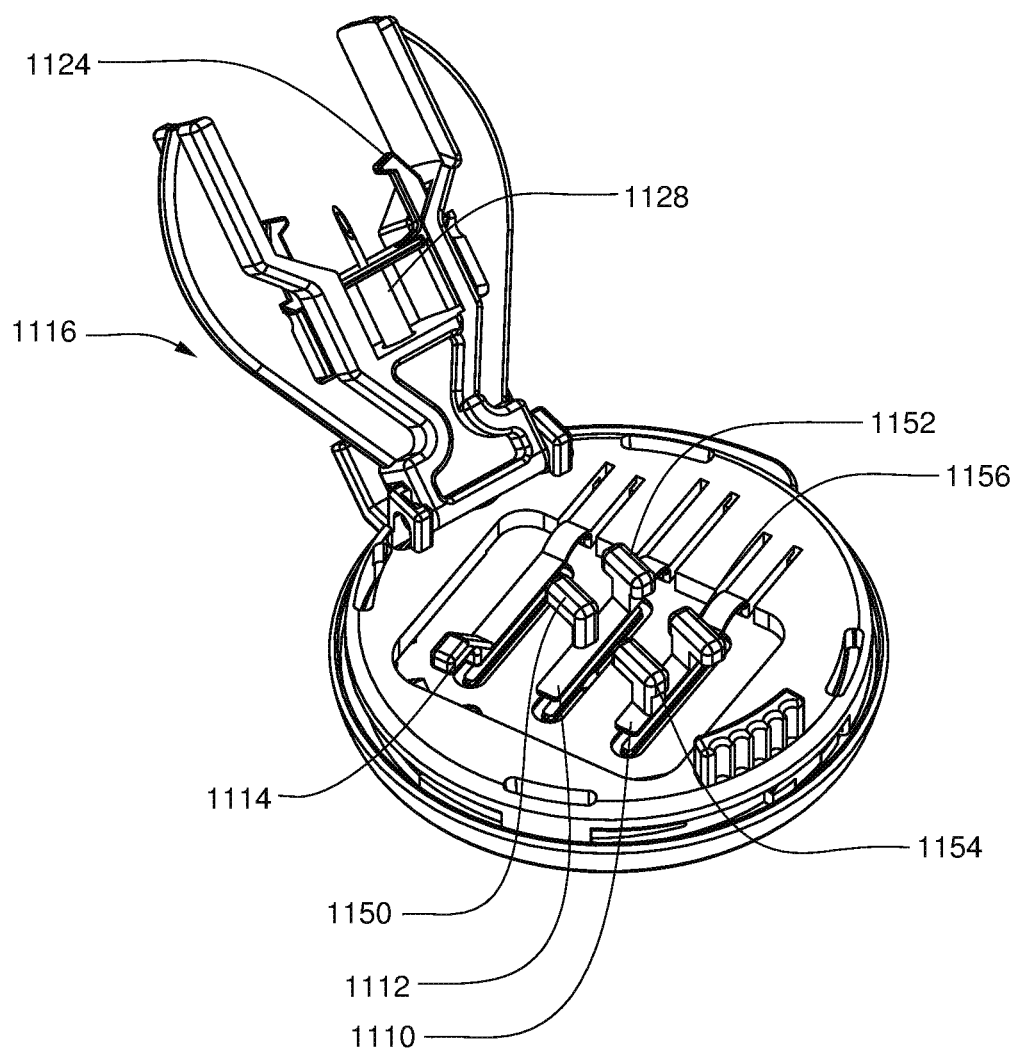

As shown in FIGS. 72-74, filling aid assembly 1116 is in a closed position. In this configuration, support member 1148 may additionally function as a needle guard. When removing filling aid assembly 1116 from disposable housing assembly 804, support member 1148 may function to safely allow a user to squeeze the ends and rotate filling aid assembly 1116 for removal. As shown in FIG. 70, in the open position, support member 1148 may function as a stop to maintain proper orientation.

Referring again to FIGS. 57-73, the exemplary embodiments of the fill adapter include a grip feature (e.g., 1166 in FIG. 72). Grip feature 1166 may provide a grip interface for removal of the fill adapter from disposable housing assembly 804. Although shown in one configuration in these figures, in other embodiments, the configuration may vary. In still other embodiments, a grip feature may not be included.

According to one embodiment, fill adapter base plate 1020 and vial fill adapter base plate 1138 may be interchangeable components. Accordingly, a single base plate (e.g., either fill adapter base plate 1020 or vial fill adapter base plate 1138 may be used with either filling aid 1010 or vial filling aid 1116. Accordingly, the number of distinct components that are required for both filling adapters may be reduced, and a user may have the ability to select the filling adapter that may be the most suitable for a given filling scenario.

The various embodiments of the fill adapters may provide many safety benefits, including but not limited to: providing a system for filling the reservoir without handling a needle; protecting the reservoir from unintentional contact with the needle, i.e., destruction of the integrity of the reservoir through unintentional puncture; designed to be ambidextrous; in some embodiments, may provide a system for maintaining air in the reservoir.

Figure 181:
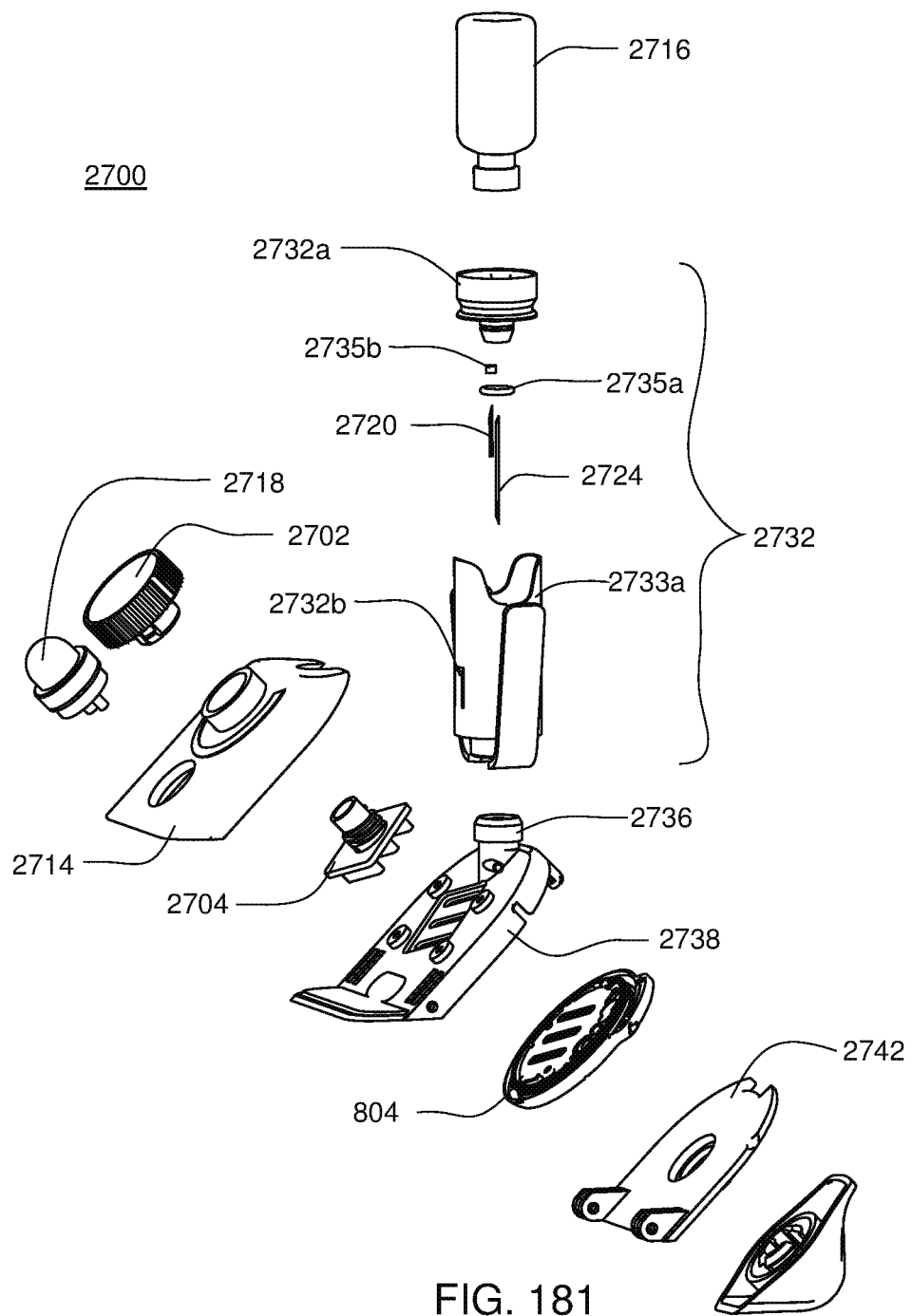
Figure 182:
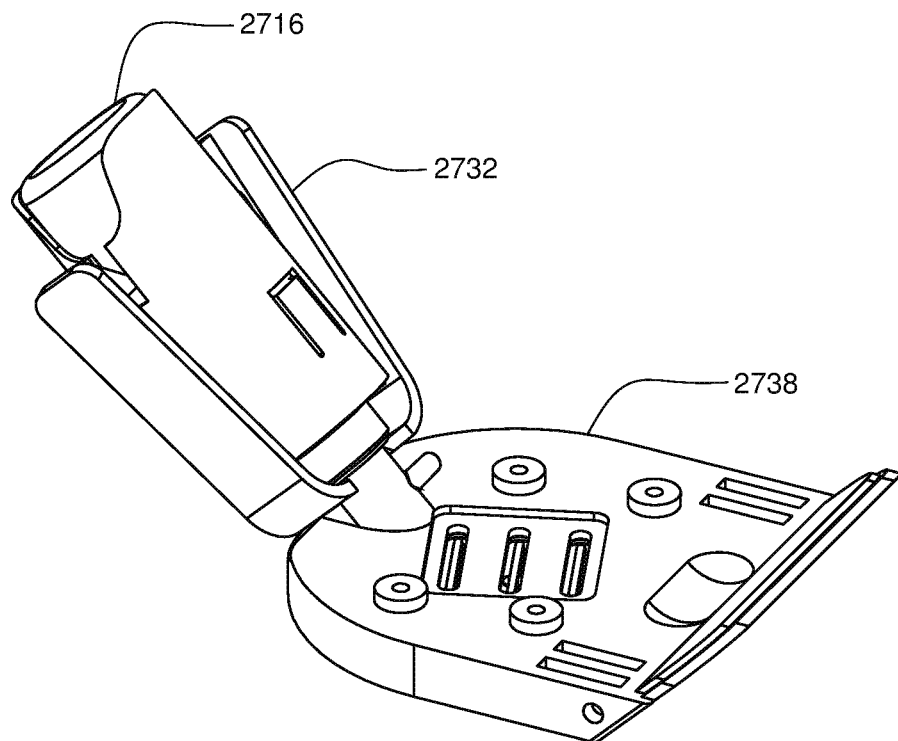
Figure 187:
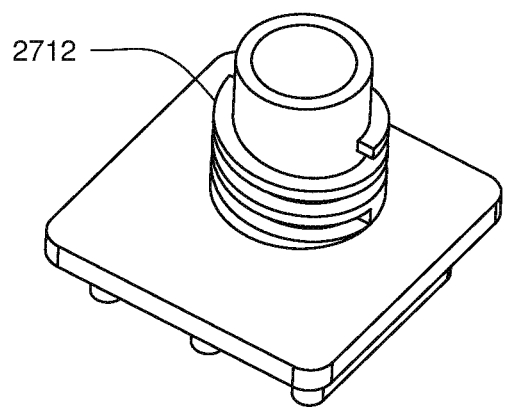
Figure 188:
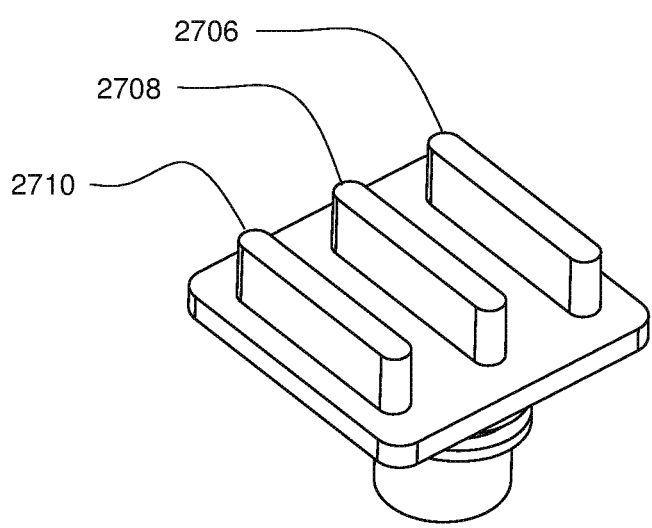
Figure 189:
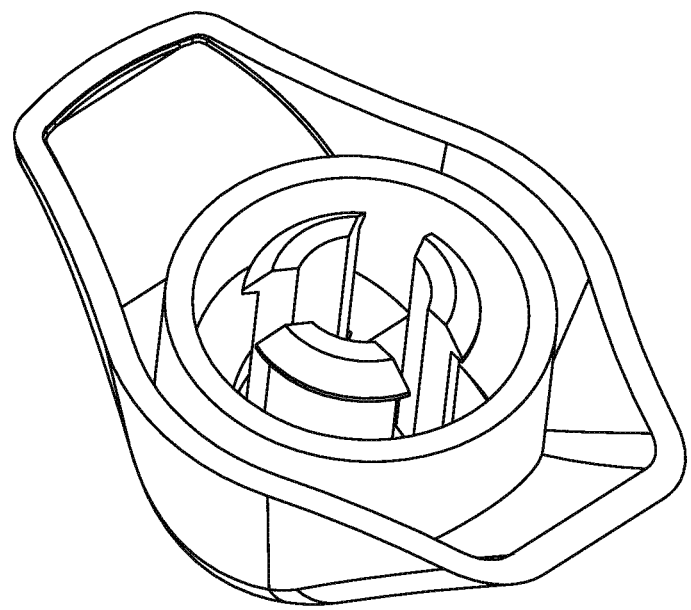
Figure 190:
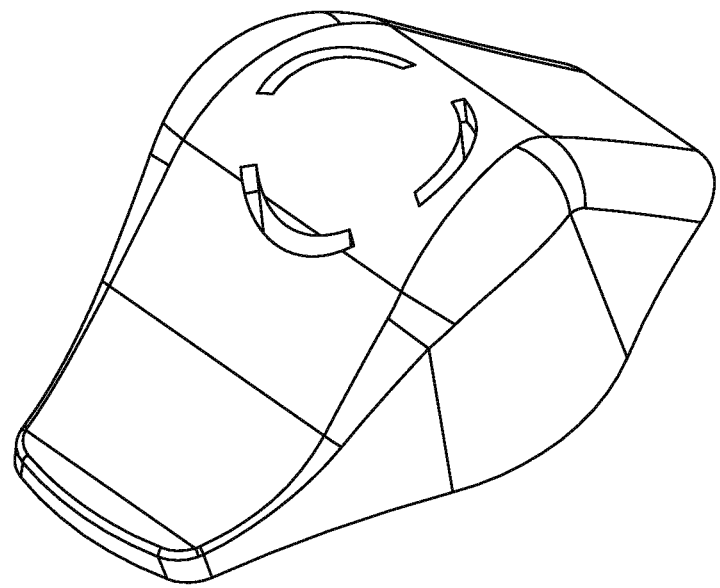
Figure 191:
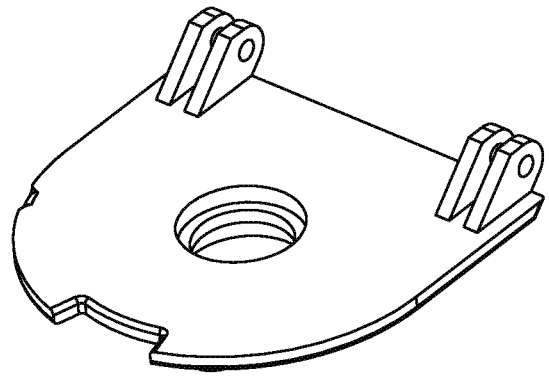
Figure 192:
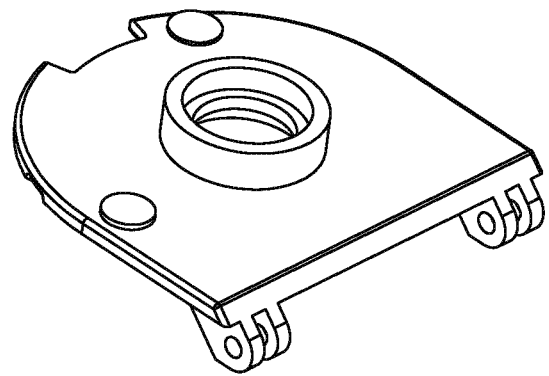

According to other embodiments, the fill adapter may be configured to meter the fluid dispensed into the reservoir or the disposable housing assembly. Additionally/alternatively, the fill adapter may be configured to positively dispense (e.g., pump) the fluid into the reservoir of the disposable housing assembly. For example, and referring also to FIGS. 174-194, fill adapter 2700 may include a metering system for controlling the amount of fluid dispensed into the reservoir of the disposable housing assembly (e.g., reservoir 908 of disposable housing assembly 804 and a pumping mechanism for positively dispensing the fluid to reservoir 908. Generally, fill adapter 2700 may include a turn dial (e.g., turn dial 2702) that may adjust the volume of fluid to be dispensed into reservoir 908. For example, turn dial 2702 may actuate push plate 2704 (FIG. 181). Push plate 2704 may include one or more button features (e.g., button features 2706, 2708, 2710 shown in FIG. 187, 188). Button features 2706, 2708, 2710 may displace one or more of ribs 964, 966, 968 associated with reservoir 908, thereby reducing the available fill volume of reservoir 908. The degree to which ribs 964, 966, 968 are displaced may determine the available fill volume of reservoir 908 (as discussed previously), and therefore also the volume of fluid that may be dispensed into reservoir 908.

Turn dial 2702 and push plate 2704 may include cooperating features that may enable turn dial 2702 to adjust the displacement of ribs 964, 966, 968 by push plate 2704. In one embodiment, turn dial 2702 and push plate 2704 may include cooperating ramp features, e.g., threads 2712 of push plate 2704 shown in FIG. 187. Turn dial 2702 may include cooperating threads, such that when turn dial 2702 is turned in a first direction (e.g., clockwise) push plate 2704 may be linearly moved in a first direction to displace ribs 964, 966, 968 into reservoir 908 to decrease the available fill volume of reservoir 908. Conversely, when turn dial 2707 is turned in a second direction (e.g., counterclockwise) push plate 2704 may be linearly moved in a second direction allowing ribs 964, 966, 968 to move to increase the available fill volume of reservoir 908. In addition to cooperating ramp features, various additional/alternative features may be utilized, including, but not limited to, cam features, rack and pinion features, etc. Further, fill adapter 2700 may include one or more return features (such as springs, or other bias members; not shown) that may ensure that push plate 2704 is biased to increase the available fill volume of reservoir 908 in response to turn dial 2702 being adjusted from a smaller available fill volume to a larger available fill volume (e.g., as turn dial 2702 is turned in a counterclockwise direction in foregoing example).

Additionally, while not shown, turn dial 2702 may be calibrated and turn dial 2702 and/or housing 2714 may include indicia that may indicate the available fill volume of reservoir 908 at a given rotational position of turn dial 2702. For example, turn dial 2702 may include a pointer and housing 2714 may include numerical indicia indicating available fill volume of reservoir 908. As such, the available fill volume of reservoir 908 may be the numerical value indicated by the cooperation of the pointer of turn dial 2702 and the numerical indicia of housing 2714.

As mentioned above, fill adapter 2700 may be configured to positively dispense fluid into reservoir 908. In one embodiment, fill adapter 2700 may include a pump mechanism configured to pump air into a vial (e.g., vial 2716 shown in FIG. 181). For example, pumping air into vial 2716 may pressurize vial 2716 to a pressure greater than a pressure within reservoir 908. As such, when vial 2716 is fluidly coupled with reservoir 908, the greater pressure within vial 2716 may force fluid contained within vial 2716 into reservoir 908. Consistent with the foregoing description, the volume of fluid transferred from vial 2716 into reservoir 908 may be controlled by turn dial 2702 and push plate 2704 (e.g., based upon, at least in part, the interaction between button features 2706, 2708, 2710 and fingers 964, 966, 968).

The fill adapter may include a pump mechanism. According to one embodiment, fill adapter 2700 may include pump bulb 2718, which may include a flexible convex member that may be biased toward a first volume, and compressible to a second volume that is less than the first volume. For example, pump bulb 2718 may be compressed from the first volume to the second volume when pump bulb 2718 is pressed by a user's thumb or finger. While not shown, a pumping volume (e.g., the difference between the first volume and the second volume of pump bulb 2718) may be controlled at least in part, by turn dial 2702. For example, the pumping volume may be controlled by turn dial 2702 to correspond to the available fill volume of reservoir 908 (e.g., the pumping volume may be a pumping volume of air that may result a transfer of a volume of fluid generally equal to the available fill volume of reservoir 908).

Further, while not shown, pump bulb 2718 may include an inlet having an associated one-way valve that may allow air to enter pump bulb 2718 via the inlet when pump bulb 2718 expands from the second volume to the first volume, and may prevent air from exiting inlet when pump bulb 2718 is compressed from the first volume to the second volume. Additionally, while also not shown, pump bulb 2718 may include an outlet having an associated one-way valve that may allow air to exit pump bulb 2718 via the outlet when pump bulb 2718 is compressed from the first volume to the second volume, and may prevent air from entering pump bulb 2718 via the outlet when pump bulb 2718 expands from the second volume to the first volume. Various valve mechanisms may be employed for the one-way inlet valve and the one-way outlet valve, including, but not limited to, ball valves, flap valves, diaphragm valves, and the like.

In various additional/alternative embodiments the pump mechanism may include, but is not limited to, a piston pump, a diaphragm pump, or the like. Further, while pump bulb 2718 has been described as being compressed by a user's thumb or finger, various additional/alternative embodiments of a pump mechanism may be actuated by a turn crank, a lever, a pair of squeeze handles, a foot pump, and/or various other means of actuation.

Figure 194:
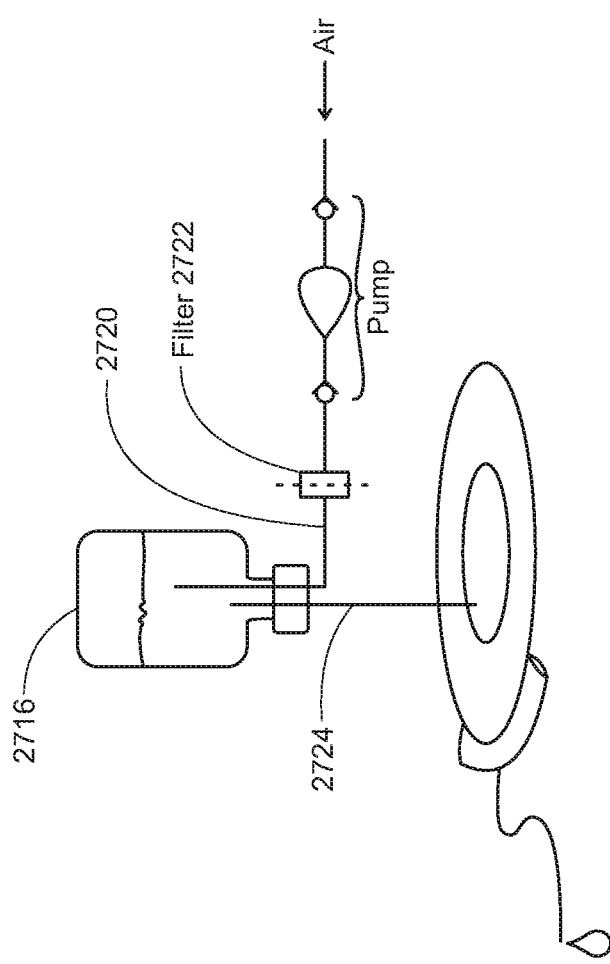
Figure 195A:
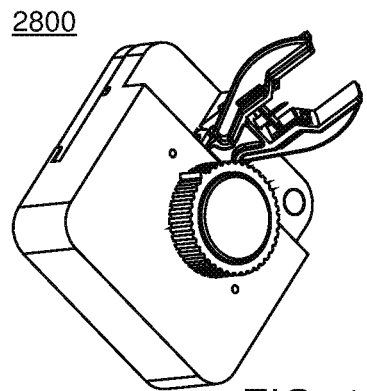
Figure 195E:
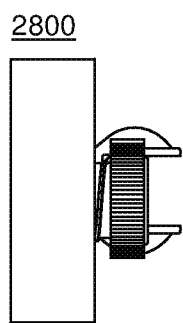
Figure 195B:
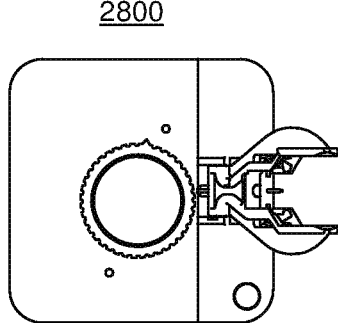
Figure 195C:
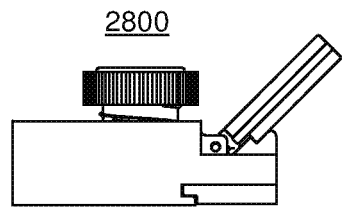
Figure 195D:
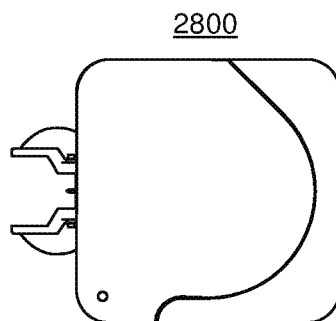
Figure 196A:
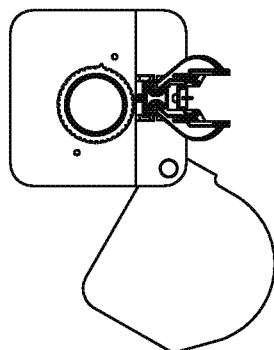
Figure 196B:
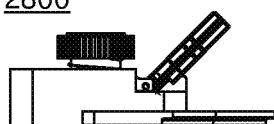
Figure 196C:
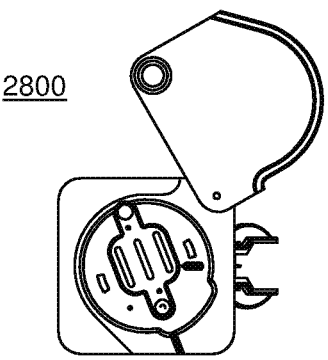
Figure 196E:
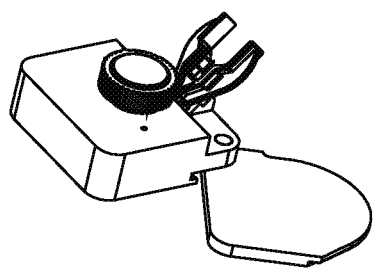
Figure 196D:
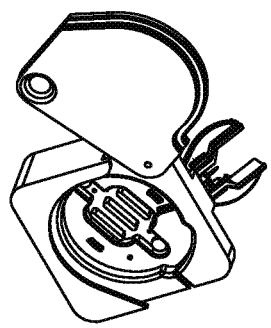

The outlet of pump bulb 2718 may be fluidly coupled to pressure needle 2720 (FIG. 181). Pressure needle 2720 may be configured to penetrate a septum of vial 2716. As such, when pressure needle 2720 has penetrated the septum of vial 2716 and pump bulb 2718 is pumped (e.g., by compressing pump bulb 2718 from the first volume to the second volume) air may be transferred from pump bulb 2718 into vial 2716. The transfer of air from pump bulb 2718 into vial 2716 may increase the internal pressure within vial 2716. The one way valve associated with the outlet of pump bulb 2718 may prevent the retrograde flow of fluid from vial 2716 into pump bulb 2718 via pressure needle 2720. Additionally, as schematically shown in FIG. 194, hydrophobic filter 2722 may be associated with pressure needle 2720. Hydrophobic filter 2722 may include any variety of gas-permeable hydrophobic materials, such as a POREX™ material, a GORE™ material, or the like (POREX is a trademark of Porex Corporation in the United States and/or other countries, GORE is a trade mark of W. L. Gore & Associates, Inc. in the Unites States and/or other countries). Hydrophobic filter 2722 may allow the transmission of gaseous fluids (such as air), but may resist/prevent the passage of liquids (such as insulin or various other infusion fluids). Additionally, hydrophobic filter 2722 may have a restricted flow rate of gaseous fluids, and may, therefore, control the rate at which air can be pumped out of pump bulb 2718 and into vial 2716.

Figure 183:
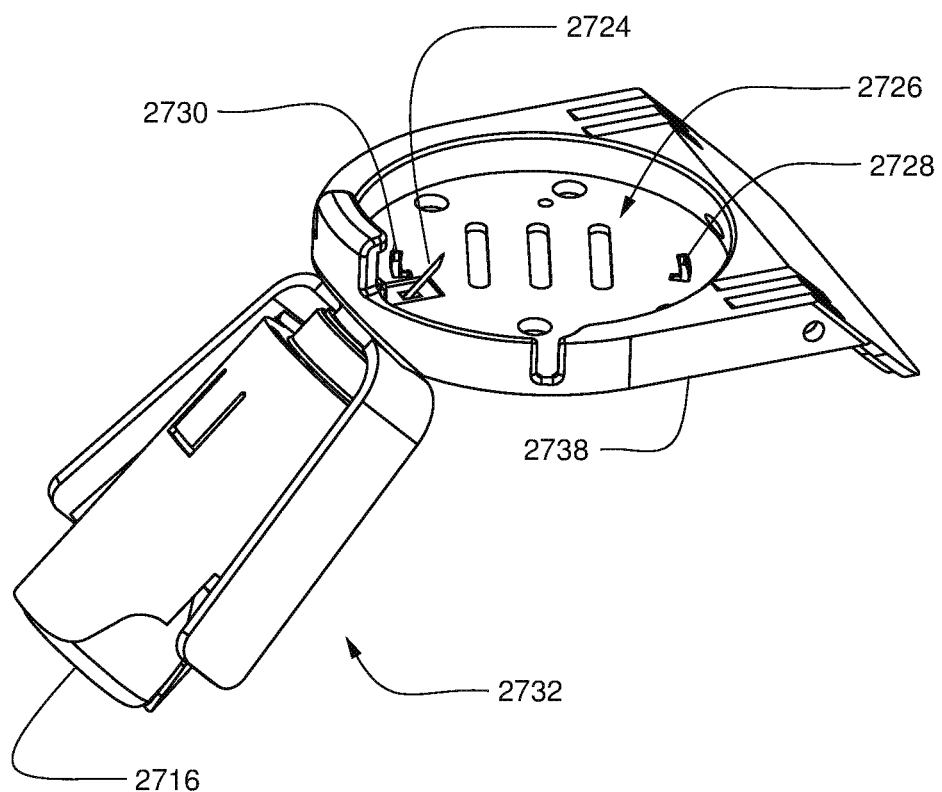

Fill adapter 2700 may further include a transfer needle (e.g., transfer needle 2724 shown in FIG. 181). Transfer needle 2724 may allow fluid to be transferred from vial 2716 to reservoir 908 of disposable housing assembly 804. Referring also to FIG. 183, in a "fill configuration" of fill adapter 2700, transfer needle 2724 may extend into recess 2726 of fill adapter 2700. Recess 2726 of fill adapter 2700 may be configured to at least partially receive disposable housing assembly 804. Further, fill adapter 2700 may be configured to align (e.g., via openings 2728, 2730 configured to cooperate with alignment tabs 930, 932 of disposable housing assembly 804) disposable housing assembly 804 relative to fill adapter 2700, such that transfer needle 2724 may be aligned to penetrate a septum of disposable housing assembly 804 to transfer fluid from vial 2716 into reservoir 908 of disposable housing assembly 804.

As shown in the schematic view of FIG. 194, pressure needle 2720 may be configured to extend farther into vial 2716 than transfer needle 2724. The foregoing configuration may reduce the likelihood that air introduced into vial 2716 by pump bulb 2718 may be transferred via transfer needle 2724. That is, in operation pressure needle 2720 may be at a higher relative position within vial 2716 as compared to transfer needle 2724. As such, air bubble rising within vial 2716 (which may contain a liquid to be transferred to reservoir 908) may not pass by, and be drawn into, transfer needle 2724, as transfer needle 2724 may be at a lower relative position within vial 2617 as compared to pressure needle.

Figure 193:
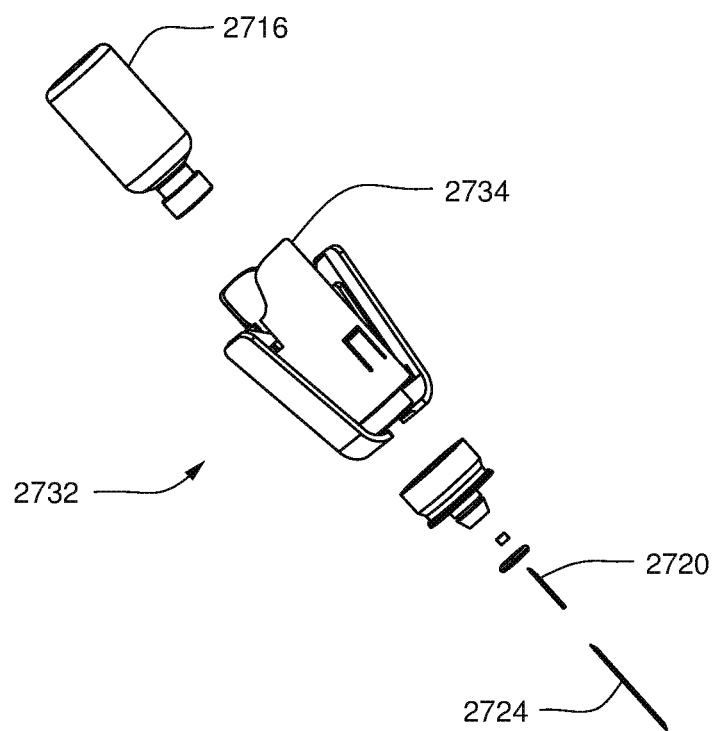

Pressure needle 2720 and transfer needle 2724 may be retained by vial adapter 2732 (FIG. 193). Additionally, vial adapter 2732 may include vial receptacle 2734 that may be configured to at least partially receive vial 2716 and align pressure needle 2720 and transfer needle 2724 with the septum of vial 2716. As such, insertion of vial 2716 into vial receptacle 2734 may align pressure needle 2720 and transfer needle 2724 with the septum of vial 2716 without the need for further alignment by the user. Further, vial adapter 2732 may retain pressure needle 2720 and transfer needle 2724 in a desired relative alignment, such that pressure needle 2720 may extend farther into vial 2716 than transfer needle 2724, as described above.

Also referring to FIGS. 199A-199H, vial adapter 2732 may be configured to be received in receptacle 2736 of main plate 2738 of fill adapter 2700 (also see FIG. 181). Vial adapter 2732 may include needle carriage 2732a as well as one or more tabs (e.g., tabs 2732b, 2732c). In some embodiments, vial 2716 may be removed from vial adapter 2732 by pulling up on vial 2716. Pulling up on vial 2716 may also cause needle carriage 2732a to move upwards until being engaged by the tabs 2732b, 2732c. Fingers 2733a, 2733b may be depressed by the user. In some embodiments, depressing fingers 2733a, 2733b may push vial 2716 further upward, and may disconnect vial 2716 from needles 2720, 2724. As such, the safety of removing vial 2716 from vial adapter 2732 may be improved. In some embodiments, vial adapter 2732 may additionally include seal 2735a and hydrophobic filter 2735b. However, in other embodiments, the vial adapter 2732 may include a check valve.

Figure 184:
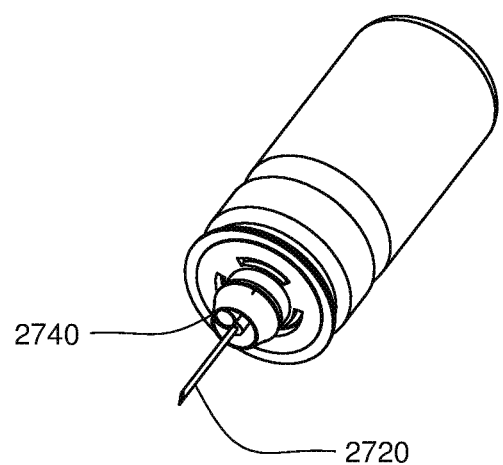
Figure 185:
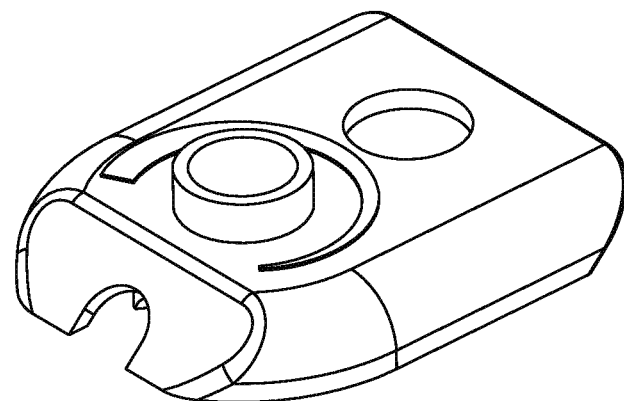
Figure 186:
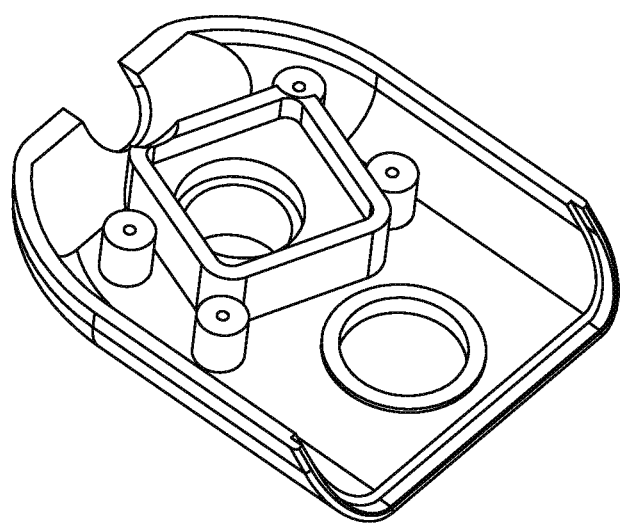

Referring also to FIG. 184, in an embodiment pressure needle 2720 may terminate within vial adapter 2732, and may be fluidly coupled to opening 2740 of vial adapter 2732. When vial adapter 2732 is assembled with main plate 2738, opening 2740 may be fluidly coupled with the outlet of pump bulb 2718 such that air pumped out of pump bulb 2718 may be received through opening 2740 and transferred to vial 2716 via pressure needle 2720.

In operation, to fill a disposable housing assembly 804, a user couples the vial adapter 2732 to the main plate 2738. The vial 2716 is then coupled to the vial adapter 2732. In performing these steps (see also FIGS. 199A-199H) the transfer needle 2724 penetrates the septum of the disposable housing assembly 804 (see 199D) and also, the septum of the vial 2716 (see FIG. 199E). Thus, in various embodiments, the transfer needle 2724 does not penetrate the septum of the vial 2716 until the transfer needle 2724 also penetrates the septum of the disposable housing assembly 804. This ensures that if the vial 2716 is pressurized, the contents of the vial 2716 will not begin to flow until the transfer needle 2724 has penetrated the septum of the disposable housing assembly 804, thereby limiting the amount of wasted vial contents.

Thus, to fill a disposable housing assembly 804, the user may couple disposable housing assembly 804 in recess 2726 of main plate 2738 (e.g., including aligning disposable housing assembly 804 relative to fill adapter 2700 via openings 2728, 2730 configured to at least partially receive alignment tabs 930, 932 of disposable housing assembly 804). Disposable housing assembly 804 may be retained relative to fill adapter 2700 using bottom door 2742, which may pivotally close to at least partially cover recess 2726 to retain disposable housing assembly 804 at least partially within recess 2726. A user may then couple the vial adapter 2732 to the main plate 2738 and then, couple a vial 2716 to the vial adapter 2732. Coupling vial adapter 2732 to main plate 2738 may result in transfer needle 2724 penetrating the septum of disposable housing assembly 804. Additionally, coupling vial adapter 2732 to main plate 2738 may couple opening 2740 with the outlet of pump bulb 2718. The user may then adjust turn dial 2702 (e.g., which may thereby cause movement of push plate 2704) to the desired available fill volume of reservoir 908. The user may then actuate pump bulb 2718 (e.g., by compressing and releasing pump bulb 2718). The user may continue to actuate pump bulb 2718 until no more bubbles are observed rising within vial 2716 (e.g., rising from pressure needle 2720). Additionally/alternatively, pump bulb 2718 may be configured such that a single complete actuation of pump bulb 2718 may be sufficient to effect a complete transfer (e.g., the volume of air transferred from pump bulb 2718 to vial 2716 during a single actuation of pump bulb 2718 may be sufficient to produce the transfer of the maximum fill volume of reservoir 908). According to one embodiment, fill adapter 2700 may be configured to overfill reservoir 908 (e.g., to transfer a volume of fluid from vial 2716 that is at least partially greater than the available fill volume of reservoir 908, as determined by the settings of turn dial 2702). Overfilling reservoir 908 may allow the fluid passages associated with disposable housing assembly 804 to be primed with fluid, thereby obviating the need to later prime the fluid lines of disposable housing assembly 804.

Still referring to FIGS. 199A-199H, in some embodiments, the fill adapter 2700 includes vial fingers 2744a, 2744b. As shown in FIGS. 199A-199H, as the vial 2716 is introduced to the vial adapter 2732, the vial 2716 overcomes the spring force of the vial fingers 2744a, 2744b. However, as the vial 2716 reaches a end on the needle carriage 2732a, the vial fingers 2744a, 2744b return force and act to maintain the position of the vial 2716.

Referring now to FIGS. 200-202B, another embodiment of the fill adapter is 2750 is shown. In various embodiments of this embodiment of the fill adapter, the vial adapter 2762 includes a needle carriage 2754 which includes vial needles 2756a, 2756b and transfer needle 2756c. In some embodiments, the needles 2756a, 2756b, 2756c are 24 gauge stainless steel. However, in other embodiments, the gauge of the needles may vary. In various embodiments, the gauge of needle is a balance between flexibility and efficiency.

The needle carriage 2754 is slidably engaged to the interior of the vial adapter housing 2752. The vial adapter 2762 includes a check valve 2758 and a filter 2766. In some embodiments, the filter 2766 may be a 0.2 micron filter, or any other filter that prevents dust and other unwanted particulate matter, from entering the air line and the vial (not shown). In the exemplary embodiment, the filter 2766 is a hydrophobic filter which may include any variety of gas-permeable hydrophobic materials, such as a POREX™ material, a GORE™ material, or the like (POREX is a trademark of Porex Corporation in the United States and/or other countries, GORE is a trade mark of W. L. Gore & Associates, Inc. in the Unites States and/or other countries). In some embodiments, the check valve 2758 is a duck bill valve. The duck bill valve serves as a check valve and a seal. However, in other embodiments, the check valve may be any type of check valve. In other embodiments, the check valve is not included and only a hydrophobic filter is used. In some embodiments, the hydrophobic filter my be as described above, and in these embodiments, a separate seal may also be used.

The vial adapter 2762 further includes a vial adapter housing 2752. The housing contains the needle carriage 2754 and is adapted to removably attach to the fill adapter base 2768 by way of the receptacle 2770. The fill adapter base 2768 includes a main plate 2760 which includes the receptacle 2770. The receptacle 2770 includes at least one key, and in the exemplary embodiment, the receptacle 2770 includes two keys 2764b. The keys 2764b in the exemplary embodiment, are differently sized, however, in other embodiments, they may be the same size. The different sizes of the keys 2764b allows for the vial adapter 2762 to be located in the intended orientation. The keys 2764b fit into locking features 2764a located inside the vial adapter housing 2752. Once the keys 2764b and locking features 2764a are fit together, a clockwise turn of the vial adapter 2762 locks the vial adapter 2762 to the receptacle 2770. However, in various other embodiments, the locking features 2764a located inside the vial adapter housing 2752 may be designed such that a counterclockwise turn of the vial adapter 2762 locks the vial adapter 2762 to the receptacle 2770.

Locking the vial adapter 2762 to the receptacle 2770 may be desirable for many reasons, including, but not limited to, maintaining the correct orientation during fill and preventing the needles from bending or twisting during fill. The locking system described above also ensures correct orientation of the vial adapter with respect to the fill adapter base 2768.

Referring now to FIGS. 203A-203J, in operation, to fill a disposable housing assembly 804, a user couples the vial adapter 2762 to the receptacle 2770. The vial adapter 2762 is then rotated clockwise, locking the vial adapter 2762 to the receptacle 2770 (see FIG. 203C). The vial 2716 is then coupled to the vial adapter 2762. In performing these steps the transfer needle 2756c penetrates the septum of the disposable housing assembly 804 (see 203E) and also, the septum of the vial 2716 (see FIG. 203F). Thus, in various embodiments, the transfer needle 2756c does not penetrate the septum of the vial 2716 until the transfer needle 2756c also penetrates the septum of the disposable housing assembly 804. This ensures that if the vial 2716 is pressurized, the contents of the vial 2716 will not begin to flow until the transfer needle 2756c has penetrated the septum of the disposable housing assembly 804, thereby limiting the amount of wasted vial contents.

Thus, to fill a disposable housing assembly 804, in this embodiment, the user couples the disposable housing assembly 804 to the fill adapter base 2768 in a similar fashion as described above with respect to the fill adapter 2700. A user may then couples the vial adapter 2762 to the receptacle 2770, turns the vial adapter 2762, locking the vial adapter 2762 to the receptacle, and then, couples a vial 2716 to the vial adapter 2762. The user may then adjust the turn dial and follow similar a similar process as described above with respect to the fill adapter 2700 for filling the disposable housing assembly 804.

Figure 203A:
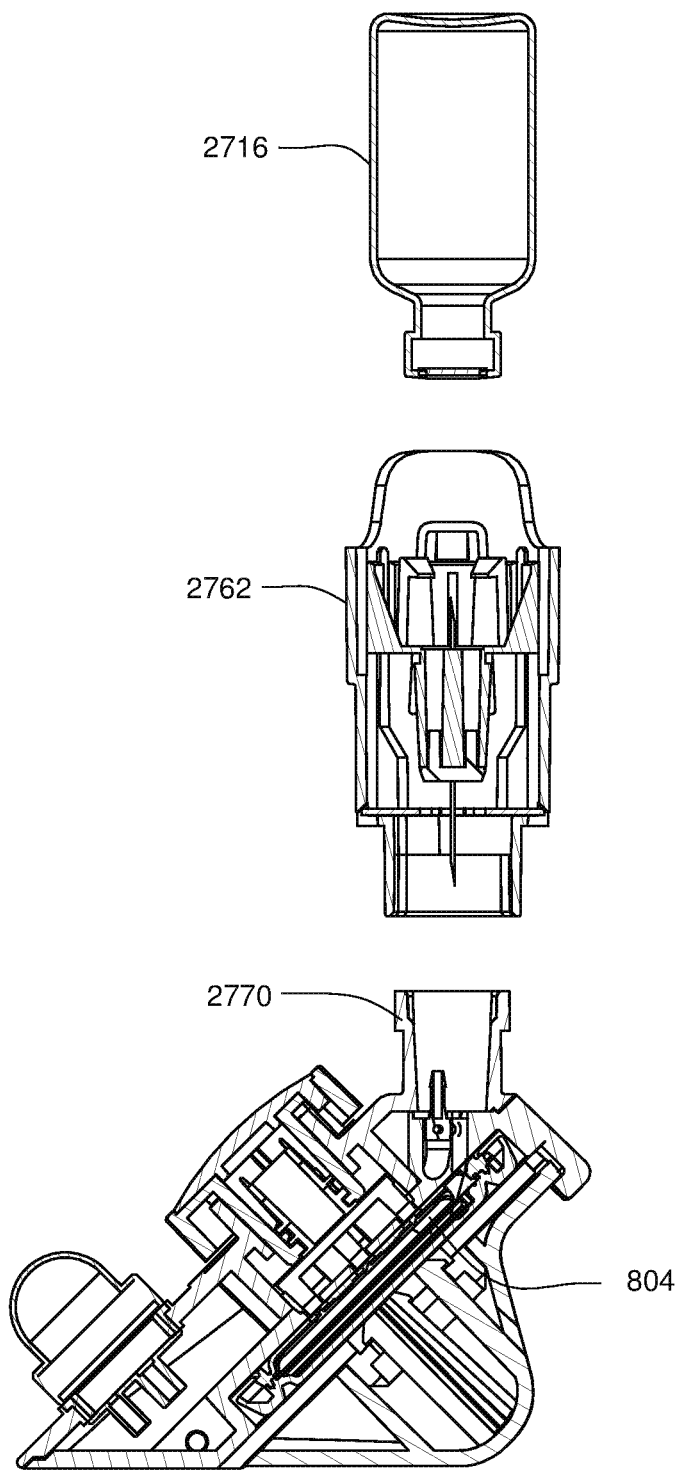
Figure 203B:
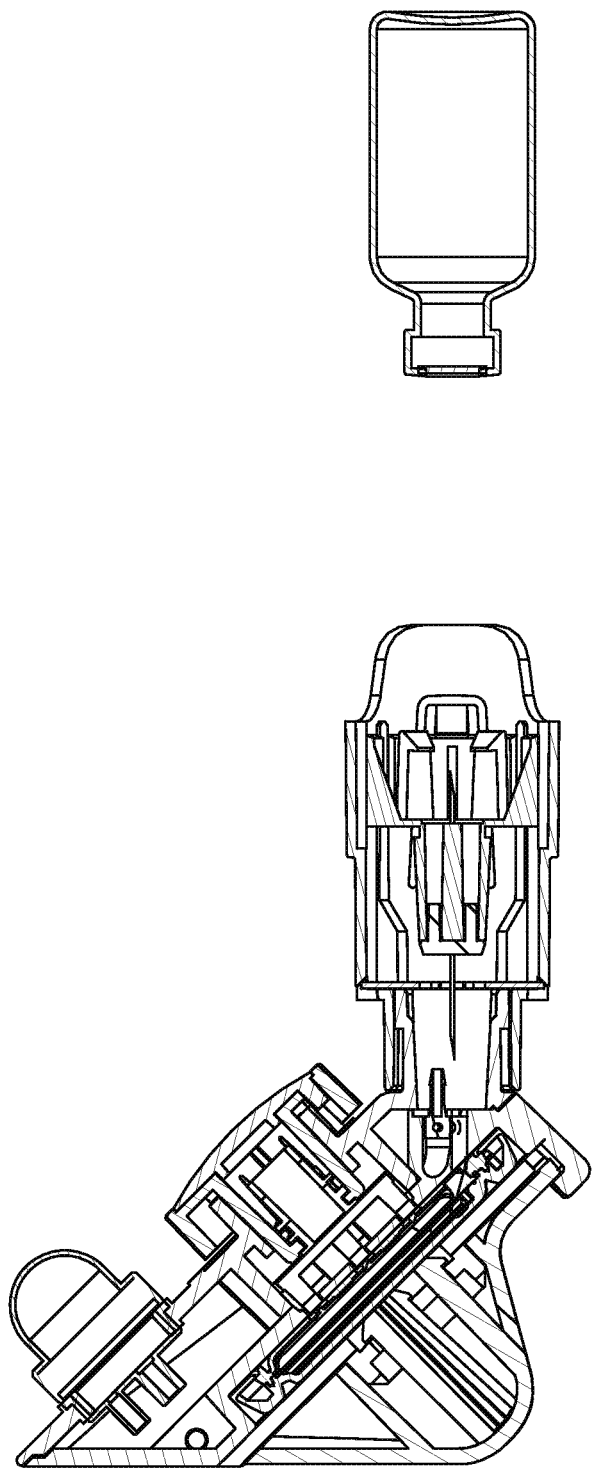
Figure 203C:
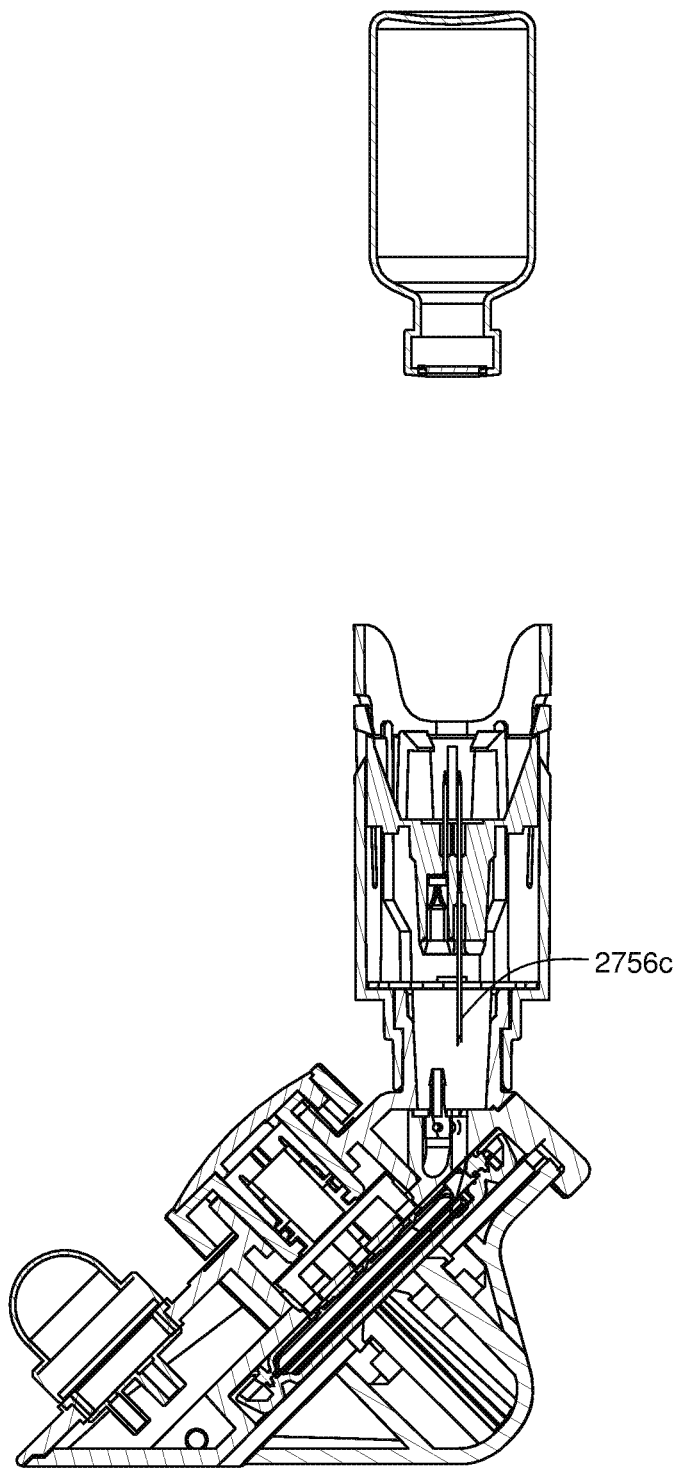
Figure 203D:
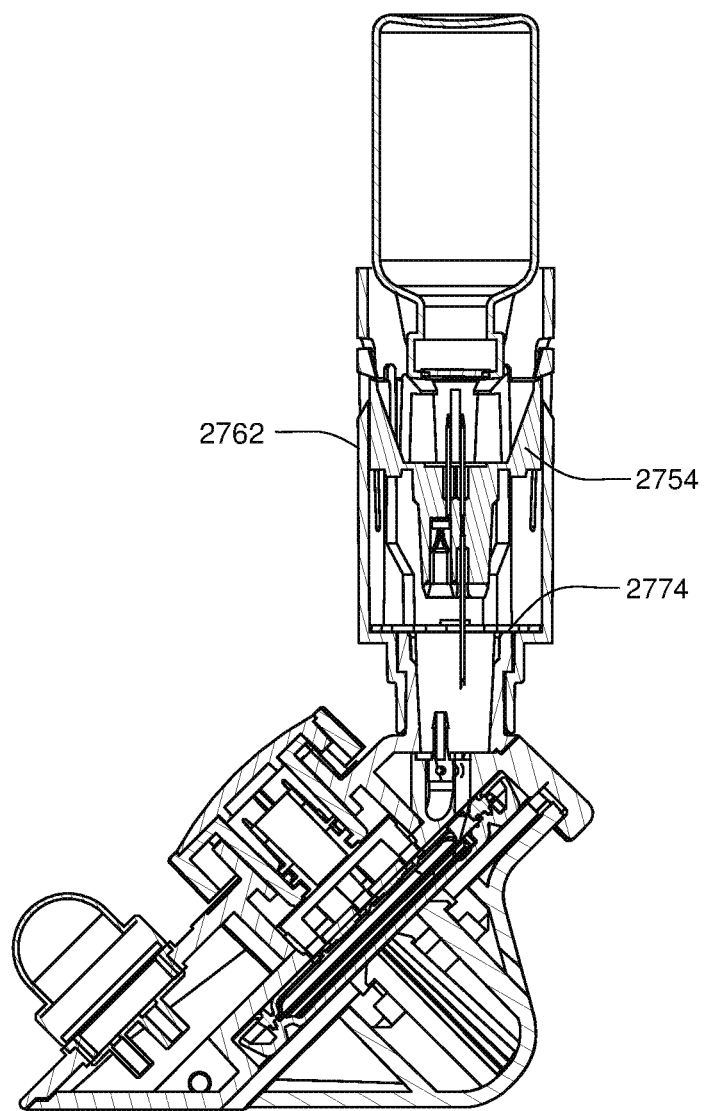
Figure 203E:
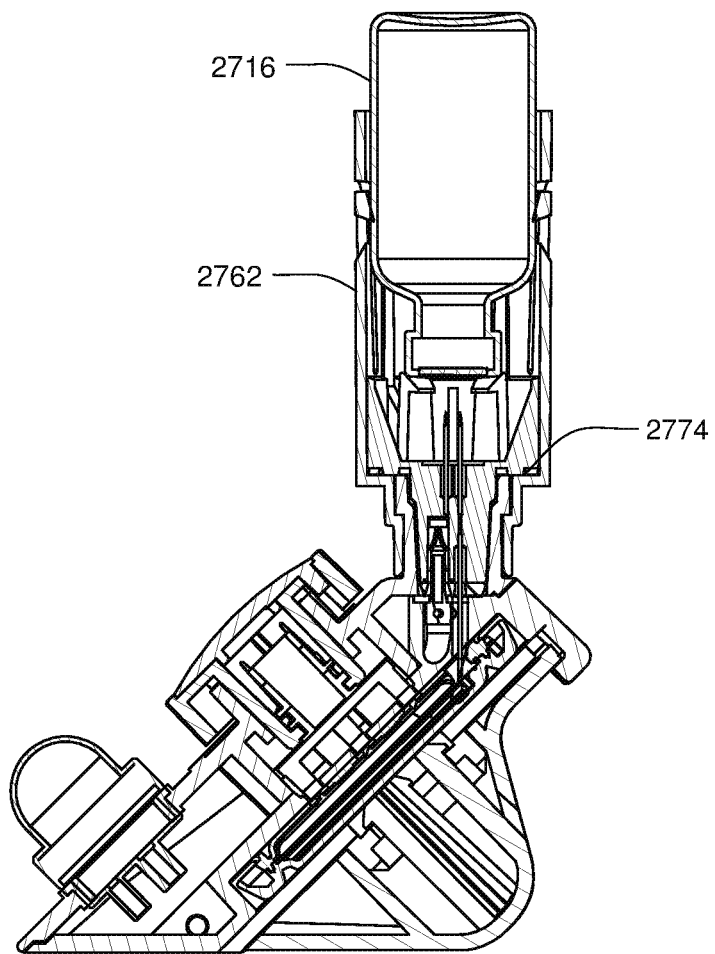
Figure 203F:
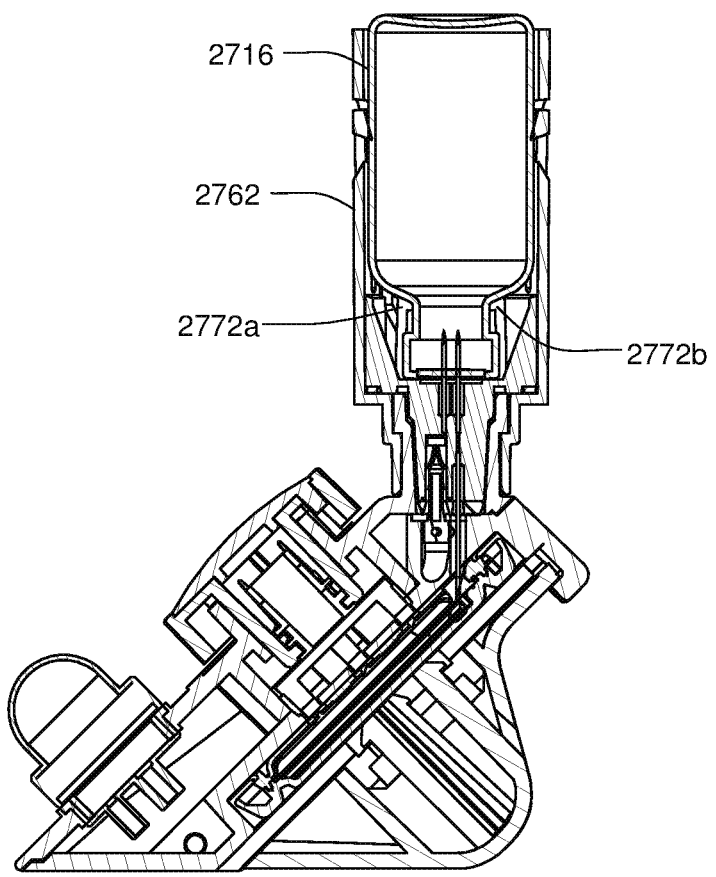
Figure 203G:
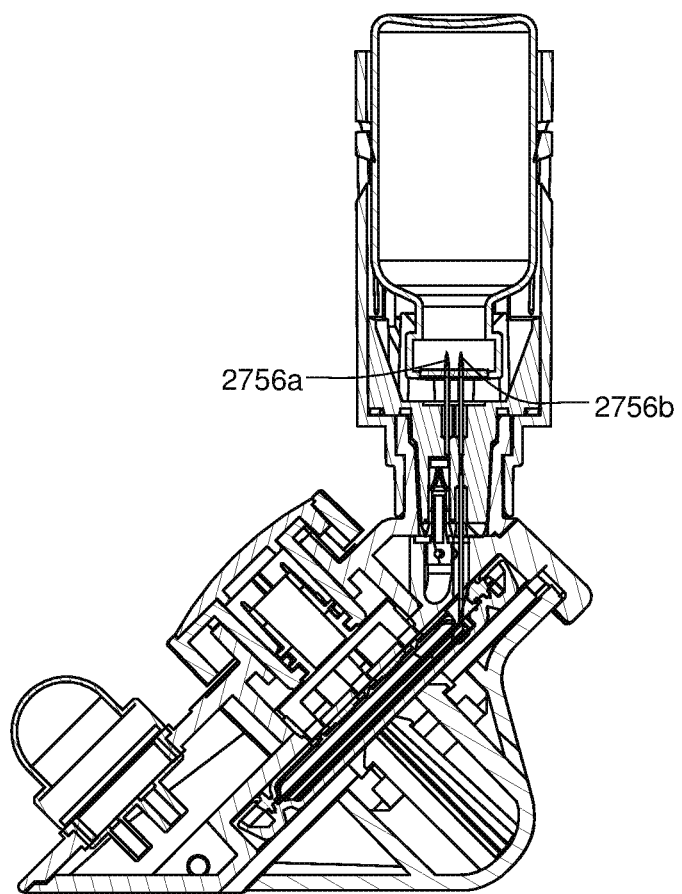

Referring to FIGS. 203D-203F, introducing the vial 2716 to the vial adapter 2762, vial fingers 2772a, 2772b, including a bent portion that grasps and holds the narrow portion of the vial 2716. However, as shown in FIG. 203F, in some embodiments, a distance remains between the top of the vial 2716 (i.e., the area including the septum) and the bent portion of the vial fingers 2772a, 2772b. As shown in FIG. 203G, to remove the vial, a user applies force to the vial 2716 in an upward direction. The upward force first pulls the vial 2716 upwards such that the needles 2756a, 2756b are no longer in contact with the contents of the vial 2716, rather, the needles 2756a, 2756b are inside the septum of the vial 2716. This ensures that if the vial 2716 is pressurized, the contents of the vial 2716 will not continue to flow while the vial 2716 is being removed from the vial adapter 2756 thereby limiting the amount of wasted vial contents.

Figure 200:
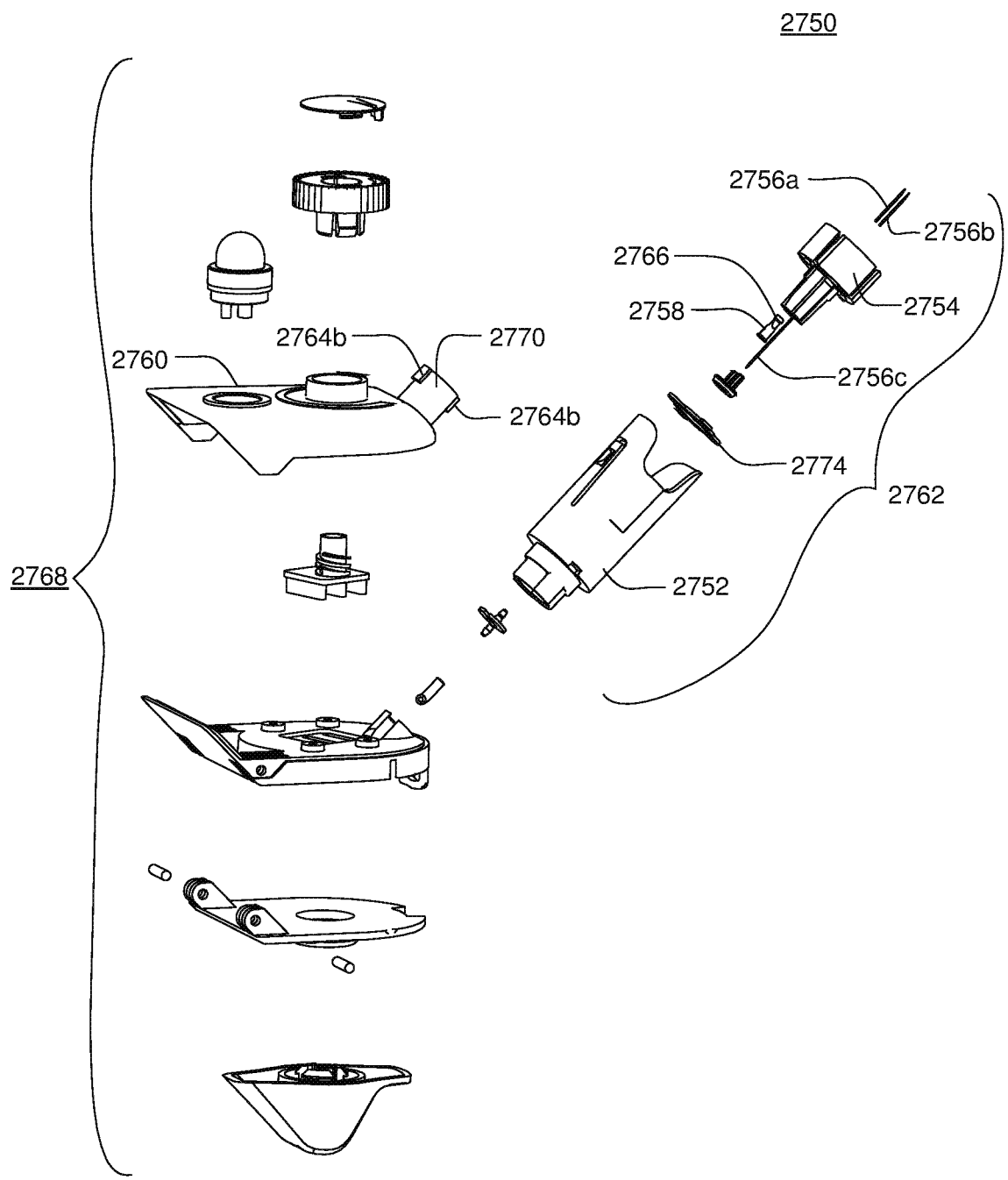
Figure 201:
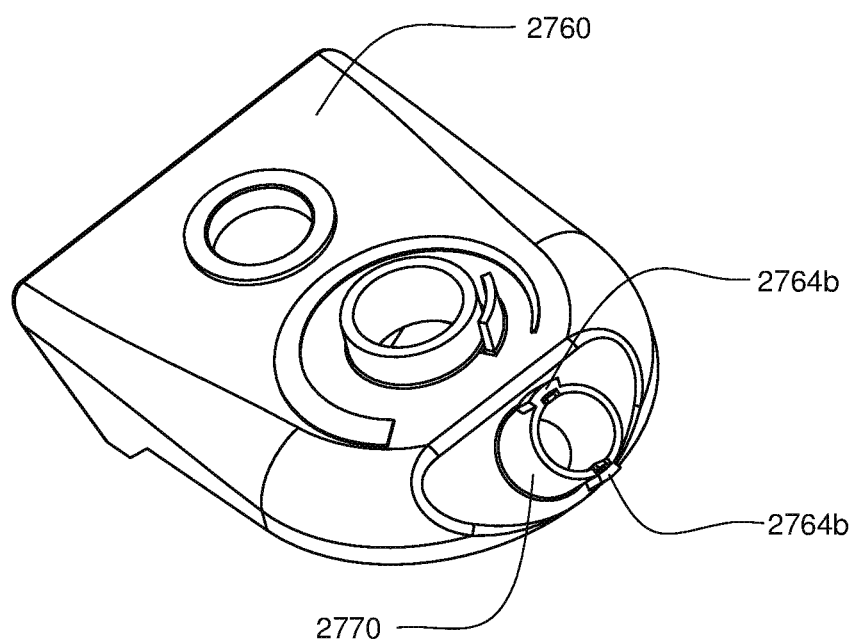
Figure 202A:
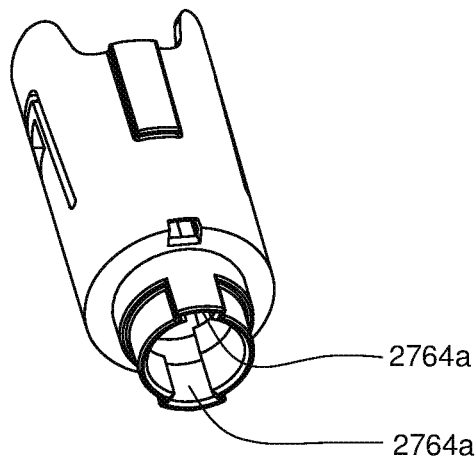
Figure 202B:
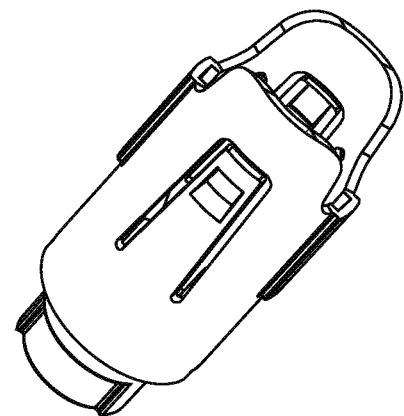
Figure 203H:
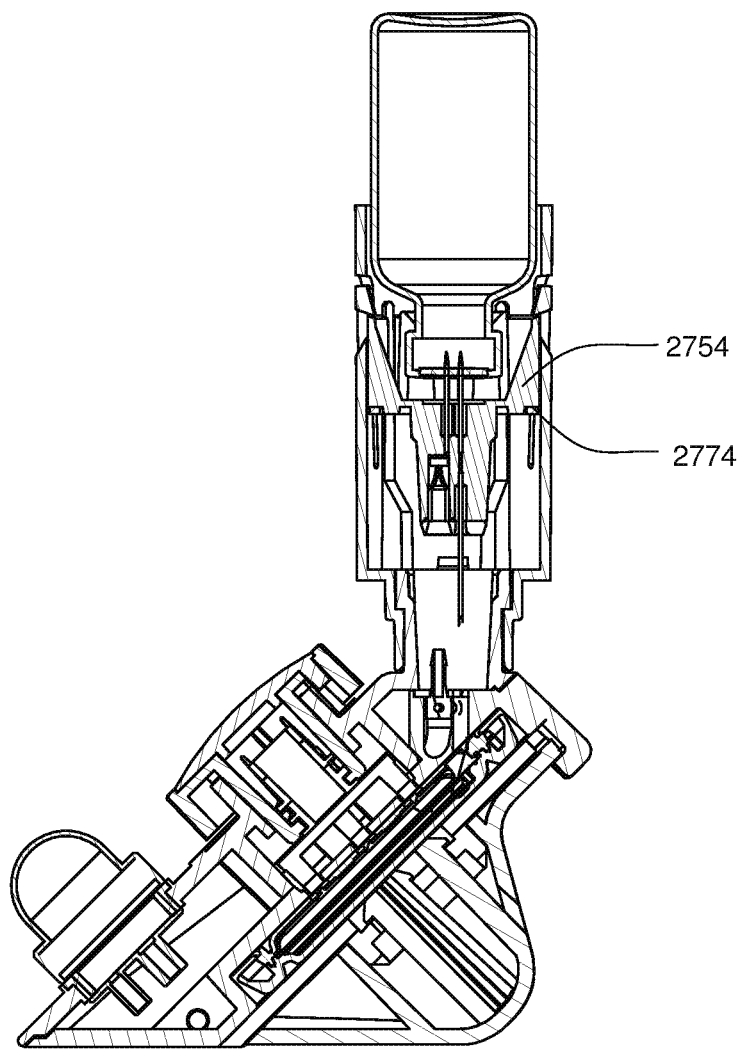

Referring to FIG. 203E, the vial adapter 2762 additionally includes a disc 2774 (see also FIG. 200). The disc 2774 remains at the bottom of the vial adapter 2762 (which may also be referred to as the receptacle end of the vial adapter 2762) until the needle carriage 2754 reaches the bottom of the vial adapter 2762. Referring to FIG. 203E, the needle carriage 2754 having reached the bottom of the vial adapter 2762, the needle carriage 2754 is now connected to the disc 2774. The disc 2774 includes features which mate with the needle carriage 2754 such that, when the needle carriage 2754 moves upward, or towards the top or vial end of the vial adapter 2762, as seen in FIG. 203H, the disc 2774 accompanies the needle carriage 2754.

Referring now to FIGS. 204A-204C, a sequence showing the progression of the needle carriage 2754 and the relationship of the needle carriage 2754 with the disc 2774 is shown without a vial. As seen in FIG. 204C, once the needle carriage 2754, together with the disc 2774, reach the top section of the vial adapter 2762, the disc 2774 is locked in place by the wall features of the vial adapter 2762.

Figure 203I:
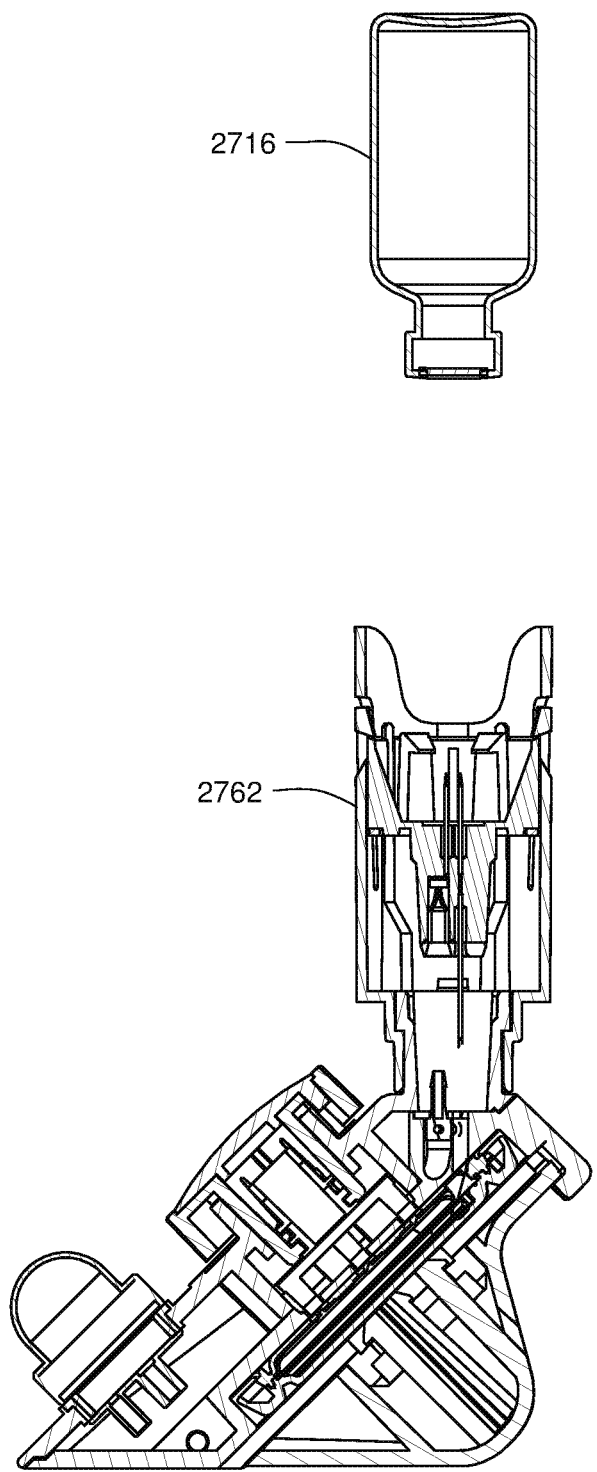
Figure 203J:
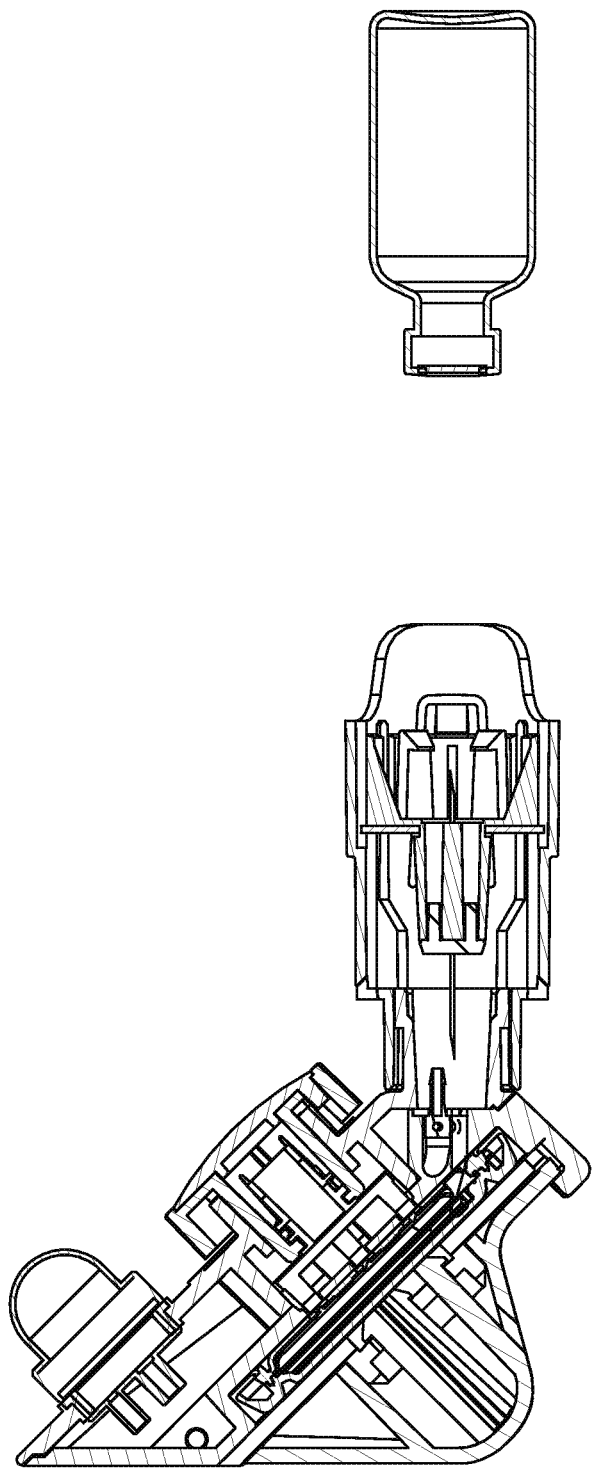
Figure 203K:
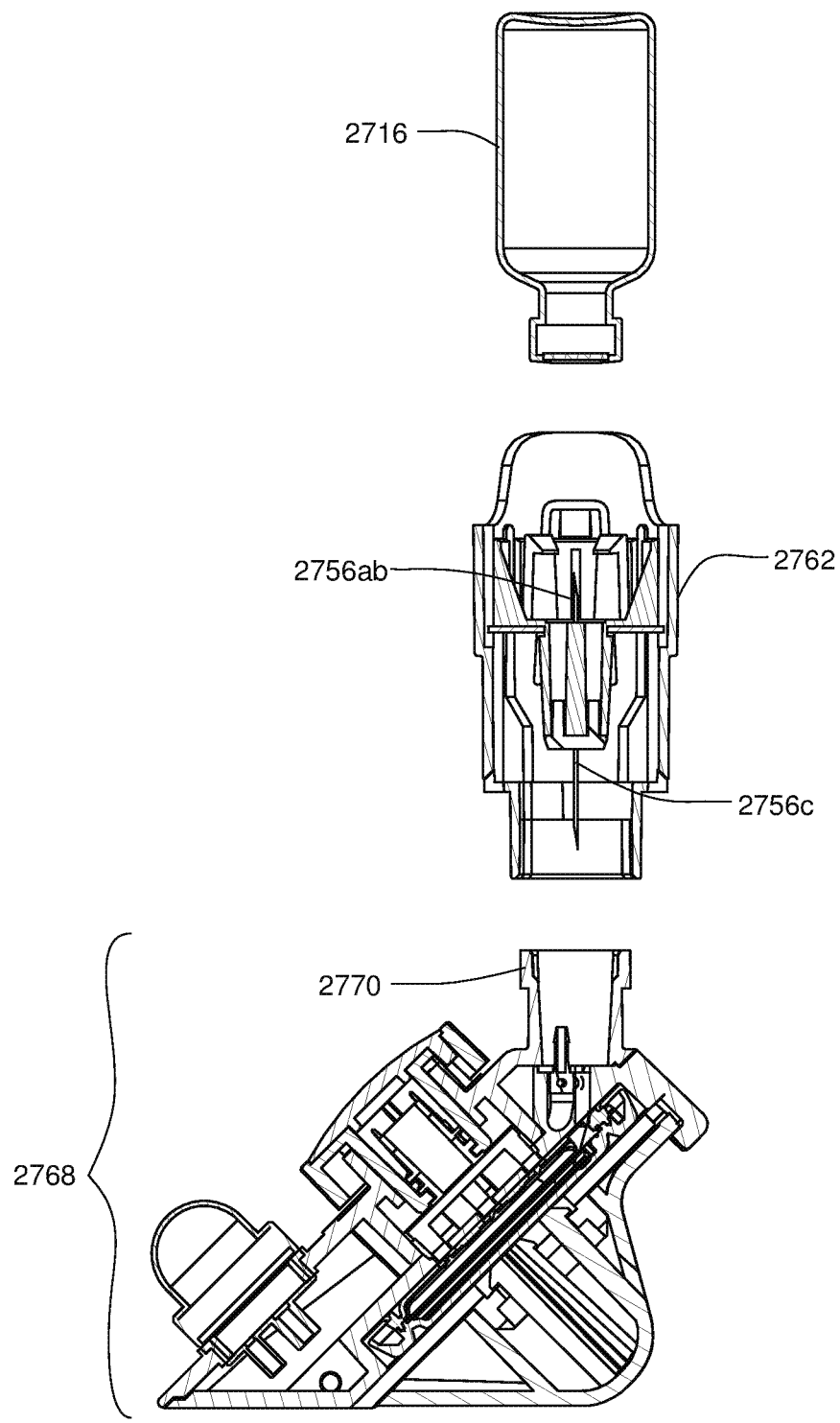

Referring now to FIGS. 203I-203K, after the vial 2716 is lifted outside of the vial adapter 2762, the vial adapter 2762 may be rotated counter clockwise (FIG. 203J), unlocking the vial adapter 2762 from the receptacle 2770, and the vial adapter 2762 may then be lifted off the fill adapter base 2768 (FIG. 203K). Additionally, as is shown in FIG. 203K, the needles 2756a, 2756b, 2756c are contained within the vial adapter 2762 thus protecting the user and others from interaction with the needles 2756a, 2756b, 2756c.

Figure 197:
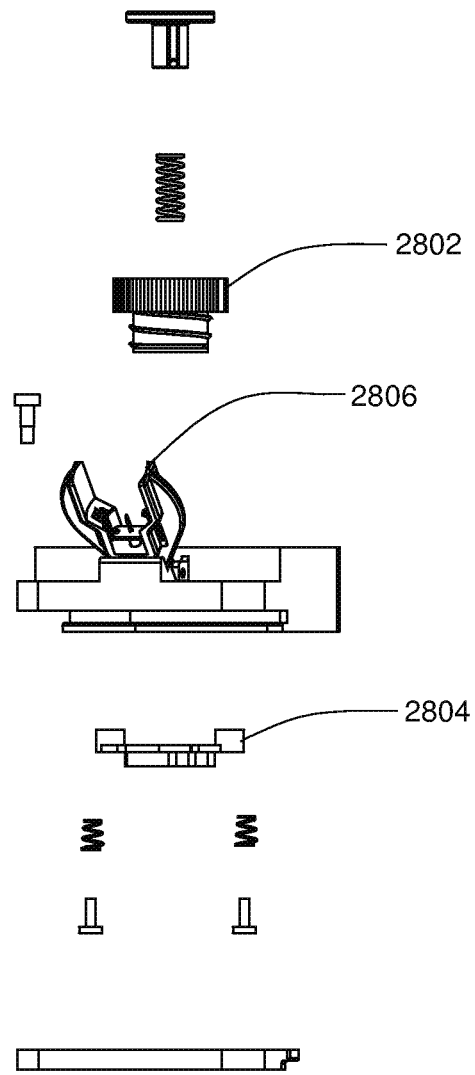
Figure 198:
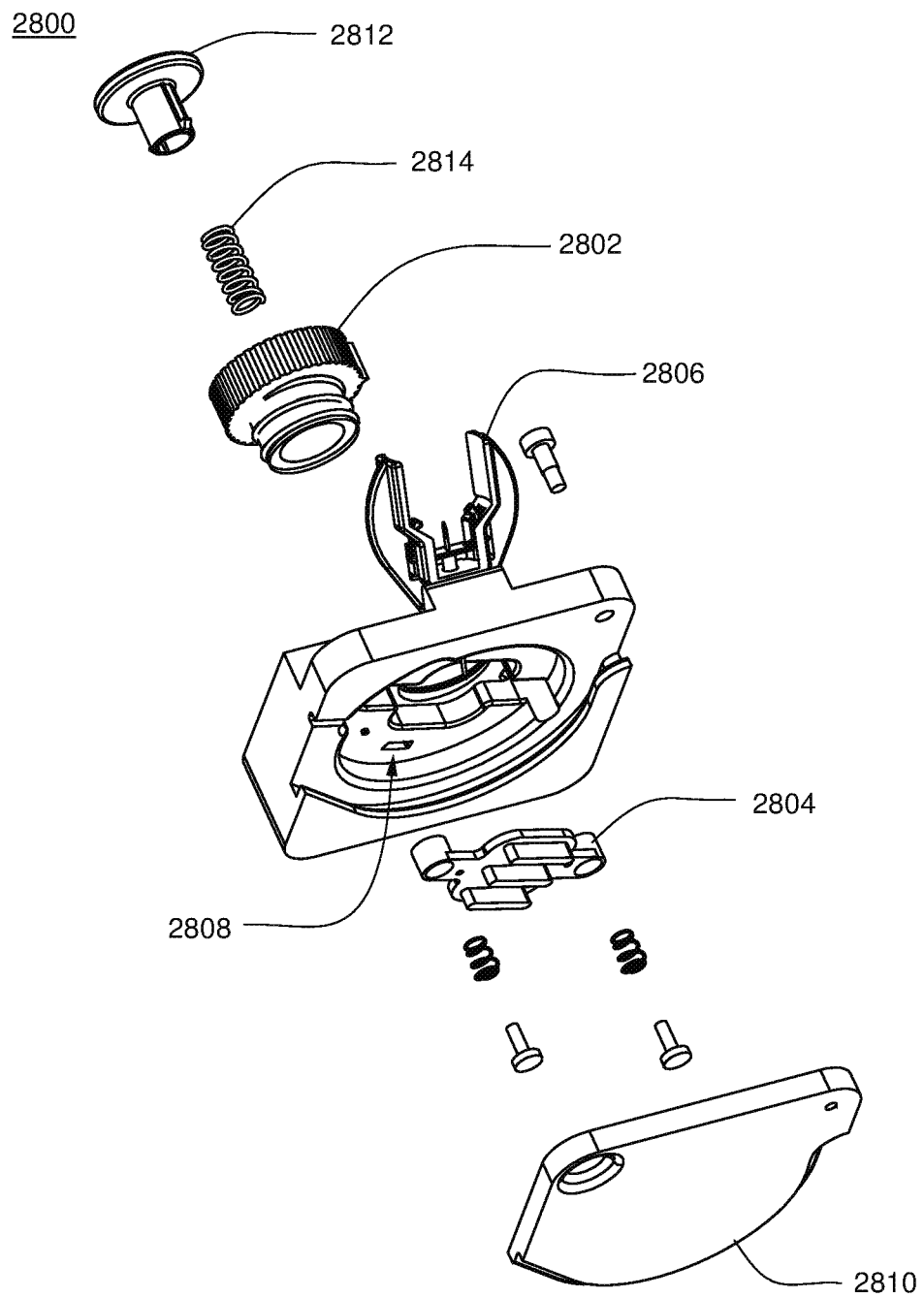
Figure 199A:
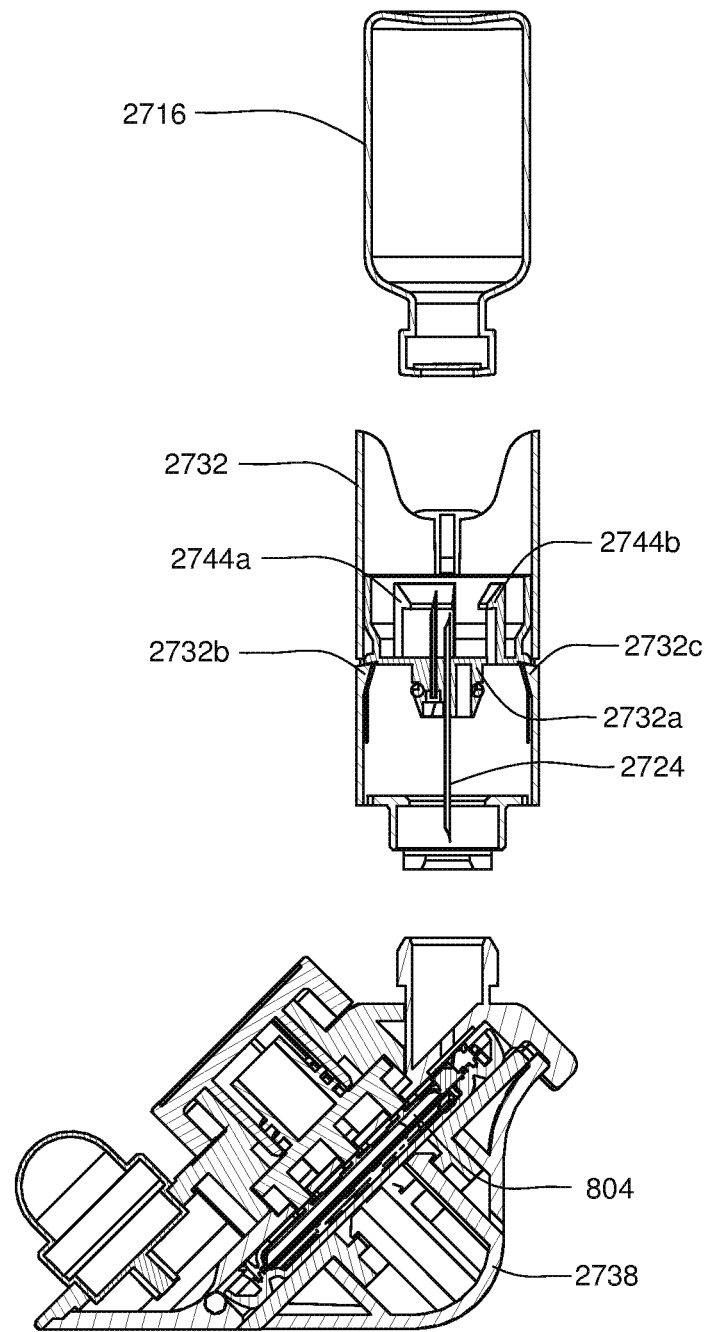
Figure 199B:
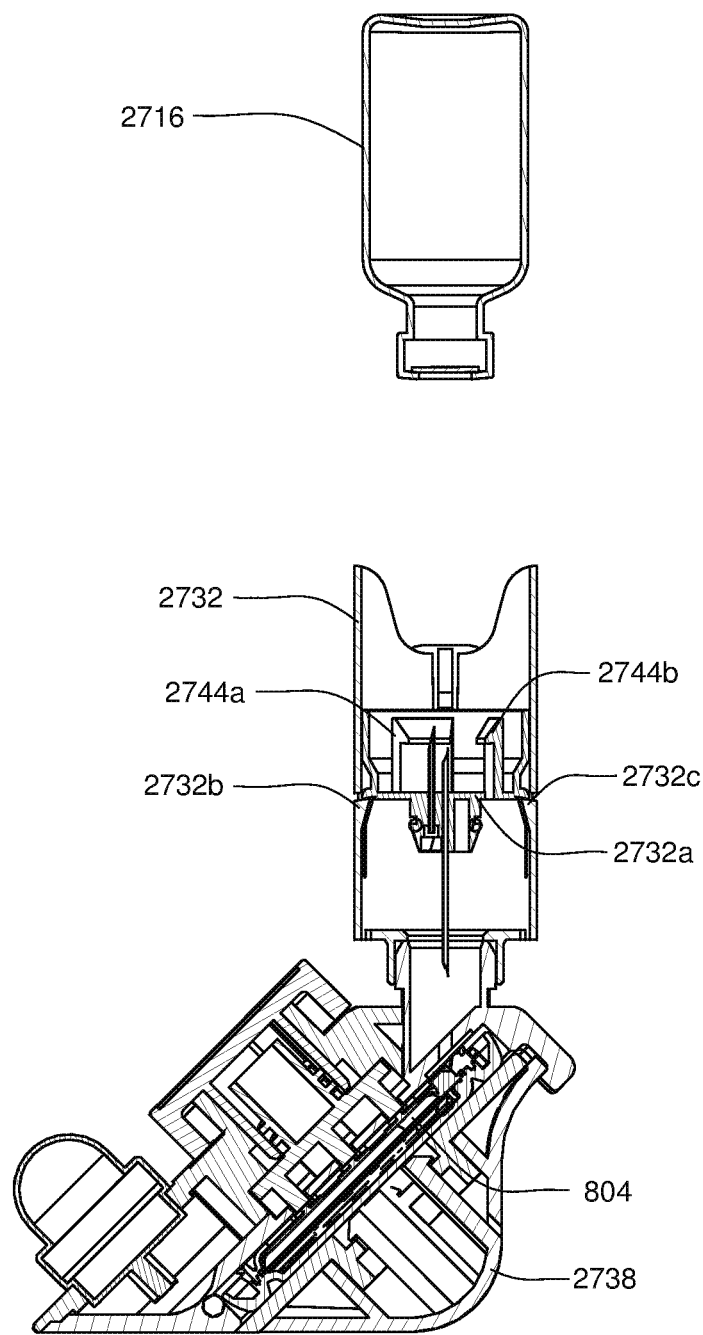
Figure 199C:
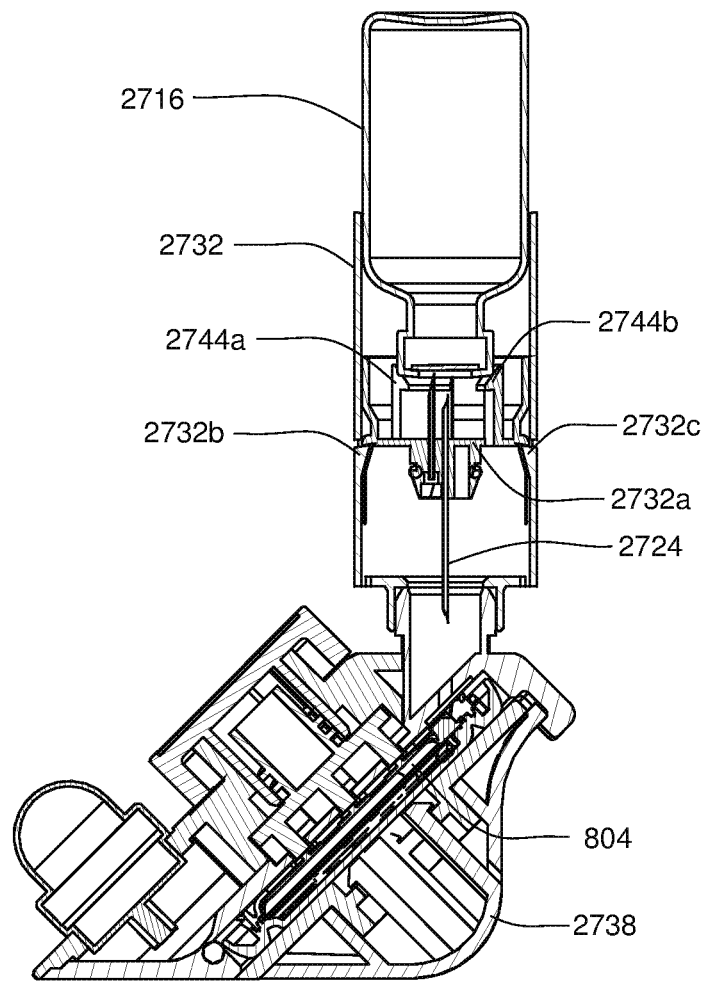
Figure 199D:
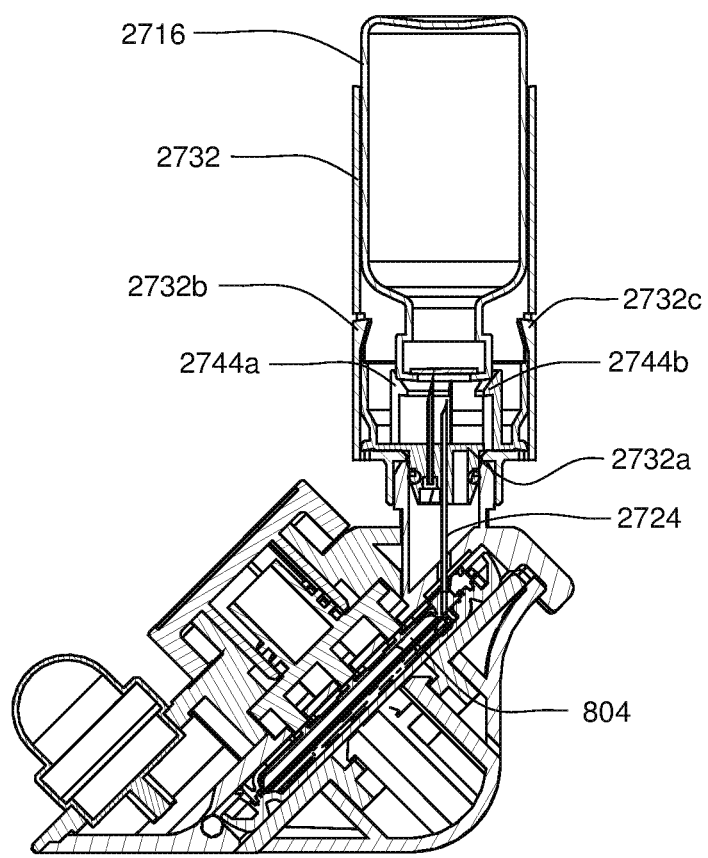
Figure 199E:
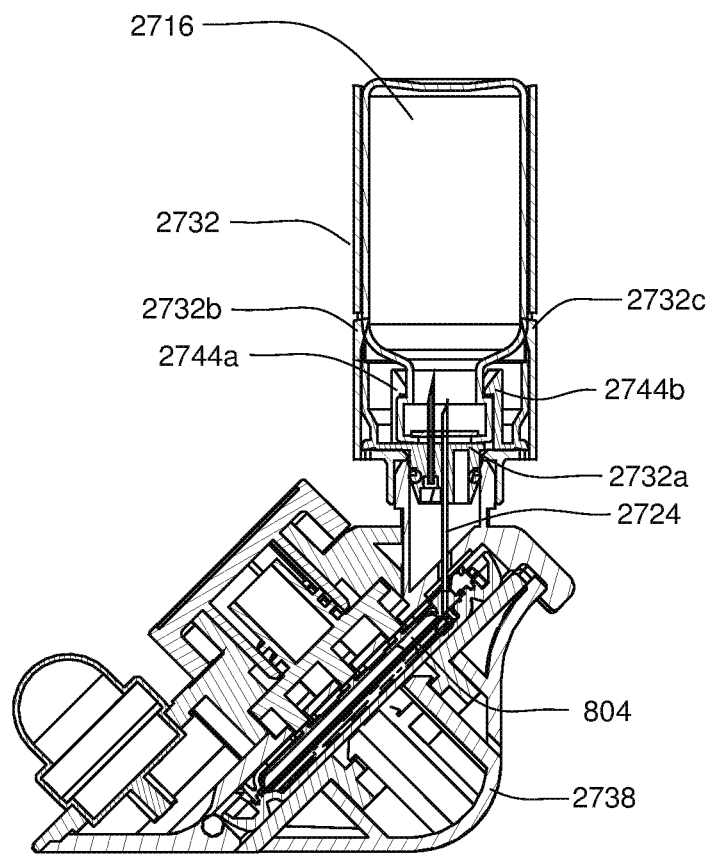
Figure 199F:
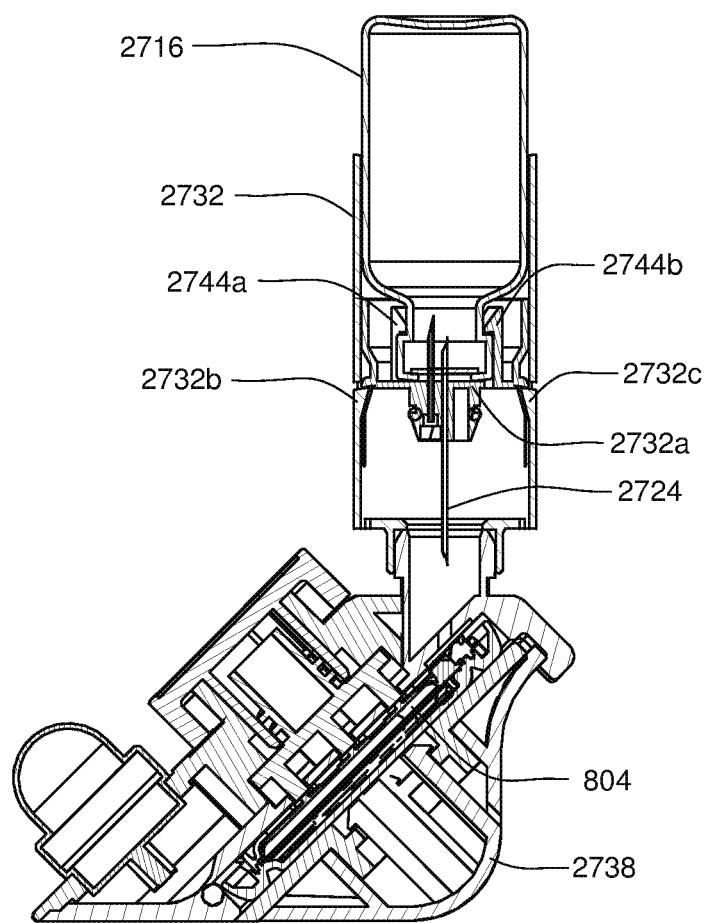
Figure 199G:
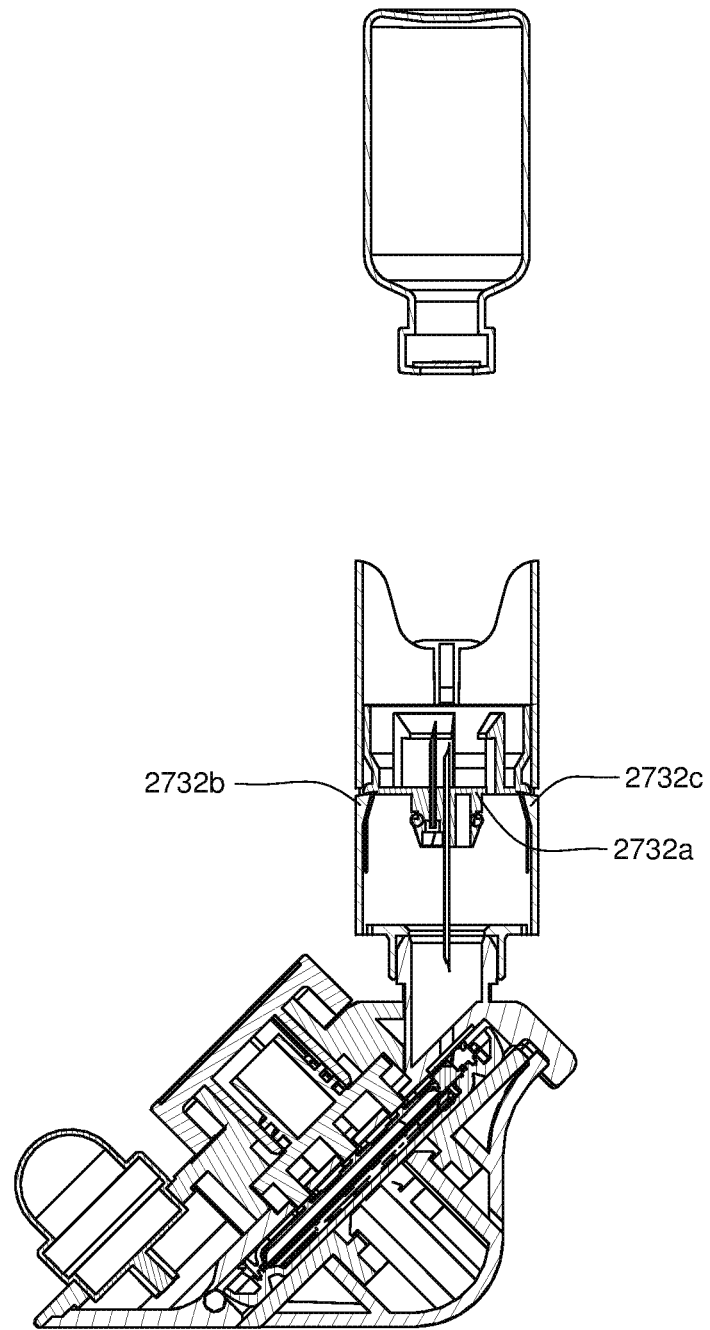
Figure 199H:
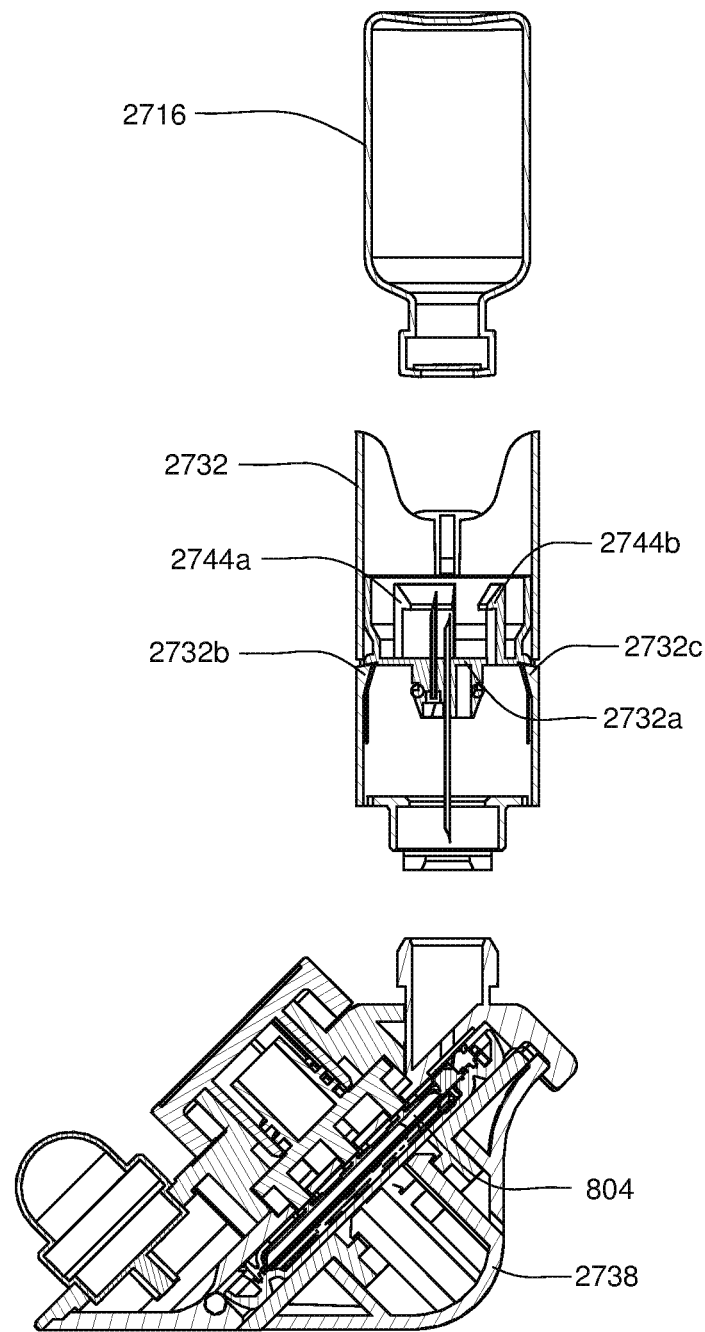

Referring also to FIGS. 195A-198, another embodiment of a fill adapter (e.g., fill adapter 2800) is shown. Fill adapter 2800 may be generally similar to fill adapter 2700, including a turn dial (e.g., turn dial 2802) that may actuate a push plate (e.g., push plate 2804) for setting an available fill volume of reservoir 908 of disposable housing assembly 804 (FIGS. 197-198). Fill adapter 2800 may also include vial to fill adapter 2806 configured to releasably couple a vial to fill adapter 2800 for transferring fluid from the vial to reservoir 908 of disposable housing assembly 804. Fill adapter 2806 may include a pressure needle and/or a transfer needle respectively configured to introduce air into the vial and allow fluid to be transferred from the vial to reservoir 908 of disposable housing assembly 804. While fill adapter 2800 is shown including recess 2808 and pivoting door 2810 for retaining disposable housing assembly to fill adapter 2800, in other embodiments, the fill adapter may utilize locking features, e.g., which may releasably engage tabs 934, 936, 938, 940 disposable housing assembly 804.

With respect to the embodiments including a vial adapter removably connectable to a fill adapter base, in some embodiments, the vial adapter may be a one-use, i.e., disposable portion, and the fill adapter base may be a multi-use, i.e., reusable, portion. In some embodiments, upon removal of the vial from the vial adapter, the needle carriage becomes locked in the end position. This may be desirable to prevent reuse and reuse may contaminate vials and disposable housing assemblies, for the transfer needle may become contaminated while stored between uses.

Fill adapter 2800 may include actuation button 2812, which may be disposed in turn dial 2802. Actuation button 2812 may be configured as a plunger pump, e.g., which may pump air into the vial to effectuate fluid transfer from the vial into reservoir 908, in a manner as described above. Various additional/alternative pumping mechanisms may similarly be used, as described above. Additionally, actuation button 2812 may operate a bias member (e.g., spring 2814) that may limit the amount of force that is transferred to reservoir 908. For example, spring 2814 may be disposed between actuation button 2812 and the pumping member that may actually pump air into the vial. As such, the force that may be transferred to reservoir 908 may be limited to the spring force of spring 2814.

Referring now to FIGS. 206A and 207A, one embodiment of a fill adapter 3000 is shown. The fill adapter 3000 may be configured to be coupled to an embodiment of the disposable housing assembly, including but not limited to, the disposable housing assembly 804, shown and described above, or the disposable housing assembly 3002, shown in FIG. 206B. The embodiments of the disposable housing assembly 3002 shown in FIG. 206B is similar to disposable housing assembly 804. However, for description purposes, disposable housing assembly 3002 will be referred to with respect to fill aid adapter 3000, however, in various other embodiments, the filling aid adapter 3000 may be coupled to any embodiment of the disposable housing assembly. Upon coupling the fill adapter 3000 to the disposable housing assembly 3002, the reservoir 908 may be filled using a syringe (not shown). Any syringe known in the art may be used, however, in the exemplary embodiments, any syringe having a size and shape to be accommodated by the filling aid 3004 may be used, including, but not limited to, a 3 cc/mL TERUMO SYRINGE without needle, made by TERUMO Europe, Belgium, together with a Becton Dickinson 26G1/2 PRECISIONGLIDE Needle, made by Becton Dickinson & Co., Franklin Lakes, N.J., U.S.A., however, in various embodiments, the syringe may be a syringe and/or a syringe and filling needle and/or a filling needle made by another manufacture and/or at a larger or smaller size. Fill adapter 1000 may include locking tabs 3006, 3008, 3010, 3012 that may be configured to engage radial tabs 3014, 3016, 3018 (and another, not shown) of disposable housing assembly 3002 in a manner generally similar to tabs 942, 944, 946, 948 of locking ring assembly 806. Accordingly, fill adapter 3000 may be releasably engaged with disposable housing assembly 3002 by aligning fill adapter 3000 with disposable housing assembly 3002 and rotating fill adapter 3000 and disposable housing assembly 3002 relative to one another to releasably engage locking tabs 3006, 3008, 3010, 3012 with radial tabs 3014, 3016, 3018 (and another, not shown).

The embodiment of the disposable housing assembly 3002 shown in FIG. 206B includes an additional radial tab that is hidden in the view shown. In various embodiment, the number of locking tabs and radial tabs may vary, for example, in various embodiments, the number of locking tabs or radial tabs may be greater than or less than the number shown in the exemplary embodiments.

Also referring to FIGS. 208-208B, the process for engaging the fill adapter 3000 with the disposable housing assembly 3002 is shown. FIG. 208A shows the fill adapter 3000 attached to the disposable housing assembly 3002 and in the non-locked position. In some embodiments of the various embodiments of the disposable housing assemblies described herein, an indication of "lock" 3020 and "unlock" 3022 may be included on the disposable housing assembly, for example, as shown in the embodiment of the disposable housing assembly 3002, for example, to indicate the direction of rotation 3024 to either "lock" 3020 or "unlock" 3022 the fill adapter 3000, for example, and/or the locking ring assembly 806, with respect to the disposable housing assembly 3002. In various embodiments, the indications 3020, 3022, 3024 may vary. Referring now to FIG. 208B, the fill adapter 3000, having rotated with respect to the disposable housing assembly 3002 in the direction shown in FIG. 208A, the direction of rotation 3024 also indicated on the disposable housing assembly 3002, which is clockwise in the exemplary embodiment, the fill adapter 3000 is in the locked position with respect to the disposable housing assembly 3002. In the exemplary embodiment, the locked position (see FIG. 208B) is a position in which the fill adapter 3000 is coupled and/or engaged with the disposable housing assembly 3002 such that the fill adapter 3000 may not easily rotate with respect to the disposable housing assembly 3002. In the exemplary embodiment, the fill adapter 3000 may rotate counterclockwise from the locked position to the unlocked position following the exertion of force onto the locking tab actuator 3026 which releases the locking tab 3030 from the disposable housing assembly 3002. In the exemplary embodiment, filling aid base 3046 (which, in some embodiments is cylindrical and includes an opening to the cavity portion of the filling aid) is located opposite the locking tab actuator 3026 such that a user may release the locking tab 3030 using an ergonomically efficient configuration, e.g., placing the thumb on the filling aid base 3026 and the forefinger on the locking tab actuator 3025 to efficiently relay force on the locking tab actuator 3026 and release the locking tab 3030. In some embodiments, the fill adapter 3000 includes a rotation direction indication 3028 to indicate the direction of rotation to unlock the fill adapter 3000 from the disposable housing assembly 3002. In some embodiments of the infusion pump apparatus and system described herein, in practice, the fill adapter 3000 may be attached to the disposable housing assembly 3002 in the locked position. A user may fill the reservoir (which may be the embodiment as shown in FIG. 49B, 908) of the disposable housing assembly 3002 using the fill adapter 3000. Following, the user may unlock the fill adapter 3000 by exerting force onto the locking tab actuator 3026, which releases the locking tab 3030, and rotating the fill adapter 3000 counterclockwise as indicated by the rotation direction indication 3028 on the fill adapter 3000 until the fill adapter 3000 is in the unlocked position, as shown in FIG. 208A.

In the exemplary embodiment, the locking tab 3030, in the locked position, prevents counterclockwise rotation of the fill adapter 3000 with respect to the disposable housing assembly 3002. In the locked position, the locking tab 3030 is located between two radial tabs, 3018 and one not shown, of the disposable housing assembly 3002. Further, fill adapter 1000 locking tabs 3006, 3008, 3010, 3012 and radial tabs 3014, 3016, 3018 (and another, not shown) of disposable housing assembly 3002 together limit the rotation of the fill adapter 3000 with respect to the disposable housing assembly 3002. Thus, the locking tabs 3006, 3008, 3010, 3012 and radial tabs 3014, 3016, 3018 (and another, not shown) limit the rotation of the fill adapter 3000 with respect to the disposable housing assembly 3002 such that in the locked position, the fill adapter 3000 is aligned and releasably engaged in the desired coupling configuration with the disposable housing assembly 3002 such that the reservoir 908 may be filled. The locking tab 3030 prevents counterclockwise rotation, or unlocking, of the coupling between the fill adapter 3000 and the disposable housing assembly 3002, which may assist the user and ensure proper alignment during reservoir 908 fill.

Fill adapter 3000 may further include filling aid 3004, which may include guide passage 3038, e.g., which may be configured to guide a needle of a syringe (not shown) to a septum of disposable housing assembly 3002 (which, in some embodiments, may be one as described above, for example, with respect to FIG. 3) to allow the reservoir 908 of the disposable housing assembly 3002 to be filled by the syringe. In some embodiments, guide passage 3038 may be an angled bevel or other gradual angled bevel to further guide a syringe to a septum. Fill adapter 3004 may facilitate filling the reservoir 908 by providing an insertion area, e.g., at the distal opening of the guide passage 3038, that is relatively large as compared with the proximal end of the guide passage 3038. In some embodiments, guide passage 3038 may generally taper to a smaller proximal opening that may be properly aligned with the septum of disposable housing assembly 3002, when fill adapter 3000 is in the locked position relative to the disposable housing assembly 3002, and therefore engaged and in the orientation for fill. Accordingly, fill adapter 3000 may reduce the dexterity and aim necessary to properly insert a needle through the septum of disposable housing assembly 3002 for the purpose of filling the reservoir 908. Further, in some embodiments, the filling aid 3004 includes a filling aid base 3046. The base may assist in maintaining stability of the fill adapter 3000 during fill with a syringe which may contribute to greater accuracy of location and angle of insertion of the needle through the septum of the disposable housing assembly 3002 and successful fill of the reservoir 908.

As discussed above with respect to various embodiments of the fill adapter, disposable housing assembly 3002 may be configured to facilitate controlling the quantity of infusible fluid delivered to reservoir 908 during filling. For example, membrane assembly 902 of disposable housing assembly 3002 may include ribs 3040, 3042, 3044, which may provide windows to the reservoir membrane 902 that are formed on the disposable housing assembly 3002. The reservoir membrane 902 may be depressed and at least partially displaced into reservoir 908, thereby reducing the volume of reservoir 908. Accordingly, when infusible fluid is delivered to reservoir 908, the volume of fluid that may be accommodated by reservoir 908 may be correspondingly reduced by at least partially displacing the reservoir membrane 902.

In some embodiments, the ribs 3040, 3042, 3044 may be sized and shaped to prevent depression of the reservoir membrane 902 by anything other than the button assemblies 3032, 3034, 3036 discussed in more detail below. This may provide addition safety to the infusion system as the disposable housing assembly 3002 does not include access to unintentional pumping of fluid by depression of the reservoir membrane 902 when the fill adapter 3000 is not attached to the disposable housing assembly 3002. Further, the ribs may additionally prevent unintentional fluid loss after fill is complete. Thus, once the fill adapter 3000 is removed from the disposable housing assembly 3002, unintentional pressure to the disposable housing assembly 3002 may not result in forcing fluid through the disposable housing assembly 3002 fluid path to the exit. Rather, the reusable housing assembly 802 may be attached to the disposable housing assembly 3002 for fluid to be forced out of the reservoir 908. Therefore, the ribs 3040, 3042, 3044 in the disposable housing assembly 3002 provide for a mechanism for safely and intentionally priming the disposable housing assembly 3002 but also, prevent the unintentional forcing of fluid from the reservoir 908.

In some embodiments, the size, shape and/or overall dimensions of the ribs 3040, 3042, 3044 may be chosen to accommodate the one or more button assemblies 3032, 3034, 3036 (described in further detail below) so as to limit the travel of the button assemblies 3032, 3034, 3036 and thereby limiting the amount of displacement of the reservoir membrane 902 by the button assemblies button assemblies 3032, 3034, 3036.

Fill adapter 1000 may include one or more button assemblies (e.g., button assemblies 3032, 3034, 3036) corresponding to ribs 3040, 3042, 3044 (which are as described in other embodiments of the disposable housing assembly having and ribs 964, 966, 968) in the disposable housing assembly 3002. In various embodiments, when fill adapter 3000 is releasably engaged with disposable housing assembly 3002, buttons 3032, 3034, 3036 may be aligned with ribs 3040, 3042, 3044. Button assemblies 3032, 3034, 3036 may be, for example, cantilever members capable of being depressed. When fill adapter 3000 is releasably engaged with disposable housing assembly 3002, one or more of button assemblies 3032, 3034, 3036 may be depressed, and may correspondingly be displaced through a respective one of ribs 3040, 3042, 3044 into reservoir 908, causing an attendant reduction in the volume of reservoir 908.

Although three ribs and three button assemblies are described and shown herein, in various embodiments, the fill adapter 3000 may include one or more button assemblies and the disposable housing assembly may include one or more corresponding ribs. In some embodiments, the button assemblies and the ribs may be similarly sized as shown in the accompanying figures. However, in various embodiments, the number, size, distribution and shape of the one or more button assemblies and the one or more ribs may be different than as shown herein. For example, in some embodiments, the button assemblies may be wider, may be round, may be square or may be thicker. Likewise, the corresponding rib may accommodate the various embodiments of the button assemblies. In some embodiments, it may be desirable to vary the distribution, number, size and shape of the button assemblies, and correspondence ribs, to accommodate the volume of fluid that is anticipated to be filled in the reservoir. This is further described below.

In some embodiments, for example, the embodiments shown in FIGS. 206A-208B, the button assemblies 3032, 3034, 3036 are actuated by at least one button assembly actuator 3046 which is hingably actuated. In some embodiments, each of the at least one button assemblies may be separately actuated by a dedicated button assembly actuator. The button assembly actuator 3046 may be any size desired, but in some embodiments, may be as shown in FIGS. 206A and 207A-211C. As shown in, for example, FIG. 207B, the button assembly actuator 3046 may include visible indicators, for example, "press", to indicate the method of actuation. In some embodiments, the button assembly actuator 3026 may include a depression and/or ergonomic finger and/or thumb accommodation 3052. In the exemplary embodiment of this embodiment of the fill adapter 3000, the button assembly actuator 3046 also includes a pump chamber plunger actuator 3048, which actuates the pump chamber plunger 3050 shown in, for example, FIG. 207B. In some embodiments, the button assembly actuator may not include any button assemblies, thus, in these embodiments; the button assembly actuator may actuate only the pump chamber plunger actuator.

Still referring to FIGS. 206A-208B, in some embodiments, in practice, following the filling of the reservoir, the syringe (not shown) may be removed from the filling aid 3004. The fill adapter 3000 remains in the locked position with respect to the disposable housing assembly 3002 (see FIG. 208B). In some embodiments, it may be desirable to "prime" the fluid lines in the disposable housing assembly 3002, i.e., to force fluid from the reservoir through the fluid path and through the exit such that air is purged from the fluid path and replaced with fluid. The button assemblies 3032, 3034, 3036, when actuated by the button assembly actuator 3046, apply pressure onto the reservoir membrane and force fluid out of the reservoir and into the fluid path.

In the exemplary embodiment of the fill adapter 3000, a pump chamber plunger actuator 3048 is hingedly connected to, and actuated by, the button assembly actuator 3046. The pump chamber plunger actuator 3048 actuates the pump chamber plunger 3050. The hinge 3054 attachment to the button assembly actuator 3046 allows for the pump chamber plunger actuator 3048 to actuate the pump chamber plunger 3050 before the button assembly actuator 3046 reaches a point in travel where it actuates the button assemblies 3032, 3034, 3036. In the exemplary embodiment, the hinge is a living hinge. Referring now also to FIGS. 209A-209C, the fill adapter 3000 is shown with a cross-section taken at "B" in 209A (see 209B) and a cross-section taken at "C" in 209A (see 209C). The button assembly actuator 3046 is shown in the non-actuated position. In practice, the button assembly actuator 3046 would likely be in this position prior to the initiation of the actuation path. As can be seen in FIG. 209B, the hinge 3054 connects the pump chamber plunger actuator 3048 to the button assembly actuator 3046. The pump chamber plunger 3050 is also shown in a non-actuated position and the button assembly 3036 is shown. Referring now also to FIG. 209C, the cross-sectional view shows the pump chamber plunger 3050, the button assembly 3034 and the button assembly actuator 3046.

Referring now also to FIGS. 210A-210C, the fill adapter 3000 is shown in a coupled and/or engaged and locked position with respect to the disposable housing assembly 3002. The cross-sectional views are taken at cross section "A" and the interaction between the pump chamber plunger actuator 3048, the button assembly actuator 3026 and button assembly 3034, and the pump chamber plunger 3050 with the pumping recess/pump chamber 926 (hereinafter "pump chamber"), the membrane 924, the rib 3042, the membrane assembly 902 and the reservoir 908 is shown. Referring now to FIG. 210B, in practice, upon force being applied to the button assembly actuator 3026, for example, upon the finger and/or thumb accommodation 3052, the button assembly actuator 3026 and the pump chamber plunger actuator 3048 begin travel in the direction of the disposable housing assembly 3002. During this travel, the pump chamber plunger 3050 reaches the membrane 924 and forces the membrane 924 into the pump chamber 926. The air in the pump chamber 926 is evacuated/forced out of the pump chamber 926 by the pump chamber plunger 3050 and the fluid flows through the pump chamber 926 rather than swirling in the pump chamber 926 during prime. This may be beneficial for many reasons including, but not limited to, reducing the occurrence of air being trapped in the pump chamber 926.

Referring now to FIG. 210C, the button assembly actuator 3026 having reached the end of travel, the membrane assembly 902 is displaced by the button assembly 3034. This displacement of the membrane assembly 902 forces fluid out of the reservoir 908 and into the fluid path. The pump chamber plunger 3050 has displaced or depressed the membrane 924. As the pump chamber plunger 3050 displaces/depresses the membrane 924 the pump chamber 926 volume is reduced and the fluid, being forced from the reservoir 908 by the at least one button assembly 3034, fills the remaining volume of the pump chamber 926. As discussed above, the pump chamber plunger actuator 3048 is hingably attached to the button assembly actuator 3026 through a living hinge 3054. However, in various embodiments, the pump chamber plunger actuator 3048 may be attached by way of a pivot hinge or any other type of hinge. The hinge 3054 provides for less force being exerted onto the pump chamber plunger actuator 3048 as compared with the button assembly actuator 3026. Thus, while force is maintained on the button assembly actuator 3026 sufficient to force fluid out of the reservoir, and sufficient to force air out of the pump chamber 926, the pump chamber plunger 3050 does not receive sufficient force to close the pump chamber 926 completely. Thus, fluid is allowed to pass through the pump chamber 926 while the button assembly actuator 3026 is fully actuated, and air will be forced out of the pump chamber 926. Thus, the pump chamber plunger actuator 3048 being separately hinged through hinge 3054, as compared with the hinge for the button assembly actuator 3026, allows the pump plunger actuator 3048 to rise up due to fluid pressure such that fluid may pass through the pump chamber 926 and through the fluid path. The fluid displaces the air. Thus, through the actuation of the button assembly actuator 3026, air in the pump chamber 926 is evacuated prior to fluid being forced from the reservoir 908 and through the pump chamber 926.

In some embodiments of priming, the button assembly actuator 3026 may be actuated multiple times. In some embodiments, the button assembly actuator 3026 is actuated until fluid exits the fluid path and the system is primed.

Referring now also to FIGS. 213A and 213B, where FIG. 213B is a magnified sectional view of section "B" as indicated in FIG. 213A, an embodiment of the disposable housing assembly 3068 is shown, with the membrane and top portion removed. In some embodiments, the pump chamber 926 may include a groove 3070 along the chamber wall. This groove 3070 allows for fluid to flow through the pump chamber 926 even while the membrane 924 is fully depressed/displaced and reaches the pump chamber 926 wall. Thus, in some embodiments, where the pump chamber plunger 3050 may depress/displace the membrane 924 such that it reaches the pump chamber 926 wall, fluid may still flow through the pump chamber 926 and through the fluid path to exit the system.

In some embodiments, the number of button assemblies, the distribution with respect to the reservoir membrane and the size of the button assemblies and the shape of the button assemblies may vary. In some embodiments, these variations may be made to accommodate the volume of fluid anticipated to be pumped from the reservoir 908. For example, in some embodiments, these accommodate a very low volume fill of the reservoir; the button assembly may be such that a prime may be completed. In some embodiments, the pump chamber actuator 3050 may actuate the membrane 924 to depress/displace the membrane 924 towards the pump chamber 926 wall. Following, the membrane 924 may springs to the starting position. This spring back of the membrane 924 may work to pump the fluid from the reservoir 908 as discussed in more detail herein with respect to pumping. Thus, in some embodiments, through the priming methods, where, for example, the button assembly actuator 3026 is actuated multiple times to prime the system, the pump chamber plunger 3050 may work to aid in the prime by not only evacuating the air from the pump chamber 926 prior to the fluid being forced from the reservoir, but the return of the membrane 924 to the starting position may contribute to priming the system with a small volume of fluid in the reservoir 908. In some embodiments, this may increase the flexibility of the system where the system may not require a minimum fill to prime the system and/or any minimum volume fill requirements may be lower as compared with systems that do not include a pump chamber plunger 3050 and/or a pump chamber plunger actuator 3048.

In some embodiments, the pump chamber plunger 3050 may be separately actuated from the button assembly actuator 3026, and in some embodiment, a method for priming may include depressing a pump chamber plunger such that air in the pump chamber is evacuated, followed by forcing fluid from the reservoir, which may be accomplished by pressing on the membrane of the reservoir, until fluid is forced through the pump chamber and fluid path and exits the system, such that the system is primed. In some embodiments, where manual actuation of the pump chamber plunger 3050 is employed, a method for prime may include actuating the pump chamber plunger 3050 before each actuation of the button assemblies 3034/button assembly actuator 3026 such that the pump chamber membrane 924 may provide the additional benefits discussed above.

Referring now to FIGS. 211A-211C, another embodiment of the fill adapter 3056 is shown. The embodiment shown in FIGS. 211A-211C may include many of the features as discussed above with respect to the embodiment of the fill adapter 3000. However, some embodiments of the fill adapter 3056 may include a removable filling aid 3058. This may be beneficial for many reasons, including but not limited to, limiting the size of the fill adapter 3056 prior to fill which may be beneficial for many reasons, including, but not limited to, storage, transport and packaging. In the embodiments shown, the fill adapter 3058 is removable from the fill adapter base 3060. The filling aid 3058 may include an attachment feature to removably attach to the fill adapter base 3060. In the embodiment shown, the attachment feature includes two tabs 3062, 3064 which include two sides around an opening that allows for a snap fit to the fill adapter base 3060. Other attachments features may include, but are not limited to, clips and latches. Referring now to FIGS. 212A-212C, another embodiment of the filling adapter 3056 is shown. In some embodiments, the filling aid 3058 may be hingably attached to the fill adapter base 3060 via a pivot hinge 3066. In other embodiments, the hinge 3066 may be a living hinge. Although shown in FIGS. 212B-212C, the filling aid 3058 folds under the fill adapter base 3060, in other embodiments, the filling aid 3058 may fold over the top of the fill adapter base 3060, including living hinge and pivot hinge.

In some embodiments, the length of the filling aid 3058 may be extended and the width of the opening wide enough such that the barrel of the syringe, rather than the needle, may guide. This may be desirable and/or beneficial for many reasons, including, but not limited to, the filling aid 3058 may be reusable due to lack of contamination, i.e., the needle may not be contaminated during the fill (as compared with where the needle guides). In some embodiments, the filling adapter may be made from any materials, including, but not limited to, one or more of the following: polypropylene, high density polypropylene, and any other materials desired. In some embodiments, the fill adapter base and the filling aid may be made from the same materials and in some embodiments, they may be made form different materials one from another.

The embodiments shown and described with respect to FIGS. 206A-213 may be used to provide a method for priming the disposable housing assembly with a low volume reservoir fill, for example, but not limited to, a 0.75 cc reservoir fill. In some embodiments, it may be desirable to provide a method for priming a reservoir filled with a lower than, for example. 1.5 cc of fluid. In some embodiments, upon filling the reservoir with, for example, 0.75 cc of fluid then repeatably pressing the button assembly actuator 3026, the disposable housing assembly may be fully primed. In some embodiments, this may be desirable, including, for those users/patient requiring a lower volume of fluid for therapy, for example, those using low daily volumes of insulin for therapy, and/or for uses of the pump assembly that may require only small volumes of fluid, the additional, and perhaps non needed, fluid may be wasted. Thus, a method for priming the disposable housing assembly with a smaller volume of fluid may be desirable.

With respect to the embodiments shown and described with respect to FIGS. 206A-213, one or more of the various features described within may be used in embodiments described throughout the specification. Thus, the features described with respect to FIGS. 206A-213 are not meant to be limited to the embodiments described with respect to those figures. Additionally, one or more of those features and embodiments described elsewhere in this specification may be incorporated into one or more embodiments described and shown in FIGS. 206A-213. For example, the pump chamber plunger 3050 may be included in any of the various fill adapters described within the specification. This example is for illustration purposes only and is not meant to be a limiting example.

In some embodiments, the filling aid may attach to the fill adapter at an angle that is beneficial for the disposable housing assembly reservoir. For example, in some embodiments, the filling aid may attach to the fill adapter at a 45 degree angle relative to the fill adapter. However, in various embodiments, the filling aid may attach to the fill adapter at other angles that may be beneficial for the reservoir fill. With respect to some embodiments where the filling aid may be hingably attached to the filling aid base, the hinge may be designed such that the filling aid will rotate to the appropriate "filling" position for the syringe.

As discussed above, reusable housing assembly 802 may include battery 832, e.g., which may include a rechargeable battery. Referring also to FIGS. 75-80, battery charger 1200 may be configured to recharge battery 832. Battery charger 1200 may include housing 1202 having top plate 1204. Top plate 1204 may include one or more electrical contacts 1206, generally, configured to be electrically coupled to electrical contacts 834 of reusable housing assembly 802. Electrical contacts 1206 may include, but are not limited to, electrical contact pads, spring biased electrical contact members, or the like. Additionally, top plate 1204 may include alignment tabs 1208, 1210, which may be configured to mate with openings 836, 838 in base plate 818 of reusable housing assembly 802 (e.g., as shown in FIG. 35C). The cooperation of alignment tabs 1208, 1210 and openings 836, 838 may ensure that reusable housing assembly 802 is aligned with battery charger 1200 such that electrical contacts 1206 of battery charger 1200 may electrically couple with electrical contacts 834 of reusable housing assembly 802.

Figure 77:
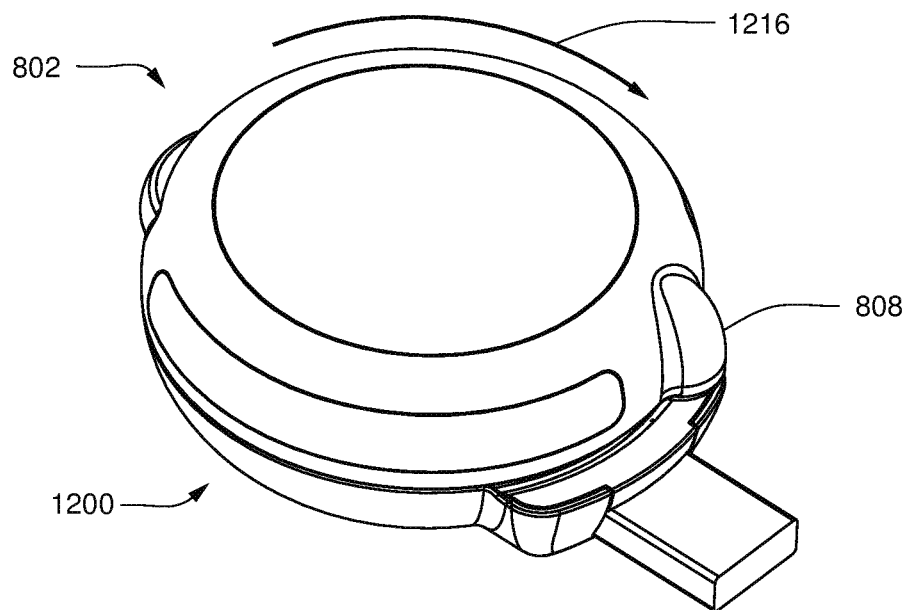
Figure 78:
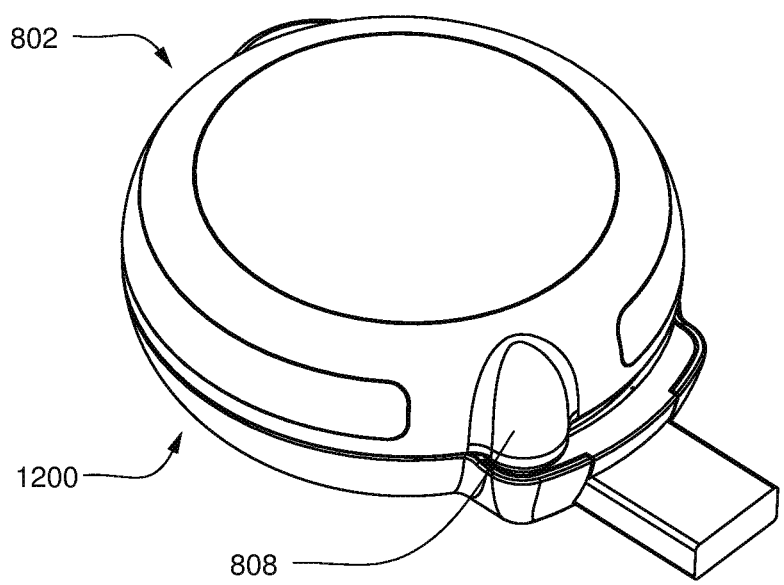

With reference also to FIGS. 77 and 78, battery charger 1200 may be configured to releasably engage reusable housing assembly 802. For example, in a similar manner as disposable housing assembly 804, battery charger 1200 may include one or more locking tabs (e.g., locking tabs 1212, 1214 shown in FIG. 76). The locking tabs (e.g., locking tabs 1212, 1214) may be engaged by tabs 942, 944, 946, 948 of locking ring assembly 806. As such, reusable housing assembly 802 may be aligned with battery charger 1200 (via alignment tabs 1208, 1210) with locking ring 806 in a first, unlocked position, as shown in FIG. 77. Locking ring 806 may be rotated relative to battery charger 1200 in the direction of arrow 1216 to releasably engage tabs 942, 944, 946, 948 of locking ring 806 with the locking tabs (e.g., locking tabs 1212, 1214) of battery charger 1200, as shown in FIG. 78.

Figure 79:
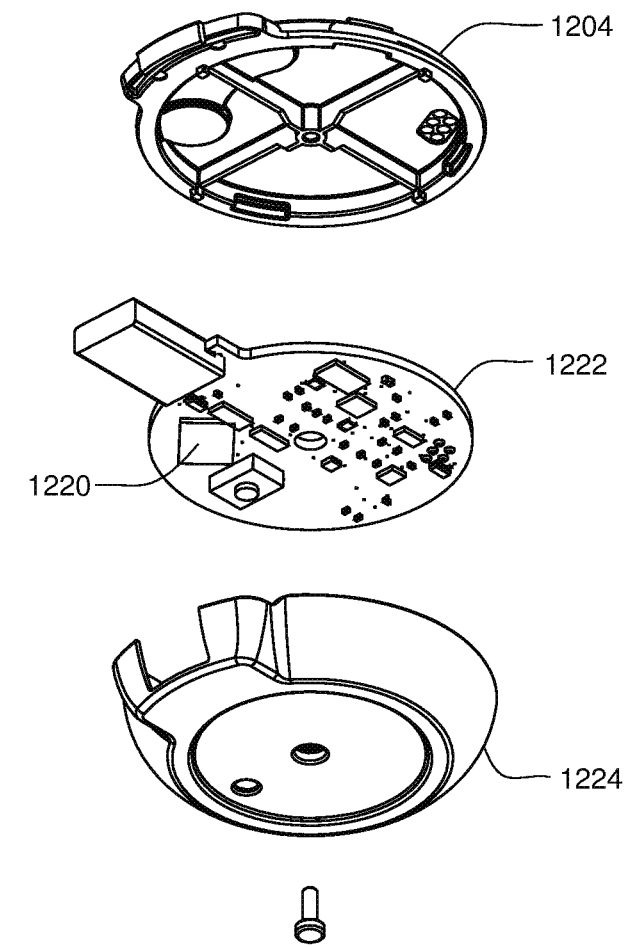
Figure 80:
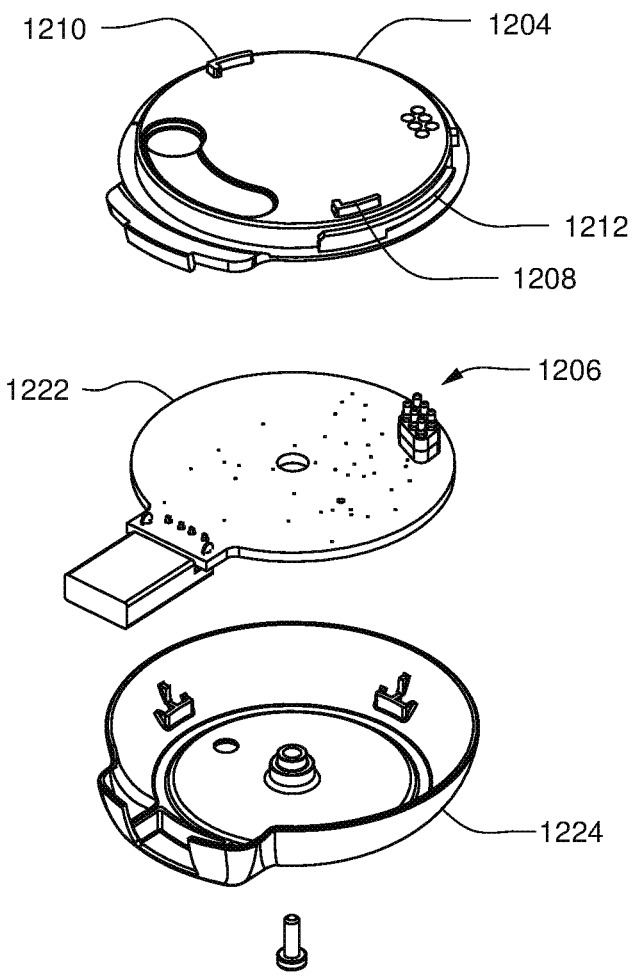

In an embodiment, battery charger 1200 may include recessed region 1218, e.g., which may, in the exemplary embodiments, provide clearance to accommodate reusable housing assembly 802 pumping and valving components. Referring also to FIGS. 79 & 80, battery charger 1200 may provide electrical current to electrical contacts 1206 (and thereby to reusable housing assembly 802 via electrical contacts 834) for recharging battery 832 of reusable housing assembly 802. In some embodiments, when a signal indicative of a fully engaged reusable housing is not provided, current may not be provided to electrical contacts 1206. According to such an embodiment, the risk associated with an electrical short circuit (e.g., resulting from foreign objects contacting electrical contacts 1206) and damage to reusable housing assembly 802 (e.g., resulting from improper initial alignment between electrical contacts 1206 and electrical contacts 834) may be reduced. Additionally, battery charger 1200 may not unnecessarily draw current when battery charger is not charging reusable housing assembly 802.

Still referring to FIGS. 79 and 80, battery charger 1200 may include a lower housing portion 1224 and top plate 1204. Printed circuit board 1222 (e.g., which may include electrical contacts 1206) may be disposed within a cavity included between top plate 1204 and lower housing portion 1224.

Figure 81:
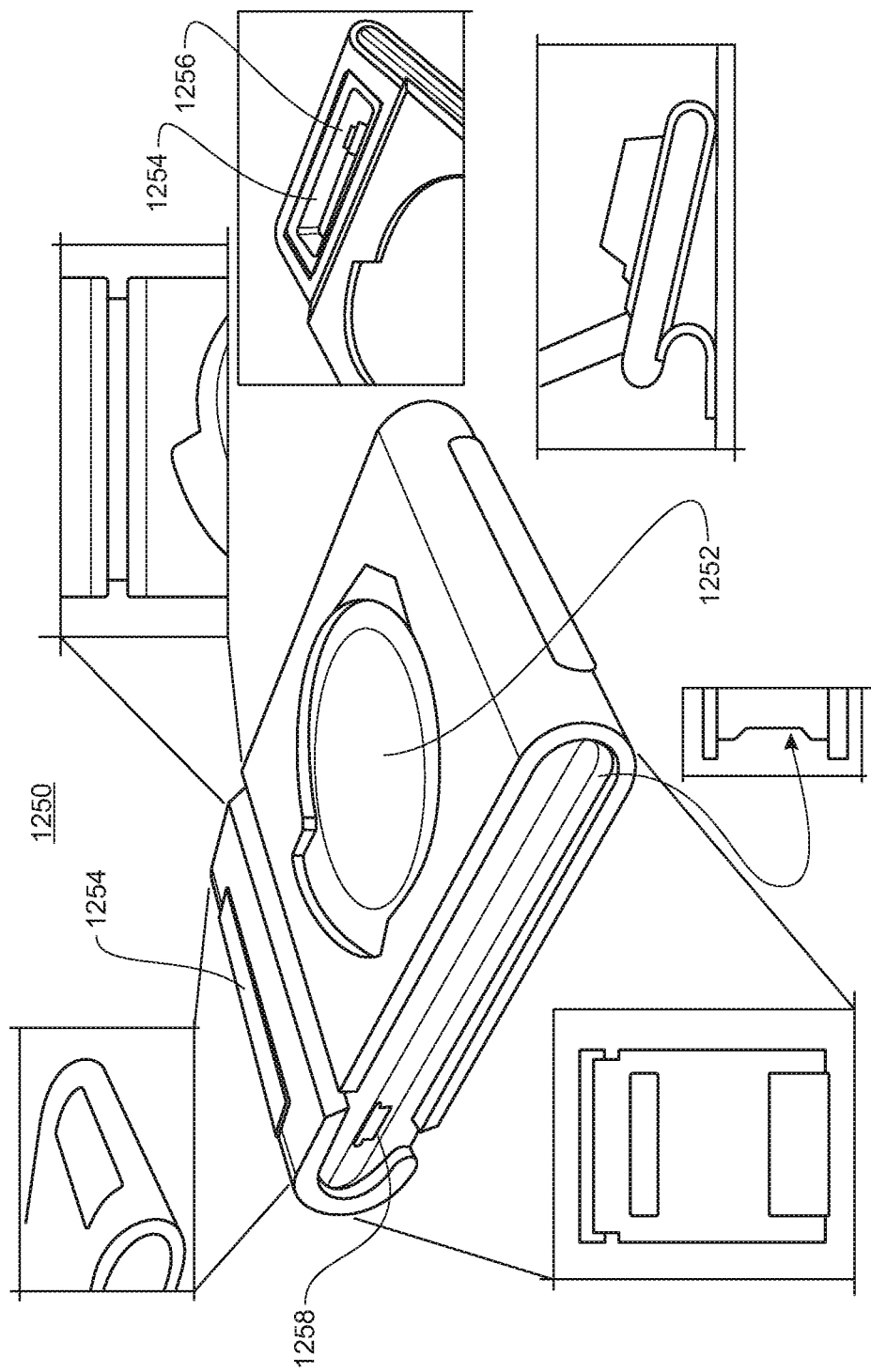
Figure 82:
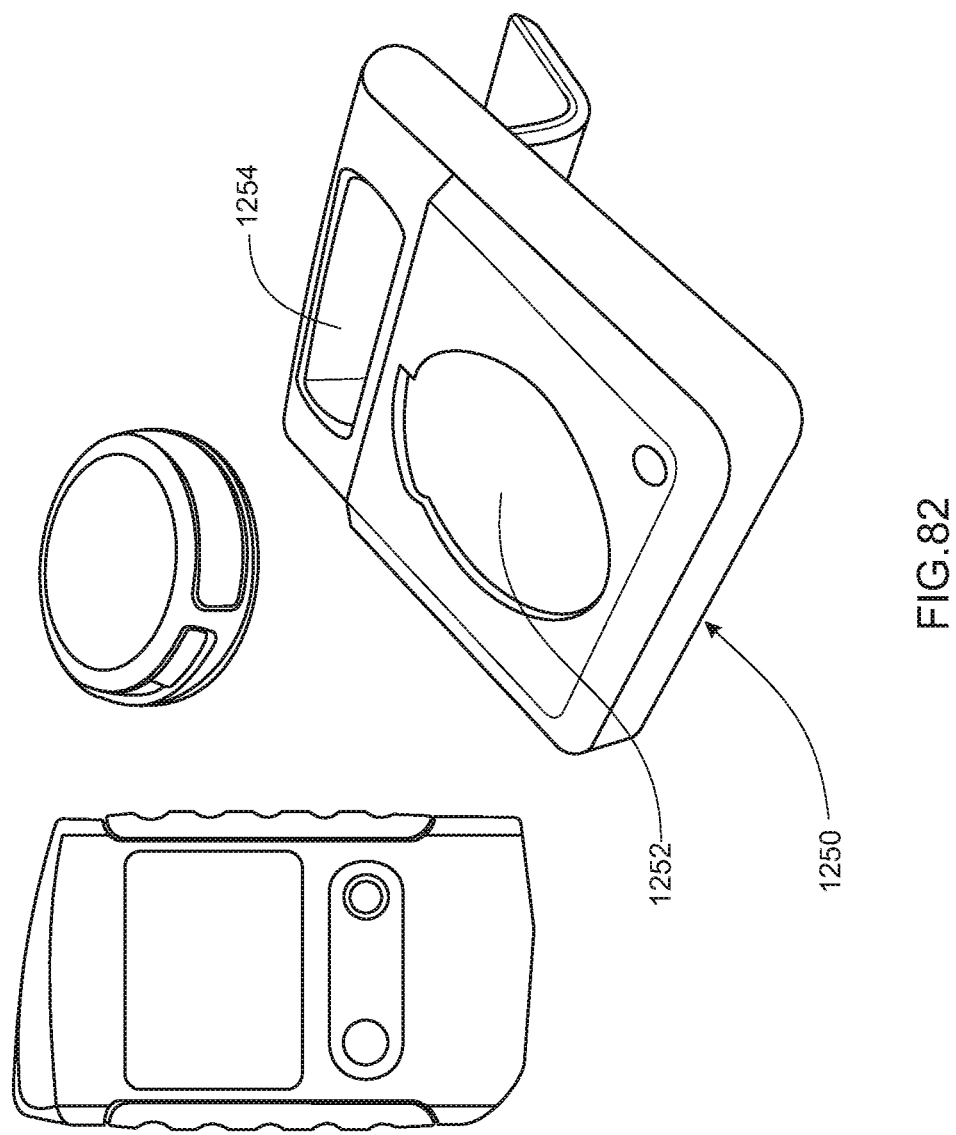

Referring also to FIGS. 81-89, various embodiments of battery charger/docking stations are shown. FIGS. 81 and 82 depicts desktop charger 1250 including recess 1252 configured to mate with and recharge a reusable housing assembly (e.g., reusable housing assembly 802). The reusable housing assembly may rest in recess 1252 and or may be releasably engaged in recess 1252, in a similar manner as discussed above. Additionally, desktop charger 1250 may include recess 1254 configured to mate with a remote control assembly (e.g., remote control assembly 300). Recess 1254 may include a USB plug 1256, e.g., which may be configured to couple with the remote control assembly when the remote control assembly is disposed within recess 1254. USB plug 1256 may allow for data transfer to/from the remote control assembly, as well as charging of remote control assembly. Desktop charger 1250 may also include USB port 1258 (e.g., which may include a mini-USB port), allowing desktop charger to receive power (e.g., for charging the reusable housing assembly and/or the remote control assembly). Additionally/alternatively USB port 1258 may be configured for data transfer to/from remote control assembly and/or reusable housing assembly, e.g., by connection to a computer (not shown).

Referring to FIGS. 83A-83B, similar to the previous embodiment, desktop charger 1260 may include recess 1262 for mating with a reusable housing assembly (e.g., reusable housing assembly 1264). Desktop charger may also include recess 1266 configured to receive a remote control assembly (e.g., remote control assembly 1268). One or more of recess 1262, 1266 may include electrical and/or data connections configure to charge and/or transfer data to/from reusable housing assembly 1262 and/or remote control assembly 1268, respectively.

Figure 84A:
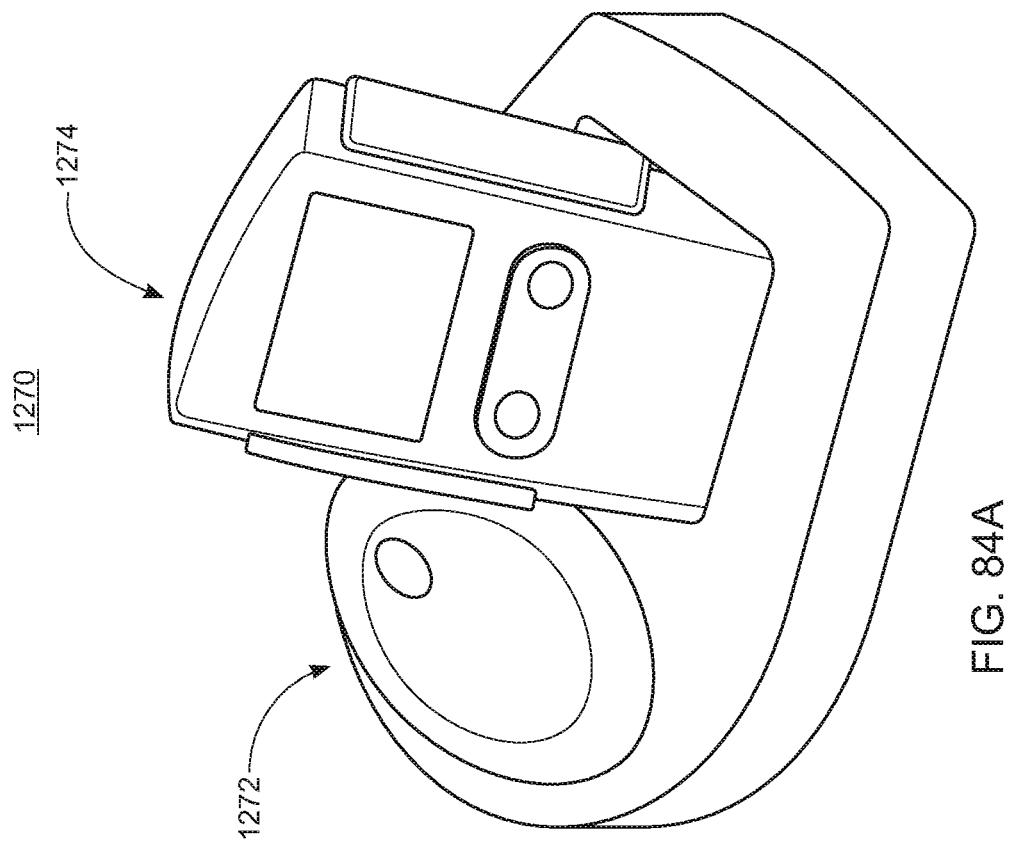
Figure 84B:
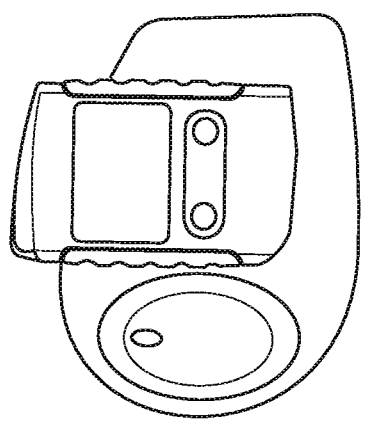

Referring to FIGS. 84A-84B, another embodiment of a desktop charger is shown. Similar to desktop charger 1260, desktop charger 1270 may include recesses (not shown) for respectively mating with reusable housing assembly 1272 and remote control assembly 1274. As shown, desktop charger 1270 may hold reusable housing assembly 1272 and remote control assembly 1274 in a side-by-side configuration. Desktop charger 1270 may include various electrical and data connection configured to charge and/or transfer data to/from reusable housing assembly 1272 and/or remote control assembly 1274, as described in various embodiments above.

Referring to FIG. 85A-85D, collapsible charger 1280 may include recess 1282 for receiving reusable housing assembly 1284 and remote control assembly 1286. Collapsible charger 1280 may include various electrical and data connection configured to charge and/or transfer data to/from reusable housing assembly 1284 and/or remote control assembly 1286, as described in various embodiments above. Additionally, as shown in FIGS. 85B-85D, collapsible charger 1280 may include pivotable cover 1288. Pivotable cover 1288 may be configured to pivot between an open position (e.g., as shown in FIG. 85B), in which reusable housing assembly 1284 and remote control assembly 1286 may be docked in collapsible charger 1280, and a closed position (e.g., as shown in FIG. 85D), in which recess 1282 may be covered by pivotable cover 1288. In the closed position, recess 1282, as well as any electrical and/or data connections disposed therein, may be protected from damage.

Figure 86:
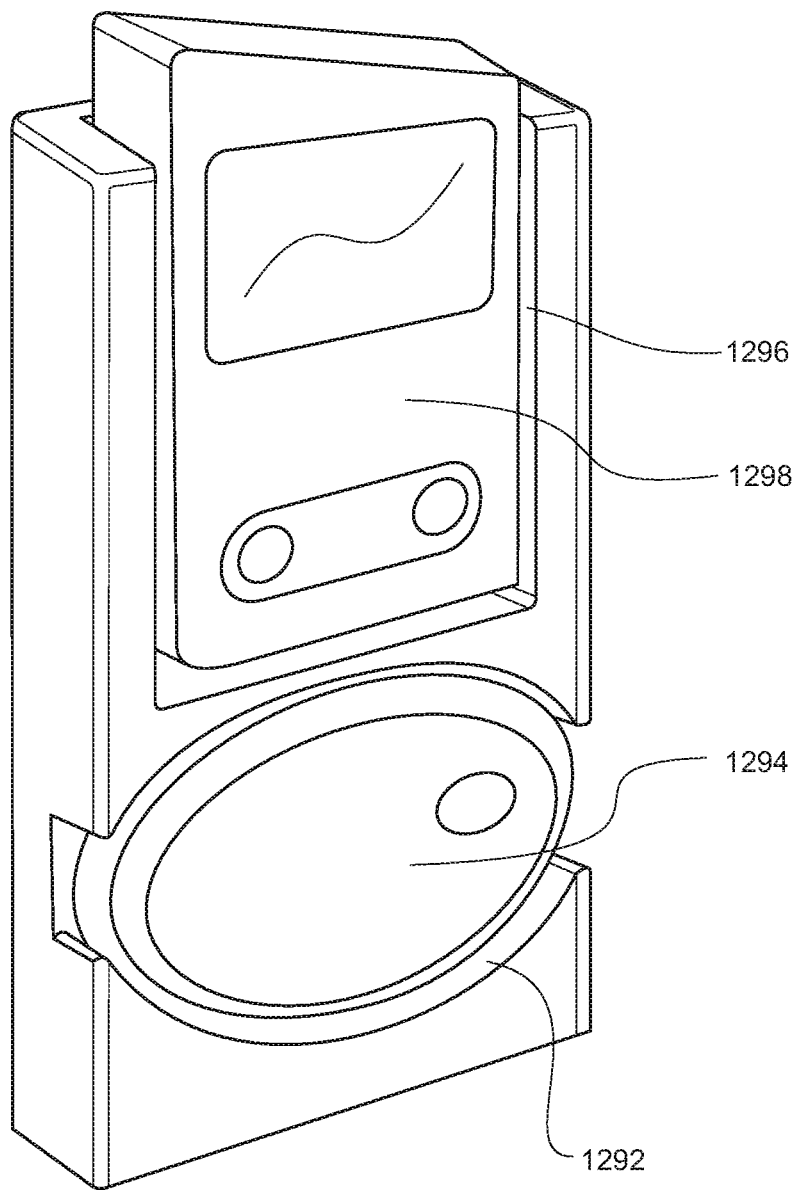

Referring to FIG. 86, wall charger 1290 may include recess 1292 configured to receive reusable housing assembly 1294. Additionally, wall charger 1290 may include recess 1296 configured to receive remote control assembly 1298. Reusable housing assembly 1294 and remote control assembly 1298 may be positioned in a stacked configuration, e.g., thereby providing a relatively slim profile. A rear portion of wall charger 1290 may include an electrical plug, configured to allow wall charger to be plugged into an electrical receptacle. As such, wall charger 1290, while plugged into the electrical receptacle, may achieve a wall mounted configuration. Additionally, while plugged into the electrical receptacle, wall charger 1290 may be provided with power for charging reusable housing assembly 1294 and/or remote control assembly 1298.

Figure 87:
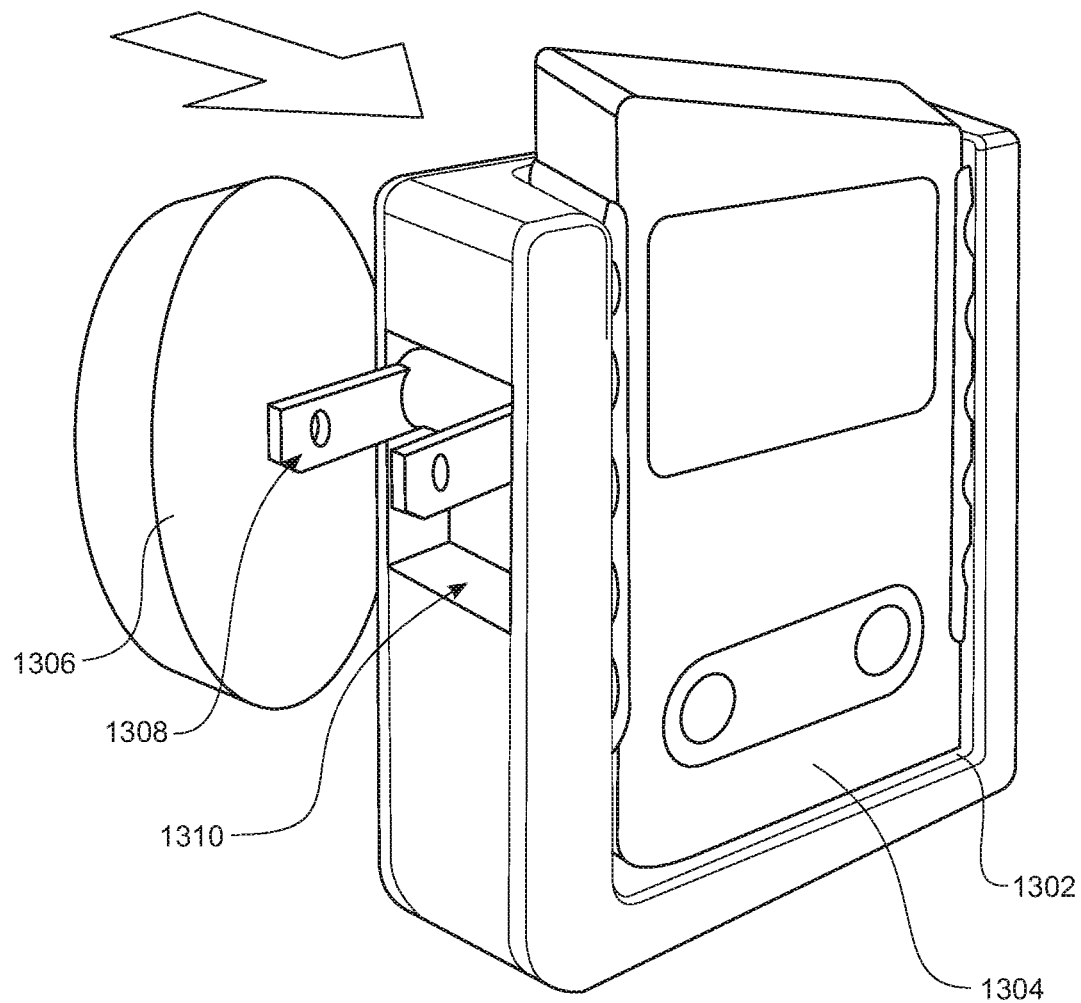

Referring to FIG. 87, wall charger 1300 may include recess 1302 configured to receive remote control assembly 1304. Additionally, wall charger may include a recess (not shown) configured to receive reusable housing assembly 1306. Wall charger 1300 may be configured to position remote control assembly 1304 and reusable housing assembly 1306 in a back-to-back configuration, which may provide a relatively thin profile. Additionally, wall charger 1300 may include an electrical plug 1308 configured to be plugged into an electrical receptacle. Electrical plug 1308 may include a stowable configuration, in which electrical plug 1308 may be pivotable between a deployed position (e.g., as shown), and a stowed position. In the deployed position, electrical plug 1308 may be oriented to be plugged into an electrical receptacle. In the stowed position electrical plug 1308 may be disposed within recess 1310, which may protect electrical plug 1308 from damage and/or from damaging other items.

Figure 88:
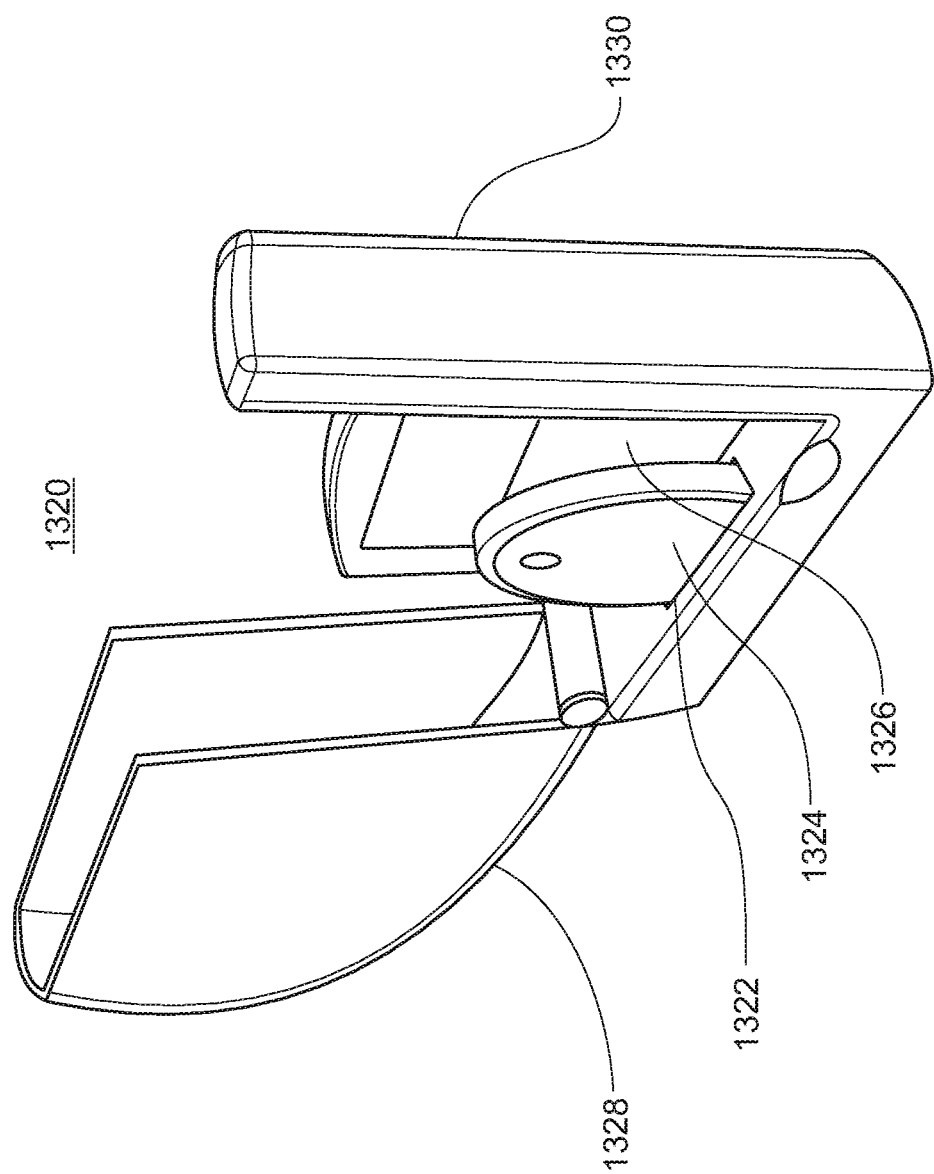

Referring to FIG. 88, charger 1320 may include recess 1322 configured to receive reusable housing assembly 1324. Charger 1320 may additionally include a recess (not shown) configured to receive remote control assembly 1326. Charger 1320 may additionally include cover 1328. Cover 1328 may be configured to pivot between an open position (as shown) and a closed position. When cover 1328 is in the open position, reusable housing assembly 1324 and remote control assembly 1326 may be accessible (e.g., allowing a user to remove/install reusable housing assembly 1324 and/or remote control assembly 1326 from/into charger 1320. When cover 1324 is in the closed position, cover 1328 and charger body 1330 may substantially enclose reusable housing assembly 1324 and/or remote control assembly 1326 and/or recess 1322 and the recess configured to receive remote control assembly 1326, thereby providing damage and/or tamper protection for reusable housing assembly 1324, remote control assembly 1326 and/or any electrical and/or data connection associated with charger 1320.

Referring to FIGS. 89A-89B, wall charger 1350 may include recess 1352 configured to receive remote control assembly 1354. Wall charger 1350 may also include recess 1356 configured to receive reusable housing assembly 1358. Wall charger 1350 may be configured to position remote control assembly 1354 and reusable housing assembly 1358 in a generally side-by-side configuration, thereby providing a relatively slim profile. Charger 1350 may additionally include electrical plug 1360, e.g., which may be configured to be plugged into an electrical receptacle. Electrical plug 1360 may include a stowable configuration, in which electrical plug 1360 may be pivotable between a deployed position (e.g., as shown), and a stowed position. In the deployed position, electrical plug 1360 may be oriented to be plugged into an electrical receptacle. In the stowed position electrical plug 1360 may be disposed within recess 1362, which may protect electrical plug 1308 from damage and/or from damaging other items.

Referring also to FIGS. 134 through 145, another embodiment of a battery charger (e.g., charger 2600), which may be used to recharge battery 832 of reusable housing assembly 802, is shown. Similar to previously discussed embodiments, charger 2600 may be configured to charge both a reusable housing assembly (e.g., reusable housing assembly 802), as well as a companion remote control assembly (e.g., remote control assembly 2602). For example, charger 2600 may include reusable housing assembly charging portion 2604 configured to cooperate with reusable housing assembly 802, for the charging thereof. As shown, reusable housing assembly charging portion 2604 may include a recess in top cover 2606 of charger 2600 that may at least partially receive reusable housing assembly 802. In a similar manner as discussed above, reusable housing assembly charging portion 2604 may include one or more alignment tabs (e.g., alignment tabs 2608, 2610) that may be configured to mate with openings 836, 838 in base plate 818 of reusable housing assembly 802 (shown in FIG. 35C). The alignment of tabs 2608, 2610 and openings 836, 838 may ensure that reusable housing assembly 802 is aligned with reusable housing assembly charging portion 2604 such that electrical contacts of charger 2600 (e.g., contacts 2612) may electrically couple with electrical contacts 834 of reusable housing assembly 802.

Also, in a similar manner as discussed above, reusable housing assembly charging portion 2604 may be configured to releasably engage reusable housing assembly 802. For example, in a similar manner as disposable housing assembly 804, reusable housing assembly charging portion 2604 may include one or more locking tabs (e.g., locking tabs 2614, 2616, 2618 visible in FIG. 134). The locking tabs (e.g., locking tabs 2614, 2616, 2618) may be engaged by tabs 942, 944, 946, 948 of locking ring assembly 806. As such, reusable housing assembly 802 may be aligned with charger 2600 (via alignment tabs 2608, 2610) with locking ring 806 in a first, unlocked position, and locking ring 806 may be rotated relative to charger 2600 in a first direction (e.g., clockwise in an exemplary embodiment) to releasably engage tabs 942, 944, 946, 948 of locking ring 806 with the locking tabs (e.g., locking tabs 2614, 2616, 2618) of charger 2600. In some embodiments, reusable housing assembly charging portion 2604 may include recess 2620 configured to receive locking ring nub 808, e.g., which may further ensure proper alignment of reusable housing assembly 802 with charger 2600. Additionally, as shown, top cover 2606 may include a recess (e.g., recess 2622) adjacent to reusable housing assembly charging portion 2604 that may facilitate removal of reusable housing assembly 802 from charger 2600 (e.g., by allowing a user to at least partially grip reusable housing assembly 802 with a thumb or finger). Additionally, recess 2622 may facilitates opening of lid 2626.

In addition to reusable housing assembly charging portion 2604, charger 2600 may include remote control assembly charging portion 2624, e.g., that may allow companion remote control assembly 2602 to be charged along with reusable housing assembly 802. In the exemplary embodiment, remote control assembly charging portion 2624 is configured to receive a remote control. In some embodiments, the remote control may include a glucose strip reader on portion of the remote control intended to be placed into remote control assembly charging portion 2624. In these embodiments, remote control assembly charging portion 2624 may accepts the remote control during charging such that the strip reader may be blocked by remote control assembly charging portion 2624. This may be desirable to prevent a user from using the glucose strip reader while the remote control is on the charger.

Remote control assembly charging portion 2624 may include a recess configured to receive at least a portion of remote control assembly 2602. Charger 2600 may include lid 2626, e.g., which may be adjacent to, and/or at least partially define, remote control assembly charging portion. For example, lid 2626 may, in an open position, extend generally upwardly relative to top cover 2606. Further, lid

2626 may include surface 2628 that may be at least generally aligned with remote control assembly charging portion 2624. As such, lid 2626 may facilitate insertion of remote control assembly 2602 into remote control assembly charging portion 2624 (e.g., by allowing remote control assembly to generally slide downwardly along surface 2628 and into remote control assembly charging portion 2624). Additionally, lid 2626 may support remote control assembly 2602 while coupled in remote control assembly charging portion 2624 (e.g., to reduce stress imparted on remote control assembly 2602 from being bumped, etc., from being transferred to electrical connection or the like associated with remote control assembly charging portion 2624).

Figure 136:
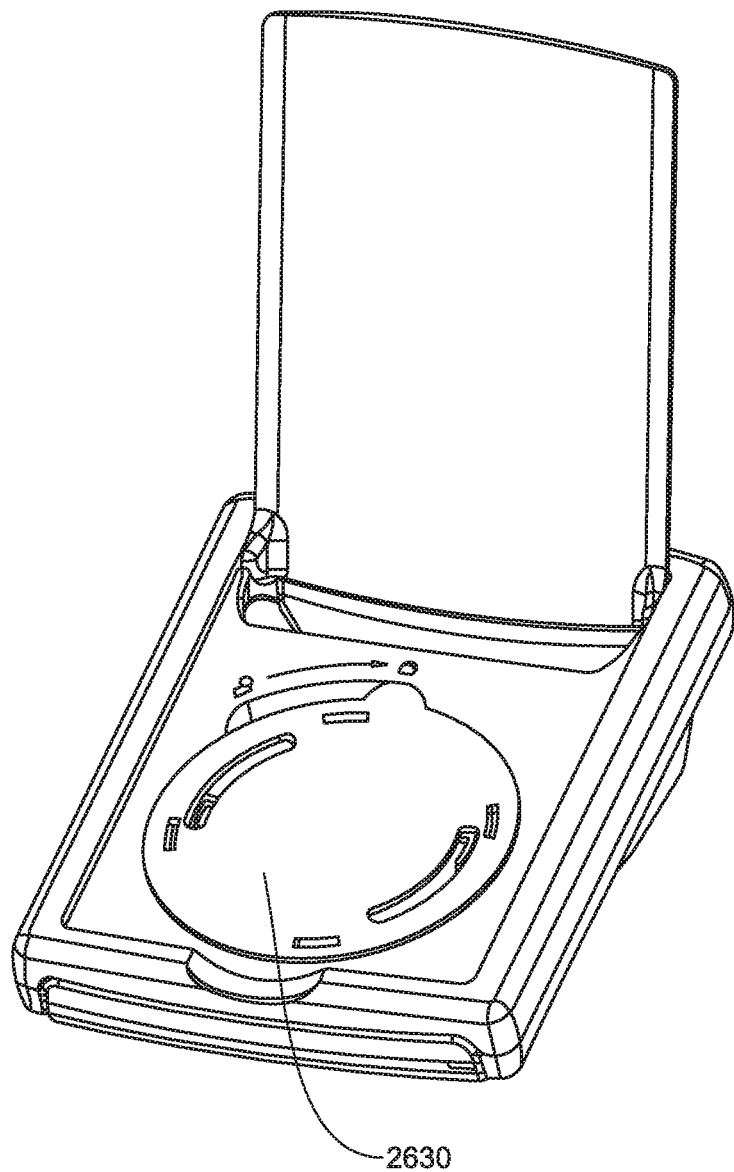
Figure 137:
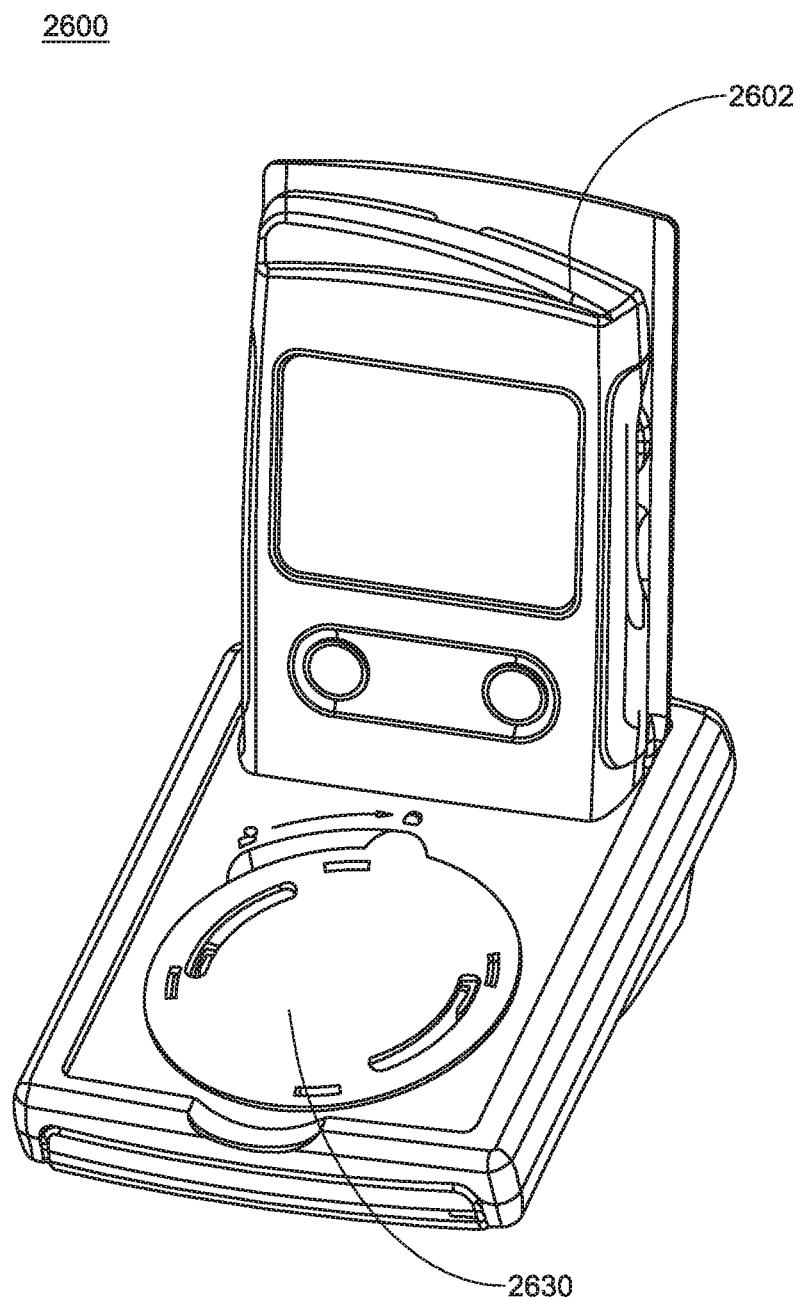
Figure 138:
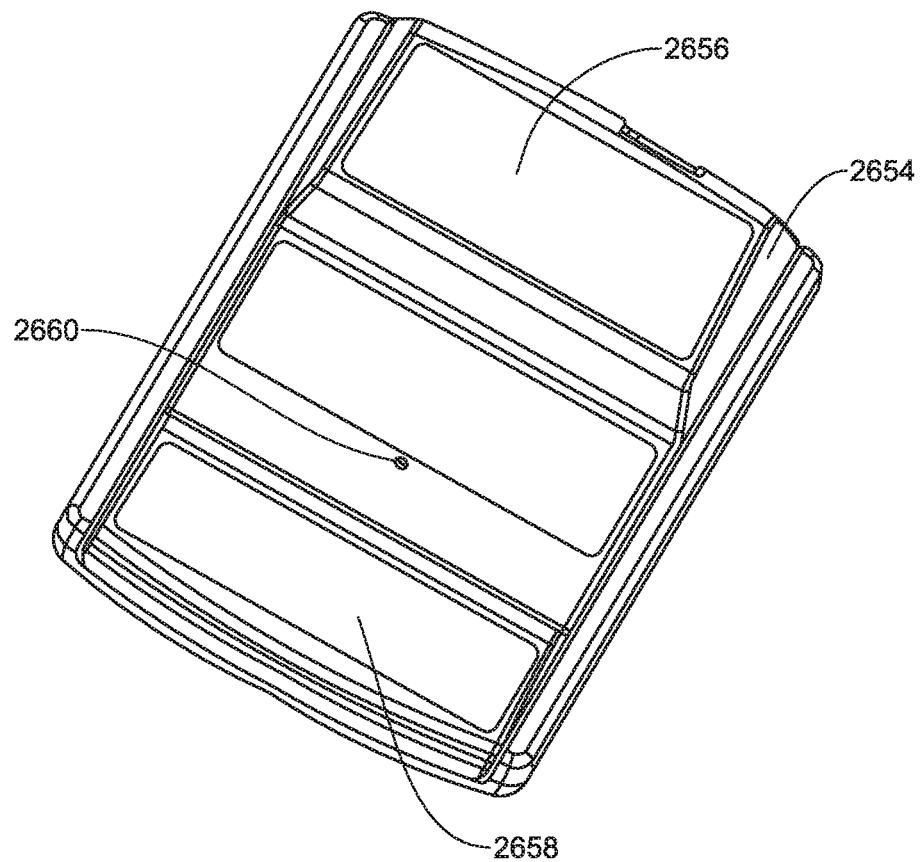
Figure 139:
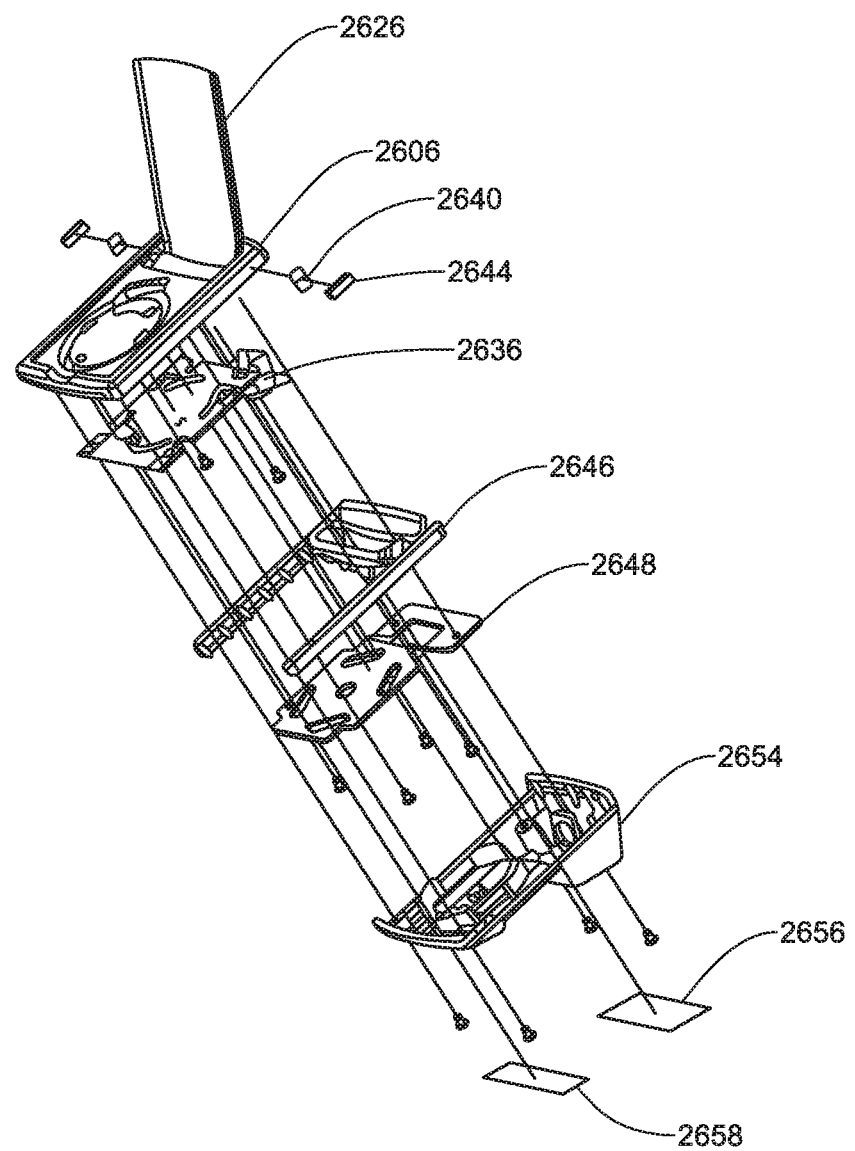

With particular reference also to FIGS. 136-137, charger 2600 may include lock cover 2630, e.g., which may at least partially conceal and/or protect reusable housing assembly charging portion 2604 when not in use (e.g., when a reusable housing assembly is not being charged or stored on charger 2600). In a similar manner to reusable housing assembly 802, lock cover 2630 may include one or more locking tabs that may interact with the locking tabs of charger 2600 (e.g., locking tabs 2614, 2616, 2618) to allow releasable engagement of lock cover 2630 with reusable housing assembly charging portion 2604. As shown in FIG. 137, lock cover 2630 may provide protection for/concealment of reusable housing assembly charging portion 2604, e.g., without impeding access to and/or the use of remote control assembly charging portion 2624. As such, reusable housing assembly charging portion 2604 may be protected/concealed while still allowing remote control assembly 2602 to be charged by/reside in charger 2600. Further, while not shown, when neither reusable housing assembly charging portion 2604 nor remote control assembly charging portion 2624 are in use, lid 2626 may be pivoted to a closed position, e.g., disposed over both reusable housing assembly charging portion 2604 and remote control assembly charging portion 2624. As such, in the closed position lid 2626 may provide protection for charger 2600 when charger 2600 is not in use.

Figure 140:
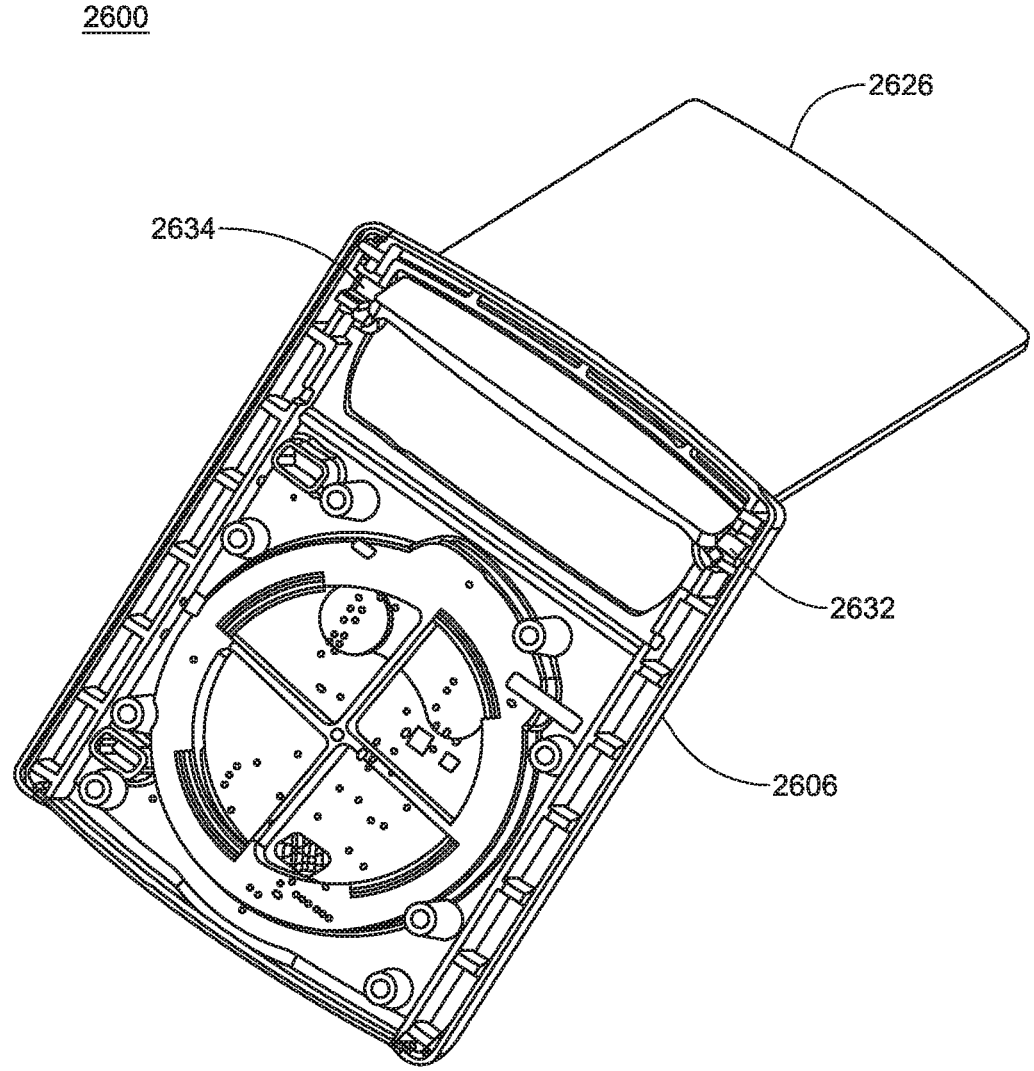
Figure 141:
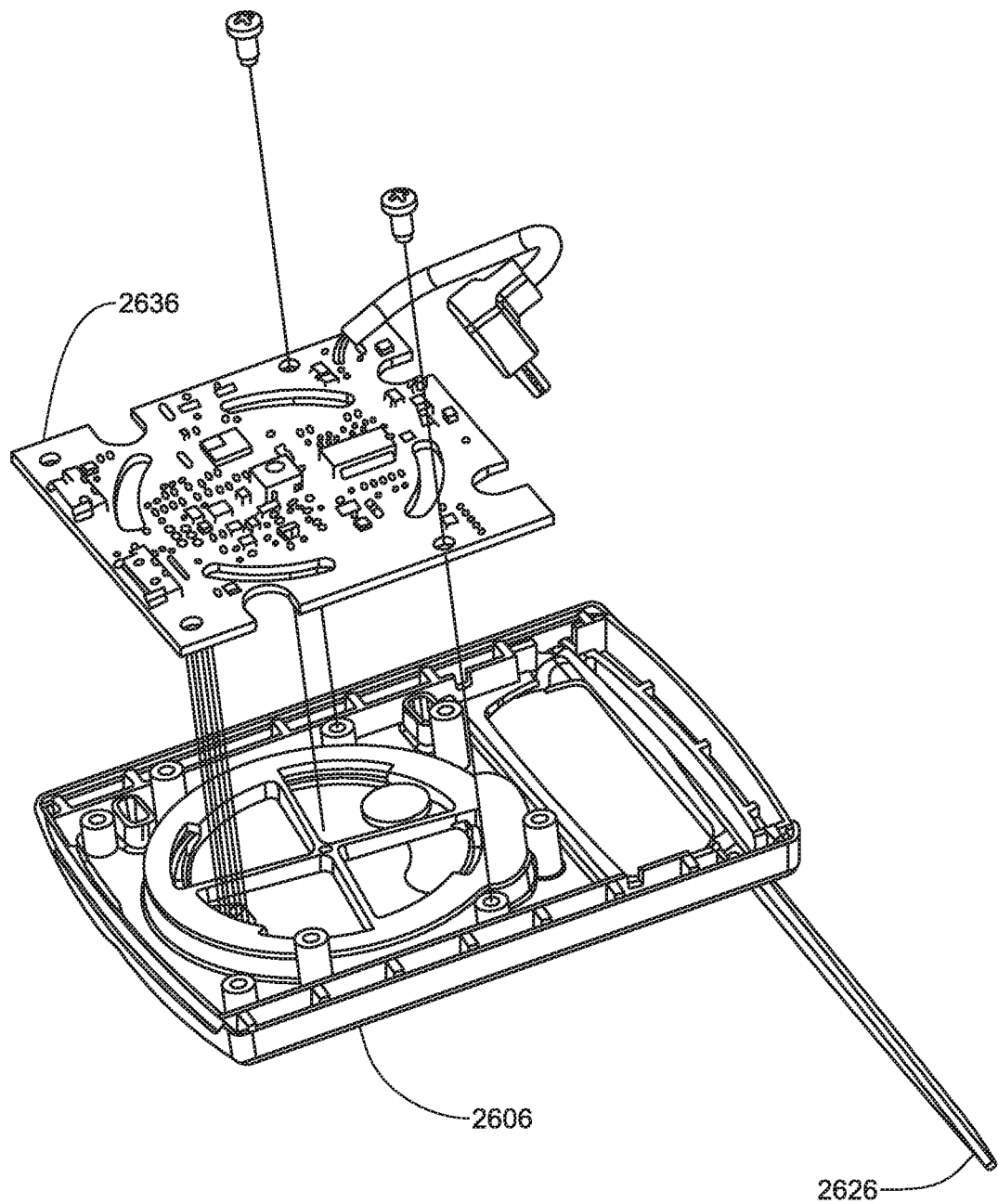
Figure 142:
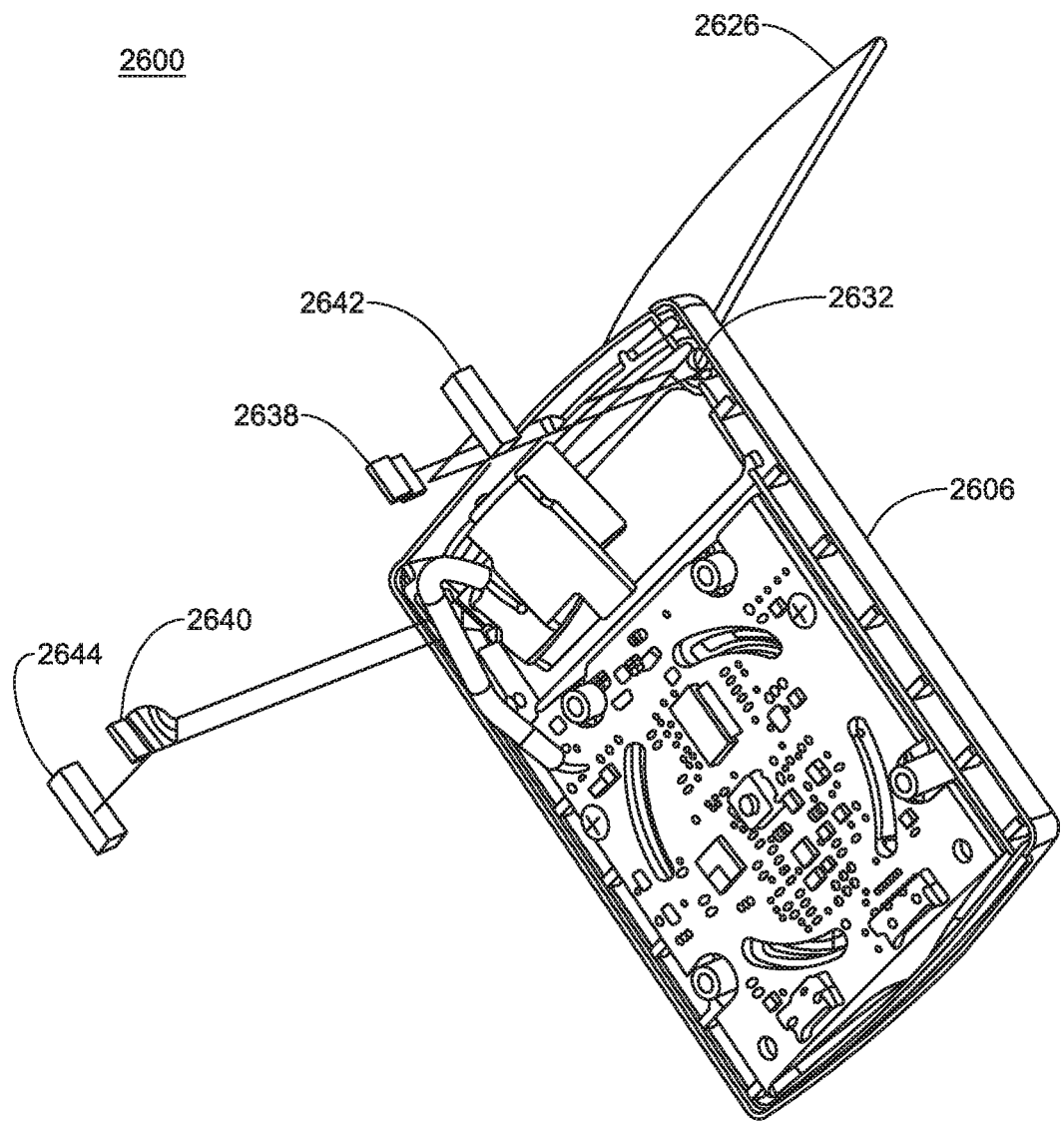

Referring also to FIGS. 139-145, charger 2600 is shown in various exploded, and partially exploded views. As shown, lid 2626 may include integrated shaft portions 2632, 2634 that may be at least partially received in cooperating recesses in the rear of top cover 2606 (FIG. 140). Printed circuit board 2636, including the various electronics associated with charger 2600, may be mounted to the rear or top cover 2606, e.g., using screws, heat-staked posts, or other suitable fastening means (FIG. 141). Lid closure features 2638, 2640 may be received in top cover 2606 at least partially engaging shaft portions 2632, 2634. Bias members 2642, 2644 may bias lid closure features 2638, 2640 into engagement with shaft portions 2632, 2634 (FIG. 142). Bias members 2642, 2644 may include a resilient material, such as silicone, rubber, or the like, and/or may include springs or other biasing structures. In one embodiment, shaft portions 2632, 2634 may include features (e.g., flatted regions, etc.) that may interact with lid closure features 2638, 2640 when lid 2626 is in, or close to, a fully open and/or a fully closed position. The interaction between lid closure features 2638, 2640 and shaft portions 2632, 2634 may bias lid 2626 to the fully open and/or the fully closed position.

Figure 143:
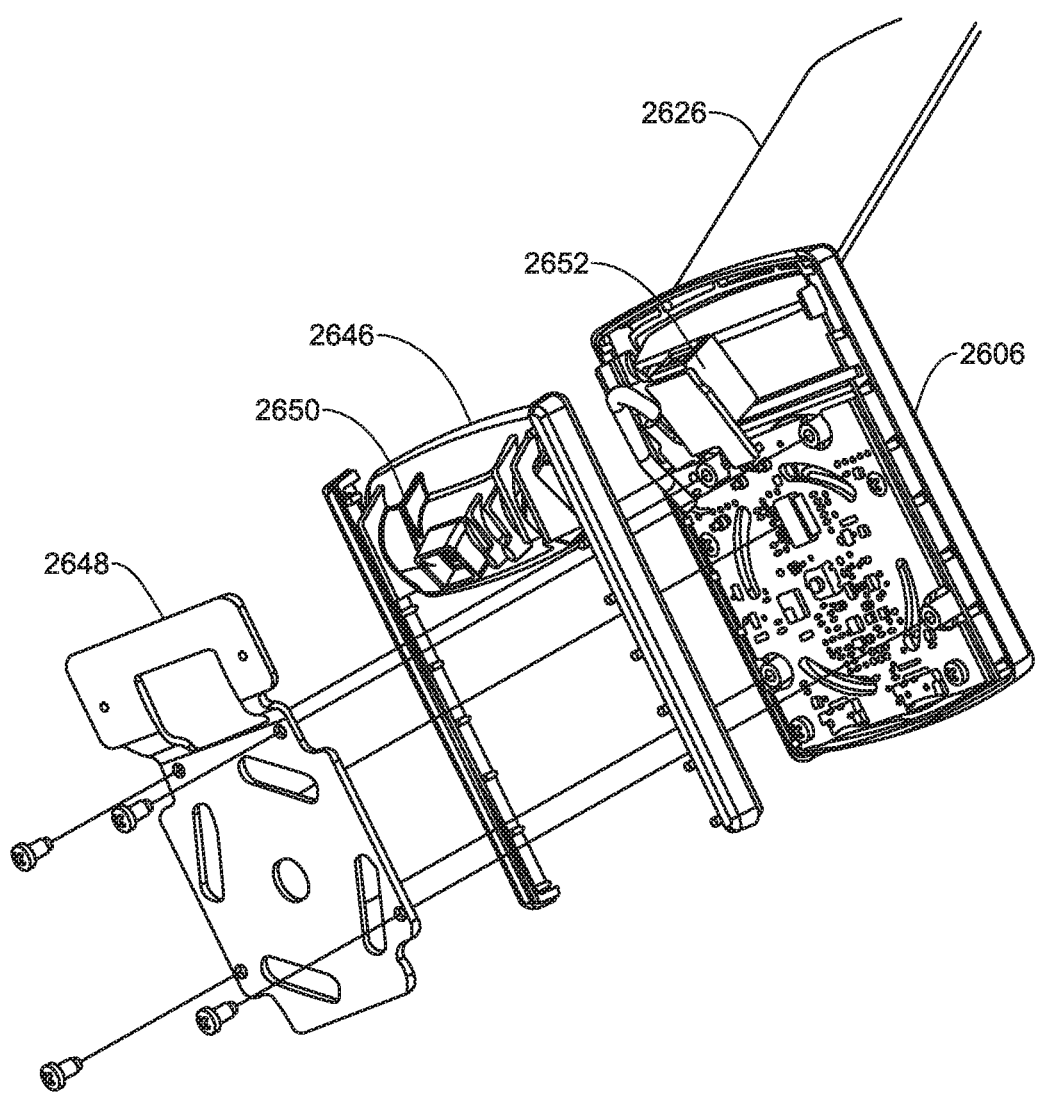

Intermediate tray 2646 may be secured to top cover 2606 via plate 2648, which may itself be secured to top cover 2606 using screws, heat-stake posts, adhesive, or other suitable fastening means (FIG. 143). Intermediate tray 2646 may include a recess at least partially defining the remote control assembly charging portion 2624 of charger 2600. Additionally, intermediate tray 2646 may include opening 2650 configured to at least partially receive electrical connector 2652 coupled to printed circuit board 2636 (e.g., capable of establishing an electrical connection between charger 2600 and remote control assembly 2602). Plate 2648 may include, for example, a stamped metal plate. Additionally, plate 2648 may increase the weight of charger 2600, which may allow charger 2600 to resist tipping and/or facilitate one handed installation/removal of reusable housing assembly 802 on charger 2600. For example, the weight added by plate 2648 may allow charger to be tilted rearwardly between about 15-30 degrees without tipping over. The degree of rearward tilt achievable before charger 2600 tips over may vary depending upon, for example, the weight of plate 2648, weight distribution, center of gravity, and the like, and may be varied according to design criteria.

Figure 144:
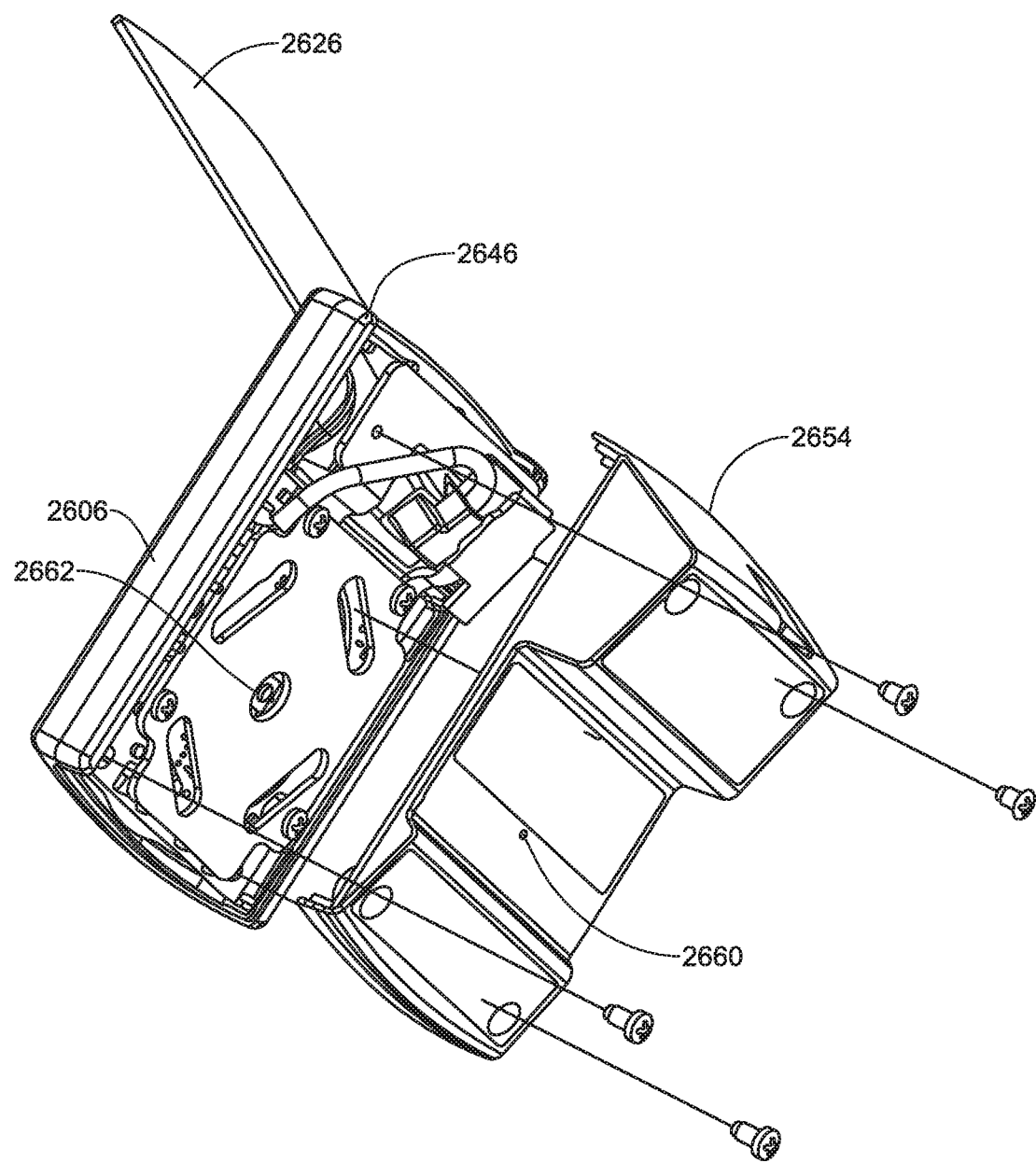
Figure 145:
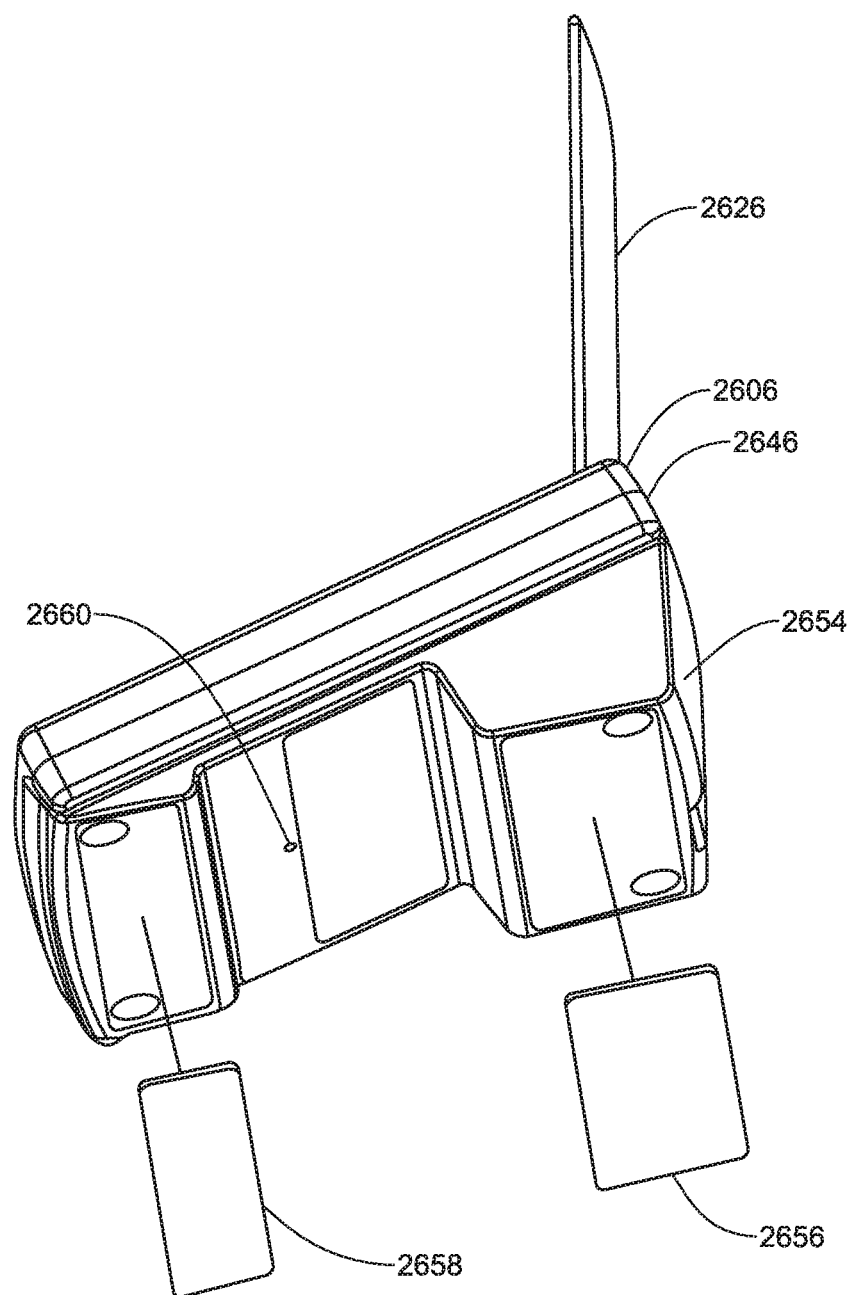
Figure 155B:
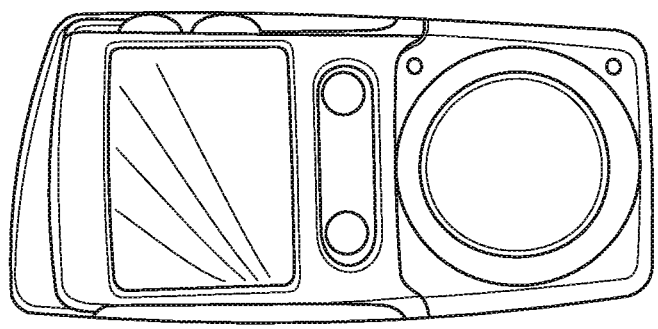
Figure 155A:
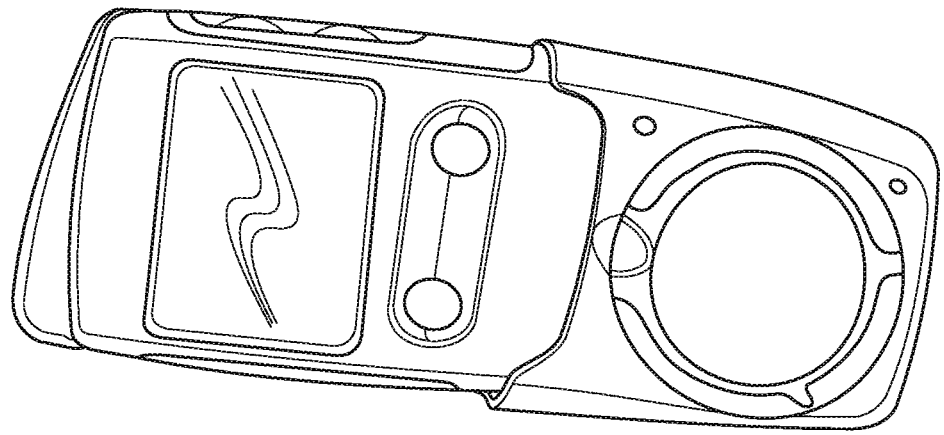
Figures 161A, 161B:
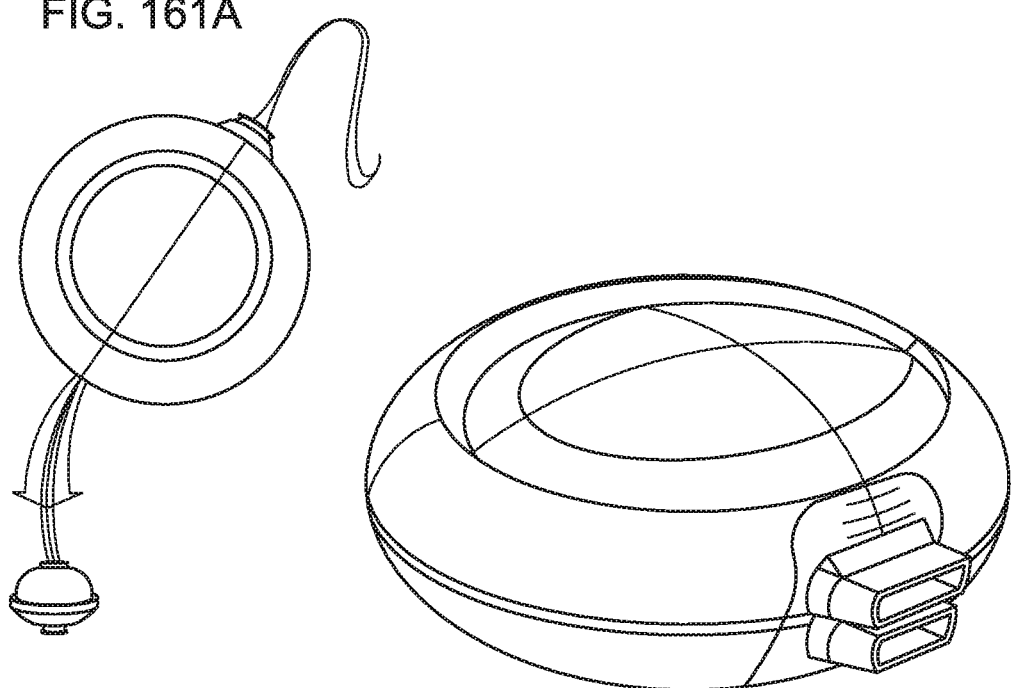
Figure 163A:
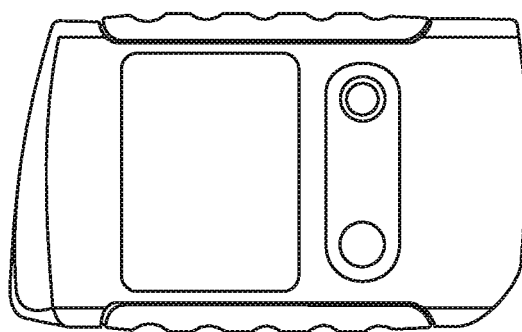
Figure 163B:
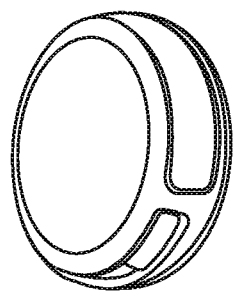
Figure 163C:
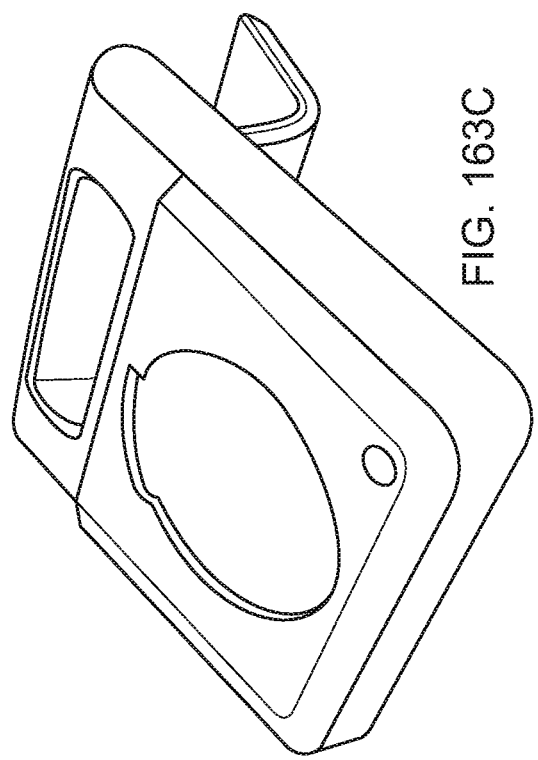
Figure 166:
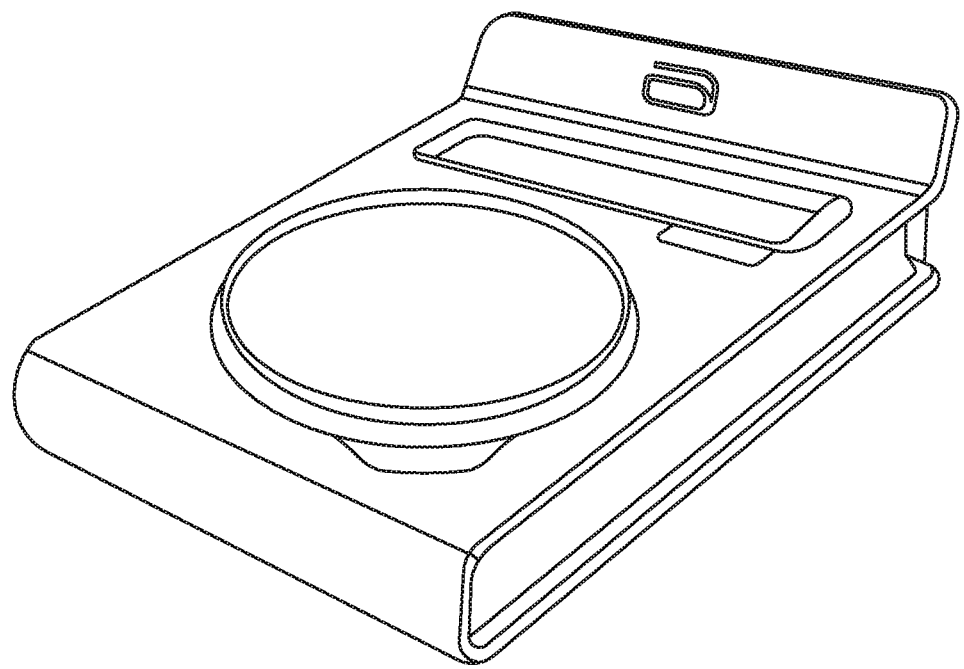
Figure 167:
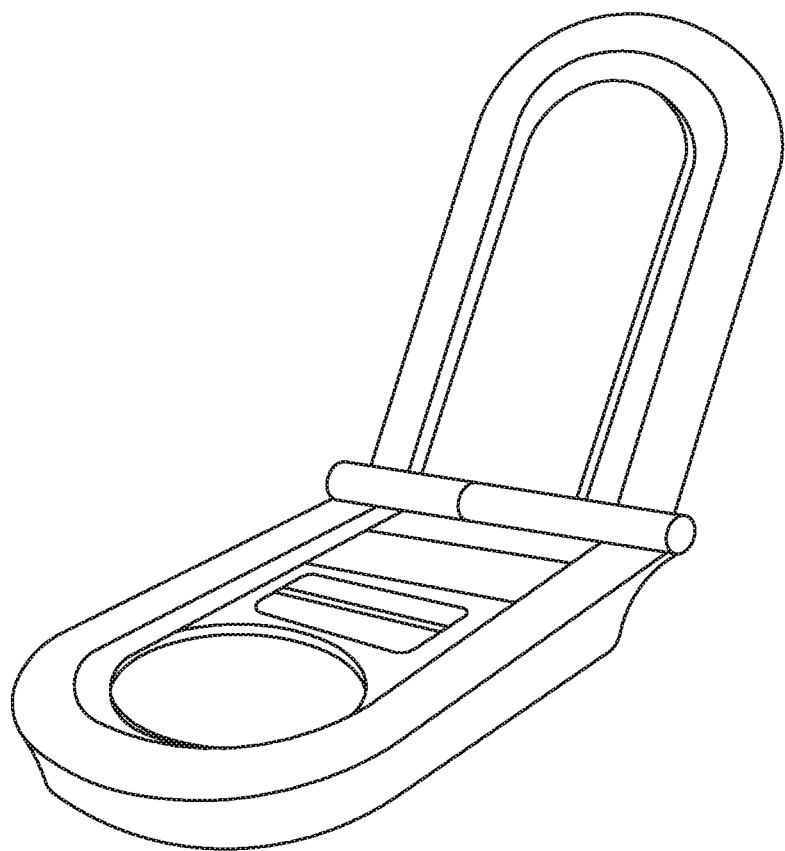
Figures 171A, 171B:
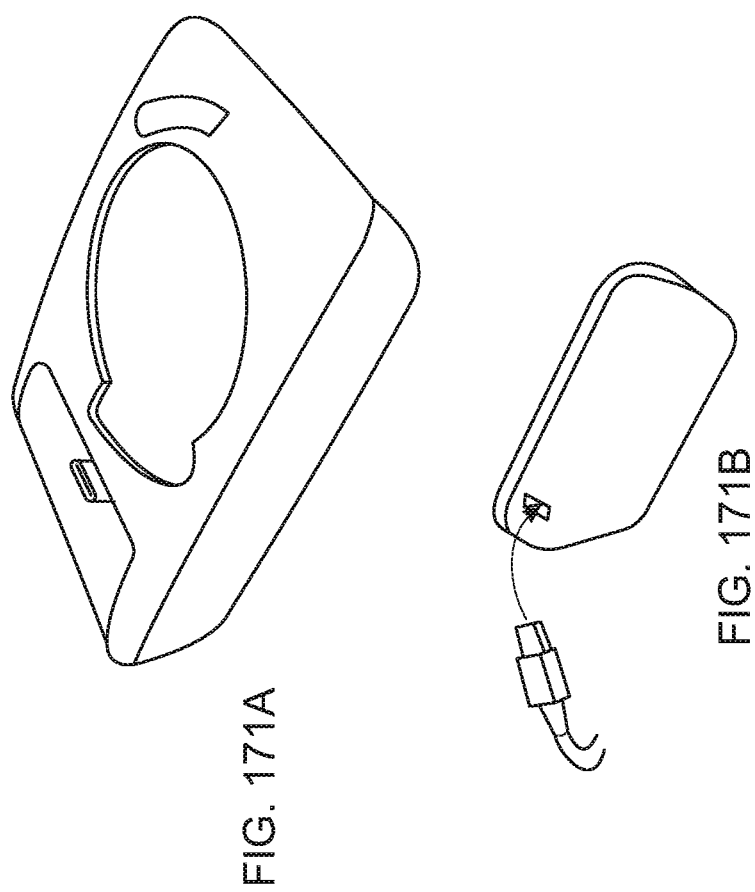
Figure 174:
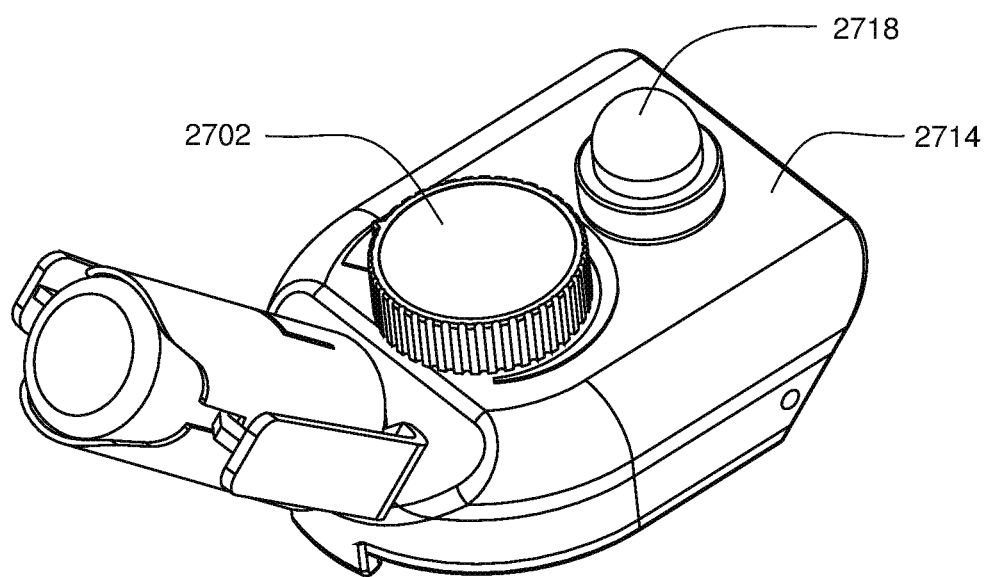
Figure 174A:
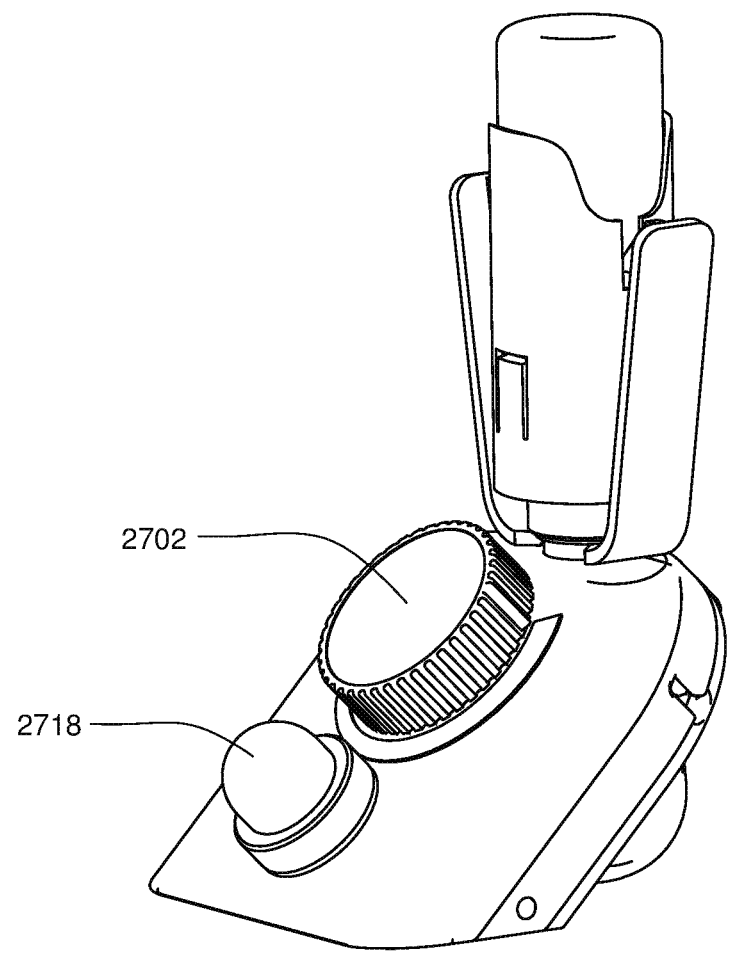
Figure 175:
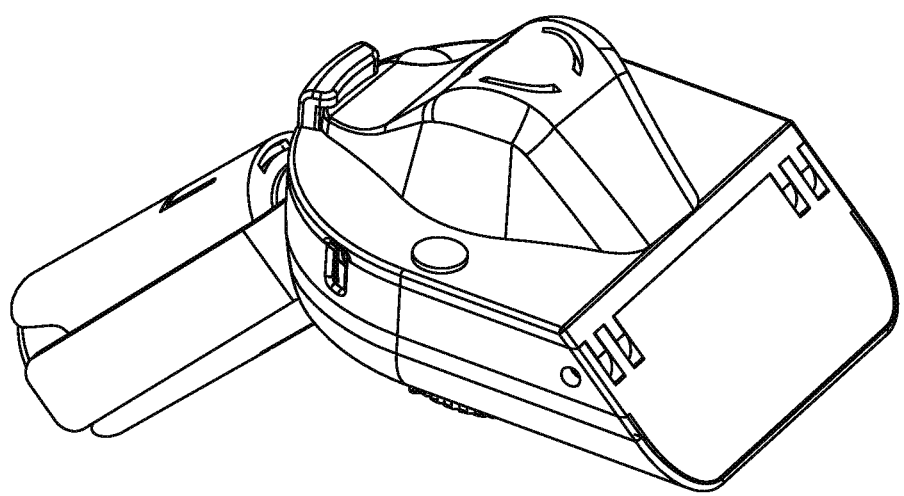
Figure 176:
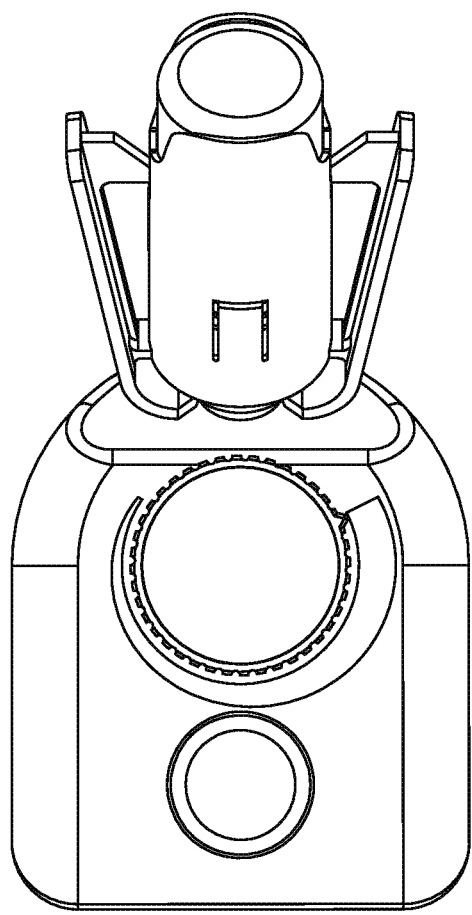
Figure 177:
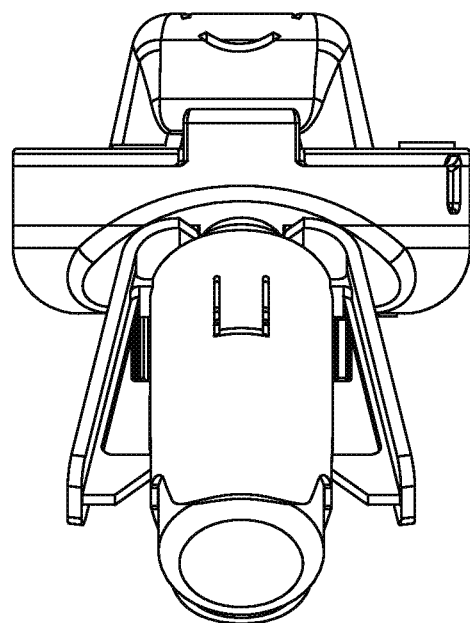
Figure 178:
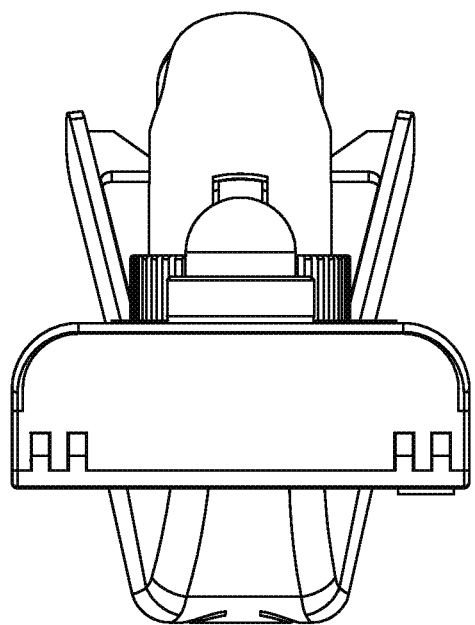
Figure 179:
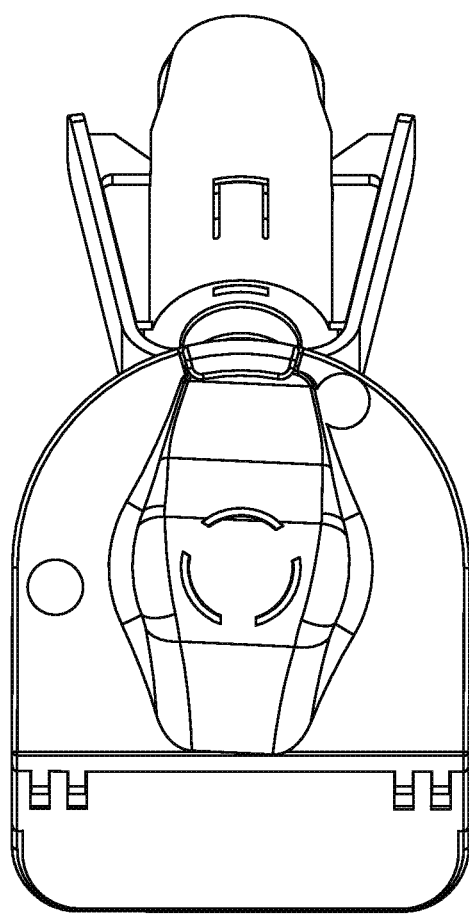
Figure 180:
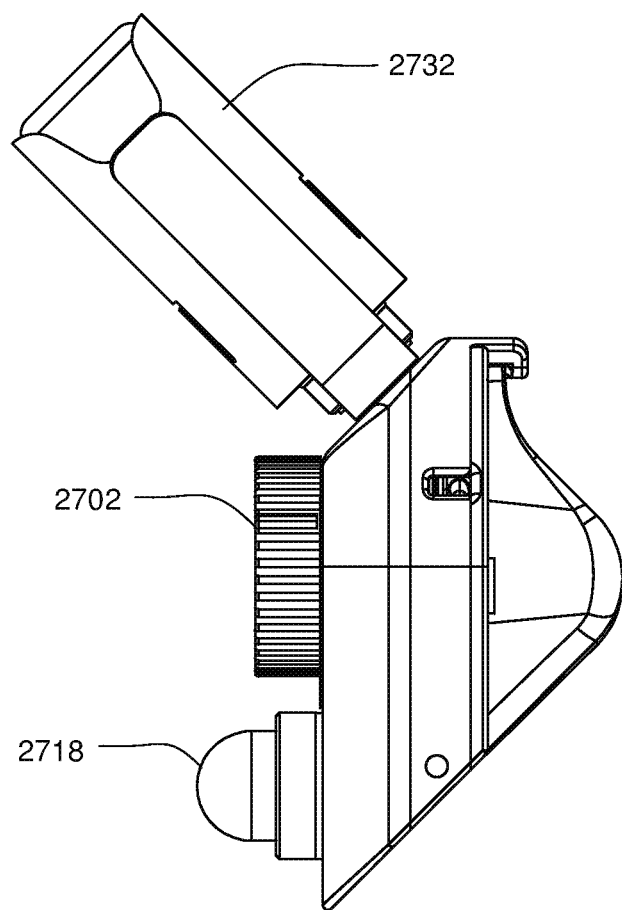

Bottom cover 2654 may be coupled to top cover 2606 and/or intermediate tray 2646 via suitable fastening means, including, but not limited to, screws that may be secured to one or more of plate 2648, top cover 2606, and/or intermediate tray 2646. In an embodiment in which bottom cover 2654 may be coupled via screws, foot pads 2656, 2658 may be disposed over the screws and/or screw recesses of bottom cover 2654 (FIGS. 144-145). Additionally, foot pads 2656, 2658 may include a relatively high friction material (e.g., urethane foam or elastomer, rubber, or the like) that may increase the slip resistance of charger 2600 relative to a surface upon which charger 2600 is disposed. Further, bottom cover 2654 may include opening 2660 that may allow access to reset button 2662, e.g., which may be disposed on printed circuit board 2636.

According to one embodiment, charger 2600 may utilize a mini-USB connection, e.g., which may provide power to charger 2600 as well as allowing data communication, e.g., between charger 2600 and an external computer (such as a personal computer, or the like). In some embodiments, charger 2600 may utilize a modified mini-USB connection, e.g., which may have the square table of the mini-USB-A plug removed to facilitate extraction of the plug from charger 2600. Accordingly, charger 2600 may allow for the charging of batteries associated with reusable housing assembly 802 and/or remote control assembly 2602, as well as communication between remote control assembly 2602, reusable housing assembly 802, and an external computer. Such communication may allow for, for example, downloading of logs from reusable housing assembly 802 (e.g., which may be transmitted via the internet, or other communication network, to a customer support service), reprogramming (e.g., upgrading software, conducting diagnostics, changing program attributes, etc.) of reusable housing assembly 802 and/or remote control assembly 2602.

Charger 2600 may include one or more status indicators (such as LEDs) that may indicate a charging status (e.g., charging in process, charging complete), as well as one or more fault conditions. For example, a red and a green LED may be utilized in connection with one or both of reusable housing assembly 802 and remote control assembly 2602. The red and green LED may be visually perceptible through top cover 2606 of charger, via a thinned region of top cover 2606, one or more openings in top cover 2606, or the like. For example, in one embodiment, a continuously glowing red LED may indicate that the reusable housing assembly is currently being charged. A continuously glowing green LED may indicate that the reusable housing assembly is completely charged. A blinking red LED may indicate a fault condition that may require user intervention. In addition to the blinking red LED, in some embodiments, the exact nature of the fault condition may be displayed on a display screen associated with the remote control assembly. The absence of the red and the green LED being illuminated may indicate that no device is coupled (or is not properly coupled) to charger 2600. Various additional/alternative status indicator arrangements may be implemented depending upon design criteria and user preference. In some embodiments, charger 2600 may include one LED as a status indicator for reusable housing assembly 802 and remote control assembly 2602 may itself indicate status via a screen of/associated with remote control assembly 2602 or other status indicators on remote control assembly 2602. Such other status indicators may include, but are note limited to, alarms (e.g., audio and/or vibration) and/or one or more LEDs.

In addition to the status indicators, which may indicate charging status and the occurrence of a fault condition, charger 2600 may include one or more overvoltage protection circuitry. In an embodiment, charger 2600 may include input overvoltage protection circuitry, which may actuate (e.g., via opening the circuit, etc.) in the event that the voltage provided by the USB connection is greater than a predetermined threshold. Additionally/alternatively, charger 2600 may include output overvoltage protection circuitry, which may actuate (e.g., via opening the circuit, etc.) in the event that the voltage provide to the reusable housing assembly and/or the remote control assembly is greater than a predetermined threshold. Additionally, the battery of the reusable housing assembly and/or of the remote control assembly may include an overvoltage protection, e.g., which may prevent battery damage resulting from an overvoltage event at the battery, which may not be prevented by either the input overvoltage protection circuitry or the output overvoltage protection circuitry. According to an embodiment, the overvoltage protection circuitry may be hardware based, i.e., may not rely upon software. As such, the overvoltage protection circuitry may provide a higher level of safety, as it may not be subject to software faults. Additionally, according to one embodiment, the occurrence of an overvoltage event may trigger a fault condition indicator (e.g., a blinking LED, or the like).

Figure 134:
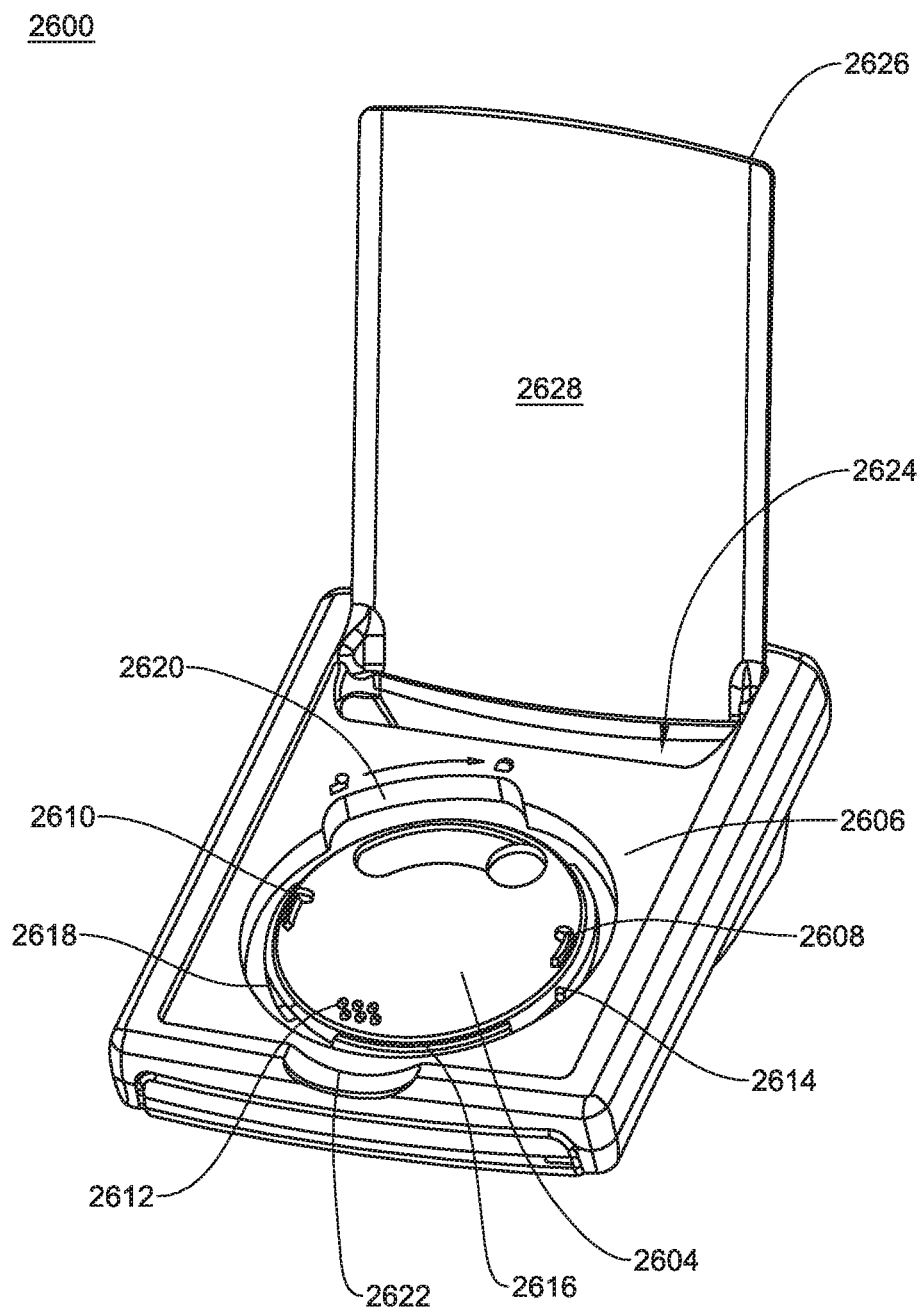
FIGS. 134-145 depict an embodiment of a charger, including various perspective views, exploded views, and partially exploded views.
Figure 135:
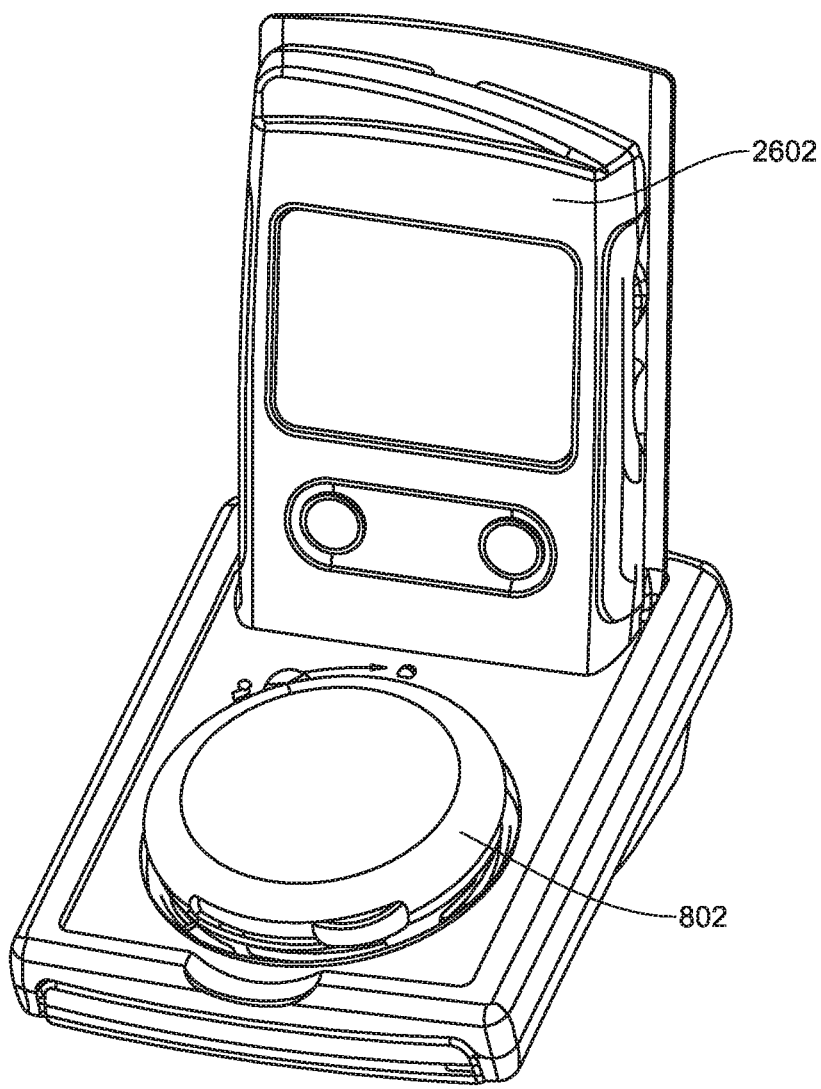

As shown, e.g., in FIG. 134, charger 2600 may utilize a six contact electrical connector (e.g., electrical contacts 2612). According to an embodiment, the six contact electrical connector may allow for power transfer between charger 2600 and reusable housing assembly 802. Additionally, the six contact electrical connector may allow connection between a battery thermister and charging circuitry (e.g., which may allow charging to be discontinued and/or provide a fault condition indication in the event that the battery temperature is out of range). Further, the six contact electrical connector may provide for two-way communication between reusable housing assembly 802 and charger 2600 (as well as between reusable housing assembly 802 and an external computer via charger 2600). The two-way communication may allow for, for example, reprogramming of reusable housing assembly 802 (e.g., to upgrade software), obtaining data from reusable housing assembly 802 (e.g., such as log information to be sent to customer service center), or the like. The six contact electrical connector may also allow reusable housing assembly 802 (e.g., circuitry within the reusable housing assembly) to be reset, either as a result of a reset signal originating from an external computer, or as a result of reset button 2662 being actuated. Resetting reusable housing assembly 802 may be utilized for certain functions, such as programming reusable housing assembly, diagnostic purposes, resetting a malfunctioning reusable housing assembly, or the like. Additionally, the six contact electrical connector may allow charger 2600 to recognize that a reusable housing assembly has been coupled to charger 2600. Similarly, the six contact electrical connector may allow reusable housing assembly 802 to recognize that it has been coupled to charger 2600. The ability of reusable housing assembly 802 to recognize that it has been coupled to charger 2600 may allow, for example, reusable housing assembly 802 to enter a low power state while charger, initiate download of logs, or the like. While the various features of the electrical connection between charger 2600 and reusable housing assembly 802 have been described, it will be appreciated that similar electrical connections may be utilized between charger 2600 and remote control assembly 2602. Additionally, while the use of a six contact electrical connector has been discussed, this is for exemplary purposes only, as the number and nature of electrical contacts and associated features may vary depending upon user need and design criteria.

According to one embodiment, the electronics of charger 2600 may include a commercially available charging circuit, such as a model L6924D Battery Charger System with Integrated Power Switch for Li-Ion/Li-Polymer, available from STMicroelectronics of Geneva, Switzerland. Various other battery charging circuits may be utilized depending upon, for example, battery characteristics, design criteria, or the like. The battery charging circuit may, for example, monitor battery voltage and temperature (e.g., via information provided by the battery thermister via the six contact electrical connector). Additionally, the battery charging circuit may adjust the battery charging parameters based upon, for example, the battery voltage, battery temperature, predetermined charging requirements (e.g., desired charge time, etc.) or the like.

In addition to the charging circuit, the electronics of charger 2600 may additionally include one or more processors (example of which may include, but is not limited to an MSP430 microcontroller, available from Texas Instruments Inc. of Dallas, Tex.) that may control charger 2600, as well as provide for communication between an external computer and reusable housing assembly 802 and/or remote control assembly 2602. The one or more microprocessors may control the overall operation of charger 2600. For example, the microprocessor may allow communication between reusable housing assembly 802 and an external computer. Similarly, the microprocessor may control the operation of the status indicators (e.g., the LEDs). Various additional/ alternative operations and features of charger 2600 may be controlled by the microprocessor.

Referring also to FIGS. 146-148, exemplary charger circuitry that may be utilized in connection with charger 2600 is schematically illustrated. The illustrated charger circuitry is intended of illustrative purposes only, as the exact configuration may vary depending upon included features (status indicators, overvoltage protection, and the like), as well the charging circuit and microcontroller utilized.

Referring also to FIGS. 149-173 various features and embodiments of chargers that may be utilized in connection with the reusable housing assembly and/or remote control assembly are depicted. Any of the depicted chargers may incorporate one or more of the above-described features.

Infusion pump therapy may include volume and time specifications. The amount of fluid dispensed together with the dispense timing may be two critical factors of infusion pump therapy. As discussed in detail below, the infusion pump apparatus and systems described herein may provide for a method of dispensing fluid together with a device, system and method for measuring the amount of fluid dispensed. However, in a circumstance where the calibration and precision of the measurement device calibration is critical, there may be advantages to determining any compromise in the precision of the measurement device as soon as possible. Thus, there are advantages to off-board verification of volume and pumping.

As discussed above, infusion pump assembly 100 may include volume sensor assembly 148 configured to monitor the amount of fluid infused by infusion pump assembly 100. Further and as discussed above, infusion pump assembly 100 may be configured so that the volume measurements produced by volume sensor assembly 148 may be used to control, through a feedback loop, the amount of infusible fluid that is infused into the user.

Figure 90B:
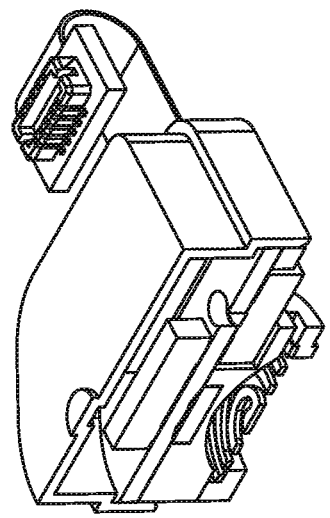
FIGS. 90A-90C are various views of a volume sensor assembly included within the infusion pump assembly of FIG. 1.
Figure 90A:
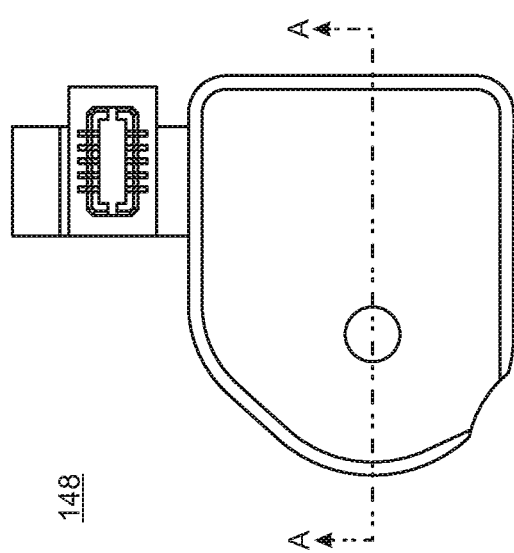
Figure 90C:
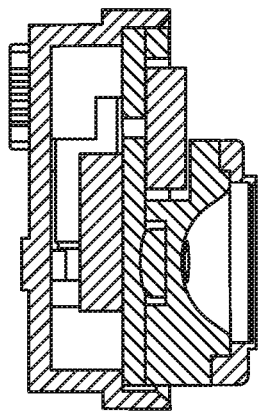
Figure 94C:
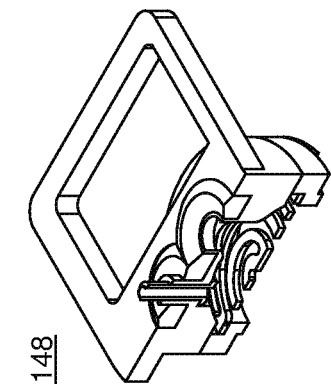
FIGS. 94A-94F are various views of a volume sensor assembly included within the infusion pump assembly of FIG. 1.
Figure 94F:
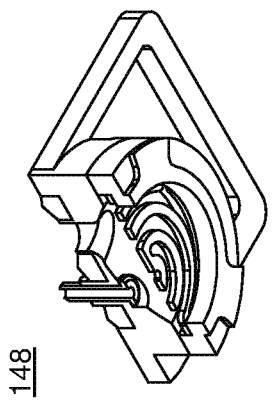
Figure 94B:
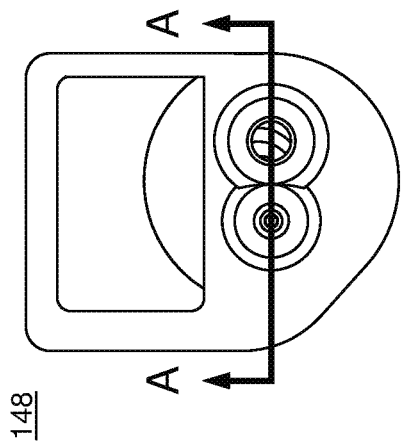
Figure 94E:
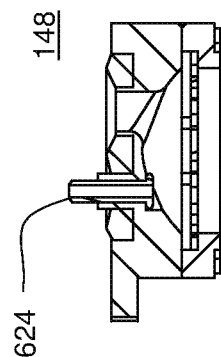
Figure 94A:
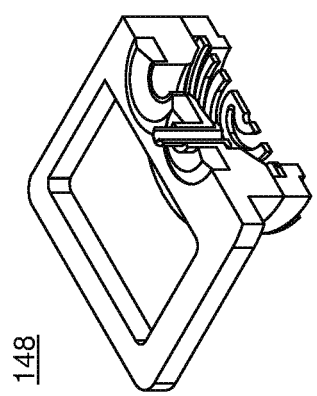
Figure 94D:
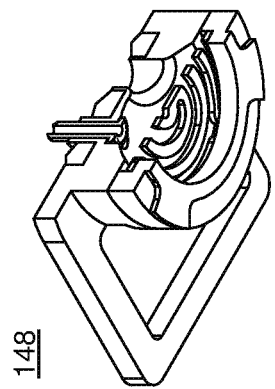
Figure 95:
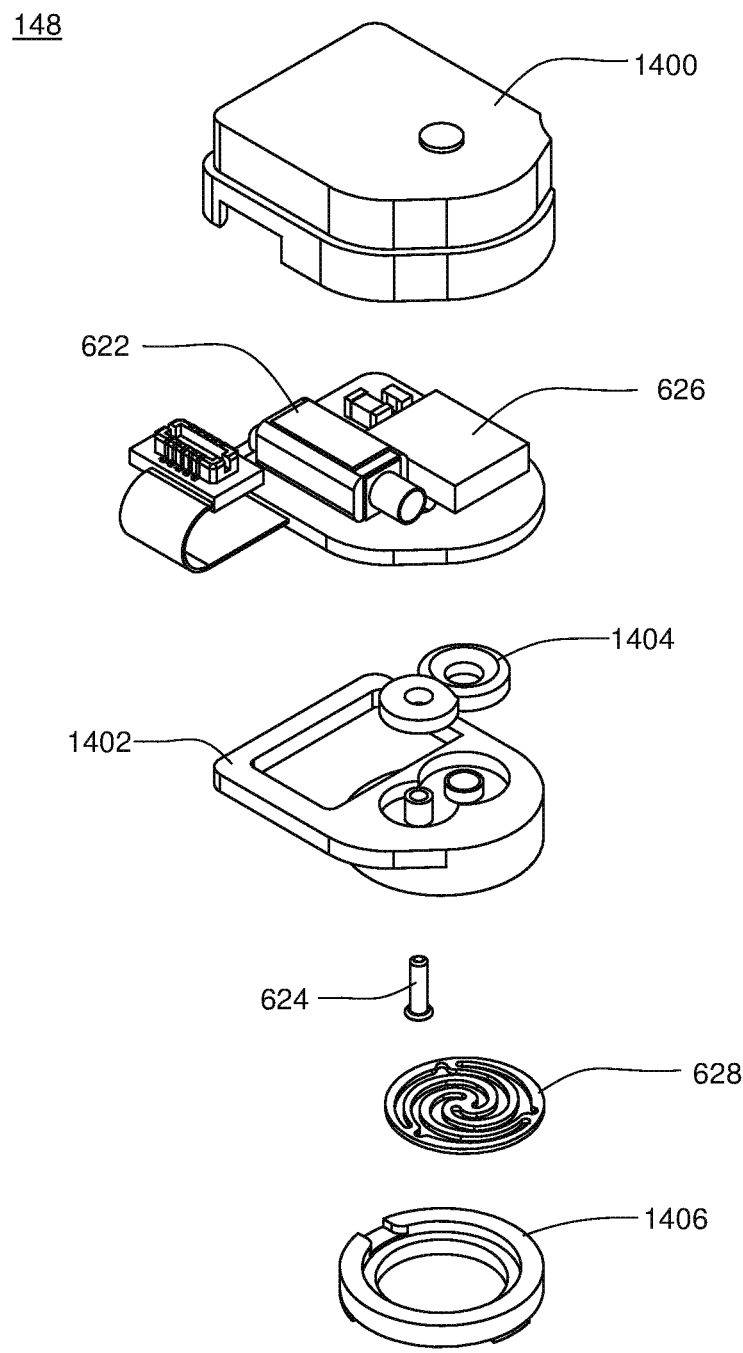
FIG. 95 is an exploded view of a volume sensor assembly included within the infusion pump assembly of FIG. 1.

Referring also to FIGS. 90A-90C, there is shown one diagrammatic view and two cross-sectional views of volume sensor assembly 148. Referring also to FIGS. 91A-91I, there is shown various isometric and diagrammatic views of volume sensor assembly 148 (which is shown to include upper housing 1400). Referring also to FIGS. 92A-92I, there is shown various isometric and diagrammatic views of volume sensor assembly 148 (with upper housing 1400 removed), exposing speaker assembly 622, reference microphone 626, and printed circuit board assembly 830. Referring also to FIGS. 93A-93I, there is shown various isometric and diagrammatic views of volume sensor assembly 148 (with printed circuit board assembly 830 removed), exposing port assembly 624. Referring also to FIGS. 94A-94F, there is shown various isometric and diagrammatic cross-sectional views of volume sensor assembly 148 (with printed circuit board assembly 830 removed), exposing port assembly 624. Referring also to FIG. 95, there are shown an exploded view of volume sensor assembly 148, exposing upper housing 1400, speaker assembly 622, reference microphone 626, seal assembly 1404, lower housing 1402, port assembly 624, spring diaphragm 628, and retaining ring assembly 1406.

Figure 96:
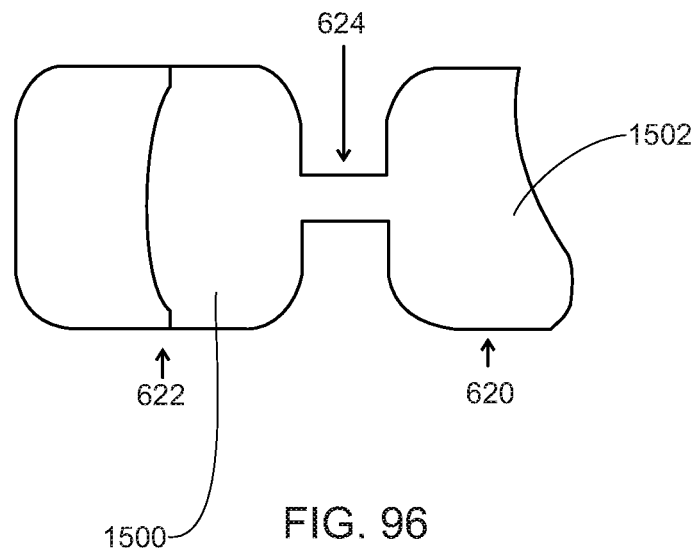
FIG. 96 is a diagrammatic view of a volume sensor assembly included within the infusion pump assembly of FIG. 1.

The following discussion concerns the design and operation of volume sensor assembly 148 (which is shown in a simplified form in FIG. 96). For the following discussion, the following nomenclature may be used:

| Symbols | |
|---|---|
| P | Pressure |
| p | Pressure Perturbation |
| V | Volume |
| v | Volume Perturbation |
| γ | Specific Heat Ratio |
| R | Gas Constant |
| ρ | Density |
| Z | Impedance |
| f | Flow friction |
| A | Cross sectional Area |
| L | Length |
| ω | Frequency |
| ζ | Damping ratio |
| α | Volume Ratio |
| Subscripts | |
| 0 | Speaker Volume |
| 1 | Reference Volume |
| 2 | Variable Volume |
| k | Speaker |
| r | Resonant Port |
| z | Zero |
| p | Pole |

Derivation of the Equations for Volume Sensor Assembly 148:

Modeling the Acoustic Volumes

The pressure and volume of an ideal adiabatic gas may be related by:

$$PV^\gamma = K \quad [\text{EQ \#1}]$$

where K is a constant defined by the initial conditions of the system.

EQ #1 may be written in terms of a mean pressure, P, and volume, V, and a small time-dependent perturbation on top of those pressures, p(t), v(t) as follows:

$$(P+p(t))(V+v(t))^\gamma = K \quad [\text{EQ \#2}]$$

Differentiating this equation may result in:

$$\dot{p}(t)V+v(t))^\gamma + \gamma(V+v(t))^{\gamma-1}(P+p(t))\dot{v}(t) = 0 \quad [\text{EQ \#3}]$$

which may simplify to:

$$\dot{p}(t) + \gamma \frac{P+p(t)}{V+v(t)} \dot{v}(t) = 0 \quad [\text{EQ\#4}]$$

If the acoustic pressure levels are much less than the ambient pressure, the equation may be further simplified to:

$$\dot{p}(t) = \frac{\gamma P}{V} \dot{v}(t) = 0 \quad [\text{EQ\#5}]$$

How good is this assumption? Using the adiabatic relation it may be shown that:

$$\frac{P}{V} = \left(\frac{P+p(t)}{V+v(t)}\right)\left(\frac{P+p(t)}{P}\right)^{-\frac{\gamma+1}{\gamma}} \quad [\text{EQ\#6}]$$

Accordingly, the error in the assumption would be:

$$\text{error} = 1 - \left(\frac{P+p(t)}{P}\right)^{-\frac{\gamma+1}{\gamma}} \quad [\text{EQ\#7}]$$

A very loud acoustic signal (120 dB) may correspond to pressure sine wave with amplitude of roughly 20 Pascal. Assuming air at atmospheric conditions (γ=1.4, P=101325 Pa), the resulting error is 0.03%. The conversion from dB to Pa is as follows:

$$\lambda = 20\log_{10}\left(\frac{p_{rms}}{p_{ref}}\right) \text{ or } p_{rms} = p_{ref} 10^{\frac{\lambda}{20}} \quad [\text{EQ\#8}]$$

where $p_{ref}$=20·μPa.

Applying the ideal gas law, P=ρRT, and substituting in for pressure may result in the following:

$$\dot{p}(t) + \frac{\gamma RT\rho}{V} \dot{v}(t) = 0 \quad [\text{EQ\#9}]$$

EQ #9 may be written in terms of the speed of sound, a=$\sqrt{\gamma RT}$ as follows:

$$\dot{p}(t) + \frac{\rho a^2}{V}\dot{v}(t) = 0 \quad [EQ\#10]$$

Acoustic impedance for a volume may be defined as follows:

$$Z_v = \frac{p(t)}{\dot{v}(t)} = -\frac{1}{\left(\frac{V}{\rho a^2}\right)s} \quad [EQ\#11]$$

Modeling the Acoustic Port

The acoustic port may be modeled assuming that all of the fluid in the port essentially moves as a rigid cylinder reciprocating in the axial direction. All of the fluid in the channel is assumed to travel at the same velocity, the channel is assumed to be of constant cross section, and the "end effects" resulting from the fluid entering and leaving the channel are neglected.

If we assume laminar flow friction of the form $\Delta p = f \rho \dot{v}$, the friction force acting on the mass of fluid in the channel may be written as follows:

$$F = f\rho A^2 \dot{x} \quad [EQ\ \#12]$$

A second order differential equation may then be written for the dynamics of the fluid in the channel:

$$\rho L A \ddot{x} = \Delta p A - f \rho A^2 \dot{x} \quad [EQ\ \#13]$$

or, in terms of volume flow rate:

$$\ddot{v} = -\frac{fA}{L}\dot{v} + \Delta p \frac{A}{\rho L} \quad [EQ\#14]$$

The acoustic impedance of the channel may then be written as follows:

$$Z_p = \frac{\Delta p}{\dot{v}} = \frac{\rho L}{A}\left(s + \frac{fA}{L}\right) \quad [EQ\#15]$$

System Transfer Functions

Using the volume and port dynamics defined above, volume sensor assembly 148 may be described by the following system of equations: (k=speaker, r=resonator)

$$\dot{p}_0 - \frac{\rho a^2}{V_0}\dot{v}_k = 0 \quad [EQ\#16]$$

$$\dot{p}_1 + \frac{\rho a^2}{V_1}(\dot{v}_k - \dot{v}_r) = 0 \quad [EQ\#17]$$

$$\dot{p}_2 + \frac{\rho a^2}{V_2}\dot{v}_r = 0 \quad [EQ\#18]$$

$$\ddot{v}_r = -\frac{fA}{L}\dot{v}_r + \frac{A}{\rho L}(p_2 - p_1) \quad [EQ\#19]$$

One equation may be eliminated if $p_0$ is treated as the input substituting in $$\dot{v}_k = \frac{V_0}{\rho a^2}\dot{p}_0.$$

$$\dot{p}_1 + \frac{V_0}{V_1}\dot{p}_0 - \frac{\rho a^2}{V_1}\dot{v}_r = 0 \quad [EQ\#20]$$

$$\dot{p}_2 + \frac{\rho a^2}{V_2}\dot{v}_r = 0 \quad [EQ\#21]$$

$$\ddot{v}_r = -\frac{fA}{L}\dot{v}_r + \frac{A}{\rho L}p_2 - \frac{A}{\rho L}p_1 \quad [EQ\#22]$$

Cross System Transfer Function

The relationship between the speaker volume and the variable volume may be referred to as the Cross System transfer function. This transfer function may be derived from the above equations and is as follows:

$$\frac{p_2}{p_0} = -\frac{V_0}{V_1}\frac{\omega_n^2}{s^2 + 2\zeta\omega_n s + \alpha\omega_n^2} \quad [EQ\#23]$$

where $$\omega_n^2 = \frac{a^2 A}{L}\frac{1}{V_2}, \zeta = \frac{fA}{2L\omega_n} \text{ and } \alpha = \left(1 + \frac{V_2}{V_1}\right) \quad [EQ\#24]$$

Figure 97:
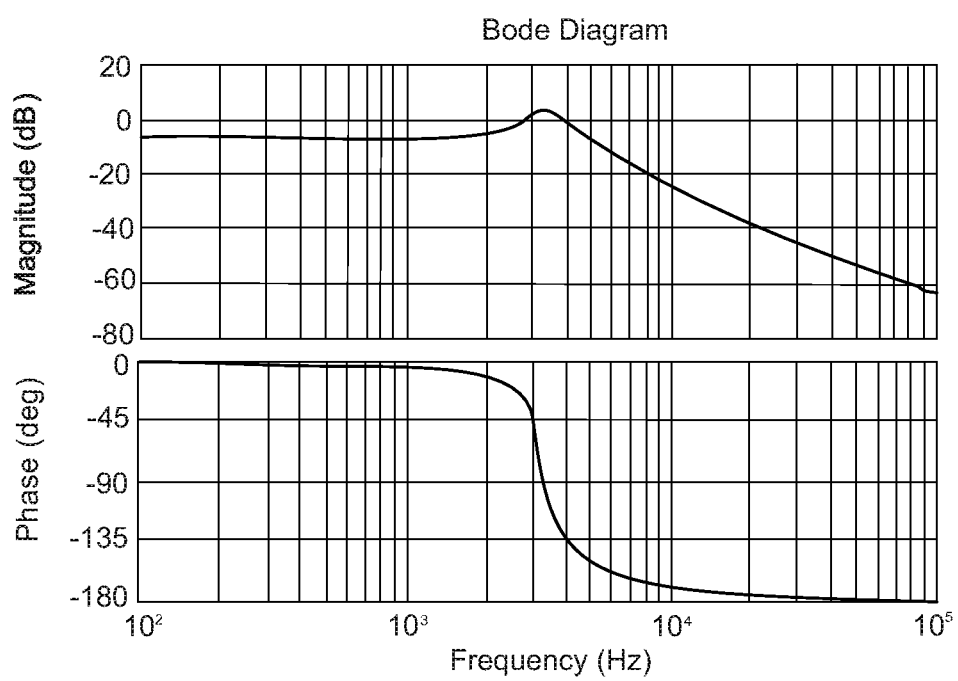
FIG. 97 is a two-dimensional graph of a performance characteristic of the volume sensor assembly of FIG. 96.

Referring also to FIG. 97, a bode plot of EQ #23 is shown.

The difficulty of this relationship is that the complex poles depend on both the variable volume, $V_2$, and the reference volume, $V_1$. Any change in the mean position of the speaker may result in an error in the estimated volume.

Cross Port Transfer Function

Figure 98:
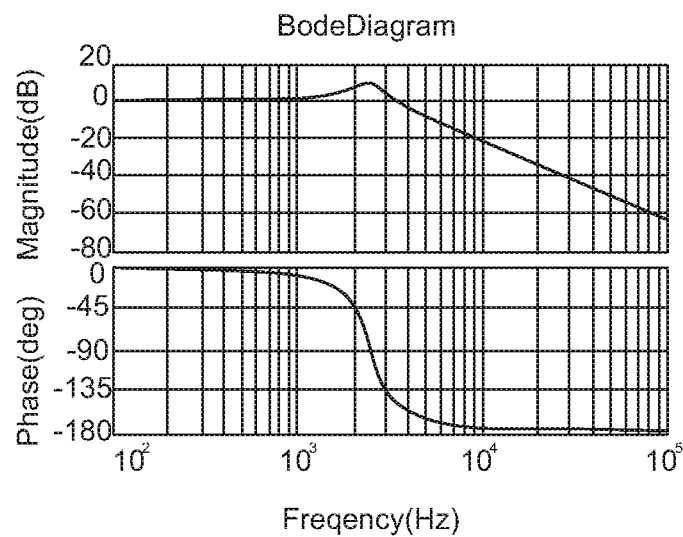
FIG. 98 is a two-dimensional graph of a performance characteristic of the volume sensor assembly of FIG. 96.

The relationship between the two volumes on each side of the acoustic port may be referred to as the Cross Port transfer function. This relationship is as follows:

$$\frac{p_2}{p_1} = \frac{\omega_n^2}{s^2 + 2\zeta\omega_n s + \omega_n^2} \quad [EQ\#25]$$

which is shown graphically in FIG. 98.

This relationship has the advantage that the poles are only dependent on the variable volume and not on the reference volume. It does, however, have the difficulty that the resonant peak is actually due to the inversion of the zero in the response of the reference volume pressure. Accordingly, the pressure measurement in the reference chamber will have a low amplitude in the vicinity of the resonance, potentially increasing the noise in the measurement.

Cross Speaker Transfer Function

Figure 99:
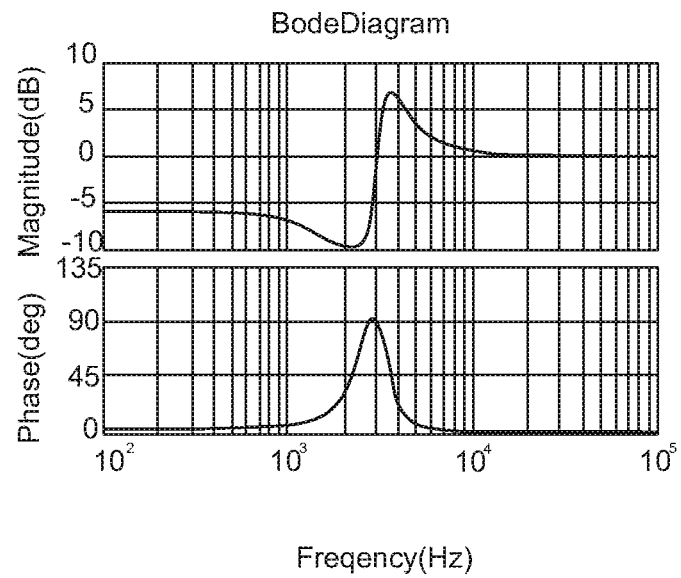
FIG. 99 is a two-dimensional graph of a performance characteristic of the volume sensor assembly of FIG. 96.

The pressures may also be measured on each side of the speaker. This is referred to as the cross speaker transfer function:

$$\frac{p_1}{p_0} = -\frac{V_0}{V_1}\frac{s^2 + 2\zeta\omega_n s + \omega_n^2}{s^2 + 2\zeta\omega_n s + \alpha\omega_n^2} \quad [EQ\#26]$$

which is shown graphically in FIG. 99.

This transfer function has a set of complex zeros in addition to the set of complex poles.

Looking at the limits of this transfer function: as $s \to 0$, $$\frac{p_1}{p_0} \to -\frac{V_0}{V_1 + V_2};$$

and as $s \to \infty$, $$\frac{p_1}{p_0} \to -\frac{V_0}{V_1}.$$

Resonance Q Factor and Peak Response

The quality of the resonance is the ratio of the energy stored to the power loss multiplied by the resonant frequency. For a pure second-order system, the quality factor may be expressed as a function of the damping ratio:

$$Q = \frac{1}{2\zeta} \quad [\text{EQ\#27}]$$

The ratio of the peak response to the low-frequency response may also be written as a function of the damping ratio:

$$|G|_{\omega_d} = \frac{1}{\zeta\sqrt{5-4\zeta}} \quad [\text{EQ\#28}]$$

This may occur at the damped natural frequency:

$$\omega_d = \omega_n\sqrt{1-\zeta} \quad [\text{EQ \#29}]$$

Volume Estimation

Volume Estimation Using Cross-Port Phase

The variable volume (i.e., within volume sensor chamber 620) may also be estimated using the cross-port phase. The transfer function for the pressure ratio across the resonant port may be as follows:

$$\frac{p_2}{p_1} = \frac{\omega_n^2}{s^2 + bs + \omega_n^2} \quad [\text{EQ\#30}]$$

At the 90° phase point, $\omega = \omega_n$; where $$\omega_n^2 = \frac{1}{V_2}\frac{a^2 A}{L}$$

The resonant frequency may be found on the physical system using a number of methods. A phase-lock loop may be employed to find the 90° phase point—this frequency may correspond to the natural frequency of the system. Alternatively, the resonant frequency may be calculated using the phase at any two frequencies:

The phase, $\phi$, at any given frequency will satisfy the following relation:

$$\tan\phi = \frac{b\omega}{\omega^2 - \omega_n^2} \quad [\text{EQ\#31}]$$

where $$b = \frac{fA}{L}.$$

Solving for $V_2$ results in:

$$V_2 = \frac{\frac{a^2 A}{L}}{\omega^2 - f\omega\cot\phi} \quad [\text{EQ\#32}]$$

Accordingly, the ratio of the phases at two different frequencies $\omega_1$ and $\omega_2$ can be used to compute the natural frequency of the system:

$$\alpha\omega_n^2 = \omega_1\omega_2 \frac{\left(\omega_1 \frac{\tan\phi_1}{\tan\phi_2} - \omega_2\right)}{\left(\omega_2 \frac{\tan\phi_1}{\tan\phi_2} - \omega_1\right)} \quad [\text{EQ\#33}]$$

For computational efficiency, the actual phase does not need to be calculated. All that is needed is the ratio of the real and imaginary parts of the response ($\tan \phi$).

Re-writing EQ #33 in terms of the variable volume results in:

$$\frac{1}{V_2} = \frac{1}{a^2}\frac{L}{A}\omega_1\omega_2 \frac{\left(\omega_1 \frac{\tan\phi_1}{\tan\phi_2} - \omega_2\right)}{\left(\omega_2 \frac{\tan\phi_1}{\tan\phi_2} - \omega_1\right)} \quad [\text{EQ\#34}]$$

Volume Estimation using Swept Sine

The resonant frequency of the system may be estimated using swept-sine system identification. In this method, the response of the system to a sinusoidal pressure variation may be found at a number of different frequencies. This frequency response data may then used to estimate the system transfer function using linear regression.

The transfer function for the system may be expressed as a rational function of s. The general case is expressed below for a transfer function with an $n^{th}$ order numerator and an $m^{th}$ order denominator. N and D are the coefficients for the numerator and denominator respectively. The equation has been normalized such that the leading coefficient in the denominator is 1.

$$G(s) = \frac{N_n s^n + N_{n-1} s^{n-1} + \ldots + N_0}{s^m + D_{m-1} s^{m-1} + D_{m-2} s^{m-2} + \ldots + D_0} \quad \text{or} \quad [\text{EQ\#35}]$$

$$G(s) = \frac{\sum_{k=0}^{n} N_k s^k}{s^m + \sum_{k=0}^{m-1} D_k s^k} \quad [\text{EQ\#36}]$$

This equation may be re-written as follows:

$$Gs^m = \sum_{k=0}^{n} N_k s^k - G \sum_{k=0}^{m-1} D_k s^k \quad [\text{EQ\#37}]$$

Representing this summation in matrix notation resulting in the following:

$$\begin{bmatrix} G_1 s_1^m \\ \vdots \\ G_k s_k^m \end{bmatrix} = \begin{bmatrix} s_1^n & \cdots & s_1^0 & -G_1 s_1^{m-1} & \cdots & -G_1 s_1^0 \\ \vdots & & \vdots & \vdots & & \vdots \\ s_k^n & \cdots & s_k^0 & -G_k s_k^{m-1} & \cdots & -G_k s_k^0 \end{bmatrix} \begin{bmatrix} N_n \\ \vdots \\ N_0 \\ D_{m-1} \\ \vdots \\ D_0 \end{bmatrix} \quad [\text{EQ\#38}]$$

where k is the number of data points collected in the swept sine. To simplify the notation, this equation may be summarized using the vectors:

$$y = Xc \quad [\text{EQ \#39}]$$

where y is k by 1, x is k by (m+n−1) and c is (m+n−1) by 1. The coefficients may then be found using a least square approach. The error function may be written as follows:

$$e = y - Xc \quad [\text{EQ \#40}]$$

The function to be minimized is the weighted square of the error function; W is a k x k diagonal matrix.

$$e^T W e = (y - Xc)^T W (y - Xc) \quad [\text{EQ \#41}]$$

$$e^T W e = y^T W y - (y^T W X c)^T - y^T W X c + c^T x^T W X c \quad [\text{EQ \#42}]$$

As the center two terms are scalars, the transpose may be neglected.

$$e^T W e = y^T W y - 2 y^T W X c + c^T x^T W X c \quad [\text{EQ\#43}]$$

$$\frac{\partial e^T W e}{\partial c} = -2 X^T W y + 2 X^T W X c = 0 \quad [\text{EQ\#44}]$$

$$c = (X^T W X)^{-1} X^T W y \quad [\text{EQ\#45}]$$

It may be necessary to use the complex transpose in all of these cases. This approach may result in complex coefficients, but the process may be modified to ensure that all the coefficients are real. The least-square minimization may be modified to give only real coefficients if the error function is changed to be $$e^T W e = \text{Re}(y - Xc)^T W \text{ Re}(y - Xc) + \text{Im}(y - Xc)^T W \text{ Im}(y - Xc) \quad [\text{EQ \#46}]$$

Accordingly, the coefficients may be found with the relation:

$$c = (\text{Re}(X)^T W \text{ Re}(X) + \text{Im}(X)^T W \text{ Im}(X))^{-1} (\text{Re}(X)^T W \text{ Re}(y) + \text{Im}(X)^T W \text{ Im}(y)) \quad [\text{EQ \#47}]$$

Solution for a 2nd Order System

For a system with a $0^{th}$ order numerator and a second order denominator as shown in the transfer function:

$$G(s) = \frac{N_0}{s^2 + D_1 s + D_0} \quad [\text{EQ\#48}]$$

The coefficients in this transfer function may be found based on the expression found in the previous section:

$$c = (\text{Re}(X)^T W \text{ Re}(X) + \text{Im}(X)^T W \text{ Im}(X))^{-1} \quad [\text{EQ\#49}]$$
$$(\text{Re}(X)^T W \text{ Re}(y) + \text{Im}(X)^T W \text{ Im}(y))$$

where:

$$y = \begin{bmatrix} G_1 s_1^2 \\ \vdots \\ G_k s_k^2 \end{bmatrix}, X = \begin{bmatrix} 1 & -G_1 s_1 & -G_1 \\ \vdots & \vdots & \vdots \\ 1 & -G_k s_k & -G_k \end{bmatrix}, \text{ and } c = \begin{bmatrix} N_0 \\ D_1 \\ D_0 \end{bmatrix} \quad [\text{EQ\#50}]$$

To simplify the algorithm, we may combine some of terms:

$$c = D^{-1} b \quad [\text{EQ \#51}]$$

where:

$$D = \text{Re}(X)^T W \text{ Re}(X) + \text{Im}(X)^T W \text{ Im}(X) \quad [\text{EQ \#52}]$$

$$b = \text{Re}(X)^T W \text{ Re}(y) + \text{Im}(X)^T W \text{ Im}(y) \quad [\text{EQ \#53}]$$

To find an expression for D in terms of the complex response vector G and the natural frequency $s = j\omega$, X may be split into its real and imaginary parts:

$$\text{Re}(X) = \begin{bmatrix} 1 & \omega_k \text{ Im}(G_1) & -\text{Re}(G_1) \\ \vdots & \vdots & \vdots \\ 1 & \omega_k \text{ Im}(G_k) & -\text{Re}(G_k) \end{bmatrix}, \quad [\text{EQ\#54}]$$

$$\text{Im}(X) = \begin{bmatrix} 0 & -\omega_k \text{ Re}(G_1) & -\text{Im}(G_1) \\ \vdots & \vdots & \vdots \\ 0 & -\omega_k \text{ Re}(G_k) & -\text{Im}(G_k) \end{bmatrix}$$

The real and imaginary portions of the expression for D above may then become:

$$\text{Re}(X)^T W \text{ Re}(X) = \begin{bmatrix} \sum_{i=1}^{k} w_i & \sum_{i=1}^{k} w_i \text{ Im}(G_i)\omega_i & -\sum_{i=1}^{k} w_i \text{ Re}(G_i) \\ \sum_{i=1}^{k} w_i \text{ Im}(G_i)\omega_i & \sum_{i=1}^{k} w_i \text{ Im}(G_i)^2 \omega_i^2 & -\sum_{i=1}^{k} w_i \text{ Im}(G_i)\text{Re}(G_i)\omega_i \\ -\sum_{i=1}^{k} w_i \text{ Re}(G_i) & -\sum_{i=1}^{k} w_i \text{ Im}(G_i)\text{Re}(G_i)\omega_i & \sum_{i=1}^{k} w_i \text{ Re}(G_i)^2 \end{bmatrix} \quad [\text{EQ\#55}]$$

$$\operatorname{Im}(X)^T \ W \ \operatorname{Im}(X) = \begin{bmatrix} 0 & 0 & 0 \\ 0 & \sum_{i=1}^{k} w_i \ \operatorname{Re}(G_i)^2 \omega_i^2 & \sum_{i=1}^{k} w_i \ \operatorname{Im}(G_i)\operatorname{Re}(G_i)\omega_i \\ 0 & \sum_{i=1}^{k} w_i \ \operatorname{Im}(G_i)\operatorname{Re}(G_i)\omega_i & \sum_{i=1}^{k} w_i \ \operatorname{Im}(G_i)^2 \end{bmatrix}$$ [EQ#56]

Combining these terms results in the final expression for the D matrix, which may contain only real values.

$$D = \begin{bmatrix} \sum_{i=1}^{k} w_i & \sum_{i=1}^{k} w_i \ \operatorname{Im}(G_i)\omega_i & -\sum_{i=1}^{k} w_i \ \operatorname{Re}(G_i) \\ \sum_{i=1}^{k} w_i \ \operatorname{Im}(G_i)\omega_i & \sum_{i=1}^{k} w_i \ (\operatorname{Re}(G_i)^2 + \operatorname{Im}(G_i)^2)\omega_i^2 & 0 \\ -\sum_{i=1}^{k} w_i \ \operatorname{Re}(G_i) & 0 & \sum_{i=1}^{k} w_i \ (\operatorname{Re}(G_1)^2 + \operatorname{Im}(G_i)^2) \end{bmatrix}$$ [EQ#57]

The same approach may be taken to find an expression for the b vector in terms of G and ω. The real and imaginary parts of y are as follows:

$$\operatorname{Re}(y) = \begin{bmatrix} -\operatorname{Re}(G_1)\omega_1^2 \\ \vdots \\ -\operatorname{Re}(G_k)\omega_k^2 \end{bmatrix}, \operatorname{Im}(y) = \begin{bmatrix} -\operatorname{Im}(G_1)\omega_1^2 \\ \vdots \\ -\operatorname{Im}(G_k)\omega_k^2 \end{bmatrix}$$ [EQ#58]

Combining the real and imaginary parts results in the expression for the b vector as follows:

$$b = \operatorname{Re}(X)^T \ W \ \operatorname{Re}(X) + \operatorname{Im}(X)^T \ W \ \operatorname{Im}(y) =$$ [EQ#59]
$$\begin{bmatrix} -\sum_{i=1}^{k} w_i \ \operatorname{Re}(G_i)\omega_i^2 \\ 0 \\ \sum_{i=1}^{k} w_i \ (\operatorname{Re}(G_i)^2 + \operatorname{Im}(G_i)^2)\omega_i^2 \end{bmatrix}$$

The next step is to invert the D matrix. The matrix is symmetric and positive-definite so the number of computations needed to find the inverse will be reduced from the general 3×3 case. The general expression for a matrix inverse is:

$$D^{-1} = \frac{1}{det(D)} adj(D)$$ [EQ#60]

If D is expressed as follows:

$$D = \begin{bmatrix} d_{11} & d_{12} & d_{13} \\ d_{12} & d_{22} & 0 \\ d_{13} & 0 & d_{33} \end{bmatrix}$$ [EQ#61]

then the adjugate matrix may be written as follows:

$$adj(D) =$$ [EQ#62]
$$\begin{bmatrix} \begin{vmatrix} d_{22} & 0 \\ 0 & d_{33} \end{vmatrix} & -\begin{vmatrix} d_{12} & 0 \\ d_{13} & d_{33} \end{vmatrix} & \begin{vmatrix} d_{12} & d_{22} \\ d_{13} & 0 \end{vmatrix} \\ -\begin{vmatrix} d_{12} & d_{13} \\ 0 & d_{33} \end{vmatrix} & \begin{vmatrix} d_{11} & d_{13} \\ d_{13} & d_{33} \end{vmatrix} & -\begin{vmatrix} d_{11} & d_{12} \\ d_{13} & 0 \end{vmatrix} \\ \begin{vmatrix} d_{12} & d_{13} \\ d_{22} & 0 \end{vmatrix} & -\begin{vmatrix} d_{11} & d_{13} \\ d_{12} & 0 \end{vmatrix} & \begin{vmatrix} d_{11} & d_{12} \\ d_{12} & d_{22} \end{vmatrix} \end{bmatrix} = \begin{bmatrix} a_{11} & a_{12} & a_{13} \\ a_{12} & a_{22} & a_{23} \\ a_{13} & a_{23} & a_{33} \end{bmatrix}$$

Due to symmetry, only the upper diagonal matrix may need to be calculated.

The Determinant may then be computed in terms of the adjugate matrix values, taking advantage of the zero elements in the original array:

$$\det(D) = a_{12}d_{12} + a_{22}d_{22}$$ [EQ#63]

Finally, the inverse of D may be written as follows:

$$D^{-1} = \frac{1}{det(D)} adj(D)$$ [EQ#64]

Since we are trying to solve:

$$c = D^{-1}b = \frac{1}{det(D)} adj(D) b$$ [EQ#65]

then:

$$c = \frac{1}{det(D)} \begin{bmatrix} a_{11} & a_{12} & a_{13} \\ a_{12} & a_{22} & a_{23} \\ a_{13} & a_{23} & a_{33} \end{bmatrix} \begin{bmatrix} b_1 \\ 0 \\ b_3 \end{bmatrix} = \frac{1}{det(D)} \begin{bmatrix} a_{11}b_1 + a_{13}b_3 \\ a_{12}b_1 + a_{23}b_3 \\ a_{13}b_1 + a_{33}b_3 \end{bmatrix}$$ [EQ#66]

The final step is to get a quantitative assessment of how well the data fits the model. Accordingly, the original expression for the error is as follows:

$$e^T W e = \operatorname{Re}(y - Xc)^T W \operatorname{Re}(y - Xc) + \operatorname{Im}(y - Xc)^T W \operatorname{Im}(y - Xc)$$ [EQ #67]

This may be expressed in terms of the D matrix and the b and c vectors as follows:

$$e^T W e = h = 2c^T b + c^T D c \qquad [\text{EQ\#68}]$$

where:

$$h = \text{Re}(y^T) W \text{ Re}(y) + \text{Im}(y^T) W \text{ Im}(y) \qquad [\text{EQ\#69}]$$

$$h = \sum_{i=1}^{k} w_i (\text{Re}(G_i)^2 + \text{Im}(G_i)^2) \omega_i^4 \qquad [\text{EQ\#70}]$$

The model fit error may also be used to detect sensor failures.

Alternate Solution for a 2nd Order System $$G(s) = \frac{N_n s^n + N_{n-1} s^{n-1} + \ldots + N_0}{s^m + D_{m-1} s^{m-1} + D_{m-2} s^{m-2} + \ldots + D_0} \qquad [\text{EQ\#71}]$$

or $$G(s) = \frac{\sum_{k=0}^{n} N_k s^k}{s^m + \sum_{k=0}^{m-1} D_k s^k} \qquad [\text{EQ\#72}]$$

This equation may be re-written as follows:

$$G = \sum_{k=0}^{n} N_k s^{k-m} - G \sum_{k=0}^{m-1} D_k s^{k-m} \qquad [\text{EQ\#73}]$$

Putting this summation into matrix notation results in the following:

$$\begin{bmatrix} G_1 \\ \vdots \\ G_k \end{bmatrix} = \begin{bmatrix} s_1^{n-m} & \cdots & s_1^{-m} & -G_1 s_1^{-1} & \cdots & -G_1 s_1^{-m} \\ \vdots & & \vdots & \vdots & & \vdots \\ s_k^{n-m} & \cdots & s_k^{-m} & -G_k s_k^{-1} & \cdots & -G_k s_k^{-m} \end{bmatrix} \begin{bmatrix} N_n \\ \vdots \\ N_0 \\ D_{m-1} \\ \vdots \\ D_0 \end{bmatrix} \qquad [\text{EQ\#74}]$$

For a system with a $0^{th}$ order numerator and a second order denominator as shown in the transfer function:

$$G(s) = \frac{N_0}{s^2 + D_1 s + D_0} \qquad [\text{EQ\#75}]$$

The coefficients in this transfer function may be found based on the expression found in the previous section:

$$c = (\text{Re}(X)^T W \text{ Re}(X) + \text{Im}(X)^T W \text{ Im}(X))^{-1} \qquad [\text{EQ\#76}]$$
$$(\text{Re}(X)^T W \text{ Re}(y) + \text{Im}(X)^T W \text{ Im}(y))$$

where $$y = \begin{bmatrix} G_1 \\ \vdots \\ G_k \end{bmatrix}, X = \begin{bmatrix} s_1^{-2} & -G_1 s_1^{-1} & -G_1 s_1^{-2} \\ \vdots & \vdots & \vdots \\ s_k^{-2} & -G_k s_k^{-1} & -G_k s_k^{-2} \end{bmatrix}, \text{ and } c = \begin{bmatrix} N_0 \\ D_1 \\ D_0 \end{bmatrix} \qquad [\text{EQ\#77}]$$

To simplify the algorithm, some terms may be combined:

$$c = D^{-1} b \qquad [\text{EQ \#78}]$$

where:

$$D = \text{Re}(X)^T W \text{Re}(X) + \text{Im}(X)^T W \text{Im}(X) \qquad [\text{EQ \#79}]$$

$$b = \text{Re}(X)^T W \text{Re}(y) + \text{Im}(X)^T W \text{Im}(y) \qquad [\text{EQ \#80}]$$

To find an expression for D in terms of the complex response vector G and the natural frequency $s=j\omega$, split X may be split into its real and imaginary parts:

$$\text{Re}(X) = \begin{bmatrix} -\omega_1^{-2} & -\omega_1^{-1} \text{Im}(G_1) & \omega_1^{-2} \text{Re}(G_1) \\ \vdots & \vdots & \vdots \\ -\omega_k^{-2} & -\omega_k^{-1} \text{Im}(G_k) & \omega_k^{-2} \text{Re}(G_k) \end{bmatrix} \qquad [\text{EQ\#81}]$$

$$\text{Im}(X) = \begin{bmatrix} 0 & -\omega_1^{-1} \text{Re}(G_1) & \omega_1^{-2} \text{Im}(G_1) \\ \vdots & \vdots & \vdots \\ 0 & -\omega_k^{-1} \text{Re}(G_k) & \omega_k^{-2} \text{Im}(G_k) \end{bmatrix} \qquad [\text{EQ\#82}]$$

The real and imaginary portions of the expression for D above may then become:

$$\text{Re}(X)^T W \text{ Re}(X) = \begin{bmatrix} \sum_{i=1}^{k} w_i \omega_i^{-4} & \sum_{i=1}^{k} w_i \text{Im}(G_i) \omega_i^{-3} & -\sum_{i=1}^{k} w_i \text{Re}(G_i) \omega_i^{-4} \\ \sum_{i=1}^{k} w_i \text{Im}(G_i) \omega_i^{-3} & \sum_{i=1}^{k} w_i \text{Im}(G_i)^2 \omega_i^{-2} & -\sum_{i=1}^{k} w_i \text{Im}(G_i) \text{Re}(G_i) \omega_i^{-3} \\ -\sum_{i=1}^{k} w_i \text{Re}(G_i) \omega_i^{-4} & -\sum_{i=1}^{k} w_i \text{Im}(G_i) \text{Re}(G_i) \omega_i^{-3} & \sum_{i=1}^{k} w_i \text{Re}(G_i)^2 \omega_i^{-4} \end{bmatrix} \qquad [\text{EQ\#83}]$$

$$\text{Im}(X)^T W \text{ Im}(X) = \begin{bmatrix} 0 & 0 & 0 \\ 0 & \sum_{i=1}^{k} w_i \text{Re}(G_i)^2 \omega_i^{-2} & -\sum_{i=1}^{k} w_i \text{Im}(G_i) \text{Re}(G_i) \omega_i^{-3} \\ 0 & -\sum_{i=1}^{k} w_i \text{Im}(G_i) \text{Re}(G_i) \omega_i^{-3} & \sum_{i=1}^{k} w_i \text{Im}(G_i)^2 \omega_i^{-4} \end{bmatrix} \qquad [\text{EQ\#84}]$$

Combining these terms results in the final expression for the D matrix, which may contain only real values.

$$D = \begin{bmatrix} \sum_{i=1}^{k} w_i \omega_i^{-4} & \sum_{i=1}^{k} w_i \, \text{Im}(G_i)\omega_i^{-3} & -\sum_{i=1}^{k} w_i \, \text{Re}(G_i)\omega_i^{-4} \\ \sum_{i=1}^{k} w_i \, \text{Im}(G_i)\omega_i^{-3} & \sum_{i=1}^{k} w_i \, (\text{Re}(G_i)^2 + \text{Im}(G_i)^2)\omega_i^{-2} & -2\sum_{i=1}^{k} w_i \, \text{Im}(G_i)\,\text{Re}(G_i)\omega_i^{-3} \\ -\sum_{i=1}^{k} w_i \, \text{Re}(G_i)\omega_i^{-4} & -2\sum_{i=1}^{k} w_i \, \text{Im}(G_i)\,\text{Re}(G_i)\omega_i^{-3} & \sum_{i=1}^{k} w_i \, (\text{Re}(G_i)^2 + \text{Im}(G_i)^2)\omega_i^{-4} \end{bmatrix}$$  [EQ#85]

The same approach may be taken to find an expression for the b vector in terms of G and ω. The real and imaginary parts of y areas follows:

$$\text{Re}(y) = \begin{bmatrix} -\text{Re}(G_1) \\ \vdots \\ -\text{Re}(G_k) \end{bmatrix}, \text{Im}(y) = \begin{bmatrix} -\text{Im}(G_1) \\ \vdots \\ -\text{Im}(G_k) \end{bmatrix}$$  [EQ#86]

Combining the real and imaginary parts results in the expression for the b vector as follows:

$$b = \text{Re}(X)^T \, W \, \text{Re}(y) + \text{Im}(X)^T \, W \, \text{Im}(y) = \begin{bmatrix} -\sum_{i=1}^{k} w_i \text{Re}(G_i)\omega_i^{-2} \\ -\sum_{i=1}^{k} w_i (\text{Im}(G_i) + \text{Re}(G_i))\omega_i^{-1} \\ \sum_{i=1}^{k} w_i (\text{Re}(G_i)^2 + \text{Im}(G_i)^2)\omega_i^{-2} \end{bmatrix}$$  [EQ#87]

Implementing Acoustic Volume Sensing
Collecting the Frequency Response Data and Computing the Complex Response To implement volume sensor assembly 148, volume sensor assembly 148 should determine the relative response of reference microphone 626 and invariable volume microphone 630 to the acoustic wave set up by speaker assembly 622. This may be accomplished by driving speaker assembly 622 with a sinusoidal output at a known frequency; the complex response of microphones 626, 630 may then be found at that driving frequency. Finally, the relative response of microphones 626, 630 may be found and corrected for alternating sampling by e.g., an analog-to-digital convertor (i.e., ADC).

Additionally, the total signal variance may be computed and compared to the variance of pure tone extracted using the discrete Fourier transform (i.e., DFT). This may result in a measure of how much of the signal power comes from noise sources or distortion. This value may then be used to reject and repeat bad measurements.

Computing the Discrete Fourier Transform The signal from the microphone may be sampled synchronously with the output to speaker assembly 622 such that a fixed number of points, N, are taken per wavelength. The measured signal at each point in the wavelength may be summed over an integer number of wavelengths, M, and stored in an array x by the ISR for processing after all the data for that frequency has been collected.

A DFT may be performed on the data at the integer value corresponding to the driven frequency of the speaker. The general expression for the first harmonic of a DFT is as follows:

$$x_k = \frac{2}{MN} \sum_{n=0}^{N-1} x_n e^{-\frac{2\pi i}{N} kn}$$  [EQ#88]

The product MN may be the total number of points and the factor of two may be added such that the resulting real and imaginary portions of the answer match the amplitude of the sine wave:

$$x_n = \text{re}(x_k)\cos\left(\frac{2\pi}{N}kn\right) + \text{im}(x_k)\sin\left(\frac{2\pi}{N}kn\right)$$  [EQ#89]

This real part of this expression may be as follows:

$$\text{re}(x) = \frac{2}{MN} \sum_{n=0}^{N-1} x_n \cos\left(\frac{2\pi}{N}n\right)$$  [EQ#90]

We may take advantage of the symmetry of the cosine function to reduce the number of computations needed to compute the DFT. The expression above may be equivalent to:

$$\text{re}(x) = \frac{2}{MN}\left[ \left(x_0 - x_{\frac{1}{2}N}\right) + \sum_{n=1}^{\frac{1}{4}N-1} \sin\left(\frac{\pi}{2} - \frac{2\pi}{N}n\right)\left[\left(x_n - x_{\frac{1}{2}N+n}\right) - \left(x_{\frac{1}{2}N+n} - x_{N-n}\right)\right] \right]$$  [EQ#91]

Similarly, for the imaginary portion of the equation:

$$\text{im}(x) = -\frac{2}{MN} \sum_{n=0}^{N-1} x_n \sin\left(\frac{2\pi}{N}n\right)$$  [EQ#92]

which may be expressed as follows:

$$\text{im}(x) = -\frac{2}{MN}\left[\left(x_{\frac{1}{4}N} - x_{\frac{3}{4}N}\right) + \sum_{n=1}^{\frac{1}{4}N-1} \sin\left(\frac{2\pi}{N}n\right)\left[\left(x_n - x_{\frac{1}{2}N+n}\right) + \left(x_{\frac{1}{2}N+n} - x_{N-n}\right)\right]\right] \quad [\text{EQ\#93}]$$

The variance of this signal may be calculated as follows:

$$\sigma^2 = \frac{1}{2}(\text{re}(x)^2 + \text{im}(x)^2) \quad [\text{EQ \#94}]$$

The maximum possible value of the real and imaginary portions of x may be $2^{11}$; which corresponds to half the AD range. The maximum value of the tone variance may be $2^{21}$; half the square of the AD range.

Computing the Signal Variance

The pseudo-variance of the signal may be calculated using the following relation:

$$\sigma^2 = \frac{1}{NM^2}\sum_{n=0}^{N-1} x_n^2 - \frac{1}{N^2M^2}\left(\sum_{n=0}^{N-1} x_n\right)^2 \quad [\text{EQ\#95}]$$

The result may be in the units of AD counts squared. It may only be the "pseudo-variance" because the signal has been averaged over M periods before the variance is calculated over the N samples in the "averaged" period. This may be a useful metric, however, for finding if the "averaged" signal looks like a sinusoid at the expected frequency. This may be done by comparing the total signal variance to that of the sinusoid found in the discrete Fourier transform.

The summation may be on the order of $$\sum_{n=0}^{N-1} x_n^2 = O(NM^2 2^{24})$$

for a 12-bit ADC. If $N < 2^7 = 128$ and $M < 2^6 = 64$, then the summation will be less than $2^{43}$ and may be stored in a 64-bit integer. The maximum possible value of the variance may result if the ADC oscillated between a value of 0 and $2^{12}$ on each consecutive sample. This may result in a peak variance of $\frac{1}{4}(2^{12})^2 = 2^{22}$ so the result may be stored at a maximum of a $\frac{1}{2}^9$ resolution in a signed 32-bit integer.

Computing the Relative Microphone Response The relative response (G) of microphones 626, 630 may be computed from the complex response of the individual microphones:

$$G = \frac{x_{var}}{x_{ref}} = \frac{x_{var}}{x_{ref}} \frac{x_{ref}^*}{x_{ref}^*} \quad [\text{EQ\#96}]$$

$$\text{Re}(G) = \frac{\text{Re}(x_{var})\text{Re}(x_{ref}) + \text{Im}(x_{var})\text{Im}(x_{ref})}{\text{Re}(x_{ref})^2 + \text{Im}(x_{ref})^2} \quad [\text{EQ\#97}]$$

$$\text{Im}(G) = \frac{\text{Re}(x_{ref})\text{Im}(x_{var}) - \text{Re}(x_{var})\text{Im}(x_{ref})}{\text{Re}(x_{ref})^2 + \text{Im}(x_{ref})^2} \quad [\text{EQ\#98}]$$

The denominator of either expression may be expressed in terms of the reference tone variance computed in the previous section as follows:

$$\text{Re}(x_{ref})^2 + \text{Im}(x_{ref})^2 = 2\sigma_{ref}^2 \quad [\text{EQ \#99}]$$

Correcting for A/D Skew

The signals from microphones 626, 630 may not be sampled simultaneously; the A/D ISR alternates between microphones 626, 630, taking a total of N samples per wavelength for each of microphones 626, 630. The result may be a phase offset between two microphones 626, 630 of $$\frac{\pi}{N}.$$

correct for this phase offset, a complex rotation may be applied to the relative frequency response computed in the previous section:

$$G_{rotated} = G \cdot \left(\cos\left(\frac{\pi}{N}\right) + i\,\sin\left(\frac{\pi}{N}\right)\right) \quad [\text{EQ\#100}]$$

Reference Models

Second and Higher Order Models

Figure 100:
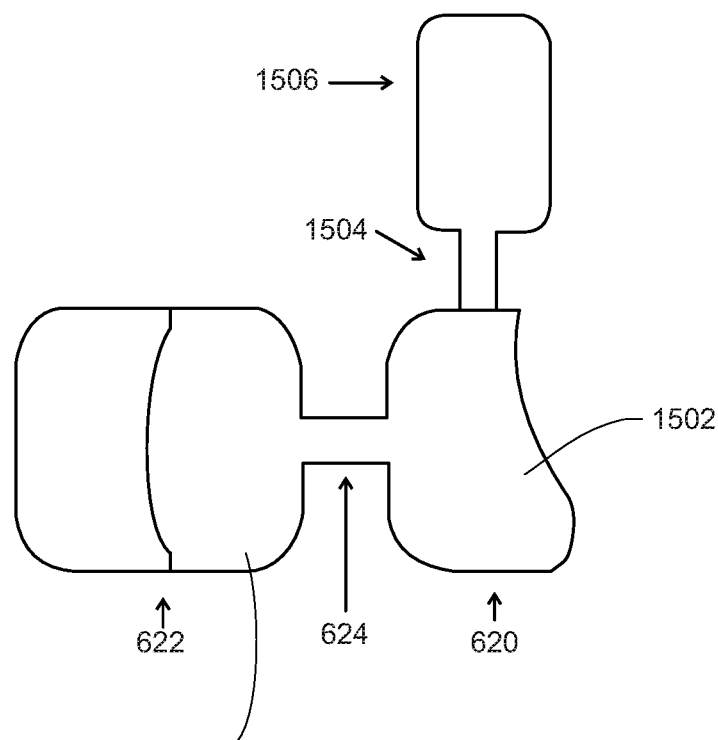
FIG. 100 is a diagrammatic view of a volume sensor assembly included within the infusion pump assembly of FIG. 1.

Leakage through the seals (e.g., seal assembly 1404) of volume sensor chamber 620 may be modeled as a second resonant port (e.g., port 1504, FIG. 100) connected to an external volume (e.g., external volume 1506, FIG. 100).

The system of equations describing the three-chamber configuration may be as follows:

$$\dot{p}_1 + \frac{\rho a^2}{V_1}(\dot{v}_k - \dot{v}_{r12}) = 0 \quad [\text{EQ\#101}]$$

$$\dot{p}_2 + \frac{\rho a^2}{V_2}(\dot{v}_{r12} - \dot{v}_{r23}) = 0 \quad [\text{EQ\#102}]$$

$$\ddot{v}_{r12} = -\frac{f_{12}A_{12}}{L_{12}}\dot{v}_{r12} + \frac{A_{12}}{\rho L_{12}}(p_2 - p_1) \quad [\text{EQ\#103}]$$

$$\dot{p}_3 + \frac{\rho a^2}{V_3}\dot{v}_{r23} = 0 \quad [\text{EQ\#104}]$$

$$\ddot{v}_{r23} = -\frac{f_{23}A_{23}}{L_{23}}\dot{v}_{r23} + \frac{A_{23}}{\rho L_{23}}(p_3 - p_2) \quad [\text{EQ\#105}]$$

Figure 101:
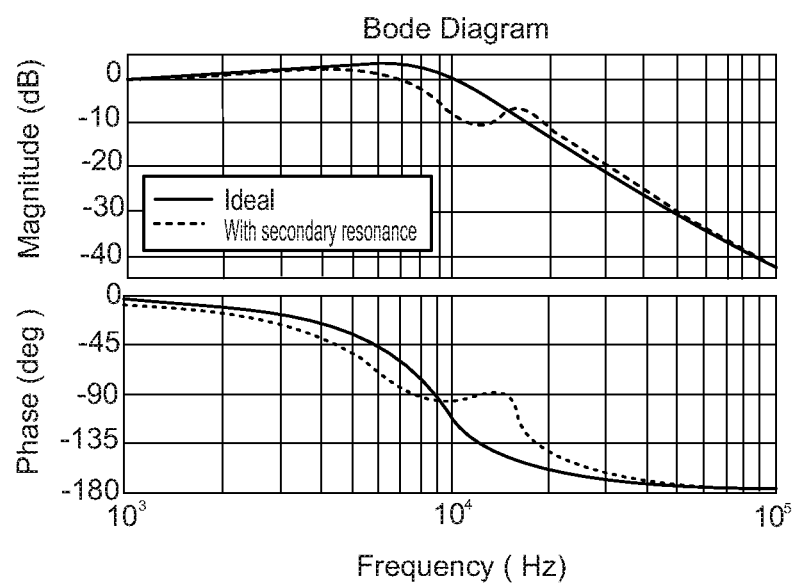
FIG. 101 is a two-dimensional graph of a performance characteristic of the volume sensor assembly of FIG. 100.

Putting these equations into state-space results in the following:

$$\begin{bmatrix}\dot{p}_1\\\dot{p}_2\\\dot{p}_3\\\dot{v}_{12}\\\dot{v}_{23}\end{bmatrix} = \begin{bmatrix}0 & 0 & 0 & \frac{\rho a^2}{V_1} & 0\\0 & 0 & 0 & -\frac{\rho a^2}{V_2} & \frac{\rho a^2}{V_2}\\0 & 0 & 0 & 0 & -\frac{\rho a^2}{V_3}\\-\frac{A_{12}}{\rho L_{12}} & \frac{A_{12}}{\rho L_{12}} & 0 & -b_{12} & 0\\0 & -\frac{A_{23}}{\rho L_{23}} & \frac{A_{23}}{\rho L_{23}} & 0 & -b_{23}\end{bmatrix} \quad [\text{EQ\#106}]$$

$$\begin{bmatrix} \dot{p}_1 \\ \dot{p}_2 \\ \dot{p}_3 \\ \dot{v}_{12} \\ \dot{v}_{23} \end{bmatrix} + \begin{bmatrix} -\frac{\rho a^2}{V_1} \\ 0 \\ 0 \\ 0 \\ 0 \end{bmatrix} [\dot{v}_k]$$

the frequency response of which may be represented graphically in the Bode diagram shown in FIG. 101 and which may also be written in transfer function form:

$$\frac{p_2}{p_1} = \frac{\omega_{12}^2(s^2 + b_{23}s + \omega_{23}^2)}{(s^2 + b_{12}s + \omega_{12}^2)(s^2 + b_{23}s + \omega_{23}^2) + \frac{V_3}{V_2}\omega_{23}^2(s + b_{12})s}$$ [EQ#107]

Expanding the denominator results in the following:

$$\frac{p_2}{p_1} = \frac{\omega_{12}^2(s^2 + b_{23}s + \omega_{23}^2)}{s^4 + (b_{12} + b_{23})s^3 + \left(b_{12}b_{23} + \omega_{12}^2 + \omega_{23}^2\left(1 + \frac{V_3}{V_2}\right)\right)s^2 + \left(b_{23}\omega_{12}^2 + b_{12}\omega_{23}^2\left(1 + \frac{V_3}{V_2}\right)\right)s + \omega_{12}^2\omega_{23}^2}$$ [EQ#108]

A bubble underneath the diaphragm material in the variable volume will follow the same dynamic equations as a leakage path. In this case, the diaphragm material may act as the resonant mass rather than the leakage port. Accordingly, the equation may be as follows:

$$m\ddot{x} = \Delta p A - b_m \dot{x}$$ [EQ #109]

wherein m is the mass of the diaphragm, A is the cross sectional area of the diaphragm that can resonate, and $b_m$ is the mechanical damping. EQ #106 may be written in terms of the volume flow rate:

$$\dot{v} = -\frac{b}{m}v + \Delta p \frac{A^2}{m}$$ [EQ#110]

wherein the volume of the air bubble is V3. If the bubble volume is substantially smaller than the acoustic volume V3<<V2 than the transfer function may be simplified to:

$$\frac{p_2}{p_1} = \frac{\omega_{12}^2(s^2 + b_{23}s + \omega_{23}^2)}{(s^2 + b_{12}s + \omega_{12}^2)\left(s^2 + b_{23}s + \omega_{23}^2\left(1 + \frac{V_3}{V_2}\right)\right)}$$ [EQ#111]

Second Order with Time Delay The volume sensor assembly 148 equations derived above assume that the pressure is the same everywhere in the acoustic volume. This is only an approximation, as there are time delays associated with the propagation of the sound waves through the volume. This situation may look like a time delay or a time advance based on the relative position of the microphone and speakers.

Figure 102:
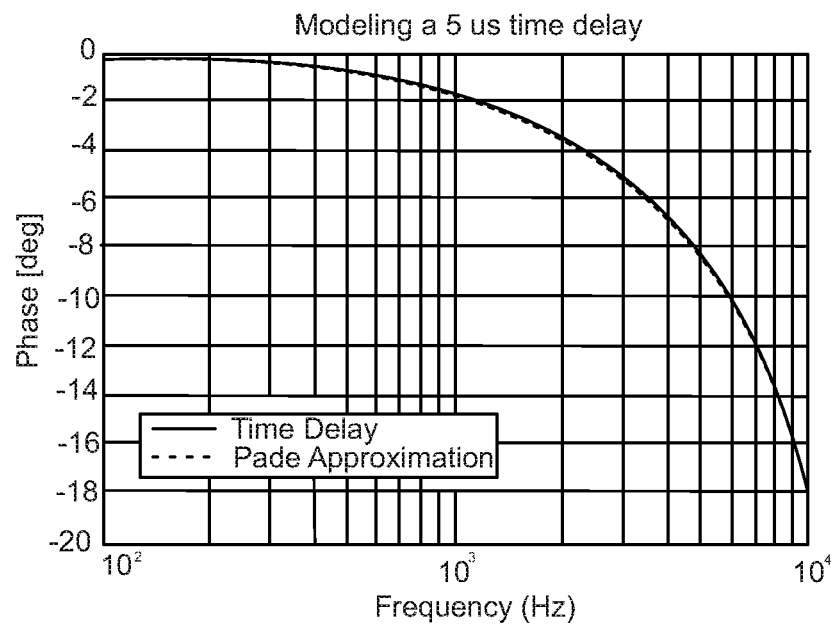
FIG. 102 is a two-dimensional graph of a performance characteristic of the volume sensor assembly of FIG. 100.

A time delay may be expressed in the Laplace domain as:

$$G(s) = e^{-\Delta T s}$$ [EQ #112]

which makes for a non-linear set of equations. However, a first-order Pade approximation of the time delay may be used as follows:

$$G(s) = -\frac{s + \frac{2}{\Delta T}}{s - \frac{2}{\Delta T}}$$ [EQ#113]

which is shown graphically in FIG. 102.

Figure 103:
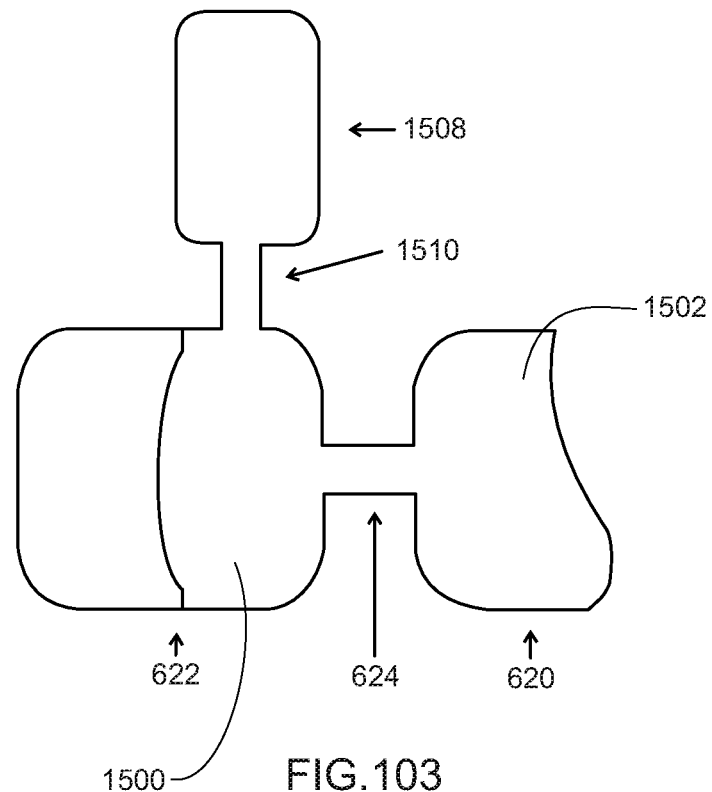
FIG. 103 is a diagrammatic view of a volume sensor assembly included within the infusion pump assembly of FIG. 1.

Three Chamber Volume Estimation Volume sensor assembly 148 may also be configured using a third reference volume (e.g., reference volume 1508; FIG. 103) connected with a separate resonant port (e.g., port 1510; FIG. 103). This configuration may allow for temperature-independent volume estimation.

The system of equations describing the three-chamber configuration are as follows:

$$\dot{p}_1 + \frac{\rho a^2}{V_1}(\dot{v}_k - \dot{v}_{r12} - \dot{v}_{r23}) = 0$$ [EQ#114]

$$\dot{p}_2 + \frac{\rho a^2}{V_2}\dot{v}_{r12} = 0$$ [EQ#115]

$$\ddot{v}_{r12} = -\frac{f_{12}A_{12}}{L_{12}}\dot{v}_{r12} + \frac{A_{12}}{\rho L_{12}}(p_2 - p_1)$$ [EQ#116]

$$\dot{p}_3 + \frac{\rho a^2}{V_3}\dot{v}_{r13} = 0$$ [EQ#117]

$$\ddot{v}_{r13} = -\frac{f_{13}A_{13}}{L_{13}}\dot{v}_{r13} + \frac{A_{13}}{\rho L_{13}}(p_2 - p_1)$$ [EQ#118]

Using these equations and solving for the transfer function across each of the resonant ports results in the following:

$$\frac{p_2}{p_1} = \frac{\omega_{n12}^2}{s^2 + 2\zeta_{12}\omega_{n12}s + \omega_{n12}^2}$$ [EQ#119]

where $$\omega_{n12} = \sqrt{\frac{1}{V_2}\frac{a^2 A_{12}}{L_{12}}} \text{ and } \zeta = \frac{f_{12}A_{12}}{2L_{12}\omega_{n12}}$$ [EQ#120]

$$\frac{p_3}{p_1} = \frac{\omega_{n13}^2}{s^2 + 2\zeta_{13}\omega_{n13}s + \omega_{n13}^2}$$ [EQ#121]

where $$\omega_{n13} = \sqrt{\frac{1}{V_3}\frac{a^2 A_{13}}{L_{13}}} \text{ and } \zeta = \frac{f_{13}A_{13}}{2L_{13}\omega_{n13}}$$ [EQ#122]

The volume of volume sensor chamber 620 may be estimated using the ratio of the natural frequency of the two resonant ports as follows:

$$\frac{\omega_{n13}^2}{\omega_{n12}^2} = \frac{V_2}{V_3}\frac{A_{13}}{A_{12}}\frac{L_{12}}{L_{13}}$$ [EQ#123]

EQ #120 illustrates that the volume of volume sensor chamber 620 may be proportional to reference volume 1508. The ratio of these two volumes (in the ideal model) may only depend on the geometry of the resonant port (e.g., port 1510; FIG. 103) and has no dependence upon temperature.

Exponential Volume Model

Assume the flow out through the flow resistance has the following form:

$$\dot{V}_{out} = \frac{V_{avs}}{\tau} \quad [\text{EQ\#124}]$$

Assuming a fixed input flow rate from the pump chamber, the volume of volume sensor chamber 620 is based upon the following differential equation:

$$\dot{V}_{avs} = \dot{V}_{in} - \dot{V}_{out} = \dot{V}_{in} - \frac{V_{avs}}{\tau} \quad [\text{EQ\#125}]$$

which gives the following solution assuming a zero initial volume:

$$V_{avs} = \dot{V}_{in}\tau\left(1 - e^{-\frac{t}{\tau}}\right) \quad [\text{EQ\#127}]$$

Accordingly, the output flow rate flows:

$$\dot{V}_{out} = \dot{V}_{in}\left(1 - e^{-\frac{t}{\tau}}\right) \quad [\text{EQ\#127}]$$

The volume delivered during the pump phase may be written:

$$V_{out} = \dot{V}_{in}\left[t - \tau\left(1 - e^{-\frac{t}{\tau}}\right)\right] \quad [\text{EQ\#128}]$$

Device Calibration

The model fit allows the resonant frequency of the port to be extracted from the sine sweep data. The next step is to relate this value to the delivered volume. The ideal relationship between the resonant frequency and the delivered volume to be expressed as follows:

$$\omega_n^2 = \frac{a^2 A}{L} \frac{1}{V_2} \quad [\text{EQ\#129}]$$

The speed of sound will vary with temperature, so it may be useful to split out the temperature effects.

$$\omega_n^2 = \frac{\gamma R A}{L} \frac{T}{V_2} \quad [\text{EQ\#130}]$$

The volume may then be expressed as a function of the measured resonant frequency and the temperature:

$$V_2 = C\frac{T}{\omega_n^2} \quad [\text{EQ\#131}]$$

Where c is the calibration constant $$C = \frac{\gamma R A}{L}$$

Implementation Details

End Effects The air resonating in the port (e.g., port assembly 624) may extend out into the acoustic volumes at the end of each oscillation. The distance the air extends may be estimated based on the fundamental volume sensor assembly equations. For any given acoustic volume, the distance the air extends into the volume may be expressed as a function of the pressure and port cross-sectional area:

$$x = \frac{V}{\rho a^2 A}p \quad [\text{EQ\#132}]$$

If we assume the following values:

$$V = 28.8 \times 10^{-6} \, L \quad [\text{EQ\#133}]$$

$$\rho = 1.292\frac{\text{kg}}{\text{m}^3} \quad [\text{EQ\#134}]$$

$$a = 340\frac{\text{m}}{\text{s}} \quad [\text{EQ\#135}]$$

$$d = 0.5 \cdot \text{mm} \quad [\text{EQ\#136}]$$

$$p = 1 \cdot \text{Pa (Approximately 100 dB)} \quad [\text{EQ\#137}]$$

Accordingly, the air will extend roughly 1.9 mm in to the acoustic chamber.

Sizing V1 (i.e., the Fixed Volume) Relative to V2 (i.e., the Variable Volume)

Sizing $V_1$ (e.g., fixed volume 1500) may require trading off acoustic volume with the relative position of the poles and zeros in the transfer function. The transfer function for both $V_1$ and $V_2$ (e.g., variable volume 1502) are shown below relative to the volume displacement of speaker assembly 622.

$$\frac{p_2}{v_k} = -\frac{\rho a^2}{V_1}\frac{\omega_n^2}{s^2 + 2\zeta\omega_n s + \alpha\omega_n^2} \quad [\text{EQ\#138}]$$

$$\frac{p_1}{v_k} = -\frac{\rho a^2}{V_1}\frac{s^2 + 2\zeta\omega_n s + \alpha\omega_n^2}{s^2 + 2\zeta\omega_n s + \omega_n^2} \quad [\text{EQ\#139}]$$

where $$\omega_n^2 = \frac{a^2 A}{L}\frac{1}{V_2}, \zeta = \frac{fA}{2L\omega_n} \text{ and } \alpha = \left(1 + \frac{V_2}{V_1}\right) \quad [\text{EQ\#140}]$$

As $V_1$ is increased the gain may decrease and the speaker may be driven at a higher amplitude to get the same sound pressure level. However, increasing $V_1$ may also have the benefit of moving the complex zeros in the $p_1$ transfer function toward the complex poles. In the limiting case where $V_1 \to \infty$, $\alpha \to 1$ and you have pole-zero cancellation and a flat response. Increasing $V_1$, therefore, may have the benefit of reducing both the resonance and the notch in the $p_1$ transfer function, and moving the $p_2$ poles toward $\omega_n$; resulting in a lower sensitivity to measurement error when calculating the $p_2/p_1$ transfer function.

Figure 104:
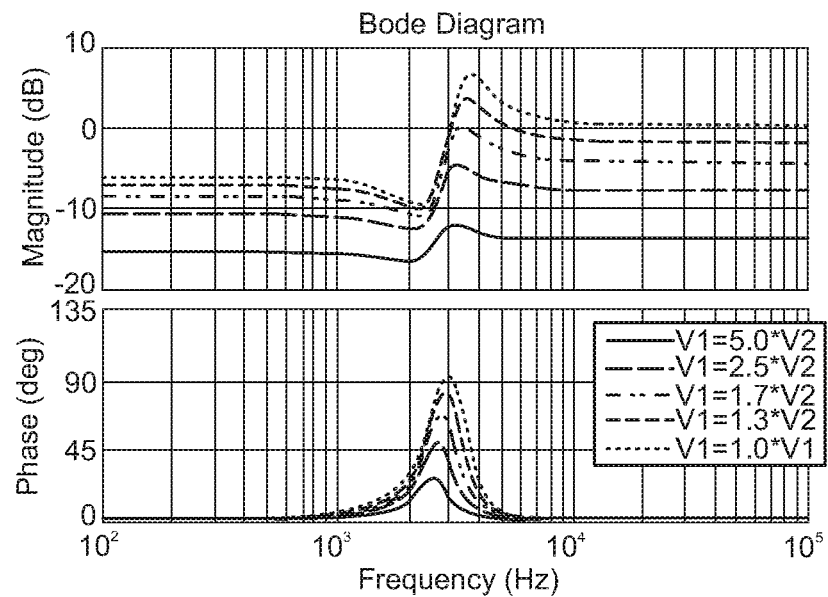
FIG. 104 is a two-dimensional graph of a performance characteristic of a volume sensor assembly included within the infusion pump assembly of FIG. 1.

FIG. 104 is a graphical representation of:

$$\frac{p_1}{v_k} \quad [EQ\#141]$$

Figure 105:
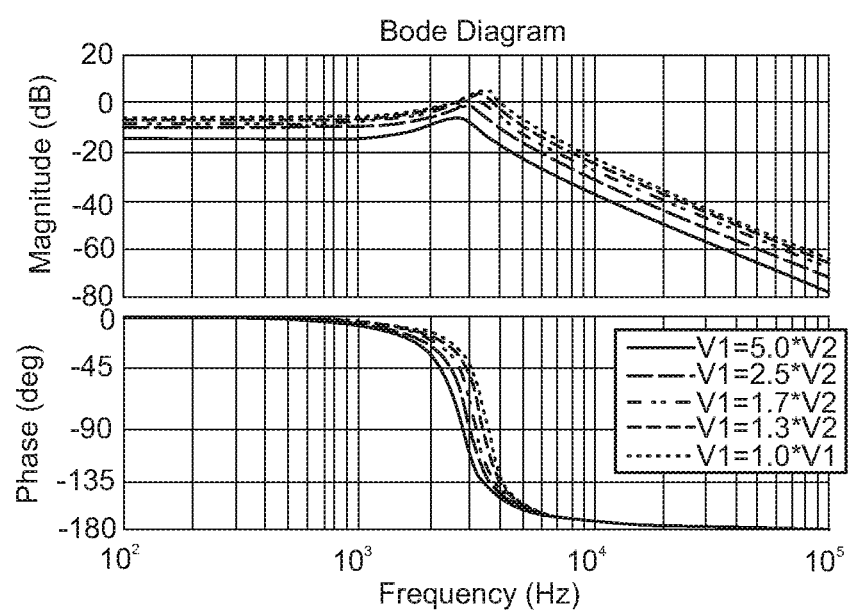
FIG. 105 is a two-dimensional graph of a performance characteristic of a volume sensor assembly included within the infusion pump assembly of FIG. 1.
Figure 106:
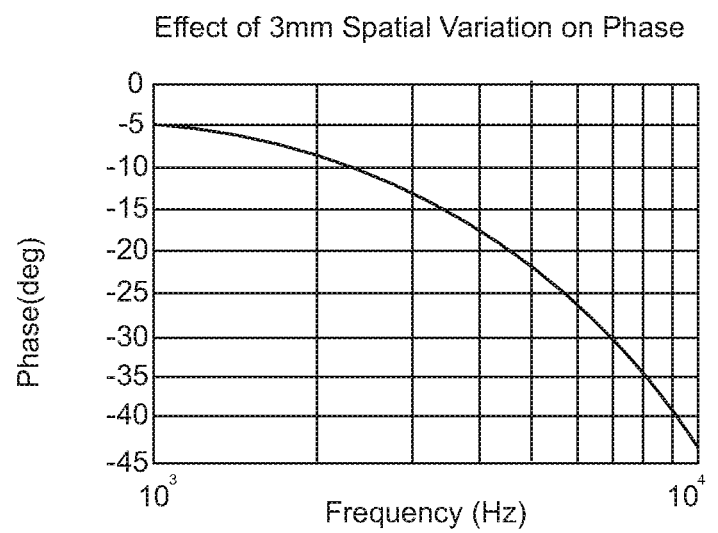
FIG. 106 is a two-dimensional graph of a performance characteristic of a volume sensor assembly included within the infusion pump assembly of FIG. 1.

FIG. 105 is a graphical representation of $$\frac{p_2}{v_k} \quad [EQ\#142]$$

Aliasing Higher frequencies may alias down to the frequency of interest, wherein the aliased frequency may be expressed as follows:

$$f = |f_n - nf_s| \quad [EQ\#143]$$

where $f_s$ is the sampling frequency, $f_n$ is the frequency of the noise source, n is a positive integer, and $f$ is the aliased frequency of the noise source.

The demodulation routine may effectively filter out noise except at the specific frequency of the demodulation. If the sample frequency is set dynamically to be a fixed multiple of the demodulation frequency, then the frequency of the noise that can alias down to the demodulation frequency may be a fixed set of harmonics of that fundamental frequency.

For example, if the sampling frequency is eight times the demodulation frequency, then the noise frequencies that can alias down to that frequency are as follows:

$$\frac{f_n}{f} = \left\{\frac{1}{n\beta+1}, \frac{1}{n\beta-1}\right\} = \left\{\frac{1}{7}, \frac{1}{9}, \frac{1}{15}, \frac{1}{17}, \frac{1}{23}, \frac{1}{25}, ...\right\} \quad [EQ\#144]$$

where $$\beta = \frac{f_s}{f} = 8.$$

For β=16, the following series would result:

$$\frac{f_n}{f} = \left\{\frac{1}{15}, \frac{1}{17}, \frac{1}{31}, \frac{1}{33}, ...\right\} \quad [EQ\#145]$$

Performance

Sensitivity to Temperature

The sensitivity to temperature may be split into a gain change and a noise change. If the temperature is off by a factor of dT, the resulting gain error may be:

$$V_2 = c\left(\frac{T_2}{\omega_2^2} - \frac{T_1}{\omega_1^2}\right) \quad [EQ\#147]$$

Accordingly, if the same temperature is used for both sine sweeps, any error in the temperature measurement may look like a gain change to the system.

$$e_{gain} = 1 - \frac{T_{measured}}{T_{actual}} \quad [EQ\#148]$$

Therefore, for a 1° K temperature error, the resulting volume error may be 0.3% at 298° K. This error may include both the error in the temperature sensor and the difference between the sensor temperature and the temperature of the air within volume sensor assembly 148.

The measurement, however, may be more susceptible to noise in the temperature measurement. A temperature change during the differential sine sweeps may result in an error that looks more like an offset rather than a gain change:

$$V_{error} = \frac{c}{\omega^2}\Delta T \quad [EQ\#149]$$

Figure 107:
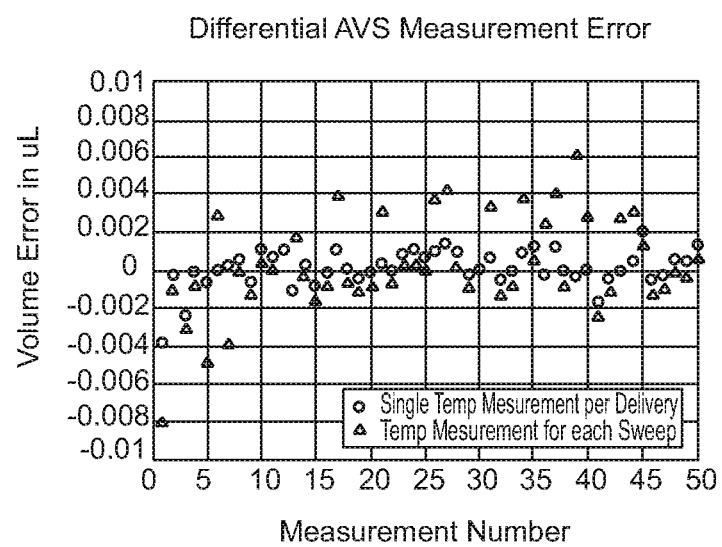
FIG. 107 is a two-dimensional graph of a performance characteristic of a volume sensor assembly included within the infusion pump assembly of FIG. 1.

Accordingly, if the measurement varies by 0.1 K during the two measurement sine sweeps, the difference may be 0.012 uL. Therefore, it may be better to use a consistent temperature estimate for each delivery rather than taking a separate temperature measurement for each sine sweep (as shown in FIG. 107).

Figure 108:
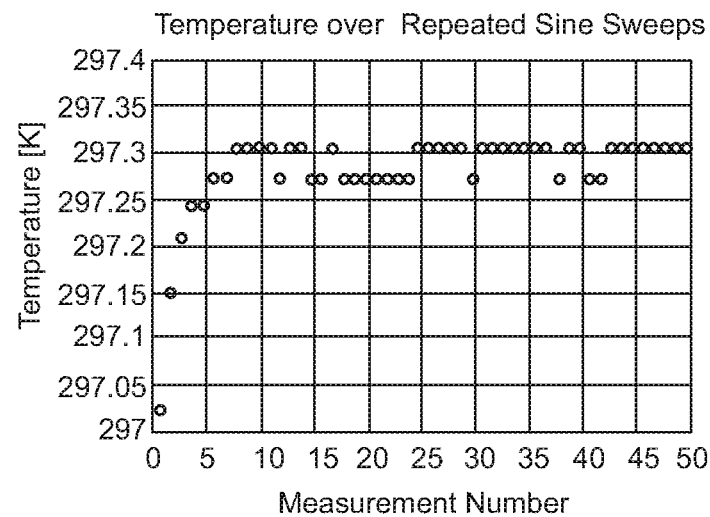
FIG. 108 is a two-dimensional graph of a performance characteristic of a volume sensor assembly included within the infusion pump assembly of FIG. 1.
Figure 109:
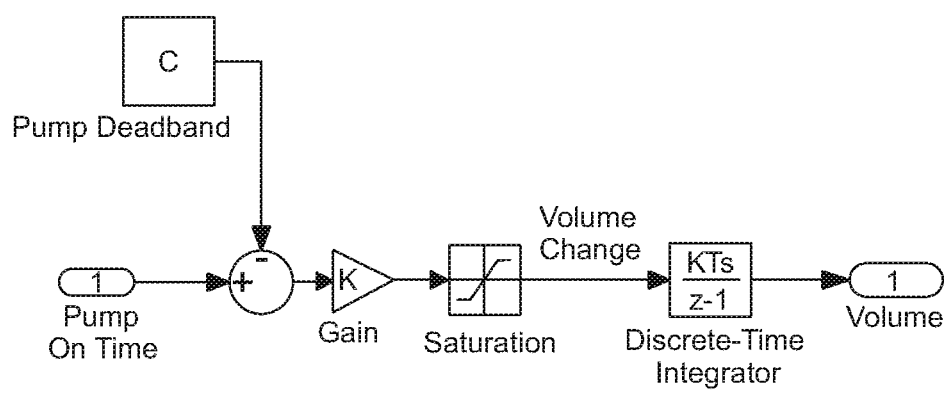
FIG. 109 is a diagrammatic view of a control model for a volume sensor assembly included within the infusion pump assembly of FIG. 1.

The LM73 temperature sensor has a published accuracy of +/−1° C. and a resolution of 0.03 C. Further, the LM73 temperature sensor seems to consistently have a startup transient of about 0.3° C. that takes about five sine sweeps to level out (as shown in FIG. 108). Since the above-described infusion pump assemblies (e.g., infusion pump assembly 100, 100', 400, 500) provides discrete deliveries of infusible fluid, the above-described infusion pump assemblies may be modeled entirely in the discrete domain (in the manner shown in FIG. 109), which may be reduced to the following:

$$G_p(z) = \frac{Kz}{z-1} \quad [EQ\#150]$$

A discrete-time PI regulator may perform according to the following:

$$G_c(z) = K_p\left(1 + \frac{T_s}{T_i}\frac{z}{z-1}\right) \quad [EQ\#151]$$

The AVS system described above works by comparing the acoustic response in fixed volume 1500 and variable volume 1502 to a speaker driven input and extracting the volume of the variable volume 1502. As such, there is a microphone in contact with each of these separate volumes (e.g., microphones 626, 630). The response of variable volume microphone 630 may also be used in a more gross manner to detect the presence or absence of disposable housing assembly 114. Specifically, if disposable housing assembly 114 is not attached to (i.e., positioned proximate) variable volume 1502, essentially no acoustic response to the speaker driven input should be sensed. The response of fixed volume 1500, however, should remain tied to the speaker input. Thus, the microphone data may be used to determine whether disposable housing assembly 114 by simply ensuring that both microphones exhibit an acoustic response. In the event that microphone 626 (i.e., the microphone positioned proximate fixed volume 1500) exhibits an acoustic response and microphone 630 (i.e., the microphone positioned proximate variable volume 1502) does not exhibit an acoustic response, it may be reasonably concluded that disposable housing assembly 114 is not attached to reusable housing assembly 102. It should be noted that a failure of variable volume microphone 630 may also appear to be indicative of disposable housing assembly 114 not being attached, as the failure of variable volume microphone 630 may result in a mid-range reading that is nearly indistinguishable from the microphone response expected when disposable housing assembly 114 is not attached.

For the following discussion, the following nomenclature may be used:

| Symbols | |
|---|---|
| $\alpha_{max}(f)$ | maximum read at a given frequency |
| $\alpha_{min}(f)$ | minimum read at a given frequency |
| δ | difference between max and min sums |
| f | individual frequency |
| F | set of sine sweep frequencies |
| N | number of frequencies in each sine sweep, F |
| φ | boolean disposable attached flag |
| σmax | sum of maximum ADC reads |
| σmin | sum of minimum ADC reads |
| T | max/min ADC difference threshold |
| Subscripts | |
| i | sweep number |
| ref | rererence volume |
| var | variable volume |

As part of the demodulation routine employed in each frequency response calculation, the minimum and maximum readings of both fixed volume microphone 626 and variable volume microphone 630 may be calculated. The sum of these maximum and minimum values may be calculated over the entire sine-sweep (as discussed above) for both microphone 626 and microphone 630 as follows.

$$\sigma max = \sum^{f \in F} \alpha_{max}(f) \quad \text{[EQ\#152]}$$

$$\sigma min = \sum^{f \in F} \alpha_{min}(f) \quad \text{[EQ\#153]}$$

and the difference between these two summations may be simplified as follows:

$$\delta = \sigma max - \sigma min \quad \text{[EQ \#154]}$$

While δ may be divided by the number of sine sweeps to get the average minimum/maximum difference for the sine sweep (which is then compared to a threshold), the threshold may equivalently be multiplied by N for computational efficiency. Accordingly, the basic disposable detection algorithm may be defined as follows:

$$\phi_i = \begin{cases} 1 & \text{if } \delta_{var} > N*T \\ 0 & \text{if } \delta_{var} < N*T \text{ \& } \delta_{ref} > N*T \end{cases} \quad \text{[EQ\#155]}$$

The additional condition that the maximum/minimum difference be greater than the threshold is a check performed to ensure that a failed speaker is not the cause of the acoustic response received. This algorithm may be repeated for any sine-sweep, thus allowing a detachment of disposable housing assembly 114 to be sensed within e.g., at most two consecutive sweeps (i.e., in the worst case scenario in which disposable housing assembly 114 is removed during the second half of an in-progress sine sweep).

Thresholding for the above-described algorithm may be based entirely on numerical evidence. For example, examination of typical minimum/maximum response differences may show that no individual difference is ever less than five hundred ADC counts. Accordingly, all data examined while disposable housing assembly 114 is detached from reusable housing assembly 102 may show that all minimum/maximum response differences as being well under five hundred ADC counts. Thus, the threshold for δ may be set at T=500.

While volume sensor assembly 148 is described above as being utilized within an infusion pump assembly (e.g., infusion pump assembly 100), this is for illustrative purposes only and is not intended to be a limitation of this disclosure, as other configurations are possible and are considered to be within the scope of this disclosure. For example, volume sensor assembly 148 may be used within a process control environment for e.g., controlling the quantity of chemicals mixed together. Alternatively, volume sensor assembly 148 may be used within a beverage dispensing system to control e.g., the quantity of ingredients mixed together.

While volume sensor assembly 148 is described above as utilizing a port (e.g., port assembly 624) as a resonator, this is for illustrative purposes only, as other configurations are possible and are considered to be within the scope of this disclosure. For example, a solid mass (not shown) may be suspended within port assembly 624 and may function as a resonator for volume sensor assembly 148. Specifically, the mass (not shown) for the resonator may be suspended on a diaphragm (not shown) spanning port assembly 624. Alternatively, the diaphragm itself (not shown) may act as the mass for the resonator. The natural frequency of volume sensor assembly 148 may be a function of the volume of variable volume 1502. Accordingly, if the natural frequency of volume sensor assembly 148 can be measured, the volume of variable volume 1502 may be calculated.

The natural frequency of volume sensor assembly 148 may be measured in a number of different ways. For example, a time-varying force may be applied to the diaphragm (not shown) and the relationship between that force and the motion of the diaphragm (not shown) may be used to estimate the natural frequency of volume sensor assembly 148. Alternately the mass (not shown) may be perturbed and then allowed to oscillate. The unforced motion of the mass (not shown) may then be used to calculate the natural frequency of volume sensor assembly 148.

The force applied to the resonant mass (not shown) may be accomplished in various ways, examples of which may include but are not limited to:
  speaker assembly 622 may create a time-varying pressure within fixed volume 1500;
  the resonant mass (not shown) may be a piezoelectric material responding to a time-varying voltage/current; and
  the resonant mass (not shown) may be a voice coil responding to a time-varying voltage/current The force applied to the resonant mass may be measured in various ways, examples of which may include but are not limited to:
  measuring the pressure in the fixed volume;
  the resonant mass (not shown) may be a piezoelectric material; and a strain gauge may be connected to the diaphragm (not shown) or other structural member supporting the resonant mass (not shown).

Similarly, the displacement of the resonant mass (not shown) may be estimated by measuring the pressure in the variable volume, or measured directly in various ways, examples of which may include but are not limited to:

via piezoelectric sensor;
via capacitive sensor;
via optical sensor;
via Hall-effect sensor;
via a potentiometer (time varying impedance) sensor;
via an inductive type sensor; and
via a linear variable differential transformer (LVDT)

Further, the resonant mass (not shown) may be integral to either the force or displacement type sensor (i.e. the resonant mass (not shown) may be made of piezoelectric material).

The application of force and measurement of displacement may be accomplished by a single device. For example, a piezoelectric material may be used for the resonant mass (not shown) and a time-varying voltage/current may be applied to the piezoelectric material to create a time-varying force. The resulting voltage/current applied to the piezoelectric material may be measured and the transfer function between the two used to estimate the natural frequency of volume sensor assembly 148.

As discussed above, the resonant frequency of volume sensor assembly 148 may be estimated using swept-sine system identification. Specifically, the above-described model fit may allow the resonant frequency of the port assembly to be extracted from the sine sweep data, which may then be used to determine the delivered volume. The ideal relationship between the resonant frequency and the delivered volume may be expressed as follows:

$$\omega_n^2 = \frac{a^2 A}{L} \frac{1}{V_2} \qquad [\text{EQ\#126}]$$

The speed of sound will vary with temperature, so it may be useful to split out the temperature effects.

$$\omega_n^2 = \frac{\gamma R A}{L} \frac{T}{V_2} \qquad [\text{EQ\#126}]$$

The volume may then be expressed as a function of the measured resonant frequency and the temperature:

$$V_2 = C \frac{T}{\omega_n^2} \qquad [\text{EQ\#127}]$$

Where c is the calibration constant $$C = \frac{\gamma R A}{L}.$$

Infusion pump assembly 100 may then compare this calculated volume $V_2$ (i.e., representative of the actual volume of infusible fluid delivered to the user) to the target volume (i.e., representative of the quantity of fluid that was supposed to be delivered to the user). For example, assume that infusion pump assembly 100 was to deliver a 0.100 unit basal dose of infusible fluid to the user every thirty minutes. Further, assume that upon effectuating such a delivery, volume sensor assembly 148 indicates a calculated volume $V_2$ (i.e., representative of the actual volume of infusible fluid delivered to the user) of 0.095 units of infusible fluid.

When calculating volume $V_2$, infusion pump assembly 100 may first determine the volume of fluid within volume sensor chamber 620 prior to the administration of the dose of infusible fluid and may subsequently determine the volume of fluid within volume sensor chamber 620 after the administration of the dose of infusible fluid, wherein the difference of those two measurements is indicative of $V_2$ (i.e., the actual volume of infusible fluid delivered to the user). Accordingly, $V_2$ is a differential measurement.

V2 may be the total air space over the diaphragm in the variable volume chamber. The actual fluid delivery to the patient may be the difference in V2 from when the chamber was full to after the measurement valve was opened and the chamber was emptied. V2 may not directly be the delivered volume. For example, the air volume may be measured and a series of differential measurements may be taken. For occlusion, an empty measurement may be taken, the chamber may be filed, a full measurement may be taken, and then a final measurement may be taken after the exit valve is open. Accordingly, the difference between the first and second measurement may be the amount pumped and the difference between the second and third is the amount delivered to the patient.

Accordingly, electrical control assembly 110 may determine that the infusible fluid delivered is 0.005 units under what was called for. In response to this determination, electrical control assembly 110 may provide the appropriate signal to mechanical control assembly 104 so that any additional necessary dosage may be pumped. Alternatively, electrical control assembly 110 may provide the appropriate signal to mechanical control assembly 104 so that the additional dosage may be dispensed with the next dosage. Accordingly, during administration of the next 0.100 unit dose of the infusible fluid, the output command for the pump may be modified based on the difference between the target and amount delivered.

Referring also to FIG. 110, there is shown one particular implementation of a control system for controlling the quantity of infusible fluid currently being infused based, at least in part, on the quantity of infusible fluid previously administered. Specifically and continuing with the above-stated example, assume for illustrative purposes that electrical control assembly 110 calls for the delivery of a 0.100 unit dose of the infusible fluid to the user. Accordingly, electrical control assembly 110 may provide a target differential volume signal 1600 (which identifies a partial basal dose of 0.010 units of infusible fluid per cycle of shape memory actuator 112) to volume controller 1602. Accordingly and in this particular example, shape memory actuator 112 may need to be cycled ten times in order to achieve the desired basal dose of 0.100 units of infusible fluid (i.e., 10 cycles×0.010 units per cycle=0.100 units). Volume controller 1602 in turn may provide "on-time" signal 1606 to SMA (i.e., shape memory actuator) controller 1608. Also provided to SMA controller 1608 is battery voltage signal 1610.

Specifically, shape-memory actuator 112 may be controlled by varying the amount of thermal energy (e.g., joules) applied to shape-memory actuator 112. Accordingly, if the voltage level of battery 606 is reduced, the quantity of joules applied to shape-memory actuator 112 may also be reduced for a defined period of time. Conversely, if the voltage level of battery 606 is increased, the quantity of joules applied to shape memory actuator 112 may also be increased for a defined period of time. Therefore, by monitoring the voltage level of battery 606 (via battery voltage signal 1610), the type of signal applied to shape-memory actuator 112 may be varied to ensure that the appropriate quantity of thermal energy is applied to shape-memory actuator 112 regardless of the battery voltage level.

SMA controller 1608 may process "on-time" signal 1606 and battery voltage signal 1610 to determine the appropriate SMA drive signal 1612 to apply to shape-memory actuator 112. One example of SMA drive signal 1612 may be a series of binary pulses in which the amplitude of SMA drive signal 1612 essentially controls the stroke length of shape-memory actuator 112 (and therefore pump assembly 106) and the duty cycle of SMA drive signal 1612 essentially controls the stroke rate of shape-memory actuator 112 (and therefore pump assembly 106). Further, since SMA drive signal 1612 is indicative of a differential volume (i.e., the volume infused during each cycle of shape memory actuator 112), SMA drive signal 1612 may be integrated by discrete time integrator 1614 to generate volume signal 1616 which may be indicative of the total quantity of infusible fluid infused during a plurality of cycles of shape memory actuator 112. For example, since (as discussed above) it may take ten cycles of shape memory actuator 112 (at 0.010 units per cycle) to infuse 0.100 units of infusible fluid, discrete time integrator 1614 may integrate SMA drive signal 1612 over these ten cycles to determine the total quantity infused of infusible fluid (as represented by volume signal 1616).

SMA drive signal 1612 may actuate pump assembly 106 for e.g. one cycle, resulting in the filling of volume sensor chamber 620 included within volume sensor assembly 148. Infusion pump assembly 100 may then make a first measurement of the quantity of fluid included within volume sensor chamber 620 (as discussed above). Further and as discussed above, measurement valve assembly 610 may be subsequently energized, resulting in all or a portion of the fluid within volume sensor chamber 620 being delivered to the user. Infusion pump assembly 100 may then make a measurement of the quantity of fluid included within volume sensor chamber 620 (as described above) and use those two measurements to determine V2 (i.e., the actual volume of infusible fluid delivered to the user during the current cycle of shape memory actuator 112). Once determined, V2 (i.e., as represented by signal 1618) may be provided (i.e., fed back) to volume controller 1602 for comparison to the earlier-received target differential volume.

Continuing with the above-stated example in which the differential target volume was 0.010 units of infusible fluid, assume that V2 (i.e., as represented by signal 1618) identifies 0.009 units of infusible fluid as having been delivered to the user. Accordingly, infusion pump assembly 100 may increase the next differential target volume to 0.011 units to offset the earlier 0.001 unit shortage. Accordingly and as discussed above, the amplitude and/or duty cycle of SMA drive signal 1612 may be increased when delivering the next basal dose of the infusible fluid to the user. This process may be repeated for the remaining nine cycles of shape memory actuator 112 (as discussed above) and discrete time integrator 1614 may continue to integrate SMA drive signal 1612 (to generate volume signal 1616) which may define the total quantity of infusible fluid delivered to the user.

Figure 111:
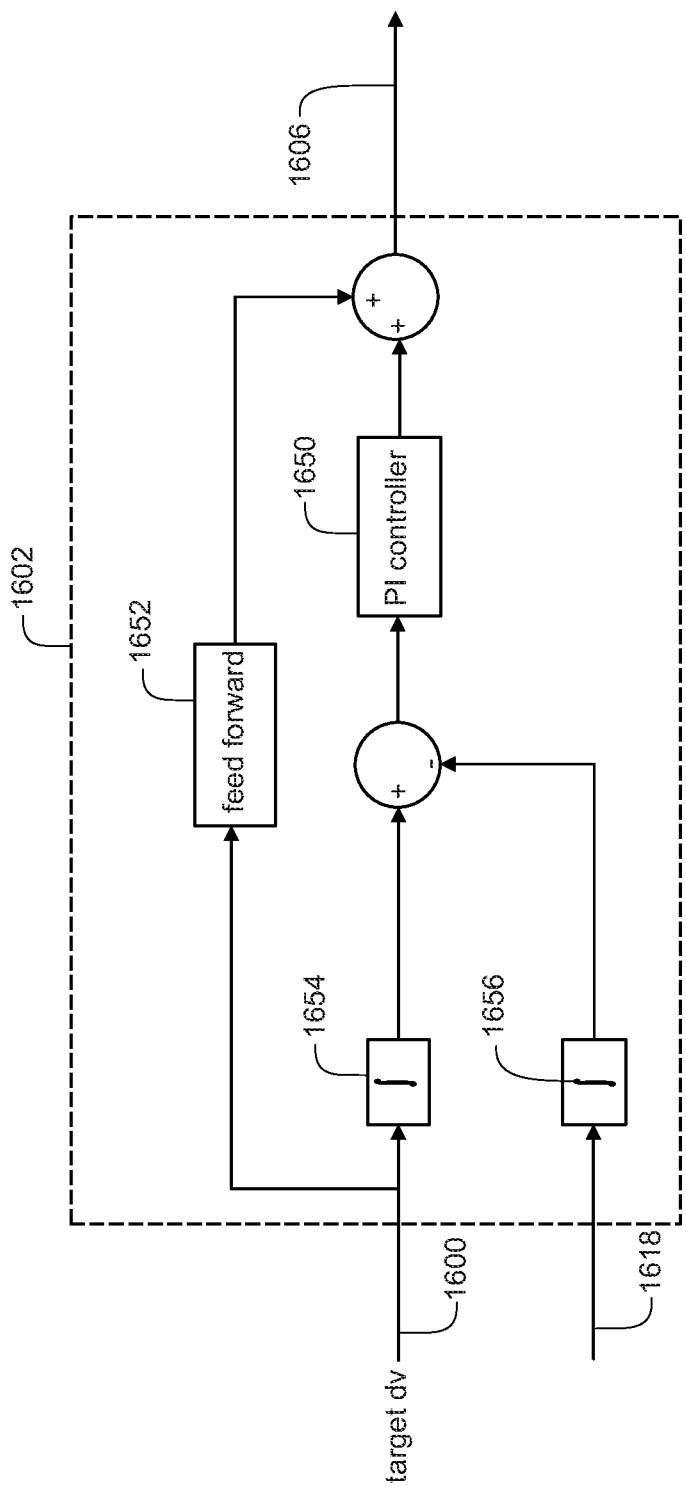
FIG. 111 is a diagrammatic view of a volume controller for the volume sensor assembly included within the infusion pump assembly of FIG. 1.

Referring also to FIG. 111, there is shown one possible embodiment of volume controller 1602. In this particular implementation, volume controller 1602 may include PI (proportional-integrator) controller 1650. Volume controller 1602 may include feed forward controller 1652 for setting an initial "guess" concerning "on-time" signal 1606. For example, for the situation described above in which target differential volume signal 1600 identifies a partial basal dose of 0.010 units of infusible fluid per cycle of shape memory actuator 112, feed forward controller 1652 may define an initial "on-time" of e.g., one millisecond. Feed forward controller 1652 may include e.g., a lookup table that define an initial "on-time" that is based, at least in part, upon target differential volume signal 1600. Volume controller 1602 may further include discrete time integrator 1654 for integrating target differential volume signal 1600 and discrete time integrator 1656 for integrating $V_2$ (i.e., as represented by signal 1618).

Figure 112:
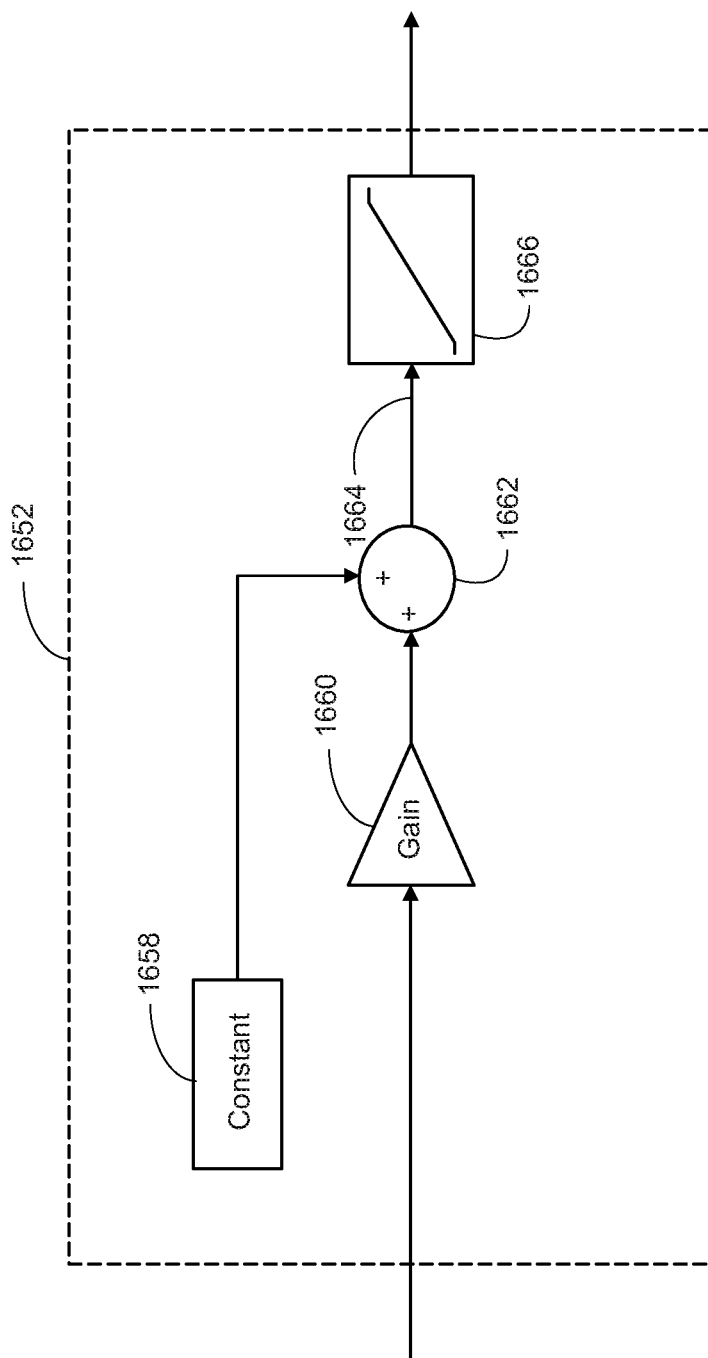
FIG. 112 is a diagrammatic view of a feed forward controller of the volume controller of FIG. 111.

Referring also to FIG. 112, there is shown one possible embodiment of feed forward controller 1652. In this particular implementation, feed forward controller 1652 may define a constant value signal 1658 and may include amplifier 1660 (e.g., a unity gain amplifier), the output of which may be summed with constant value signal 1658 at summing node 1662. The resulting summed signal (i.e., signal 1664) may be provided to as an input signal to e.g., lookup table 1666, which may be processed to generate the output signal of feed forward controller 1652.

As discussed above, pump assembly 106 may be controlled by shape memory actuator 112. Further and as discussed above, SMA controller 1608 may process "on-time" signal 1606 and battery voltage signal 1610 to determine the appropriate SMA drive signal 1612 to apply to shape-memory actuator 112.

Figure 113:
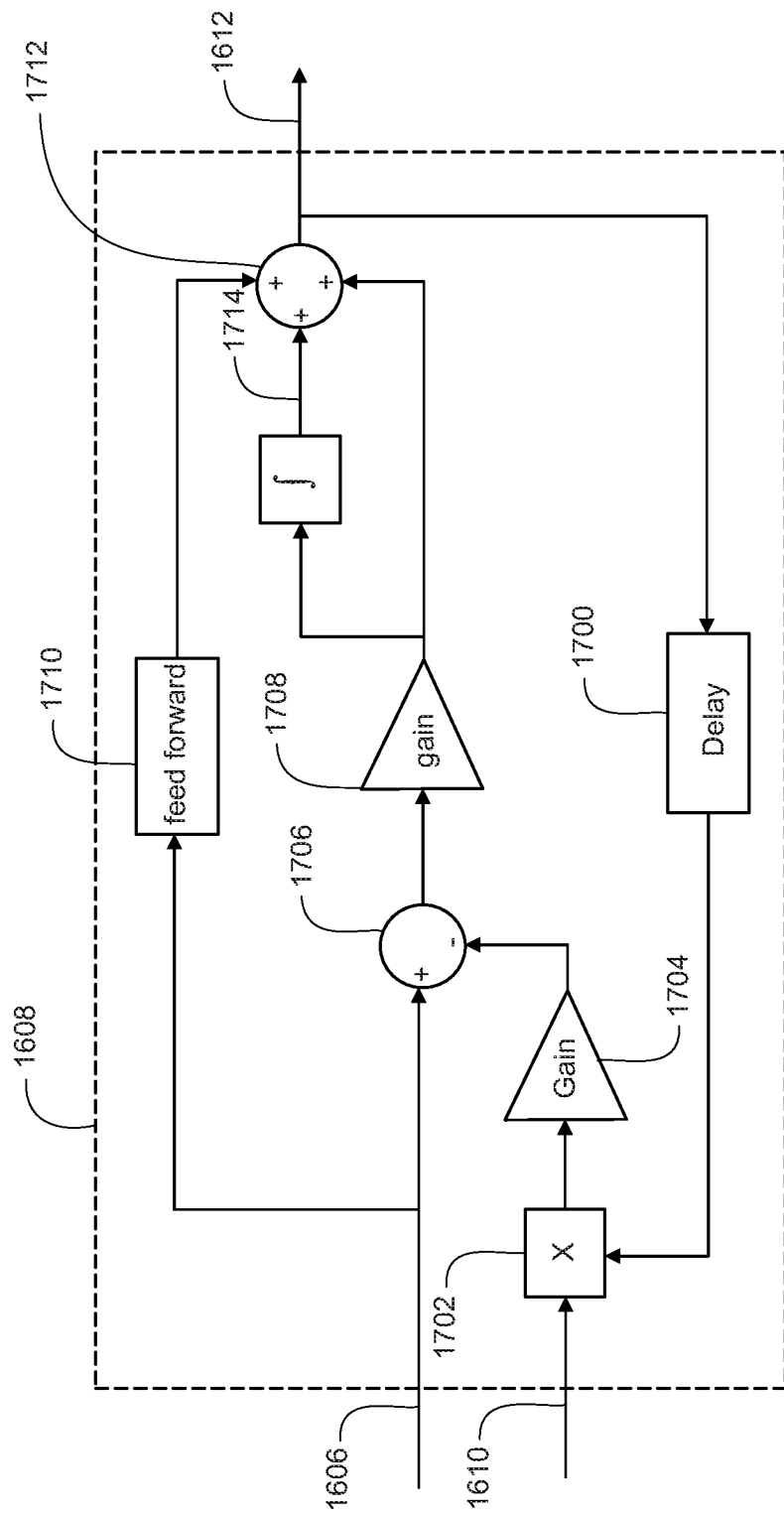
FIGS. 113-114 diagrammatically depicts an implementation of an SMA controller of the volume controller of FIG. 111.
Figure 114:
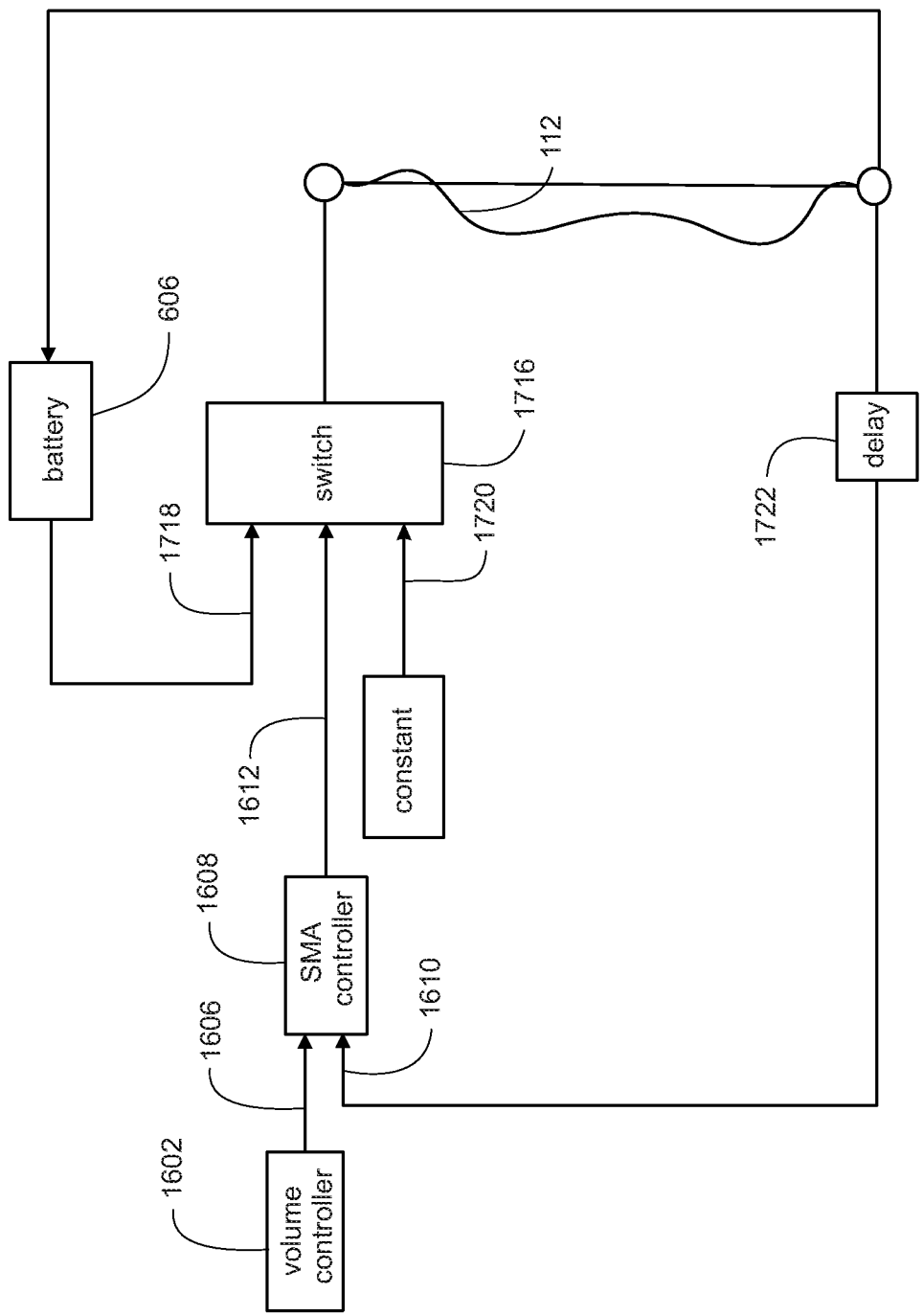

Referring also to FIGS. 113-114, there is shown one particular implementation of SMA controller 1608. As discussed above, SMA controller 1608 may be responsive to "on-time" signal 1606 and battery voltage signal 1610 and may provide SMA drive signal 1612 to shape-memory actuator 112. SMA controller 1608 may include a feedback loop (including unit delay 1700), the output of which may be multiplied with battery voltage signal 1610 at multiplier 1702. The output of multiplier 1702 may be amplified with e.g., unity gain amplifier 1704. The output of amplifier 1704 may be applied to the negative input of summing node 1706 (to which "on-time" signal 1606 is applied). The output of summing node 1706 may be amplified (via e.g., unity gain amplifier 1708). SMA controller may also include feed forward controller 1710 to provide an initial value for SMA drive signal 1612 (in a fashion similar to feed forward controller 1652 of volume controller 1602; See FIG. 112). The output of feed forward controller 1710 may be summed at summing node 1712 with the output of amplifier 1708 and an integrated representation (i.e., signal 1714) of the output of amplifier 1708 to form SMA drive signal 1612.

SMA drive signal 1612 may be provided to control circuitry that effectuates the application of power to shape-memory actuator 112. For example, SMA drive signal 1612 may be applied to switching assembly 1716 that may selectively apply current signal 1718 (supplied from battery 606) and/or fixed signal 1720 to shape-memory actuator. For example, SMA drive signal 1612 may effectuate the application of energy (supplied from battery 606 via current signal 1718) via switching assembly 1716 in a manner that achieves the duty cycle defined by SMA drive signal 1612. Unit delay 1722 may generate a delayed version of the signal applied to shape-memory actuator 112 to form battery voltage signal 1610 (which may be applied to SMA controller 1608).

When applying power to shape-memory actuator 112, voltage may be applied for a fixed amount of time and: a) at a fixed duty cycle with an unregulated voltage; b) at a fixed duty cycle with a regulated voltage; c) at a variable duty cycle based upon a measured current value; d) at a variable duty cycle based upon a measured voltage value; and e) at a variable duty cycle based upon the square of a measured voltage value. Alternatively, voltage may be applied to shape-memory actuator 112 for a variable amount of time based upon a measured impedance.

When applying an unregulated voltage for a fixed amount of time at a fixed duty cycle, inner loop feedback may not be used and shape memory actuator may be driven at a fixed duty cycle and with an on-time determined by the outer volume loop.

When applying a regulated voltage for a fixed amount of time at a fixed duty cycle, inner loop feedback may not be used and shape memory actuator 112 may be driven at a fixed duty cycle and with an on-time determined by the outer volume loop.

When applying an unregulated voltage at a variable duty cycle based upon a measured current value, the actual current applied to shape-memory actuator 112 may be measured and the duty cycle may be adjusted during the actuation of shape-memory actuator 112 to maintain the correct mean current.

When applying an unregulated voltage at a variable duty cycle based upon a measured voltage value, the actual voltage applied to shape-memory actuator 112 may be measured and the duty cycle may be adjusted during the actuation of shape-memory actuator 112 to maintain the correct mean voltage.

When applying an unregulated voltage at a variable duty cycle based upon the square of a measured voltage value, the actual voltage applied to shape-memory actuator 112 may be measured and the duty cycle may be adjusted during the actuation of shape-memory actuator 112 to maintain the square of the voltage at a level required to provide the desired level of power to shape-memory actuator 112 (based upon the impedance of shape-memory actuator 112).

Figure 114A:
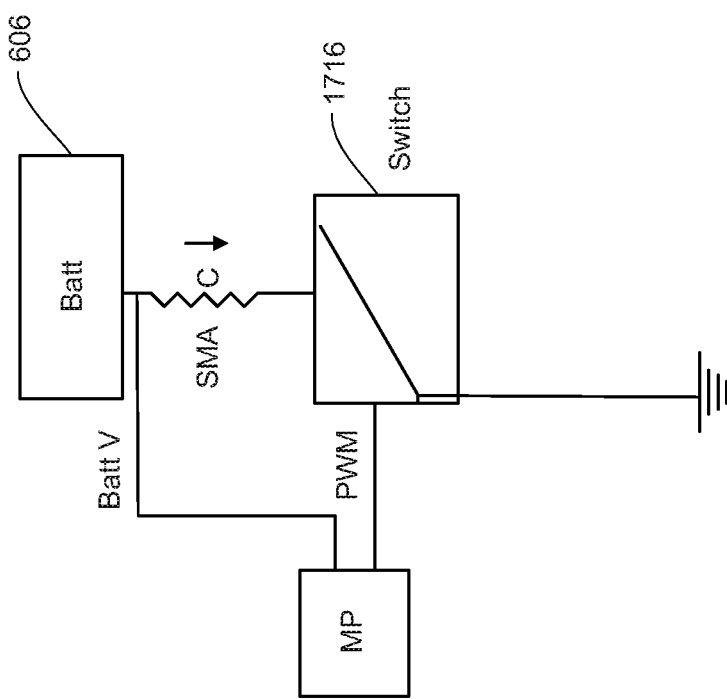

Referring also to FIG. 114A-114B, there is shown other implementations of SMA controller 1608. Specifically, FIG. 114A is an electrical schematic that includes a microprocessor and various control loops that may be configured to provide a PWM signal that may open and close the switch assembly. The switch assembly may control the current that is allowed to flow through the shape memory actuator. The battery may provide the current to the shape memory actuator. Further, 114B discloses a volume controller and an inner shape memory actuator controller. The shape memory actuator controller may provide a PWM signal to the pump, which may be modified based on the battery voltage. This may occur for a fixed ontime, the result being a volume that may be measured by volume sensor assembly 148 and fed back into the volume controller.

In our preferred embodiment, we vary the duty cycle based on the measured battery voltage to give you approximately consistent power. We adjust the duty cycle to compensate for a lower battery voltage. Battery voltage may change for two reasons: 1) as batteries are discharged, the voltage slowly decreases; and 2) when you apply a load to a battery it has an internal impedance so its voltage dips. This is something that happens in any type of system, and we compensate for that by adjusting the duty cycle, thus mitigating the lower or varying battery voltage. Battery voltage may be measured by the microprocessor. In other systems: 1) voltage may be regulated (put a regulator to maintain the voltage at a steady voltage); 2) feedback based on something else (i.e., speed or position of a motor, not necessarily measuring the battery voltage).

Other configurations may be utilized to control the shape memory actuator. For example: A) the shape memory actuator may be controlled at fixed duty cycle with unregulated voltage. As voltage varies, the repeatability of heating the shape memory actuator is reduced. B) a fixed duty cycle, regulated voltage may be utilized which compensate for changes in battery voltage. However, regulate the voltage down is less efficient due to energy of energy. C) the duty cycle may be varied based on changes in current (which may required more complicated measurement circuitry. D) The duty cycle may be varied based on measured voltage. E) The duty cycle may be varied based upon the square of the current. or the square of the voltage divided by resistance. F) the voltage may be applied for a variable amount of time based on the measured impedance (e.g., may measure impedance using Wheatstone gauge (not shown)). The impedance of the shape memory actuator may be correlated to strain (i.e., may correlate how much the SMA moves based on its impedance).

Figure 115:
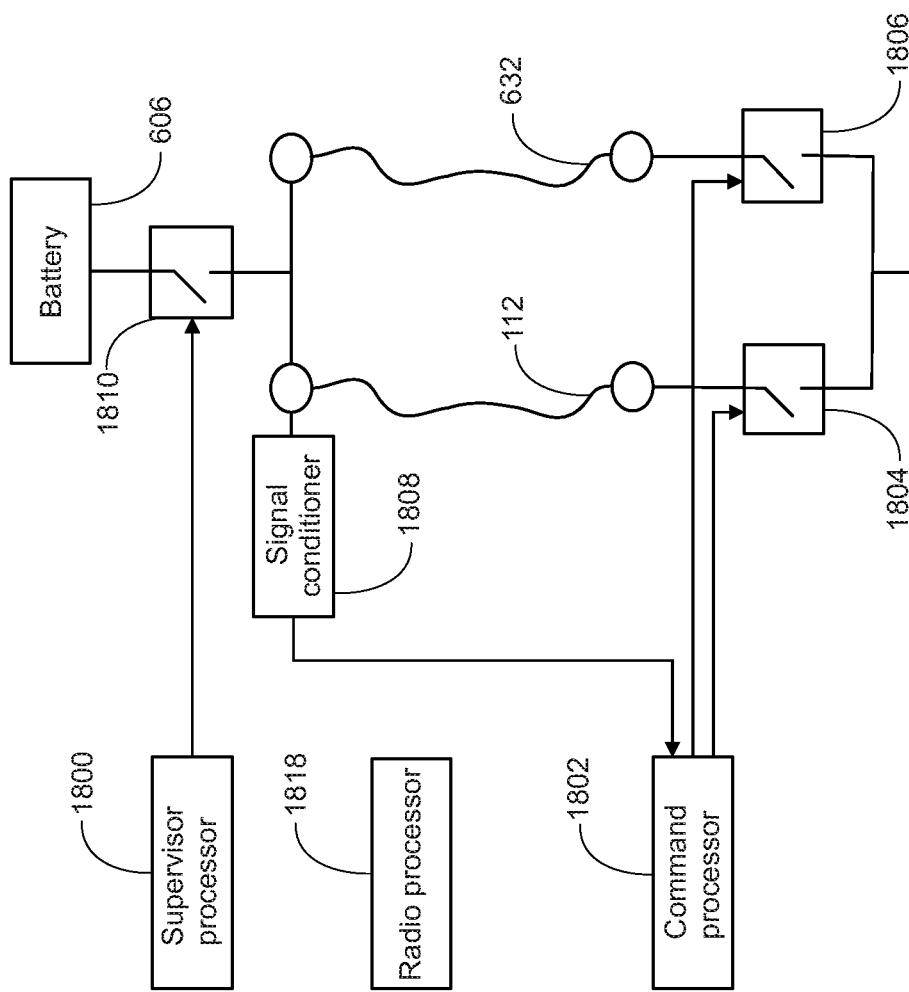
FIG. 115 diagrammatically depicts a multi-processor control configuration that may be included within the infusion pump assembly of FIG. 1.

Referring also to FIG. 115 and as discussed above, to enhance the safety of infusion pump assembly 100, electrical control assembly 110 may include two separate and distinct microprocessors, namely supervisor processor 1800 and command processor 1802. Specifically, command processor 1802 may perform the functions discussed above (e.g., generating SMA drive signal 1612) and may control relay/switch assemblies 1804, 1806 that control the functionality of (in this example) shape memory actuators 112, 632 (respectively). Command processor 1802 may receive feedback from signal conditioner 1808 concerning the condition (e.g., voltage level) of the voltage signal applied to shape memory actuators 112, 632. Command processor 1800 may control relay/switch assembly 1810 independently of relay/switch assemblies 1804, 1806. Accordingly, when an infusion event is desired, both of supervisor processor 1800 and command processor 1802 must agree that the infusion event is proper and must both actuate their respective relays/switches. In the event that either of supervisor processor 1800 and command processor 1802 fails to actuate their respective relays/switches, the infusion event will not occur. Accordingly through the use of supervisor processor 1800 and command processor 1802 and the cooperation and concurrence that must occur, the safety of infusion pump assembly 100 is enhanced.

The supervisor processor may prevent the command processor from delivering when it is not supposed and also may alarm if the command processor does not deliver when it should be delivering. The supervisor processor may deactivate the relay/switch assembly if the command processor actuates the wrong switch, or if the command processor it tries to apply power for too long.

The supervisor processor may redundantly doing calculations for how much insulin should be delivered (i.e., double checking the calculations of the command processor). Command processor may decide the delivery schedule, and the supervisor processor may redundantly check those calculations.

Supervisor also redundantly holds the profiles (delivery profiles) in RAM, so the command processor may be doing the correct calculations, but if is has bad RAM, would cause the command to come up with the wrong result. The Supervisor uses its local copy of the basal profile, etc., to double check.

Supervisor can double check AVS measurements, looks at the AVS calculations and applies safety checks. Every time AVS measurement is taken, it double checks.

Figure 116:
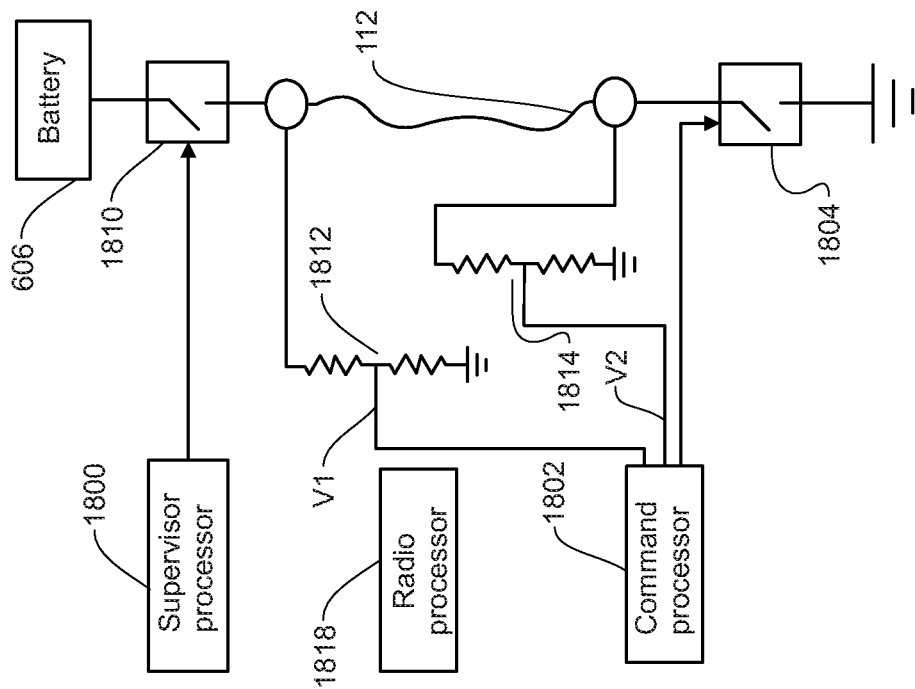
FIG. 116 is a diagrammatic view of a multi-processor control configuration that may be included within the infusion pump assembly of FIG. 1.

Referring also to FIG. 116, one or more of supervisor processor 1800 and command processor 1802 may perform diagnostics on various portions of infusion pump assembly 100. For example, voltage dividers 1812, 1814 may be configured to monitor the voltages (V1 & V2 respectively) sensed at distal ends of e.g., shape memory actuator 112. The value of voltages V1 & V2 in combination with the knowledge of the signals applied to relay/switch assemblies 1804, 1810 may allow for diagnostics to be performed on various components of the circuit shown in FIG. 116 (in a manner similar to that shown in illustrative diagnostic table 1816).

As discussed above and as illustrated in FIGS. 115-116, to enhance the safety of infusion pump assembly 100, electrical control assembly 110 may include a plurality of microprocessors (e.g., supervisor processor 1800 and command processor 1802), each of which may be required to interact and concur in order to effectuate the delivery of a dose of the infusible fluid. In the event that the microprocessors fail to interact/concur, the delivery of the dose of infusible fluid may fail and one or more alarms may be triggered, thus enhancing the safety and reliability of infusion pump assembly 100.

A master alarm may be utilized that tracks the volume error over time. Accordingly, if the sum of the errors becomes too large, the master alarm may be initiated, indicating that something may be wrong with the system. Accordingly, the master alarm may be indicative of a total volume comparison being performed and a discrepancy being noticed. A typical value of the discrepancy required to initiate the master alarm may be 1.00 milliliters. The master alarm may monitor the sum in a leaky fashion (i.e., Inaccuracies have a time horizon).

Figure 117A:
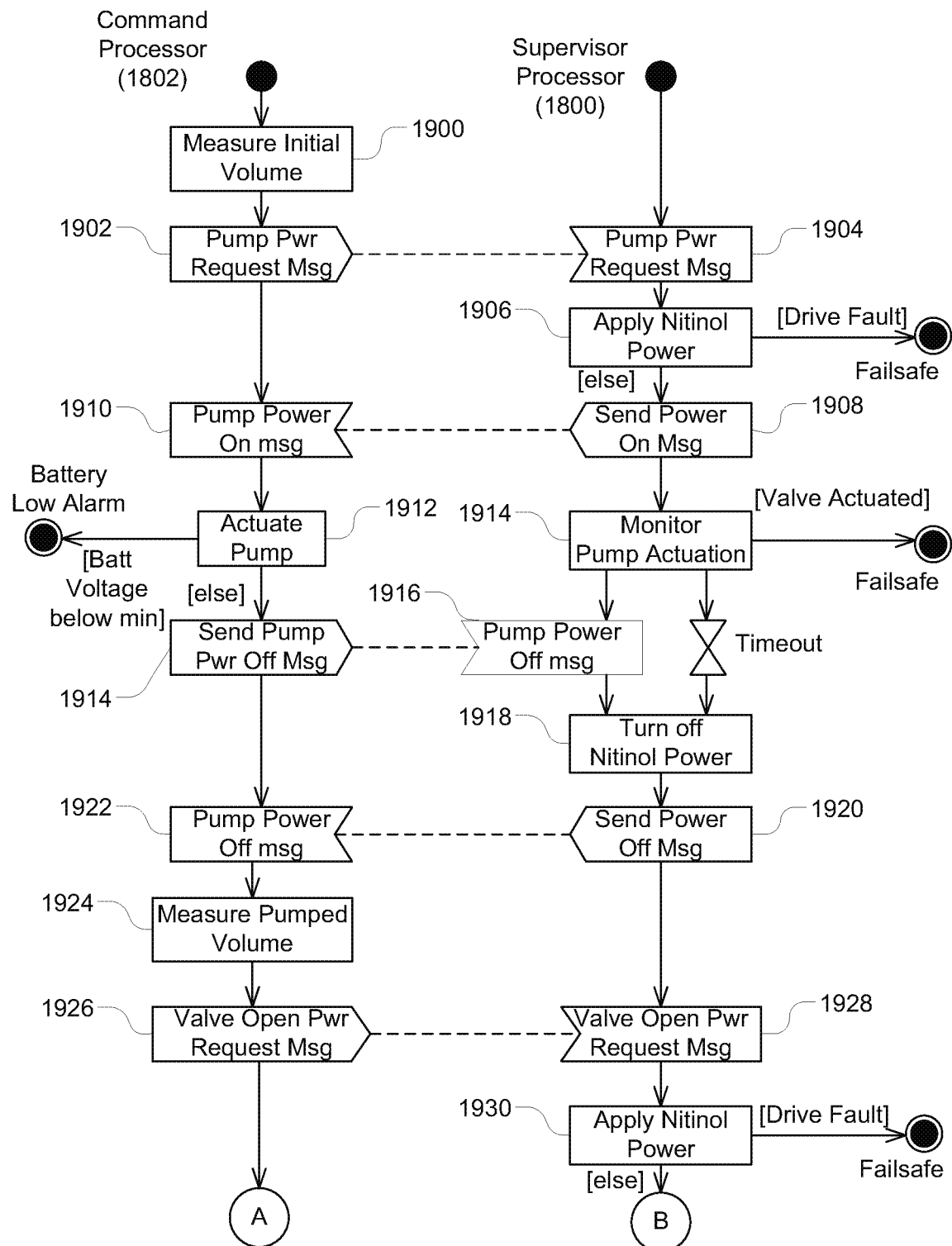
FIG. 117A-117B diagrammatically depicts multi-processor functionality.
Figure 117B:
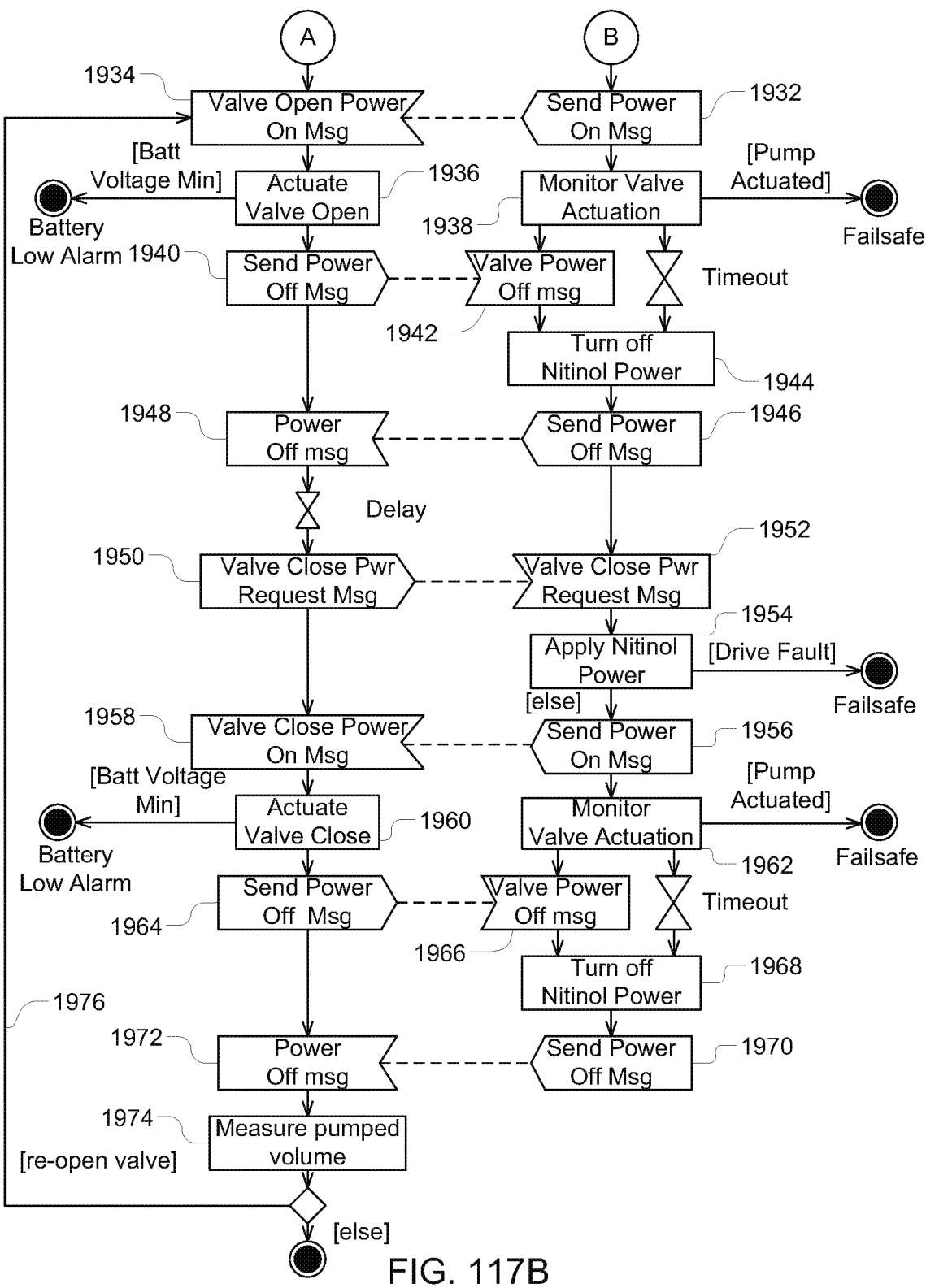

Referring also to FIGS. 117A-117B, there is shown one such illustrative example of such interaction amongst multiple microprocessors during the delivery of a dose of the infusible fluid. Specifically, command processor 1802 may first determine 1900 the initial volume of infusible fluid within volume sensor chamber 620. Command processor 1802 may then provide 1902 a "pump power request" message to supervisor processor 1800. Upon receiving 1904 the "pump power request" message, supervisor processor 1800 may e.g., energize 1906 relay/switch 1810 (thus energizing shape memory actuator 112) and may send 1908 a "pump power on" message to command processor 1802. Upon receiving 1910 the "pump power on" message, command processor 1802 may actuate 1912 e.g., pump assembly 106 (by energizing relay/switch 1804), during which time supervisor processor 1800 may monitor 1914 the actuation of e.g., pump assembly 106.

Once actuation of pump assembly 106 is complete, command processor 1802 may provide 1914 a "pump power off" message to supervisor processor 1800. Upon receiving 1916 the "pump power off" message, supervisor processor 1800 may deenergize 1918 relay/switch 1810 and provide 1920 a "pump power off" message to command processor 1802. Upon receiving 1922 the "pump power off" message, command processor 1802 may measure 1924 the quantity of infusible fluid pumped by pump assembly 106. This may be accomplished by measuring the current quantity of fluid within volume sensor chamber 620 and comparing it with the quantity determined above (in step 1900). Once determined 1924, command processor 1802 may provide 1926 a "valve open power request" message to supervisor processor 1800. Upon receiving 1928 the "valve open power request" message, supervisor processor 1800 may energize 1930 relay/switch 1810 (thus energizing shape memory actuator 632) and may send 1932 a "valve open power on" message to command processor 1802. Upon receiving 1934 the "valve open power on" message, command processor 1802 may actuate 1936 e.g., measurement valve assembly 610 (by energizing relay/switch 1806), during which time supervisor processor 1800 may monitor 1938 the actuation of e.g., measurement valve assembly 610.

Once actuation of measurement valve assembly 610 is complete, command processor 1802 may provide 1940 a "valve power off" message to supervisor processor 1800. Upon receiving 1942 the "valve power off" message, supervisor processor 1800 may deenergize 1944 relay/switch 1810 and provide 1946 a "valve power off" message to command processor 1802.

Upon receiving 1948 the "valve power off" message, command processor 1802 may provide 1950 a "valve close power request" message to supervisor processor 1800. Upon receiving 1952 the "valve close power request" message, supervisor processor 1800 may energize 1954 relay/switch 1810 (thus energizing shape memory actuator 652) and may send 1956 a "power on" message to command processor 1802. Upon receiving 1958 the "power on" message, command processor 1802 may actuate 1960 an energizing relay/switch (not shown) that is configured to energize shape memory actuator 652, during which time supervisor processor 1800 may monitor 1962 the actuation of e.g., shape memory actuator 652.

As discussed above (and referring temporarily to FIGS. 26A, 26B, 27A, 27B & 28), shape memory actuator 652 may be anchored on a first end using electrical contact 654. The other end of shape memory actuator 652 may be connected to bracket assembly 656. When shape memory actuator 652 is activated, shape memory actuator 652 may pull bracket assembly 656 forward and release valve assembly 634. As such, measurement valve assembly 610 may be activated via shape memory actuator 632. Once measurement valve assembly 610 has been activated, bracket assembly 656 may automatically latch valve assembly 610 in the activated position. Actuating shape memory actuator 652 may pull bracket assembly 656 forward and release valve assembly 634. Assuming shape memory actuator 632 is no longer activated, measurement valve assembly 610 may move to a de-activated state once bracket assembly 656 has released valve assembly 634. Accordingly, by actuating shape memory actuator 652, measurement valve assembly 610 may be deactivated.

Once actuation of shape memory actuator 652 is complete, command processor 1802 may provide 1964 a "power off" message to supervisor processor 1800. Upon receiving 1966 the "power off" message, supervisor processor 1800 may deenergize 1968 relay/switch 1810 and may provide 1970 a "power off" message to command processor 1802. Upon receiving 1972 the "power off" message, command processor 1802 may determine the quantity of infusible fluid within volume sensor chamber 620, thus allowing command processor 1802 to compare this measured quantity to the quantity determined above (in step 1924) to determine 1974 the quantity of infusible fluid delivered to the user.

In the event that the quantity of infusible fluid delivered 1974 to the user is less than the quantity of infusible fluid specified for the basal/bolus infusion event, the above-described procedure may be repeated (via loop 1976).

Figure 118:
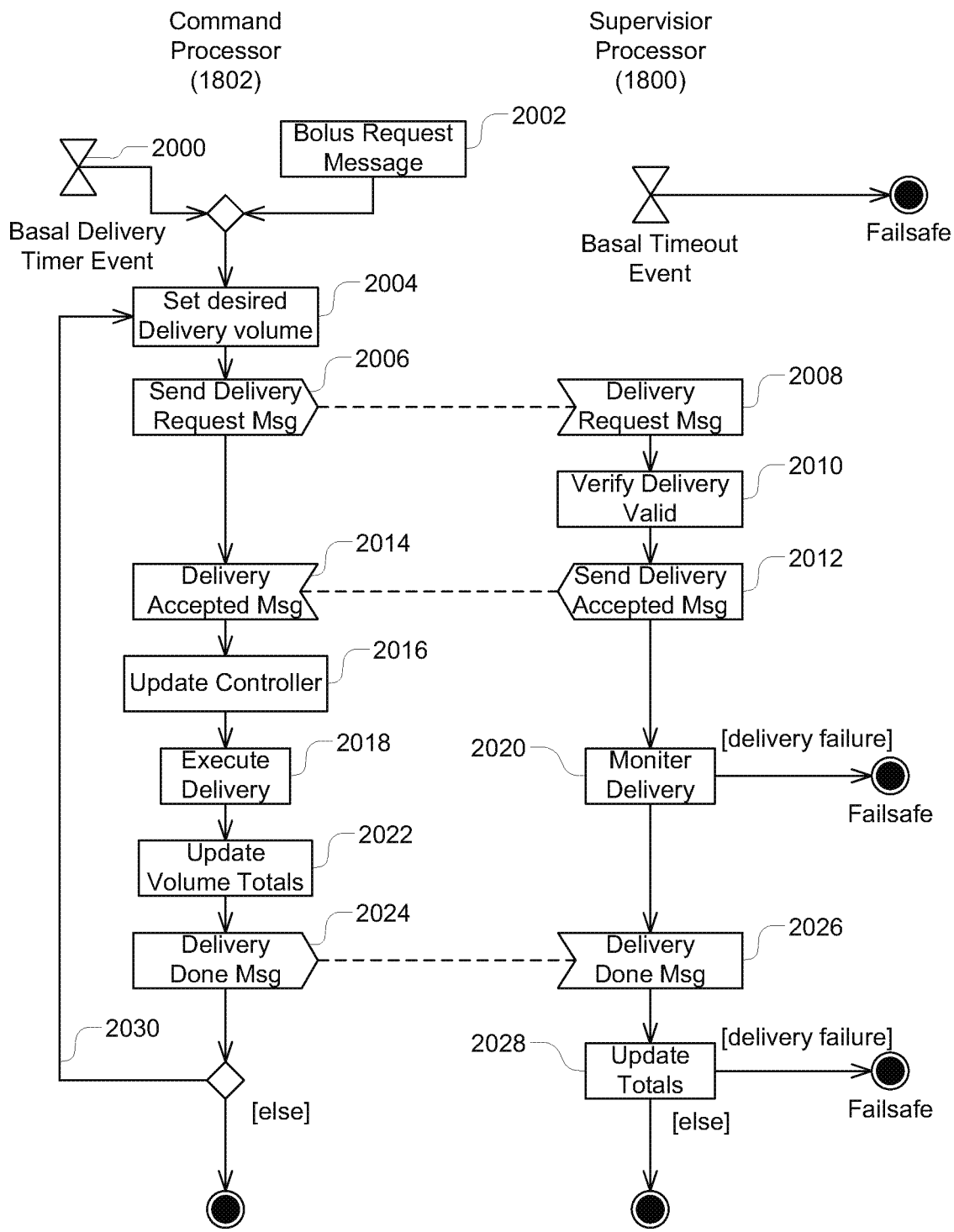
FIG. 118 diagrammatically depicts multi-processor functionality.

Referring also to FIG. 118, there is shown another illustrative example of the interaction amongst processors 1800, 1802, this time during the scheduling of a dose of infusible fluid. Command processor 1802 may monitor 2000, 2002 for the receipt of a basal scheduling message or a bolus request message (respectively). Upon receipt 2000, 2002 of either of these messages, command processor 1802 may set 2004 the desired delivery volume and may provide 2006 a "delivery request" message to supervisor processor 1800. Upon receiving 2008 the "delivery request" message, supervisor processor 1800 may verify 2010 the volume defined 2004 by command processor 1802. Once verified 2010, supervisor processor 1800 may provide 2012 a "delivery accepted" message to command processor 1802. Upon receipt 2014 of the "delivery accepted" message, command processor 1802 may update 2016 the controller (e.g., the controller discussed above and illustrated in FIG. 110) and execute 2018 delivery of the basal/bolus dose of infusible fluid. Command processor 1808 may monitor and update 2022 the total quantity of infusible fluid delivered to the user (as discussed above and illustrated in FIGS. 117A-117B). Once the appropriate quantity of infusible fluid is delivered to the user, command processor 1802 may provide 2024 a "delivery done" message to supervisor processor 1800. Upon receipt 2026 of the "delivery done" message, supervisor processor 1800 may update 2028 the total quantity of infusible fluid delivered to the user. In the event that the total quantity of infusible fluid delivered 2018 to the user is less than the quantity defined above (in step 2004), the infusion process discussed above may be repeated (via loop 2030).

Figure 119:
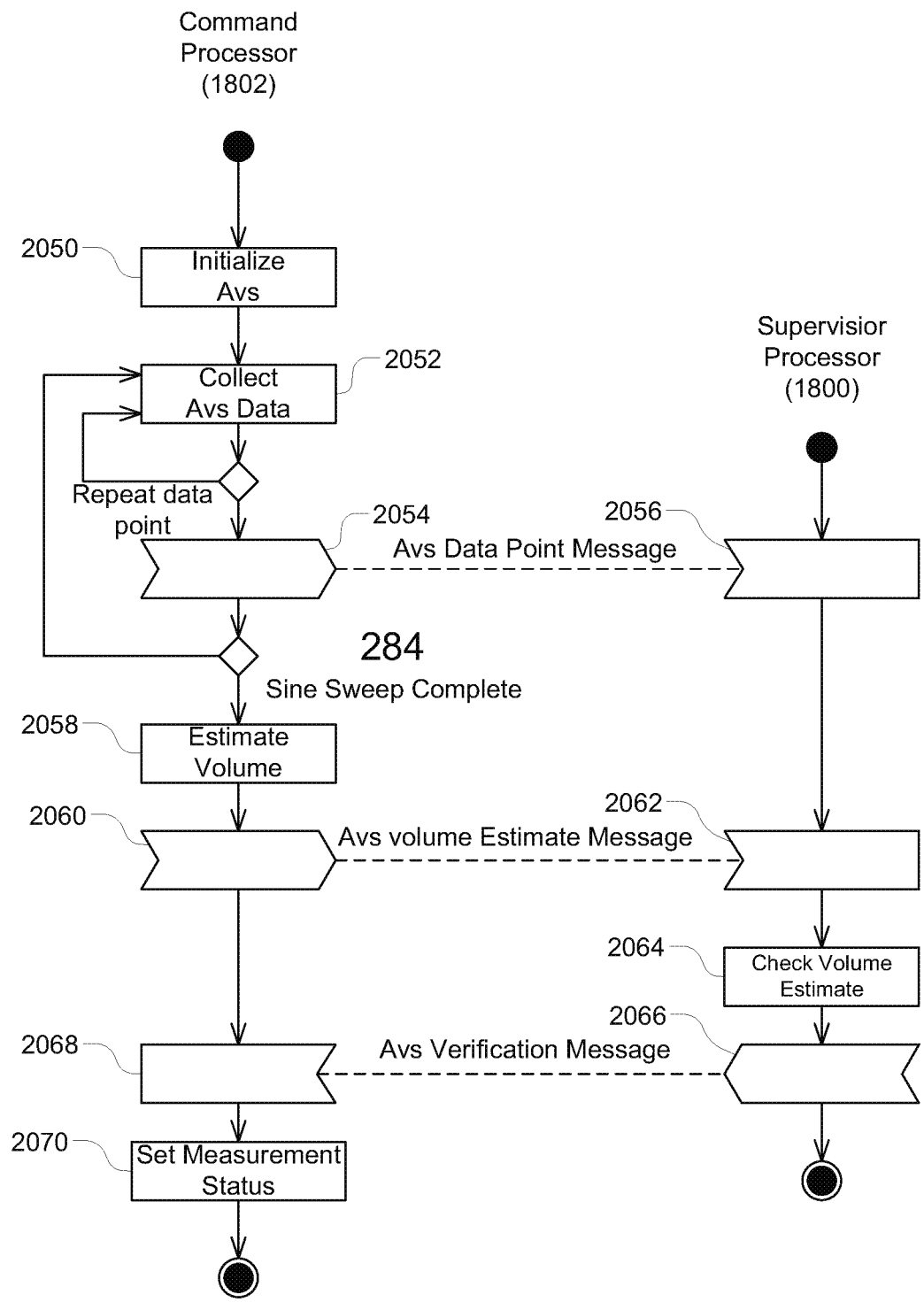
FIG. 119 diagrammatically depicts multi-processor functionality.

Referring also to FIG. 119, there is shown an example of the manner in which supervisor processor 1800 and command processor 1802 may interact while effectuating a volume measurements via volume sensor assembly 148 (as described above).

Specifically, command processor 1802 may initialize 2050 volume sensor assembly 148 and begin collecting 2052 data from volume sensor assembly 148, the process of which may be repeated for each frequency utilized in the above-described sine sweep. Each time that data is collected for a particular sweep frequency, a data point message may be provided 2054 from command processor 1802, which may be received 2056 by supervisor processor 1800.

Once data collection 2052 is completed for the entire sine sweep, command processor 1802 may estimate 2058 the volume of infusible fluid delivered by infusion pump assembly 100. Command processor 1802 may provide 2060 a volume estimate message to supervisor processor 1800. Upon receiving 2062 this volume estimate message, supervisor processor 1800 may check (i.e., confirm) 2064 the volume estimate message. Once checked (i.e., confirmed), supervisor processor 1800 may provide 2066 a verification message to command processor 1802. Once received 2068 from supervisor processor 1800, command processor 1802 may set the measurement status for the dose of infusible fluid delivered by volume sensor assembly 148.

As discussed above and referring temporarily to FIG. 11), the various embodiments of the infusion pump assembly (e.g., infusion pump assembly 100, 100', 400, 500) discussed above may be configured via a remote control assembly 300. When configurable via remote control assembly 300, the infusion pump assembly may include telemetry circuitry (not shown) that allows for communication (e.g., wired or wireless) between the infusion pump assembly and e.g., remote control assembly 300, thus allowing remote control assembly 300 to remotely control the infusion pump assembly. Remote control assembly 300 (which may also include telemetry circuitry (not shown) and may be capable of communicating with the infusion pump assembly) may include display assembly 302 and input assembly 304. Input assembly 304 may include slider assembly 306 and switch assemblies 308, 310. In other embodiments, the input assembly may include a jog wheel, a plurality of switch assemblies, or the like. Remote control assembly 300 may allow the user to program basal and bolus delivery events.

Remote control assembly 300 may include two processors, one processor (e.g., which may include, but is not limited to a CC2510 microcontroller/RF transceiver, available from Chipcon AS, of Oslo, Norway) may be dedicated to radio communication, e.g., for communicating with infusion pump assembly 100, 100', 400, 500. The second processor included within remote control assembly (which may include but are not limited to an ARM920T and an ARM922T manufactured by ARM Holdings PLC of the United Kingdom) may be a command processor and may perform data processing tasks associated with e.g., configuring infusion pump assembly 100, 100', 400, 500.

Further and as discussed above, one embodiment of electrical control assembly 816 may include three microprocessors. One processor (e.g., which may include, but is not limited to a CC2510 microcontroller/RF transceiver, available from Chipcon AS, of Oslo, Norway) may be dedicated to radio communication, e.g., for communicating with a remote control assembly 300. Two additional microprocessors (e.g., supervisor processor 1800 and command processor 1802) may effectuate the delivery of the infusible fluid (as discussed above). Examples of supervisor processor 1800 and command processor 1802 may include, but is not limited to an MSP430 microcontroller, available from Texas Instruments Inc. of Dallas, Tex.

The OS may be a non-preemptive scheduling system, in that all tasks may run to completion before the next task is allowed to run regardless of priority. Additionally, context switches may not be performed. When a task completes executing, the highest priority task that is currently scheduled to run may then be executed. If no tasks are scheduled to execute, the OS may place the processor (e.g., supervisor processor 1800 and/or command processor 1802) into a low power sleep mode and may wake when the next task is scheduled. The OS may only be used to manage main loop code and may leave interrupt-based functionality unaffected.

The OS may be written to take advantage of the C++ language. Inheritance as well as virtual functions may be key elements of the design, allowing for easy creation, scheduling and managing of tasks.

At the base of the OS infrastructure may be the ability to keep track of system time and controlling the ability to place the processor in Low Power Mode (LPM; also known as sleep mode). This functionality along with the control and configuration of all system clocks may be encapsulated by the SysClocks class.

The SysClocks class may contain the functionality to place the processor (e.g., supervisor processor 1800 and/or command processor 1802) into LPM to reduce energy consumption. While in LPM, the slow real time clock may continue to run while the fast system clock that runs the CPU core and most peripherals may be disabled.

Placing the processor into LPM may always be done by the provided SysClocks function. This function may contain all required power down and power up sequences resulting in consistency whenever entering or exiting LPM. Waking from LPM may be initiated by any interrupts based on the slow clock.

The OS may keep track of three aspects of time: seconds, milliseconds and the time of day. Concerning seconds, SysClocks may count seconds starting when the processor comes out of reset. The second counter may be based on the slow system clocks and, therefore, may increment regardless of whether the processor is in LPM or at full power. As a result, it is the boundary at which the processor may wake from sleep to execute previously scheduled tasks. If a task is scheduled to run immediately from an interrupt service routine (ISR), the ISR may wake the processor from LPM on exit and the task may be executed immediately. Concerning milliseconds, in addition to counting the seconds since power on, SysClocks may also count milliseconds while the processor is in full power mode. Since the fast clock is stopped during LPM, the millisecond counter may not increment. Accordingly, whenever a task is scheduled to execute based on milliseconds, the processor may not enter LPM. Concerning time of day, the time of day may be represented within SysClocks as seconds since a particular point time (e.g., seconds since 1 Jan. 2004).

The SysClocks class may provide useful functionality to be used throughout the Command and Supervisor project code base. The code delays may be necessary to allow hardware to settle or actions to be completed. SysClocks may provide two forms of delays, a delay based on seconds or a delay based on milliseconds. When a delay is used, the processor may simply wait until the desired time has passed before continue with its current code path. Only ISRs may be executed during this time. SysClocks may provide all of the required functionality to set or retrieve the current time of day.

The word "task" may be associated with more complex scheduling systems; therefore within the OS, task may be represented by and referred to as Managed Functions. The ManagedFunc class may be an abstract base class that provides all the necessary control members and functionality to manage and schedule the desired functionality.

The ManagedFunc base class may have five control members, two scheduling manipulation member functions, and one pure virtual execute function that may contain the managed functionality. All of the ManagedFunc control members may be hidden from the derived class and may only be directly set by the derived class during creation, thus simplifying the use and enhancing the safety of infusion pump assembly 100, 100', 400, 500.

The Function ID may be set at the time of creation and may never be changed. All Function IDs may be defined within a single.h file, and the base ManagedFunc constructor may strongly enforce that the same ID may not be used for more than one managed function. The ID may also define the priority of a function (with respect to other functions) based upon the function ID assigned, wherein higher priority functions are assigned lower function IDs. The highest priority task that is currently scheduled to execute may execute before lower priority tasks.

All other control members may be used to represent the function's current scheduled state, when it should be executed, and if (upon execution) the function should be rescheduled to execute in a previously set amount of time. Manipulation of these controls and states may be allowed but only through the public member functions (thus enforcing safety controls on all settings).

To control the scheduling of a managed function, the set start and set repeat functions may be used. Each of these member functions may be a simple interface allowing the ability to configure or disable repeat settings as well as control whether a managed function is inactive, scheduled by seconds, milliseconds, or time of day.

Through inheritance, creating a Managed Function may be done by creating a derived class and defining the pure virtual 'execute' function containing the code that needs to be under scheduling control. The ManagedFunc base class constructor may be based upon the unique ID of a function, but may also be used to set default control values to be used at start up.

For example to create a function that runs thirty seconds after start up and every 15 seconds thereafter, the desired code is placed into the virtual execute function and the function ID, scheduled by second state, thirty second start time, and repeat setting of fifteen seconds is provided to the constructor.

The following is an illustrative code example concerning the creation of a managed function. In this particular example, a "heartbeat" function is created that is scheduled to execute for the first time one second after startup of infusion pump assembly 100, 100', 400, 500 and execute every ten seconds thereafter:

```
#include "ManagedFunc.h"
// The SendGoodFunc is a "heartbeat" status message
class SendGoodFunc : public ManagedFunc
{
public:
    // Initialize the managed func to run 2 seconds after
      start up
    // and repeat every second.
    SendGoodFunc( ) :
        ManagedFunc(IPC_SEND_GOOD, SCHEDULED_SEC, 1, true,
        10) { };
    ~SendGoodFunc( ) { };
protected:
    void execute (void);
};
void SendGoodFunc::execute(void)
{
    // << code to send the heartbeat >>
}
SendGoodFunc g_sendGoodFunc;
// to manipulate the heartbeat timing simply call:
//     g_sendGoodFunc.setFuncStart(...)         or
g_sendGoodFunc.setRepeat( ... )
```

The actual execution of the Managed Functions may be controlled and performed by the SleepManager class. The SleepManager may contain the actual prioritized list of managed functions. This prioritized list of functions may automatically be populated by the managed function creation process and may ensure that each function is created properly and has a unique ID.

The main role of the SleepManager class may be to have its 'manage' function called repeatedly from the processors main loop and/or from a endless while loop. Upon each call of manage, the SleepManager may execute all functions that are scheduled to run until the SleepManager has exhausted all scheduled functions; at which time the SleepManager may place the processor in LPM. Once the processor wakes from LPM, the manage function may be reentered until the processor is again ready to enter LPM (this process may be repeated until stopped, e.g., by a user or by the system).

If the processor has to be kept in full power mode for an extended period of time (e.g., while an analog-to-digital conversion is being sampled), the SleepManager may provide functionality to disable entering LPM. While LPM is disabled, the manage function may continuously search for a scheduled task.

The SleepManager may also provide an interface to manipulate the scheduling and repeat settings of any managed function through the use of the unique ID of the function, which may allow any section of code to perform any required scheduling without having direct access to or unnecessary knowledge of the desired ManagedFunc object.

Radio circuitry included within each of infusion pump assembly 100, 100', 400, 500 and remote control assembly 300 may effectuate wireless communication between remote control assembly 300 and infusion pump assembly 100, 100', 400, 500. A 2.4 GHz radio communications chip (e.g., a Texas Instruments CC2510 radio transceiver) with an internal 8051 microcontroller may be used for radio communications.

The radio link may balance the following three objectives: link availability; latency; and energy.

Concerning link availability, remote control assembly 300 may provide the primary means for controlling the infusion pump assembly 100, 100', 400, 500 and may provide detailed feedback to the user via the graphical user interface (GUI) of remote control assembly 300. Concerning latency, the communications system may be designed to provide for low latency to deliver data from remote control assembly 300 to the infusion pump assembly 100, 100', 400, 500 (and vice versa). Concerning energy, both remote control assembly 300 and infusion pump assembly 100, 100', 400, 500 may have a maximum energy expenditure for radio communications.

The radio link may support half-duplex communications. Remote control assembly 300 may be the master of the radio link, initiating all communications. Infusion pump assembly 100, 100', 400, 500 may only respond to communications and may never initiate communications. The use of such a radio communication system may provide various benefits, such as: increased security; a simplified design (e.g., for airplane use); and coordinated control of the radio link.

Figure 120A:
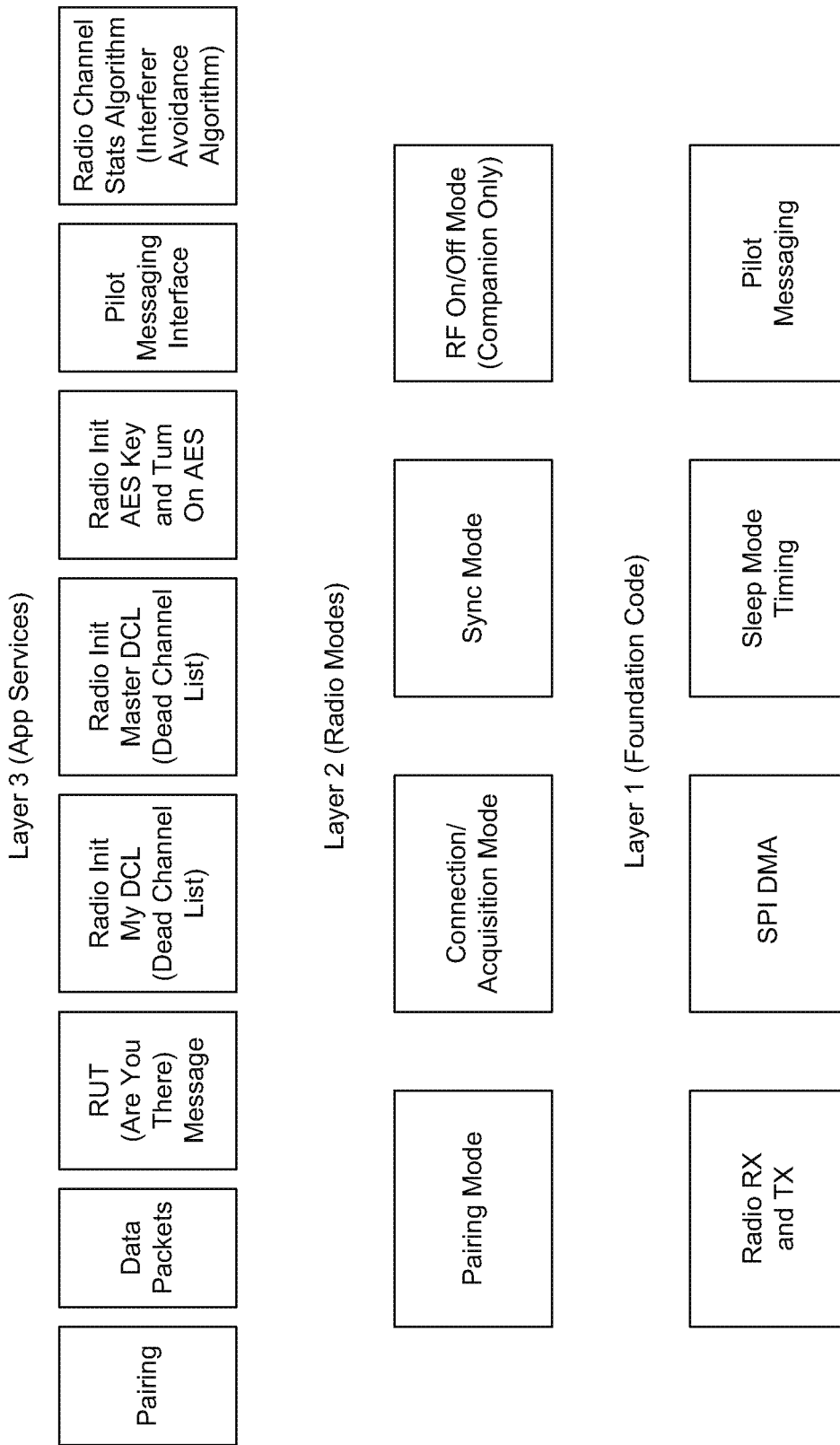
FIG. 120A graphically depicts various software layers.

Referring also to FIG. 120A, there is shown one illustrative example of the various software layers of the radio communication system discussed above.

The radio processors included within remote control assembly 300 and infusion pump assembly 100, 100', 400, 500 may transfer messaging packets between an SPI port and a 2.4 GHz radio link (and vice versa). The radio may always be the SPI slave. On infusion pump assembly 100, 100', 400, 500, radio processor (PRP) 1818 (See FIGS. 115-116) may service two additional nodes over the SPI port that are upstream (namely command processor 1800 and supervisor processor 1802. In some embodiments, on remote control assembly 300, the radio processor (CRP) may service at least one additional node over the SPI port that may be either upstream or down stream, for example, in some embodiments, the above-described remote control processor (UI) and the Continuous Glucose Engine (CGE).

A messaging system may allow for communication of messages between various nodes in the network. The UI processor of remote control assembly 300 and e.g., supervisor processor 1800 may use the messaging system to configure and initiate some of the mode switching on the two system radios. It may be also used by the radios to convey radio and link status information to other nodes in the network.

When the radio of remote control assembly 300 wishes to gather channel statistics from the infusion pump assembly 100, 100', 400, 500 or update the master channel list of the radio of infusion pump assembly 100, 100', 400, 500, the radio of remote control assembly 300 may use system messages. Synchronization for putting the new updated list into effect may use flags in the heartbeat messages to remove timing uncertainty.

The radio communication system may be written in C++ to be compatible with the messaging software. A four byte radio serial number may be used to address each radio node. A hash table may be used to provide a one-to-one translation between the device "readable" serial number string and the radio serial number. The hash table may provide a more randomized 8-bit logical address so that pumps (e.g., infusion pump assembly 100, 100', 400, 500) or controllers with similar readable serial numbers are more likely to have unique logical addresses. Radio serial numbers may not have to be unique between pumps (e.g., infusion pump assembly 100, 100', 400, 500) and controllers due to the unique roles each has in the radio protocol.

The radio serial number of remote control assembly 300 and the radio serial number of infusion pump assembly 100, 100', 400, 500 may be included in all radio packets except for the RF Pairing Request message that may only include the radio serial number of remote control assembly 300, thus ensuring that only occur with the remote control assembly/infusion pump assembly to which it is paired. The CC2510 may support a one byte logical node address and it may be advantageous to use one byte of the radio serial number as the logical node address to provide a level of filtering for incoming packets.

The Quiet_Radio signal may be used by the UI processor of remote control assembly 300 to prevent noise interference on the board of remote control assembly 300 by other systems on the board. When Quiet_Radio is asserted, the radio application of remote control assembly 300 may send a message to the radio of infusion pump assembly 100, 100', 400, 500 asserting Radio Quiet Mode for a pre-determined period of time. The Quiet_Radio feature may not be required based on noise interference levels measured on the PC board of remote control assembly 300. During this period of time, the radio of remote control assembly 300 may stay in Sleep Mode 2 for up to a maximum of 100 ms. The radio of remote control assembly 300 may come out of Sleep Mode 2 when the Quiet_Radio signal is de-asserted or the maximum time period has expired. The UI processor of remote control assembly 300 may assert Quiet_Radio at least one radio communication's interval before the event needs to be asserted. The radio of remote control assembly 300 may inform the radio of infusion pump assembly 100, 100', 400, 500 that communications will be shutdown during this quiet period. The periodic radio link protocol may have status bits/bytes that accommodate the Quiet_Radio feature unless Quiet_Radio is not required.

The radio software may integrate with the messaging system and radio bootloader on the same processor, and may be verified using a throughput test. The radio software may integrate with the messaging system, SPI Driver using DMA, and radio bootloader, all on the same processor (e.g., the TI CC2510).

The radio of remote control assembly 300 may be configured to consume no more than 32 mAh in three days (assuming one hundred minutes of fast heartbeat mode communications per day). The radio of infusion pump assembly 100, 100', 400, 500 may be configured to consume no more than 25 mAh in three days (assuming one hundred minutes of fast heartbeat mode communications per day).

The maximum time to reacquire communications may be <6.1 seconds including connection request mode and acquisition mode. The radio of remote control assembly 300 may use the fast heartbeat mode or slow heartbeat mode setting to its advantage in order to conserve power and minimize latency to the user. The difference between the infusion pump assembly 100, 100', 400, 500 and remote control assembly 300 entering acquisition mode may be that the infusion pump assembly 100, 100', 400, 500 needs to enter acquisition mode often enough to ensure communications may be restored within the maximum latency period. However, the remote control assembly 300 may change how often to enter acquisition mode with the infusion pump assembly 100, 100', 400, 500 when in slow heartbeat mode and heartbeats are lost. The radio of remote control assembly 300 may have knowledge of the user GUI interaction, but the infusion pump assembly 100, 100', 400, 500 may not.

The radio of remote control assembly 300 may set the heartbeat period for both radios. The period may be selectable in order to optimize power and link latency depending on activity. The desired heartbeat period may be communicated in each heartbeat from the radio of remote control assembly 300 to the radio of infusion pump assembly 100, 100', 400, 500. This may not exclusively establish the heartbeat rate of infusion pump assembly 100, 100', 400, 500 due to other conditions that determine what mode to be in. When in fast heartbeat mode, the radio of remote control assembly 300 may set the heartbeat period to 20 ms if data packets are available to send or receive, thus providing low link latency communications when data is actively being exchanged.

When in fast heartbeat mode, the radio of remote control assembly 300 may set the heartbeat period to 60 ms four heartbeats after a data packet was last exchanged in either direction on the radio. Keeping the radio heartbeat period short after a data packet has been sent or received may assure that any data response packet may be also serviced using a low link latency. When in slow heartbeat mode, the heartbeat rate may be 2.00 seconds or 6.00 second, depending upon online or offline status respectively.

The infusion pump assembly 100, 100', 400, 500 may use the heartbeat rate set by the radio of remote control assembly 300. The radio of remote control assembly 300 may support the following mode requests via the messaging system:
Pairing Mode
Connection Mode
Acquisition Mode (includes the desired paired infusion pump assembly 100, 100', 400, 500 radio serial number)
Sync Mode—Fast Heartbeat
Sync Mode—Slow Heartbeat
RF Off Mode The radio of infusion pump assembly 100, 100', 400, 500 may support the following mode requests via the messaging system:
Pairing Mode
Acquisition Mode
RF Off Mode The radio may use a system message to obtain the local radio serial number. On remote control assembly 300, the radio may get the serial number from the UI processor of remote control assembly 300. The radio may use a system message to store the paired radio serial number.

Remote control assembly 300 and the radio of infusion pump assembly 100, 100', 400, 500 may issue a status message using the messaging system to the UI processor of remote control assembly 300 and command processor 1802 whenever the following status changes:
Online Fast: Successful connection
Online Fast: Change from Acquisition Mode to Fast Heartbeat Mode
Online Slow: Successful request change from Fast Heartbeat to Slow Heartbeat
Offline: Automatic change to Search Sync mode due to lack of heartbeat exchanges.
Online Fast: Successful request change from Slow Heartbeat to Fast Heartbeat
Offline: Bandwidth falls below 10% in Sync Mode
Online: Bandwidth rises above 10% in Search Sync mode
Offline: Successful request change to RF Off Mode The radio configuration message may be used to configure the number of radio retries. This message may be sent over the messaging system. The UI processor of remote control assembly 300 will send this command to both the radio of remote control assembly 300 and the radio of infusion pump assembly 100, 100', 400, 500 to configure these radio settings.

There may be two parameters in the radio configuration message: namely the number of RF retries (e.g., the value may be from 0 to 10); and the radio offline parameters (e.g., the value may be from 1 to 100 in percent of bandwidth).

The radio application on both the remote control assembly 300 and infusion pump assembly 100, 100', 400, 500 may have an API that allows the messaging system to configure the number of RF retries and radio offline parameters.

The following parameters may be recommended for the radio hardware configuration:
Base Radio Specifications
MSK
250 kbps over air baud rate
Up to 84 channels
Channel spacing 1000 kHz
Filter bandwidth 812 kHz
No Manchester encoding
Data whitening
4 byte preamble
4 byte sync (word)
CRC appended to packet
LQI (Link Quality Indicator) appended to packet
Automatic CRC filtering enabled
Forward Error Correction (FEC) may or may not be utilized. Although Forward Error Correction (FEC) may be used to increase the effective signal dynamic range by approximately 3 dB, FEC requires fixed packet sizes and doubles the number of over the air bits for the same fixed size message.

The radio may function within 1.83 meters distance under nominal operating conditions (except in pairing mode). It may be a goal that the radio function within 7.32 meters distance under nominal operating conditions. The transmit power level may be 0 dBm (except in pairing mode) and the transmit power level in pairing mode may be −22 dBm. Since the desired radio node address of infusion pump assembly 100, 100', 400, 500 may be not known by the remote control assembly 300 in pairing mode, both infusion pump assembly 100, 100', 400, 500 and remote control assembly 300 may use a lower transmit power to reduce the likelihood of inadvertently pairing with another infusion pump assembly.

AES Encryption may be used for all packets but may not be required, as the Texas Instruments CC2510 radio transceiver includes this functionality. If AES encryption is used, fixed keys may be utilized, as fixed keys provide a quick way to enable encryption without passing keys. However, key exchange may be provided for in future versions of infusion pump assembly 100, 100', 400, 500. The fixed keys may be contained in one separate header source file with no other variables but the fixed keys data, thus allowing for easier management of read access of the file.

Figure 120B:
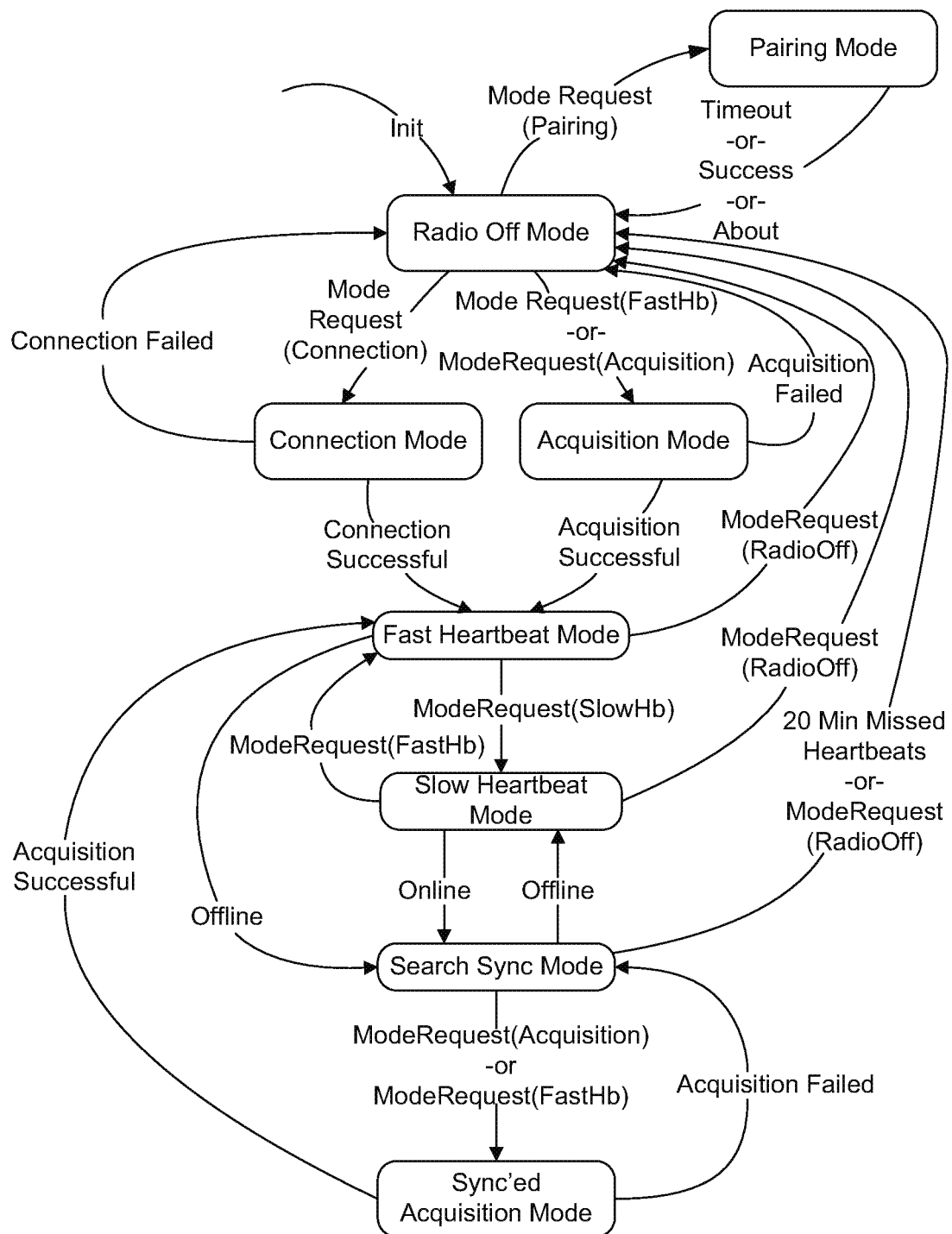
FIGS. 120B-120C depict various state diagrams.
Figure 120C:
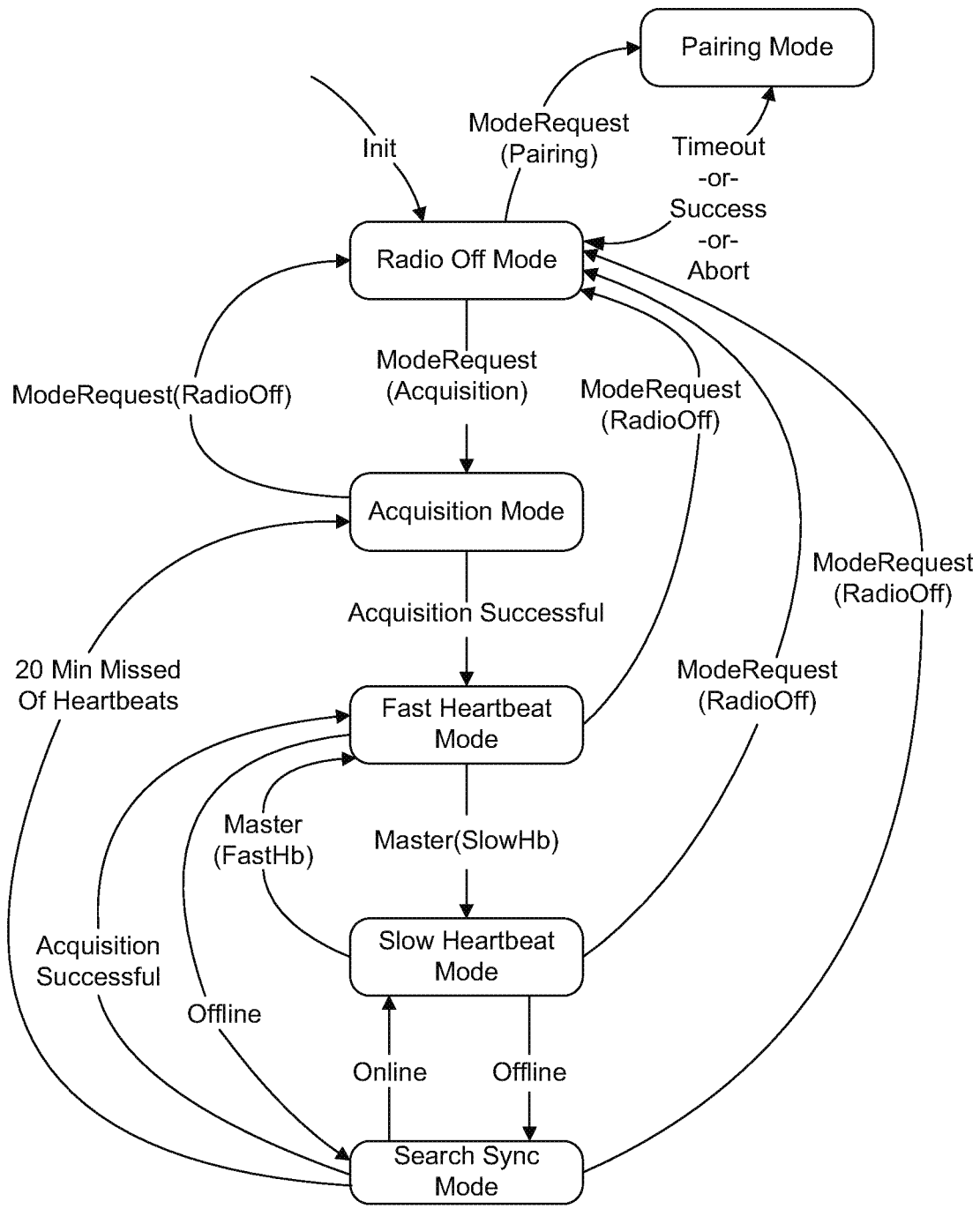

The radio software may support the following eight modes:
Pairing Mode
RF Off Mode
Connection Mode
Acquisition Mode Fast Heartbeat Mode
Slow Heartbeat Mode
Search Sync Mode
Sync'ed Acquisition Mode which are graphically depicted in FIGS. 120B-120C.

Pairing may be the process of exchanging radio serial numbers between remote control assembly 300 and infusion pump assembly 100, 100', 400, 500. Remote control assembly 300 may be "paired" with infusion pump assembly 100, 100', 400, 500 when infusion pump assembly 100, 100', 400, 500 knows its serial number. Infusion pump assembly 100, 100', 400, 500 may be "paired" with remote control assembly 300 when remote control assembly 300 knows its serial number.

Figure 120D:
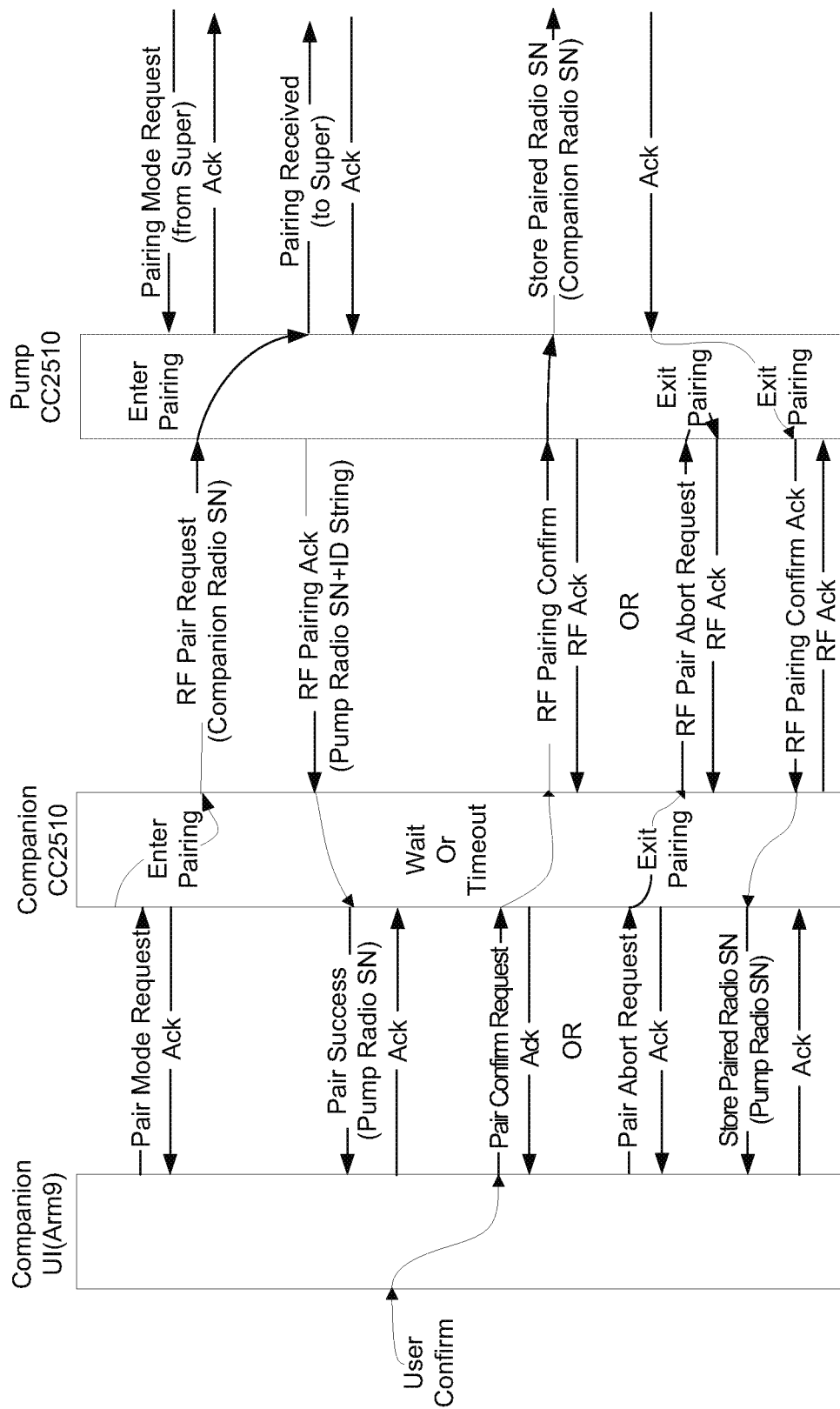
FIG. 120D graphically depicts device interaction.

Pairing mode (which is graphically depicted in FIG. 120D) may require that four messages to be exchanged over the RF link:
  RF Pairing Request (broadcast from Remote control assembly 300 to any Infusion pump assembly 100, 100', 400, 500)
  RF Pairing Acknowledge (from Infusion pump assembly 100, 100', 400, 500 to Remote control assembly 300)
  RF Pairing Confirm Request (from Remote control assembly 300 to Infusion pump assembly 100, 100', 400, 500)
  RF Pairing Confirm Acknowledge (from Infusion pump assembly 100, 100', 400, 500 to Remote control assembly 300)

Additionally, remote control assembly 300 may cancel the pairing process at any time via the RF pairing abort message (from remote control assembly 300 to infusion pump assembly 100, 100', 400, 500. Pairing mode may not support messaging system data transfers.

The radio of infusion pump assembly 100, 100', 400, 500 may enter pairing mode upon receiving a pairing mode request message. It may be the responsibility of supervisor processor 1800 on infusion pump assembly 100, 100', 400, 500 to request the radio to enter pairing mode if there is no disposable attached to infusion pump assembly 100, 100', 400, 500 and the user has pressed the button of infusion pump assembly 100, 100', 400, 500 for six seconds. The radio of infusion pump assembly 100, 100', 400, 500 may set the appropriate transmit power level for pairing mode. Infusion pump assembly 100, 100', 400, 500 may only be paired with one remote control assembly 300 at a time.

Upon receiving the first valid RF pairing request message while in pairing mode, the radio of infusion pump assembly 100, 100', 400, 500 may use the serial number of remote control assembly 300 for the duration of pairing mode and respond with an RF pairing acknowledge message containing the radio serial number infusion pump assembly 100, 100', 400, 500.

The radio of infusion pump assembly 100, 100', 400, 500 may timeout of pairing mode automatically after 2.0±0.2 seconds if no RF pairing request is received. The radio of infusion pump assembly 100, 100', 400, 500 may issue a pairing request received message after transmitting the RF pairing acknowledge. This message to supervisor processors will allow feedback to the user during the pairing confirm process. The radio of infusion pump assembly 100, 100', 400, 500 may automatically timeout of pairing mode in 1.0±0.1 minutes after sending an RF pairing acknowledge unless an RF pairing confirm request is received. The radio of infusion pump assembly 100, 100', 400, 500 may issue a store paired radio serial number message if an RF pairing confirm request message is received after receiving a RF pairing request message. This action may store the radio serial number of remote control assembly 300 in the non-volatile memory of infusion pump assembly 100, 100', 400, 500 and may overwrite the existing pairing data for the infusion pump assembly 100, 100', 400, 500.

The radio of infusion pump assembly 100, 100', 400, 500 may transmit an RF pairing confirm acknowledge and exit pairing mode after the acknowledgment from the store paired radio serial number message is received. This may be the normal exit of pairing mode on infusion pump assembly 100, 100', 400, 500 and may result in infusion pump assembly 100, 100', 400, 500 powering down until connection mode or paring mode entered by the user.

If the radio of infusion pump assembly 100, 100', 400, 500 exits pairing mode upon successfully receiving a pairing confirm request message, then the radio of infusion pump assembly 100, 100', 400, 500 may revert to the newly paired remote control assembly 300 and may send a pairing completion success message to command processor 1802. The radio of infusion pump assembly 100, 100', 400, 500 may exit pairing mode upon receiving an RF pairing abort message. The radio of infusion pump assembly 100, 100', 400, 500 may exit pairing mode upon receiving a pairing abort request message addressed to it. This may allow command processor 1802 or supervisor processor 1800 to abort the pairing process locally on the infusion pump assembly 100, 100', 400, 500.

The radio of remote control assembly 300 may enter pairing mode upon receiving a pairing mode request message. It may be the responsibility of the UI processor of remote control assembly 300 to request that the radio enter pairing mode under the appropriate conditions. The radio of remote control assembly 300 may set the appropriate transmit power level for pairing mode. The radio of remote control assembly 300 may transmit RF pairing requests until an RF pairing acknowledge is received or pairing is aborted.

The radio of remote control assembly 300 may automatically abort pairing mode if the RF pairing acknowledge message is not received within 30.0±1.0 seconds after entering pairing mode. Upon receiving the first valid RF pairing acknowledge message while in pairing mode, the radio of remote control assembly 300 may send a pairing success message to the UI processor of remote control assembly 300 that includes the serial number of infusion pump assembly 100, 100', 400, 500 and may use that serial number for the duration of pairing mode. This message may provide a means for the UI processor of remote control assembly 300 to have the user confirm the serial number of the desired infusion pump assembly 100, 100', 400, 500. If the radio of remote control assembly 300 receives multiple responses (concerning a single pairing request) from infusion pump assembly 100, 100', 400, 500, the first valid one may be used.

The Radio of remote control assembly 300 may only accept an RF pairing confirm acknowledge messages after an RF pairing acknowledge is received while in pairing mode. The radio of remote control assembly 300 may transmit the RF pairing confirm message upon receiving a pair confirm request message from the UI processor of remote control assembly 300.

The radio of remote control assembly 300 may check that infusion pump assembly 100, 100', 400, 500 confirms the pairing before adding infusion pump assembly 100, 100', 400, 500 to the pairing list. The radio of remote control assembly 300 may issue a store paired radio serial number message if an RF pairing complete message is received. This action may allow the UI processor of remote control assembly 300 to store the new serial number of infusion pump assembly 100, 100', 400, 500 and provide user feedback of a successful pairing. It may be the responsibility of the UI processor of remote control assembly 300 to manage the list of paired infusion pump assemblies.

The radio of remote control assembly 300 may send an RF pairing abort message and exit pairing mode upon receiving a pairing abort request message. This may allow the UI processor of the remote control assembly 300 to abort the pairing process on both the remote control assembly 300 and acknowledged infusion pump assembly 100, 100', 400, 500.

Figure 120E:
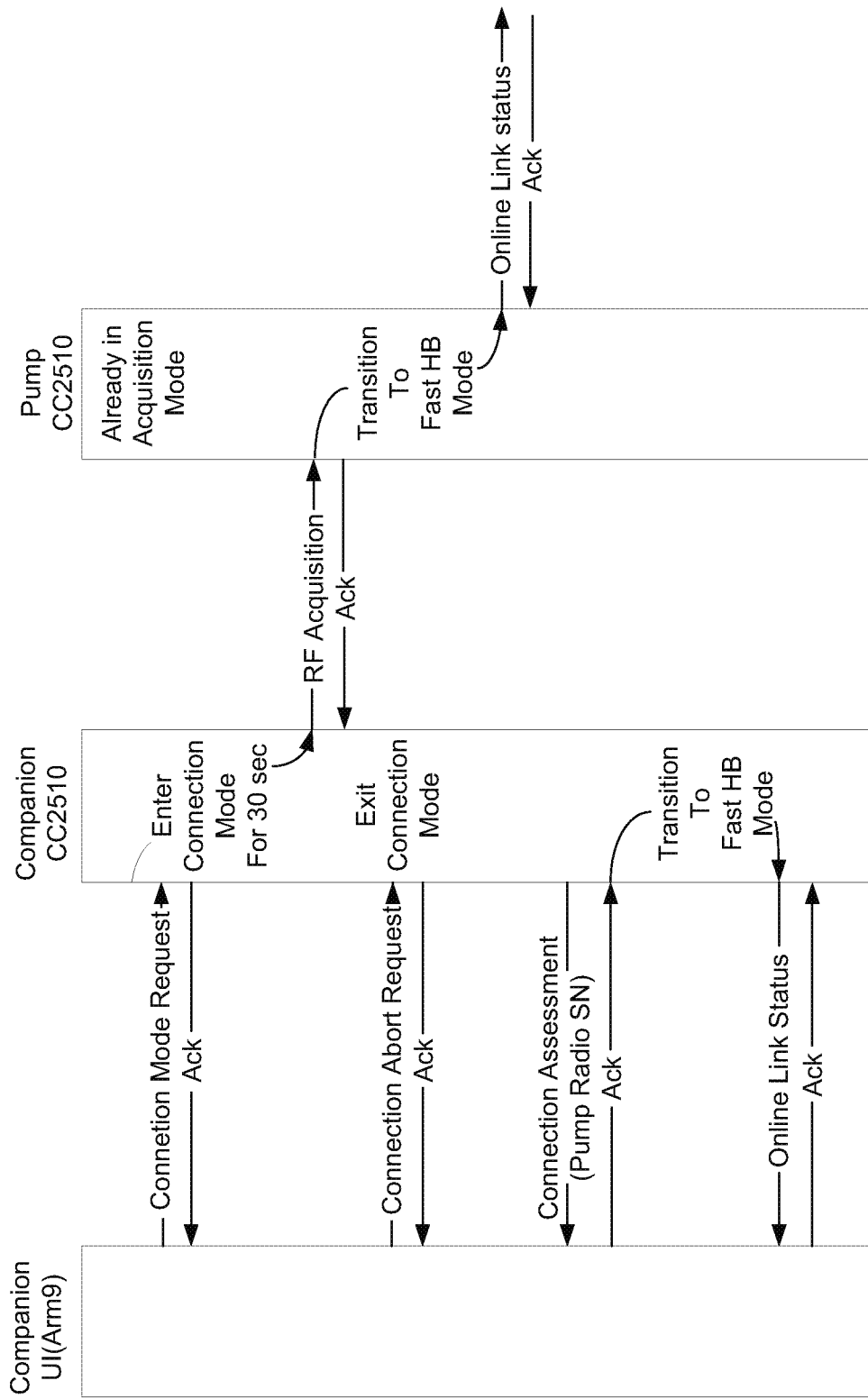
FIG. 120E graphically depicts device interaction.

In connection request mode, the radio of remote control assembly 300 may attempt to acquire each infusion pump assembly 100, 100', 400, 500 in its paired infusion pump assembly list and retrieve its "connection ready" status. The "connection" process (which is graphically depicted in FIG. 120E) may allow remote control assembly 300 to quickly identify one of its paired infusion pump assemblies that may be ready to be used. The radio of remote control assembly 300 may be capable of performing the connection request mode with up to six paired infusion pump assemblies. Connection request mode may be only supported on remote control assembly 300 and may be a special form of acquisition mode. In connection request mode, remote control assembly 300 may connect with the first infusion pump assembly to respond. However, each message may be directed to a specific infusion pump assembly serial number.

The radio of remote control assembly 300 may obtain the latest paired infusion pump assembly serial number list upon entering connection mode. The radio of remote control assembly 300 may enter connection mode upon receiving a connection mode request message. It may be the responsibility of the UI processor of remote control assembly 300 to request that the radio enter connection mode when it desires communications with a paired infusion pump assembly. The radio of remote control assembly 300 may issue a connection assessment message to the UI processor of remote control assembly 300 containing the radio serial number of the first infusion pump assembly, if any, that is "connection ready". The radio of remote control assembly 300 may generate the connection assessment message within thirty seconds of entering connection request mode. The radio of remote control assembly 300 may exit connection request mode upon receipt of the connection assessment acknowledgement and transition to fast heartbeat mode. The radio of remote control assembly 300 may exit connection request mode upon receipt of a connection request abort message from the UI processor of remote control assembly 300.

On remote control assembly 300, acquisition mode may be used to find a particular paired infusion pump assembly. The radio of remote control assembly 300 may send RF RUT (aRe yoU There) packets to the desired paired infusion pump assembly. If the infusion pump assembly receives the RF RUT message, it may respond to the radio of remote control assembly 300. Multiple channels may be used in the acquisition mode algorithm to improve the opportunity for the radio of remote control assembly 300 to find the paired infusion pump assembly.

The radio of remote control assembly 300 may enter acquisition mode upon receiving an acquisition mode request or fast heartbeat mode request message while in RF Off Mode. The radio of remote control assembly 300 may enter sync'ed acquisition mode upon receiving an acquisition mode request or fast heartbeat mode request message while in search sync mode. It may be the responsibility of the UI processor of remote control assembly 300 to request that the radio enter acquisition mode when the RF link is off-line and remote control assembly 300 desires communications with infusion pump assembly 100, 100', 400, 500.

The radio of remote control assembly 300 may only communicate with one paired infusion pump assembly 100, 100', 400, 500 (except in pairing and connection modes). When communications are lost, the UI processor of remote control assembly 300 may use acquisition mode (at some periodic rate limited by the power budget) to attempt to restore communications.

Infusion pump assembly 100, 100', 400, 500 may enter acquisition mode under the following conditions:
 When in Radio Off Mode and Acquisition Mode may be requested
 When Search Sync Mode times out due to lack of heartbeats Upon entering acquisition mode, the radio of infusion pump assembly 100, 100', 400, 500 may obtain the serial number of the last stored paired remote control assembly 300. The radio of infusion pump assembly 100, 100', 400, 500 may only communicate with the remote control assembly to which it has been "paired" (except while in the "pairing request" mode). The radio of infusion pump assembly 100, 100', 400, 500 may transition from acquisition mode to fast heartbeat mode upon successfully acquiring synchronization with the remote control assembly 300. The acquisition mode of infusion pump assembly 100, 100', 400, 500 may be capable of acquiring synchronization within 6.1 seconds, which may implies that the infusion pump assembly 100, 100', 400, 500 may always be listening at least every ~6 seconds when in acquisition mode.

Data packets may be sent between two paired devices when the two devices are in sync mode and online. The two devices may sync via a heartbeat packet before data packets are exchanged. Each radio may send data packets at known time intervals after the heartbeat exchange. The infusion pump assembly 100, 100', 400, 500 may adjust its timing to anticipate reception of a packet. The radio may support one data packet in each direction on each heartbeat. The radio may provide a negative response to a fast heartbeat mode request if the radio if offline. The radio of remote control assembly 300 may change to fast heartbeat mode if a system request for fast heartbeat mode is received while in slow heartbeat mode and the radio is online.

Upon transitioning to fast heartbeat mode from acquisition mode, the radio of remote control assembly 300 may send the master channel list message. The master channel list may be built by the radio of remote control assembly 300 and sent to the radio of infusion pump assembly 100, 100', 400, 500 to allow a selection of frequency hopping channels based on historical performance. When in fast heartbeat mode or slow heartbeat mode, periodic heartbeat messages may be exchanged between the radio of remote control assembly 300 and the radio of infusion pump assembly 100, 100', 400, 500. The periodicity of these messages may be at the heartbeat rate. The heartbeat messages may allow data packet transfers to take place and may also exchange status information. The two radios may exchange the following status information: Quiet Mode, data availability, buffer availability, heartbeat rate, and prior channel performance. It may be a goal to keep the packet size of the heartbeat messages small in order to conserve power. The radio may provide for a maximum data packet size of eighty-two bytes when in Sync Mode. The messaging system may be designed to support packet payload sizes up to sixty-four bytes. This maximum size was selected as an optimal trade-off between minimum messages types and non-fragmented messages. The eighty-two bytes may be the maximum packet size of the messaging system including packet overhead.

The messaging system has an API that may allow the radio protocol to send an incoming radio packet to it. The messaging system may also have an API that allows the radio protocol to get a packet for transmission over the radio network. The messaging system may be responsible for packet routing between the radio protocol and the SPI port. Data packets may be given to the messaging system for processing. The messaging system may have an API that allows the radio protocol to obtain a count of the number of data packets waiting to be sent over the radio network. The radio protocol may query the messaging system on each heartbeat to determine if data packets are available to send over the radio network. It may be desirable for the software to check the availability of a message just before the heartbeat is sent to minimize round trip message latency.

The radio protocol may be capable of buffering one incoming radio data packet and passing the packet to the messaging system. The radio protocol may send the data packet to the messaging system upon receipt of the data packet. The message system may be responsible for routing radio data packets to the proper destination node. The radio protocol may be capable of buffering one packet from the messaging system.

The radio protocol may be responsible for acknowledging receipt of valid data packets over the RF link via an RF ACK reply packet to the sending radio. The RF ACK packet may contain the source and destination radio serial numbers, RF ACK command identification, and sequence number of the data packet being acknowledged.

The radio transmitting a radio data packet may retransmit that radio data packet on the next heartbeat with the same sequence number if an RF ACK is not received and the retry count is within the maximum RF retries allowed. It may be expected that, from time to time, interference will corrupt a transmission on a particular frequency. An RF retry allows the same packet to be retransmitted at the next opportunity at a different frequency. The sequence number provides a means of uniquely identifying the packet over a short time window. The number of radio packet retries may be configurable using the radio configuration command. Allowing more retries may increase the probability of a packet being exchanged but introduces more latency for a round trip messages. The default number of radio retries at power up may be ten (i.e., the maximum transmission attempts before dropping the message).

A one byte (modulo 256) radio sequence number may be included in all radio data packets over the RF link. Since the radio may be responsible for retrying data packet transmission if not acknowledged, the sequence number may provide a way for the two radios to know if a data packet is a duplicate. The transmitted sequence number may be incremented for each new radio data packet and may be allowed to rollover. When a data packet is successfully received with the same sequence number as the previous successfully received data packet (and in the same direction), the data packet may be ACK'd and the received data packet discarded. This may remove duplicate packets generated by the RF protocol before they are introduced into the network. Note that it may be possible that multiple data packets in a row may need to be dropped with the same sequence number under extreme situations.

If a heartbeat is missed, the radio of remote control assembly 300 and the radio of infusion pump assembly 100, 100', 400, 500 may attempt to send and listen respectively for subsequent heartbeats. The radio of remote control assembly 300 and the radio of infusion pump assembly 100, 100', 400, 500 may automatically change from fast heartbeat mode or slow heartbeat mode to search sync mode if heartbeats are missed for two seconds. This may minimize power consumption when the link is lost by allowing the radios to continue to use their synchronization information, as two seconds allows sufficient time to hop through all channels.

The radio may be considered online while in the following modes:
Fast Heartbeat mode
Slow Heartbeat mode
as these are the only conditions where messaging system traffic may be exchanged. All other conditions may be considered offline.

The radio may initialize to radio off mode at the start of code execution from reset. When code first executes on the radio processor, the initial state may be the radio off mode to allow other processors to perform self-tests before requesting the radio to be active. This requirement does not intend to define the mode when waking from sleep mode. The radio may cease RF communications when set to radio off mode. On remote control assembly 300, this mode may be intended for use on an airplane to suppress RF emissions. Since infusion pump assembly 100, 100', 400, 500 only responds to transmissions from remote control assembly 300 (which will have ceased transmitting in airplane mode), radio off mode may only be used on infusion pump assembly 100, 100', 400, 500 when charging.

Command processor 1802 may be informed of airplane mode and that, therefore, the RF was intentionally turned off on remote control assembly 300 so that it does not generate walk-away alerts. However, this may be completely hidden from the radio of infusion pump assembly 100, 100', 400, 500.

The radio of remote control assembly 300 and the radio of infusion pump assembly 100, 100', 400, 500 may periodically attempt to exchange heartbeats in order to reestablish data bandwidth while in search sync mode. The radio of remote control assembly 300 may transition to radio off mode after twenty minutes of search sync mode with no heartbeats successfully exchanged.

The radio of infusion pump assembly 100, 100', 400, 500 may transition to acquisition mode after twenty minutes of search sync mode with no heartbeats successfully exchanged. Listening during pre-agreed time slots may be the most efficient use of power for infusion pump assembly 100, 100', 400, 500 to re-establish the RF link. After a loss of communications, the crystal tolerance and temperature drift may make it necessary to expand the receive window of infusion pump assembly 100, 100', 400, 500 over time. Staying in search sync mode for extended periods (e.g., 5-20 minutes) after communications loss may cause the instantaneous power consumed to exceed the average power budgeted for the radio of infusion pump assembly 100, 100', 400, 500. The radio of remote control assembly 300 may not be forced to expand its window, so staying in search sync mode may be very power efficient. Acquisition mode may consume more power for remote control assembly 300. Twenty minutes may be used as a compromise to balance power consumption on both the radio of remote control assembly 300 and the radio of infusion pump assembly 100, 100', 400, 500.

The radio of remote control assembly 300 and the radio of infusion pump assembly 100, 100', 400, 500 may transition to slow heartbeat mode if they successfully exchange three of the last five heartbeats. Approximately every six seconds, a burst of five heartbeats may be attempted. If three of these are successful, the bandwidth may be assumed to be sufficient to transition to slow heartbeat mode. The radio of infusion pump assembly 100, 100', 400, 500 may be acquirable while in search sync mode with a latency of 6.1 seconds. This may imply that the infusion pump assembly 100, 100', 400, 500 may always be listening at least every ~6 seconds when in search sync mode.

Radio protocol performance statistics may be necessary to promote troubleshooting of the radio and to assess radio performance. The following radio performance statistics may be maintained by the radio protocol in a data structure:

A #define DEBUG option (compiler option) may be used to gather the following additional radio performance statistics per each channel (16 bit numbers):

Number of missed hops

CCA good count

CCA bad count

Average RSSI (accumulated for good RX packets only)

Dropped from Frequency Hop List count

Acquisition Mode count (found pair on this channel)

The debug option may be used to gather engineering only statistics. If processor performance, power, and memory

| NAME | SIZE | DESCRIPTION |
|---|---|---|
| TX Heartbeat Count | 32 Bits | Total transmitted heartbeats |
| RX Heartbeat Count | 32 bits | Total valid received heartbeats |
| CRC Errors | 16 bits | Total packets received over the RF link which were dropped due to bad CRC. This may be a subset of RX Packets Nacked. |
| First Retry Count | 32 bits | Total number of packets which were successfully acknowledged after 1 retry |
| Second Retry Count | 32 bits | Total number of packets which were successfully acknowledged after 2 retries |
| Third Retry Count | 32 bits | Total number of packets which were successfully acknowledged after 3 retries |
| Fourth Retry Count | 32 bits | Total number of packets which were successfully acknowledged after 4 retries |
| Fifth Retry Count | 16 bits | Total number of packets which were successfully acknowledged after 5 retries |
| Sixth Retry Count | 16 bits | Total number of packets which were successfully acknowledged after 6 retries |
| Seventh Retry Count | 16 bits | Total number of packets which were successfully acknowledged after 7 retries |
| Eighth Retry Count | 16 bits | Total number of packets which were successfully acknowledged after 8 retries |
| Ninth Retry Count | 16 bits | Total number of packets which were successfully acknowledged after 9 retries |
| Tenth Retry Count | 16 bits | Total number of packets which were successfully acknowledged after 10 retries |
| Dropped Retry Count | 16 bits | Total number of packets which were dropped after maximum retries attempts |
| Duplicate Packet Count | 16 bits | Total number of received packets dropped due to duplicate packet |
| 1 to 5 Missed Fast Mode Hops | 16 bits | Count of 1 to 5 consecutive missed hops in Fast mode (i.e. not received) |
| 6 to 16 Missed Fast Mode Hops | 16 bits | Count of 6 to 16 consecutive missed hops in Fast mode. |
| 17 to 33 Missed Fast Mode Hops | 16 bits | Count of 17 to 33 consecutive missed hops in Fast mode |
| 34+ Missed Fast Mode Hops | 16 bits | Count of 34 or more consecutive missed hops in Fast mode |
| 1 to 2 Missed Slow Mode Hops | 16 bits | Count of 1 to 2 consecutive missed hops in Slow mode (i.e. not received) |
| 3 to 5 Missed Slow Mode Hops | 16 bits | Count of 3 to 5 consecutive missed hops in Slow mode |
| 5 to 7 Missed Slow Mode Hops | 16 bits | Count of 5 to 7 consecutive missed hops in Slow mode |
| 8+ Missed Slow Mode Hops | 16 bits | Count of 8 or more consecutive missed hops in Slow mode |
| Destination Radio Serial Number Mismatch | 16 bits | Count of received packets in which the destination made it past the hardware filtering but does not match this radio's serial number. This may be not an error but indicates that the radio may be waking up and receiving (but not processing) packets intended for other radios |
| Total Walkaway Time (minutes) | 16 bits | |
| Total Walkaway Events | 16 bits | Together with total walkaway time provides an average walkaway time |
| Number of Pairing Attempts | 16 bits | |
| Total Time in Acquisition Mode (Infusion pump assembly 100, 100', 400, 500 Only) | 16 bits | |
| Total Acquisition Mode Attempts (Remote control assembly 300 Only) | 16 bits | Successful Acquisition Count 16 bits Count of transitions from Connect or Acquisition Mode to Fast Heartbeat Mode |
| Requested Slow Heartbeat Mode Transitions | 16 bits | |
| Automatic Slow Heartbeat Mode Transitions | 16 bits | |
| Radio offline messages sent | 16 bits | |
| Radio online messages sent | 16 bits | | allow, it may be desirable to keep this information at runtime. The radio statistics may be made available to the messaging system.

Link quality may be intended to be used on remote control assembly 300 to provide a bar indicator, similar to a cell phone, of the radio link quality. Link quality may be made available to both remote control assembly 300 and infusion pump assembly 100, 100', 400, 500. It may be anticipated that the link quality status will consist of a one byte indicator of the quality of the radio link.

The radio may change frequency for each heartbeat. An adaptive pseudo random frequency hopping algorithm may be used for sync mode and heartbeat attempts in search sync mode. It may be a goal to use sixty-four channels for frequency hopping. An algorithm may be developed to adaptively generate a channel list on remote control assembly 300 for frequency hopping. The radio of remote control assembly 300 may build, maintain, and distribute the master channel list. Prior channel statistics and historical performance information may be obtained from the radio of infusion pump assembly 100, 100', 400, 500 by the radio of remote control assembly 300 using the messaging system as needed to meet performance requirements. By building the channel list from the perspective of both units, the radio interference environment of both units may be considered. The radios may adaptively select hopping channels to meet the round trip message latency, while operating in a desirable RF environment.

Figure 121:
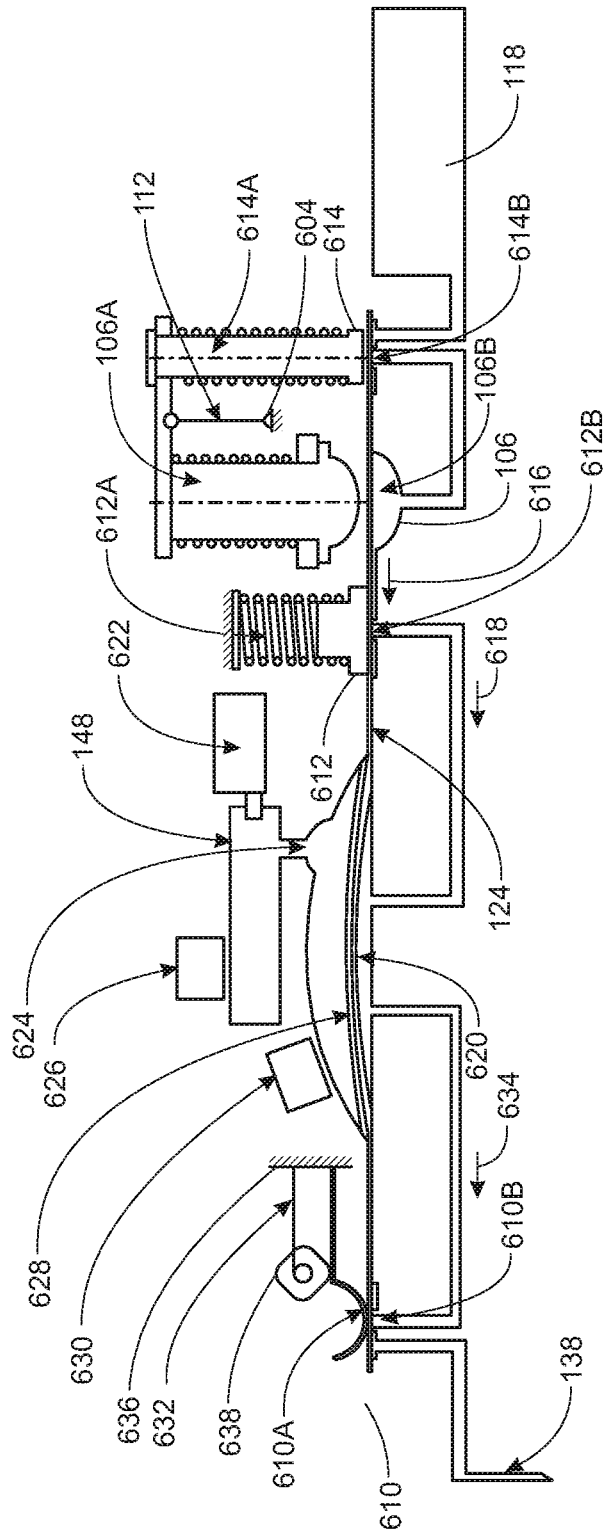
FIG. 121 diagrammatically depicts a volume sensor assembly included within the infusion pump assembly of FIG. 1.

Occlusions and/or leaks may occur anywhere along the fluid delivery path of infusion pump assembly 100. For example and referring to FIG. 121, occlusions/leaks may occur: in the fluid path between reservoir 118 and reservoir valve assembly 614; in the fluid path between reservoir valve assembly 614 and pump assembly 106; in the fluid path between pump assembly 106 and volume sensor valve assembly 612; in the fluid path between volume sensor valve assembly 612 and volume sensor chamber 620; in the fluid path between volume sensor chamber 620 and measurement valve assembly 610; and in the fluid path between measurement valve assembly 610 and the tip of disposable cannula 138. Infusion pump assembly 100 may be configured to execute one or more occlusion/leak detection algorithms that detect and locate such occlusions/leaks and enhance the safety/reliability of infusion pump assembly 100.

As discussed above, when administering the infusible fluid, infusion pump assembly 100 may first determine the volume of infusible fluid within volume sensor chamber 620 prior to the administration of the dose of infusible fluid and may subsequently determine the volume of infusible fluid within volume sensor chamber 620 after the administration of the dose of infusible fluid. By monitoring these values, the occurrence of occlusions/leaks may be detected.

Occlusion Type—Total:

When a total occlusion is occurring, the difference between the initial measurement prior to the administration of the dose of infusible fluid and the final measurement after the administration of the dose of infusible fluid will be zero (or essentially zero), indicating a large residual quantity of infusible fluid within volume sensor chamber 620. Accordingly, no fluid may be leaving volume sensor chamber 620.

Specifically, if the tip of disposable cannula is occluded, the fluid path down stream of volume sensor chamber 620 will fill with fluid and eventually become pressurized to a level equivalent to the mechanical pressure exerted by spring diaphragm 628. Accordingly, upon measurement valve assembly 610 opening, zero (or essentially zero) fluid will be dispensed and, therefore, the value of the initial and final measurements (as made by volume sensor assembly 148) will essentially be equal.

Upon detecting the occurrence of such a condition, a total occlusion flag may be set and infusion pump assembly 100 may e.g., trigger an alarm, thus indicating that the user needs to seek alternative means for receiving their therapy.

Occlusion Type—Partial:

When a partial occlusion is occurring, the difference between the initial measurement prior to the administration of the dose of infusible fluid and the final measurement after the administration of the dose of infusible fluid will indicate that less than a complete dose of infusible fluid was delivered. For example, assume that at the end of a particular pumping cycle, volume sensor assembly 148 indicated that 0.10 microliters of infusible fluid were present in volume sensor chamber 620. Further, assume that measurement value assembly 610 is subsequently closed and pump assembly 106 is subsequently actuated, resulting in volume sensor chamber 620 being filed with the infusible fluid. Further assume that volume sensor assembly 148 determines that volume sensor chamber 620 is now filled with 1.00 microliters of infusible fluid (indicating a pumped volume of 0.90 microliters).

Accordingly, upon the opening of measurement valve assembly 610, the quantity of infusible fluid included within volume sensor chamber would be expected to drop to 0.10 microliters (or reasonably close thereto). However, in the event of a partial occlusion, due to a slower-than-normal flow rate from volume sensor chamber 620, the quantity of infusible fluid within volume sensor chamber 620 may only be reduced to 0.40 microliters (indicating a delivered volume of 0.60 microliters). Accordingly, by monitoring the difference between the pumped volume (0.90 microliters) and the delivered volume (0.60 microliters), the residual volume may be defined and the occurrence of a partial occlusion may be detected.

Upon detecting the occurrence of such a condition, a partial occlusion flag may be set and infusion pump assembly 100 may e.g., trigger an alarm, thus indicating that the user needs to seek alternative means for receiving their therapy. However, as this is indicative of a partial occlusion (as opposed to a complete occlusion), the issuance of an alarm may be delayed, as the partial occlusion may clear itself.

Alternatively, infusion pump assembly 100 may: calculate a pump ontime to volume delivered ratio; track it through time; and track by using a fast moving and a slow moving exponential average of the pump ontime. The exponential average may be tracked, in a fashion similar to the leaky sum integrator. The infusion pump assembly 100 may filter signal and look for a fast change. The rate of fluid outflow and/or residual volume may be monitored. If the residual volume does not change, then there may be a total occlusion. If the residual volume changed, they may be a partial occlusion. Alternatively still, the residual values may be summed. If the number of valve actuations or the latch time is being varied, the fluid flow rate may be examined, even if you build up pressure in volume sensor assembly 148.

Total/Partial Empty Reservoir:

When reservoir 118 is becoming empty, it will become more difficult to fill volume sensor chamber 620 to the desired level. Typically, pump assembly 106 is capable of pumping 1.0 microliters per millisecond. For example, assume that an "empty" condition for volume sensor chamber 620 is 0.10 microliters and a "full" condition for volume sensor chamber 620 is 1.00 microliters. However, as reservoir 118 begins to empty, it may become harder for pump assembly 106 to fill volume sensor chamber 620 to the "full" condition and may consistently miss the goal. Accordingly, during normal operations, it may take one second for pump assembly 106 to fill volume sensor chamber 620 to the "full" condition and, as reservoir 118 empties, it may take three seconds to fill volume sensor chamber 620 to the "full" condition. Eventually, if reservoir 118 completely empties, volume sensor chamber 620 may never be able to achieve a "full condition". Accordingly, the inability of pump assembly 106 to fill volume sensor chamber 620 to a "full" condition may be indicative of reservoir 118 being empty. Alternatively, the occurrence of such a condition may be indicative of other situations (e.g., the failure of pump assembly 106 or an occlusion in the fluid path prior to volume sensor chamber 620). Infusion pump assembly 100 may determine the difference between the "full" condition and the amount actually pumped. These differences may be summed and the made up for once the reservoir condition is addressed.

Upon detecting the occurrence of such a condition, an empty flag may be set and infusion pump assembly 100 may e.g., trigger an alarm, thus indicating that the user needs to e.g., replace disposable housing assembly 114.

Additionally, as reservoir 118 empties, reservoir 118 will eventually result in a "vacuum" condition and the ability of pump assembly 106 to deliver fluid to volume sensor chamber 620 may be compromised. As discussed above, volume controller 1602 may include feed forward controller 1652 for setting an initial "guess" concerning "on-time" signal 1606, wherein this initial guess is based upon a pump calibration curve. For example, in order for pump assembly 106 to deliver 0.010 units of infusible fluid, feed forward controller 1652 may define an initial "on-time" of e.g., one millisecond. However, as reservoir 118 begins to empty, due to compromised pumping conditions, it may take two milliseconds to deliver 0.010 units of infusible fluid. Further, as reservoir 118 approaches a fully empty condition, it make take ten milliseconds to deliver 0.010 units of infusible fluid. Accordingly, the occurrence of reservoir 118 approaching an empty condition may be detected by monitoring the level at which the actual operation of pump assembly 106 (e.g., two milliseconds to deliver 0.010 units of infusible fluid) differs from the anticipated operation of pump assembly 106 (e.g., one millisecond to deliver 0.010 units of infusible fluid).

Upon detecting the occurrence of such a condition, a reserve flag may be set and infusion pump assembly 100 may e.g., trigger an alarm, thus indicating that the user will need to e.g., replace disposable housing assembly 114 shortly.

Leak Detection:

In the event of a leak (e.g., a leaky valve or a rupture/perforation) within the fluid path, the ability of the fluid path to retain fluid pressure may be compromised. Accordingly, in order to check for leaks within the fluid path, a bleed down test may be performed in which pump assembly 106 is used to pressurize volume sensor chamber 620. Volume sensor assembly 148 may then perform a first volume measurement (as described above) to determine the volume of infusible fluid within volume sensor chamber 620. Infusion pump assembly 100 may then wait a defined period of time to allow for bleed down in the event of a leak. For example, after a sixty second bleed down period, volume sensor assembly 148 may perform a second volume measurement (as described above) to determine the volume of infusible fluid within volume sensor chamber 620. If there are no leaks, the two volume measurements should be essentially the same. However, in the event of a leak, the second measurement may be less then the first measurement. Additionally, depending on the severity of the leak, pump assembly 106 may be incapable of filling volume sensor chamber 620. Typically, a leak check may be performed as part of a delivery of infusible fluid.

In the event that the difference between the first volume measurement and the second volume measurement exceeds an acceptable threshold, a leak flag may be set and infusion pump assembly 100 may e.g., trigger an alarm, thus indicating that the user needs to seek alternative means for receiving their therapy.

As discussed above, infusion pump assembly 100 may include supervisor processor 1800, command processor 1802, and radio processor 1818. Unfortunately, once assembled, access to electrical control assembly 110 within infusion pump assembly 100 very limited. Accordingly, the only means to access electrical control assembly 110 (e.g., for upgrading flash memories) may be through the communication channel established between infusion pump assembly 100, 100', 400, 500 and remote control assembly 300, or via electrical contacts 834 used by battery charger 1200.

Electrical contacts 834 may be directly coupled to radio processor 1818 and may be configured to provide I2C communication capability for erasing/programming any flash memory (not shown) included within radio processor 1818. The process of loading a program into radio processor 1818 may provide a means for erasing/programming of the flash memories in both the supervisor processor 1800 and command processor 1802.

When programming supervisor processor 1800 or command processor 1802, the program (i.e., data) to be loaded into flash memory accessible by supervisor processor 1800 or command processor 1802 may be provided in a plurality of data blocks. This is because the radio processor 1818 may not have enough memory to hold the entire flash image of the software as one block.

Figure 122:
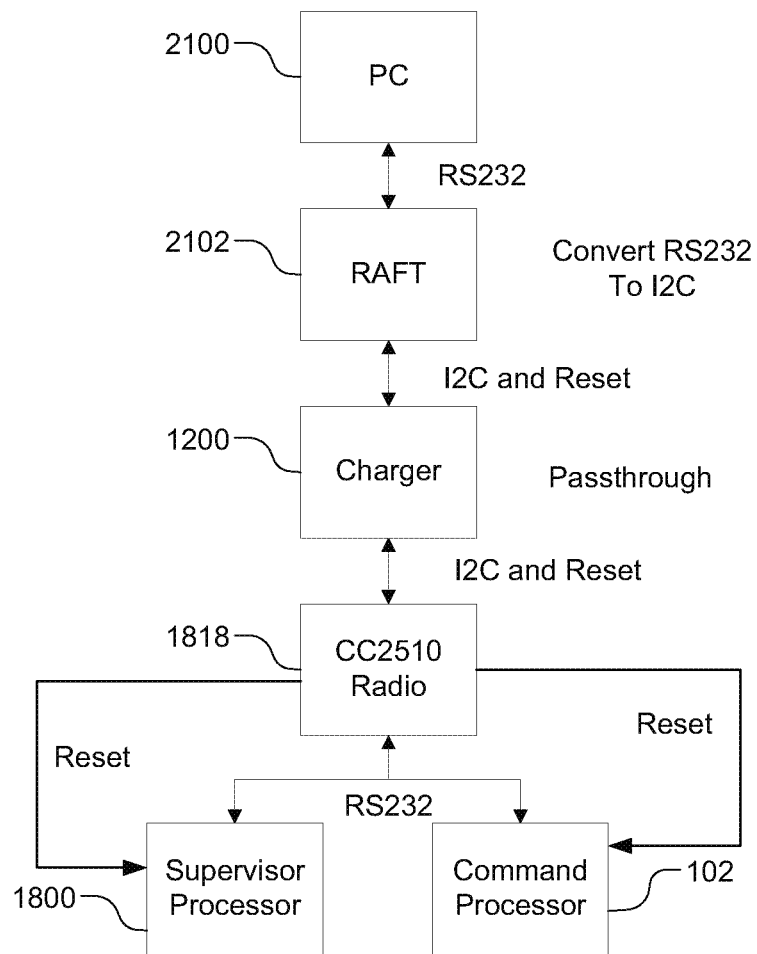
FIG. 122 diagrammatically depicts an inter-connection of the various systems of the infusion pump assembly of FIG. 1.

Referring also to FIG. 122, there is shown one illustrative example of the manner in which the various systems within infusion pump assembly 100, 100', 400, 500 may be interconnected. For example, battery charger 1200 may be coupled to computing device 2100 (e.g., a personal computer) via bus translator 2102, which converts e.g., RS232 formatted data to e.g., I2C formatted data. Bus translator 2102 may execute a pass-through program that effectuates the above-described translation. Battery charger 1200 may be coupled to radio processor 181 via electrical contacts 834 (described above). Radio processor 1818 may then be coupled to supervisor processor 1800 and command processor 1802 via e.g., an RS232 bus. Radio processor 1818 may execute an update program that allows radio processor 1818 to control/orchestrate the updating of the flash memories accessible by supervisor processor 1800 and command processor 1802. Accordingly, through the use of the above-described coupling, software updates obtained by computing device 2100 may be uploaded to flash memory (not shown) accessible by supervisor processor 1800 and command processor 1802. The above-described software updates may be command line program that may be automatically invoked by a script process.

As discussed above, infusion pump assembly 100, 100' 400, 500 may be configured to deliver an infusible fluid to a user. Further and as discussed above, infusion pump assembly 100, 100' 400, 500 may deliver the infusible fluid via sequential, multi-part, infusion events (that may include a plurality of discrete infusion events) and/or one-time infusion events. However, in some embodiments, infusion pump assembly 100, 100' 400, 500 may deliver stacking bolus infusion events. For example, a user may request the delivery of a bolus, e.g., 6 units. While the 6 units are in the process of being delivered to the user, the user may request a second bolus, e.g., 3 units. In some embodiments of infusion pump assembly 100, 100' 400, 500 may deliver the second bolus at the completion of the first bolus.

Examples of other such sequential, multi-part, infusion events may include but are not limited to a basal infusion event and an extended-bolus infusion event. As is known in the art, a basal infusion event refers to the repeated injection of small (e.g. 0.05 unit) quantities of infusible fluid at a predefined interval (e.g. every three minutes) that may be repeated until stopped, e.g., by a user or by the system. Further, the basal infusion rates may be pre-programmed and may include specified rates for pre-programmed timeframes, e.g., a rate of 0.50 units per hour from 6:00 am-3:00 pm; a rate of 0.40 units per hour from 3:00 pm-10:00 pm; and a rate of 0.35 units per hour from 10:00 pm-6:00 am. However, the basal rate may be 0.025 units per hour, and may not change according to pre-programmed time-frames. The basal rates may be repeated regularly/daily until otherwise changed.

Further and as is known in the art, an extended-bolus infusion event may refer to the repeated injection of small (e.g. 0.05 unit) quantities of infusible fluid at a predefined interval (e.g. every three minutes) that is repeated for a defined number of intervals (e.g., three intervals) or for a defined period of time (e.g., nine minutes). An extended-bolus infusion event may occur simultaneously with a basal infusion event.

If multiple infusion events conflict with each other, infusion pump assembly 100, 100' 400, 500 may prioritize the infusion event in the follow manner.

Figure 123:
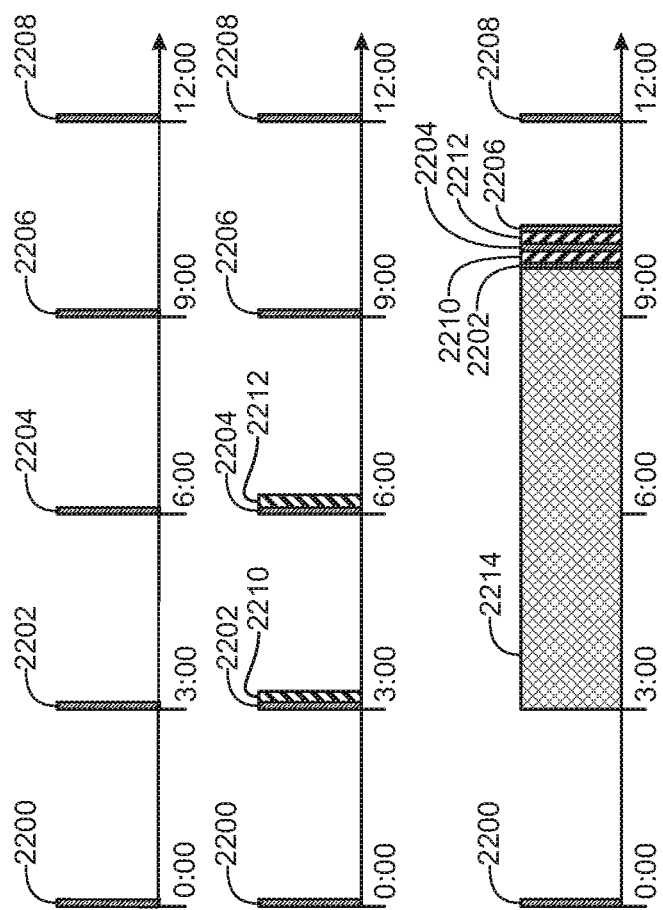
FIG. 123 diagrammatically depicts basal-bolus infusion events.

Referring also to FIG. 123, assume for illustrative purposes only that the user configures infusion pump assembly 100, 100' 400, 500 to administer a basal dose (e.g. 0.05 units) of infusible fluid every three minutes. The user may utilize remote control assembly 300 to define a basal infusion event for the infusible fluid (e.g., 1.00 units per hour).

Infusion pump assembly 100, 100' 400, 500 may then determine an infusion schedule based upon the basal infusion event defined. Once determined, infusion pump assembly 100, 100' 400, 500 may administer the sequential, multi-part, infusion event (e.g., 0.05 units of infusible fluid every three minutes). Accordingly, while administering the sequential, multi-part, infusion event, infusion pump assembly 100, 100' 400, 500: may infuse a first 0.05 unit dose 2200 of the infusible fluid at t=0:00 (i.e., a first discrete infusion event), may infuse a second 0.05 unit dose 2202 of the infusible fluid at t=3:00 (i.e., a second discrete infusion event); may infuse a third 0.05 unit dose 2204 of the infusible fluid at t=6:00 (i.e., a third discrete infusion event); may infuse a fourth 0.05 unit dose 2206 of the infusible fluid at t=9:00 (i.e., a fourth discrete infusion event); and may infuse a fifth 0.05 unit dose 2208 of the infusible fluid at t=12:00 (i.e., a fifth discrete infusion event). As discussed above, this pattern of infusing 0.05 unit doses of the infusible fluid every three minutes may be repeated until stopped, e.g., by a user or by the system, in this example, as this is an illustrative example of a basal infusion event.

Further, assume for illustrative purposes that the infusible fluid is insulin and sometime after the first 0.05 unit dose 2200 of infusible fluid is administered (but before the second 0.05 unit dose 2202 of infusible fluid is administered), the user checks their blood glucose level and realizes that their blood glucose level is running a little higher than normal. Accordingly, the user may define an extended bolus infusion event via remote control assembly 300. An extended bolus infusion event may refer to the continuous infusion of a defined quantity of infusible fluid over a finite period of time. However, as such an infusion methodology is impractical/undesirable for an infusion pump assembly, when administered by such an infusion pump assembly, an extended bolus infusion event may refer to the infusion of additional small doses of infusible fluid over a finite period of time.

Accordingly, the user may utilize remote control assembly 300 to define an extended bolus infusion event for the infusible fluid (e.g., 0.20 units over the next six minutes), which may be confirmed in a manner discussed above. While, in this example, the extended bolus infusion event is described as 0.20 units over the next six minutes, this is for illustrative purposes only and is not intended to be a limitation of this disclosure, as either or both of the unit quantity and total time interval may be adjusted upward or downward. Once defined and/or confirmed, infusion pump assembly 100, 100' 400, 500 may determine an infusion schedule based upon the extended bolus infusion event defined; and may administer the infusible fluid. For example, infusion pump assembly 100, 100' 400, 500 may deliver 0.10 units of infusible fluid every three minutes for the next two interval cycles (or six minutes), resulting in the delivery of the extended bolus dose of infusible fluid defined by the user (i.e., 0.20 units over the next six minutes).

Accordingly, while administering the second, sequential, multi-part, infusion event, infusion pump assembly 100, 100' 400, 500 may infuse a first 0.10 unit dose 2210 of the infusible fluid at t=3:00 (e.g., after administering the second 0.05 unit dose 2202 of infusible fluid). Infusion pump assembly 100, 100' 400, 500 may also infuse a second 0.10 unit dose 2212 of the infusible fluid at t=6:00 (e.g., after administering the third 0.05 unit dose 2204 of infusible fluid).

Assume for illustrative purposes only that after the user programs infusion pump assembly 100, 100' 400, 500 via remote control assembly 300 to administer the first sequential, multi-part, infusion event (i.e., 0.05 units infused every three minute interval repeated continuously) and administer the second sequential, multi-part, infusion event (i.e., 0.10 units infused every three minute interval for two intervals), the user decides to eat a very large meal. Predicting that their blood glucose level might increase considerably, the user may program infusion pump assembly 100, 100' 400, 500 (via remote control assembly 300) to administer a one-time infusion event. An example of such a one-time infusion event may include but is not limited to a normal bolus infusion event. As is known in the art, a normal bolus infusion event refers to a one-time infusion of the infusible fluid.

For illustrative purposes only, assume that the user wishes to have infusion pump assembly 100, 100' 400, 500 administer a bolus dose of thirty-six units of the infusible fluid. Infusion pump assembly 100, 100' 400, 500 may monitor the various infusion events being administered to determine whether a one-time infusion event is available to be administered. If a one-time infusion event is available for administration, infusion pump assembly 100, 100' 400, 500 may delay the administration of at least a portion of the sequential, multi-part, infusion event.

Continuing with the above-stated example, once the user completes the programming of infusion pump assembly 100, 100' 400, 500 to deliver one-time infusion event 2214 (i.e., the thirty-six unit bolus dose of the infusible fluid), upon infusion pump assembly 100, 100' 400, 500 determining that the one-time infusion event is available for administration, infusion pump assembly 100, 100' 400, 500 may delay the administration of each sequential, multi-part infusion event and administer the available one-time infusion event.

Specifically and as discussed above, prior to the user programming infusion pump assembly 100, 100' 400, 500 to deliver one-time infusion event 2214, infusion pump assembly 100, 100' 400, 500 was administering a first sequential, multi-part, infusion event (i.e., 0.05 units infused every three minute interval repeated continuously) and administering a second sequential, multi-part, infusion event (i.e., 0.10 units infused every three minute interval for two intervals).

For illustrative purposes only, the first sequential, multi-part, infusion event may be represented within FIG. 123 as 0.05 unit dose 2200 @ t=0:00, 0.05 unit dose 2202 @ t=3:00, 0.05 unit dose 2204 @ t=6:00, 0.05 unit dose 2206 @ t=9:00, and 0.05 unit dose 2208 @ t=12:00. As the first sequential, multi-part, infusion event as described above is a basal infusion event, infusion pump assembly 100, 100' 400, 500 may continue to infuse 0.05 unit doses of the infusible fluid at three minute intervals indefinitely (i.e., until the procedure is cancelled by the user).

Further and for illustrative purposes only, the second sequential, multi-part, infusion event may be represented within FIG. 123 as 0.10 unit dose 2210 @ t=3:00 and 0.10 unit dose 2212 @ t=6:00. As the second sequential, multi-part, infusion event is described above as an extended bolus infusion event, infusion pump assembly 100, 100' 400, 500 may continue to infuse 0.10 unit doses of the infusible fluid at three minute intervals for exactly two intervals (i.e., the number of intervals defined by the user).

Continuing with the above-stated example, upon infusion pump assembly 100, 100' 400, 500 determining that the thirty-six unit normal bolus dose of the infusible fluid (i.e., one-time infusion event 2214) is available for administration, infusion pump assembly 100, 100' 400, 500 may delay the administration of each sequential, multi-part infusion event and may start administering one-time infusion event 2214 that is available for administration.

Accordingly and for illustrative purposes only, assume that upon completion of the programming of infusion pump assembly 100, 100' 400, 500 to deliver the thirty-six unit normal bolus does of the infusible fluid (i.e., the one-time infusion event), infusion pump assembly 100, 100' 400, 500 begins administering one-time infusion event 2214. Being that one-time infusion event 2214 is comparatively large, it may take longer than three minutes (i.e., the time interval between individual infused doses of the sequential, multi-part, infusion events) and one or more of the individual infused doses of the sequential, multi-part, infusion events may need to be delayed.

Specifically, assume that it will take infusion pump assembly 100, 100' 400, 500 greater than six minutes to infuse thirty-six units of the infusible fluid. Accordingly, infusion pump assembly 100, 100' 400, 500 may delay 0.05 unit dose 2202 (i.e., scheduled to be infused @ t=3:00), 0.05 unit dose 2204 (i.e., scheduled to be infused @ t=6:00), and 0.05 unit dose 2206 (i.e., scheduled to be infused @ t=9:00) until after one-time infusion event 2214 (i.e., the thirty-six unit normal bolus dose of the infusible fluid) is completely administered. Further, infusion pump assembly 100, 100' 400, 500 may delay 0.10 unit dose 2210 (i.e., scheduled to be infused @ t=3:00 and 0.10 unit dose 2212 (i.e., scheduled to be infused @ t=6:00) until after one-time infusion event 2214.

Once administration of one-time infusion event 2214 is completed by infusion pump assembly 100, 100' 400, 500, any discrete infusion events included within the sequential, multi-part, infusion event that were delayed may be administered by infusion pump assembly 100, 100' 400, 500. Accordingly, once one-time infusion event 2214 (i.e., the thirty-six unit normal bolus dose of the infusible fluid) is completely administered, infusion pump assembly 100, 100' 400, 500 may administer 0.05 unit dose 2202, 0.05 unit dose 2204, 0.05 unit dose 2206, 0.10 unit dose 2210, and 0.10 unit dose 2212.

While infusion pump assembly 100, 100' 400, 500 is shown to administer 0.05 unit dose 2202, then 0.10 unit dose 2210, then 0.05 unit dose 2204, then 0.10 unit dose 2212, and then 0.05 unit dose 2206, this is for illustrative purposes only and is not intended to be a limitation of this disclosure, as other configurations are possible and are considered to be within the scope of this disclosure. For example, upon infusion pump assembly 100, 100' 400, 500 completing the administration of one-time infusion event 2214 (i.e., the thirty-six unit normal bolus dose of the infusible fluid), infusion pump assembly 100, 100' 400, 500 may administer all of the delayed discrete infusion events associated with the first sequential, multi-part infusion event (i.e., namely 0.05 unit dose 2202, 0.05 unit dose 2204, and 0.05 unit dose 2206). Infusion pump assembly 100, 100' 400, 500 may then administer all of the delayed discrete infusion events associated with the second sequential, multi-part infusion event (i.e., 0.10 unit dose 2210, and 0.10 unit dose 2212).

While one-time infusion event 2214 (i.e., the thirty-six unit normal bolus dose of the infusible fluid) is shown as being infused beginning at t=3:00, this is for illustrative purposes only and is not intended to be a limitation of this disclosure. Specifically, infusion pump assembly 100, 100' 400, 500 may not need to begin infusing one-time infusion event 2214 at one of the three-minute intervals (e.g., t=0:00, t=3:00, t=6:00, t=9:00, or t=12:00) and may begin administering one-time infusion event 2214 at any time.

While each discrete infusion event (e.g., 0.05 unit dose 2202, 0.05 unit dose 2204, 0.05 unit dose 2206, 0.10 unit dose 2210, and 0.10 unit dose 2212) and one-time infusion event 2214 are shown as being a single event, this is for illustrative purposes only and is not intended to be a limitation of this disclosure. Specifically, at least one of the plurality of discrete infusion events e.g., 0.05 unit dose 2202, 0.05 unit dose 2204, 0.05 unit dose 2206, 0.10 unit dose 2210, and 0.10 unit dose 2212) may include a plurality of discrete infusion sub-events. Further, one-time infusion event 2214 may include a plurality of one-time infusion sub-events.

Figure 124:
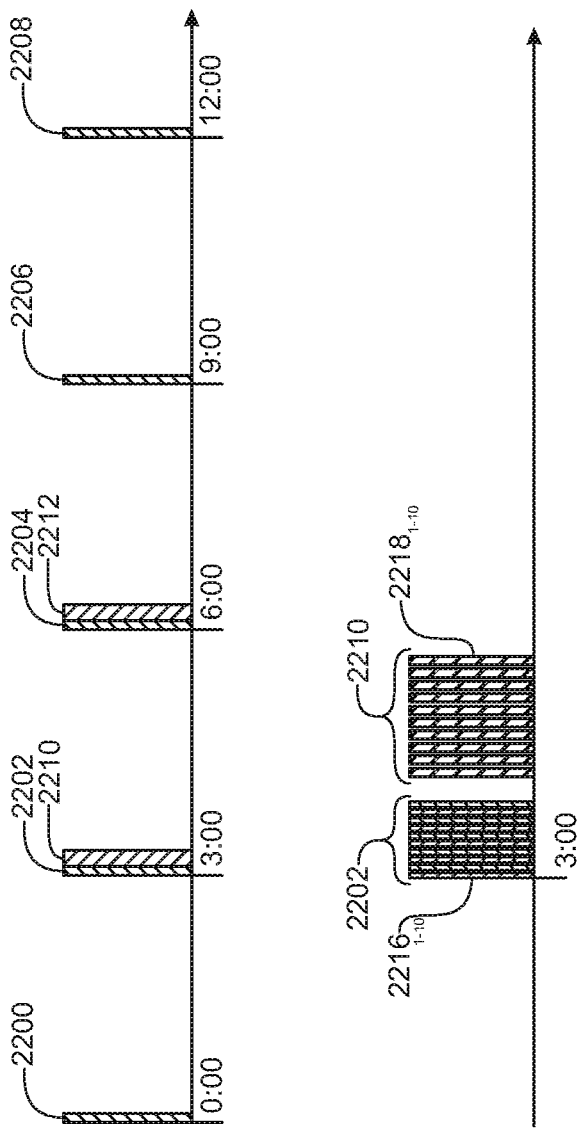
FIG. 124 diagrammatically depicts basal-bolus infusion events.
Figure 125A:
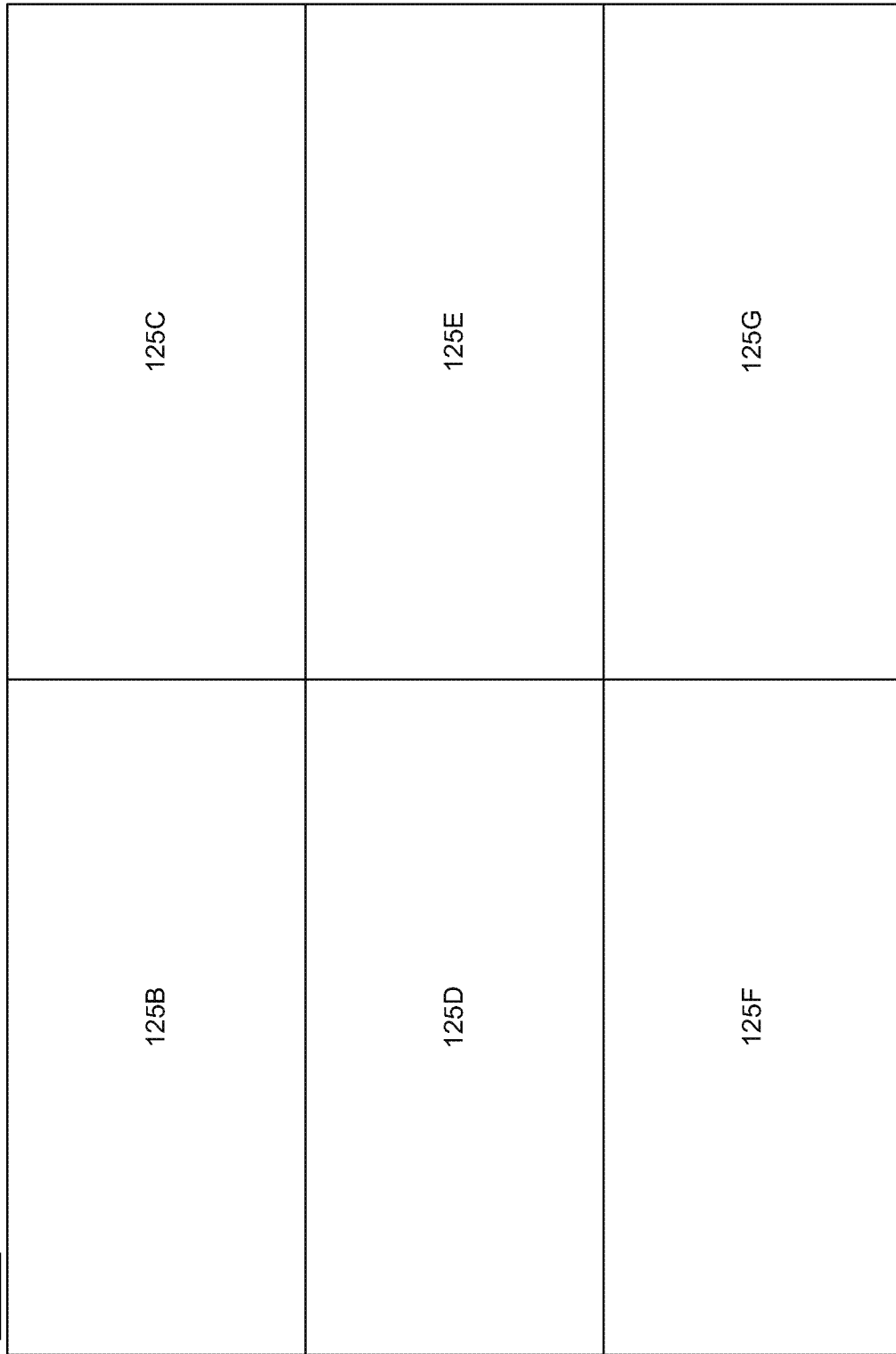
Figure 125B:
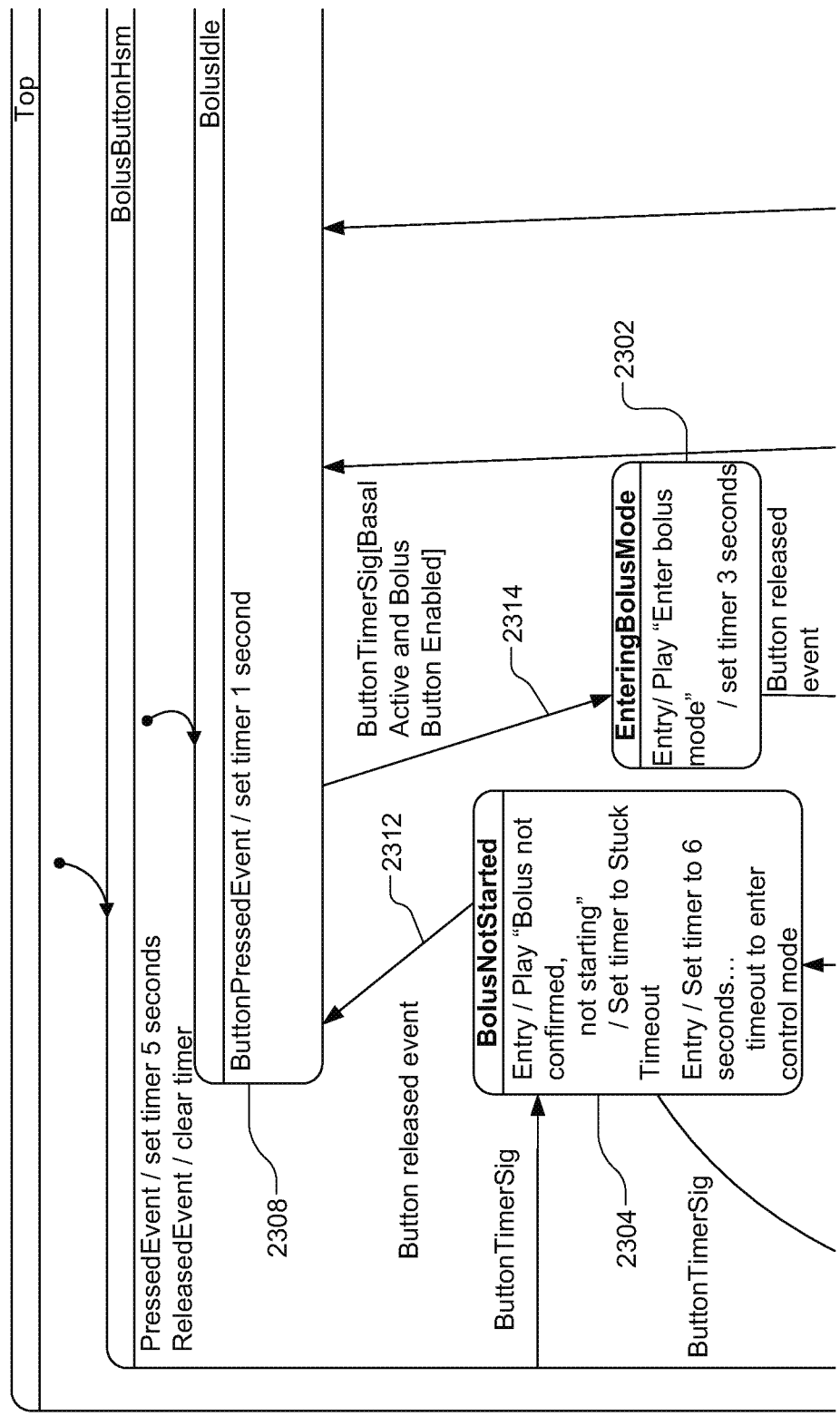
Figure 125C:
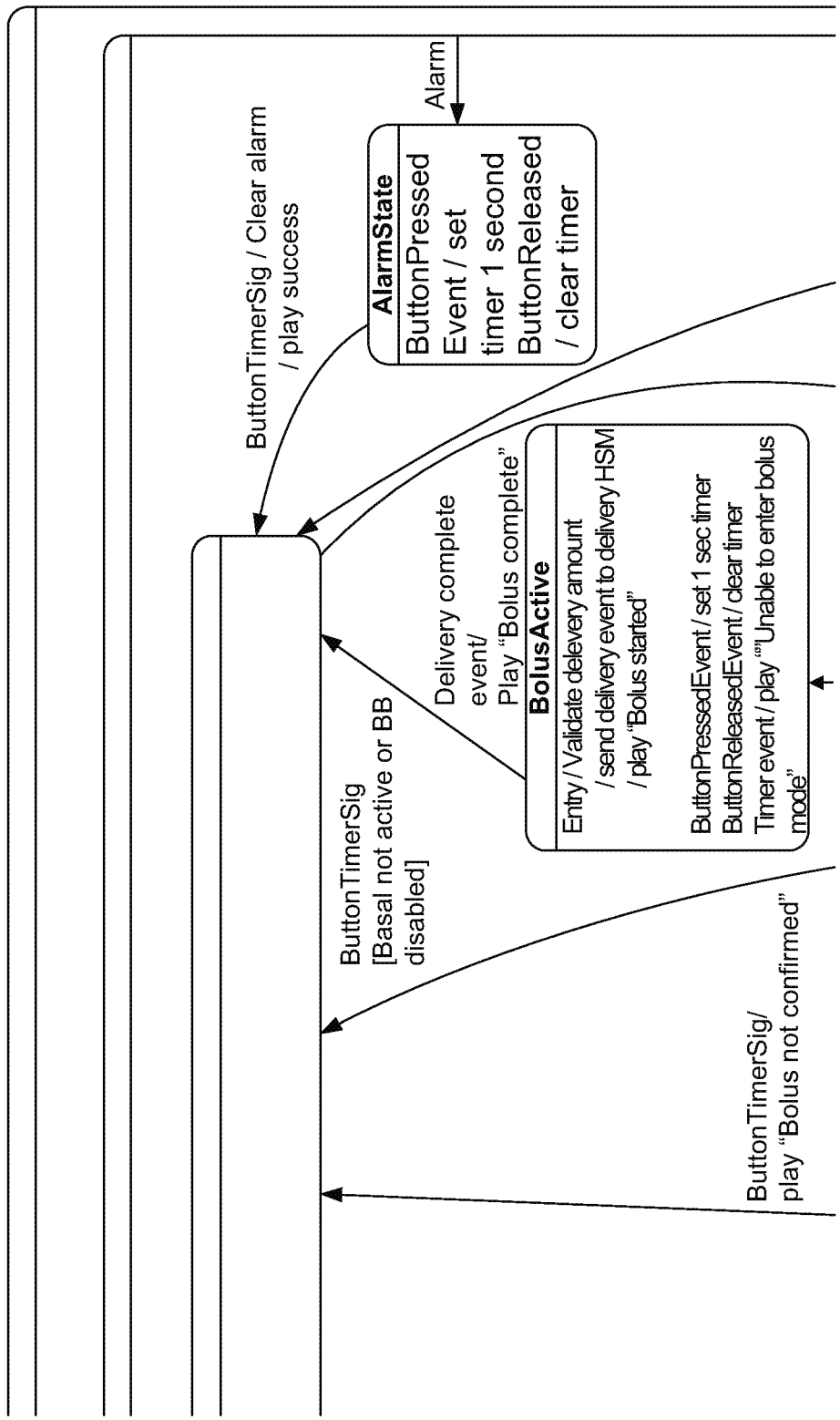
Figure 125D:
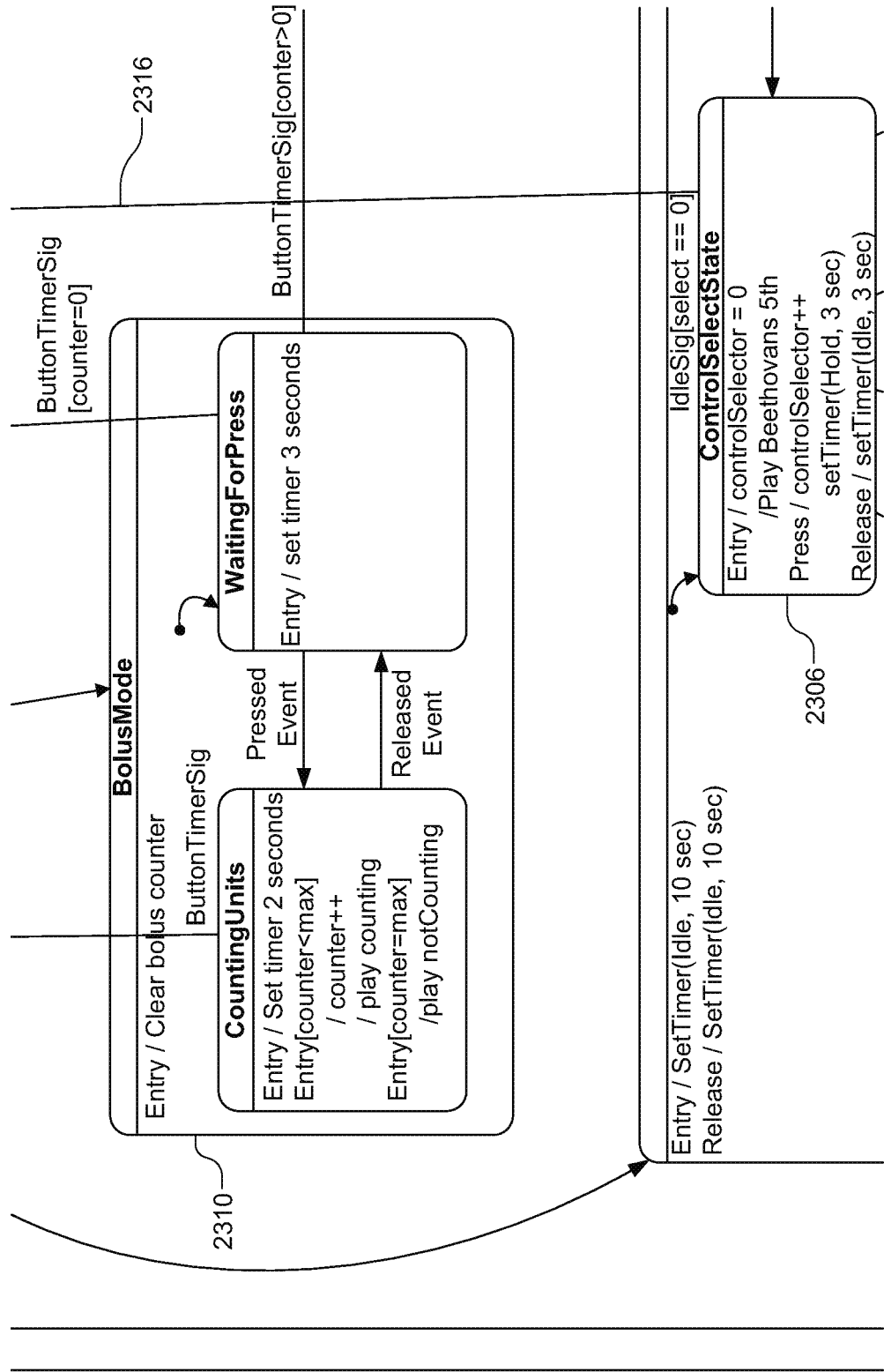
Figure 125F:
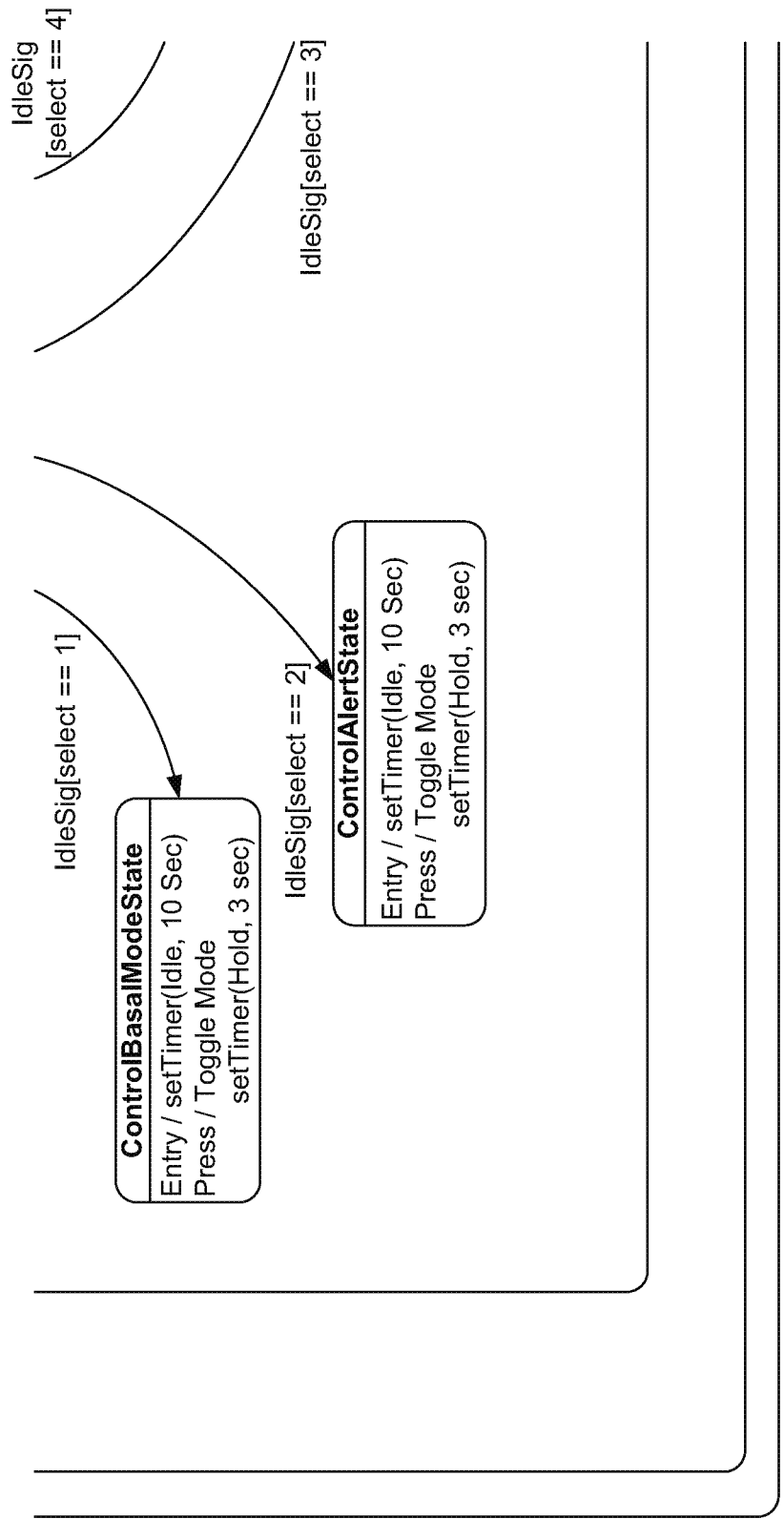
Figure 125G:
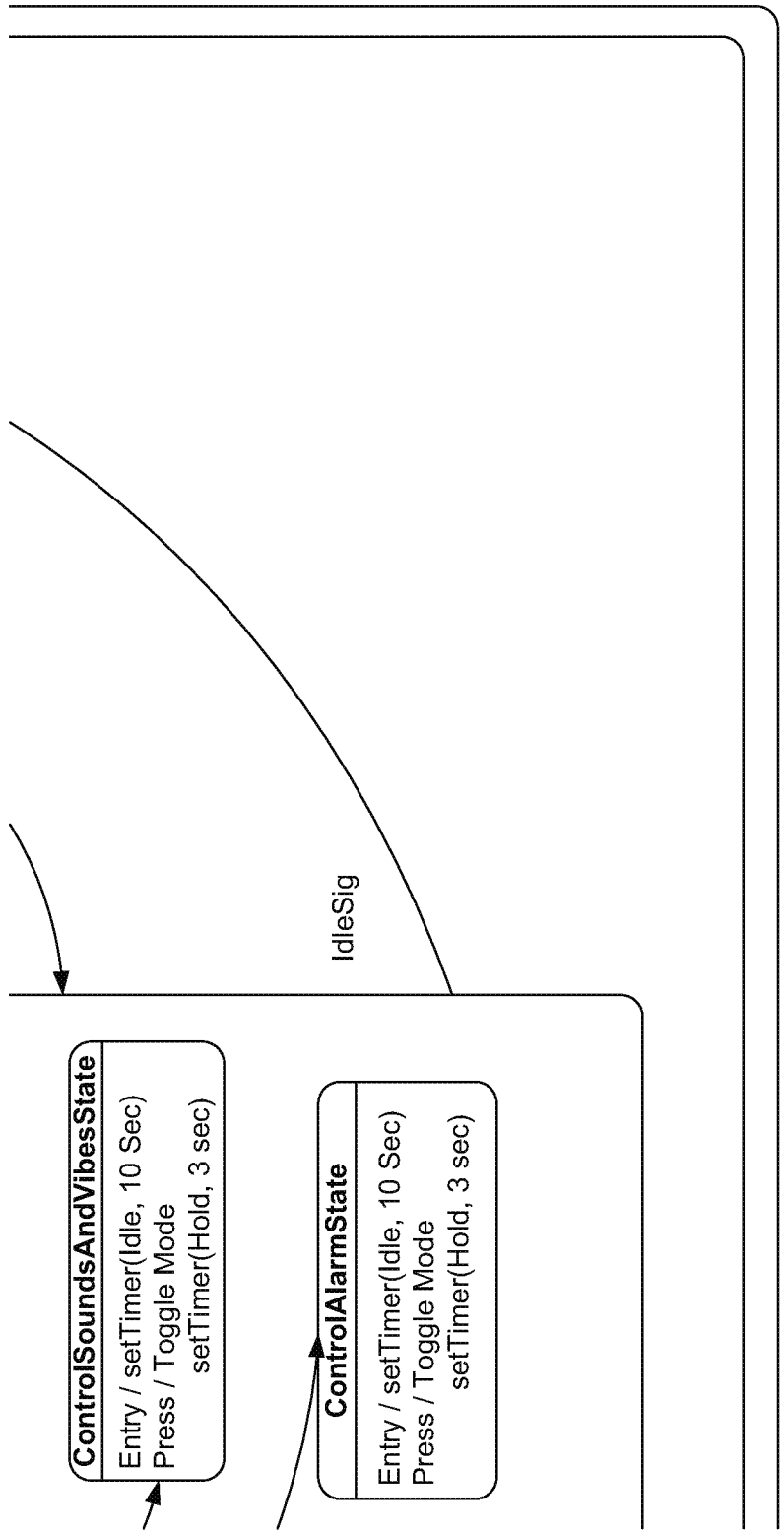
Figure 126B:
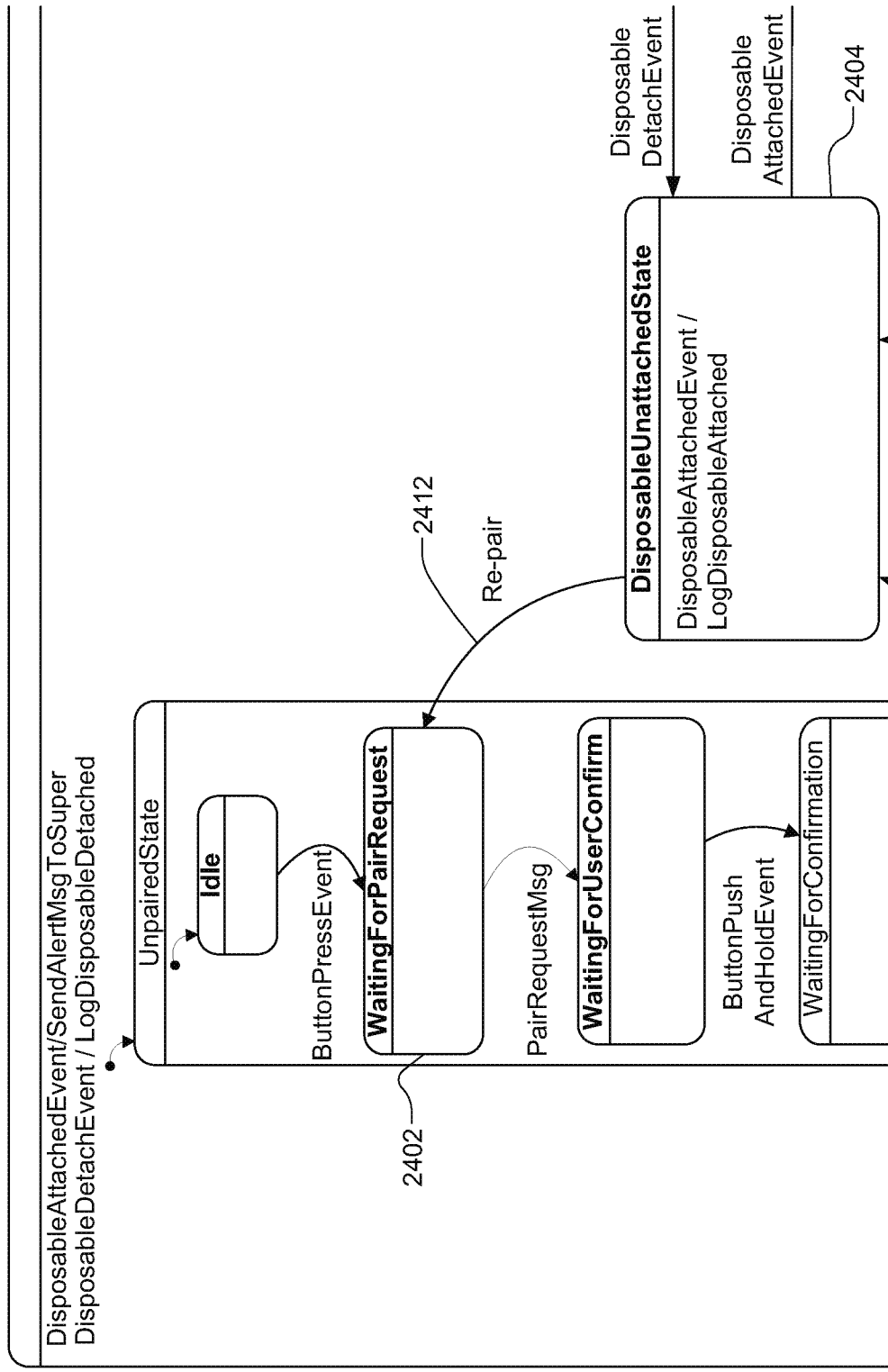
Figure 126C:
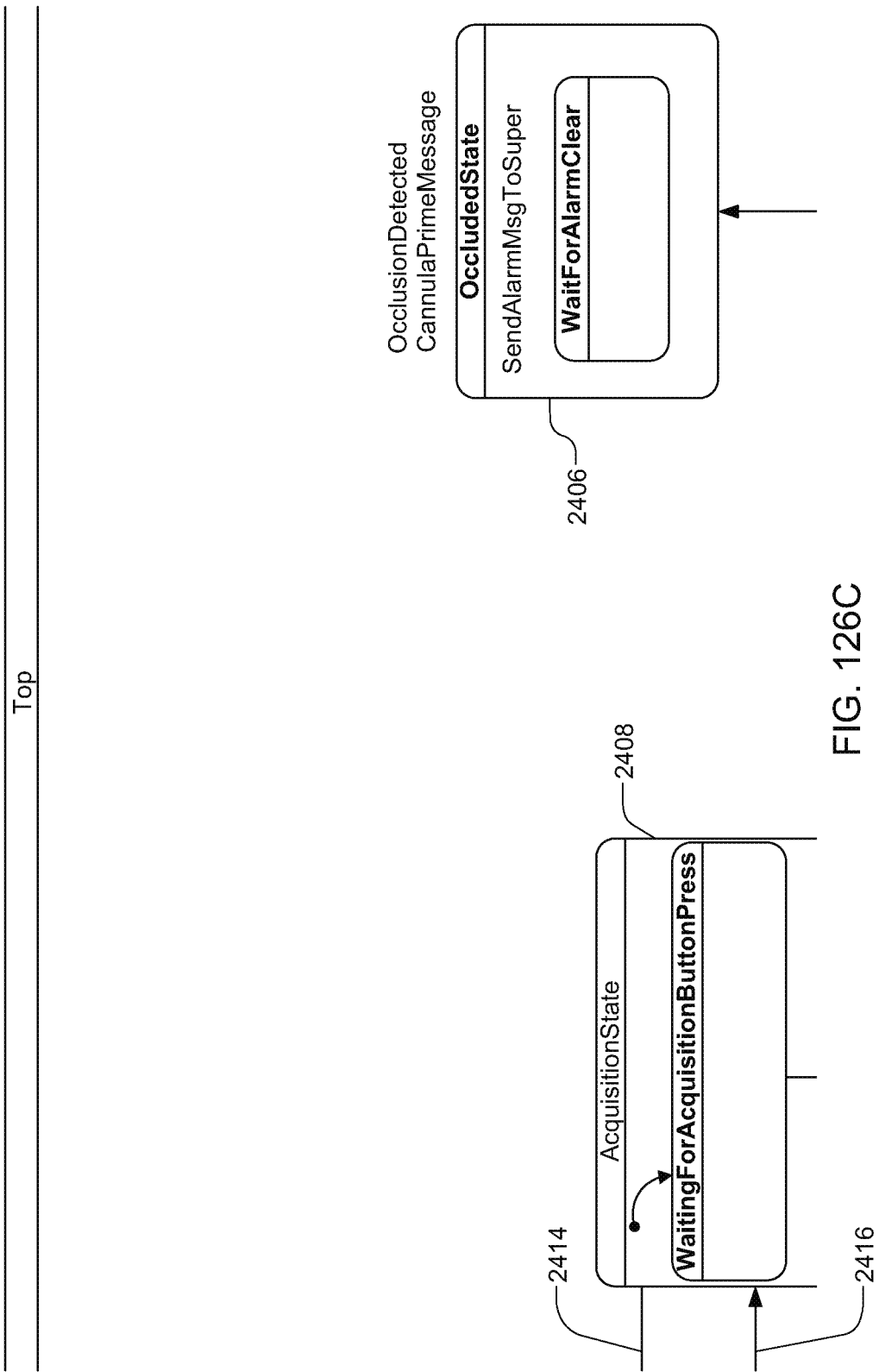
Figure 126D:
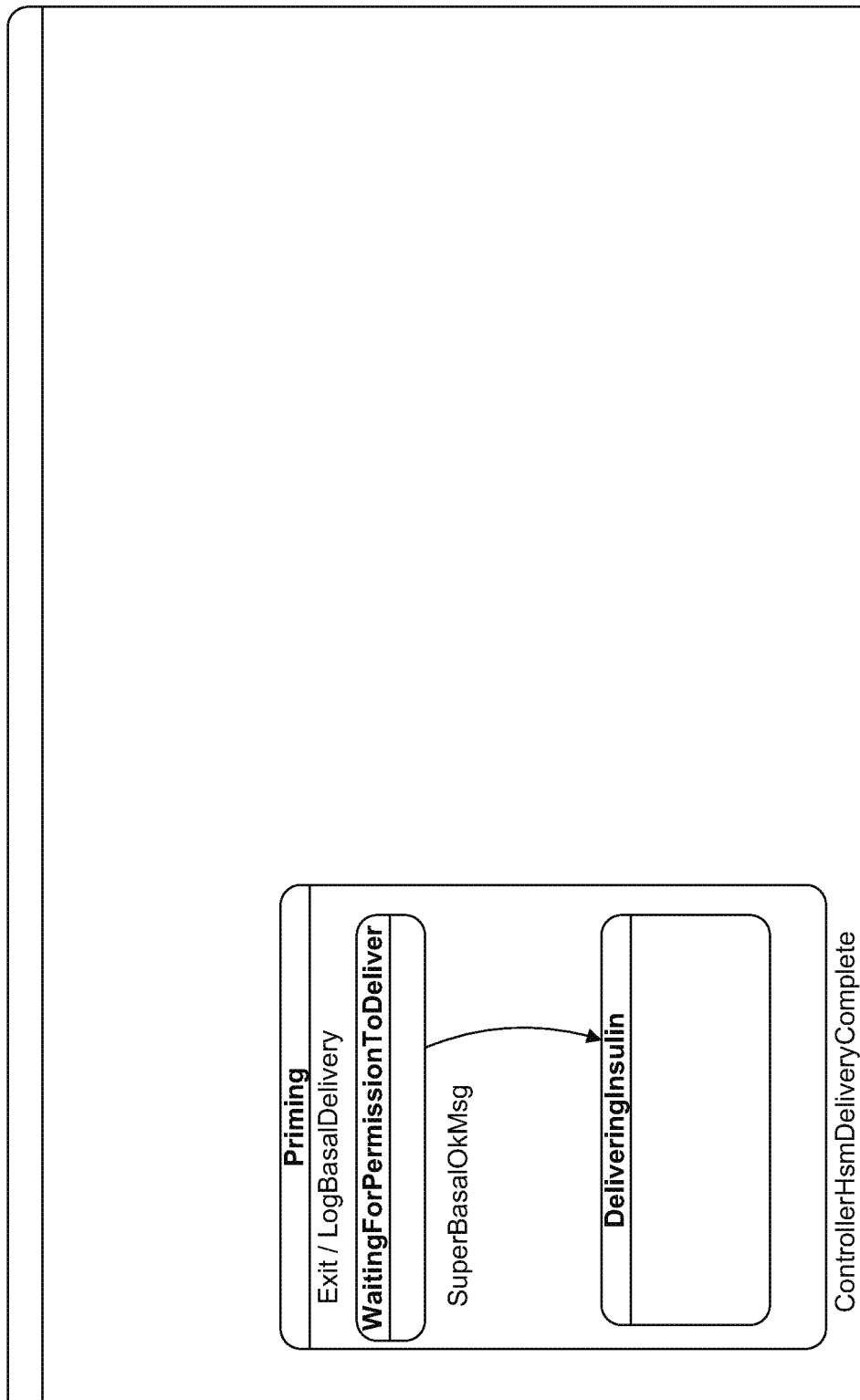
Figure 126F:
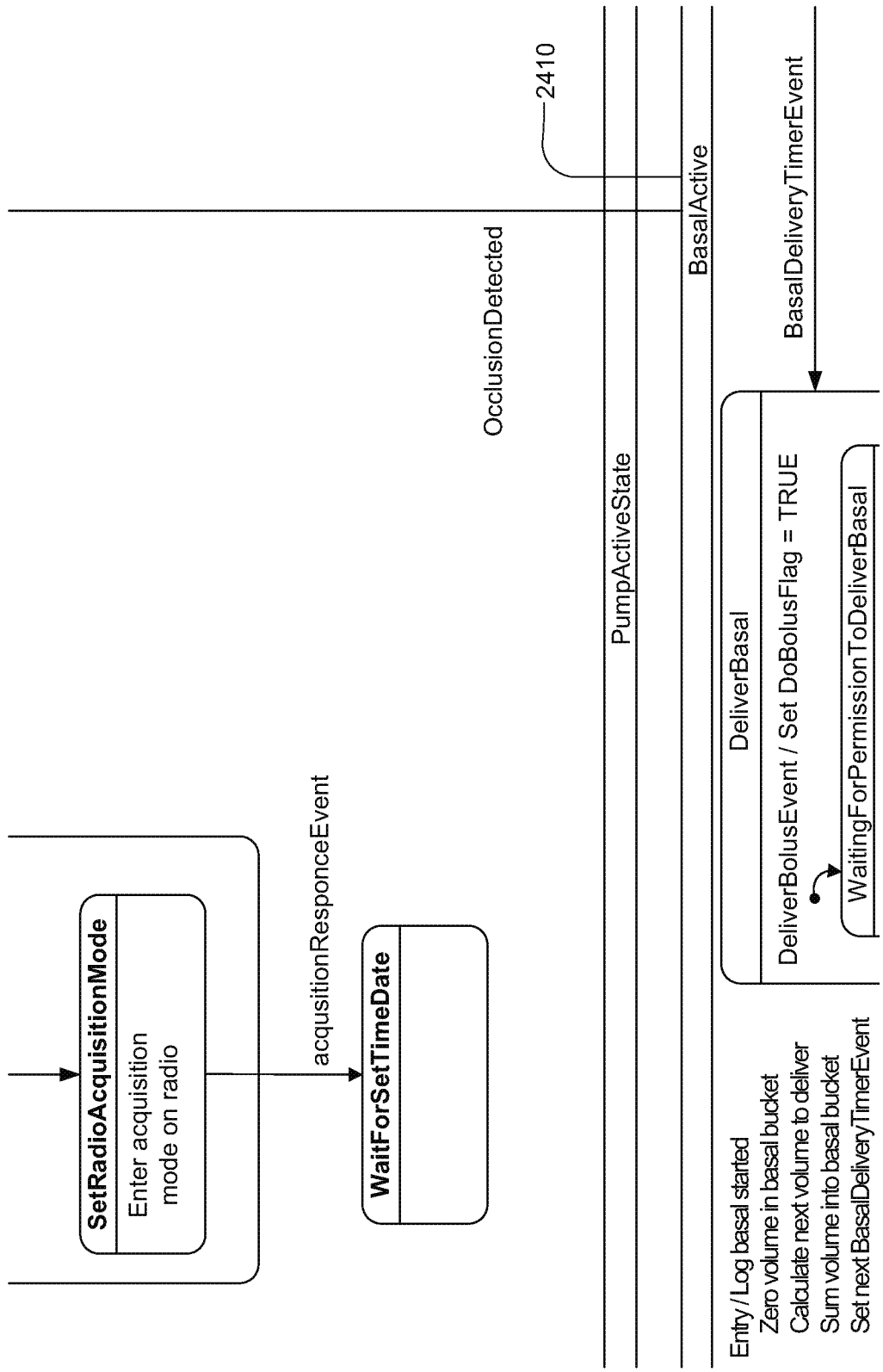
Figure 126G:
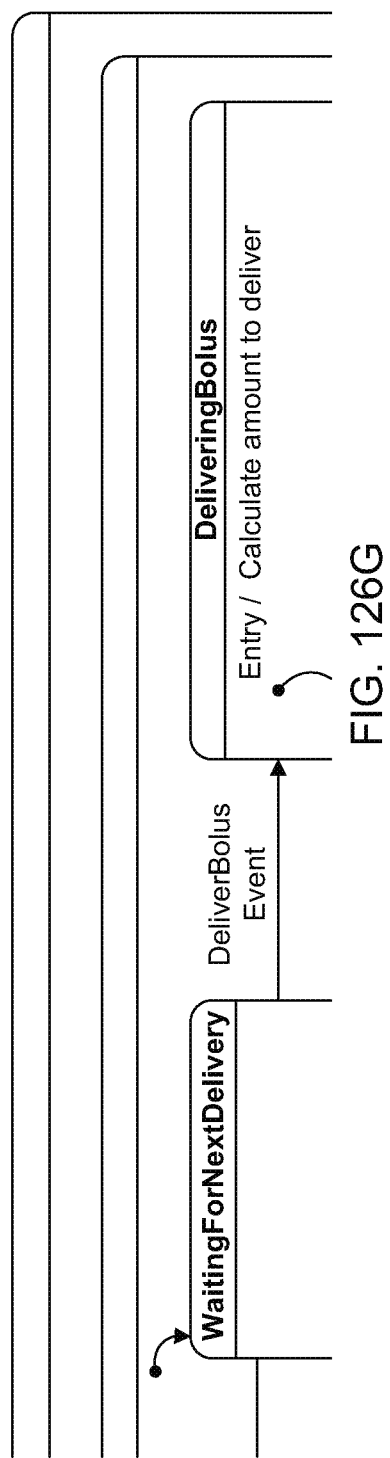
Figure 126H:
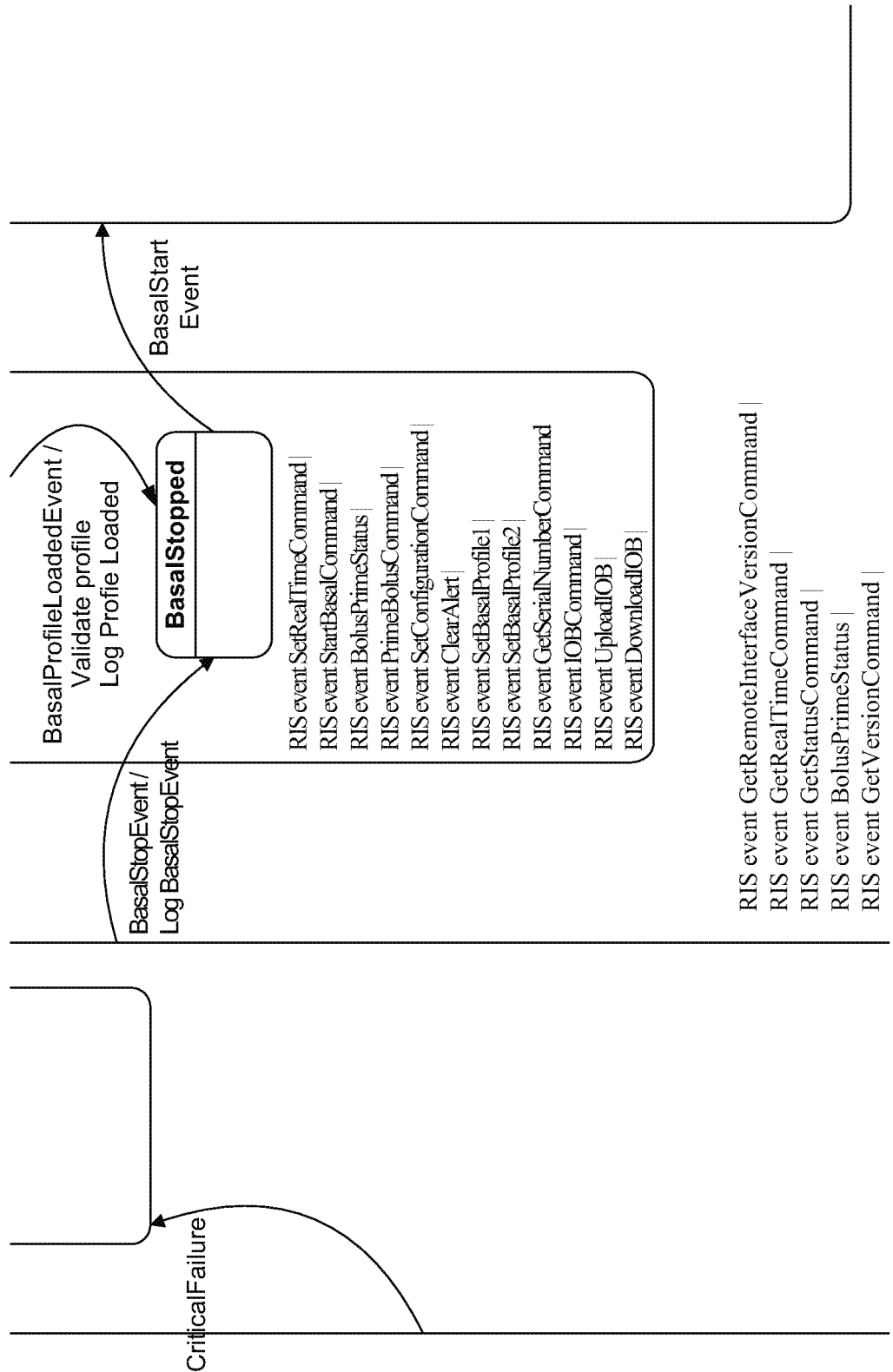
Figure 126I:
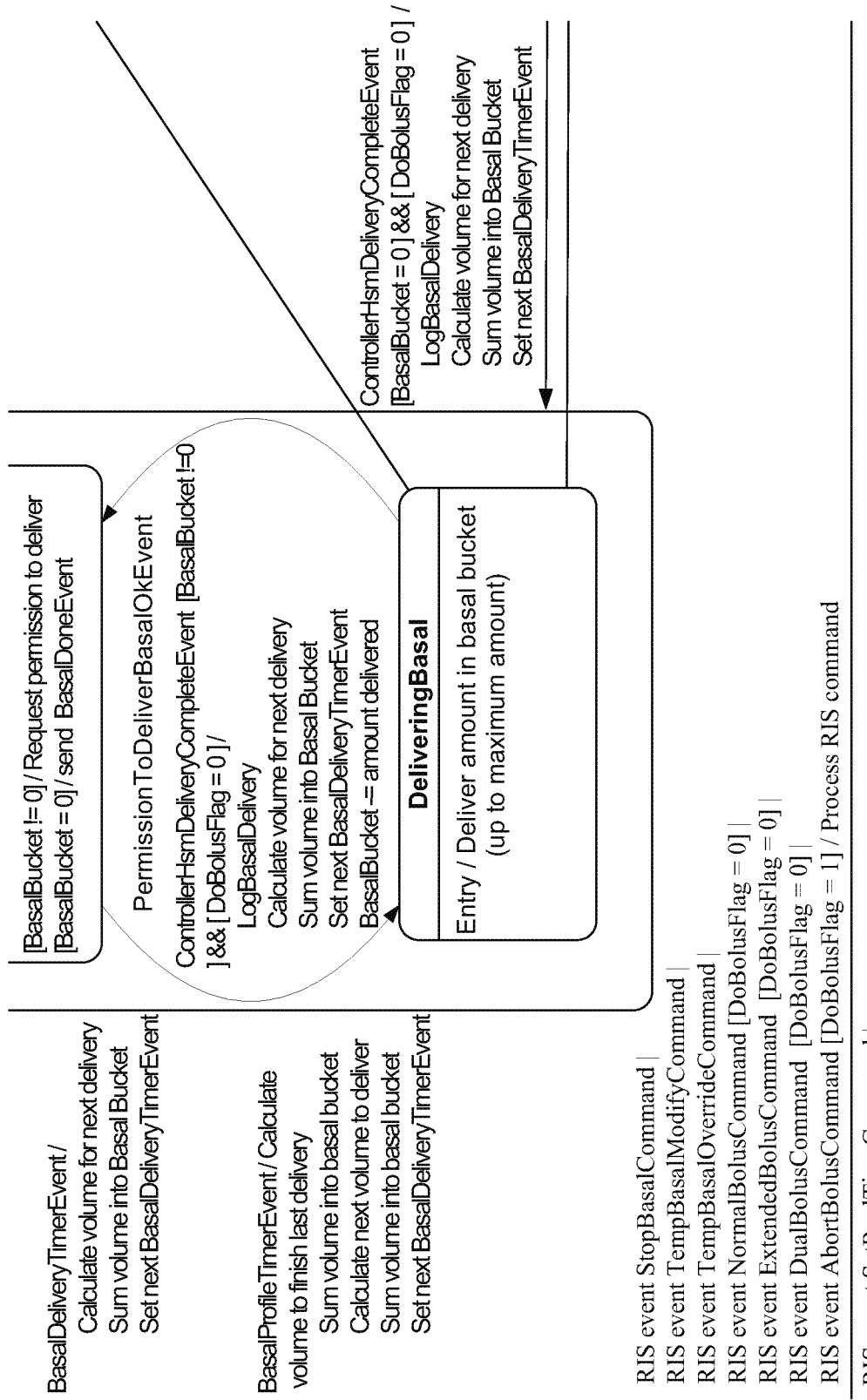
Figure 126J:
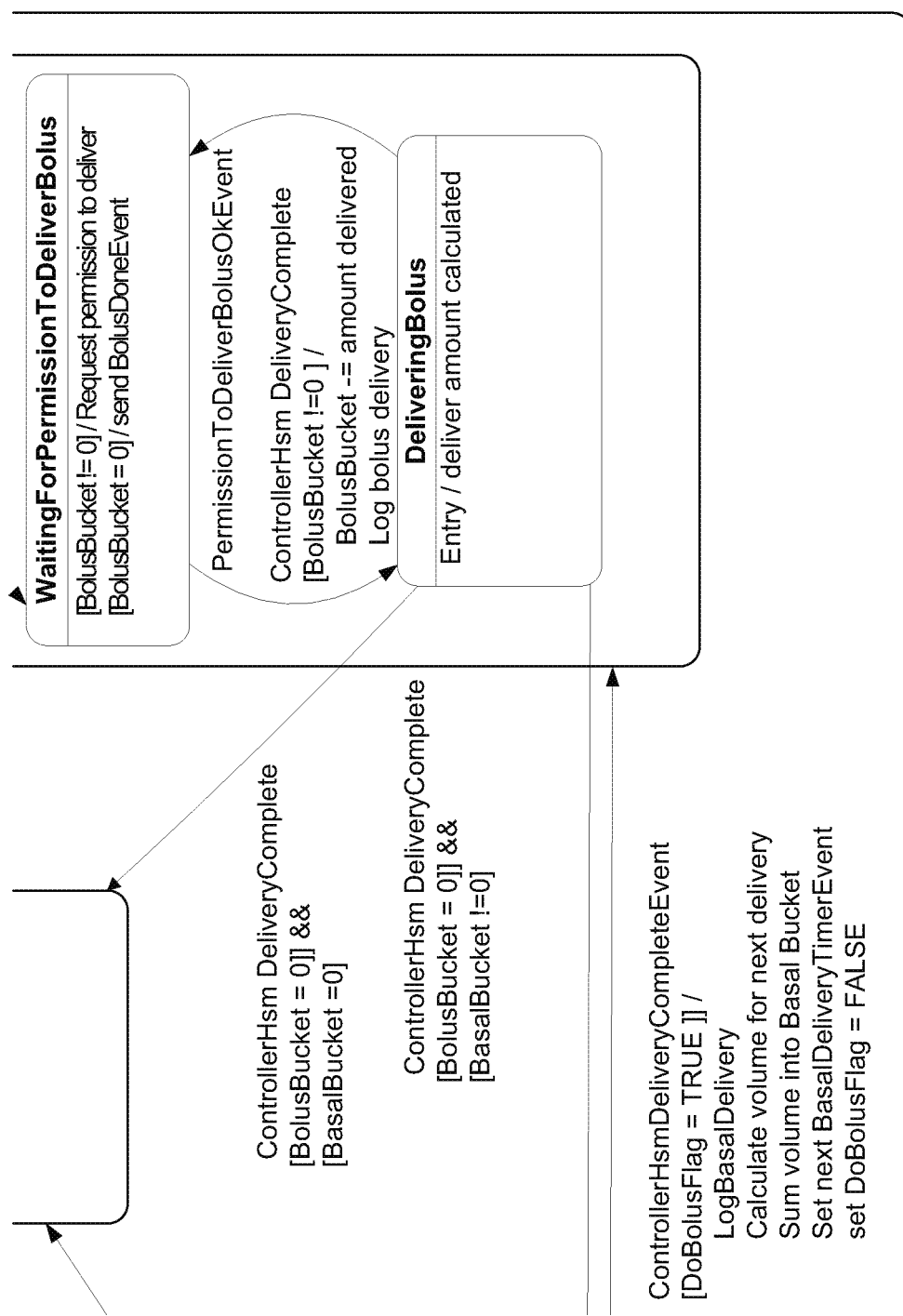
Figure 126K:
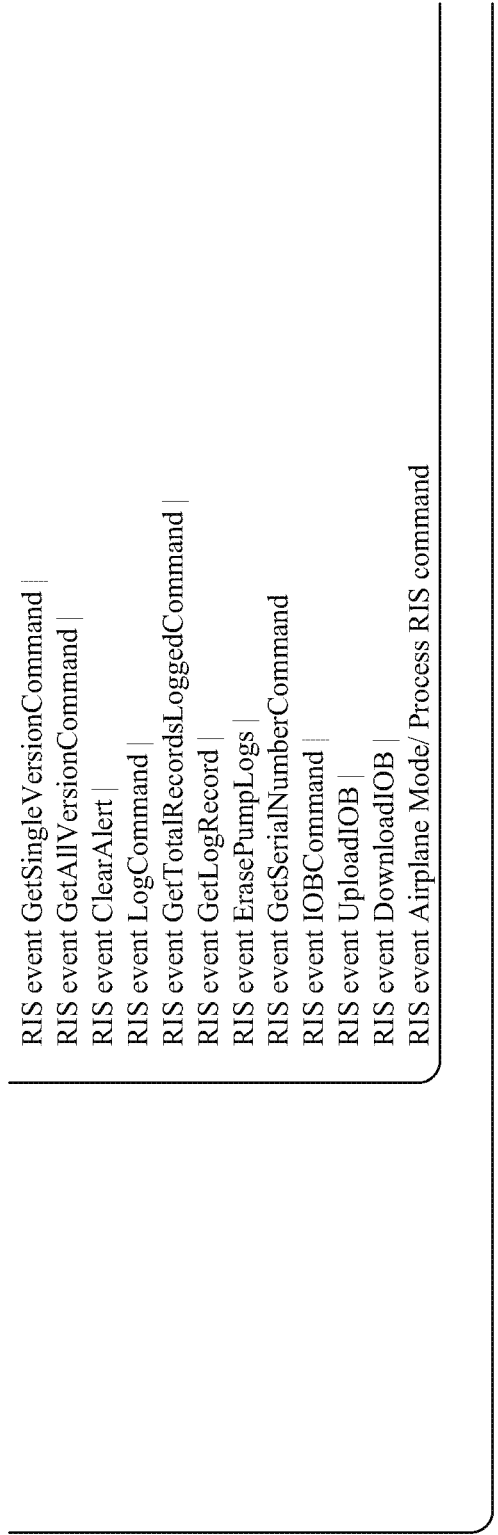
Figure 126M:
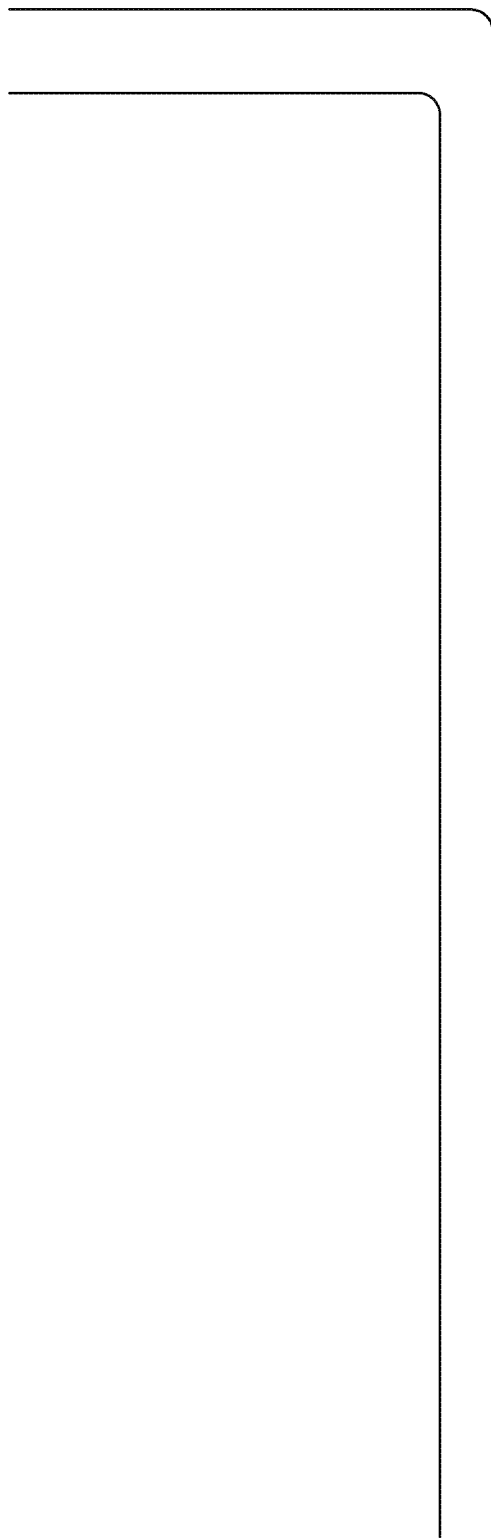

Referring also to FIG. 124 and for illustrative purposes, 0.05 unit dose 2202 is shown to include ten discrete infusion sub-events (e.g., infusion sub-events $2216_{1-10}$), wherein a 0.005 unit dose of the infusible fluid is infused during each of the ten discrete infusion sub-events. Additionally, 0.10 unit dose 2210 is shown to include ten discrete infusion sub-events (e.g., infusion sub-events $2218_{1-10}$), wherein a 0.01 unit dose of the infusible fluid is delivered during each of the ten discrete infusion sub-events. Further, one-time infusion event 2214 may include e.g., three-hundred-sixty one-time infusion sub-events (not shown), wherein a 0.1 unit dose of the infusible fluid is delivered during each of the three-hundred-sixty one-time infusion sub-events. The number of sub-events defined above and the quantity of the infusible fluid delivered during each sub-event is solely for illustrative purposes only and is not intended to be a limitation of this disclosure, as the number of sub-events and/or the quantity of the infusible fluid delivered during each sub-event may be increased or decreased depending upon e.g., the design criteria of infusion pump assembly 100, 100' 400, 500.

Before, after, or in between the above-described infusion sub-events, infusion pump assembly 100, 100' 400, 500 may confirm the proper operation of infusion pump assembly 100, 100' 400, 500 through the use of any of the above-described safety features (e.g., occlusion detection methodologies and/or failure detection methodologies).

In the exemplary embodiments, the infusion pump assembly may be wirelessly controlled by a remote control device. In the exemplary embodiments, a split ring resonator antenna may be used for wireless communication between the infusion pump assembly and the remote control device (or other remote device). The term "wirelessly controlled" refers to any device that may receive input, instructions, data, or other, wirelessly. Further, a wirelessly controlled insulin pump refers to any insulin pump that may wirelessly transmit and/or receive data from another device. Thus, for example, an insulin pump may both receive instructions via direct input by a user and may receive instructions wirelessly from a remote controller.

Figure 127:
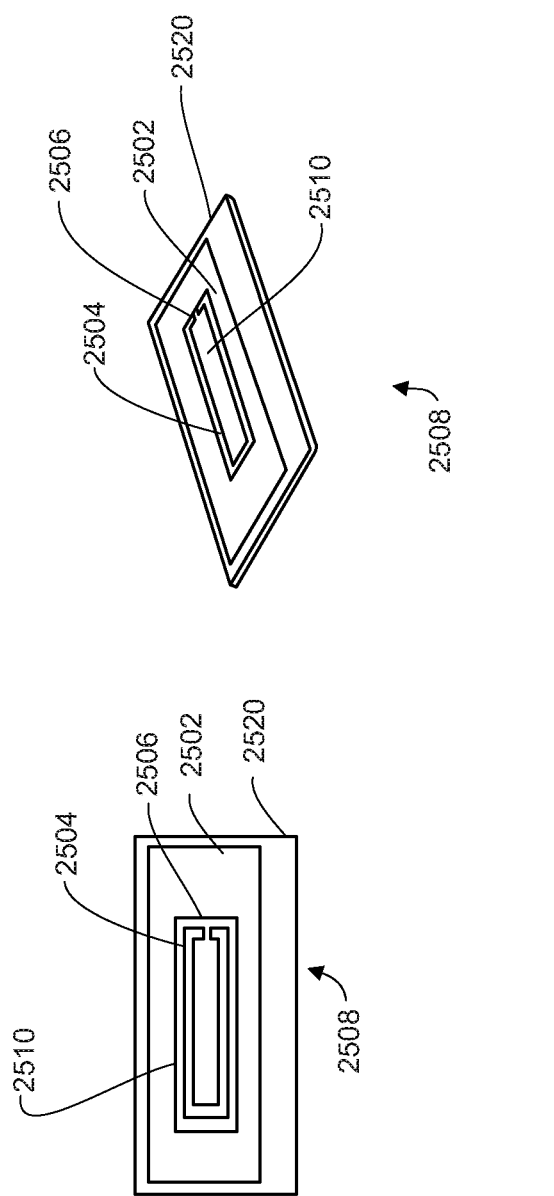
FIG. 127 is an exemplary diagram of a split ring resonator antenna.

Referring to FIG. 127, an exemplary embodiment of a split ring resonator antenna adapted for use in a wirelessly controlled medical device, and is used in the exemplary embodiment of the infusion pump assembly, includes at least one split ring resonator antenna (hereinafter "SRR antenna") 2508, a wearable electric circuit, such as a wirelessly controlled medical infusion apparatus (hereinafter "infusion apparatus") 2514, capable of powering the antenna, and a control unit 2522.

In various embodiments, a SRR antenna 2508 may reside on the surface of a non-conducting substrate base 2500, allowing a metallic layer (or layers) to resonate at a predetermined frequency. The substrate base 2500 may be composed of standard printed circuit board material such as Flame Retardant 2 (FR-2), FR-3, FR-4, FR-5, FR-6, G-10, CEM-1, CEM-2, CEM-3, CEM-4, CEM-5, Polyimide, Teflon, ceramics, or flexible Mylar. The metallic resonating bodies comprising a SRR antenna 2508 may be made of two rectangular metallic layers 2502, 2504, made of, for example, platinum, iridium, copper, nickel, stainless steel, silver or other conducting materials. In other various embodiments, a SRR antenna 2508 may contain only one metallic resonating body.

In the exemplary embodiment, a gold-plated copper outer layer 2502, surrounds, without physically contacting, a gold-plated copper inner ring 2504. That is, the inner ring 2504 resides in the cavity 2510 (or aperture) formed by the outer layer 2502. The inner ring 2504 may contain a gap, or split 2506, along its surface completely severing the material to form an incomplete ring shape. Both metallic resonating bodies 2502, 2504 may reside on the same planar surface of the substrate base 2500. In such a configuration, the outer layer 2502 may by driven via a transmission line 2512 coupled to the outer layer 2502, for example. Additionally, in various other embodiments, a transmission line 2512 may be coupled to the inner ring 2504.

Figure 132:
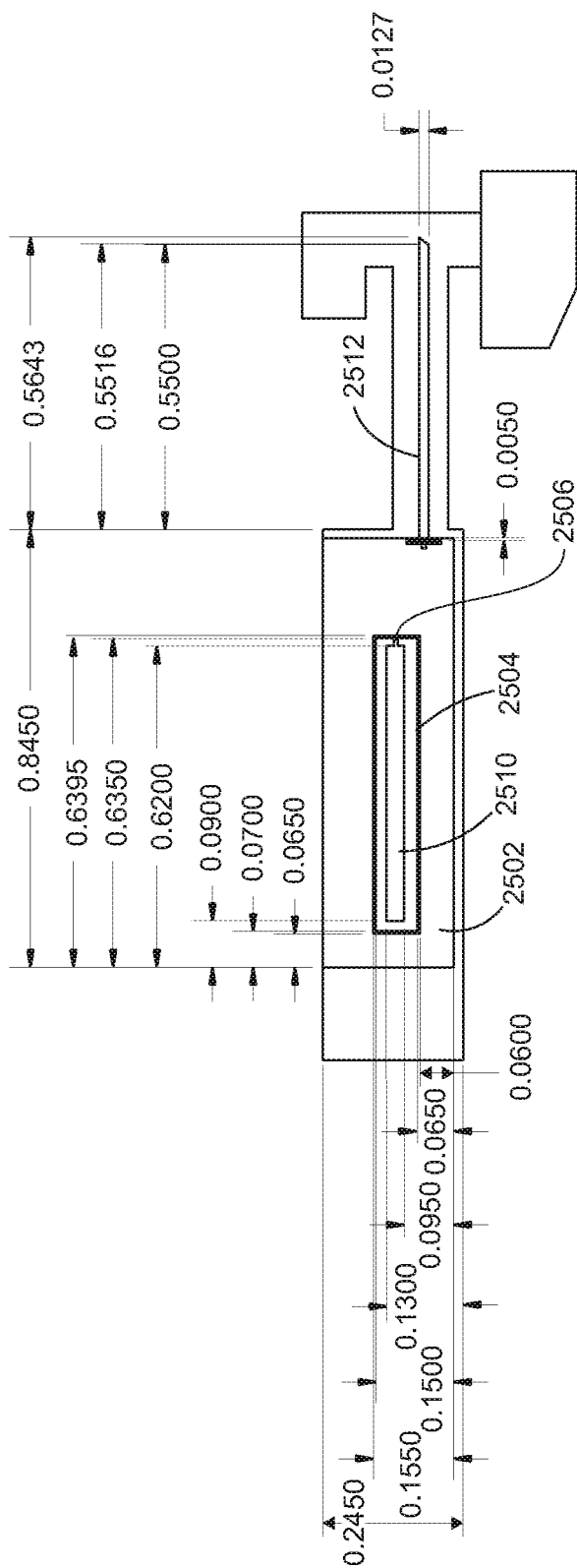
FIG. 132 is a diagram of the dimensions of the inner and outer portion of the exemplary embodiment.

Antenna design software, such as AWR Microwave Office, capable of simulating electromagnetic geometries, such as, antenna performance, may significantly decrease the time required to produce satisfactory dimensions compared to physically fabricating and testing antennas. Accordingly, with aid of such software, the SRR antenna 2508 may be designed such that the geometric dimensions of the resonant bodies 2502, 2504 facilitate an operational frequency of the 2.4 GHz ISM Band. FIG. 132 depicts the exemplary dimensions of the inner ring 2504 and outer layer 2502, and the positioning of the cavity 2510 in which the inner ring 2504 resides. The distance in between the outer layer 2502 and the inner ring 2504 is a constant 0.005 inches along the perimeter of the cavity 2510. However, in other embodiments, the distance between the outer layer and the inner ring may vary and in some embodiments, the operational frequency may vary.

In various embodiments, a SRR antenna 2508 may have dimensions such that it could be categorized as electrically small, that is, the greatest dimension of the antenna being far less than one wavelength at operational frequency.

In various other embodiments, a SRR antenna 2508 may be composed of one or more alternatively-shaped metallic outer layers, such as circular, pentagonal, octagonal, or hexagonal, surrounding one or more metallic inner layers of similar shape. Further, in various other embodiments, one or more metallic layers of a SRR antenna 2508 may contain gaps in the material, forming incomplete shapes.

Figure 130:
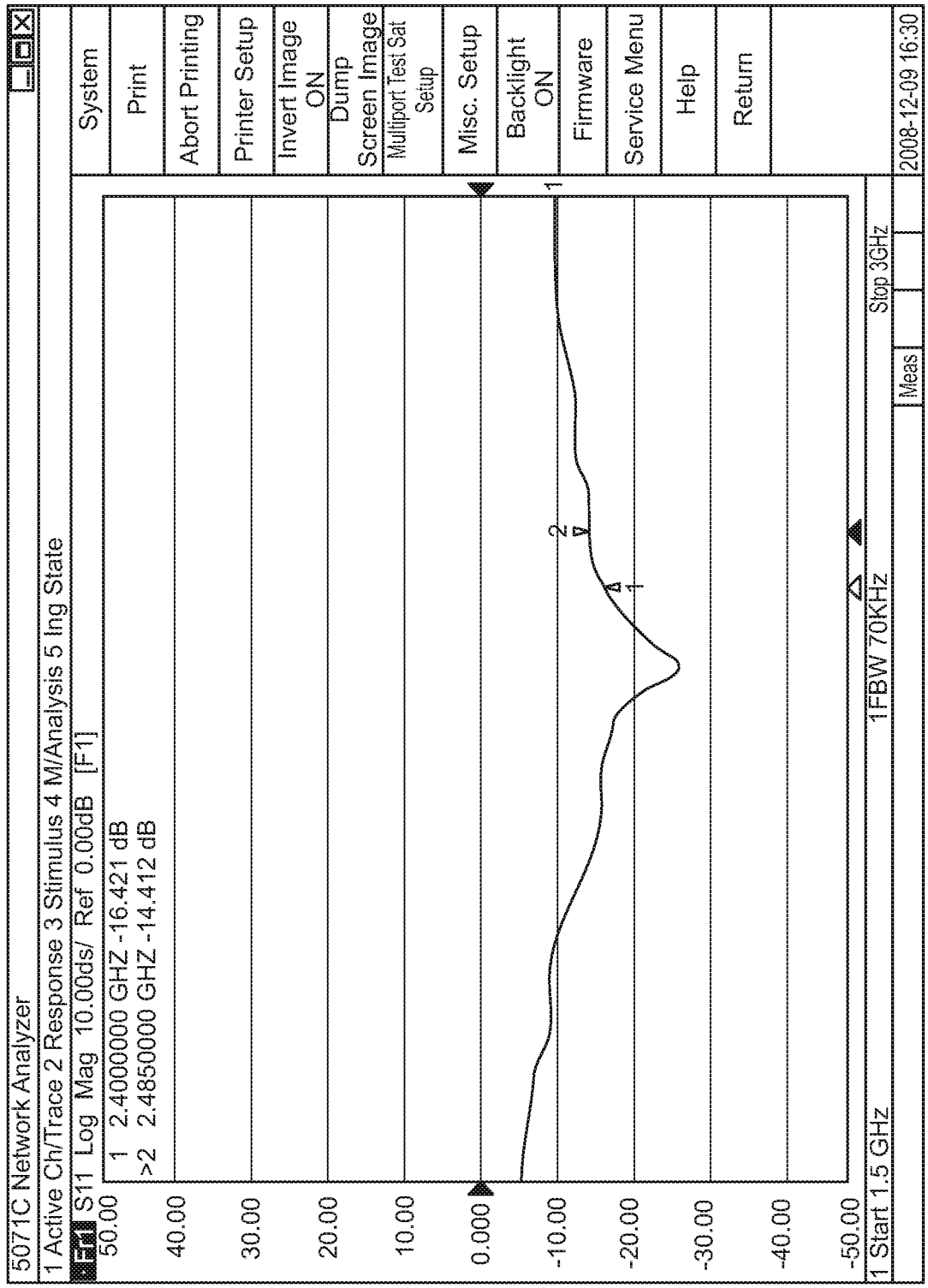
FIG. 130 is a graph of the return loss of a split ring resonator antenna prior to contact with human skin.
Figure 130A:
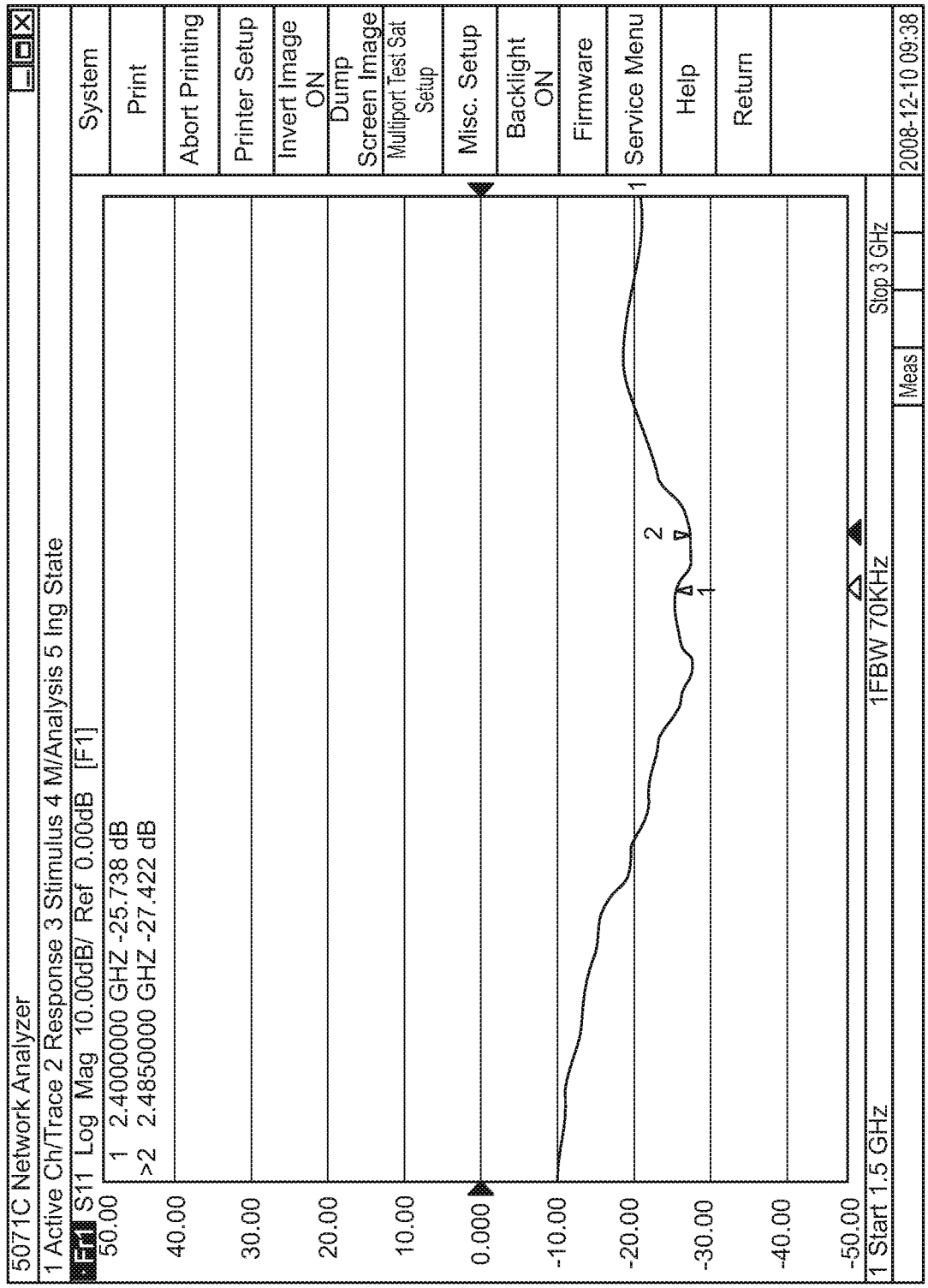
FIG. 130A is a graph of the return loss of a split ring resonator antenna during contact with human skin.

Referring to FIG. 130, a SRR antenna 2508 having the exemplary geometry exhibits acceptable return loss and frequency values when placed in contact with human skin. As shown in FIG. 130, focusing on the band of interest denoted by markers 1 and 2 on the graph, return loss prior to contact with human skin is near −15 dB while monitoring a frequency band centered around 2.44 GHz ISM Band. Return loss during contact with human skin, as shown in FIG. 130A, remains a suitable value near −25 dB at the same frequency, yielding approximately 97% transmission power.

Figure 133:
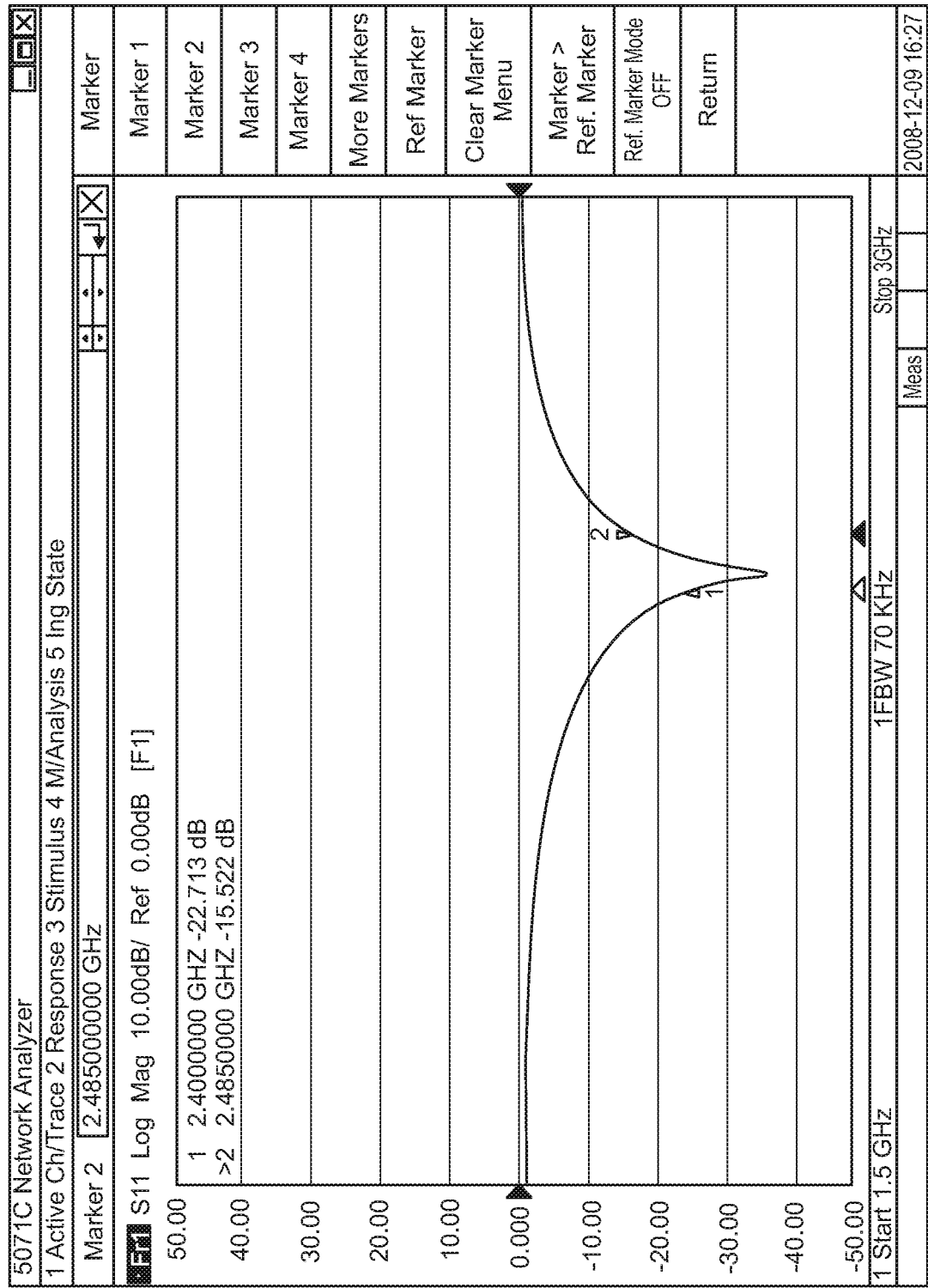
FIG. 133 is a graph of the return loss of a non-split ring resonator antenna prior to contact with human skin.
Figure 133A:
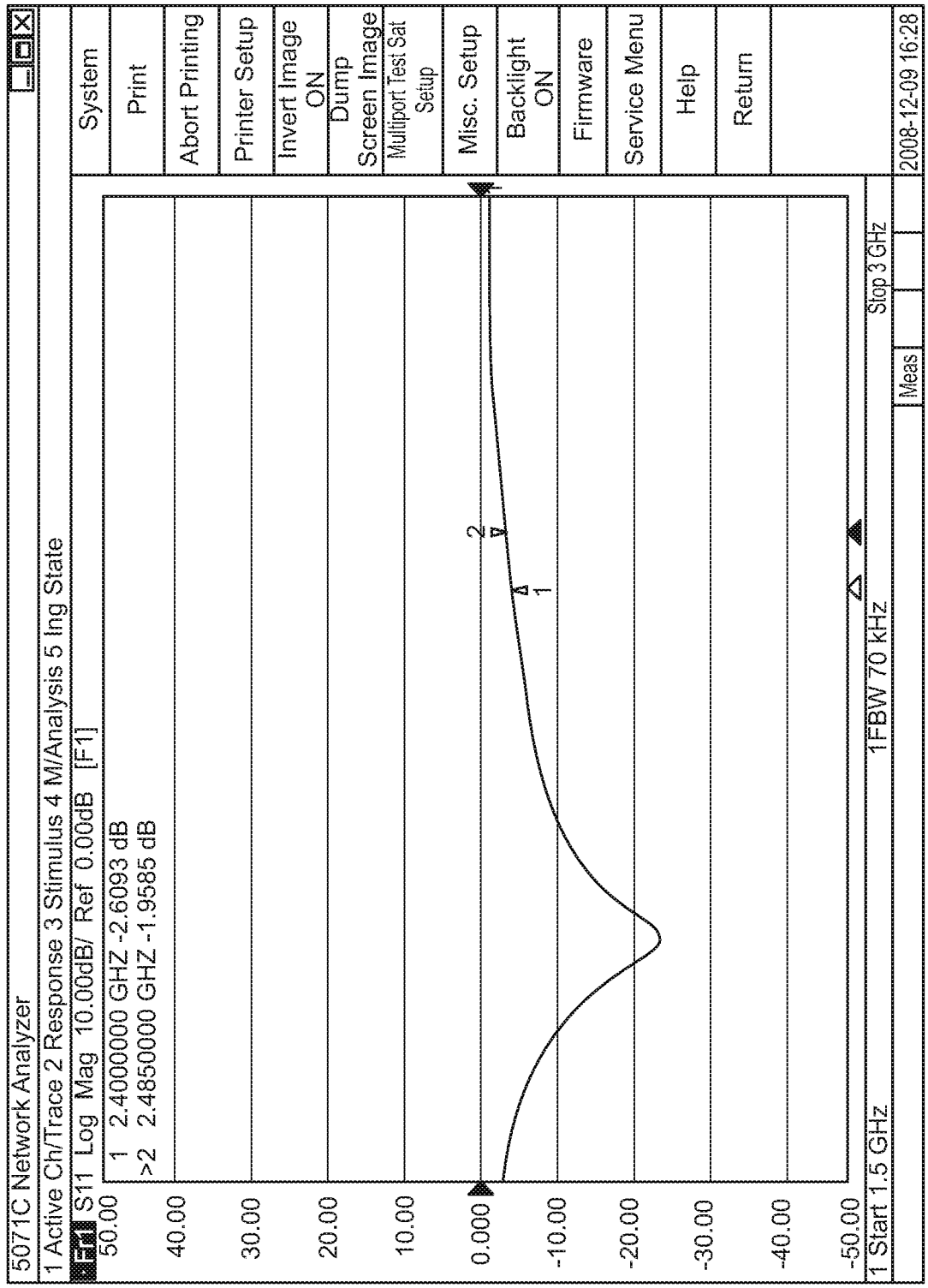
FIG. 133A is a graph of the return loss of a non-split ring resonator antenna during contact with human skin.

These results are favorable especially as compared with a non-split ring resonator antenna type, such as the Inverted-F. Return loss of an Inverted-F antenna may exhibit a difference when the antenna contacts human skin, resulting in a low percentage of power transmitted outward from the antenna. By way of example, as shown in FIG. 133, and again focusing on the band of interest denoted by markers 1 and 2 on the graph, return loss of an Inverted-F antenna prior to contact with human skin is near −25 dB at a frequency centered around 2.44 GHz. Return loss during contact with human skin is nearly −2 dB at the same frequency, yielding approximately 37% power transmission.

Integration with a Wireless Medical Device

Figure 128:
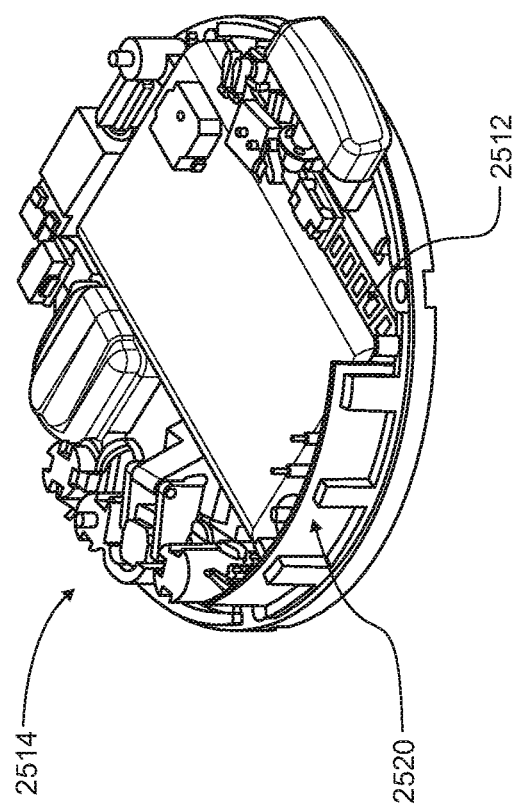
FIG. 128 is an exemplary diagram of a medical device configured to utilize a split ring resonator antenna.

In the exemplary embodiment, referring to FIG. 132 and FIG. 128, one application of a SRR antenna 2508 may be integration into a wearable infusion apparatus 2514 capable of delivering fluid medication to a user/patient 2524. In such an application, the safety of the user/patient is dependent on fluid operation between these electrical components, thus reliable wireless transmission to and from a control unit 2522 is of great importance.

Figure 131:
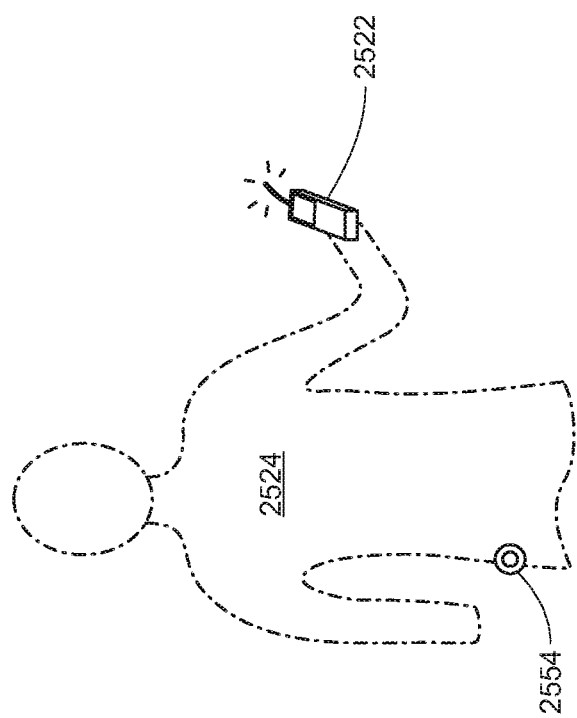
FIG. 131 is an exemplary diagram of a split ring resonator antenna integrated into a device which operates within close proximity to dielectric material.

An infusion apparatus 2514 may be worn directly on the human body. By way of example, such a device may be attached on or above the hip joint in direct contact with human skin, placing the SRR antenna 2508 at risk of unintended dielectric loading causing a frequency shift in electrical operation. However, in such an application, electrical characteristics of the SRR antenna 2508 which allow it to be less sensitive to nearby parasitic objects are beneficial in reducing or eliminating degradation to the performance. A controlling component, such as a control unit 2522 (generally shown in FIG. 131), may be paired with an infusion apparatus 2514, and may be designed to transmit and receive wireless signals to and from the infusion apparatus 2514 at a predetermined frequency, which, in the exemplary embodiment, is the 2.4 GHz Industrial Scientific and Medical Band ("ISM band"). In the exemplary embodiment, the control unit 2522 serves as the main user interface through which a patient or third party may manage insulin delivery. In other embodiments, infusion apparatus 2514 may utilize a SRR antenna 2508 to communicate with one or more control units 2522.

In various embodiments, a number of different wireless communication protocols may be used in conjunction with the SRR antenna 2508, as the protocol and data types to be transferred are independent of the electrical characteristics of the antenna. However, in the exemplary embodiment, a bi-directional master/slave means of communication organizes the data transfer through the SRR antenna 2508. The control unit 2522 may act as the master by periodically polling the infusion apparatus 2514, or slave, for information. In the exemplary embodiment, only when the slave is polled, the slave may send signals to the control unit 2522 only when the slave is polled. However, in other embodiments, the slave may send signals before being polled. Signals sent by way of this system may include, but are not limited to, control, alarm, status, patient treatment profile, treatment logs, channel selection and negotiation, handshaking, encryption, and check-sum. In some embodiments, transmission through the SRR antenna 2508 may also be halted during certain infusion operations as an added precaution against electrical disruption of administration of insulin to the patient.

In the exemplary embodiment, the SRR antenna 2508 may be coupled to electrical source circuitry via one or more pins 2516 on a transmission line 2512. In various other embodiments a transmission line may comprise a wire, pairs of wire, or other controlled impedance methods providing a signal path to the SRR antenna 2508. The transmission line 2512 may reside on the surface of the substrate base 2500 and may be composed of the same material as the SRR antenna 2508, such as gold-plated copper. Additionally, a ground plane may be attached to the surface of the substrate base opposite the transmission line 2512.

The electrical circuitry coupled to the SRR antenna 2508 may apply an RF signal to the end of the transmission line 2512 nearest the circuitry, creating an electromagnetic field throughout, and propagating from, the SRR antenna 2508. The electrical circuitry coupled to the SRR antenna 2508 facilitates resonance at a predetermined frequency, which, in the exemplary embodiment, is the 2.4 GHz ISM band. Preferably, transmission line 2512 and SRR antenna 2508 both have impedances of 50 Ohms to simplify circuit simulation and characterization. However, in other various embodiments, the transmission line and split ring resonator antenna may have other impendence values, or a different resonating frequency.

Figure 129:
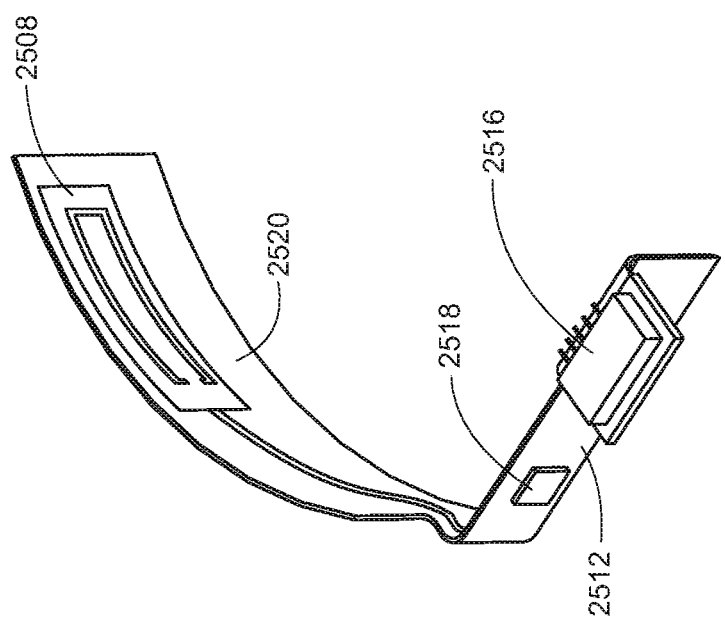
FIG. 129 is an exemplary diagram of a split ring resonator antenna and transmission line from a medical infusion device.

Referring to FIG. 129, a signal processing component(s) 2518, such as, a filter, amplifier, or switch, may be integrated into the transmission line 2512, or at some point between the signal source connection pins 2516 and the SRR antenna 2508. In the exemplary embodiment, the signal processing component 2518 is a band-pass filter to facilitate desired signal processing, such as, allowing only the exemplary frequency to be transmitted to the antenna, and rejecting frequencies outside that range. In the exemplary embodiment, a Combline band-pass filter 2518 may be included in the transmission line 2512 between the antenna and the signal source. However in other embodiments, any other signal processing device, for example, but not limited to, filters, amplifiers, or any other signal processing devices known in the art.

In various embodiments, a SRR antenna 2508 may be composed of metallic bodies capable of resonating on a flexible or rigid substrate. As shown in FIG. 128 and FIG. 129, the exemplary embodiment incorporates a curved SRR antenna on a flexible Polyimide substrate 2520. Polyimide may be the exemplary material because it tends to be more flexible than alternative substrates. This configuration may allow for simplified integration into circular-shaped devices (such as a wirelessly controlled medical infusion apparatus 2514), devices with irregular-shaped external housing, or devices in which saving space is paramount.

In various embodiments, both control unit 2522 and base unit 2514 may incorporate a split SRR antenna 2508. This configuration may prove beneficial where the control unit is meant to be handheld, in close proximity to human skin, or is likely to be in close proximity to a varying number of materials with varying dielectric constants.

In various other embodiments, a SRR antenna 2508 may be integrated into a human or animal limb replacement. As prosthetic limbs are becoming more sophisticated the electrical systems developed to control and simulate muscle movements require much more wiring and data transfer among subsystems. Wireless data transfer within a prosthetic limb may reduce weight through reduced physical wiring, conserve space, and allow greater freedom of movement. However, common antennas in such a system may be susceptible to dielectric loading. Similar to the previously mentioned benefits of integrating a SRR antenna 2508 into a wirelessly controlled medical infusion apparatus, a prosthetic limb, such as a robotic arm, may also come into contact with human skin or other dielectric materials and benefit from the reduction of electrical disturbances associated with such an antenna. In other various embodiments, the SRR antenna 2508 may be integrated into any device comprised of the electrical components capable of powering and transmitting/receiving data to an antenna and susceptible to electrical disturbances associated with proximity to dielectric materials.

In various embodiments, a SRR antenna 2508 may be integrated into a configuration of medical components in which one or more implantable medical devices, operating within the human body, communicate wirelessly to a handheld, body-mounted, or remote control unit. In certain embodiments, both body-mounted and in-body wireless devices may utilize a SRR antenna 2508 for wireless communication. Additionally, one or more of the components utilizing a SRR antenna 2508 may be completely surrounded by human skin, tissue or other dielectric material. By way of example, such a configuration may be used in conjunction with a heart monitoring/control system where stability and consistency of wireless data transmission are of fundamental concern.

In various other embodiments, a SRR antenna 2508 may be integrated into the embodiments of the infusion pump assembly. In some embodiments, the SRR antenna 2508 may be integrated into a configuration of medical components in which one or more electrical sensors positioned on, or attached to, the human body wirelessly communicate to a remote transceiving unit. By way of example, a plurality of electrodes positioned on the body may be coupled to a wireless unit employing a SRR antenna 2508 for wireless transmission to a remotely located electrocardiogram machine. By way of further example, a wireless temperature sensor in contact with human skin may employ SRR antenna 2508 for wireless communication to a controller unit for temperature regulation of the room in which the sensor resides.

System for Verification of Volume and Pumping

Infusion pump therapy includes volume and time specifications. The amount of fluid dispensed together with the dispense timing are two critical factors of infusion pump therapy. As discussed in detail below, the infusion pump apparatus and systems shown and described herein provide for a method of dispensing fluid together with a device, system and method for measuring the amount of fluid dispensed. However, in a circumstance where the calibration and precision of the measurement device calibration is critical, there are advantages to determining any compromise in the precision of the measurement device as soon as possible. Thus, there are advantages to off-board verification of volume and pumping.

As shown in the figures, the disposable assembly includes a reservoir for holding the infusible fluid for pumping. There are various methods and devices for filling the reservoir with infusible fluid, many embodiments are discussed above. An additional embodiment and system for both verifying the volume of fluid filled in the reservoir and verifying the integrity of the pumping system is discussed below.

In one embodiment, a weight scale is used to determine the volume of fluid filled into the disposable and may also be used for verification by comparing the before-use volume with the after-use volume of the disposable. In some embodiments, this is accomplished by weighing the disposable before and after reservoir filling is complete. In some embodiments, the weight scale may be reset to zero (i.e., tared) to the disposable prior to filling. In other embodiments, a weight may be taken before the fill and afterwards. In some embodiments, a processor may calculate the weight of the fluid filled and correlate the weight to a volume of fluid. In some embodiments, the display on the scale may automatically display the volume of fluid that has been filled in the reservoir. The method of filling may be any discussed above, or an automatic fill, as discussed below. In addition, in some embodiment, a pre-filled reservoir may be used and thus, filling is not necessary, rather, the weight would be taken prior to loading the reservoir and after reservoir loading.

An exact calculation of the volume of fluid in a reservoir may be used to verify the measurement system of the pumping device. For example, following the use of the disposable, where the system either stores, or, receives via an input the before-use weight at fill of the disposable, the system, taking the after-use weight, may determine the volume of fluid difference between before-use and after-use. This information may be used as a check to the pumping system to verify the amount of fluid pumped from the given reservoir.

Additionally, the exact volume of fluid filled may be entered into the pumping system which may be used by the system to warn the user of low-volume reservoir or present to the user an accurate volume of fluid remaining in the reservoir at any given time.

Figure 205:
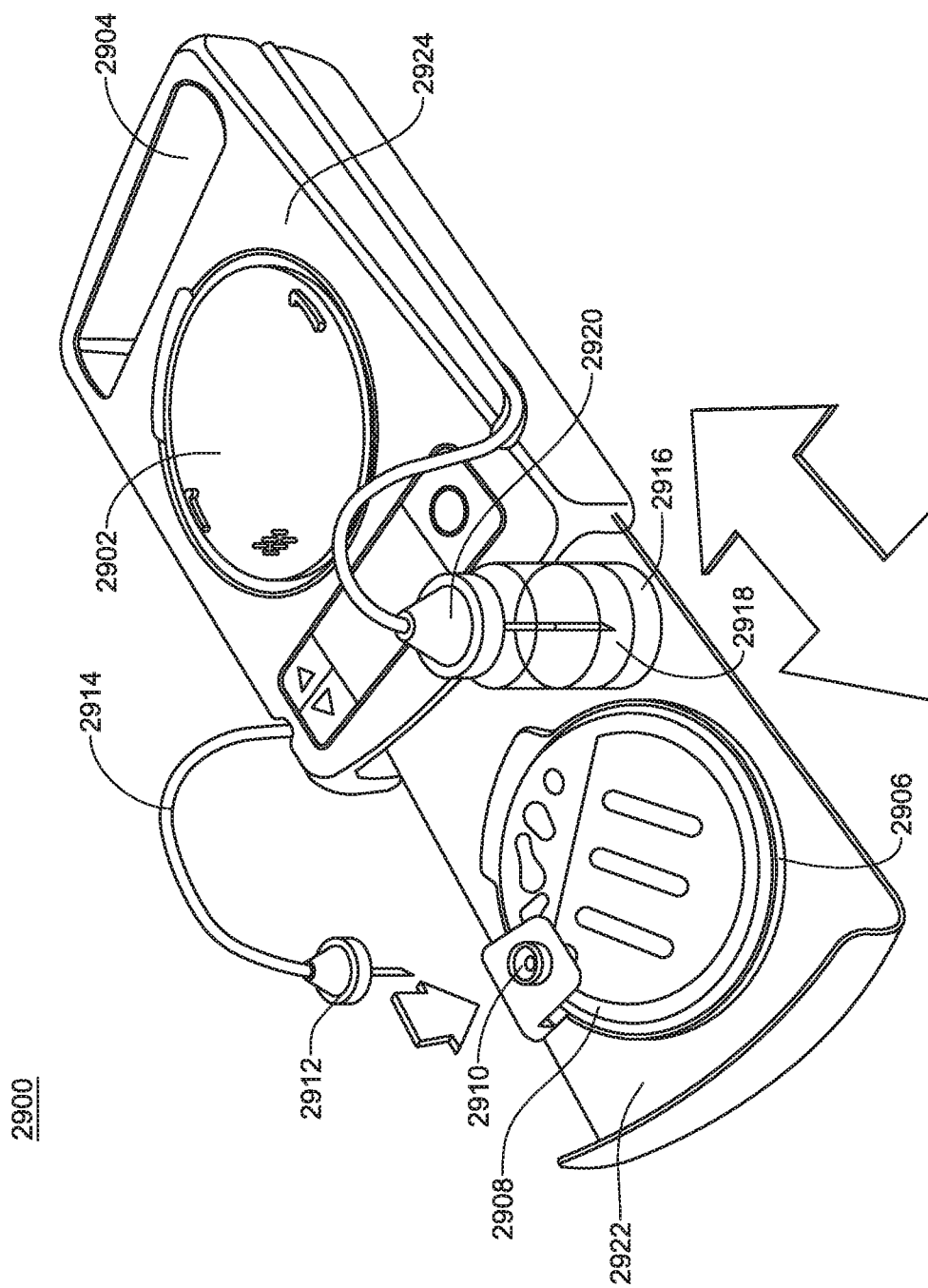

Referring now to FIG. 205, one embodiment of the system includes a combination charger, disposable fill and integrity verification station 2900. The charger station 2900 includes a charging section 2902 for a reusable assembly, a charging section 2904 for a remote control device, and a weight scale 2906. The weight scale 2906 in some embodiments may be sized to accommodate a disposable assembly 2908. In the exemplary embodiment, the station also includes a fill adapter septum 2910 that accepts a filling cap 2912 (including a filling needle for piercing the septum 2910). In some embodiments, the filling needle is attached to a fluid line 2914 which may be a flexible tubing of a predetermined length suitable for reaching around the station 2900 to, in some embodiments, a fluid vial or fluid container holder 2916. The container holder 2916 may be sized to accommodate a fluid vial 2918. In addition to the features shown in FIG. 205, in some embodiments, the station 2900 may include a pump for pumping the fluid from the container 2918 into the disposable assembly 2908. In some embodiments, the pump may be a peristaltic pump. However, in other embodiments, the pump may be a diaphragm pump or any of pump known in the art. The pump may be used to automatically fill the reservoir in the disposable 2908. In some embodiment, a user attaches the container cap 2920 (including a needle) to the fluid container 2918 as well as the filling cap 2912 to the fill adapter septum 2910. The pump evacuates air from the disposable and uses it to pressurize the vial. The pump then pulls fluid from the container 2918 and fills the disposable 2908 reservoir. Also, whilst filling the reservoir, the system may provide enough positive pressure to additionally prime the fluid path and the cannula of the disposable.

In some embodiments, the station 2900 may also include a display for communication to a user of the volume of fluid currently in the disposable 2908. This may be used to fill the reservoir to a desired volume. Additionally, in some embodiments, the station 2900 may wirelessly communicate to a remote controller (not shown) or other device, the volume of fluid filled into the reservoir. In some embodiments, when a user is finished with a disposable, the user will weight the after-use disposable. The system will communicate with the pumping system and correlating the data, an integrity verification test may be performed. Where a system integrity error is determined, the system may alarm the user appropriately.

In other embodiments, a station may include a weight scale and any one or more of the various other components of the station 2900 as discussed above. Still referring to FIG. 205, the system may be portable and the scale portion 2922 may slide into the charger portion 2924, protecting the integrity of the scale as well as providing convenient portability.

Thus, this system has many benefits, including, but not limited to, off-board integrity verification of volume sensing at each disposable change; accurate determination of volume at fill to both accurately track current reservoir volume and thus alarm user when volume is low; method for avoiding under-desired-volume filling or over-desired-volume filling; method of filling a disposable with fluid while also pre-priming (or purging the air) the disposable fluid line; and verification of volume regardless of disposable manufacture variability.

Removable Filling Aid with Sliding Filling Needle Assembly

Referring now also to FIGS. 214-220F, another embodiment of a fill adapter 4000 is shown. The fill adapter 4000 may be configured to be coupled to an embodiment of the disposable housing assembly, including but not limited to, the disposable housing assembly 804, shown and described above, or the disposable housing assembly 4002, shown in FIG. 216. The embodiments of the disposable housing assembly 4002 shown in FIG. 217 are similar to disposable housing assembly 804. However, for description purposes, disposable housing assembly 4002 will be referred to with respect to fill aid adapter 4000, however, in various other embodiments, the filling aid adapter 4000 may be coupled to any embodiment of the disposable housing assembly. Upon coupling the fill adapter 4000 to the disposable housing assembly 4002, the reservoir 908 may be filled using a filling syringe 4062. Any syringe known in the art may be used, however, in the exemplary embodiments, any syringe having a size and shape to be accommodated by the filling aid

4004 may be used, including, but not limited to, a 3 cc/mL TERUMO SYRINGE without needle, made by TERUMO Europe, Belgium, together with a Becton Dickinson 26G1/2 PRECISIONGLIDE Needle, made by Becton Dickinson & Co., Franklin Lakes, N.J., U.S.A., however, in various embodiments, the filling syringe 4062 may be a syringe made by another manufacture and/or at a larger or smaller size. Fill adapter 4000 may include locking tabs 4006, 4008, 4010, 4012 that may be configured to engage radial tabs 3014, 3016, 3018 (shown in FIG. 206B) of disposable housing assembly 4002 in a manner generally similar to tabs 942, 944, 946, 948 of locking ring assembly 806. Accordingly, fill adapter 4000 may be releasably engaged with disposable housing assembly 4002 by aligning fill adapter 4000 with disposable housing assembly 4002 and rotating fill adapter 4000 and disposable housing assembly 4002 relative to one another to releasably engage locking tabs 4006, 4008, 4010, 4012 with radial tabs 3014, 3016, 3018 (and another, not shown).

The embodiment of the disposable housing assembly 4002 (and as shown in FIG. 206B) include an additional radial tab that is hidden in the view shown. In various embodiments, the number of locking tabs and radial tabs may vary, for example, in various embodiments, the number of locking tabs or radial tabs may be greater than or less than the number shown in the exemplary embodiments.

Also referring to FIGS. 208-208B, the process for engaging the fill adapter 4000 with the disposable housing assembly 4002 is similar to the process shown with respect to the embodiment of the fill adapter 3000 and the disposable housing assembly 3002. Thus, although reference is made to fill adapter 3000 and disposable housing assembly 3002, in various embodiments, the embodiment of the fill adapter 4000 shown in, for example, FIGS. 214-217 may be attached to the disposable housing assembly 4002 following a process similar to that described below with respect to fill adapter 3000 and disposable housing assembly 3002. For example, in some embodiments, and referring again also to FIG. 208A, the fill adapter 3000 is attached to the disposable housing assembly 3002 and in the non-locked position. In some embodiments of the various embodiments of the disposable housing assemblies described herein, an indication of "lock" 3020 and "unlock" 3022 may be included on the disposable housing assembly, for example, as shown in the embodiment of the disposable housing assembly 3002, for example, to indicate the direction of rotation 3024 to either "lock" 3020 or "unlock" 3022 the fill adapter 3000, for example, and/or the locking ring assembly 806, with respect to the disposable housing assembly 3002. In various embodiments, the indications 3020, 3022, 3024 may vary. Referring now to FIG. 208B, the fill adapter 3000, having rotated with respect to the disposable housing assembly 3002 in the direction shown in FIG. 208A, the direction of rotation 3024 also indicated on the disposable housing assembly 3002, which is clockwise in the exemplary embodiment, the fill adapter 3000 is in the locked position with respect to the disposable housing assembly 3002. In the exemplary embodiment, the locked position (see FIG. 208B) is a position in which the fill adapter 3000 is coupled and/or engaged with the disposable housing assembly 3002 such that the fill adapter 3000 may not easily rotate with respect to the disposable housing assembly 3002. In the exemplary embodiment, the fill adapter 3000 may rotate counterclockwise from the locked position to the unlocked position following the exertion of force onto the locking tab actuator 3026 which releases the locking tab 3030 from the disposable housing assembly 3002. However, in some embodiments, as shown in FIGS. 214-217, the fill adapter 4000 may rotate counterclockwise from the locked position to the unlocked position following the exertion of force onto the locking tab actuator 4026 which releases the locking tab 4030 from the disposable housing assembly 4002.

In some embodiments, filling aid base 4046 is located opposite the locking tab actuator 4026 such that a user may release the locking tab 4030 using an ergonomically efficient configuration, e.g., placing the thumb on the filling aid base 4026 and the forefinger on the locking tab actuator 4025 to efficiently relay force on the locking tab actuator 4026 and release the locking tab 4030. In some embodiments, the fill adapter 4000 includes a rotation direction indication (as shown in FIGS. 208A-208B as 3028) to indicate the direction of rotation to unlock the fill adapter 4000 from the disposable housing assembly 4002. In some embodiments of the infusion pump apparatus and system described herein, in practice, the fill adapter 4000 may be attached to the disposable housing assembly 4002 in the locked position. A user may fill the reservoir (which may be the embodiment as shown in FIG. 49B, 908) of the disposable housing assembly 4002 using the fill adapter 4000. Following, the user may unlock the fill adapter 4000 by exerting force onto the locking tab actuator 4026, which releases the locking tab 4030, and rotating the fill adapter 4000 counterclockwise as indicated by the rotation direction indication 4028 on the fill adapter 4000 until the fill adapter 4000 is in the unlocked position, as depicted, with respect to another embodiment of the fill adapter 3000 and the disposable housing assembly 3002, in FIG. 208A. However, in various embodiments, the locking tab actuator may be as shown in FIG. 208A, for example, or as shown in FIG. 215, for example, or may take on various shapes and configurations that impart a similar functionality.

In various embodiments, the locking tab 4030, in the locked position, prevents counterclockwise rotation of the fill adapter 4000 with respect to the disposable housing assembly 4002. In the locked position, the locking tab 4030 is located between two radial tabs, (for example, as 3018, similar to the embodiment shown in FIG. 206B with respect to the disposable housing assembly 3002). Further, fill adapter 4000 locking tabs 4006, 4008, 4010, 4012 and disposable housing assembly radial tabs (shown in FIG. 206B as 3014, 3016, 3018 and another, not shown) of disposable housing assembly 4002 together limit the rotation of the fill adapter 4000 with respect to the disposable housing assembly 4002. Thus, the locking tabs 4006, 4008, 4010, 4012 and the radial tabs on the disposable housing assembly 4002 limit the rotation of the fill adapter 4000 with respect to the disposable housing assembly 4002 such that in the locked position, the fill adapter 4000 is aligned and releasably engaged in the desired coupling configuration with the disposable housing assembly 4002 such that the reservoir 908 may be filled. The locking tab 4030 prevents counterclockwise rotation, or unlocking, of the coupling between the fill adapter 4000 and the disposable housing assembly 4002, which may assist the user and ensure proper alignment during reservoir 908 fill.

Fill adapter 4000 may further include filling aid 4004, which may include a needle housing 4038 which may be configured to guide a filling needle 4014 held by a filling needle cradle 4016 to a septum of disposable housing assembly 4002 (which, in some embodiments, may be one as described above, for example, with respect to FIG. 3) to allow the reservoir 908 of the disposable housing assembly 4002 to be filled by the syringe. In some embodiments, the needle housing 4038 is configured to attach to the filling aid base 4046.

In some embodiments, the filling needle 4014 may be attached and/or held by a connector 4060 which may be configured to attach to the needle end 4064 of a filling syringe 4062. In various embodiments, the attachment may be a rotational attachment (e.g., twist to connect), a snap fit attachment (e.g. press parts to connect), a press fit attachment or other luer-type attachment. In some embodiments, the connector 4060 may be configured to be removably attached to the filling syringe 4062. In some embodiments, the connector may be configured to be attached to the filling syringe in a non-removable fashion.

In some embodiments, the needle housing may include end tabs 4070, 4072, 4074, 4076 which may accommodate a vial of fluid, e.g., therapeutic fluid, e.g., insulin, such that once the filling syringe 4062 needle end 4064 is attached to the connector 4060, the needle housing 4038 may clip onto a vial having a septum (for example, as shown in FIGS. 199A-199H in 2716) and the filling needle 4014 may penetrate the septum and the fluid may flow from the vial to the filling syringe 4062 by way of the filling needle 4014. Once a desired volume of fluid flows from the vial to the filling syringe 4062, the vial may be removed from the needle housing, e.g., by exerting opposing force onto the filling syringe 4062 so as to disconnect the end tabs 4070, 4072, 4074, 4076 from the vial.

These embodiments may be advantageous, beneficial and/or desirable for many reasons including that the filling needle 4014 remains inside the needle housing 4038 while the filling syringe 4062 is being filled by the fluid from the vial. Therefore, the likelihood of unintentional needle pricks and/or contamination is minimized and/or reduced. Also, in these embodiments, there is no "cover" to be removed from the filling needle 4014, therefore, the likelihood of unintentional needle pricks and/or contamination is minimized and/or reduced before and after the filling needle 4014 is inserted into the vial. However, in some embodiments, a removable cover may be included on the filling needle.

Thus, in various embodiments, the filling needle cradle 4016 remains in the starting position while the filling aid 4004 is attached to a vial.

Although the embodiments are described above with respect to a "vial" in some embodiments, the filling aid 4004 may be used in conjunction with any source of fluid, which may include, but is not limited to, a bag of fluid.

In various embodiments, once the filling syringe 4062 is removed from the vial, the filling syringe 4062, still attached to the filling aid 4004 may then be connected to the filling aid base 4046. In some embodiments, connection of the filling aid 4004 to the filling aid base 4046 may be made by sliding the filling aid 4004 over the filling aid base 4046. Thus, in various embodiments, the filling aid base 4046 may include a smaller diameter than the filling aid 4004 such that the filling aid base 4046 may be received by the filling aid 4004. In some embodiments, the connection between the filling aid 4004 and the filling aid base 4046 may include the filling aid 4004 sliding onto to the filling aid base 4046 and then the filling aid 4004 being rotated with respect to the filling aid base 4046. In some embodiments, the rotation may attach or lock the filling aid 4004 to the filling aid base 4046 such that the filling aid 4004 may not be removed from the filling aid base 4046 unless the filling aid 4004 is rotated back. Therefore, in some embodiments, the filling aid base 4046 may remain connected the filling aid 4004 while the reservoir is being filled, but may be removed from the each other once the filling is completed. Thus, in some embodiments, the filling aid 4004 may maintain a locked position with respect to the filling aid base 4046 may include an unlocked position with respect to the filling aid base 4046.

In various embodiments, the ability to lock the filling aid 4004 to the filling aid base 4046 such that the connection is maintained may be accomplished by using various mechanisms in various embodiments. For example, in the embodiments shown herein, the connection may be maintained using a tongue and groove-type connection. For example, referring again to FIG. 214, the needle housing 4038 may include one or more tongue features 4086 inside the end of the needle housing 4038 that attaches to the filling aid base 4046. The filling aid base 4046 may include one or more groove features 4088 that receive the tongue feature 4086 such that the tongue feature 4086, once rotated with respect to the groove feature 4088 becomes "locked into" the groove feature 4088. Although one embodiment of features for connecting or "locking" the filling aid base 4046 to the filling aid 4004 is shown, in various embodiments, other mechanisms may be used. In various embodiments, one of more features may be used. In some embodiments of the embodiment shown, there may be two tongue features on the filling aid and two accommodating groove features on the filling aid base. In some embodiments, a particular orientation of the tongue feature with respect to the groove feature may be required for the filling aid 4004 to connect over the filling aid base 4046. However, in various embodiments, a particular orientation for attachment may not be required.

In some embodiments, when the filling aid 4004 is connected to the filling aid base 4046, the filling needle cradle 4016 may be in a starting position. The starting position means that the filling needle 4014 remains fully inside the filling needle cradle 4016 and therefore, although the filling aid 4004 is attached to the filling needle base 4046, the filling needle 4014 has not pierced the septum of the reservoir. Referring also to FIG. 219, the disposable is shown connected to the fill adapter 4000 and the filling aid 4000 is connected to the filling aid base. The filling needle cradle 4016 is in the starting position.

In some embodiments, the filling needle cradle 4016 includes flexible tabs 4066, 4068 which are accommodated in corresponding windows 4090, 4092 on the filling aid 4004 needle housing 4038. However, in some embodiments, more than two or less than two flexible tabs and/or windows may be included. In various embodiments, when the filling needle cradle 4016 is in the starting position, the flexible tabs 4066, 4068 may be located within the windows 4090, 4092 and the relationship between the flexible tabs 4066, 4068 and the windows 4090, 4092 are such that the flexible tabs 4066, 4068 anchor the filling needle cradle 4016 in the starting position by their relationship to the windows 4090, 4092.

In various embodiments, to advance the filling needle 4014 towards the septum, the filling needle cradle 4016 flexible tabs 4066, 4068 need to be disengaged from the windows 4090, 4092. In some embodiments, this may occur automatically once the filling aid 4004 is locked onto the filling aid base 4046. However, in various embodiments, this may be accomplished manually, where a user presses on each of the flexible tabs 4066, 4068, for example, using the thumb and forefinger, and exerts force on the filling syringe 4062. This, in various embodiments, advances the filling needle cradle 4016 towards the septum such that the filling needle cradle 4016 is in the filling position. In this position, the filling needle 4014 pierces the septum.

Referring now also to FIG. 218, in various embodiments, the filling needle cradle and the filling aid base 4046 may include features that, when in contact with each other (i.e., when the filling needle cradle 4016 is in the filling position), prevent addition rotation of the filling aid 4004 with respect to the filling aid base 4046. Thus, as discussed above, the needle housing 4038 of the filling aid 4004 may be rotated, with respect to the filling needle base 4046 so as to lock the two parts together. In addition, in some embodiments, once the filling needle cradle 4016 is advanced to the filling position, features on the filling needle cradle and the filling aid base may lock prevent rotation of the filling aid 4004 with respect to the filling aid base 4046. In some embodiments, locking feature grooves 4082, 4084 on the filling needle cradle 4016 may accommodate locking feature posts 4078, 4080 in the filling aid base 4046. Although in the embodiments shown, there are two locking feature grooves 4082, 4084 on the filling needle cradle 4016 and two locking feature posts 4078, 4080 in the filling aid base 4046, in various embodiments, there may be one or more. In some embodiments, there may be more than two, for example, or less than two. In various embodiments, the mechanism for locking the filling needle cradle 4016 from rotation with respect to the filling aid base 4046 may vary and embodiments may not include locking features. In various embodiments locking the filling aid 4004 from rotation with respect to the filling aid base 4046 when the filling needle cradle 4016 is in the filling position may be desirable for many reasons, including, but not limited to, once the filling needle 4014 pierces the septum, rotation of the filling aid 4004 with respect to the filing aid base 4046 may cause damage to the septum and/or the reservoir and/or cause leakage.

Once the filling needle 4014 pierces the septum, the plunger portion of the syringe may be advanced to provide flow of fluid from the syringe barrel 4062 to the reservoir.

Figure 220A:
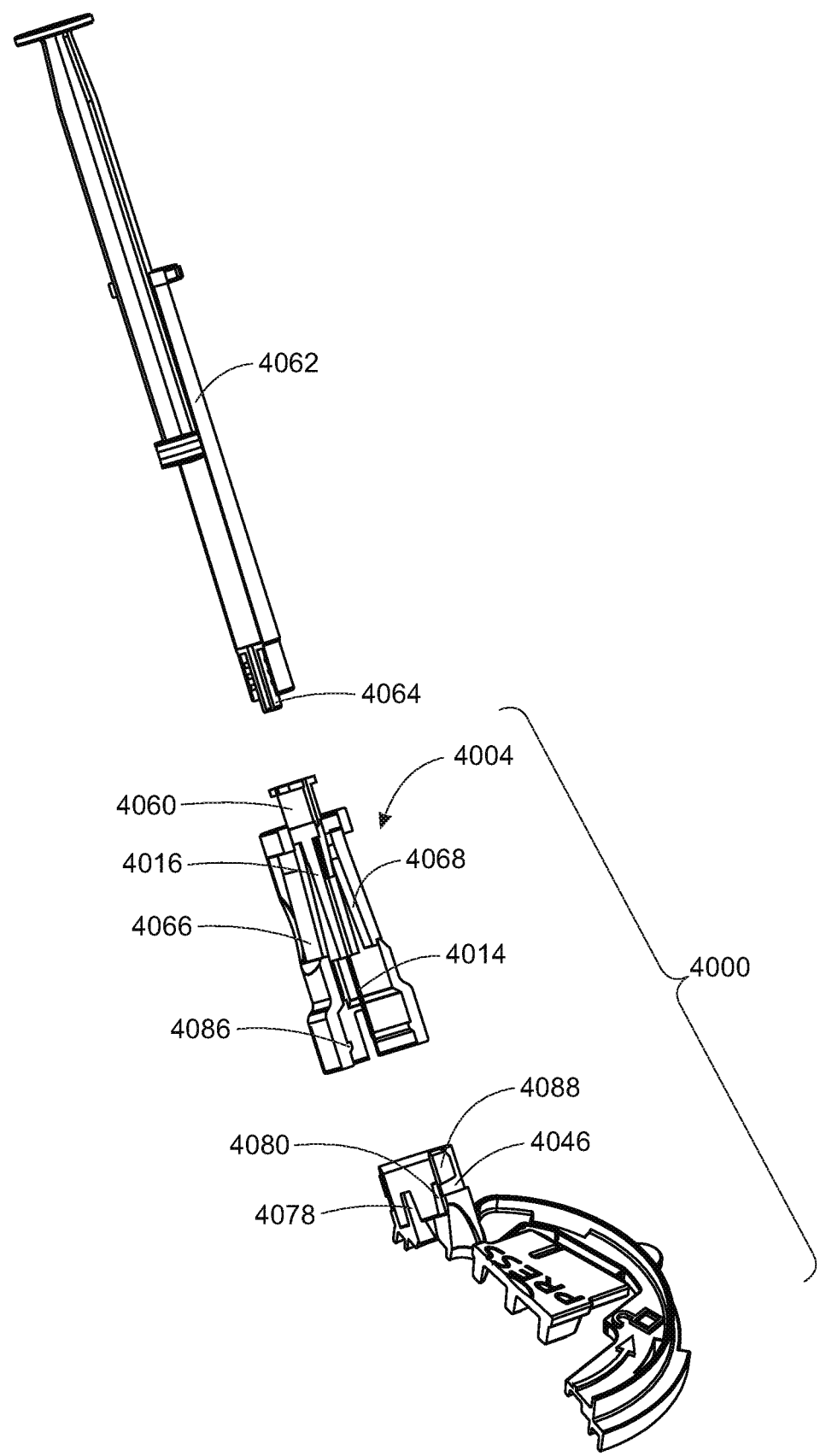
Figure 220B:
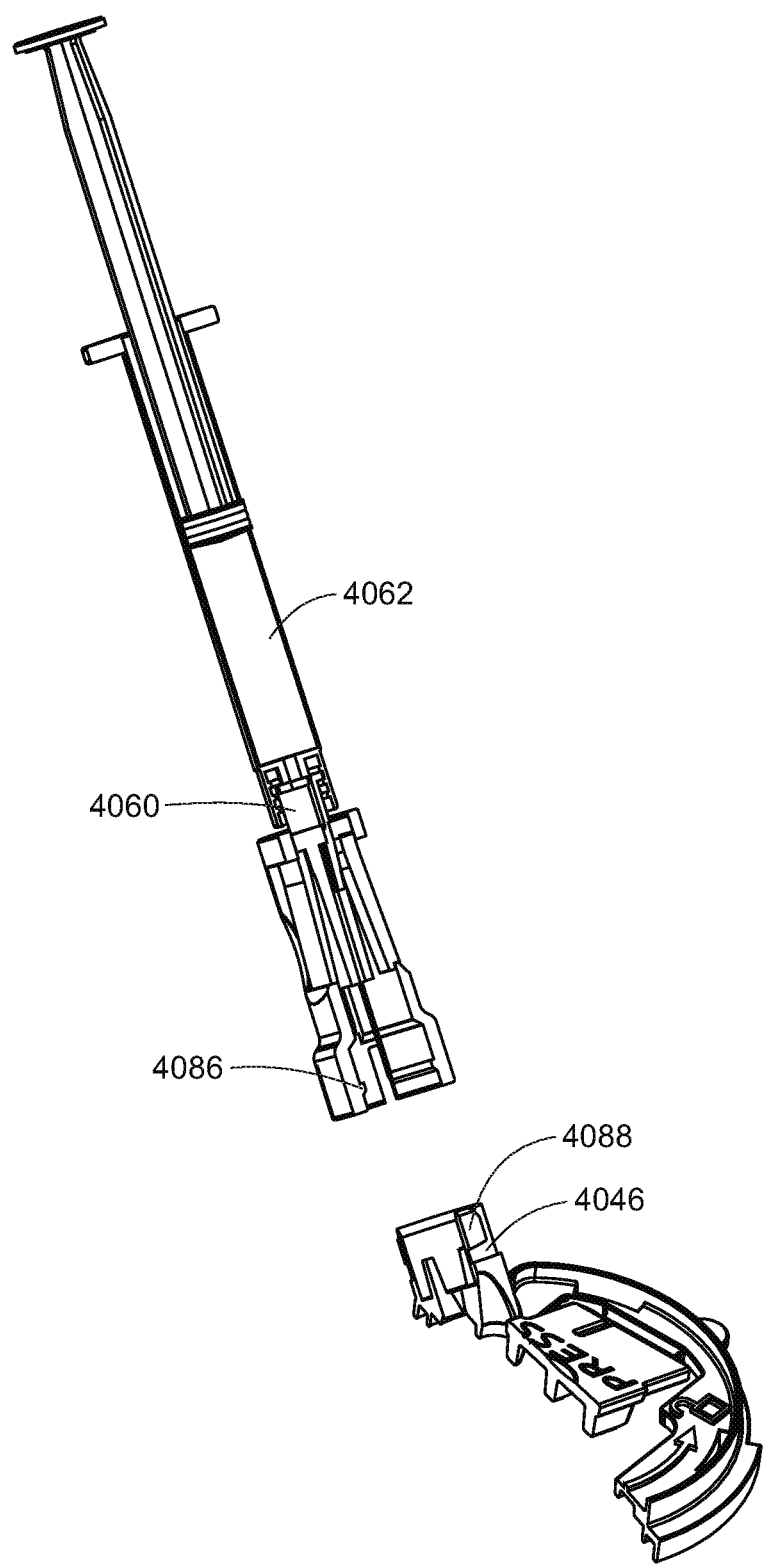
Figure 220C:
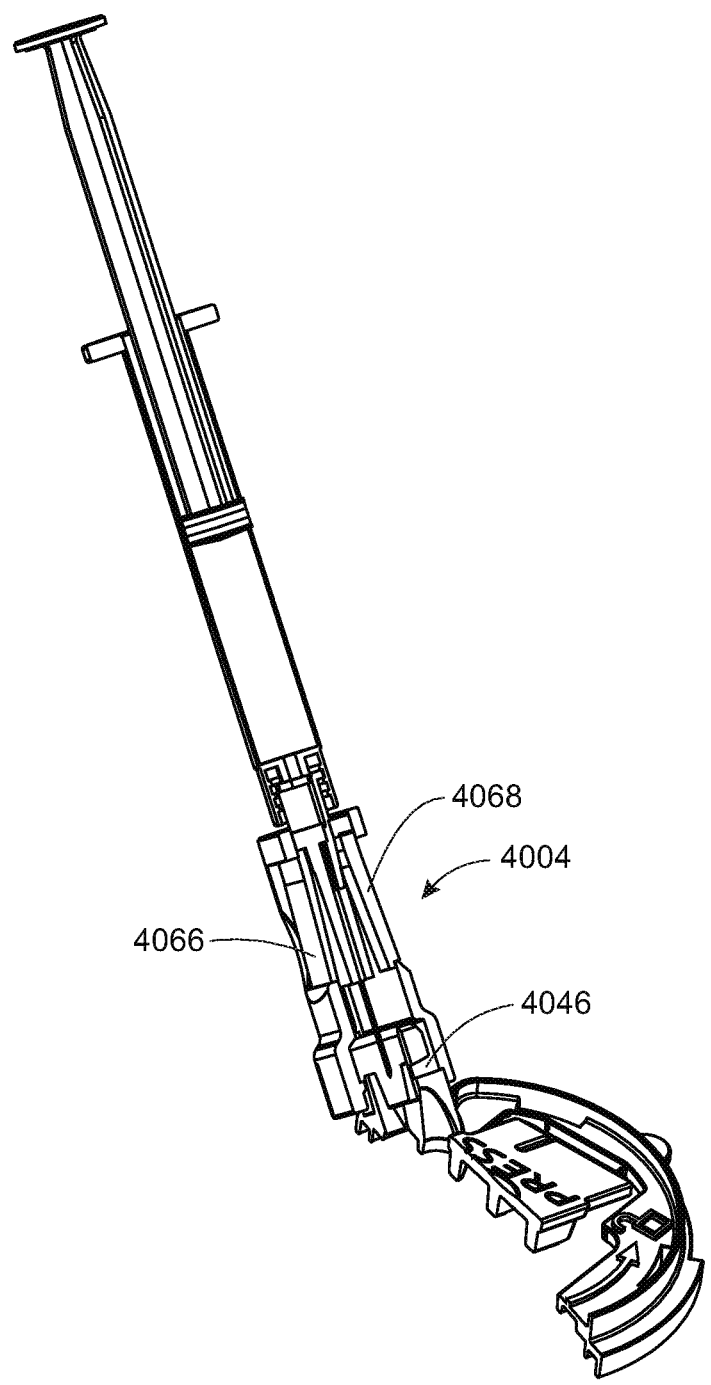
Figure 220D:
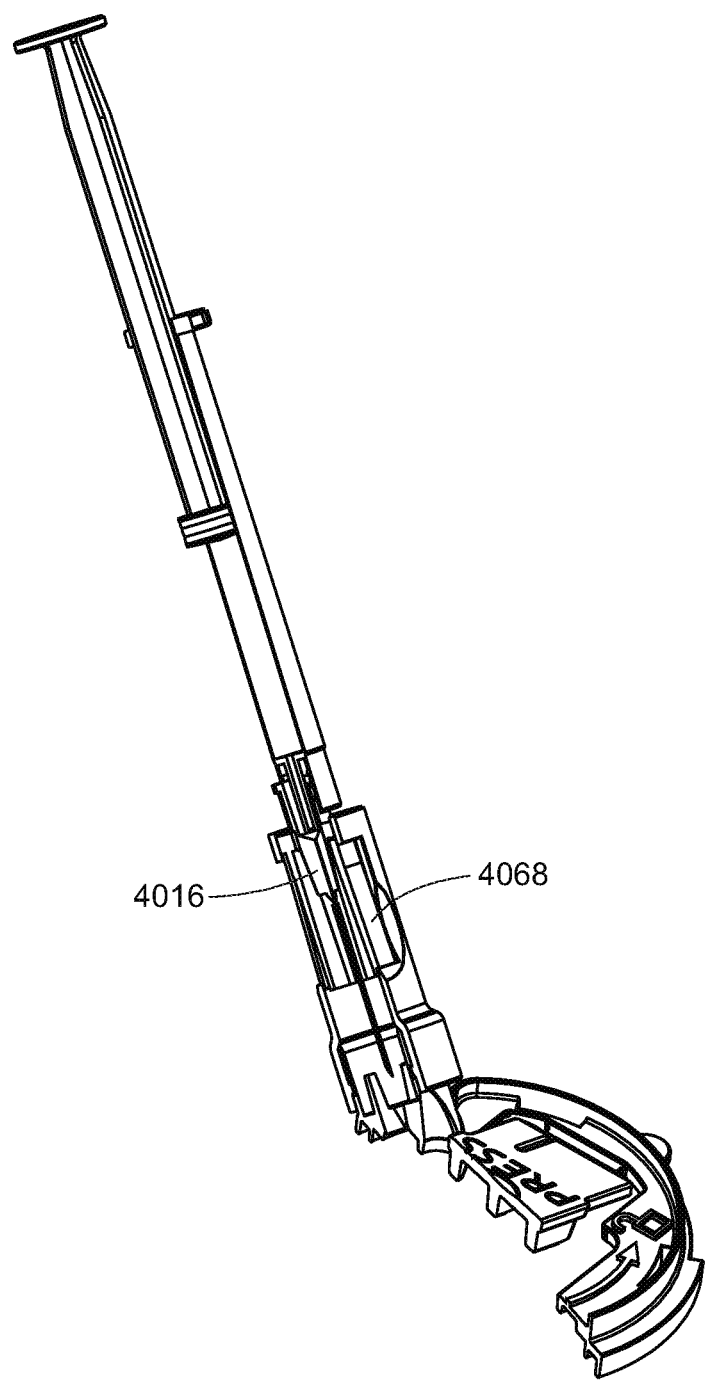
Figure 220E:
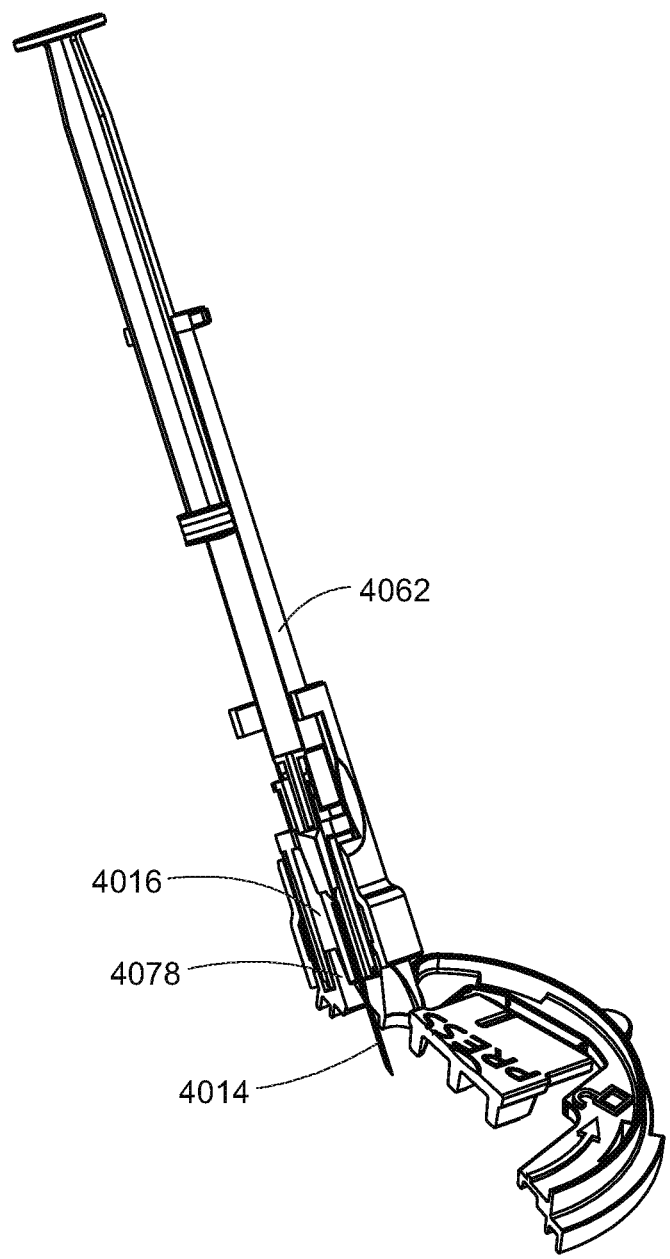
Figure 220F:
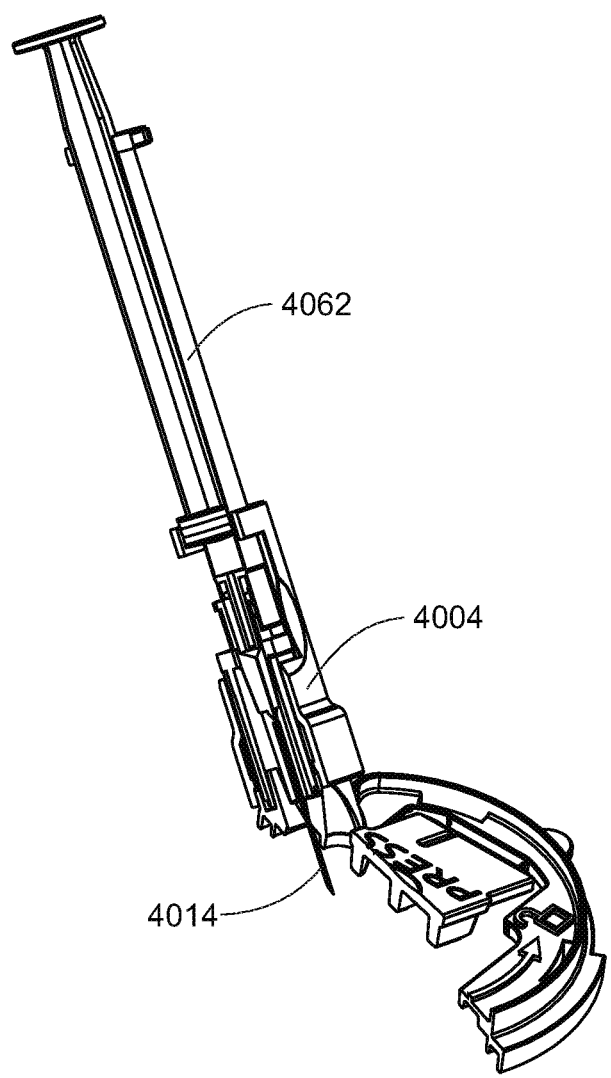

Referring now also to FIGS. 220A-220F, cross sections views of the various stages of filling the disposable using the fill adapter 4000 and a filling syringe 4062 are shown. FIG. 220A shows the filling syringe 4062, the filling aid 4004, and the base portion of the fill adapter 4000. In FIG. 220B, the filling syringe 4062 is connected to the filling aid 4004. As shown in FIG. 220B, the filling aid base 4046 includes at least one groove feature 4088 which interacts with the at least one tongue feature 4086 such that the filling aid 4004 is locked onto the filling aid base 4046. FIG. 220C shows the filling aid 4004 connected to the filling aid base 4046. FIG. 220D shows a view where the filling aid 4004 has been rotated with respect to the filling aid base 4046. In various embodiments, the filling aid base 4046 may be locked onto the filling aid 4004 after this rotation. To remove the filling aid 4004 from the filling aid base 4046, rotation in the opposite direction may be required. At this stage, the filling needle cradle 4016 is in the starting position and the flexible tab 4068 (4066 is obscured by view) is in the window of the needle housing 4038. Referring now also to FIG. 220E, the flexible tabs 4066, 4068 (obscured by view) have been pressed and force exerted onto the filling syringe 4062 such that the filling needle cradle 4016 has advanced towards the filling aid base and the needle cradle 4016 is in the filling position. The locking feature posts 4078, 4080 in the filling aid base are within the locking feature grooves (not shown, shown in FIG. 218) of the filling needle cradle 4016. The filling needle 4014 has advanced and may pierce the septum (not shown) of the disposable assembly (not shown). Referring now also to FIG. 220F, the plunger of the filling syringe 4062 has been advanced and the contents of the syringe barrel flow through the filling needle 2014 and into the reservoir (not shown).

In various embodiments, to remove the filling aid 4004 from the filling aid base 4046, the filling needle cradle 4016 is moved from the filling position to the starting position, due to the locking features described above, such that the filling aid 4004 may be rotated from the locked position to the unlocked position with respect to the filling aid base 4046. Thus, in various embodiments, the filling aid 4004 may not be removed from the filling aid base 4046 (i.e., the filling aid 4004 may not rotate with respect to the filling aid base 4046) unless and until the filling needle cradle 4016 is moved to the starting position (where the filling needle 4014 is not longer outside of the needle housing 4038), and it is only in this configuration that the filling aid 4004 may be removed from the filling aid base 4046. Thus, the filling needle 4014 is not exposed outside the needle housing unless the filling aid 4004 is attached to the filling aid base 4046. In various embodiments, the filling needle cradle 4016 may be moved back to the starting position by exerting force onto the filling syringe 4062 in a direction away from the filling aid base 4046. Once the filling needle cradle 4016 reaches the starting position, the flexible tabs 4066, 4068 may spring into the corresponding windows 4090, 4092 on the filling aid 4004 needle housing 4038, which may, again, maintain and/or lock the filling needle cradle 4016 in the starting position. In various embodiments, when the filling needle cradle 4016 is in the starting position, the filling needle 4014 is inside the needle housing 4038, and therefore, the needle housing 4038 serves as a sharps container for the filling needle 4014. In various embodiments, the filling aid 4004 may be removed from the filling syringe 4062 or the filling aid 4004 may remain on the filling syringe 4062 for disposal.

In some embodiments, the flexible tabs 4066, 4068 and the corresponding windows 4090, 4092 may be covered by such that user action may not unlock the filling needle cradle 4016 flexible tabs 4066, 4068 from the corresponding windows 4090, 4092.

In various embodiments, once the disposable housing assembly is filled to the desired volume, the fill adapter may be used to prime the disposable housing assembly in a fashion similar to those described in one or more embodiments herein.

Referring now also to FIG. 221, in some embodiments, the disposable housing assembly described above may, as described, include a reservoir which includes a septum. However, in some embodiments, the septum in the disposable housing assembly may be located on the side of the disposable housing assembly. In some embodiments, the reservoir may be filled using a fill adapter 5000. In some embodiments, the fill adapter may include disposable receiving tabs 5020, 5022 which are configured to removably receive and maintain the disposable housing assembly 5002 into a desired orientation for filling the reservoir. The fill adapter 5000, in some embodiments, includes a filling needle assembly 5006 slidably connected inside the fill adapter 5000. The filling needle assembly 5006 includes a needle including two ends, a reservoir end 5018 and a vial end 5016. In various embodiments, the filling needle assembly 5006 includes fingers to assist with maintaining the needle in a centered position with respect to the fill adapter 5000. In various embodiments, the filling needle assembly 5006 includes a first lock plate 5044 and a second lock plate 5042. In various embodiments, either the fill adapter 5000 system or the vial may also include a plunger pusher 5012 configured to be connected to one side of a vial 5010 and push the plunger 5014, which is located inside the vial 5010. The fill adapter 5000 in various embodiments includes locking features 5024, 5026 and, in various embodiments, each of these locking features 5024, 5026 includes a corresponding locking feature on the opposite side of the fill adapter 5000, but these corresponding features are not shown in the views in FIG. 221. The first lock plate 5044 and the second lock plate 5042 interact with the locking features 5024, 5026 of the fill adapter 5000 so that once the filling needle assembly 5006 slides over the locking features 5024, 5026, while moving from a starting position to a filling position, the filling needle assembly 5006 will be unable to return to the starting position.

In various embodiments, the vial 5010 is a vial containing a therapeutic or other fluid. The vial 5010 includes an elastomeric and/or rubber and/or plastic plunger 5014 which is movable within the vial 5010. In various embodiments, the vial includes a septum 5028. The pusher 5012 which, in various embodiments, may be made from plastic, attaches to the vial.

Figure 222A:
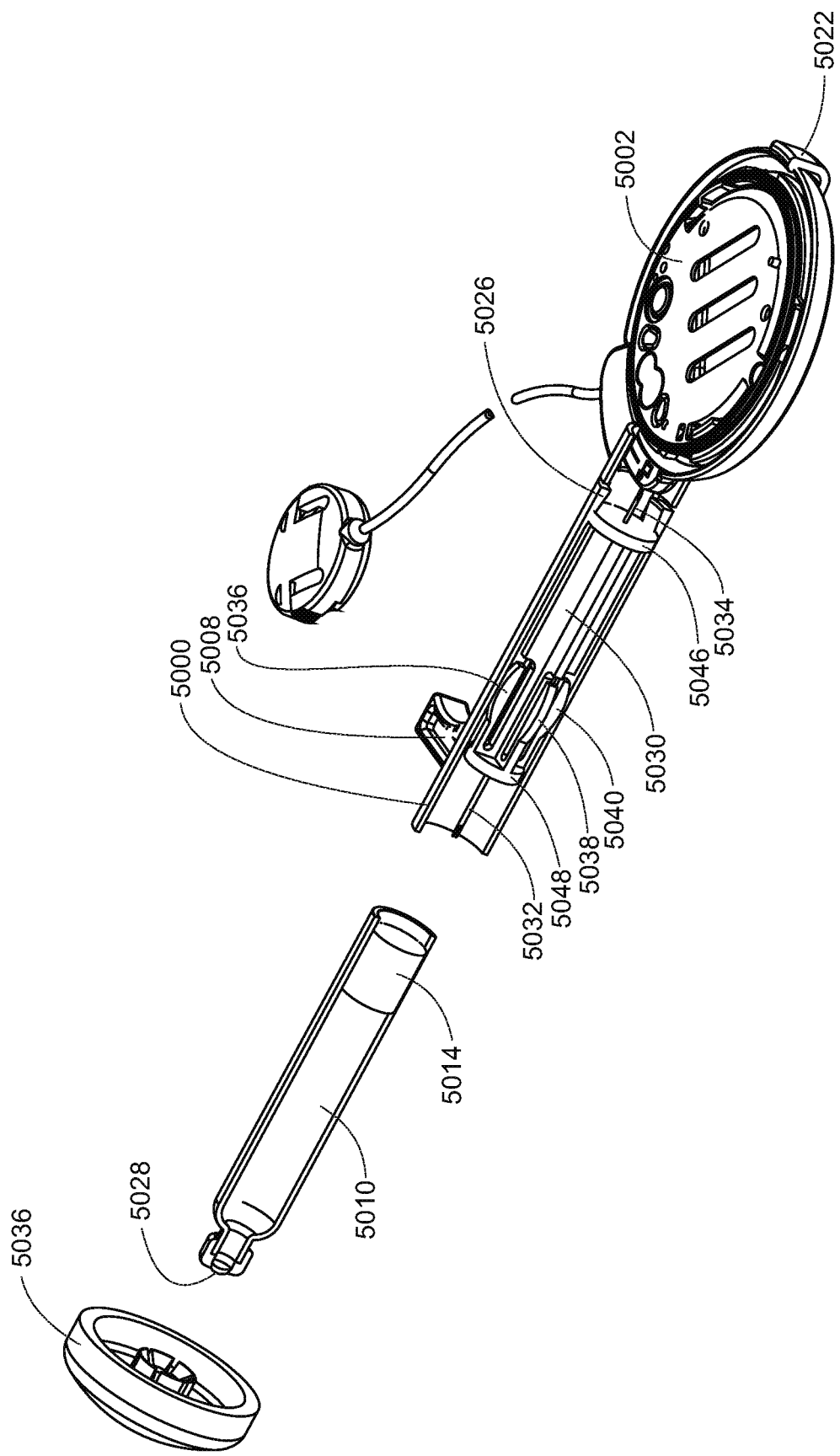
Figure 222B:
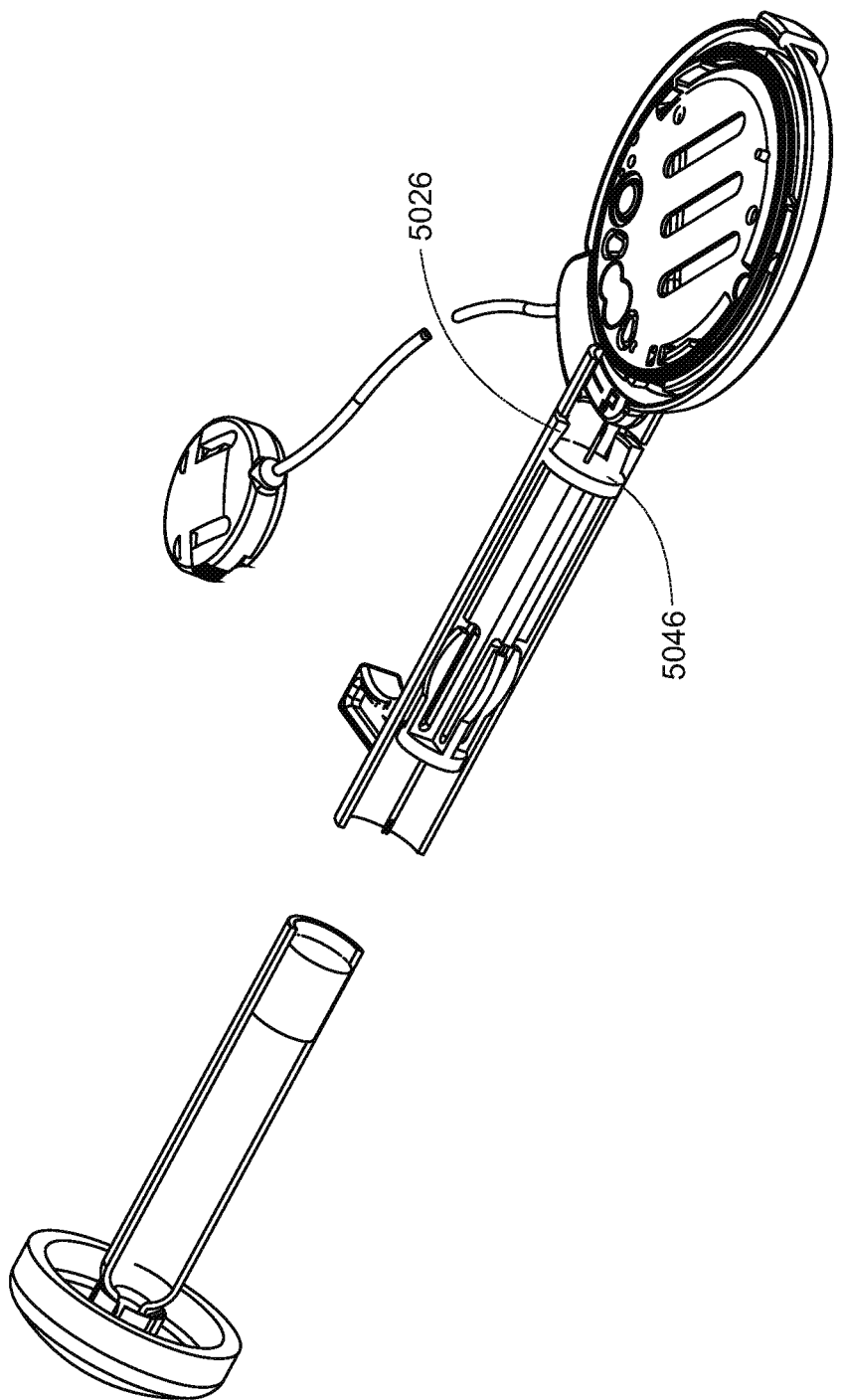
Figure 222C:
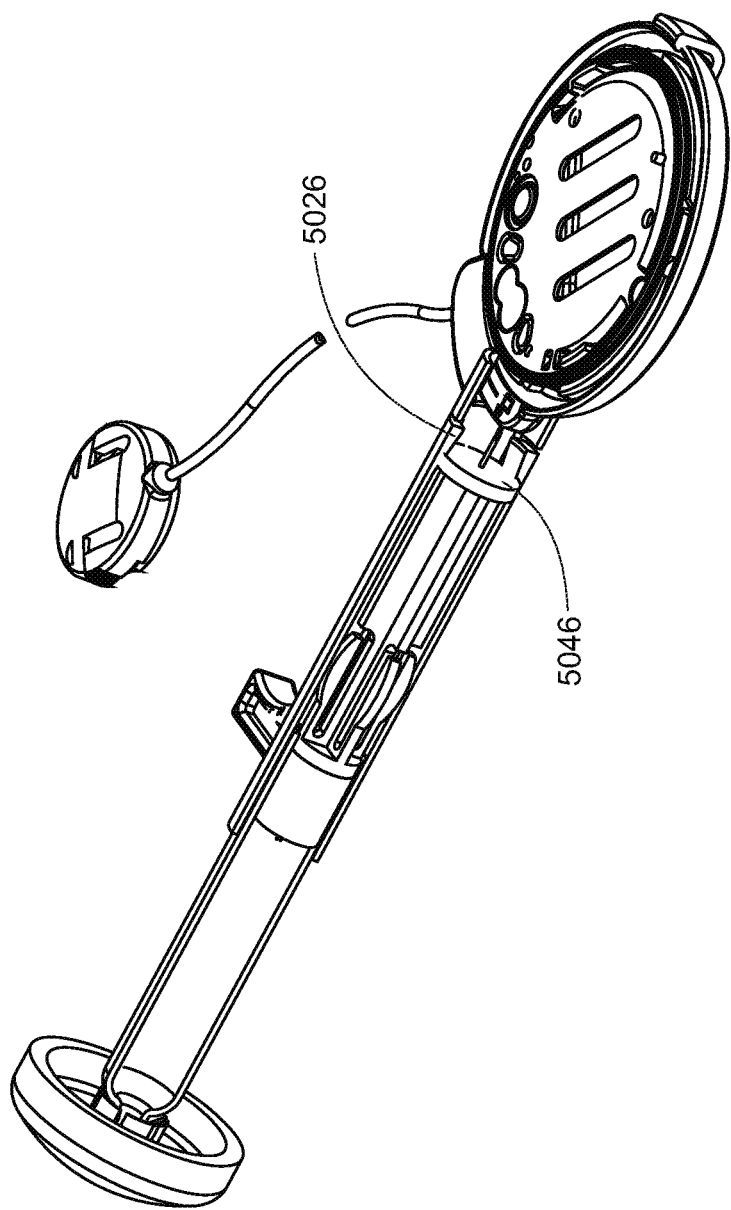
Figure 222D:
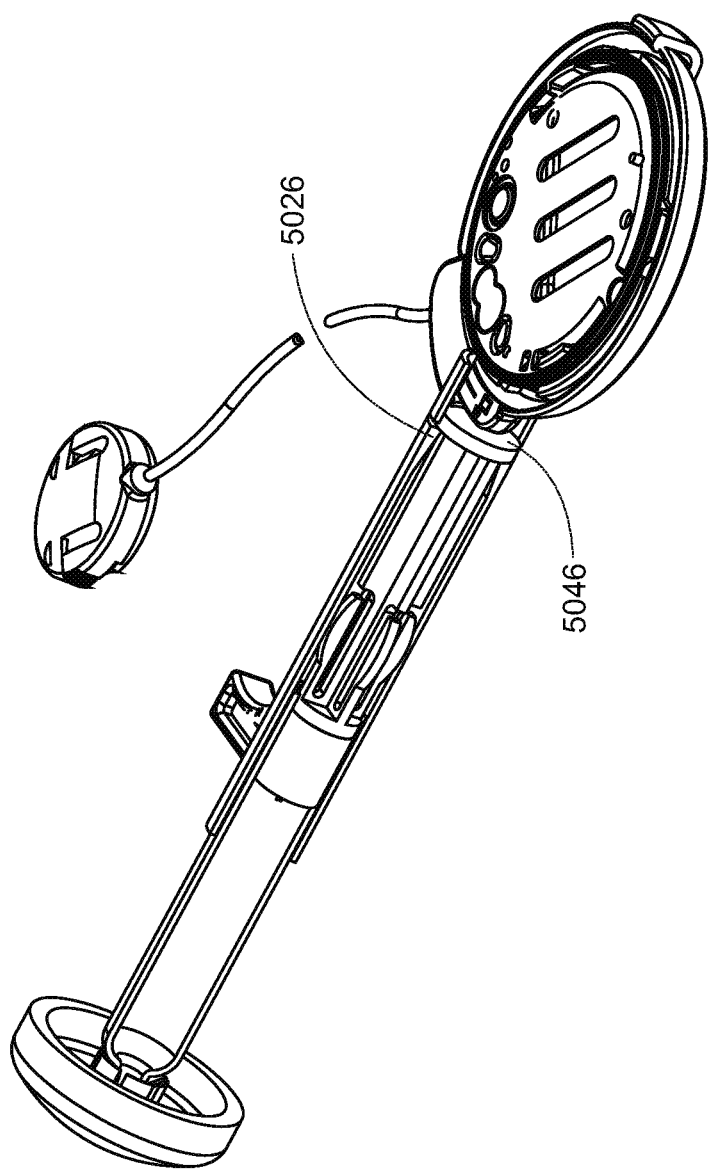
Figure 222E:
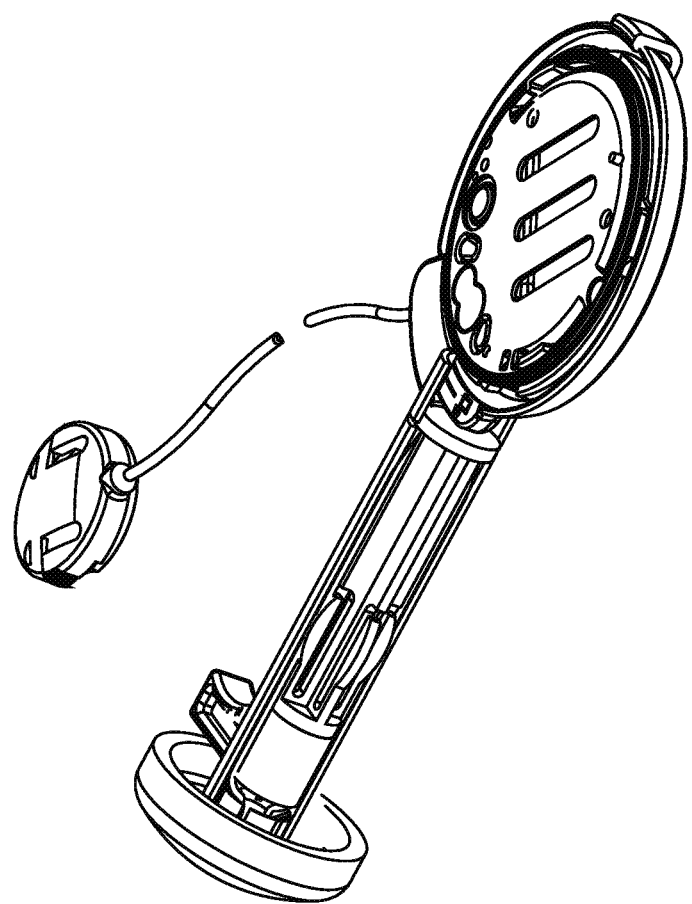
Figure 222F:
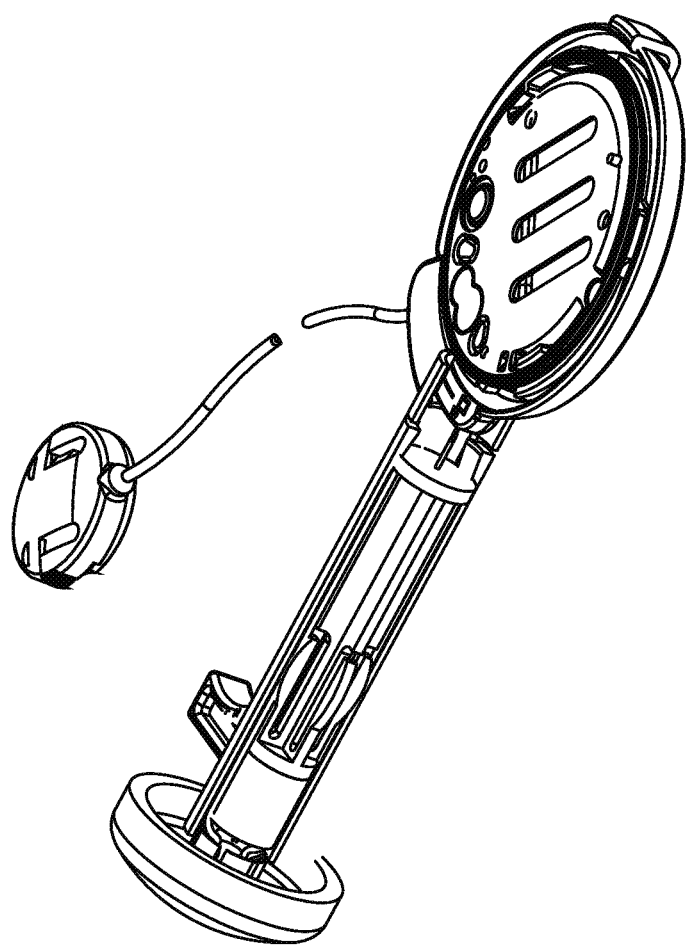

Referring now also to FIG. 222A, another embodiment of the embodiment of the fill adapter 5000 shown in FIG. 221, is shown. In various embodiments, the fill adapter 5000 shown in FIG. 221 may include a different embodiment of a filling needle assembly 5030 which include fingers 5036, 5038, 5040 to assist with maintaining the needle in a centered position with respect to the fill adapter 5000. In these embodiments, the filling needle assembly 5030 includes a first lock plate 5048 and a second lock plate 5046. The fill adapter 5000 in various embodiments includes locking features (similar to those shown in FIG. 221 as 5024, 5026 and, in various embodiments, each of these locking features 5024, 5026 includes a corresponding locking feature on the opposite side of the fill adapter 5000, but these corresponding features are not shown in the views in FIG. 221). The first lock plate 5048 and the second lock plate 5046 interact with the locking features of the fill adapter 5000 so that once the filling needle assembly 5030 slides over the locking features while moving from a starting position to a filling position, the filling needle assembly 5030 will be unable to return to the starting position.

Referring again to FIG. 221, in practice, the pusher 5012 connects to the vial 5010 such that the pusher may push the plunger 5014 (which is located inside the vial 5010). While force is exerted on the push such that force is imparted onto the fill adapter 5000, the septum 5028 makes contact with the filling needle assembly 5006 and filling needle assembly 5006 moves towards the reservoir septum. The reservoir end 5018 of the needle pierces the reservoir septum and the vial end 5016 of the needle pierces the vial septum 5028 of the vial 5010. By further exerting force onto the pusher 5012, movement of the plunger 5014 within the vial 5010 causes fluid from the vial 5010 to flow through the vial end 5016 of the needle and through the reservoir end 5018 and into the reservoir. Once a desired volume of fluid has been transferred to the reservoir (which, in some embodiments, may be determined by suing volumetric indications on the vial, in some embodiments) force exerted onto the pusher 5012 in the direction opposite the disposable housing assembly 5002 works to pull the reservoir end 5018 of the needle out of the reservoir septum. The first lock plate 5044 and the second lock plate 5042 interact with the locking features 5024, 5026 of the fill adapter 5000 so that once the filling needle assembly 5006 slides over the locking features 5024, 5026, while moving from a filling position towards the starting position, the filling needle assembly 5006 will be unable to return to the starting position, but will move at least far enough towards the starting position so that the reservoir end 5018 of the needle is not touching the reservoir septum. The filing needle assembly 5006 being locked in place provides opposite force to allow ease of removal of the vial 5010 from the vial end 5016 of the filling needle. Once the disposable housing assembly 5002 is removed from the fill adapter 5000 (by exerting an opposite force on the disposable housing assembly 5002 such that the disposable receiving tabs 5020, 5022 release the disposable housing assembly 5002) the needle in the filling needle assembly 5006 is completely inside the fill adapter and therefore, unintentional pricks may be avoided.

In various embodiments, the fill adapter 5000 may include one or more ergonomic finger rests 5008. In the embodiments shown, the fill adapter 5000 includes two ergonomic finger rests 5008. In various embodiments, the ergonomic finger rests 5008 may be shaped as shown or the shape may vary. In various embodiments, the ergonomic finger rests 5008 may be used, in conjunction with the vial 5010 and the pusher 5012 to stabilize the fill adapter 5000 while filling the disposable housing assembly 5002. In various embodiments, the ergonomic finger rests 5008 may be made from the same material as the fill adapter 5000. In various embodiments, the fill adapter 5000 may be made from plastic or other material.

Referring now also to FIGS. 222A-222G, another embodiment of the fill adapter 5000 is shown. In this embodiment, the pusher 5036 is configured to attach to the septum 5028 end of the vial 5010. The filling needle assembly 5030 includes a filling needle including a vial end 5032 and a reservoir end 5034. The vial end 5032 of the filling needle is longer than in the previously described embodiment. The vial end 5032 of the filling needle is configures to pierce the plunger 5014 in the vial 5010 such that fluid from inside the vial 5010 may flow from the inside of the vial 5010 through the vial end 5032 of the filling needle to the reservoir end 5034 of the filling needle. In embodiments similar to this embodiment, the pusher 5036 is attached to the vial 5010 on the septum 5028 end. With force being applied onto the pusher 5036 the vial 5010 comes into contact with the fill adapter 5000 and the vial end 5032 of the filling needle pierces the plunger 5014 while the filling needle assembly 5030 is pushed forward such that the reservoir end 5034 of the filling needle pierces the septum of the reservoir in the disposable housing assembly 5002. Continuing to apply pressure to the pusher 5036 in a direction towards the vial 5010, the plunger 5014 is pushed further into the vial 5010 and fluid flows from the vial 5010 to the reservoir. As shown in FIG. 222A-222G, the filling needle assembly 5030 includes fingers 5036, 5038, 5040 which act to maintain the filling needle in the center of the fill adapter 5000. In various embodiments, the fingers may be configured differently than shown and in some embodiments, there may be one or more. In various embodiments, the fingers may additionally work in conjunction with the locking features 5026, 5024, together with the second lock plate 5046 to, while the filling is in progress, lock the filling needle assembly 5040 in the filling position. Also, once the filling is completed and force in the opposing direction is applied to the pusher 5036, and the vial 5010 is pulled out of the fill adapter 5000, the second lock plate 5046 catches on one or more locking features 5026, 5024 and this prevents the filling needle assembly 5030 from being pulled out of the fill adapter 5000, and provides enough opposite force to allow the removal of the vial 5010 from the fill adapter 5000 (and allows the removal of the vial end 5032 of the filling needle from the plunger 5014. Thus, the fill adapter 5000 serves as a sharps container after filling and therefore, unintentional pricks may be avoided. FIGS. 222A-222F show one embodiment of this process. Thus, in the various embodiments, the locking features perform a similar function, they allow the filling needle assembly to move from a starting position (for example, as shown in FIG. 222A) to a filling position (for example, shown in FIG. 222D), but limit the total travel of the filling needle assembly with respect to the fill adapter 5000.

Figure 222G:
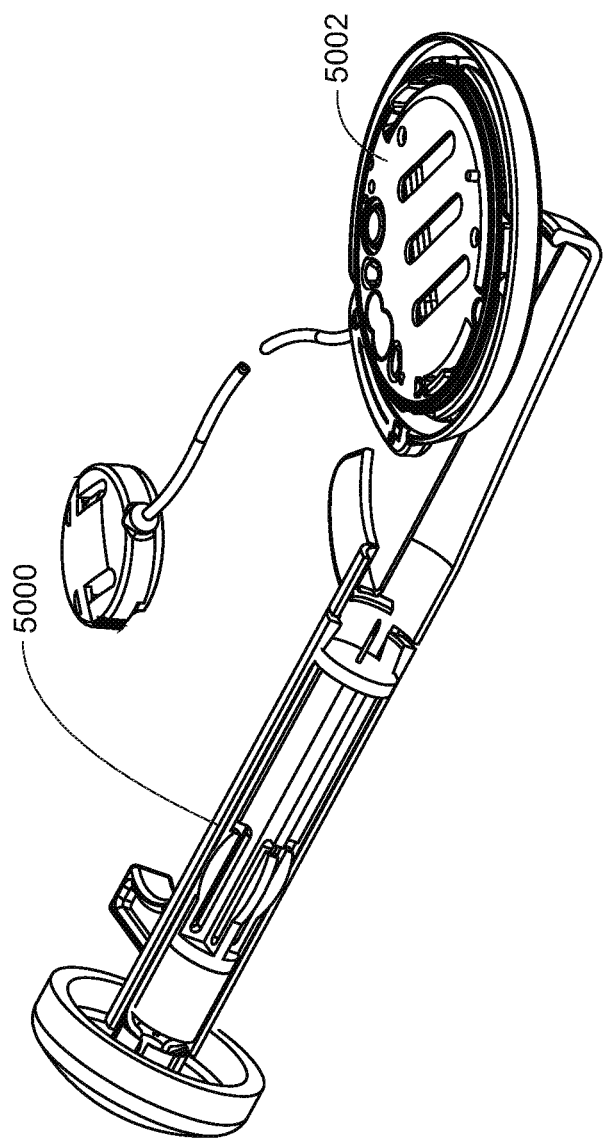

Following, as shown in FIG. 222G, the disposable housing assembly 5002 may be removed from the fill adapter 5000 and primed.

Referring to FIG. 223, an embodiment of the pusher, attached to the vial, and the vial inside the fill adapter 5000 is shown.

Referring now to FIG. 224, another embodiment of the fill adapter 5050 is shown. In these embodiments, rather than a filling needle assembly, the fill adapter 5050 is configured to receive a filling syringe 5052 and maintain the filling syringe 5052 in a desired orientation to lead the filling needle 5054 to the reservoir septum in the disposable housing assembly 5002. Thus, the fill adapter 5050 in these embodiment may be desirable for many reasons, including, but not limited to, being used with a filling syringe and assuring that the filling needle 5054 is inserted in the correct location and at the correct orientation during fill, which may be desirable for many reasons, including, but not limited to, the ability to fill the reservoir without damaging the septum or disposable housing assembly 5002 and therefore, prevent leaks, amongst other undesirable conditions.

In various embodiments, the vial end of the needle may not penetrate the septum of the vial until the reservoir end of the needle penetrates the septum of the disposable housing assembly. This ensures that if the vial is pressurized, the contents of the vial may not begin to flow until the reservoir end of the needle has penetrated the septum of the disposable housing assembly, thereby limiting the amount of wasted vial contents.

Referring now also to FIGS. 225-240B, another embodiment of a fill adapter 6000 is shown. The fill adapter 6000 may be configured to be coupled to an embodiment of the disposable housing assembly 6002, including but not limited to, the disposable housing assembly 804, shown and described above, or the disposable housing assembly 6002, shown in FIG. 228. The embodiments of the disposable housing assembly 6002 shown in FIG. 228 are similar to disposable housing assembly 804. However, for description purposes, disposable housing assembly 6002 will be referred to with respect to fill adapter 6000, however, in various other embodiments, the filling adapter 6000 may be coupled to any embodiment of the disposable housing assembly.

Fill adapter 6000 may work in conjunction with filling aid 6004, which may be configured to guide a needle of a filling syringe 6062 to a septum of disposable housing assembly 6002, which, in some embodiments, may be one as described above, for example, with respect to FIG. 3, however, in some embodiments, for example, the exemplary embodiment described with respect to FIGS. 225-240B, the embodiment of the disposable housing assembly 6002 may be used as it includes apertures 6039, 6040, 6041, 6042, 6043, 6044, 6045, 6047, rather than, for example, ribs, which are configured to interact with the button assemblies 6031, 6032, 6033, 6034, 6035, 6036, 6037, 6038. In some embodiments, the disposable housing assembly 6002 may include one or more of the features described with respect to various embodiments of the disposable housing assemblies, however, the disposable housing assembly 6002 includes apertures 6039, 6040, 6041, 6042, 6043, 6044, 6045, 6047 to allow the reservoir 908 of the disposable housing assembly 6002 to be filled by the filling syringe 6062. In various embodiments, the disposable housing assembly 6002 may be any of the disposable housing assemblies described herein or may be one or more of the disposable housing assemblies described in co-pending U.S. patent application Ser. No. 13/788,260, now U.S. Published Application No. 2014/0107579, entitled Infusion Pump Assembly, filed on Mar. 7, 2013, published Apr. 17, 2014, assigned to DEKA Products Limited Partnership, which is herein incorporated by reference in its entirety. Fill adapter 6000, together with filling aid 6004, may reduce the dexterity and aim necessary to properly insert a needle through the septum of disposable housing assembly 6002 for the purpose of filling the reservoir 908.

As discussed above with respect to various embodiments of the fill adapter, disposable housing assembly 6002 may be configured to facilitate controlling the quantity of infusible fluid delivered to reservoir 908 during filling. For example, membrane assembly 902 of disposable housing assembly 6002 may include apertures 6039, 6040, 6041, 6042, 6043, 6044, 6045, 6047 which may provide windows to the reservoir membrane 902 that are formed on the disposable housing assembly 6002. The reservoir membrane 902 may be depressed and at least partially displaced into reservoir 908, thereby reducing the volume of reservoir 908. Accordingly, when infusible fluid is delivered to reservoir 908, the volume of fluid that may be accommodated by reservoir 908 may be correspondingly reduced by at least partially displacing the reservoir membrane 902.

In some embodiments, the apertures 6039, 6040, 6041, 6042, 6043, 6044, 6045, 6047 may be sized and shaped to prevent depression of the reservoir membrane 902 by anything other than the button assemblies 6031, 6032, 6033, 6034, 6035, 6036, 6037, 6038 discussed in more detail below. This may provide addition safety to the infusion system as the disposable housing assembly 6002 does not include access to unintentional pumping of fluid by depression of the reservoir membrane 902 when the fill adapter 6000 is not attached to the disposable housing assembly 3002. Further, the apertures 6039, 6040, 6041, 6042, 6043, 6044, 6045, 6047 may additionally prevent unintentional fluid loss after fill is complete. Thus, once the fill adapter 6000 is removed from the disposable housing assembly 6002, unintentional pressure to the disposable housing assembly 6002 may not result in forcing fluid through the disposable housing assembly 6002 fluid path to the exit. Rather, the reusable housing assembly 802 may be attached to the disposable housing assembly 6002 for fluid to be forced out of the reservoir 908. Therefore, the apertures 6039, 6040, 6041, 6042, 6043, 6044, 6045, 6047 in the disposable housing assembly 6002 may provide for a mechanism for safely and intentionally priming the disposable housing assembly 6002 but also, prevent the unintentional forcing of fluid from the reservoir 908.

In some embodiments, the size, shape and/or overall dimensions of the apertures 6039, 6040, 6041, 6042, 6043, 6044, 6045, 6047 may be chosen to accommodate the one or more button assemblies 6031, 6032, 6033, 6034, 6035, 6036, 6037, 6038 (described in further detail below) so as to limit the travel of the button assemblies 6031, 6032, 6033, 6034, 6035, 6036, 6037, 6038 and thereby limiting the amount of displacement of the reservoir membrane 902 by the button assemblies 6031, 6032, 6033, 6034, 6035, 6036, 6037, 6038.

Fill adapter 6000 may include one or more button assemblies (e.g., button assemblies 6031, 6032, 6033, 6034, 6035, 6036, 6037, 6038) corresponding to apertures 6039, 6040, 6041, 6042, 6043, 6044, 6045, 6047 (which are similar to other embodiments described and shown herein with respect to the embodiments as described in other embodiments of the disposable housing assembly having and ribs 964, 966, 968) in the disposable housing assembly 6002. In various embodiments, when fill adapter 6000 is releasably engaged with disposable housing assembly 6002, buttons assemblies 6031, 6032, 6033, 6034, 6035, 6036, 6037, 6038 may be aligned with apertures 6039, 6040, 6041, 6042, 6043, 6044, 6045, 6047. Button assemblies 6031, 6032, 6033, 6034, 6035, 6036, 6037, 6038 may be, for example, members attached to a button assembly actuator 6046, capable of being depressed. When fill adapter 3000 is releasably engaged with disposable housing assembly 3002, one or more of button assemblies 6031, 6032, 6033, 6034, 6035, 6036, 6037, 6038 may be depressed, and may correspondingly be displaced through a respective one of apertures 6039, 6040, 6041, 6042, 6043, 6044, 6045, 6047 into reservoir 908, causing an attendant reduction in the volume of reservoir 908.

Although eight apertures and eight corresponding button assemblies are described and shown herein, in various embodiments, the fill adapter 6000 may include one or more button assemblies and the disposable housing assembly may include one or more corresponding apertures. In some embodiments, the button assemblies and the apertures may be similarly sized as shown in the accompanying figures. However, in various embodiments, the number, size, distribution and shape of the one or more button assemblies and the one or more apertures may be different than as shown herein. For example, in some embodiments, the button assemblies may be wider, may be round, may be square or may be thicker. Likewise, the corresponding aperture may accommodate the various embodiments of the button assemblies. In some embodiments, it may be desirable to vary the distribution, number, size and shape of the button assemblies, and correspondence apertures, to accommodate the volume of fluid that is anticipated to be filled in the reservoir.

In some embodiments, for example, the embodiments shown in FIGS. 206A-208B, the button assemblies 6031, 6032, 6033, 6034, 6035, 6036, 6037, 6038 are actuated by at least one button assembly actuator 6046 which is actuated by applying a downward force upon the button assembly actuator 6046. In some embodiments, each of the at least one button assemblies 6031, 6032, 6033, 6034, 6035, 6036, 6037, 6038 may be separately actuated by a dedicated button assembly actuator. The button assembly actuator 6046 may be any size desired, but in some embodiments, may be as shown in FIGS. 226A and 226B. As shown in, for example, FIG. 226B, the button assembly actuator 6046 may include visible indicators, for example, a fluid drop icon, other icons, for example, a "press" icon, to indicate the method of actuation. In some embodiments, the button assembly actuator 6026 may include a depression and/or ergonomic finger and/or thumb accommodation.

In the exemplary embodiment of this embodiment of the fill adapter 6000, the fill adapter 6000 includes a housing, the button assembly actuator 6046 springingly attached to the housing. The fill adapter 6000 may include a pump chamber plunger 6050 shown in, for example, FIG. 229, on the underside of the fill adapter 6000 housing.

Upon coupling the fill adapter 6000 to the disposable housing assembly 6002, the reservoir 908 may be filled using a filling syringe 4062. Any syringe known in the art may be used, however, in the exemplary embodiments, any syringe having a size and shape to be accommodated by the filling aid 6004 may be used, including, but not limited to, a 3 cc/mL TERUMO SYRINGE without needle, made by TERUMO Europe, Belgium, together with a Becton Dickinson 26G1/2 PRECISIONGLIDE Needle, made by Becton Dickinson & Co., Franklin Lakes, N.J., U.S.A., however, in various embodiments, the filling syringe 6062 may be a syringe made by another manufacture and/or at a larger or smaller size. Fill adapter 6000 may include an outside portion and a cavity portion. The cavity portion is the portion that mates with the disposable housing assembly 6002. The fill adapter 6000 may include locking tabs 6006, 6008 that may be configured to engage the disposable housing assembly 6002 in a manner such that the disposable housing assembly 6002 may be held in the cavity portion of the fill adapter 6000. Accordingly, fill adapter 6000 may be releasably engaged with disposable housing assembly 6002 by aligning fill adapter 6000 with disposable housing assembly 6002 and applying force such that force is applied to the disposable housing assembly 6002 relative to the fill adapter 6000 or vice versa.

In various embodiments, the locking tabs 6006, 6008 may include a ramping portion 6010 that works to maintain the disposable housing assembly 6002 relative to the fill adapter 6000 when the disposable housing assembly 6002 and fill adapter 6000 are releasably engaged.

In various embodiments, the locking tabs 6006, 6008 are movable such that they provide a pinch release for releasing the disposable housing assembly 6002 when engaged with the fill adapter 6000. In various embodiments, the number of locking tabs may vary, for example, in various embodiments; the number of locking tabs may be greater than or less than the number shown in the exemplary embodiments.

In some embodiments of the infusion pump apparatus and system described herein, in practice, the fill adapter 6000 may be attached to the disposable housing assembly 6002 in the locked position. A user may fill the reservoir (which may be the embodiment as shown in FIG. 49B, 908) of the disposable housing assembly 6002 using the fill adapter 6000. Following, the user may unlock the fill adapter 6000 by exerting force onto the locking tabs 6006, 6008, which releases the disposable housing assembly 6002.

In various embodiments, while the disposable housing assembly 6002 is releasably engaged with the fill adapter 6000 (which may be referred to as the locked position), the locking tabs 6006, 6008 maintain the disposable housing assembly 6002 in the engaged position with the fill adapter 6000. Thus, the locking tabs 6006, 6008 prevent rotation of the fill adapter 6000 with respect to the disposable housing assembly 6002, and vice versa, which may assist the user and ensure proper alignment during reservoir 908 fill.

As the disposable housing assembly 6002 is engaged with the fill adapter 6000 and in the locked position, the pump chamber plunger 6050 of the fill adapter 6000 interferes with the pump chamber and pushed air out of the pump chamber. Thus, in this embodiment, the pump chamber plunger 6050 engages with the pump chamber when the disposable housing assembly 6002 is locked onto the fill adapter 6000.

Fill adapter 6000 may further include filling aid 6004, which may include a needle housing 6038 which may be configured to guide a filling needle 6014 held by a filling needle cradle 6016 to a septum of disposable housing assembly 6002 to allow the reservoir 908 of the disposable housing assembly 6002 to be filled by the filling syringe 6062. In some embodiments, the needle housing 6038 is configured to attach to the filling aid base 6046. The filling aid base 6046, in various embodiments, is a structure that may, in some embodiments, be cylindrical and provides an opening from the outside of the fill adapter 6000 to the cavity portion (underside) of the fill adapter 6000. The opening is configured to allow a filling syringe/filling needle to enter the cavity portion and pierce the septum in the reservoir/enter the reservoir/fill the reservoir when a reservoir/disposable housing assembly 6002 is connected/engaged with the fill adapter 6000.

In some embodiments, the filling needle 6014 may be attached and/or held by a connector 6060 which may be configured to attach/connect to the end of a filling syringe 6062. In various embodiments, the attachment may be a rotational attachment (e.g., twist to connect), a snap fit attachment (e.g. press parts to connect), a press fit attachment or other luer-type attachment. In some embodiments, the connector 6060 may be configured to be removably attached to the filling syringe 6062. In some embodiments, the connector 6060 may be configured to be attached to the filling syringe 6062 in a non-removable fashion.

In some embodiments, the needle housing 6038 may include end tabs 6070, 6072 which may accommodate a vial of fluid, e.g., therapeutic fluid, e.g., insulin, such that once the filling syringe 6062 end (see 4064 in FIG. 220A) is attached to the connector 6060, the needle housing 6038 may clip onto a vial 6080 having a septum 6082 (also, for example, as shown in FIGS. 199A-199H in 2716) and the filling needle 6014 may penetrate the septum 6082 and the fluid may flow from the vial 6080 to the filling syringe 6062 by way of the filling needle 6014. Once a desired volume of fluid flows from the vial 6080 to the filling syringe 6062, the vial 6080 may be removed from the needle housing 6038, e.g., by exerting opposing force onto the needle housing 6038 and the vial 6080 so as to disconnect the end tabs 6070, 6072 from the vial 6080.

These embodiments may be advantageous, beneficial and/or desirable for many reasons including that the filling needle 6014 remains inside the needle housing 6038 while the filling syringe 6062 is being filled by the fluid from the vial 6080. Therefore, the likelihood of unintentional needle pricks and/or contamination is minimized and/or reduced. Also, in these embodiments, there is no "cover" to be removed from the filling needle 6014, therefore, the likelihood of unintentional needle pricks and/or contamination is minimized and/or reduced before and after the filling needle 6014 is inserted into the vial 6080. However, in some embodiments, a removable cover may be included on the filling needle 6014. Thus, in various embodiments, the filling needle cradle 6016 remains in the starting position (see FIGS. 235A and 235B) while the filling aid 6004 is attached to a vial 6080.

Although the embodiments are described above with respect to a "vial" in some embodiments, the filling aid 6004 may be used in conjunction with any source of fluid, which may include, but is not limited to, a bag of fluid.

In various embodiments, once the filling syringe 6062 is removed from the vial 6080, the filling syringe 6062, still attached to the filling aid 6004 may then be connected to the filling aid base 6046. In some embodiments, connection of the filling aid 6004 to the filling aid base 6046 may be made by sliding the filling aid 6004 over the filling aid base 6046. Thus, in various embodiments, the filling aid base 6046 may include a smaller diameter than the filling aid 6004 such that the filling aid base 6046 may be received by the filling aid 6004.

In some embodiments, the connection between the filling aid 6004 and the filling aid base 6046 may include the filling aid 6004 sliding onto to the filling aid base 6046 and then the filling aid 4004 being rotated with respect to the filling aid base 6046. In some embodiments, the rotation may attach or lock the filling aid 6004 to the filling aid base 6046 such that the filling aid 4004 may not be removed from the filling aid base 6046 unless the filling aid 4004 is rotated back. Therefore, in some embodiments, the filling aid base 6046 may remain connected the filling aid 6004 while the reservoir is being filled, but may be removed from the each other once the filling is completed. Thus, in some embodiments, the filling aid 6004 may include a locked position with respect to the filling aid base 6046 and may include an unlocked position with respect to the filling aid base 6046.

Referring now also to FIG. 236, in the embodiment shown, the needle housing 6038 locking tabs 6070, 6072 engage the filling aid base 6046. As shown, in some embodiments, the filling aid base 6046 includes a groove 6074. The locking tabs 6070, 6072 clip over the groove 6074.

In various embodiments, the ability to lock the filling aid 6004 to the filling aid base 6046 such that the connection and orientation of the filling aid 6004 with respect to the filling aid base 6046 is maintained may be accomplished using one or more mechanisms in various embodiments. For example, in the embodiments shown herein, the connection may be maintained using the locking tabs 6070, 6073 and groove 6074. However, in some embodiments, the connection and orientation may also be maintained by a tongue and groove-type connection. Or, in some embodiments, a tongue and groove-type connection may be used rather than the locking tabs 6070, 6073 and groove 6074. For example, the needle housing 6038 may include one or more groove features 6086 that accommodates one or more features on the filling aid base 6046. The filling aid base 6046 may include one or more tongue features 6088 that receive the groove feature 6086 such that the groove feature 6086 becomes "locked over" the tongue feature 6088. This arrangement is beneficial for many reasons, including, but not limited to, maintaining the orientation of the filling aid 4004 with respect to the filling adapter 6000. Although one embodiment of features for connecting or "locking" the filling aid base 6046 to the filling aid 6004 is shown, in various embodiments, other mechanisms may be used. In various embodiments, one of more features may be used. In some embodiments of the embodiment shown, there may be two groove features on the filling aid and one or more accommodating tongue features on the filling aid base. In some embodiments, a particular orientation of the tongue feature with respect to the groove feature may be required for the filling aid 6004 to connect over the filling aid base 6046. However, in various embodiments, a particular orientation for attachment may not be required.

Figure 239A:
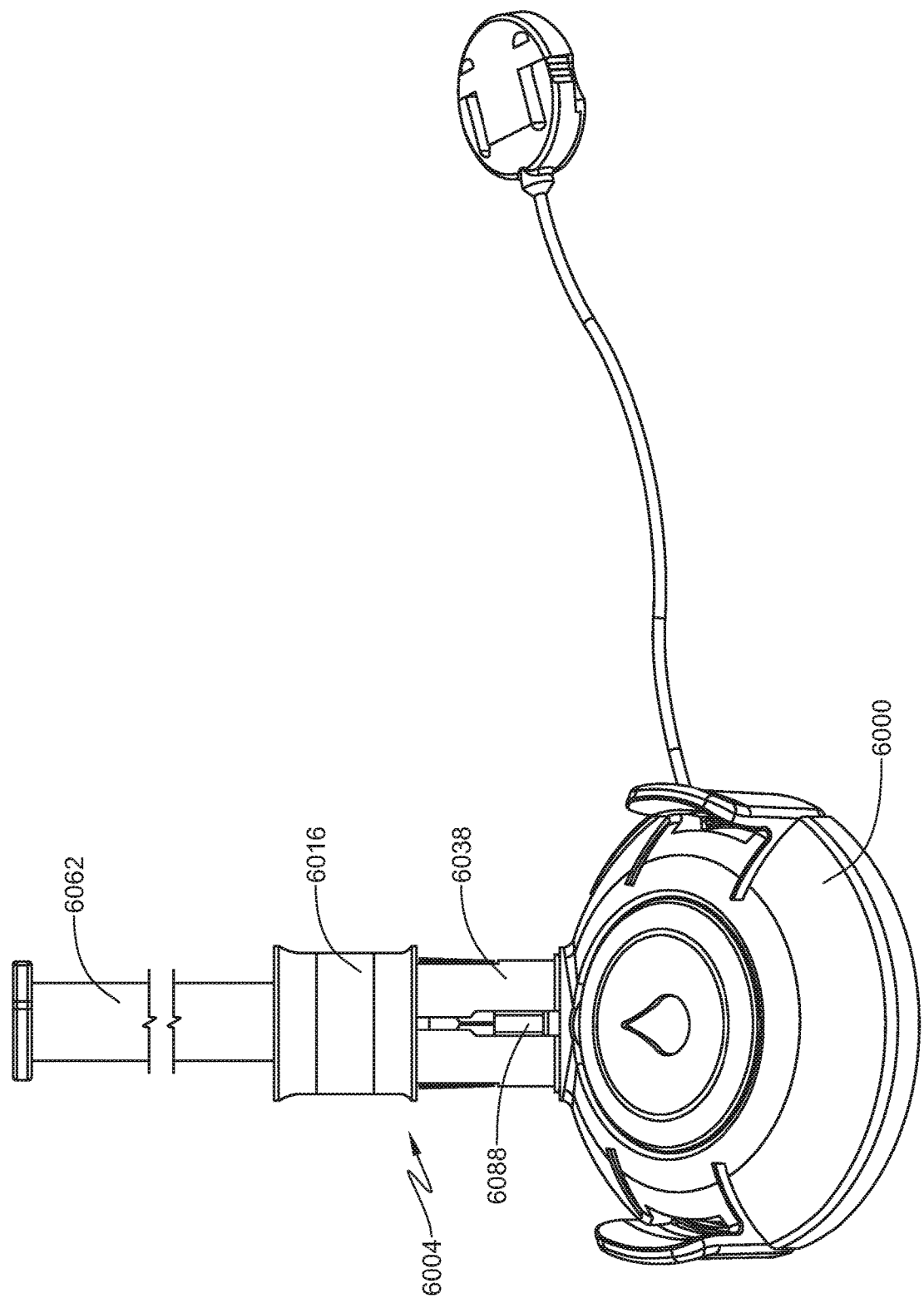
Figure 239B:
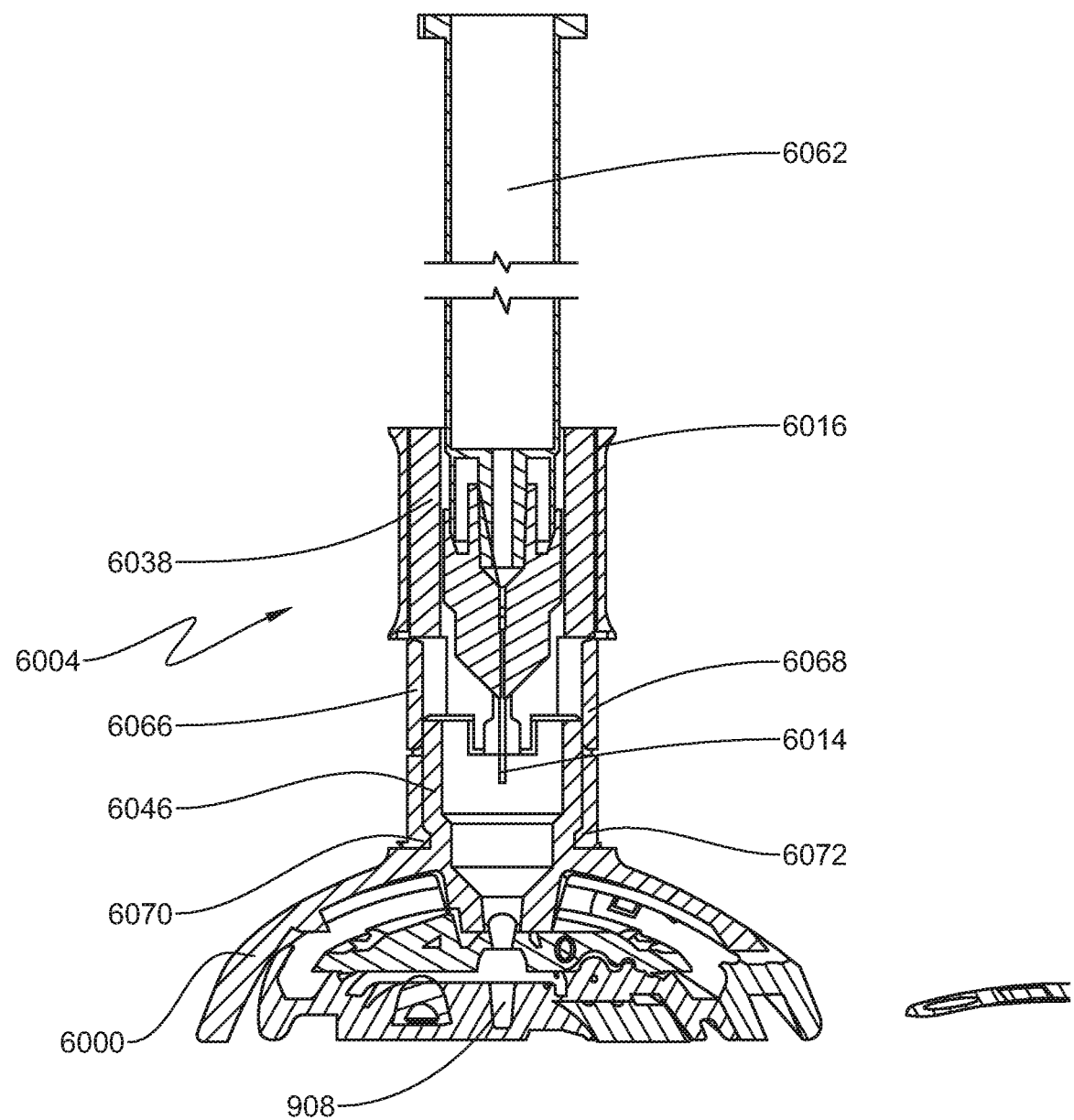

In some embodiments, when the filling aid 6004 is connected to the filling aid base 6046, the filling needle cradle 6016 may be in a starting position. The starting position means that the filling needle 6014 remains fully inside the filling needle cradle 6016 and therefore, although the filling aid 6004 is attached to the filling needle base 6046, the filling needle 6014 has not pierced the septum of the reservoir. Referring now also to FIG. 239A-239B, the filling needle cradle 6016 is in the starting position.

In some embodiments, the needle housing 6038 includes flexible tabs 6066, 6068. However, in some embodiments, more than two or less than two flexible tabs may be included. In various embodiments, when the filling needle cradle 6016 is in the starting position, the flexible tabs 6066, 6068 are in the starting position and the relationship between the flexible tabs 6066, 6068 and the filling needle cradle 6016 is such that the flexible tabs 6066, 6068 anchor the filling needle cradle 6016 in the starting position. In various embodiments, the flexible tabs 6066, 6068

As the needle housing 6038 is attached to the filling aid base 6046, the filling aid base 6046 interacts with the flexible tabs 6066, 6068 and causes the flexible tabs 6066, 6068 to flex such that the filling needle cradle 6016 may slide towards the filling aid base 6046, sliding with respect to the needle housing 6038. Thus, the filling needle cradle 6016 is prevented from sliding with respect to the needle housing 6038 until and unless the flexible tabs 6066, 6068 are flexed by the filling aid base 6046. Therefore, the filling needle 6014 is maintained within the needle housing 6038 until the filling aid 6004 is attached to the filling aid base 6046. This embodiment may be beneficial for many reasons, including, but not limited to, prevention of needle contamination and/or damage and/or prevention of unintentional needle sticks, etc.

The filling needle cradle 6016 includes orientation bars 6076 which are accommodated on the grooves 6086, 6090 of the needle housing 6038 such that the filling needle cradle 6016 may slide along the grooves 6086, 6090 and therefore the filling needle cradle 6016 is slidably engaged and/or slidaby attached to the needle housing 6038. The orientation bars 6076 additionally maintain the orientation of the filling needle cradle 6016 with respect to the needle housing 6038.

In various embodiments, to advance the filling needle 6014 towards the septum of the disposable housing assembly 6002, the needle housing 6038 flexible tabs 6066, 6068 need to be flexed by the filling aid base 6046. This, in various embodiments, advances the filling needle cradle 6016 towards the septum such that the filling needle cradle 6016 is in the filling position. In this position, the filling needle 6014 pierces the septum.

In various embodiments locking the filling aid 6004 from rotation with respect to the filling aid base 6046 when the filling needle cradle 6016 is in the filling position may be desirable for many reasons, including, but not limited to, once the filling needle 6014 pierces the septum, rotation of the filling aid 6004 with respect to the filing aid base 6046 may cause damage to the septum and/or the reservoir and/or cause leakage.

Once the filling needle 6014 pierces the septum of the disposable housing assembly 6002, the plunger portion of the filling syringe 6062 may be advanced to provide flow of fluid from the filling syringe 6062 to the reservoir 908.

Figure 237:
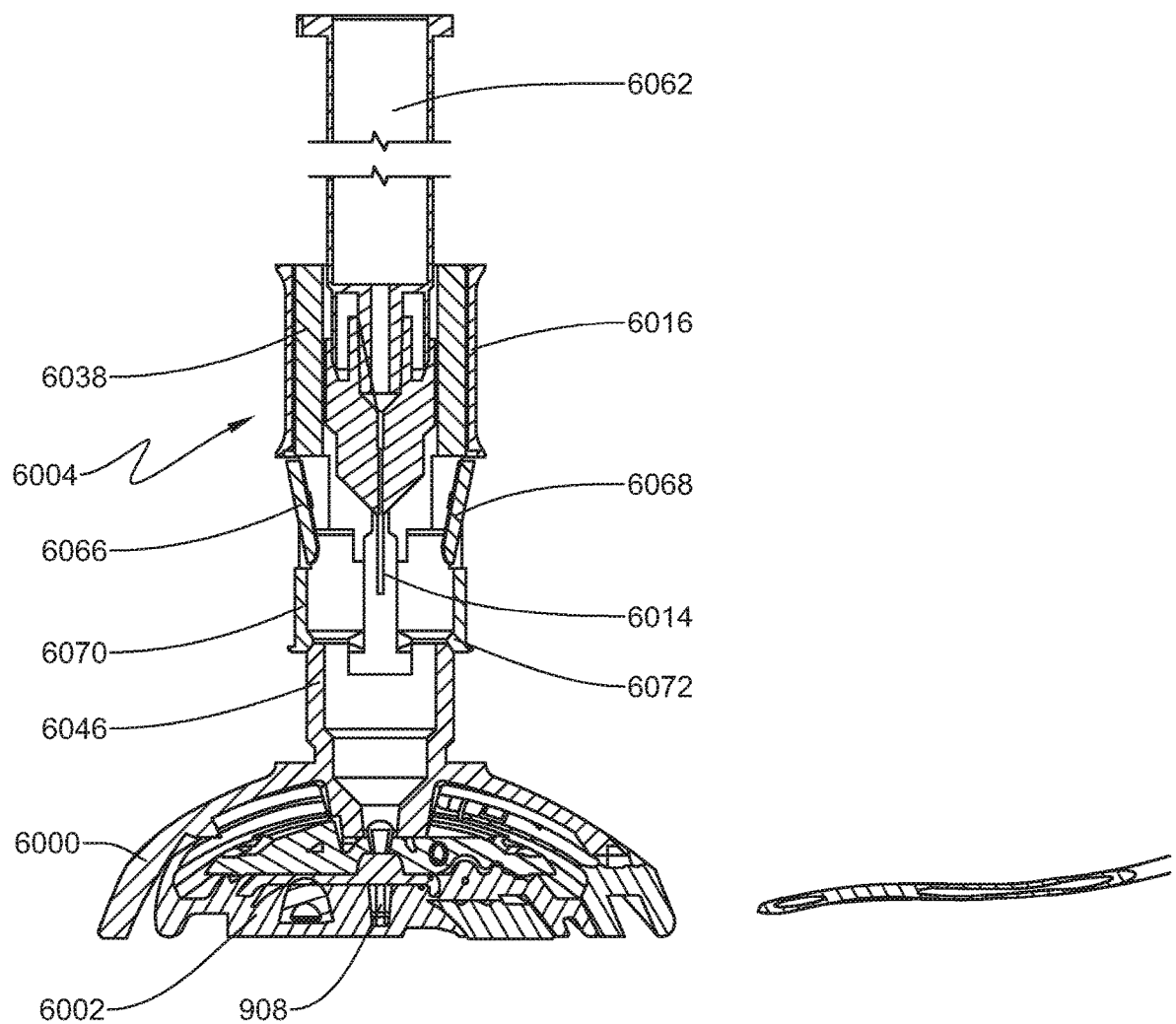
Figure 238A:
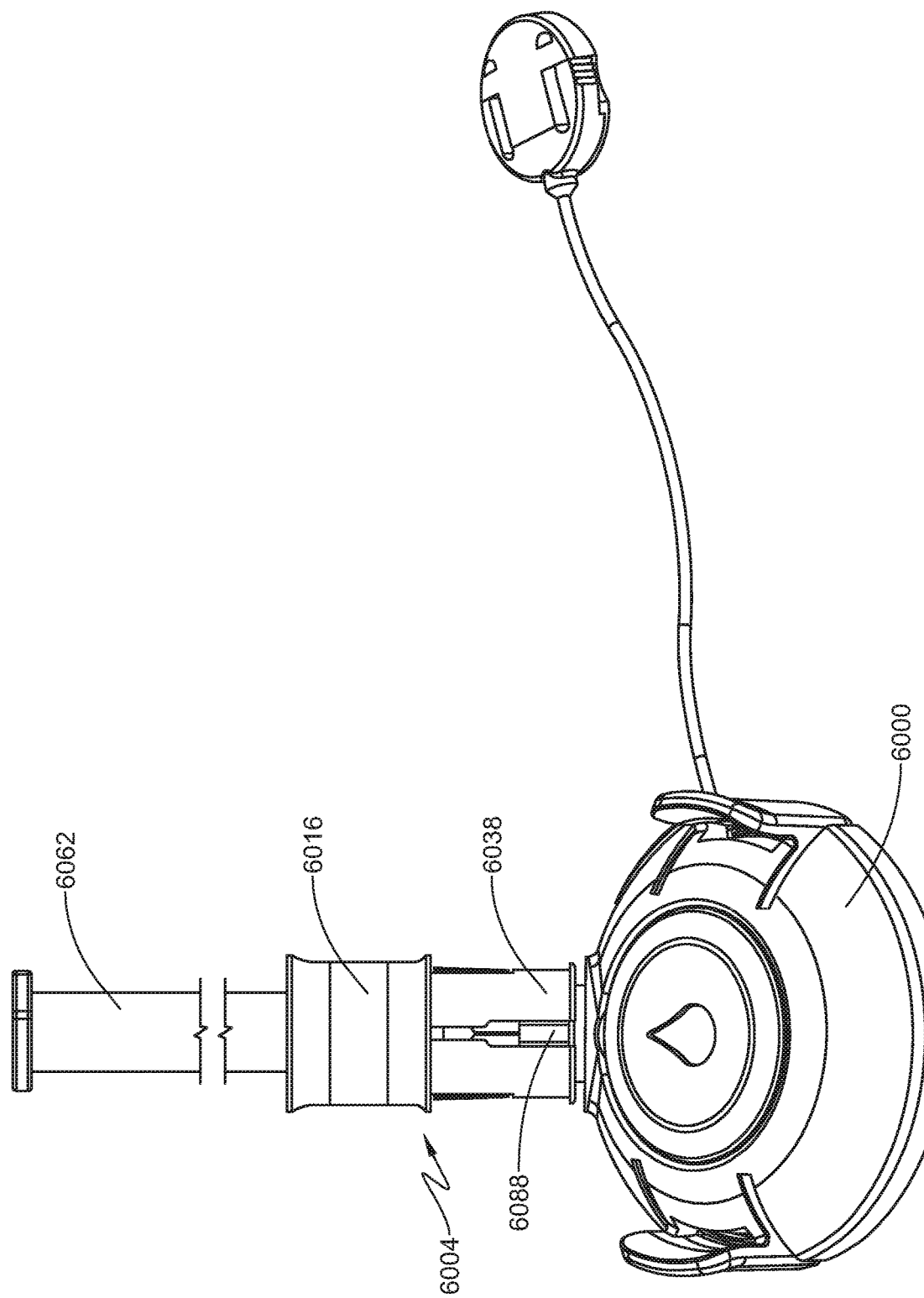
Figure 238B:
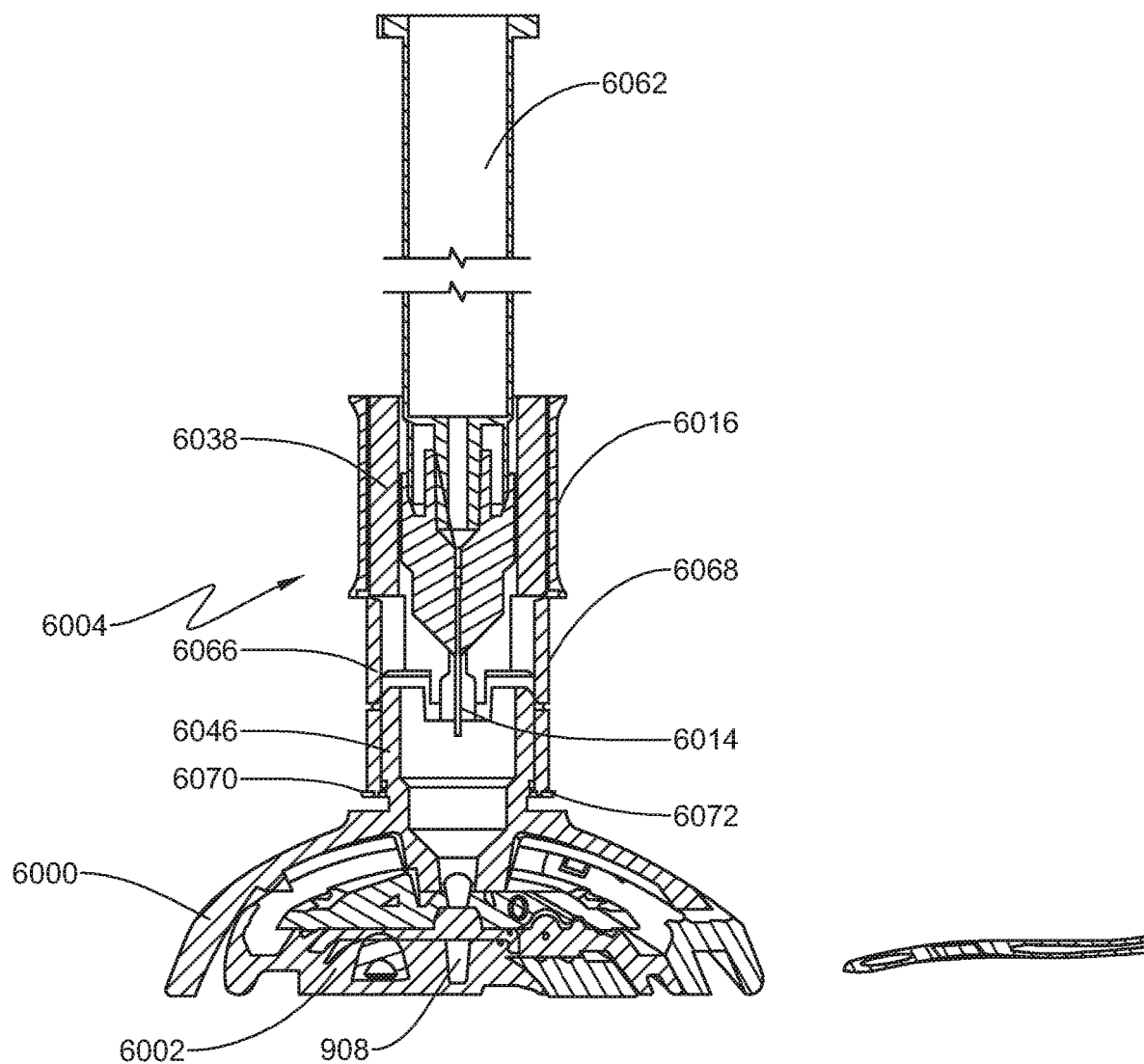
Figure 240A:
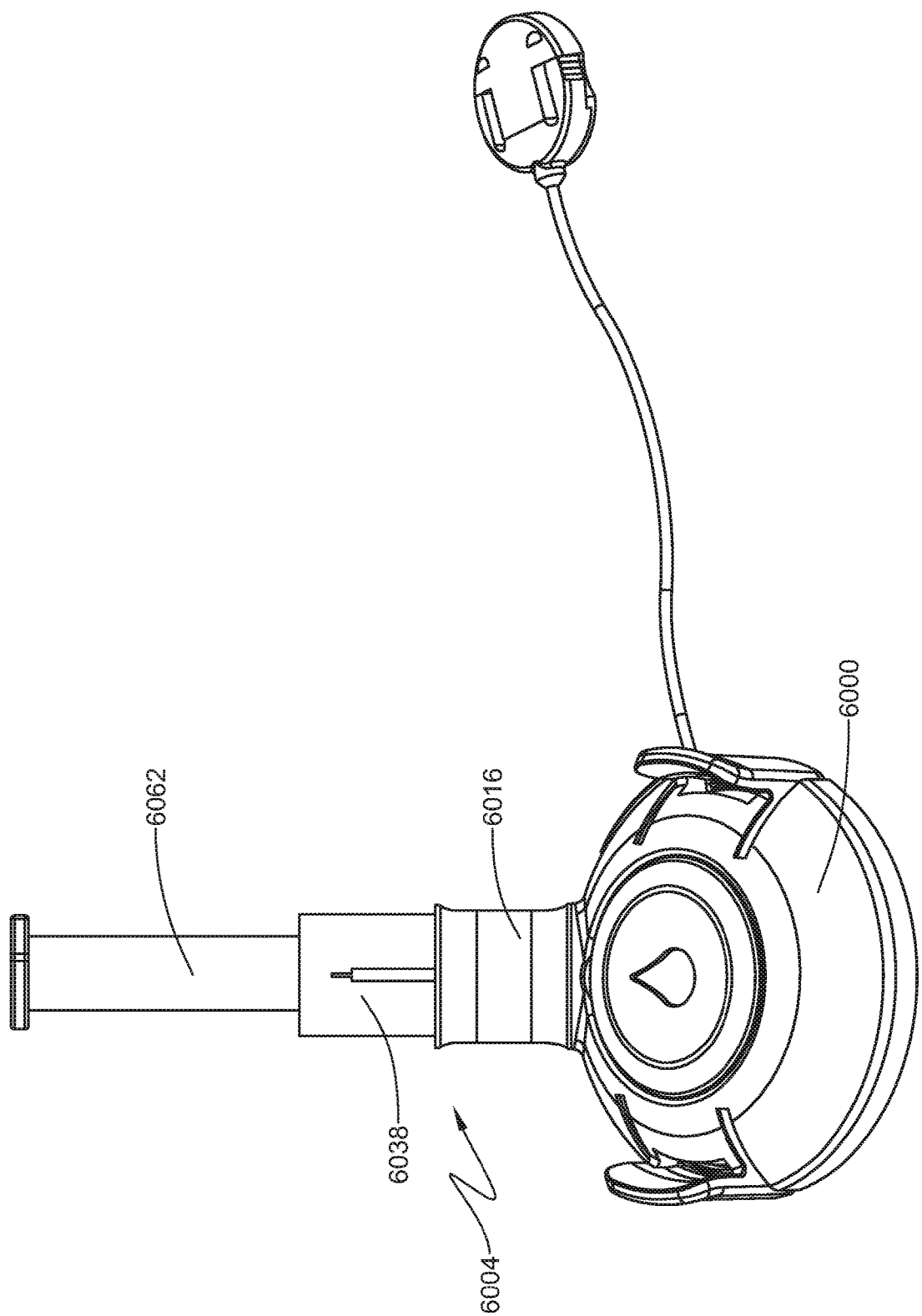
Figure 240B:
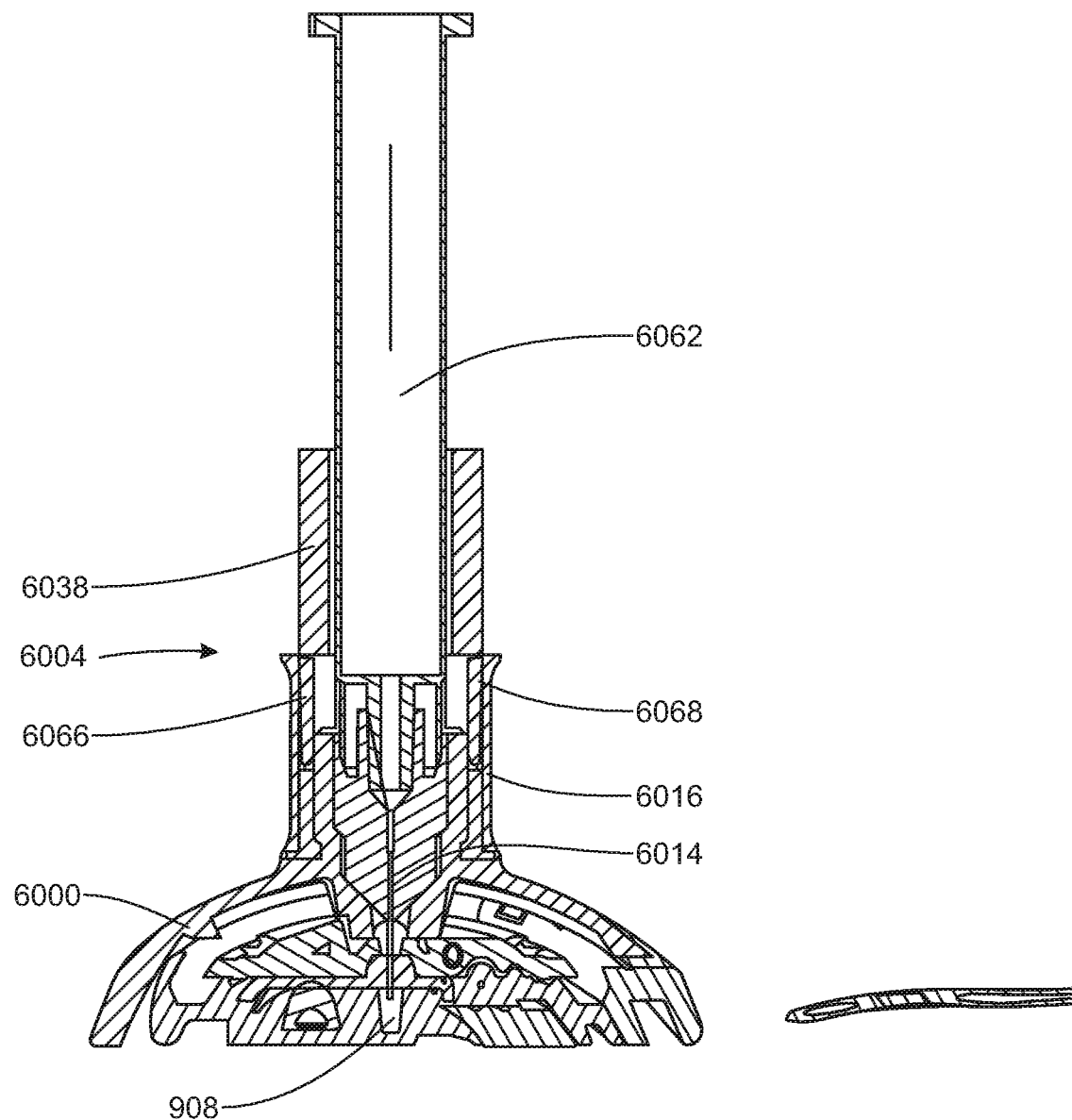

Referring now also to FIGS. 236-240B, both isometric and cross sectional views of the various stages of filling the disposable using the fill adapter 6000, filling aid 6004 and a filling syringe 6062 are shown. FIG. 236 shows the filling syringe 6062, the filling aid 4004, and the the fill adapter 6000. In FIG. 237, the filling syringe 6062 is connected to the filling aid 6004, and the filling aid 6004 is touching the filling aid base 6046, however, the flexible tabs 6066, 6068 are not flexed. The filling needle 6014 and the filling needle cradle 6016 are shown in the starting position. As shown in FIGS. 238A and 238B, the needle housing 6038 of the filling aid 6004 has advanced over the filling aid base 6046 and the flexible tabs 6066, 6068 are in the flexed position. The tabs 6070, 6072 have not clipped over the groove 6074 on the filling aid base 6046. The needle housing 6038 groove 6086 feature is shown adjacent to the tongue feature 6088 of the filling aid base 6046. FIGS. 239A and 239B show the filling aid 6004 connected to the filling aid base 6046 such that the filling aid 6004 is locked onto the filling aid base 6046. The tabs 6070, 6072 are clipped over the groove 6074 of the filling aid base 6046. The filling needle cradle 6016 remains in the starting position. FIGS. 240A and 240B show views where the filling needle cradle 6016 has advanced towards the filling aid base 6046 and the filling needle cradle 6016 is in the filling position. The filling needle 6014 has advanced and pierces the septum of the disposable assembly 6002. Once the plunger of the filling syringe 6062 is advanced, the contents of the filling syringe 6062 will flow through the filling needle 6014 and into the reservoir 908.

In various embodiments, to remove the filling aid 4004 from the filling aid base 4046, the filling needle cradle 6016 is moved from the filling position to the starting position, such that the filling aid 6004 may be removed from the filling aid base 6046. Thus, in various embodiments, the filling aid 6004 may not be removed from the filling aid base 6046 unless and until the filling needle cradle 6016 is moved to the starting position (where the filling needle 6014 is not longer outside of the needle housing 6038), and it is only in this configuration that the filling aid 6004 may be removed from the filling aid base 6046. Thus, the filling needle 6014 is not exposed outside the needle housing 6038 unless the filling aid 6004 is attached to the filling aid base 6046. In various embodiments, the filling needle cradle 6016 may be moved back to the starting position by exerting force onto the filling syringe 6062 in a direction away from the filling aid base 6046. Once the filling needle cradle 6016 reaches the starting position, the flexible tabs 6066, 6068 may spring back to the starting position on the needle housing 6038, which may, again, maintain and/or lock the filling needle cradle 6016 in the starting position. In various embodiments, when the filling needle cradle 6016 is in the starting position, the filling needle 6014 is inside the needle housing 6038, and therefore, the needle housing 6038 serves as a sharps container for the filling needle 6014. In various embodiments, the filling aid 6004 may be removed from the filling syringe 6062 or the filling aid 6004 may remain on the filling syringe 6062 for disposal.

In some embodiments, the flexible tabs 6066, 6068 and may be covered such that user action may not unlock the filling needle cradle 6016 flexible tabs 6066, 6068, i.e., only interaction between the filling aid base 6046 and the flexible tabs 6066, 6068 unlocks the filling needle cradle 6016.

In various embodiments, once the disposable housing assembly 6002 is filled to the desired volume, the fill adapter 6000 may be used to prime the disposable housing assembly 6002 in a fashion similar to those described in one or more embodiments herein.

Still referring to FIGS. 240A-240B, in some embodiments, in practice, following the filling of the reservoir 908, the filling syringe 6062 may be removed from the filling aid 6004. The fill adapter 6000 remains in the locked position with respect to the disposable housing assembly 6002 (see FIG. 230). In some embodiments, it may be desirable to "prime" the fluid lines in the disposable housing assembly 6002, i.e., to force fluid from the reservoir 908 through the fluid path and through the exit such that air is purged from the fluid path and replaced with fluid. The button assemblies 6031, 6032, 6033, 6034, 6035, 6036, 6037, 6038, of the fill adapter 6000, when actuated by the button assembly actuator 6046, apply pressure onto the reservoir membrane and force fluid out of the reservoir and into the fluid path.

Referring now also to FIG. 226A, the button assembly actuator 6046 is springedly attached by at least one spring assembly 6092 to the remainder of the filling aid 6000 such that upon force being applied to the button assembly actuator 6046, the button assembly actuator 6046 is depressed into the cavity portion of the filling aid 6000. Upon the disposable housing assembly 6002 being engaged with the filling aid 6000, upon force being applied to the button assembly actuator 6046, the button assembly actuator 6046 is depressed into the cavity portion of the filling aid 6000 and the button assemblies 6031, 6032, 6033, 6034, 6035, 6036, 6037, 6038 interact with the apertures 6039, 6040, 6041, 6042, 6043, 6044, 6045, 6047 on the disposable housing assembly 6002. As force continues to be applied to the button assembly actuator 6046, the disposable housing assembly 6002 will be primed with fluid from the reservoir 908.

Referring now also to FIGS. 241A and 241B, in some embodiments, the fill adapter 7000 may include "scalloped" edges which may be desirable for many reasons, including, but not limited to, ergonomic handling of the fill adapter 7000. Another embodiment of the filling aid 7004 is shown attached to a filling syringe 6062. In some embodiments, the button assembly actuator 7046 may actuate button assemblies 7032, 7034, 7036. In some embodiments, the button assembly actuator 7046 may include a pump chamber plunger 6050, which functions as discussed above with respect to various embodiments where the button assembly actuator 7046 includes a pump chamber plunger 6050. Various embodiments of the fill adapter 7000 may include icons to indicate the direction to rotate the fill adapter 7000 with respect to the disposable housing assembly 6002. For example, in some embodiments, the fill adapter 7000 may include "locked" and/or "unlocked" icons and/or directional "arrows" to indicate the direction rotate the fill adapter 7000 with respect to the disposable housing assembly 6002. In some embodiments of this embodiment of the fill adapter 7000, the fill adapter 7000 may include locking tabs 7052 to lock the fill adapter 7000 to the disposable housing assembly 6002.

Referring now also to FIG. 242A-242E, in some embodiments, the fill adapter 8000 may include a top portion 8010, including a button assembly actuator 8046 and a catch feature 8008, and a bottom portion 8012, including a locking feature 8006, wherein the top portion 8010 and bottom portion 8012 are hingably connected. The disposable housing assembly 6002 may be inserted between the top portion 8010 and bottom portion 8012 and the top portion 8010 and bottom portion 8012 may move towards one another by applying force either to one with respect to the other, or to both the top portion 8010 and the bottom portion 8012, such that the fill adapter 8000 is in a closed position. In the closed position, the locking feature 8006 on the bottom portion 8012 interlocks with the catch feature 8008 to maintain the fill adapter 8000 in the closed/locked positions. Once the reservoir has been filled as desired, the button assembly actuator 8046 may be pressed to prime the disposable housing assembly as described herein. In various embodiments, once the filling aid 6004 is attached to the fill adapter 8000 in the closed position, the fill adapter 8000 may not be unlocked/opened as the filling aid interferes with releasing the catch feature 8008. This may be desirable for many reasons, including, but not limited to, preventing the removal of the disposable housing assembly while the filling needle 8014/filling syringe 8062 is engaged with the septum in the reservoir. This may prevent unintentional tearing of the septum or other damage.

In some embodiments, the fill adapter 8000 may include a foot 8014 which may provide the fill adapter 8000 in an angled position above horizon. This may be desirable/beneficial for many reasons, including, but not limited to, air management and/or holding the fill adapter 8000 at an ergonomic angle for filling by a user.

Figure 242A:
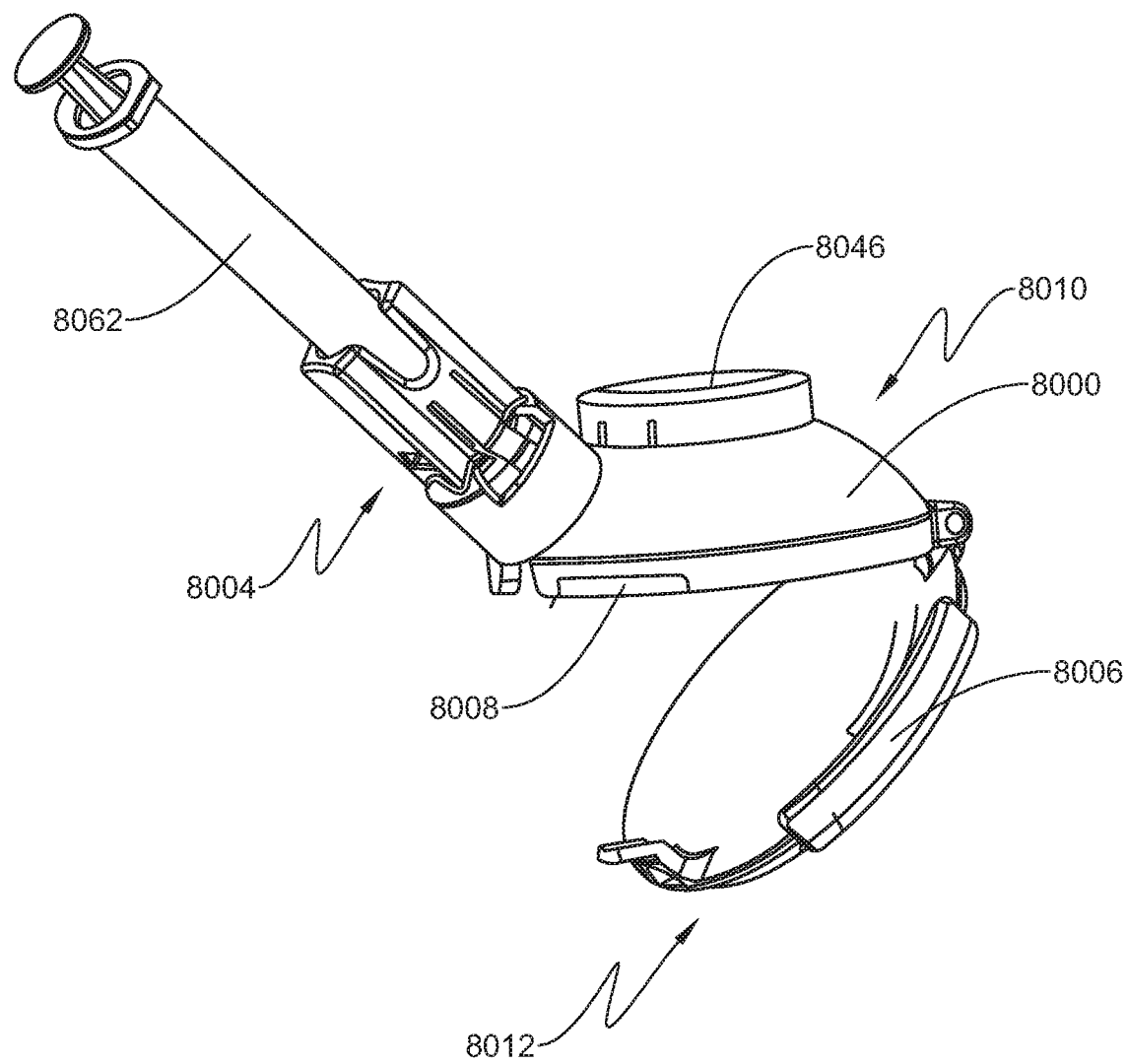
Figure 242B:
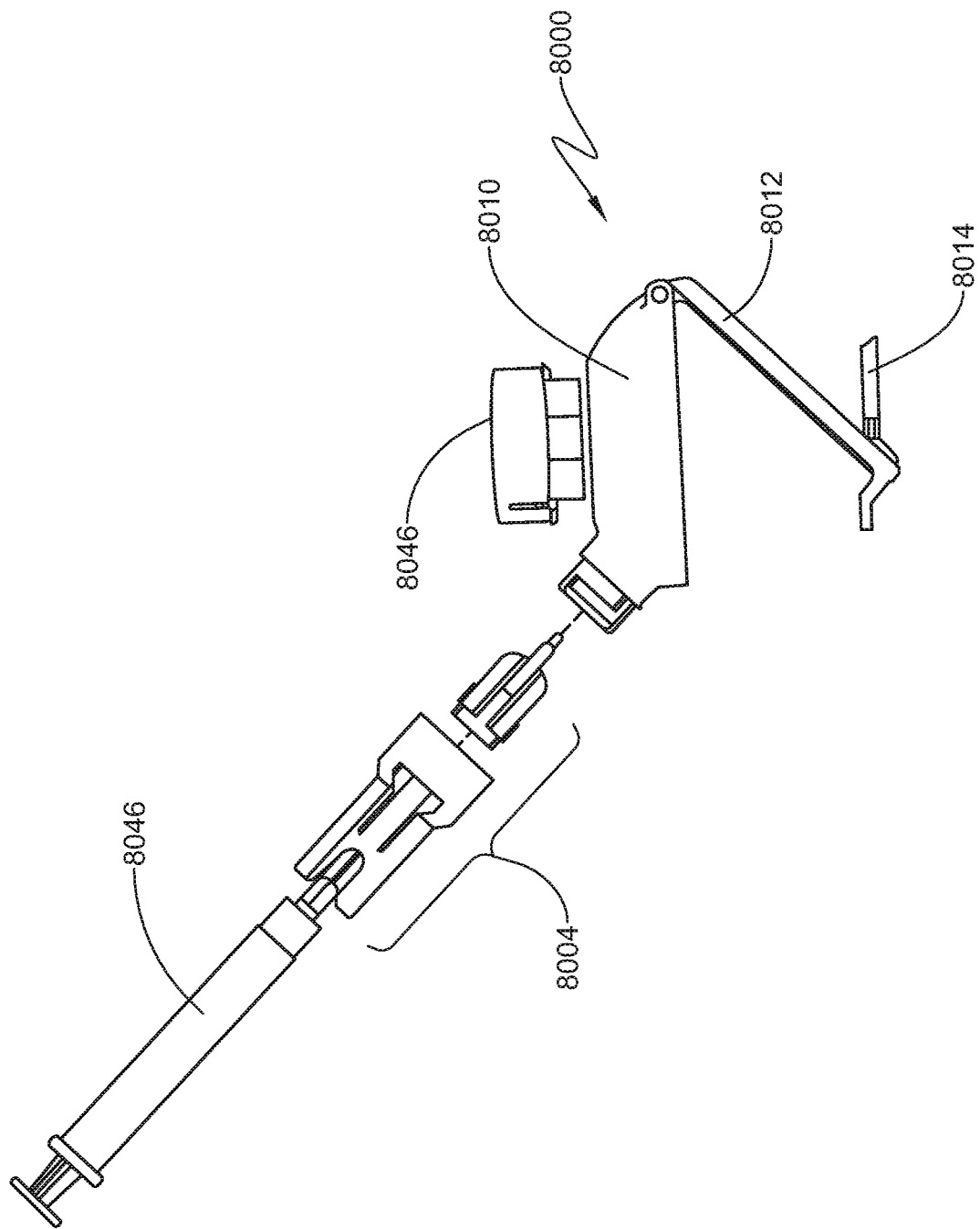
Figure 242C:
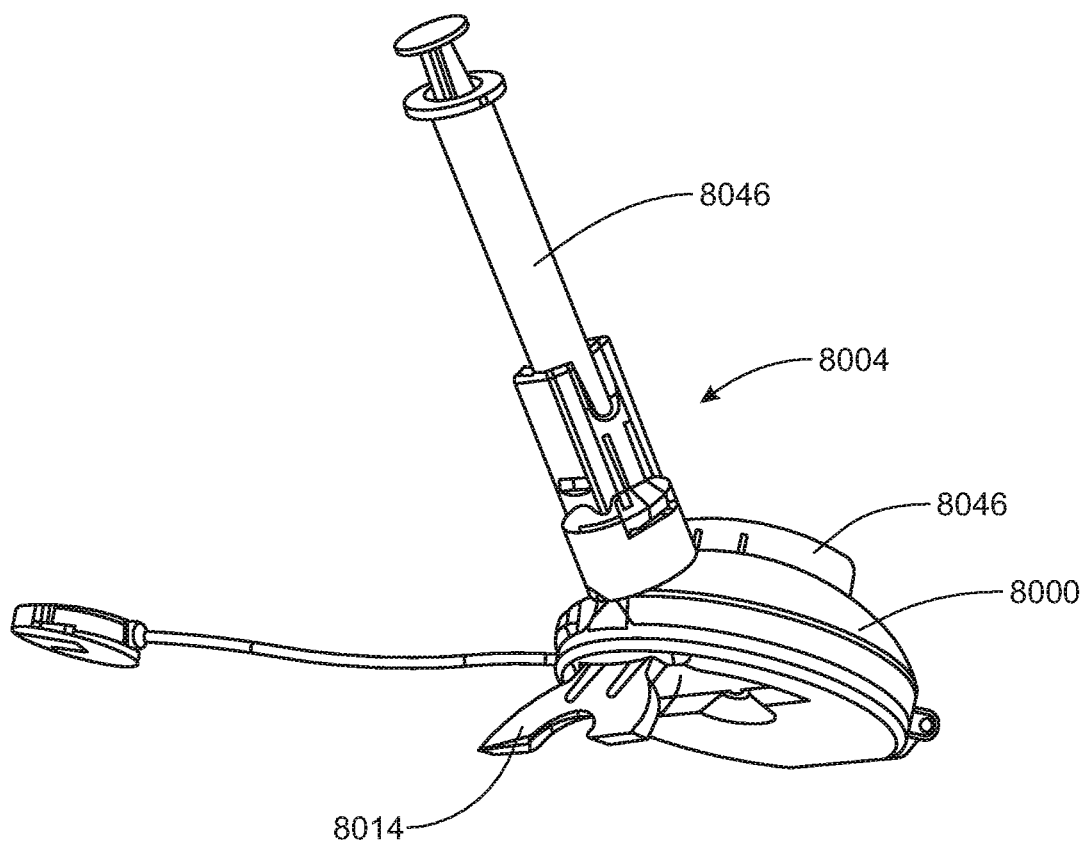
Figure 242D:
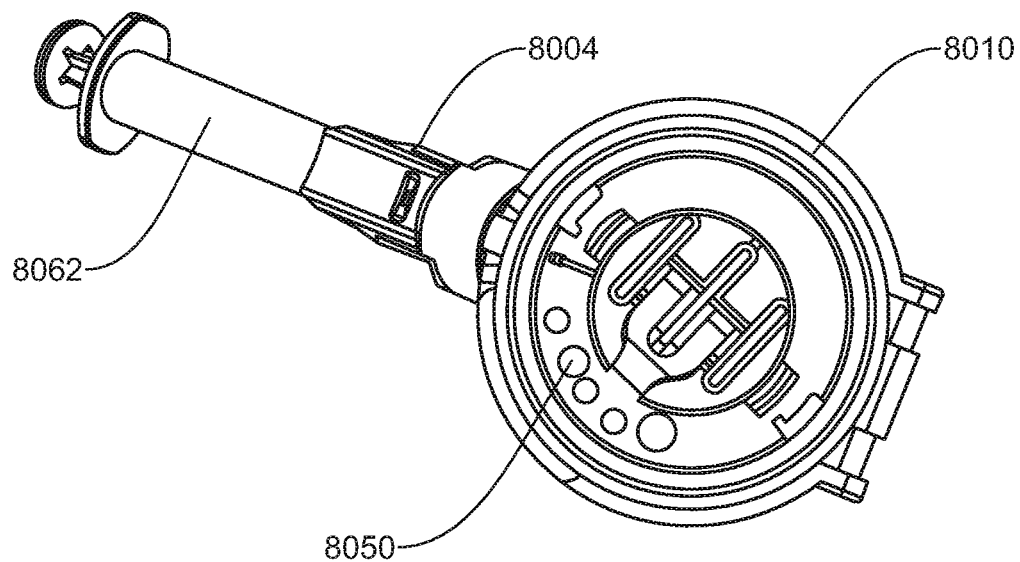
Figure 242E:
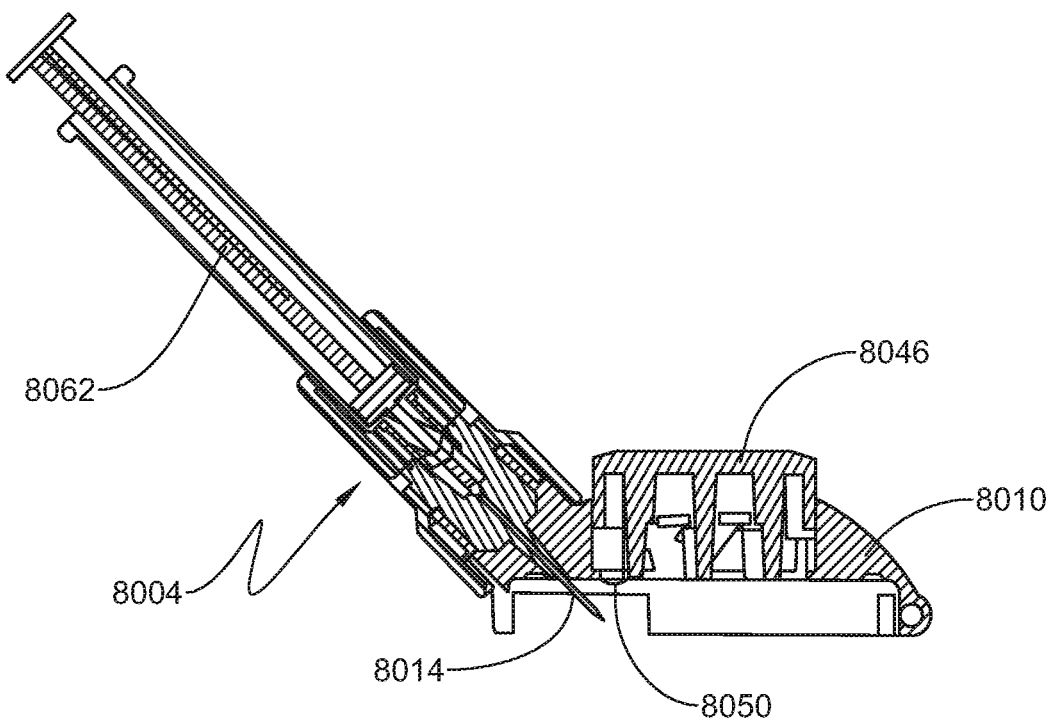

The underside of the top portion 8010 of the fill adapter 8000 is shown in FIG. 242D. The underside includes a pump chamber plunger 8050 which works as discussed above with respect to the embodiment shown in FIG. 226A.

Referring now also to FIGS. 243A-243B, another embodiment of the fill adapter 9000 is shown. In this embodiment, the fill adapter 9000 includes guide features 9032 to guide the button assemblies.

Referring now also to FIGS. 244A-244F, another embodiment of the filling aid 9004 is shown. In this embodiment, the filling aid 9004 is configured to receive a filling syringe (not shown, shown as 9062 in FIGS. 245A-245B), which includes a filling needle (not shown, shown as 9014 in FIG. 245A) attached to the filling syringe 9062. The filling aid 9004 in this embodiment includes a filling needle cradle 9016

In some embodiments, the needle housing 9038 may include one or more of the features described above with respect to various embodiments of the needle housing. However, in the embodiment shown in FIGS. 244A-244F, the needle housing 9038 includes needle housing locking features 9066 which interact with the filling needle cradle 9016 to lock the filling needle cradle 9016 either in a starting or filling position. The filling needle cradle 9016 may be unlocked from its position by rotating the filling needle cradle 9016 with respect to the needle housing 9038.

In various embodiments, the filling needle cradle 9016 includes filling needle cradle ribs 9060 which capture the filling syringe 9062 and maintain the filling syringe 9062 in an attached position with respect to the filling needle cradle 9016.

In various embodiments, the filling needle cradle 9016 also includes a stop feature 9068 which limits the distance the filling syringe 9062 may travel within the filling needle cradle 9016. However, the filling needle 9014 itself may travel through the stop feature 9068.

Referring now also to FIGS. 245A-248, in practice, the filling syringe 9062 is attached to the filling aid 9004 by pressing the filling syringe 9062 through the opening of the filling aid 9004. The filling needle 9014 cap may then be removed. Next, the filling aid 9004 is attached to a vial of fluid 9080 by using the end tabs of the needle housing. The vial of fluid may contain e.g., therapeutic fluid, e.g., insulin. The filling needle 9014 may penetrate the septum 9082 and the fluid may flow from the vial 9080 to the filling syringe 9062 by way of the filling needle 9014. Once a desired volume of fluid flows from the vial 9080 to the filling syringe 9062, the vial 9080 may be removed from the needle housing 9038, e.g., by exerting opposing force onto the needle housing 9038 and the vial 9080 so as to disconnect the end tabs of the needle housing 9038 from the vial 9080.

These embodiments may be advantageous, beneficial and/or desirable for many reasons including that the filling needle 9014 remains inside the needle housing 9038 while the filling syringe 9062 is being filled by the fluid from the vial 9080. Therefore, the likelihood of unintentional needle pricks and/or contamination is minimized and/or reduced. Thus, in various embodiments, the filling needle cradle 9016 remains in the starting position (see FIGS. 245A and 245B) while the filling aid 9004 is attached to a vial 9080.

Although the embodiments are described above with respect to a "vial" in some embodiments, the filling aid 9004 may be used in conjunction with any source of fluid, which may include, but is not limited to, a bag of fluid.

In various embodiments, once the filling syringe 9062 is removed from the vial 9080, the filling syringe 9062, still attached to the filling aid 9004 may then be connected to the filling aid base 9046. In some embodiments, connection of the filling aid 9004 to the filling aid base 9046 may be made by sliding the filling aid 9004 over the filling aid base 9046. Thus, in various embodiments, the filling aid base 9046 may include a smaller diameter than the filling aid 9004 such that the filling aid base 9046 may be received by the filling aid 9004.

In some embodiments, the connection between the filling aid 9004 and the filling aid base 9046 may include the filling aid 9004 sliding onto the filling aid base 9046 and then the filling aid 9004 being rotated with respect to the filling aid base 9046. In some embodiments, the rotation may attach or lock the filling aid 9004 to the filling aid base 9046 such that the filling aid 9004 may not be removed from the filling aid base 9046 unless the filling aid 9004 is rotated back. Therefore, in some embodiments, the filling aid base 9046 may remain connected the filling aid 9004 while the reservoir is being filled, but may be removed from the each other once the filling is completed. Thus, in some embodiments, the filling aid 9004 may include a locked position with respect to the filling aid base 9046 and may include an unlocked position with respect to the filling aid base 9046.

In some embodiments, when the filling aid 9004 is connected to the filling aid base 9046, the filling needle cradle 9016 may be in a starting position. The starting position means that the filling needle 9014 remains fully inside the filling needle cradle 9016 and therefore, although the filling aid 9004 is attached to the filling needle base 9046, the filling needle 9014 has not pierced the septum of the reservoir. Referring now also to FIG. 247, the filling needle cradle 9016 is in the starting position.

In some embodiments, the needle housing 9038 includes needle housing locking features 9066. In various embodiments, when the filling needle cradle 9016 is in the starting position, the needle housing locking features 9066 are in the starting position and the relationship between the needle housing locking features 9066 and the filling needle cradle 9016 is such that the needle housing locking features 9066 anchor the filling needle cradle 9016 in the starting position.

As the needle housing 9038 is attached to the filling aid base 9046, to unlock the needle housing locking features 9066, the filling needle cradle 9016 may be rotated and unlocked. The filling needle cradle 9016 may then slide towards the filling aid base 9046, sliding with respect to the needle housing 9038. Thus, the filling needle cradle 9016 is prevented from sliding with respect to the needle housing 9038 until and unless it is rotated. Therefore, the filling needle 9014 is maintained within the needle housing 9038 until the filling aid 9004 is attached to the filling aid base 9046. This embodiment may be beneficial for many reasons, including, but not limited to, prevention of needle contamination and/or damage and/or prevention of unintentional needle sticks, etc.

In various embodiments, to advance the filling needle 9014 towards the septum of the disposable housing assembly 9002, the filling needle cradle 9016 needs to be rotated, unlocking with respect to the needle housing locking features 9066 This, in various embodiments, advances the filling needle cradle 9016 towards the septum such that the filling needle cradle 9016 is in the filling position. In this position, the filling needle 9014 pierces the septum (see FIG. 248)

In various embodiments locking the filling aid 9004 from rotation with respect to the filling aid base 9046 when the filling needle cradle 9016 is in the filling position may be desirable for many reasons, including, but not limited to, once the filling needle 9014 pierces the septum, rotation of the filling aid 9004 with respect to the filing aid base 9046 may cause damage to the septum and/or the reservoir and/or cause leakage.

Once the filling needle 9014 pierces the septum of the disposable housing assembly 9002, the plunger portion of the filling syringe 9062 may be advanced to provide flow of fluid from the filling syringe 9062 to the reservoir 908.

In various embodiments, the disposable housing assembly 9002 may have a tubing assembly 9090 and/or a tubing assembly 9090 connected to a cannula assembly 9092 (which, in some embodiments, may be a connection to a cannula assembly) attached.

In various embodiments, the fill adapter may be a reusable portion and the filling aid and filling syringe may be disposable/limited (e.g., one time) use portions. In some embodiments, the disposable housing assembly may be packaged with a filling aid and/or with a filling syringe. In some embodiments, the fill adapter may be packaged with a predetermined number of filling aids and/or with a predetermined number of filling syringes, e.g., 1 fill adapter packaged with 10 filling aids and 10 disposable housing assemblies. These numbers are examples only, and in various embodiments, the numbers may vary including being higher or lower than the examples given.

Referring now also to FIGS. 249A-249F, another embodiment of the filling aid 9100 is shown. In this embodiment, the filling aid 9100 is configured to receive a filling syringe (not shown, shown as 9132 in FIGS. 252A-252D and FIGS. 254A-254C), which includes a filling needle (not shown, shown as 9134 in FIG. 252A) attached to the filling syringe 9132. The filling aid 9100 in this embodiment includes a filling syringe holder 9102, which includes a filling needle cradle portion 9106 and a frame portion 9108. In various embodiments, the frame portion 9108 maintains the filling syringe such that it is attached to the filling aid 9100 and is not pulled out of the filling aid 9100. In some embodiments, the frame portion 9108 includes a half moon portion 9110 that accommodates the sliding portion of the filling syringe and also, provides a stop for the filling syringe such that if a user applies force in a direction opposite from the filling needle cradle portion 9106, the filling syringe will not be pulled out from the filling aid 9100. However, in various other embodiments, this portion may be shaped differently and some embodiments of the frame portion 9108 may not include a half moon (or differently shaped) portion 9110. In some embodiments, the filling syringe holder 9102 also include grips 9112, 9114 which, in various embodiments, may be shaped to ergonomically accommodate a portion of a user's thumb and forefinger. Some embodiments of the grips 9112, 9114 may include gripping features 9116 that may provide better traction for gripping the grips 9112, 9114. In various other embodiments, different features may be used, which may include, but is not limited to, ribs, raised circular features, embossed features and/or any type of feature in any shape and any quantity desired.

In some embodiments, the filling aid 9100 also includes a locking portion 9104 which may include one or more of the features described above with respect to various embodiments of the needle housing. In various embodiments, the filing syringe holder 9106 is slidably attached to the locking portion 9104, wherein, in various embodiments, the locking portion 9104 includes a groove feature 9130 on each side of the locking portion 9104 which accommodates a tongue feature 9128 from the filling needle cradle portion 9106 of the filling syringe holder 9102. These features work together to maintain the orientation of the locking portion 9104 with respect to the filling syringe holder 9102 and also, to provide a slidable relationship between the locking portion 9104 and the filling syringe holder 9102.

In the embodiments shown in FIGS. 249A-251B, the locking portion 9104 includes locking features 9118 which interact with the filling syringe holder 9102 to lock the filling syringe holder 9102 either in a starting or filling position, with respect to the locking portion 9104. The filling syringe holder 9102 may be unlocked from its position by attaching the filling aid 9100 onto the filling aid base 9142. As the locking portion 9104 is attached to the filling aid base 9142, the locking features 9118 move to an unlocked position and the filling syringe holder 9102 may slide towards the filling aid base 9142. This occurs when the locking features 9118 are pushed out by the filling aid base 9142, which allows the filling syringe holder 9102 to become unlocked and slide with respect to the locking portion 9104.

Still referring to FIGS. 249A-251B, in various embodiments, the filling syringe holder 9102 includes a filling syringe cradle portion 9106 which includes filling needle cradle ribs 9124 which capture the filling syringe 9132 and maintain the filling syringe 9132 in an attached position with respect to the filling needle cradle 9106.

In various embodiments, the filling needle cradle 9106 also includes a stop feature 9126 which limits the distance the filling syringe 9132 may travel within the filling needle cradle 9016. However, the filling needle 9134 itself may travel through the stop feature 9126.

In various embodiments, once the filling syringe 9132 is attached to the filling aid 9100, the filling needle 9134 is attached to the end of the filling syringe 9132. In some embodiments, attaching the filling needle 9134 to the filling syringe 9132 may be done using a rotating motion. In some embodiments, the filling needle 9134 is attached to the filling syringe 9132 using a lure connection and is pressed onto the filling syringe 9132. However, in various other embodiments, any mechanism for attachment of a filling needle 9134 to a filling syringe 9132 may be used. In some embodiments, the filling needle 9134 is already attached to the filling syringe 9132.

Still referring to FIGS. 249A-251B, in various embodiments, the locking portion 9104 includes one or more tab features 9120. In various embodiments, the locking portion 9104 may include four tab features 9120 (two of which are shown in FIGS. 251A-251B). The tab features 9120 interact with either a vial (shown as 9136 in FIG. 252A) or a filling aid base 9142 and grip either the vial or filling base to secure the filling aid 9100 onto either the vial or the filling base. In various embodiments, the locking portion 9104 includes a syringe support 9122 which, in various embodiments, supports the filling syringe and, together with the frame portion 9108 of the filling syringe holder 9102, maintains the position of the filling syringe with respect to the filling aid 9100. These features prevent the filling syringe from moving with respect to the filling aid 9100 and therefore, maintain alignment of the filling needle 9134 with respect to the septum in the disposable housing assembly 9002.

Referring now also to FIGS. 252A-252D, in practice, the filling syringe 9132 is attached to the filling aid 9100. In some embodiments, the filling needle 9134 may be attached to the filling syringe 9132, however, in some embodiments, the filling needle 9134 may have already been attached to the filling syringe 9132, for example, at manufacture. The cap (not shown) of the filling needle 9134 may then be removed. Next, the filling aid 9100 is attached to a vial of fluid 9136 by using the tabs features 9120 of the locking portion 9104. The vial of fluid may contain e.g., therapeutic fluid, e.g., insulin. The filling needle 9134 may penetrate the septum 9138 and the fluid may flow from the vial 9136 to the filling syringe 9132 by way of the filling needle 9134. Once a desired volume of fluid flows from the vial 9136 to the filling syringe 9132, the vial 9136 may be removed from the locking portion 9104, e.g., by exerting opposing force onto the locking housing 9104 and the vial 9136 so as to disconnect the tabs features 9120 of the locking portion 9104 from the vial 9136.

These embodiments may be advantageous, beneficial and/or desirable for many reasons including that the filling needle 9134 remains inside the locking portion 9104 while the filling syringe 9132 is being filled by the fluid from the vial 9136. Therefore, the likelihood of unintentional needle pricks and/or contamination is minimized and/or reduced. Thus, in various embodiments, the filling syringe holder 9102 remains in the starting and/or locked position while the filling aid 9100 is attached to a vial 9136.

Although the embodiments are described above with respect to a "vial" in some embodiments, the filling aid 9100 may be used in conjunction with any source of fluid, which may include, but is not limited to, a bag of fluid.

Referring now also to FIGS. 253A-254C, in various embodiments, once the filling syringe 9132 is removed from the vial 9136, the filling syringe 9132, still attached to the filling aid 9100 may then be connected to the filling aid base 9142 of the fill adapter 9140. The fill adapter 9140 may be connected to a disposable housing assembly 9002 (which, in various embodiments, includes a tubing and a cannula connection or a cannula at the end of the tubing). The fill adapter 9140 may be any one of the various embodiments of fill adapters described and shown herein. Further, in various embodiments, the fill adapter 9140 may be modified to include the embodiment of the filling aid base 9142 shown in FIGS. 253A-254C. In some embodiments, connection of the filling aid 9100 to the filling aid base 9140 may be made by sliding the filling aid 9100 over the filling aid base 9142. Thus, in various embodiments, the filling aid base 9142 may include a smaller diameter than the filling aid 9100 such that the filling aid base 9142 may be received by the filling aid 9100.

In some embodiments, the connection between the filling aid 9100 and the filling aid base 9142 may include the filling aid 9100 sliding onto the filling aid base 9142. The tab features 9120 slide over a groove on the filling aid base 9142. The filling aid base then interacts with the locking features 9118 and the locking features 9118 are moved to their unlocked position. The filling syringe holder 9102 then slides over the locking portion 9104 and towards the filling aid base 9142. At this point, the filling aid 9100 is attached or locked to the filling aid base 9142 such that the filling aid 9100 may not be removed from the filling aid base 9142 unless the filling aid 9100 is pulled back from the filling aid base 9142. Therefore, in some embodiments, the filling aid base 9142 may remain connected the filling aid 9100 while the disposable housing assembly 9002 reservoir 908 is being filled, but may be removed from each other once the filling is completed. Thus, in some embodiments, the filling aid 9100 may include a locked position with respect to the filling aid base 9142 and may include an unlocked position with respect to the filling aid base 9142.

In some embodiments, when the filling aid 9100 is connected to the filling aid base 9142, the filling needle cradle portion 9106 may be in a starting position. The starting position means that the filling needle 9134 remains fully inside the filling needle cradle portion 9106 and therefore, although the filling aid 9100 is attached to the filling needle base 9142, the filling needle 9134 has not pierced the septum of the reservoir 908. Referring now also to FIG. 954B, the filling needle cradle portion 9106 is in the starting position.

In various embodiments, when the filling needle cradle portion 9106 is in the starting position, the locking features 9118 are in the starting position and the relationship between the locking features 9118 and the filling needle cradle portion 9106 is such that the locking features 9118 anchor the filling needle cradle portion 9106 in the starting position.

As the locking portion 9104 is attached to the filling aid base 9142, to unlock the locking features 9118, the filling aid base 9142 interacts with the locking features 9118 such that they are moved to the unlocked position. The filling needle cradle portion 9106 may then slide towards the filling aid base 9142, sliding with respect to the locking portion 9104. Thus, the filling needle cradle portion 9106 is prevented from sliding with respect to the locking portion 9104 until and unless the locking portion 9104 is attached to the filling aid base 9142. Therefore, the filling needle 9134 is maintained within the filling needle cradle portion 9106 until the filling aid 9100 is attached to the filling aid base 9142. This embodiment may be beneficial for many reasons, including, but not limited to, prevention of needle contamination and/or damage and/or prevention of unintentional needle sticks, etc.

In various embodiments, to advance the filling needle 9134 towards the septum of the disposable housing assembly 9002, the filling needle cradle portion 9106 needs to be unlocked with respect to the locking portion 9104. This, in various embodiments, advances the filling needle cradle portion 9106 towards the septum such that the filling needle cradle portion 9106 is in the filling position. In this position, the filling needle 9134 pierces the septum of the reservoir 908 of the disposable housing assembly 9002.

In various embodiments locking the filling aid 9100 from movement with respect to the filling aid base 9142 when the filling needle cradle portion 9106 is in the filling position may be desirable for many reasons, including, but not limited to, once the filling needle 9134 pierces the septum, movement or rotation of the filling aid 9100 with respect to the filing aid base 9142 may cause damage to the septum and/or the reservoir and/or cause leakage.

Once the filling needle 9134 pierces the septum of the disposable housing assembly 9002, the plunger portion of the filling syringe 9132 may be advanced to provide flow of fluid from the filling syringe 9132 to the reservoir 908 of the disposable housing assembly 9002.

In various embodiments, the disposable housing assembly 9002 may have a tubing assembly 9090 and/or a tubing assembly 9090 connected to a cannula assembly 9092 (which, in some embodiments, may be a connection to a cannula assembly) attached.

In various embodiments, the fill adapter may be a reusable portion and the filling aid and filling syringe may be disposable/limited (e.g., one time) use portions. In some embodiments, the disposable housing assembly may be packaged with a filling aid and/or with a filling syringe. In some embodiments, the fill adapter may be packaged with a predetermined number of filling aids and/or with a predetermined number of filling syringes, e.g., 1 fill adapter packaged with 10 filling aids and 10 disposable housing assemblies. These numbers are examples only, and in various embodiments, the numbers may vary including being higher or lower than the examples given. In some embodiments, the filling aid 9100 may be packaged with the filling syringe 9132 and the filling syringe 9132 may be attached to the filling 9100. In some embodiments, the filling needle 9134 may be attached to the filling syringe 9132 in packaging and in some embodiments, the filling needle 9134 may not be attached to the filling syringe 9132 in packaging however, in some embodiments of this embodiment, the filling needle 9134 may be provided in the same package as the filling syringe 9132 and/or the filling aid 9100.

Referring now also to FIGS. 255A-256B, another embodiment of a fill adapter 9144 is shown. In this embodiment, the fill adapter 9144 includes a single piece frame which, in some embodiments, may be molded. The fill adapter 9144 frame includes one or more button assemblies 9148 corresponding to apertures 6039, 6040, 6041, 6042, 6043, 6044, 6045, 6047 (which are similar to other embodiments described and shown herein with respect to the embodiments as described in other embodiments of the disposable housing assembly having and ribs 964, 966, 968) in the disposable housing assembly 9002. In various embodiments, when fill adapter 9144 is releasably engaged with disposable housing assembly 9002, buttons assemblies 9148 may be aligned with apertures 6039, 6040, 6041, 6042, 6043, 6044, 6045, 6047. Button assemblies 9148 may be, for example, members attached to a button assembly actuator 9146, capable of being depressed. When fill adapter 9144 is releasably engaged with disposable housing assembly 9002, one or more of button assemblies 9148 may be depressed, and may correspondingly be displaced through a respective one of apertures 6039, 6040, 6041, 6042, 6043, 6044, 6045, 6047 into reservoir 908, causing an attendant reduction in the volume of reservoir 908.

Although eight apertures and eight corresponding button assemblies are described and shown herein, in various embodiments, the fill adapter 9144 may include one or more button assemblies and the disposable housing assembly may include one or more corresponding apertures. In some embodiments, the button assemblies and the apertures may be similarly sized as shown in the accompanying figures. However, in various embodiments, the number, size, distribution and shape of the one or more button assemblies and the one or more apertures may be different than as shown herein. For example, in some embodiments, the button assemblies may be wider, may be round, may be square or may be thicker. Likewise, the corresponding aperture may accommodate the various embodiments of the button assemblies. In some embodiments, it may be desirable to vary the distribution, number, size and shape of the button assemblies, and correspondence apertures, to accommodate the volume of fluid that is anticipated to be filled in the reservoir.

In some embodiments, for example, the embodiments shown in FIGS. 206A-208B, the button assemblies 9148 are actuated by at least one button assembly actuator 9146 which is actuated by applying a downward force upon the button assembly actuator 9146. In some embodiments, each of the at least one button assemblies 9148 may be separately actuated by a dedicated button assembly actuator. The button assembly actuator 9146 may be any size desired, but in some embodiments, may be as shown in FIGS. 255A-255C. As shown in, for example, FIG. 255A, the button assembly actuator 9146 may include visible indicators, for example, a fluid drop icon, other icons, for example, a "press" icon, to indicate the method of actuation. In some embodiments, the button assembly actuator 9146 may include a depression and/or ergonomic finger and/or thumb accommodation.

In the exemplary embodiment of this embodiment of the fill adapter 9144, the fill adapter 9144 includes a housing, the button assembly actuator 9146 springingly attached to the housing. The fill adapter 9144 may include a pump chamber plunger 9150 shown in, for example, FIG. 255D, on the underside of the fill adapter 9144 housing. In various embodiments, the pump chamber plunger 9150 may be actuated together with the button assemblies 9148 via the button assembly actuator 9146.

Referring now also to FIGS. 256A-256B, upon coupling the fill adapter 9144 to the disposable housing assembly 9002, the reservoir 908 may be filled using a filling syringe 9132. Any syringe known in the art may be used, however, in the exemplary embodiments, any syringe having a size and shape to be accommodated by the filling aid 6004 may be used, including, but not limited to, a 3 cc/mL TERUMO SYRINGE without needle, made by TERUMO Europe, Belgium, together with a Becton Dickinson 26G1/2 PRECISIONGLIDE Needle, made by Becton Dickinson & Co., Franklin Lakes, N.J., U.S.A., however, in various embodiments, the filling syringe 9132 may be a syringe made by another manufacture and/or at a larger or smaller size. Fill adapter 9144 may include an outside portion and a cavity portion. The cavity portion is the portion that mates with the disposable housing assembly 9002. The fill adapter 9144 may include locking tabs 9152 that may be configured to engage the disposable housing assembly 9002 in a manner such that the disposable housing assembly 9002 may be held in the cavity portion of the fill adapter 9144. Accordingly, fill adapter 9144 may be releasably engaged with disposable housing assembly 9002 by aligning fill adapter 9144 with disposable housing assembly 9002 and applying force such that force is applied to the disposable housing assembly 9002 relative to the fill adapter 9144 or vice versa. In some embodiments, the fill adapter 9144 may attach to the disposable housing assembly 9002 by rotating the fill adapter 9144 with respect to the disposable housing assembly 9002 in a similar fashion as described above with respect to attaching the reusable pump assembly to the disposable housing assembly.

In various embodiments, the fill adapter 9144 includes a filling aid base 9142.

Referring now also to FIGS. 257A-257C, another embodiment of a fill adapter 9244 is shown. In this embodiment, the fill adapter 9244 includes a single piece frame which, in some embodiments, may be molded. The fill adapter 9244 frame includes one or more button assemblies 9248 corresponding to apertures 6039, 6040, 6041, 6042, 6043, 6044, 6045, 6047 (which are similar to other embodiments described and shown herein with respect to the embodiments as described in other embodiments of the disposable housing assembly having and ribs 964, 966, 968) in the disposable housing assembly (not shown, and embodiment is shown in various other figures, for example, 9002). In various embodiments, when fill adapter 9244 is releasably engaged with disposable housing assembly 9002, buttons assemblies 9248 may be aligned with apertures 6039, 6040, 6041, 6042, 6043, 6044, 6045, 6047. Button assemblies 9248 may be, for example, members attached to a button assembly actuator 9246, capable of being depressed. When fill adapter 9244 is releasably engaged with disposable housing assembly 9002, one or more of button assemblies 9248 may be depressed, and may correspondingly be displaced through a respective one of apertures 6039, 6040, 6041, 6042, 6043, 6044, 6045, 6047 into reservoir (not shown, and embodiment is shown in various other figures, for example, 908), causing an attendant reduction in the volume of reservoir 908.

Although eight apertures and eight corresponding button assemblies are described and shown herein, in various embodiments, the fill adapter 9244 may include one or more button assemblies and the disposable housing assembly may include one or more corresponding apertures. In some embodiments, the button assemblies and the apertures may be similarly sized as shown in the accompanying figures. However, in various embodiments, the number, size, distribution and shape of the one or more button assemblies and the one or more apertures may be different than as shown herein. For example, in some embodiments, the button assemblies may be wider, may be round, may be square or may be thicker. Likewise, the corresponding aperture may accommodate the various embodiments of the button assemblies. In some embodiments, it may be desirable to vary the distribution, number, size and shape of the button assemblies, and correspondence apertures, to accommodate the volume of fluid that is anticipated to be filled in the reservoir.

In some embodiments, for example, the embodiments shown in FIGS. 206A-208B, the button assemblies 9248 are actuated by at least one button assembly actuator 9246 which is actuated by applying a downward force upon the button assembly actuator 9246. In some embodiments, each of the at least one button assemblies 9248 may be separately actuated by a dedicated button assembly actuator. The button assembly actuator 9246 may be any size desired, but in some embodiments, may be as shown in FIGS. 257A-257C. As shown in, for example, FIG. 257A, the button assembly actuator 9246 may include visible indicators, for example, a fluid drop icon, other icons, for example, a "press" icon, to indicate the method of actuation. In some embodiments, the button assembly actuator 9246 may include a depression and/or ergonomic finger and/or thumb accommodation.

In the exemplary embodiment of this embodiment of the fill adapter 9244, the fill adapter 9244 includes a housing, the button assembly actuator 9246 springingly attached to the housing. The fill adapter 9244 may include a pump chamber plunger 9250 shown in, for example, FIG. 257C, on the underside of the fill adapter 9244 housing. In various embodiments, the pump chamber plunger 9250 may be actuated together with the button assemblies 9248 via the button assembly actuator 9246.

Upon coupling the fill adapter 9244 to a disposable housing assembly 9002, the reservoir 908 may be filled using a filling syringe. Any syringe known in the art may be used, however, in the exemplary embodiments, any syringe having a size and shape to be accommodated by the filling aid 6004 may be used, including, but not limited to, a 3 cc/mL TERUMO SYRINGE without needle, made by TERUMO Europe, Belgium, together with a Becton Dickinson 26G1/2 PRECISIONGLIDE Needle, made by Becton Dickinson & Co., Franklin Lakes, N.J., U.S.A., however, in various embodiments, the filling syringe may be a syringe made by another manufacture and/or at a larger or smaller size. Fill adapter 9244 may include an outside portion and a cavity portion. The cavity portion is the portion that mates with the disposable housing assembly 9002. The fill adapter 9244 may include a locking tabs 9252 that may be configured to engage the disposable housing assembly 9002 in a manner such that the disposable housing assembly 9002 may be held in the cavity portion of the fill adapter 9244. Accordingly, fill adapter 9244 may be releasably engaged with disposable housing assembly 9002 by aligning fill adapter 9244 with disposable housing assembly 9002 and applying force such that force is applied to the disposable housing assembly 9002 relative to the fill adapter 9244 or vice versa. In some embodiments, the fill adapter 9244 may attach to the disposable housing assembly 9002 by rotating the fill adapter 9244 with respect to the disposable housing assembly 9002 in a similar fashion as described above with respect to attaching the reusable pump assembly to the disposable housing assembly.

In some embodiments, the fill adapter 9144 includes a filling aid base 9242. In some embodiments, the filling aid base 9242 may include a tapered area 9254 that may be beneficial/desirable for many reasons, including, but not limited to, controlling the entry of a filling needle such that the filling needle is maintained in an aligned position while filling the disposable housing assembly 9002 reservoir 908. In various embodiments, the tapered area 9254 may be sized and shaped as shown or the size and/or the shape may vary in some embodiments. Any one of more of the various embodiments of the filling aid base shown herein may also include a tapered area as shown and describe herein.

Referring now to FIGS. 258-272, another embodiment of a filling aid 9300 is shown. In various embodiments of this embodiment of the filling aid 9300, the filling aid 9300 attaches to a disposable housing assembly 9302, which, in various embodiment, may be any disposable housing assembly 9302 shown and/or described herein, and/or any variation of a disposable housing assembly. In various embodiments, the disposable housing assembly 9302 includes a reservoir. The reservoir is empty until and unless a user/patient/caregiver fills the reservoir with a fluid. In various embodiments, the user/patient/caregiver may fill the reservoir with any volume of fluid desirable and may fill the reservoir with any fluid desired, including, but not limited to, an infusible fluid, including but not limited to, insulin.

In various embodiments the disposable housing assembly 9302 has a predetermined length of tubing 9308 attached. The length of the tubing 9308 may be any length desired. In various embodiment, the tubing 9308 may be attached to a luer connector 9310 which in various embodiment is configured to attach to a cannula, such that a fluid pathway is established from the reservoir (in the disposable housing assembly 9302) to the cannula (not shown). However, in some embodiments, a length of tubing may not be attached to the disposable housing assembly 9302, and in some embodiments of these embodiment, a length of tubing may be attached at a later time. In some embodiments, a luer connector may not be attached to the length of tubing, but in some embodiments of these embodiments, a luer connector is attached at a later time.

Still referring to FIGS. 258-272, in various embodiments, the filling aid 9300 includes a cover portion 9304 and a bottom portion 9306. In various embodiments, the filling aid 9300 may include one or more indicators and/or indicia indicating to a user/patient/caregiver instructions on how to operate the filling aid 9300. In some embodiments, for example, the cover portion 9304 may include an arrow/indicia 9312 to indicate that a user/patient/caregiver push downward/exert downward force on the cover portion 9304. However, in various other embodiments, the indicia can be any indicia desired.

In some embodiments, in practice, the filling aid 9300 may be attached to the disposable housing assembly 9302 in the locked position. In various embodiments, the bottom portion 9306 is configured to be removably attached to the disposable housing assembly 9302. A user may fill the reservoir (which may be the embodiment as shown in FIG. 49B, 908) of the disposable housing assembly 9302 using the filling aid 9300. Following, the user may prime the disposable housing assembly 9302, then remove the filling aid 9300 from the disposable housing assembly 9302.

Figure 264:
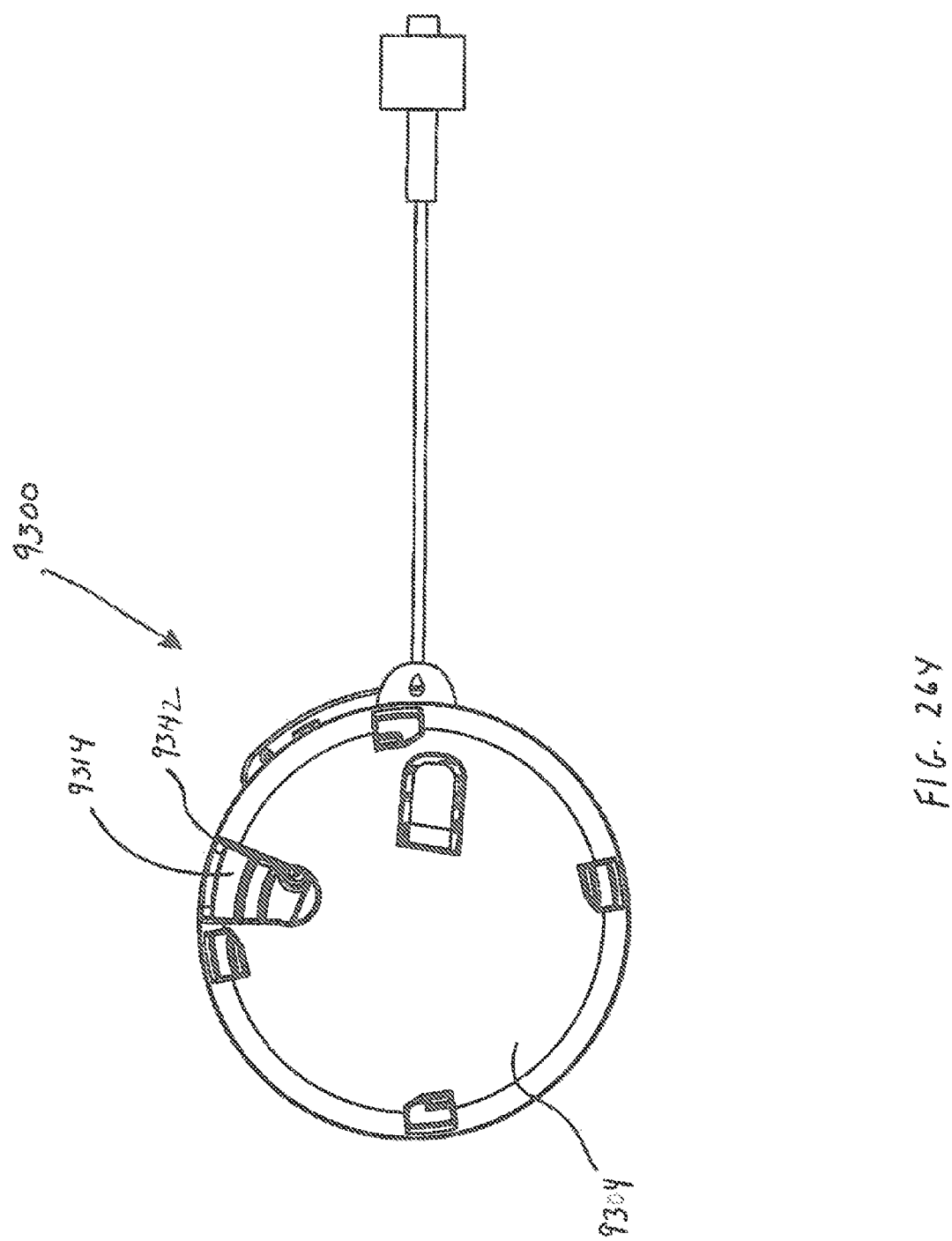
Figure 265:
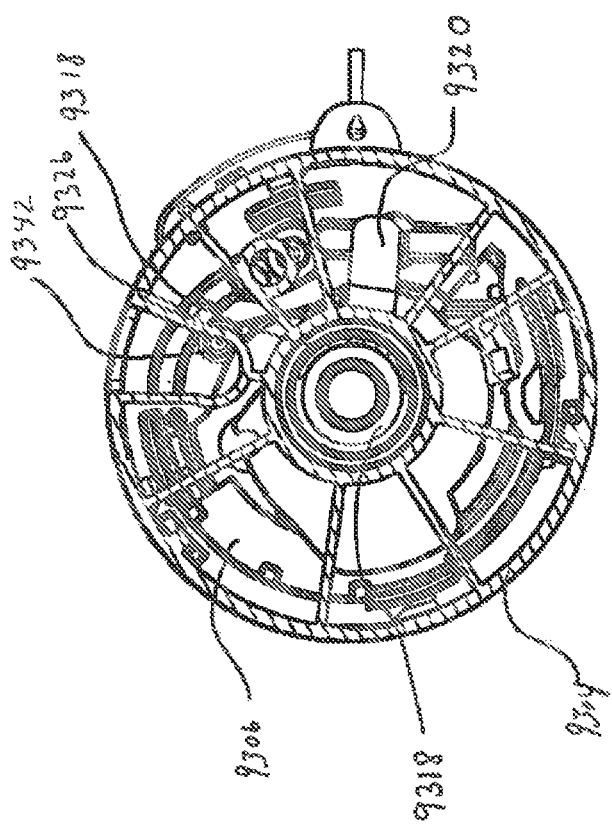
Figure 266:
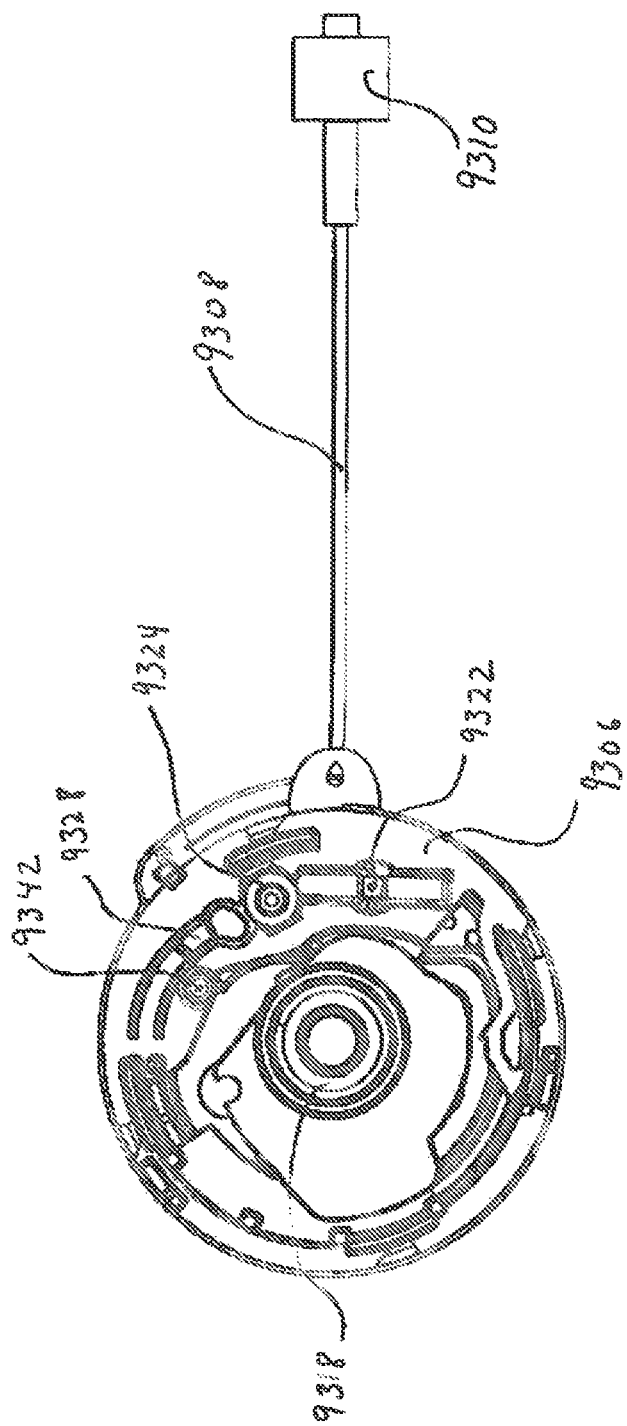
Figure 267:
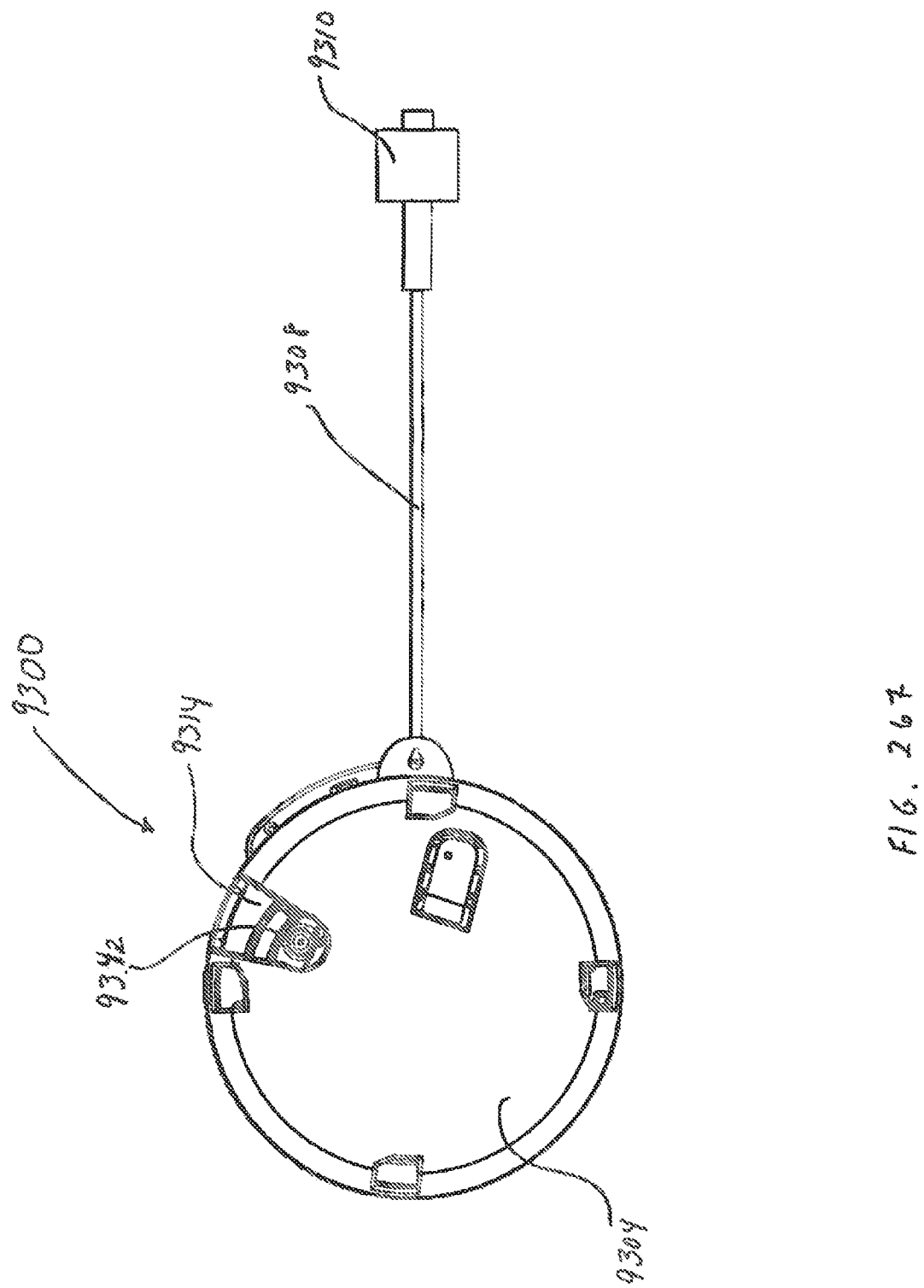
Figure 268:
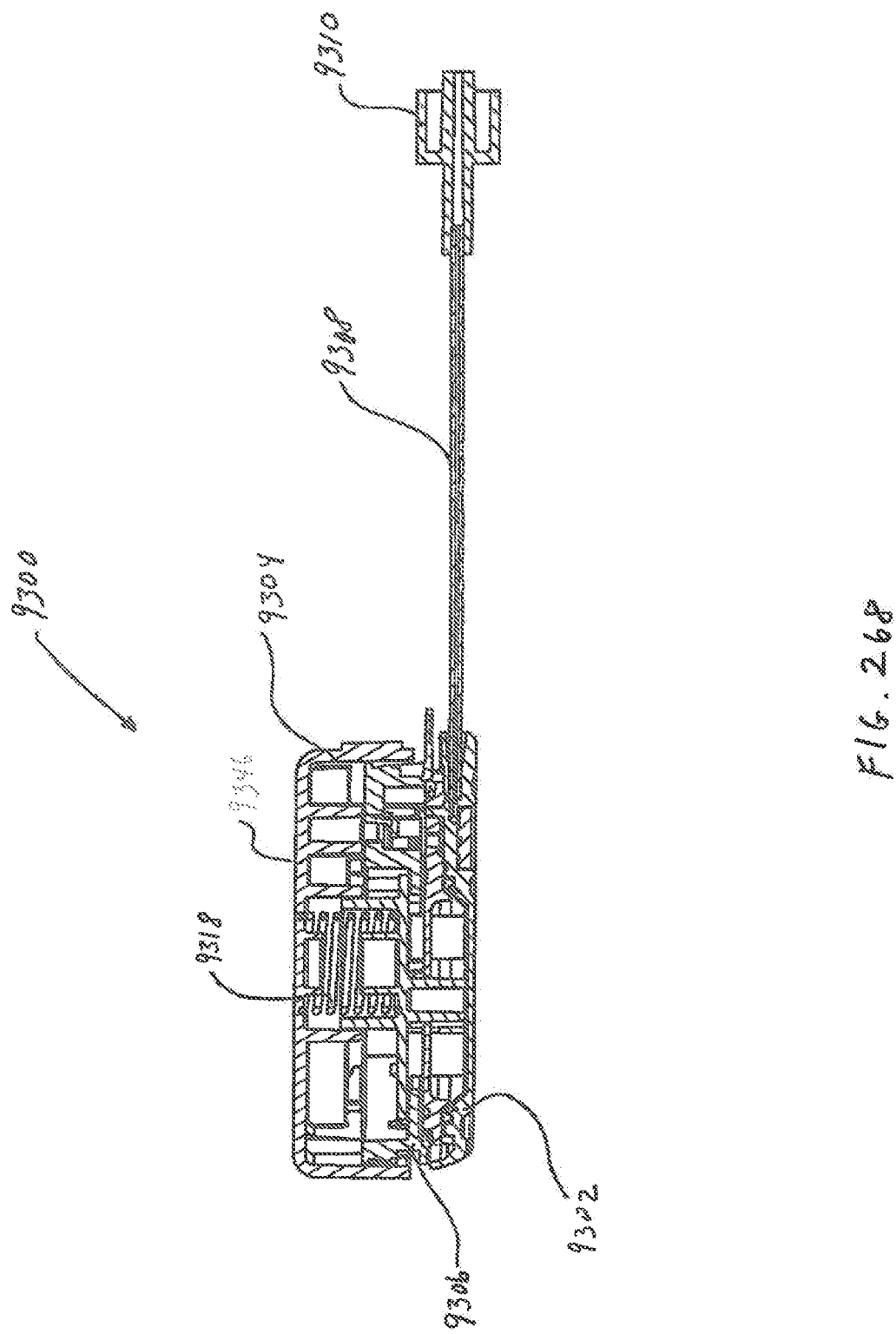
Figure 269:
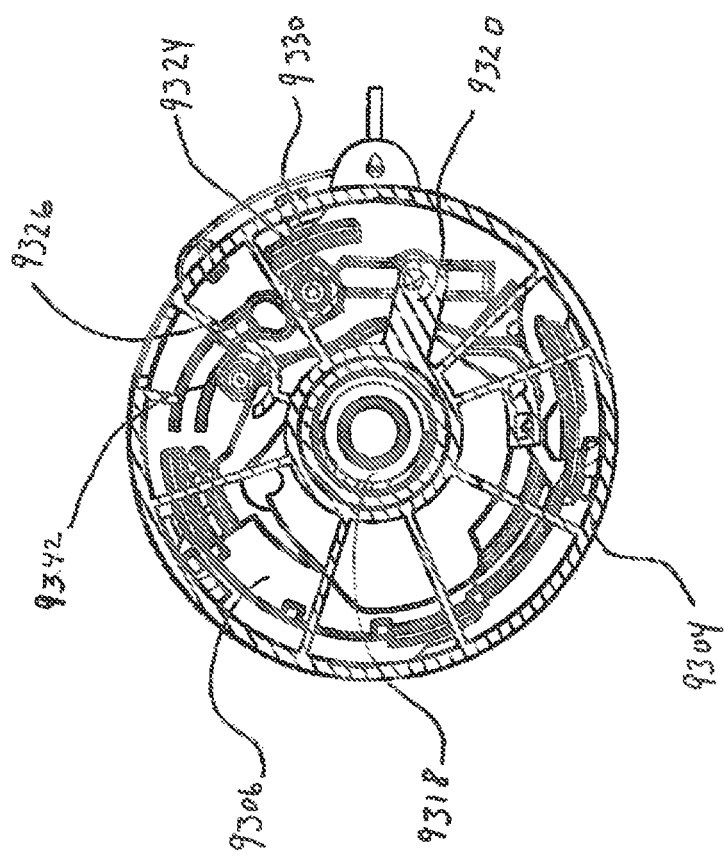

Still referring to FIGS. 258-272, in various embodiments, the filling aid 9300 is attached to the disposable housing assembly 9302. The cover portion 9304 and the bottom portion 9306 are rotatably attached. The cover portion 9304 includes a septum window 9314. When the filling aid 9300 is first attached, and in the starting position, the cover portion 9304 and the bottom portion 9306 are in the position shown, for example, in FIG. 259. In the starting position, as shown in FIG. 264, the septum window 9314 obscures the needle funnel 9342. The needle funnel 9342 is located adjacent to the reservoir port, which is the inlet to the reservoir, and is therefore connected to the reservoir. The needle funnel 9342 is the entrance to the reservoir port and is used to fill the reservoir. Using a syringe, or other needle, a needle is inserted through the needle funnel 9342 and the contents of the syringe may be transferred into the reservoir. The starting position, without the cover, is shown in FIG. 265. In this position, the reservoir may not be filled because the needle funnel 9342 is obscured. FIG. 266 is a view of the filling aid 9300 bottom portion 9306 without the cover portion 9304. The check valve beam 9322, pump chamber plunger 9324, reservoir valve beam 9328 and needle guide 9316 are shown.

The cover portion also includes a spring 9318. The spring 9318 is always in the loaded position, resting against the membrane of the disposable housing assembly 9302. This is beneficial/desirable for many reasons, including but not limited to, before the disposable housing assembly 9302 reservoir is filled, the parts of the filling aid 9300 are always pushed all the way down/forward. Therefore, there is less load on the parts of the filling aid 9300 in storage. This is beneficial/desirable for many reasons, including but not limited to, this ensures that the filling aid 9300 does not become deformed in storage. Also, the spring 9318 being loaded against the reservoir/reservoir membrane keeps air out of the reservoir.

In the starting position, the cover portion 9304 and the bottom portion 9306 are locked in position and therefore, the cover portion 9304 and the bottom portion 9306 are in a locked configuration. Referring also to FIGS. 266-269, to unlock the cover portion 9304 and the bottom portion 9306, a downward force is exerted onto the cover portion 9304 and the cover portion 9304 slides downward over the bottom portion 9306. The cover portion 9304 may then be rotated, with respect to the bottom portion 9306 and therefore, the cover portion 9304 and the bottom portion 9306 are in an unlocked configuration. Upon rotation, the septum window 9314 is positioned such that the needle funnel 9342 is no longer obscured and is accessible. The rotation also positions a valve beam cover 9320 (or first valve beam cover) over the check valve beam 9322 (or a first check valve beam), a pump chamber plunger beam 9330 over the pump chamber plunger 9324 and a reservoir valve beam cover 9326 (or a second valve beam cover) over the reservoir valve beam 9328 (or a second valve beam). The terms first and second valve beam, valve or valve beam cover may be used throughout this specification. The reservoir valve beam cover 9326, pump chamber plunger beam 9330 and the valve beam cover 9320 are part of the cover portion 9304 and exert pressure onto the reservoir valve beam 9328, pump chamber plunger 9324 and the check valve beam 9322, part of the bottom portion 9306, respectively. Thus, as the reservoir is being filled by inserting a syringe through the needle guide 9342, the inlet check valve beam 9322, the pump chamber plunger beam 9330 and the reservoir valve beam 9328 ensure that the check valve, pump chamber and the reservoir valve, in the disposable housing assembly 9302, are closed/evacuated. This also ensures that all the pressure is held in the reservoir until priming is desired. This ensures that the fluid being loaded into the reservoir is not openly flowing out of the reservoir as the reservoir is being filled. Additionally, this also ensures that air or fluid is not retained in any valves or the pump chamber.

Referring now also to FIGS. 288-289, the filling aid 9400 is attached to the disposable housing assembly 9402. In FIG. 288, the system is shown in the open and fillable position. In this position, the user/patient/caregiver may access the needle guide 9442 and fill the reservoir. In FIG. 289, the system is shown in the closed position. In this position, the user/patient/caregiver may not access the needle guide 9442, as the slider 9450 is in a position that blocks the needle guide 9442 from access.

Figure 270:
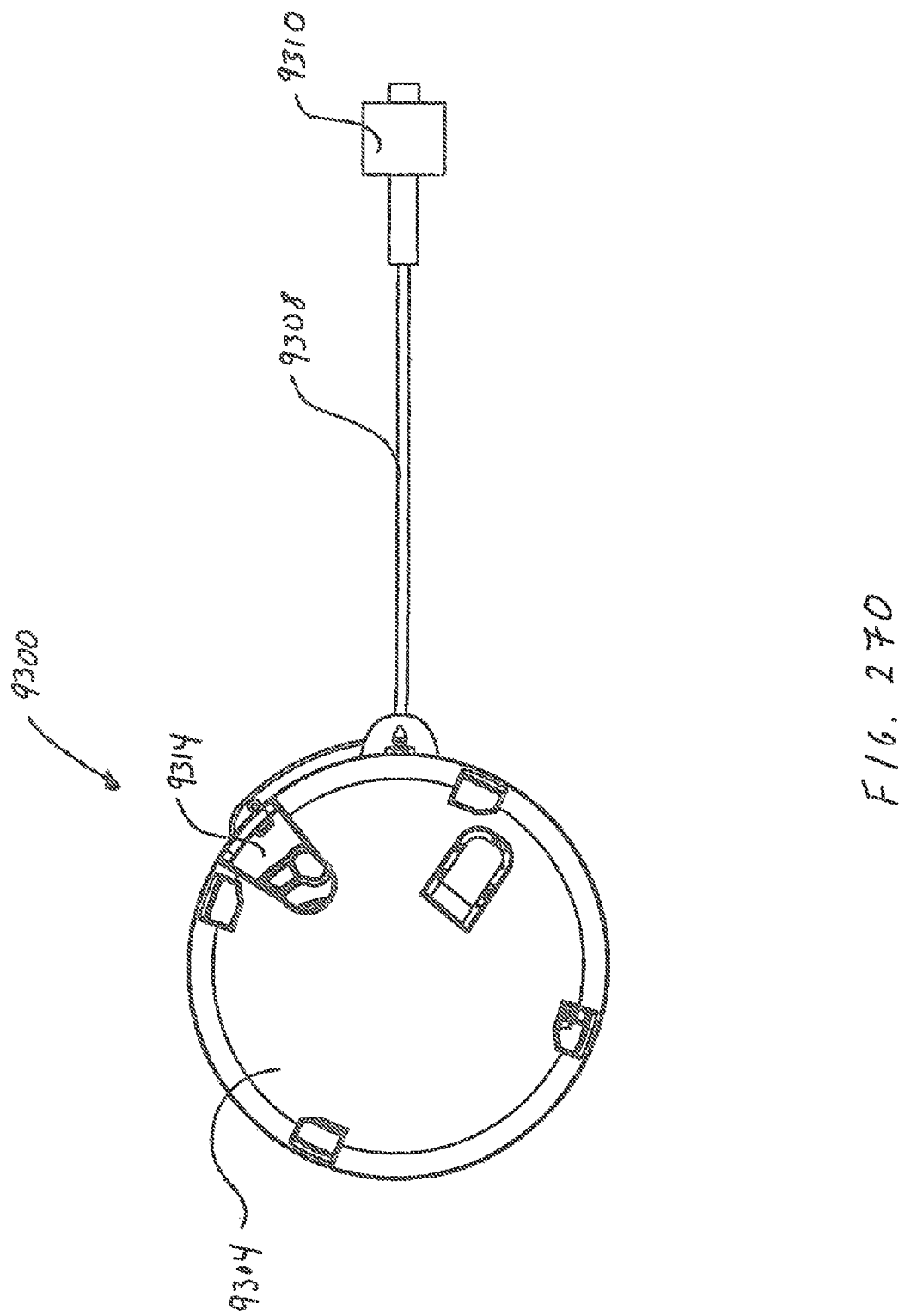
Figure 271:
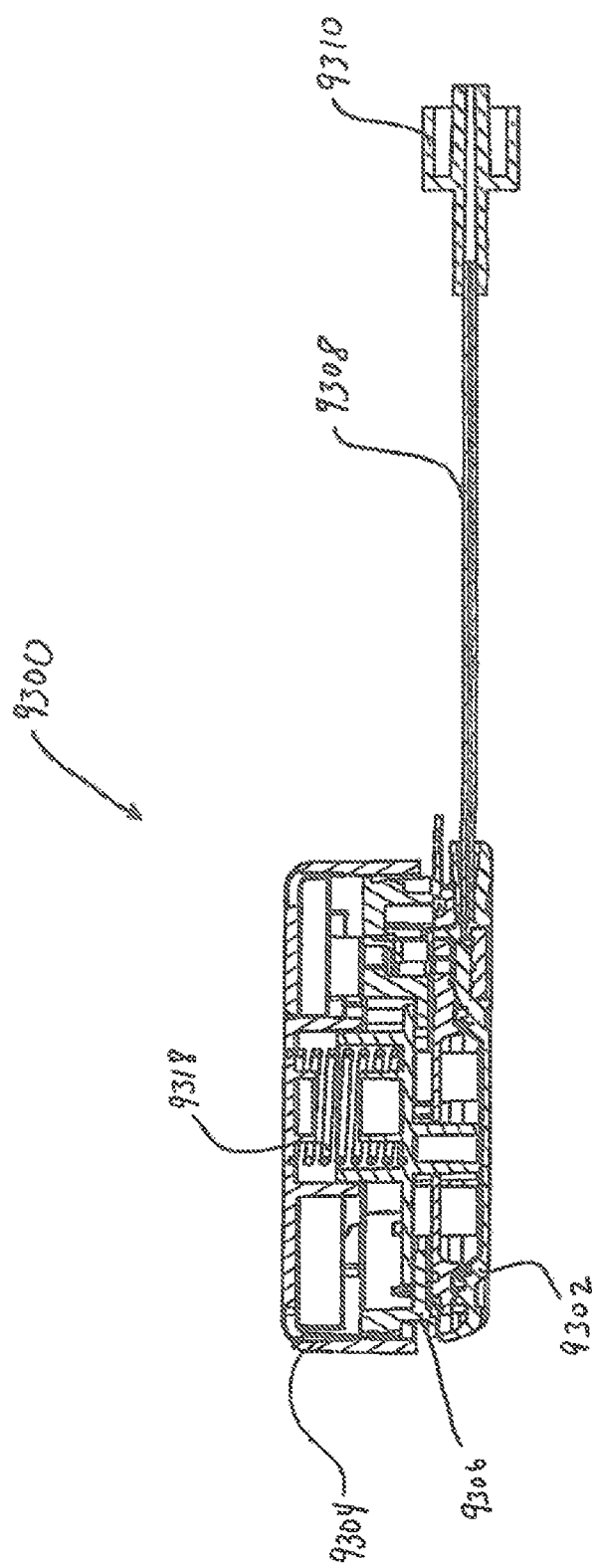
Figure 272:
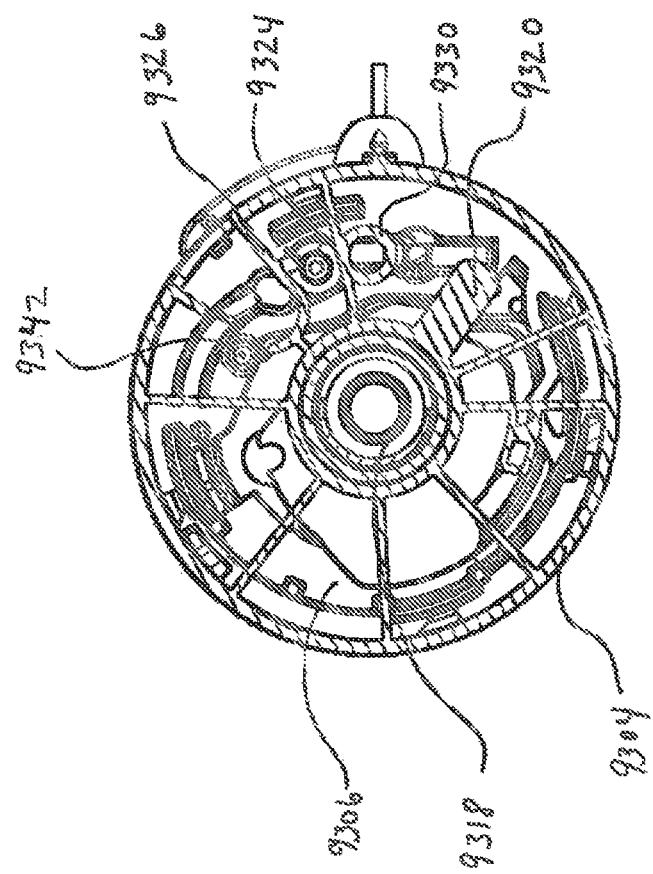

Once the user/patient/caregiver has filled the reservoir a desired amount, and referring also to FIGS. 270-272, to prime the disposable housing assembly 9302, the cover portion 9304 may be rotated with respect to the bottom portion 9306. This places the filling aid 9300 in the priming configuration. The user/patient/caregiver or other watches the luer 9310 until fluid appears (or, in embodiments not including a luer, the user/patient/caregiver watches the exit of the disposable housing assembly 9302). This indicates the disposable housing assembly 9302 is primed. Once the disposable housing assembly 9302 is primed, the user/patient/caregiver removes the cover portion 9304 from the disposable housing assembly 9302 and priming stops. In other embodiments, the user/patient/caregiver may rotate the cover portion 9304 back to the filling position, which stops the priming. The cover portion 9304 may then be removed from the disposable housing assembly 9302.

Thus, when the filling aid 9300 is in the starting position, the reservoir valve, inlet valve and pump chamber are in their opened position. When the filling aid 9300 is in the filling position, the check valve is in the closed position. When the filling aid 9300 is in the priming position, reservoir valve, check valve and pump chamber are in their opened position.

Referring now to FIG. 273, a partial view of one embodiment of a disposable housing assembly 9302 is shown. In some embodiments of the disposable housing assembly 9302, the AVS, acoustic volume sensing, assembly includes an over mold.

The user/patient/caregiver may remove the filling aid 9300 from the disposable housing assembly 9302 by rotating the entire filling aid 9300 counterclockwise. This unlocks the disposable housing assembly 9302 and allows for the filling aid 9300 to be removed.

Referring now to FIGS. 274-287, another embodiment of a filling aid 9400 is shown. In various embodiments of this embodiment of the filling aid 9400, the filling aid 9400 attaches to a disposable housing assembly 9402, which, in various embodiments, may be any disposable housing assembly 9402 shown and/or described herein, and/or any variation of a disposable housing assembly. In various embodiments, the disposable housing assembly 9402 includes a reservoir. The reservoir is empty until and unless a user/patient/caregiver fills the reservoir with a fluid. In various embodiments, the user/patient/caregiver may fill the reservoir with any volume of fluid desirable and may fill the reservoir with any fluid desired, including, but not limited to, an infusible fluid, including but not limited to, insulin.

In various embodiments the disposable housing assembly 9402 has a predetermined length of tubing 9408 attached. The length of the tubing 9408 may be any length desired. In various embodiment, the tubing 9408 may be attached to a luer connector 9410 which in various embodiments is configured to attach to a cannula, such that a fluid pathway is established from the reservoir (in the disposable housing assembly 9402) to the cannula (not shown). In some embodiments, tubing 9408 is connected to the disposable housing assembly 9402 after the reservoir in the disposable housing assembly 9402 is filled. In various views shown in FIGS. 274-287, tubing 9408 is not shown, however, in various embodiments of these embodiments, the disposable housing assembly 9402 is configured to received tubing 9408 and/or tubing may be attached, only is not shown.

Still referring to FIGS. 274-287, in various embodiments, the filling aid 9400 includes a cover portion 9404 and a bottom portion 9406. In various embodiments, the filling aid 9400 may include one or more indicators and/or indicia indicating to a user/patient/caregiver instructions on how to operate the filling aid 9400. In some embodiments, for example, the cover portion 9404 may include an arrow/indicia (similar to those shown here as 9412 on the disposable housing assembly 9402) to indicate that a user/patient/caregiver move the first filling aid tab 9432 towards the second filling aid tab 9436. In various embodiments, additional indicia may be shown, for example, but not limited to, indicia indicating a locked and unlocked position (shown as 9436 on the disposable housing assembly 9402, however, in various embodiments, various indicia may be located on the cover portion 9404) of the first filling aid tab 9432 (see FIG. 274). However, in various other embodiments, the indicia may be any indicia desired.

In some embodiments, in practice, the filling aid 9400 may be attached to the disposable housing assembly 9402 while the first filling aid tab 9432 is in the locked position. In various embodiments, the bottom portion 9406 is configured to be removably attached to the disposable housing assembly 9402. A user may fill the reservoir (which may be the embodiment as shown in FIG. 49B, 908) of the disposable housing assembly 9402 using the filling aid 9400. Following, the user may prime the disposable housing assembly 9402, then remove the filling aid 9400 from the disposable housing assembly 9402.

Figure 274:
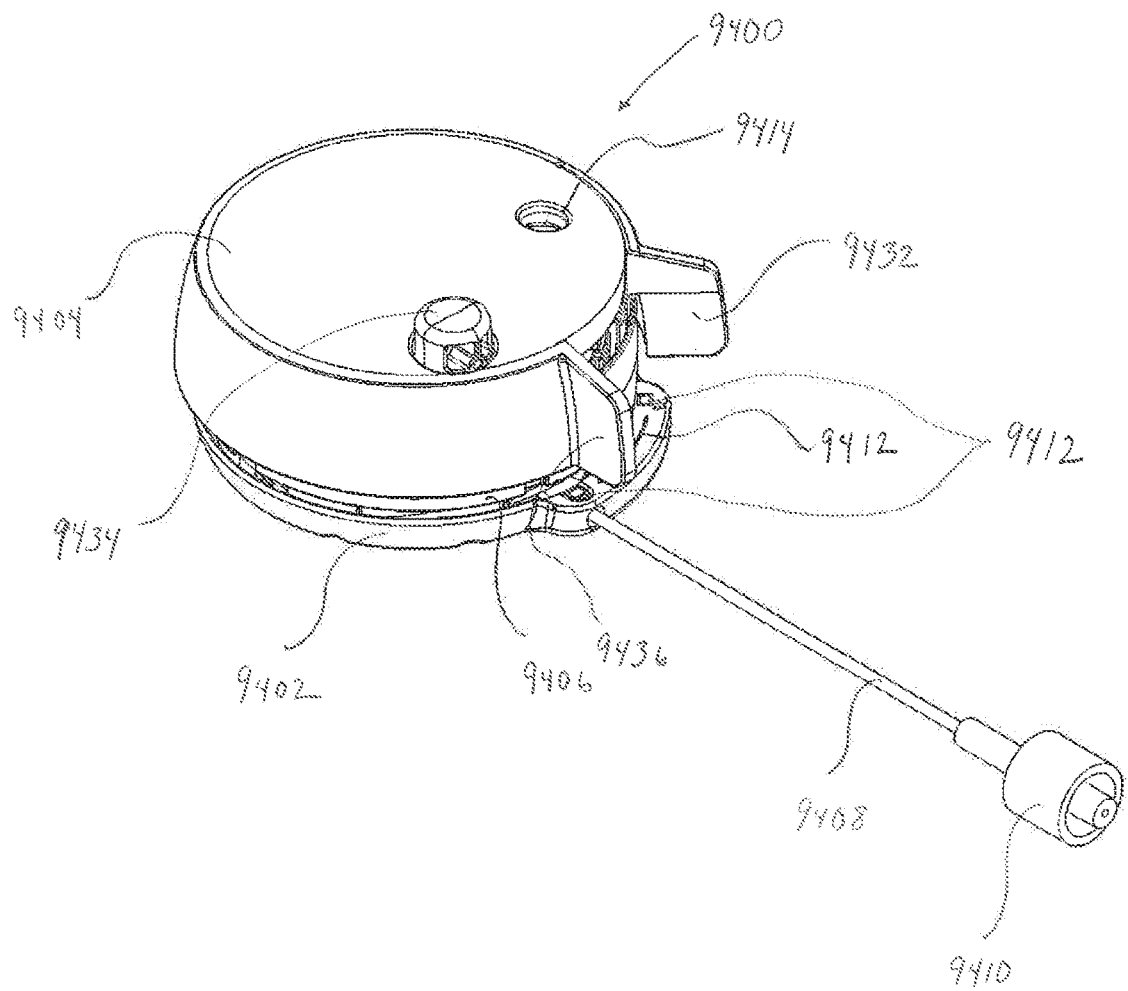
Figure 275A:
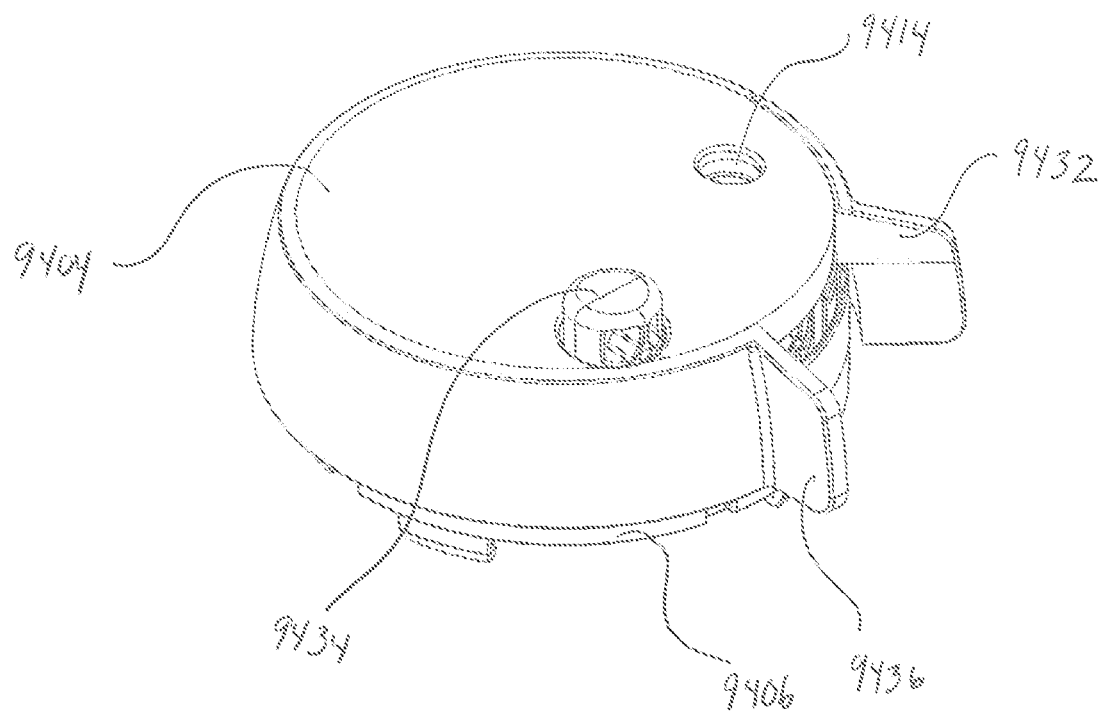
Figure 275B:
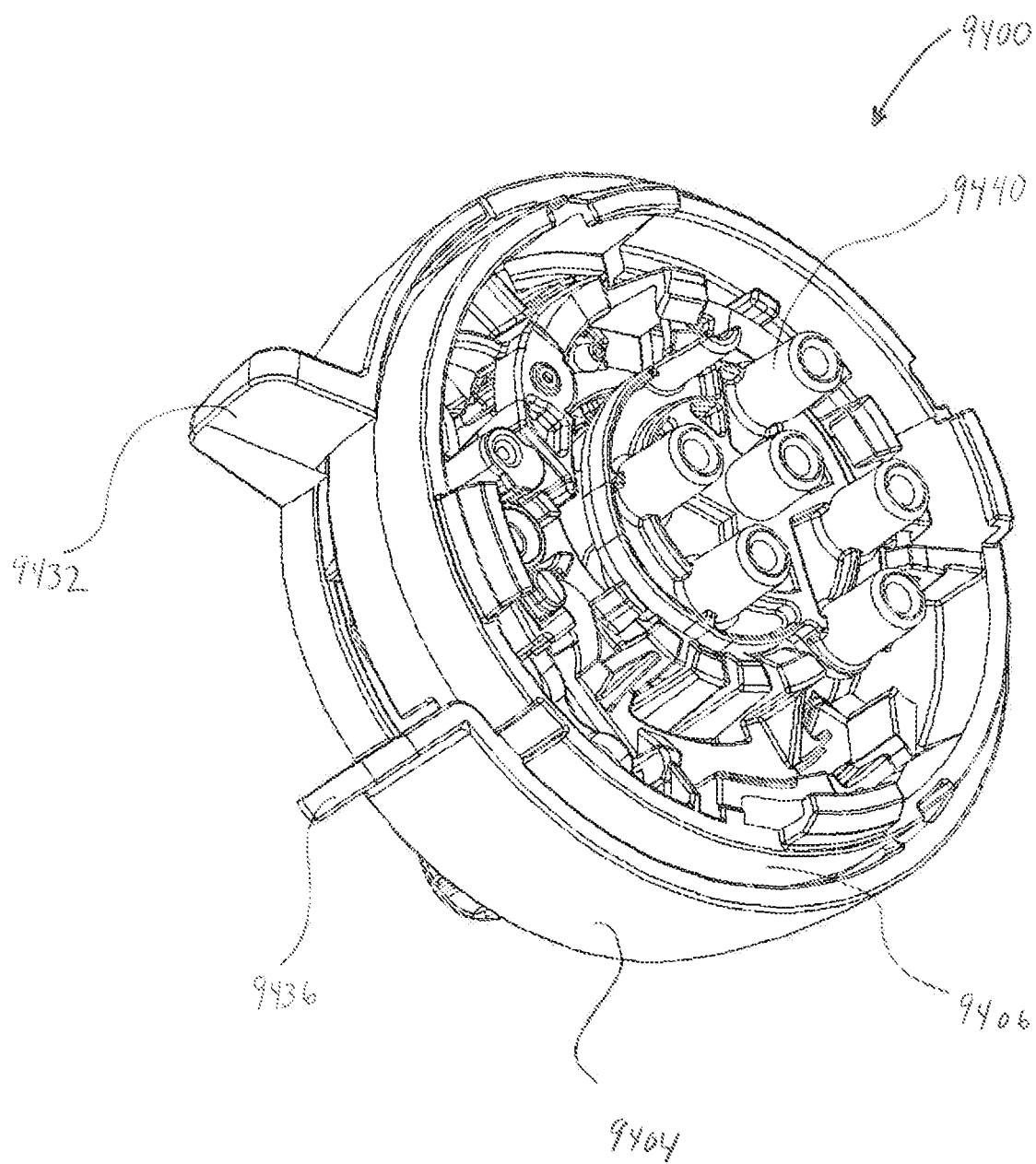
Figure 276:
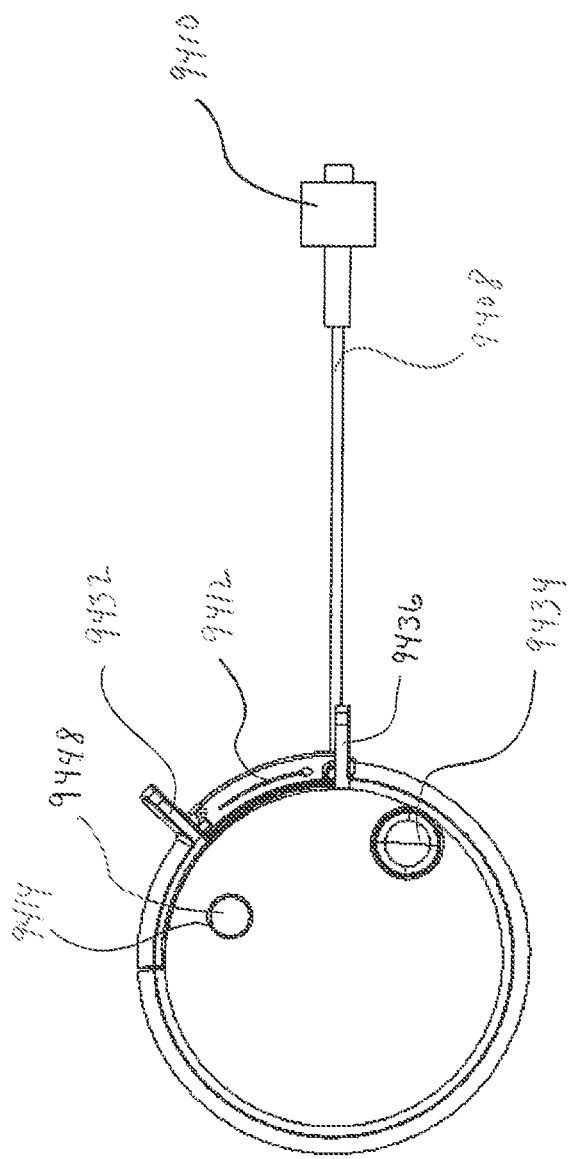
Figure 277:
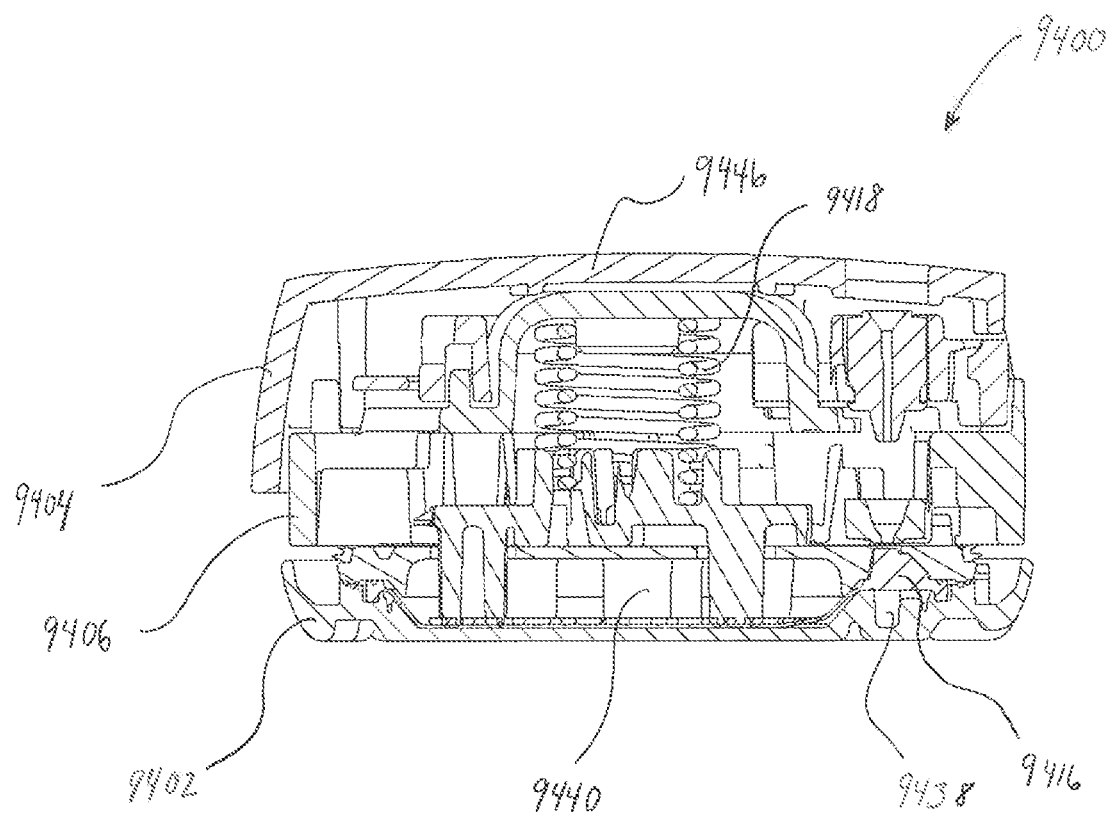
Figure 278:
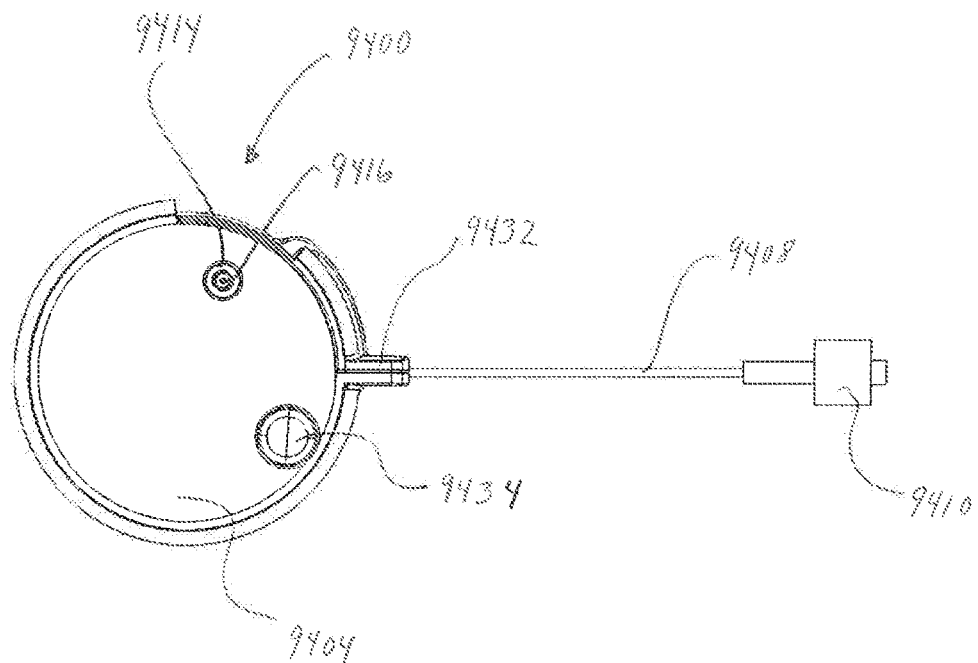
Figure 279:
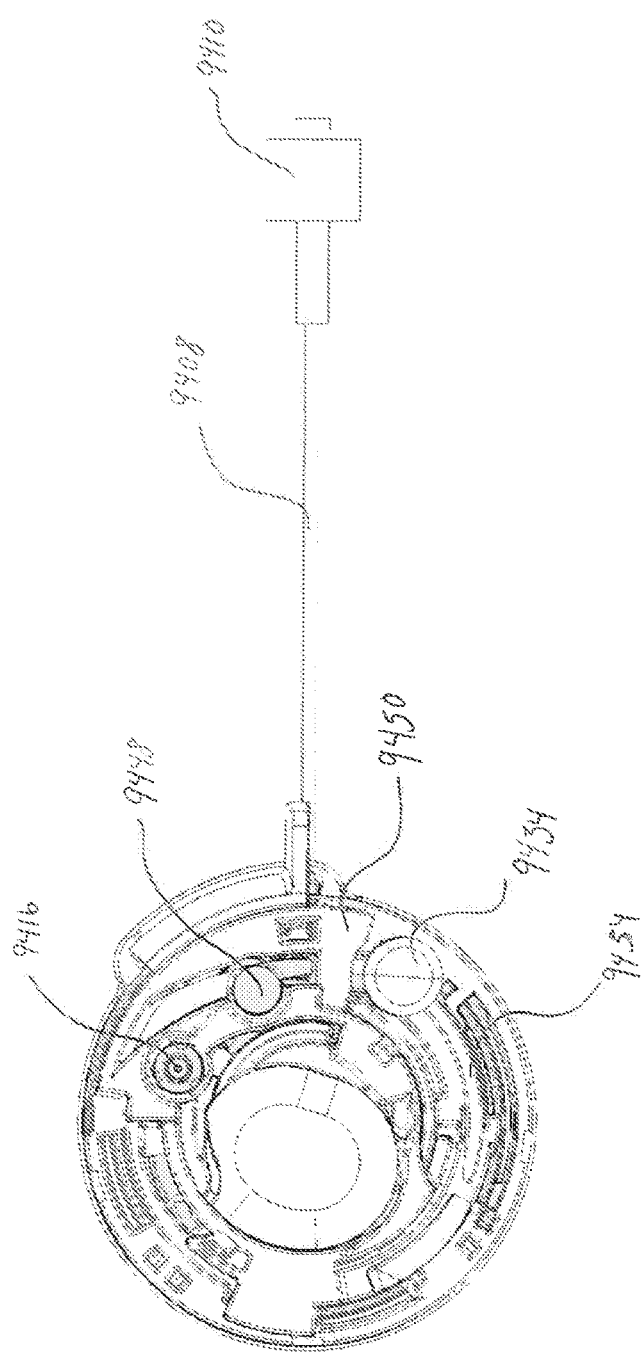

Still referring to FIGS. 274-287, in various embodiments, the filling aid 9400 is attached to the disposable housing assembly 9402. The cover portion 9404 and the bottom portion 9406 are rotatably attached to one another such that the cover portion 9404 may rotate with respect to the bottom portion 9406. The cover portion 9404 includes a septum window 9414. The septum cover 9448 is located on the slider beam 9450. When the filling aid 9400 is first attached to the disposable housing assembly 9402, and in the starting and unlocked position (see, for example, FIGS. 274 and 276), the cover portion 9404 and the bottom portion 9406 are in the position shown. In the starting and unlocked position, as shown in FIGS. 274 and 276, the septum 9416 is obscured by the septum cover 9448 and therefore, the septum 9416 is inaccessible in this position. The septum 9416 is connected to the reservoir in the disposable housing assembly 9402 and the septum 9416 is connected to the reservoir port 9438, which is the entrance to the reservoir, and is used to fill the reservoir. Using a syringe, or other, a needle is inserted through the septum 9416 and into the reservoir port 9438 and the contents of the syringe may be transferred into the reservoir. The starting position is shown, for example, in FIG. 274. In this position, the reservoir may not be filled because the septum 9416 is obscured. As shown in FIG. 278, in the locked position, the septum 9416 is accessible through the septum window 9414. Thus, in the locked position, the septum 9416 may be accessed and the reservoir in the disposable housing assembly 9402 may be filled.

Still referring to FIGS. 274-287, the cover portion 9404 also includes a spring 9418. The spring 9418 is in a starting position while the filling aid 9400 is in a starting position. The spring 9418 maintains the position of the priming interface 9440. The priming interface 9440 is in the bottom portion 9406 of the filling aid 9400.

In the starting position, the bottom portion 9406 is locked in position. Still referring to FIGS. 274-287, to begin the filling process, the first filling aid tab 9432 is rotated such that it meets the second filling aid tab 9436 (see, for example, FIG. 278). Thus, the cover portion 9304 may be rotated, with respect to the bottom portion 9306, from a starting position (see, for example, FIG. 276) to a locked or filling position (see, for example, FIG. 278). Upon rotation, the septum cover 9448 rotates with the first filling aid tab 9432, and the septum window 9414 is now positioned such that the septum 9416 is no longer obscured and is now accessible (see, for example, FIG. 279).

The first filling aid tab 9432 is part of a slider beam 9450. The slider beam 9450 includes ramps and various tab that interact and actuate a pump chamber plunger 9424, a check valve beam 9422, and a check valve plunger 9452.

Figure 280:
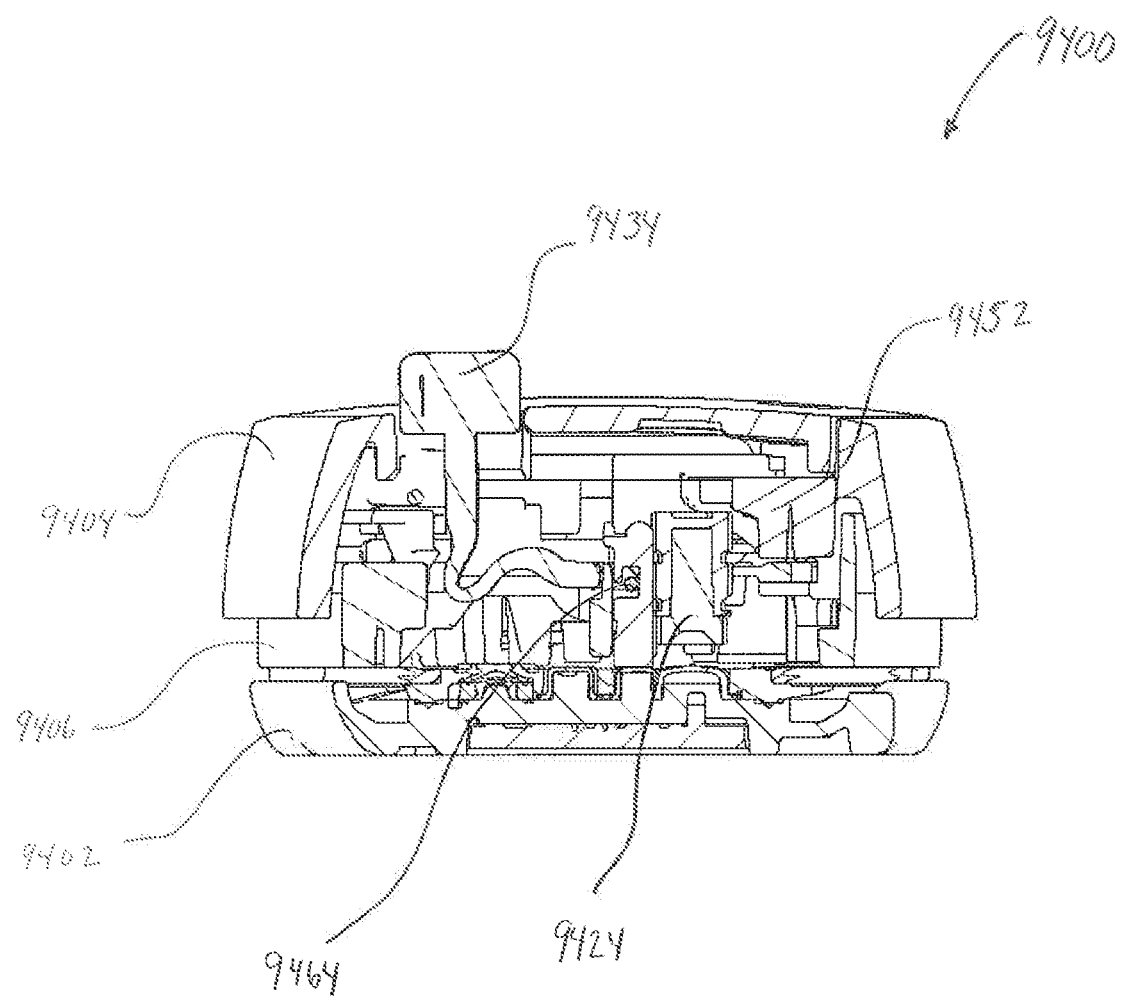
Figure 281:
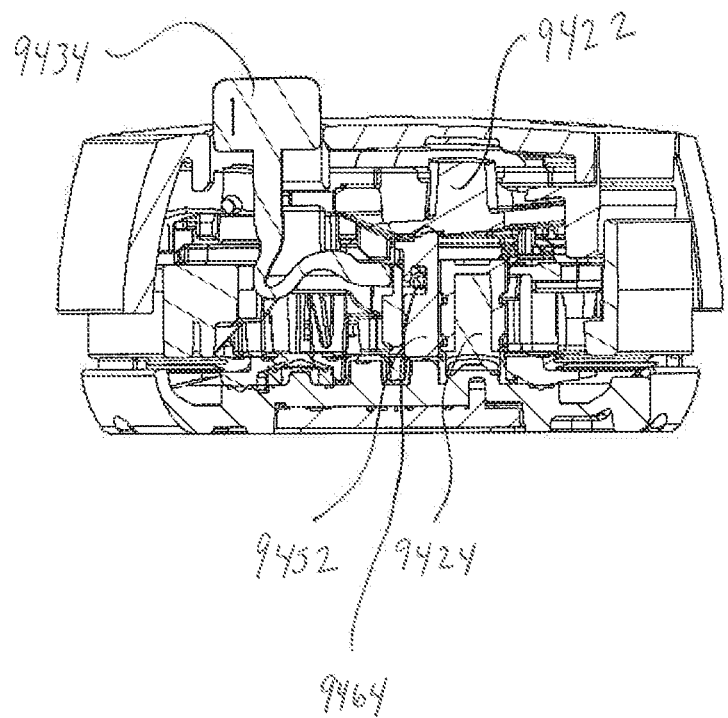

Referring now also to FIGS. 280-281, rotating the first filling aid tab 9432 from the starting position to the locked or filling position also causes the entire slider beam 9450 to rotate, wherein the pump chamber plunger ramp 9470 rotates causing the pump chamber plunger ramp 9470 to first actuate the pump chamber plunger 9424 (see FIG. 280) and then, as the slider beam 9450 continues in its rotation, it actuates the check valve beam 9422 (see FIG. 281) and moves it into position. The pump chamber plunger 9424 and the check valve plunger 9452 evacuate the pump chamber and maintain the check valve in the closed position, respectively. Both the pump chamber and the check valve are located in the disposable housing assembly 9402. The inlet check valve beam 9422 ensures the pump chamber and the check valve remain in the evacuated or closed position, respectively. Thus, as the reservoir is being filled by inserting a syringe through the septum guide 9416, the pump chamber plunger 9424 and the check valve plunger, in the disposable housing assembly 9402, are evacuated/closed. The inlet check valve beam 9422 also ensures that all the pressure is held in the reservoir until priming is desired. This ensures that the fluid being loaded into the reservoir is not openly flowing out of the reservoir as the reservoir is being filled. Additionally, the pump chamber plunger 9424 and reservoir and reservoir valve beam 9328 ensures that air or fluid is not stuck in any valves or the pump chamber.

Thus, as the first filling aid tab 9432 is being rotated towards the second filling aid tab 9436, the slider beam 9450, being rotated, causes the pump chamber plunger ramp 9470 to actuate the pump chamber plunger 9424, and the check valve beam 9422 actuates the check valve plunger 9452 such that both the pump chamber plunger 9424 and the check valve plunger 9452 are in the evacuated/closed position, respectively. Also, as the first filling aid tab 9432 is being rotated toward the second filling tab 9436, the slider beam 9450 is rotated such that the septum cover 9448 rotates and the septum window 9314 is now positioned such that the septum guide 9316 is no longer obscured and is now accessible. Thus, once the first filling tab 9432 meets the second filling aid tab 9436, the filling aid 9400 is in the unlocked, or filling, position.

Referring now also to FIG. 280, in various embodiments, the priming button 9434 and the check valve plunger 9452 may be manufactured as a single part that accomplishes both actions. However, in embodiments where the priming button 9434 and the check valve plunger 9452 are separate parts (as shown in FIG. 280, for example), there may be a delay between when the priming button 9434 is pushed and the priming response. This may be beneficial and/or desirable for many reasons, including, but not limited to, providing a tactile response to the user/patient/caregiver when pressing the priming button 9434 and therefore, the user/patient/caregiver may receive tactile feedback that the priming button 9434 was pressed and priming will initiate.

Figure 282:
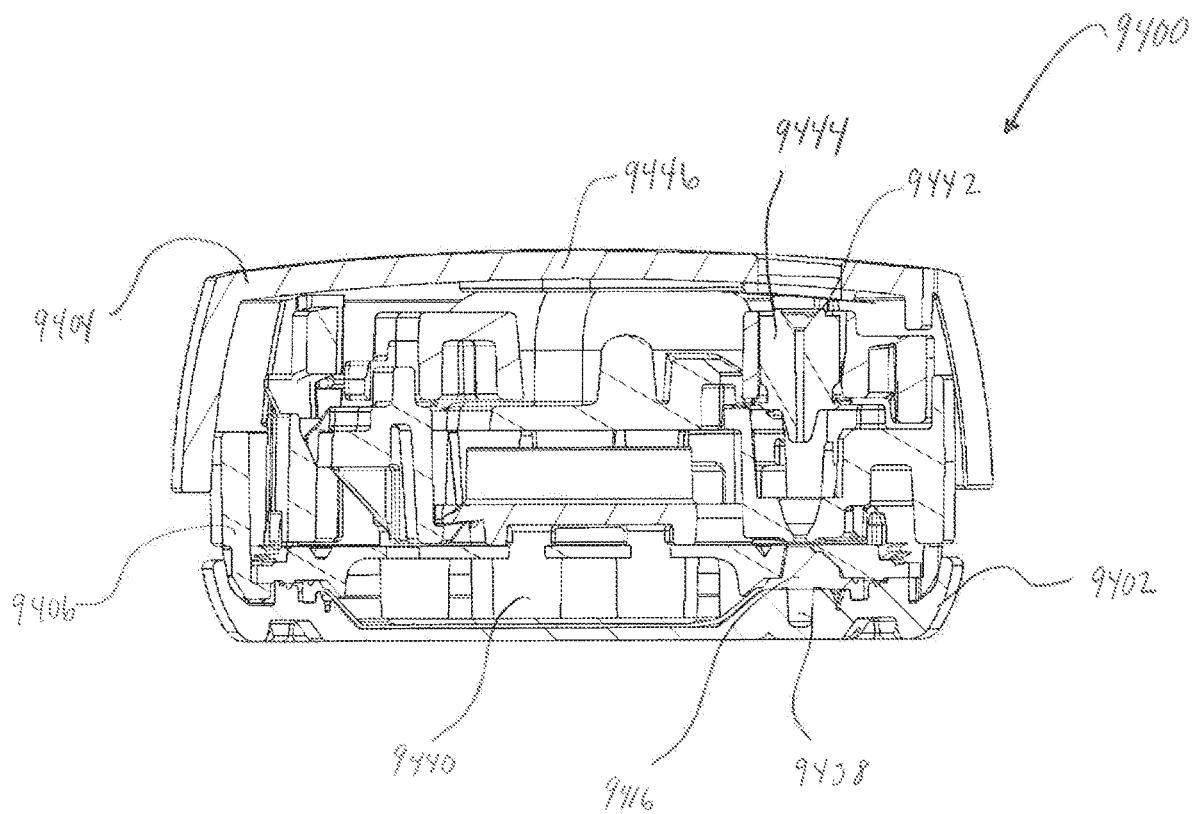
Figure 283:
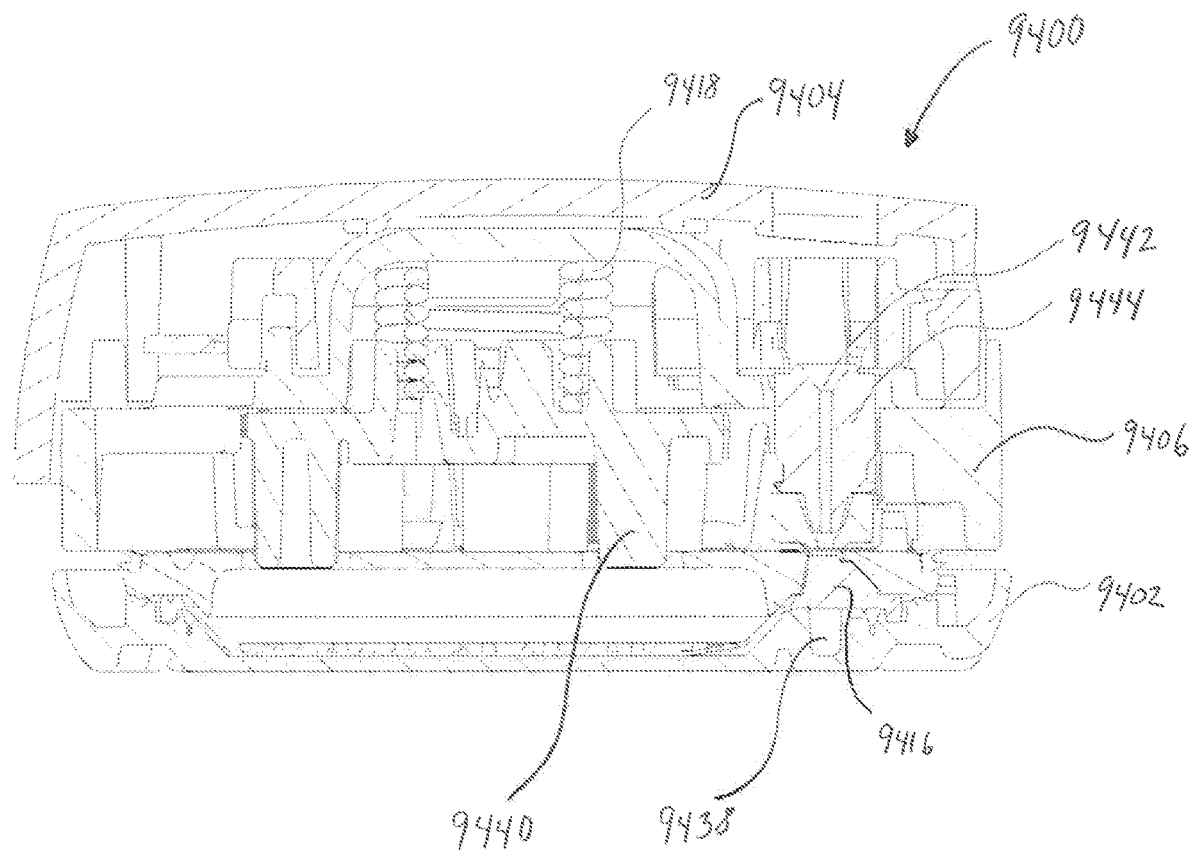
Figure 284:
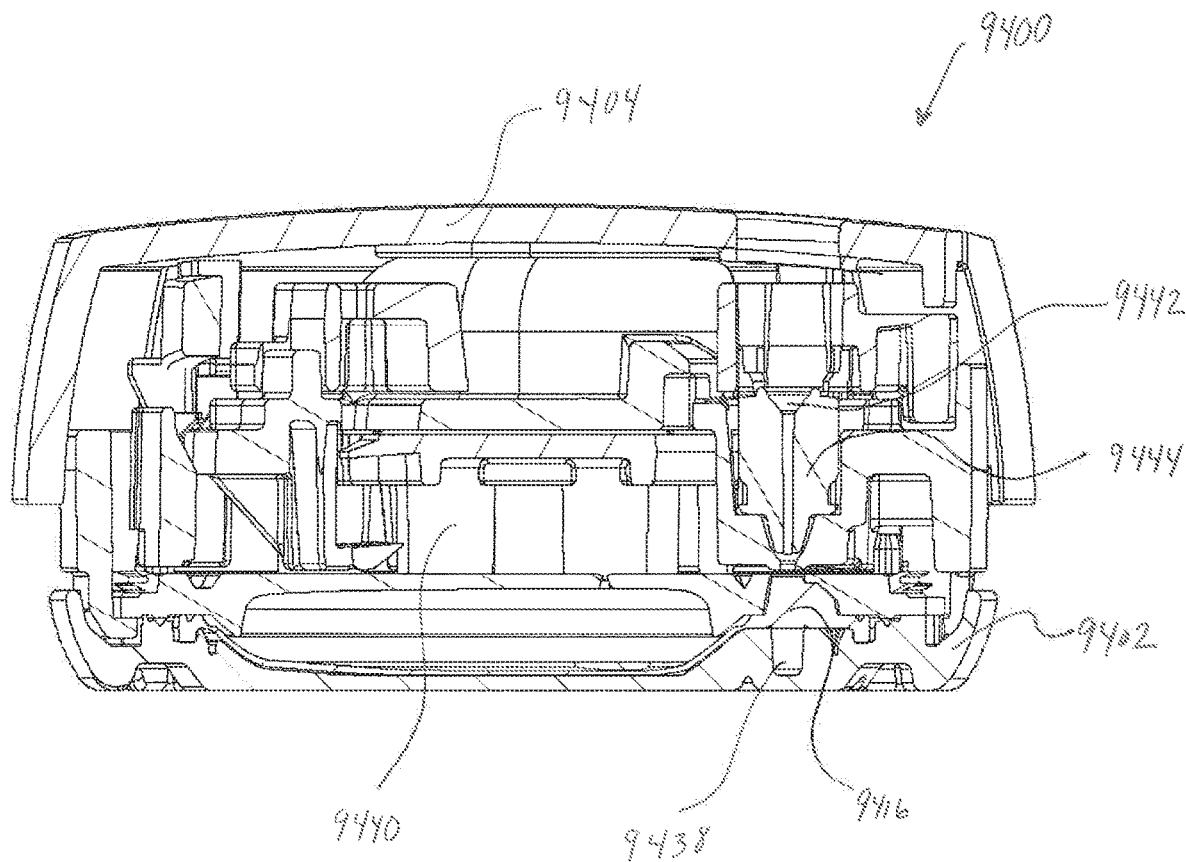

Referring now also to FIGS. 282-284, in various embodiments, the filling aid 9400 includes a needle guide 9442 which, in some embodiments, is located within a needle shuttle 9444. In various embodiments, the needle guide 9442 may be shaped as shown or shaped differently. In some embodiments, the needle guide 9442 may be made from ABS. In other embodiments, the needle funnel 9442 may be made from any rigid material, including, but not limited to, 316 Stainless Steel or any other metal or other material that is rigid. A syringe containing a needle, or a needle, is used to fill the reservoir in the disposable housing assembly 9402. The syringe/needle enters the filling aid 9400 through the septum window 9414. The needle guide 9442 ensures that the needle enters the filling aid 9400 and is guided to the correct location such that the needle may pierce the septum 9416 and fill the reservoir through the reservoir port 9438 (see FIG. 282). Once pressure is exerted onto the needle guide 9442/needle shuttle 9444, (see FIGS. 283-284), the needle shuttle 9444 moves downward, towards the bottom portion 9406 of the filling aid 9400 and such that the needle guide 9442/needle shuttle 9444 is positioned adjacent the septum 9416.

Referring now also to FIGS. 288-289, in various embodiments, the needle guide 9442 may be stationary and in these embodiments, a needle shuttle 9444 is not included. As discussed in more detail above, in these embodiments, the slider beam 9450 provides a structural means to prevent filling when the filling aid 9400 is in the closed position.

Still referring to FIGS. 274-287, as fluid is filled into the reservoir of the disposable housing assembly 9402, the membrane of the reservoir rises. The priming interface 9440 is located adjacent to the reservoir and maintains contact with the reservoir. As discussed above, as the priming interface 9440 is attached to a spring 9418, the spring ensures a constant amount of pressure is maintained by the priming interface 9440 on the reservoir.

Referring again also to FIG. 279, in various embodiments, the priming button 9434 is attached to a button arm 9454. A portion of the slider beam 9450, at the starting position (see, for example, FIG. 276, is located under the button arm 9454, and the slider beam 9450 holds the button arm 9454 up, preventing the priming button 9434 from being actuated/pressed/depressed. As discussed above, when filling of the reservoir is desired, the user/patient/caregiver rotates the slider beam 9450. This rotation, amongst other functions discussed above, moves the slider beam 9450 such that the slider beam 9450 is no longer under the button arm 9454 and therefore, the priming button 9434 is now free to be actuated/pressed/depressed. Thus, unless and until the slider beam 9450 is rotated fully such that the first filling aid tab 9432 meets the second filling aid tab 9436, the priming button 9434 cannot be actuated/pressed/depressed and, as discussed above, the reservoir cannot be filled as the septum 9416 is not accessible. This may be beneficial/desirable for many reasons, including, but not limited to, ensuring the septum 9416 is protected until filling is desired, and decreasing potential user/patient/caregiver confusion of when to push the priming button.

Figure 285:
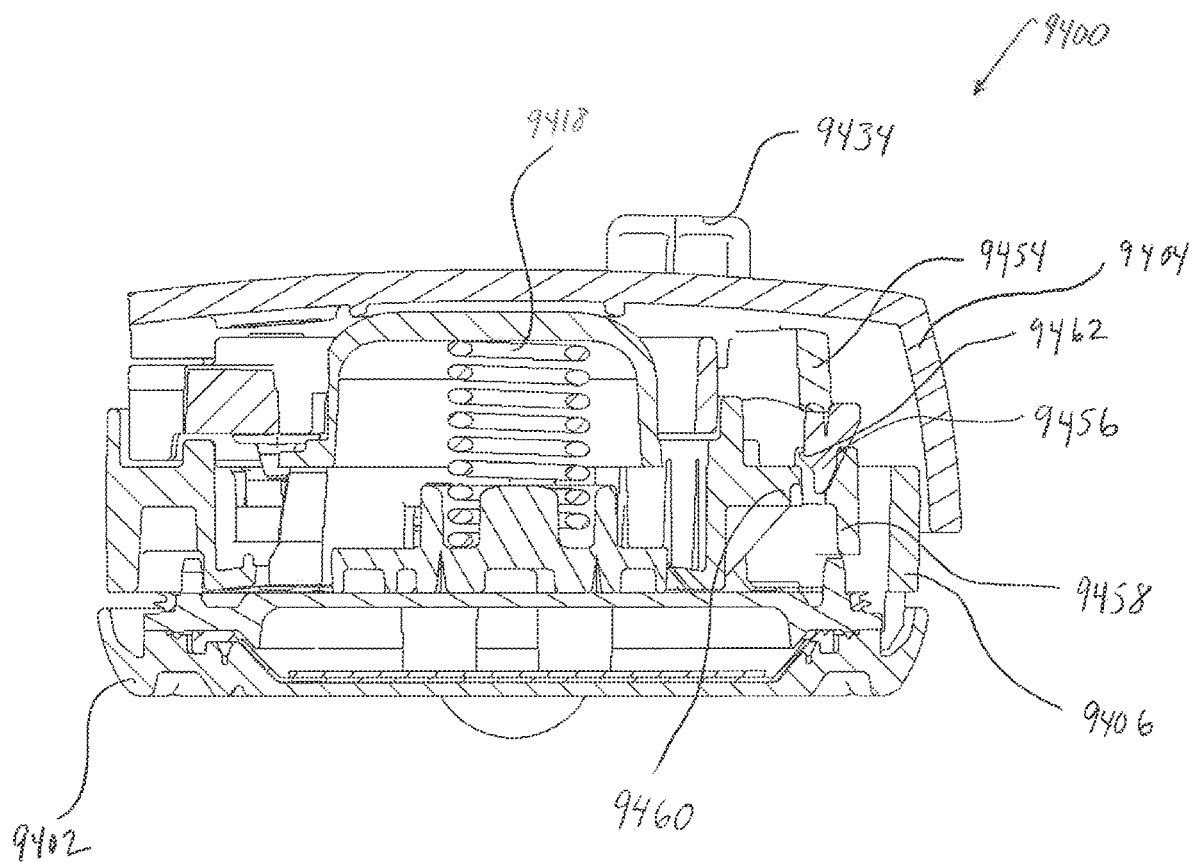

Referring now also to FIG. 285, in various embodiments, the filling aid 9400 includes an anti-rotation arm 9458 which, before the priming button 9434 is actuated, prevents the removal of the filling aid 9400 from the disposable housing assembly 9402. The anti-rotation arm 9458 interacts with an alignment tab on the disposable housing assembly 9402. Thus, this ensures that the filling aid 9400 cannot be removed from the disposable housing assembly 9402 until and unless the priming button 9434 has been actuated, which prevents removal of the filling aid until the disposable housing assembly 9402 is primed. This may be desirable/beneficial to ensure that the disposable housing assembly 9402 is primed which may be desirable/beneficial for many reason, including, but not limited to, priming is required to ensure a user/patient receives the amount of fluid they require from the reservoir. If the disposable housing assembly 9402 is not primed, then when a user/patient/caregiver requests a volume of fluid from the disposable housing assembly 9402, the first volume of fluid pumped may be used to prime the disposable housing assembly 9402, therefore, the user/patient does not receive the amount of fluid requested/required to be delivered to them. In various embodiments of the filling aid and system, however, the filling aid does not include an anti-rotation arm.

Still referring to FIG. 285, the priming button 9434 is attached to a button wedge 9456. The slider beam 9450 also includes a slider clip 9462 and an anti-rotation arm 9458. The bottom portion 9406 of the filling aid 9400 includes a bottom clip 9460. Actuating the priming button 9434 actuates the button arm 9454 which pushes the button wedge 9456 down which in turn pushes the anti-rotation arm 9458 out of the way. The slider clip 9462 hooks with the bottom clip 9460 and this ensures that the anti-rotation arm 9458 remains pushed out of the way. The slider beam 9450 clicks and locks in place and helps maintain the anti-rotation arm 9458 in its place. This enables the filling aid 9400 to be removed from the disposable housing assembly 9402. Additionally, because the slider beam 9450 is locked in place, the slider beam 9450 can not be rotated back to its starting position. This may be desirable/beneficial for many reasons, including, but not limited to, the filling aid 9400 cannot be reattached to the disposable housing assembly 9402, or any other disposable housing assembly 9402, which may be desirable/beneficial for many reasons, including, but not limited to, preventing reuse which may be unsafe for it may lead to cross-contamination as a used filling aid 9400 will no longer be sterile.

Figure 286:
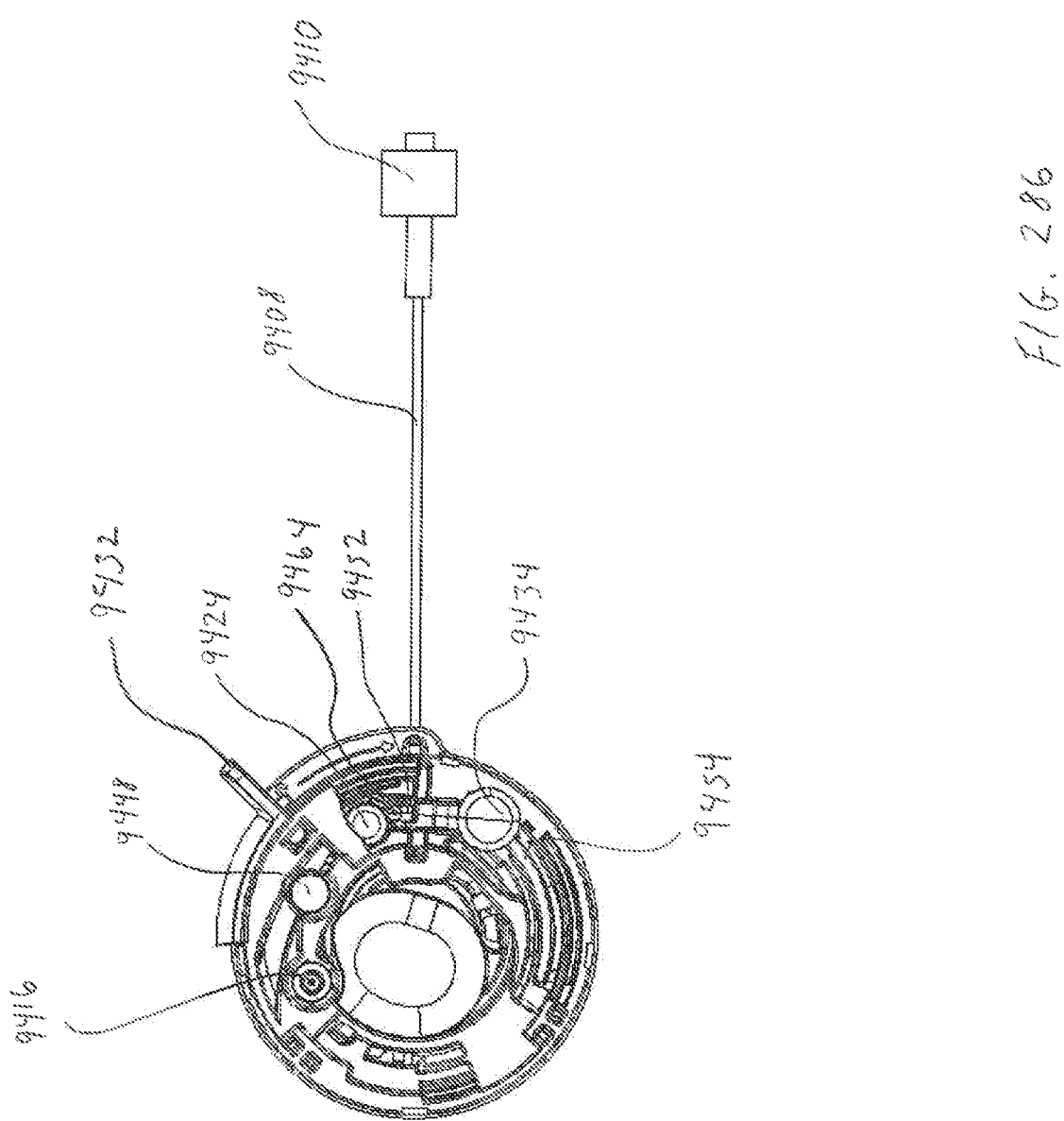

Referring now also to FIGS. 280, 281 and 286, the priming button 9434 includes a button lift pin 9464 located in the check valve plunger 9452. As the priming button 9434 is actuated/pressed/depressed the button lift pin 9464 lifts. The button lift pin 9464 moves upwards and lifts the check valve plunger 9452. This allows priming to commence. In various embodiments, the priming button 9434 may be directly attached to the button lift pin 9464. As the priming button 9434 is actuated/pressed/depressed, the priming interface 9440 continue to interact with the reservoir and apply pressure to the reservoir. This allows priming of the disposable housing assembly 9402.

A user/patient/caregiver primes the disposable housing assembly 9402 by actuating/pressing/depressing the priming button 9434. In various embodiments, priming may only be accomplished while the priming button 9434 is actuated/pressed/depressed. Thus, once pressure is exerted onto the priming button 9434, fluid will be forced out of the reservoir and through the disposable housing assembly 9402. The user/patient/caregiver may maintain the priming button 9434 in the actuated/pressed/depressed position as long as they wish and the fluid will continue to be forced out of the reservoir. To stop the priming process, the user/patient/caregiver may release pressure from the priming button 9434 such that the priming button 9434 is no longer actuated/pressed/depressed. In some embodiments, as soon as the user/patient/caregiver sees fluid coming out of the luer connector 9410 (or, in embodiments where a luer connector 9410 is not included at the base of the tubing 9408, when fluid is seen coming out of the tubing) the user/patient/caregiver may release the priming button 9434 and the priming process stops. If the user/patient/caregiver wishes to continue priming after the priming button 9434 is released, the priming button 9434 may be actuated/pressed/depressed and the priming process will continue.

In various embodiments, to remove the filling aid 9400 from the disposable housing assembly 9402, after priming, the filling aid 9400 may be rotated counter clockwise and will separate from the disposable housing assembly 9402. In various embodiments, the priming interface 9440 does not rotate, but rather, the bottom portion 9406 rotates independently from the priming interface 9440. However, in other embodiment, wherein the disposable housing assembly 9402 and/or the priming interface 9440 are shaped differently, the priming interface 9440 may rotate with the bottom portion 9406.

Referring again also to FIG. 275B, the priming interface 9440 is shown in the isometric view of the bottom of the filling aid 9400. The priming interface 9440 may be shaped as shown, or may be shaped differently. In various embodiment, the priming interface 9440 is shaped and/or configured to interact with the reservoir in the disposable housing assembly 9402. Thus, in some embodiments, the priming interface 9440 includes posts that mate with openings in the reservoir so that the priming interface 9440 may exert pressure onto the top of the reservoir.

Figure 287:
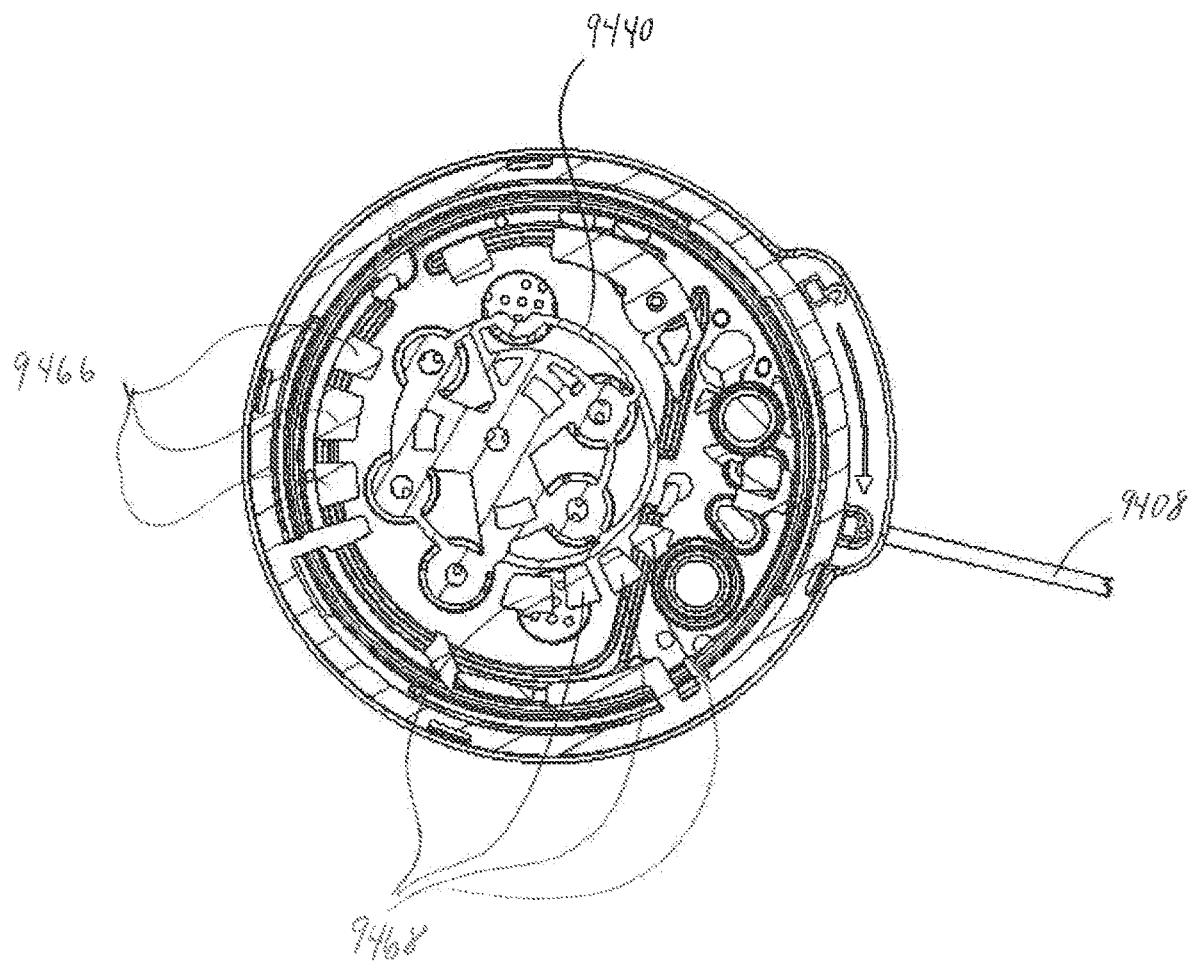

Referring now also to FIG. 287, in various embodiments of the filling aid 9400, which is shown in FIG. 287 with elements of the cover portion removed, various filling aid clips 9466, 9468 are included. These filling aid clips 9466, 9468 may be desirable/beneficial for many reasons, including, but not limited to, aiding in assembly and alignment in manufacture. Also, when the filling aid 9400 is removed from the disposable housing assembly 9402, the filling aid clips 9466, 9468 assist in pulling the priming interface 9440 off the disposable housing assembly 9402.

Once the user/patient/caregiver has filled the reservoir a desired amount, to prime the disposable housing assembly 9402, the cover portion 9404 may be rotated with respect to the bottom portion 9406. The user/patient/caregiver watches the luer 9410 until fluid appears. This indicates the disposable housing assembly 9402 is primed. At this point, the user/patient/caregiver removes the filling aid 9400 from the disposable housing assembly 9402.

Thus, when the filling aid 9400 is in the starting position, the reservoir valve, inlet valve and pump chamber are in their opened position. When the filling aid 9400 is in the filling position, the inlet check valve is in its closed position. When the filling aid 9400 is in the priming position, reservoir valve, inlet valve and pump chamber are in their opened position.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. A filling aid device for filling a reservoir comprising:
a cover portion comprising a septum window;
a slider beam comprising a septum cover; and
a first filling aid tab attached to the slider beam, the first filling aid tab in slidable relation to the cover from a first position to a second position,
wherein when the filling aid device is in an unlocked position, the septum cover is located below the septum window,
wherein when the first filling aid tab is moved from the first position to the second position, the septum cover is moved from below the septum window, and the filling aid device is in the locked position.

2. The device of claim 1, further comprising a second filling aid tab attached to the cover.

3. The device of claim 1, further comprising a bottom portion wherein the cover portion slides downward over the bottom portion and wherein when the cover portion slides downward over the bottom portion, the device is in an unlocked configuration.

4. The device of claim 3, wherein the cover portion slides downward over the bottom portion and wherein when the cover portion slides downward over the bottom portion, the device is in an unlocked configuration.

5. The device of claim 3, further comprising a first valve beam cover and a first check valve beam, wherein when the cover portion and the bottom portion are in the unlocked position, the first valve beam cover is rotated over the first check valve beam.

6. The device of claim 3, further comprising a first check valve beam, wherein when the cover portion and the bottom portion are in the unlocked position, the first valve beam is actuated.

7. The device of claim 6, wherein when the cover portion and the bottom portion are in the priming position, the first valve beam is unactuated.

8. The device of claim 3, further comprising a pump chamber plunger beam and a pump chamber plunger, wherein when the cover portion and the bottom portion are in the unlocked position, the pump chamber plunger beam is rotated over the pump chamber plunger.

9. The device of claim 3, further comprising a pump chamber plunger, wherein when the cover portion and the bottom portion are in the unlocked position, the pump chamber plunger is actuated.

10. The device of claim 3, further comprising a second valve beam cover and a second valve beam, wherein when the cover portion and the bottom portion are in the unlocked position, the second valve beam cover is rotated over the second valve beam.

11. The device of claim 10, wherein when the cover portion and the bottom portion are in the priming position, the second valve beam is unactuated.

12. The device of claim 3, further comprising a second valve beam, wherein when the cover portion and the bottom portion are in the unlocked position, the second valve beam is actuated.

13. The device of claim 3, wherein when the cover portion and the bottom portion are placed in a priming configuration, the device primes a disposable housing assembly.

14. The device of claim 3, wherein when the cover portion and the bottom portion are in a priming configuration, a first valve and a second valve are in their opened positions.

15. A system for filling a reservoir comprising:
a disposable housing assembly comprising the reservoir and a septum;
a filling aid comprising:
a cover portion comprising a septum window;
a slider beam comprising a septum cover; and
a first filling aid tab attached to the slider beam, the first filling aid tab in slidable relation to the cover from a first position to a second position,
wherein when the filling aid device is in an unlocked position, the septum cover is located below the septum window,
wherein when the first filling aid tab is moved from the first position to the second position, the septum cover is moved from below the septum window, and the filling aid device is in the locked position.

16. The system of claim 15, further comprising a needle guide accessible through the septum window.

17. The device of claim 15, further comprising a second filling aid tab attached to the cover.

18. The device of claim 15, further comprising a bottom portion wherein the cover portion slides downward over the bottom portion and wherein when the cover portion slides downward over the bottom portion, the device is in an unlocked configuration.

19. The device of claim 18, wherein the cover portion slides downward over the bottom portion and wherein when the cover portion slides downward over the bottom portion, the device is in an unlocked configuration.

20. The device of claim 18, further comprising a first valve beam cover and a first check valve beam, wherein when the cover portion and the bottom portion are in the unlocked position, the first valve beam cover is rotated over the first check valve beam.

21. The device of claim 18, further comprising a first check valve beam, wherein when the cover portion and the bottom portion are in the unlocked position, the first valve beam is actuated.

22. The device of claim 21, wherein when the cover portion and the bottom portion are in the priming position, the first valve beam is unactuated.

23. The device of claim 18, further comprising a pump chamber plunger beam and a pump chamber plunger, wherein when the cover portion and the bottom portion are in the unlocked position, the pump chamber plunger beam is rotated over the pump chamber plunger.

24. The device of claim 18, further comprising a pump chamber plunger, wherein when the cover portion and the bottom portion are in the unlocked position, the pump chamber plunger is actuated.

25. The device of claim 18, further comprising a second valve beam cover and a second valve beam, wherein when the cover portion and the bottom portion are in the unlocked position, the second valve beam cover is rotated over the second valve beam.

26. The device of claim 25, wherein when the cover portion and the bottom portion are in the priming position, the second valve beam is unactuated.

27. The device of claim 18, further comprising a second valve beam, wherein when the cover portion and the bottom portion are in the unlocked position, the second valve beam is actuated.

28. The device of claim 18, wherein when the cover portion and the bottom portion are placed in a priming configuration, the device primes a disposable housing assembly.

29. The device of claim 18, wherein when the cover portion and the bottom portion are in a priming configuration, a first valve and a second valve are in their opened positions.

* * * * *